United States Patent
Planken et al.

(10) Patent No.: US 10,662,204 B2
(45) Date of Patent: May 26, 2020

(54) SUBSTITUTED QUINAZOLINE AND PYRIDOPYRIMIDINE DERIVATIVES USEFUL AS ANTICANCER AGENTS

(71) Applicant: PFIZER INC., New York, NY (US)

(72) Inventors: Simon Planken, San Marcos, CA (US); Hengmiao Cheng, San Diego, CA (US); Michael Raymond Collins, San Diego, CA (US); Jillian Elyse Spangler, San Diego, CA (US); Alexei Brooun, San Diego, CA (US); Andreas Maderna, Escondido, CA (US); Cynthia Palmer, La Mesa, CA (US); Maria Angelica Linton, San Diego, CA (US); Asako Nagata, San Diego, CA (US); Ping Chen, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/263,185

(22) Filed: Jan. 31, 2019

(65) Prior Publication Data

US 2019/0233440 A1 Aug. 1, 2019

Related U.S. Application Data

(60) Provisional application No. 62/795,062, filed on Jan. 22, 2019, provisional application No. 62/685,383, filed on Jun. 15, 2018, provisional application No. 62/624,829, filed on Feb. 1, 2018.

(51) Int. Cl.
| | | |
|---|---|---|
| *C07D 403/12* | (2006.01) | |
| *C07D 403/14* | (2006.01) | |
| *C07D 407/14* | (2006.01) | |
| *C07D 487/10* | (2006.01) | |
| *A61P 35/00* | (2006.01) | |
| *C07D 519/00* | (2006.01) | |
| *C07D 471/04* | (2006.01) | |
| *C07D 487/04* | (2006.01) | |
| *C07D 417/14* | (2006.01) | |
| *C07D 413/14* | (2006.01) | |
| *A61P 25/00* | (2006.01) | |

(52) U.S. Cl.
CPC ............ *C07D 519/00* (2013.01); *A61P 25/00* (2018.01); *A61P 35/00* (2018.01); *C07D 403/12* (2013.01); *C07D 403/14* (2013.01); *C07D 407/14* (2013.01); *C07D 413/14* (2013.01); *C07D 417/14* (2013.01); *C07D 471/04* (2013.01); *C07D 487/04* (2013.01); *C07D 487/10* (2013.01)

(58) Field of Classification Search
CPC .. C07D 471/04; C07D 403/12; C07D 403/14; C07D 407/14
See application file for complete search history.

(56) References Cited

U.S. PATENT DOCUMENTS 6,106,864 A  8/2000  Dolan et al.

FOREIGN PATENT DOCUMENTS

| WO | 91/11172 | 8/1991 |
| WO | 94/02518 | 2/1994 |
| WO | 98/55148 | 12/1998 |
| WO | 00/35298 | 6/2000 |
| WO | 2015/054572 A1 | 4/2015 |
| WO | 2016/164675 A1 | 10/2016 |
| WO | 2017/087528 A1 | 5/2017 |
| WO | 2017/201161 A1 | 11/2017 |

OTHER PUBLICATIONS

Tan et al. World J Gastroenterol Oct. 7, 2012; 18(37): 5171-5180.*
Zeitouni et al. Cancers 2016, 8, 45, p. 1-22.*
Liu et al. Acta Pharmaceutica Sinica B 2019;9(5):871-879.*
Cancer Drug Design and Discovery, Neidle,Stephen,ed. (Elsevier/Academic Press), pp. 427-431 (2008).*
Feramisco, et al., "Transient reversion of ras oncogene-induced cell transformation by antibodies specific for amino acid 12 of ras protein", Nature, 314(18), 639-642 (1985).
Finnin, et al., "Transdermal Penetration Enhancers: Applications, Limitations, and Potential", Journal of Pharmaceutical Sciences, 88(10), 955-958 (1999).
Flaherty, et al., "Inhibition of Mutated, Activated BRAF in Metastatic Melanoma", The New England Journal of Medicine, 363(9), 809-819 (2010).
Haleblian, "Characterization of Habits and Crystalline Modification of Solids and Their Pharmaceutical Applications", Journal of Pharmaceutical Sciences, 64(8), 1269-1288 (1975).
Hunter, et al., "Biochemical and Structural Analysis of Common Cancer-Associated KRAS Mutations", Molecular Cancer Research, 13(9), 1325-1335 (2015).
Janne, et al., "Selumetinib Plus Docetaxel Compared With Docetaxel Alone and Progression-Free Survival in Patients with KRAS-Mutant Advanced Non-Small Cell Lung Cancer. The Select-1 Randomized Clinical Trial", JAMA, 317(18), 1844-1853 (2017).

(Continued)

*Primary Examiner* — Emily A Bernhardt
(74) *Attorney, Agent, or Firm* — David Rubin

(57) ABSTRACT

Compounds of the general formula:

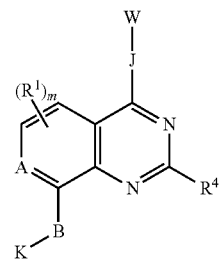

Formula (I)

processes for the preparation of these compounds, compositions containing these compounds, and administration of these compounds to patients to treat pancreatic, lung, colon and other cancers.

21 Claims, No Drawings

(56) References Cited

OTHER PUBLICATIONS

Liang, et al., "Fast-dissolving intraoral drug delivery systems", Expert Opinion on Therapeutic Patents, 11(6), 981-986 (2001).
Longshaw, et al., "Design and Synthesis of Potent "Sulfur-Free" Transition State Analogue Inhibitors of 5'-Methylthioadenosine Nucleosidase and 5'-Methylthioadenosine Phosphorylase", J. Med Chem., 53, 6730-6746 (2010).
McCormick, "KRAS as a Therapeutic Target", Clinical Cancer Research, 21(8), 1797-1802 (2015).
Ostrem, et al., "K-Ras (G12C) inhibitors allosterically control GTP affinity and effector interactions", Nature, 503, 548-561 (2013).
Prior et al., "A Comprehensive Survey of Ras Mutations in Cancer", Cancer Research, 72(10), 2457-2467 (2012).
Rajalingam et al., "Ras oncogenes and their downstream targets", Biochimica Biophysica Acta, 1773, 1177-1195 (2007).
Turke et al., "MEK inhibition leads to PI3K/AKT activation by relieving a negative feedback on ERBB", Cancer Research, 72(13), 3228-3237 (2012).
Verma et al., "Drug Delivery Technologies and Future Directions", Pharmaceutical Technology On-Line, 25(2), 1-14 (2001).
International Search Report and the Written Opinion of the International Searching Authority, PCT/IB2019/050795, dated Apr. 15, 2019.

\* cited by examiner

SUBSTITUTED QUINAZOLINE AND PYRIDOPYRIMIDINE DERIVATIVES USEFUL AS ANTICANCER AGENTS

FIELD OF THE INVENTION

This invention relates to novel quinazoline and pyridopyrimidine derivatives useful as inhibitors of the KRAS protein. This invention also relates to a method of using such compounds in the treatment of abnormal cell growth in mammals, especially humans, and to pharmaceutical compositions as anticancer agents.

BACKGROUND OF THE INVENTION

Kirsten Rat Sarcoma Oncogene Homolog (KRAS) is a small GTPase that integrates signals from outside the cell to proliferation and survival signals within the cell. This occurs through growth factor mediated activation of Guanine Exchange Factors (GEFs) which remove GDP from Ras and allow the entry of GTP which resides in high concentrations in the cytoplasm. Upon binding of the GTP nucleotide, two disordered switch regions (switch I and switch II) interact with the gamma phosphate of the nucleotide allowing Ras to interact with effector enzymes via a Ras Binding Domain (RBD) which start signalling cascades which alter gene expression. Binding of a GTPase activating protein (GAP) accelerates the intrinsic conversion of GTP to GDP and renders the protein in an inactive state thus terminating the signal (Rajalingam, K., R. Schreck, U. R. Rapp and S. Albert (2007). "Ras oncogenes and their downstream targets." Biochim Biophys Acta 1773(8): 1177-1195.)

Ras is mutated in up to 20% of human tumors at the codon 12, 13, and 61 positions which serve to promote the GTP bound form of the protein. These include colon, pancreas and lung tumors, the latter of which show KRAS mutation in up to 25-30% of all tumors with 40% of these harboring a G12C mutation thought to be promoted by carcinogens in cigarette smoke. KRAS with G12C mutations activate the Mapk pathway and promote Non-Small Cell Lung Cancer (NSCLC) growth and survival. (Prior, I. A., P. D. Lewis and C. Mattos (2012). "A comprehensive survey of Ras mutations in cancer." Cancer Res 72(10): 2457-2467.)

Since the discovery of KRAS mutations in human tumors and that inhibiting signalling by these proteins caused inhibition of the cancer phenotype there has been a strong desire by both academic groups and industry to find Ras inhibitors (Feramisco, J. R., R. Clark, G. Wong, N. Arnheim, R. Milley and F. McCormick (1985). "Transient reversion of ras oncogene-induced cell transformation by antibodies specific for amino acid 12 of ras protein." Nature 314(6012): 639-642.) and (McCormick, F. (2015). "KRAS as a Therapeutic Target." Clin Cancer Res 21(8): 1797-1801. Specific Inhibitors of the KRAS effector BRaf alone and combined with other inhibitors the Mapk pathway have shown dramatic responses in melanoma where this BRaf is frequently activated via mutation (Flaherty, K. T., I. Puzanov, K. B. Kim, A. Ribas, G. A. McArthur, J. A. Sosman, P. J. O'Dwyer, R. J. Lee, J. F. Grippo, K. Nolop and P. B. Chapman (2010). "Inhibition of mutated, activated BRAF in metastatic melanoma." N Engl J Med 363(9): 809-819.) In contrast, general Mapk inhibitors have not shown dramatic responses in cancers with mutant KRAS potentially because of the lack of an appropriate therapeutic index over normal tissues or compensatory signalling by other Ras pathways (Turk Turke, A. B., Y. Song, C. Costa, R. Cook, C. L. Arteaga, J. M. Asara and J. A. Engelman (2012). "MEK inhibition leads to PI3K/AKT activation by relieving a negative feedback on ERBB receptors." Cancer Res 72(13): 3228-3237.e, Song et al. 2012) and (Janne, P. A., M. M. van den Heuvel, F. Barlesi, M. Cobo, J. Mazieres, L. Crino, S. Orlov, F. Blackhall, J. Wolf, P. Garrido, A. Poltoratskiy, G. Mariani, D. Ghiorghiu, E. Kilgour, P. Smith, A. Kohlmann, D. J. Carlile, D. Lawrence, K. Bowen and J. Vansteenkiste (2017). "Selumetinib Plus Docetaxel Compared With Docetaxel Alone and Progression-Free Survival in Patients With KRAS-Mutant Advanced Non-Small Cell Lung Cancer: The SELECT-1 Randomized Clinical Trial." Jama 317(18): 1844-1853.)

Compounds that selectively bind mutant KRAS are highly desirable as they would spare impact on normal tissues and for adequate inhibition of Ras signalling within the tumor to elicit antitumor activity. Recently G12C has been shown to retain cycling both biochemically and in cancer cells creating an opportunity to disrupt activation (Hunter, J. C., A. Manandhar, M. A. Carrasco, D. Gurbani, S. Gondi and K. D. Westover (2015). "Biochemical and Structural Analysis of Common Cancer-Associated KRAS Mutations." Mol Cancer Res 13(9): 1325-1335.) Compounds that utilize the cysteine substitution in G12C and for binding and prevent the GDP to GTP exchange were described (Ostrem, J. M., U. Peters, M. L. Sos, J. A. Wells and K. M. Shokat (2013). "K-Ras(G12C) inhibitors allosterically control GTP affinity and effector interactions." Nature 503(7477): 548-551.) This makes utilizing G12C binding compounds that lock KRAS in the inactive state an attractive opportunity for cancer treatment.

SUMMARY OF THE INVENTION

Given its role in regulating various biological processes, KRAS is an attractive target for modulation with small molecule inhibitors. To date, few effective KRAS inhibitors have been developed, and no KRAS inhibitors have entered the clinic.

Each of the embodiments of the compounds of the present invention described below can be combined with any other embodiment of the compounds of the present invention described herein not inconsistent with the embodiment with which it is combined. Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

The invention includes embodiments wherein there is provided a compound of Formula (I):

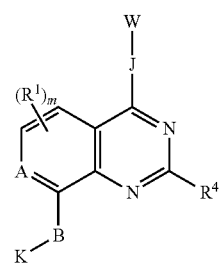

Formula (I)

or a pharmaceutically acceptable salt thereof; wherein:
A is —C(H)— or nitrogen;
B is oxygen, sulfur, $NR^6$ or $C(R^6)_2$;

J is a heterocycle having 3-12 ring atoms, where J is optionally substituted with 1, 2, 3, 4, 5 or 6 $R^2$;

K is $C_6$-$C_{12}$ aryl, or K is heteroaryl having 5-12 ring atoms, where K is optionally substituted with 1, 2, 3, 4, 5, 6 or 7 $R^3$;

W is selected from the group consisting of:

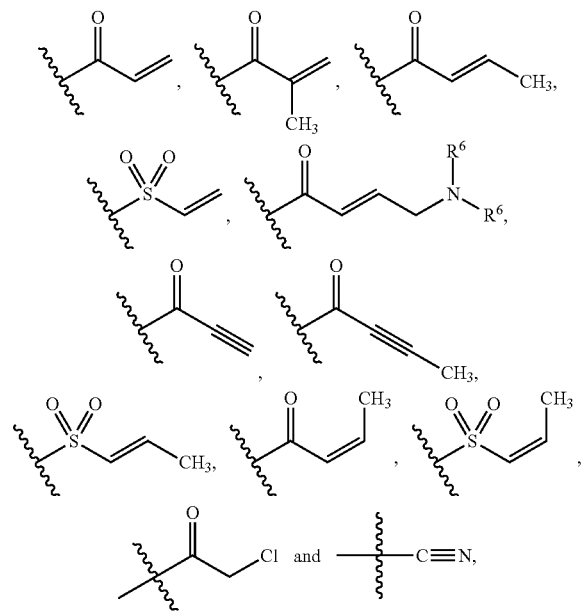

where W is optionally substituted with 1, 2 or 3 $R^5$;

each $R^1$ is independently selected from the group consisting of $C_1$-$C_6$ alkyl, $C_3$-$C_6$ cycloalkyl, $C_1$-$C_6$ alkyl-hydroxy, $C_1$-$C_6$ alkoxy, $C_1$-$C_6$ alkyl-$C_1$-$C_6$alkoxy, hydroxy, $C_2$-$C_6$ alkenyl, $C_2$-$C_6$ alkynyl, halogen, $C_1$-$C_6$ haloalkyl, cyano and $N(R^6)_2$, or two $R^1$ optionally join to form a heterocycle having 3-12 ring atoms or a $C_3$-$C_6$ cycloalkyl;

each $R^2$ is independently selected from the group consisting of $C_1$-$C_6$ alkyl, $C_3$-$C_6$ cycloalkyl, hydroxy, $C_1$-$C_6$ alkyl-hydroxy, $C_1$-$C_6$ alkoxy, halogen, $C_1$-$C_6$ haloalkyl, cyano, $C_1$-$C_6$ alkyl-cyano and oxo, or two $R^2$ optionally join to form a heterocycle having 3-12 ring atoms or a $C_3$-$C_6$ cycloalkyl;

each $R^3$ is independently selected from the group consisting of $C_1$-$C_6$ alkyl, $C_3$-$C_6$ cycloalkyl, hydroxy, $C_1$-$C_6$ alkoxy, halogen, $C_1$-$C_6$ halo-alkyl, $N(R^6)_2$, oxo and cyano, or two $R^3$ optionally join to form a heterocycle having 3-12 ring atoms or $C_3$-$C_6$ cycloalkyl;

$R^4$ is —X—Y—Z where:

X is absent or is selected from the group consisting of oxygen, sulfur and —$NR^6$—, Y is absent or $C_1$-$C_6$ alkylenyl, and Z is selected from H, —$N(R^6)_2$, —C(O)—$N(R^6)_2$, —$OR^6$, heterocycle having 3-12 ring atoms, heteroaryl having 5-12 ring atoms, and $C_3$-$C_6$ cycloalkyl, where $R^4$ is optionally substituted with one or more $R^7$;

each $R^5$ is independently selected from the group consisting of: $C_1$-$C_6$ alkyl, hydroxy, $C_1$-$C_6$ alkoxy, halogen and —$N(R^6)_2$;

each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl, hydroxy, $C_1$-$C_6$ alkoxy, halogen, —$N(R^6)_2$, heterocycle having 3-12 ring atoms and oxo; and m is 0, 1, 2 or 3.

The invention also includes embodiments wherein there is provided a compound of Formula (I):

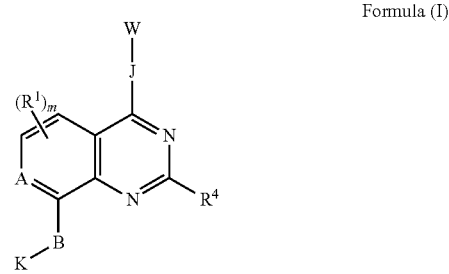

Formula (I)

or a pharmaceutically acceptable salt thereof; wherein:

A is —C(H)— or nitrogen;

B is oxygen, sulfur, $NR^6$ or $C(R^6)_2$;

J is heterocycle having 3-12 ring atoms and is selected from the group consisting of:

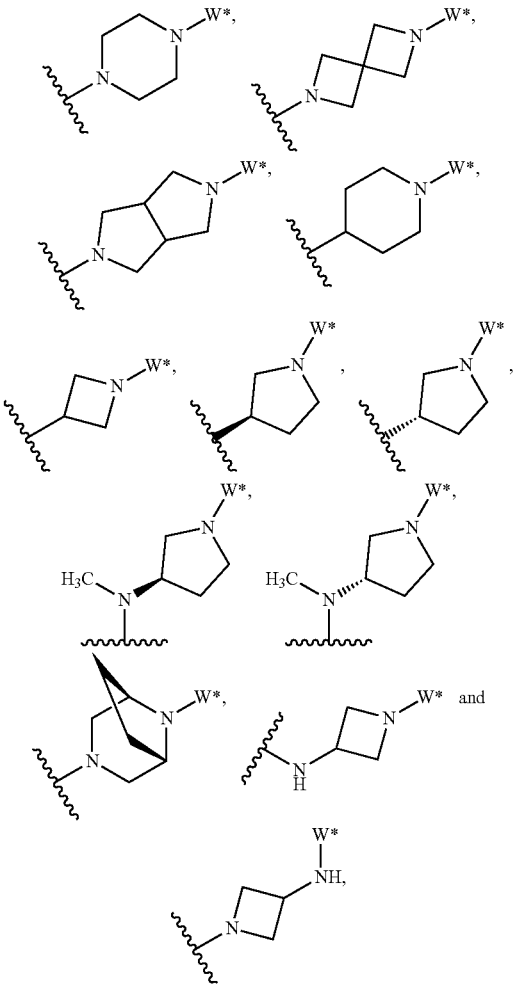

where W* represents the point of attachment to W, and where J is optionally substituted with 1, 2, 3, 4, 5 or 6 $R^2$;

K is $C_6$-$C_{12}$ aryl and is selected from the group consisting of:

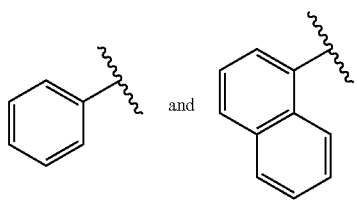

or

K is heteroaryl having 5-12 ring atoms and is selected from the group consisting of:

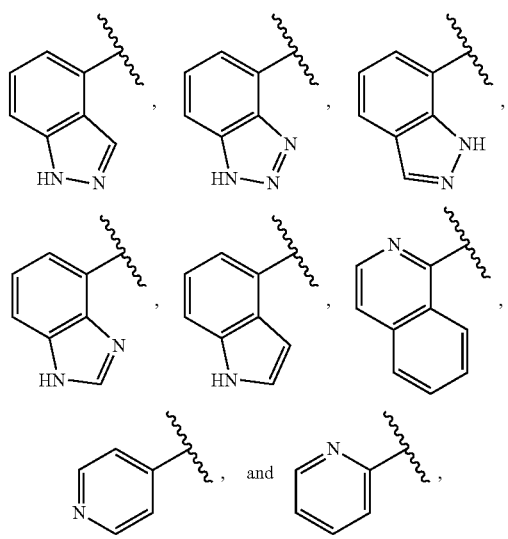

where K is optionally substituted with 1, 2, 3, 4, 5, 6 or 7 $R^3$;

W is selected from the group consisting of:

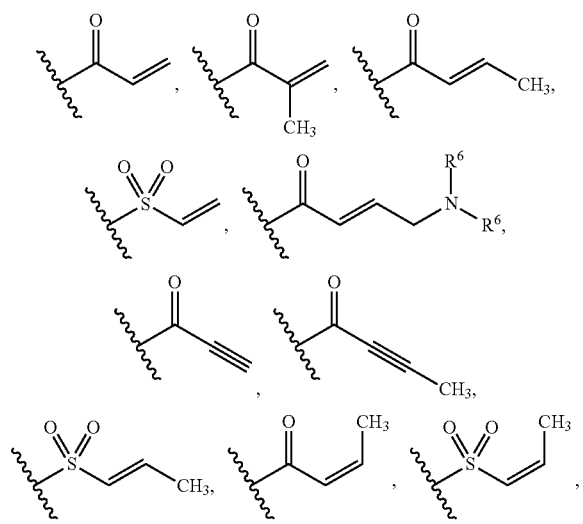

-continued

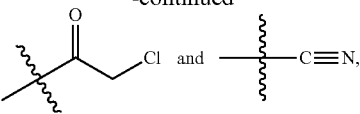

where W is optionally substituted with 1, 2 or 3 $R^5$;

each $R^1$ is independently selected from the group consisting of $C_1$-$C_6$ alkyl, $C_3$-$C_6$ cycloalkyl, $C_1$-$C_6$ alkyl-hydroxy, $C_1$-$C_6$ alkoxy, $C_1$-$C_6$ alkyl-$C_1$-$C_6$alkoxy, hydroxy, $C_2$-$C_6$ alkenyl, $C_2$-$C_6$ alkynyl, halogen, $C_1$-$C_6$ haloalkyl, cyano and $N(R^6)_2$, or two $R^1$ optionally join to form a heterocycle having 3-12 ring atoms or a $C_3$-$C_6$ cycloalkyl;

each $R^2$ is independently selected from the group consisting of $C_1$-$C_6$ alkyl, $C_3$-$C_6$ cycloalkyl, hydroxy, $C_1$-$C_6$ alkyl-hydroxy, $C_1$-$C_6$ alkoxy, halogen, $C_1$-$C_6$ haloalkyl, cyano, $C_1$-$C_6$ alkyl-cyano and oxo, or two $R^2$ optionally join to form a heterocycle having 3-12 ring atoms or a $C_3$-$C_6$ cycloalkyl;

each $R^3$ is independently selected from the group consisting of $C_1$-$C_6$ alkyl, $C_3$-$C_6$ cycloalkyl, hydroxy, $C_1$-$C_6$ alkoxy, halogen, $C_1$-$C_6$ halo-alkyl, $N(R^6)_2$, oxo and cyano, or two $R^3$ optionally join to form a heterocycle having 3-12 ring atoms or $C_3$-$C_6$ cycloalkyl;

$R^4$ is —X—Y—Z where:
X is absent or is selected from the group consisting of oxygen, sulfur and —$NR^6$—,
Y is absent or $C_1$-$C_6$ alkylenyl, and
Z is selected from H, —$N(R^6)_2$, —C(O)—$N(R^6)_2$, —$OR^6$, heterocycle having 3-12 ring atoms, heteroaryl having 5-12 ring atoms, and $C_3$-$C_6$ cycloalkyl,
where $R^4$ is optionally substituted with one or more $R^7$;

each $R^5$ is independently selected from the group consisting of: $C_1$-$C_6$ alkyl, hydroxy, $C_1$-$C_6$ alkoxy, halogen and —$N(R^6)_2$;

each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl, hydroxy, $C_1$-$C_6$ alkoxy, halogen, —$N(R^6)_2$, heterocycle having 3-12 ring atoms and oxo; and m is 0, 1, 2 or 3.

The invention also includes embodiments wherein there is provided a compound of Formula (I):

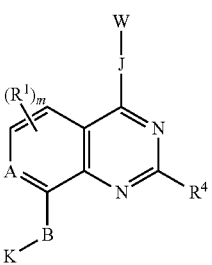

Formula (I)

or a pharmaceutically acceptable salt thereof; wherein:
A is —C(H)— or nitrogen;
B is oxygen or $C(R^6)_2$;
J is heterocycle having 3-12 ring atoms and is selected from the group consisting of:

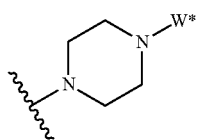

where W*' represents the point of attachment to W, and where J is optionally substituted with 1 R²;
K is C₆-C₁₂ aryl and is:

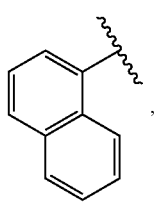 [SMILES: *c1cccc2ccccc12]

or
K is heteroaryl having 5-12 ring atoms and is selected from the group consisting of:

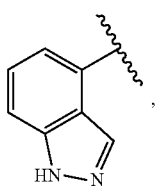

where K is optionally substituted with 1 or 2 R³;
W is selected from the group consisting of:

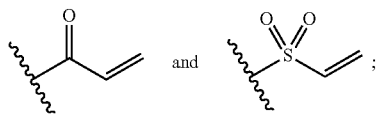

each R¹ is independently selected from the group consisting of C₁-C₆ alkyl, halogen, C₁-C₆ haloalkyl cyano and N(R⁶)₂;
each R² is C₁-C₆ alkyl;
each R³ is independently selected from the group consisting of C₁-C₆ alkyl, hydroxy, halogen, and C₁-C₆ halo-alkyl;
R⁴ is —X—Y—Z where:
X is absent or is oxygen,
Y is absent or C₁-C₆ alkylenyl, and
Z is selected from H, heterocycle having 3-12 ring atoms and C₃-C₆ cycloalkyl,
where R⁴ is optionally substituted with R⁷;
each R⁶ is independently selected from the group consisting of hydrogen, hydroxyl, C₁-C₆ alkoxy and C₁-C₆ alkyl, or two R⁶ optionally join to form heterocycle having 3-12 ring atoms or C₃-C₆ cycloalkyl;
each R⁷ is independently R⁷' or C₁-C₆ alkyl-R⁷', where each R⁷' is independently selected from the group consisting of: C₁-C₆ alkyl and —N(R⁶)₂; and
m is 0, 1, 2 or 3.

It is noted that embodiments include compounds of Formula (I) wherein two R³ substituents join to form a heterocycle having 3-12 ring atoms wherein said heterocycle having 3-12 ring atoms is a lactam. Exemplary lactams fused to K (in the below instances K is aryl, but K may also be heteroaryl) include but are not limited to:

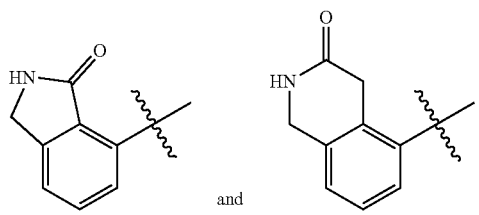 [SMILES: *c1cccc2c1C(=O)NC2 ; *c1cccc2c1CC(=O)NC2]

and

It is also the case that embodiments include compounds of Formula (I) and pharmaceutically acceptable salts thereof wherein K is selected from:

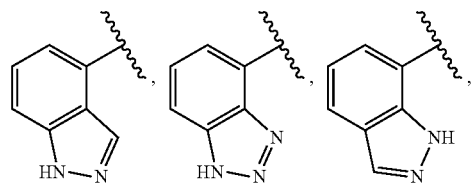

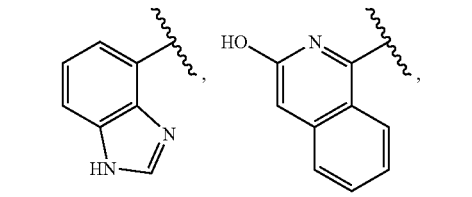

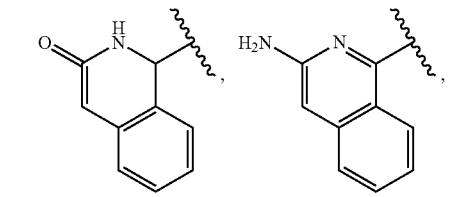

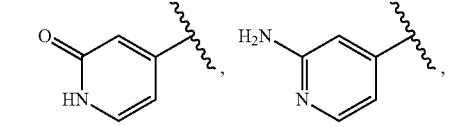

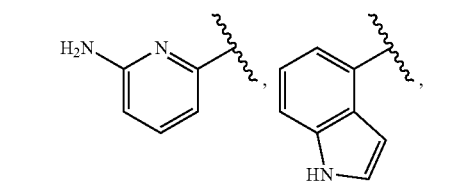

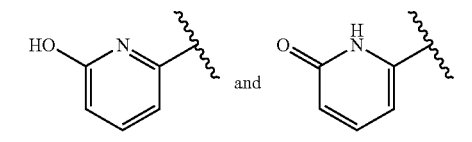

and compounds of Formula (I) and pharmaceutically acceptable salts thereof wherein K is selected from:

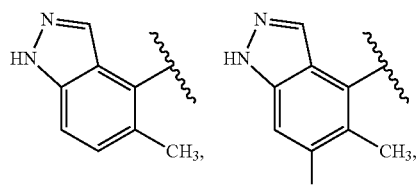

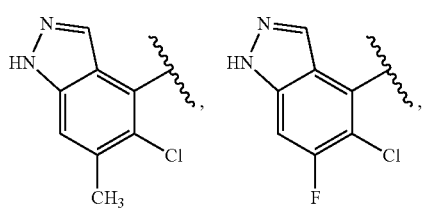

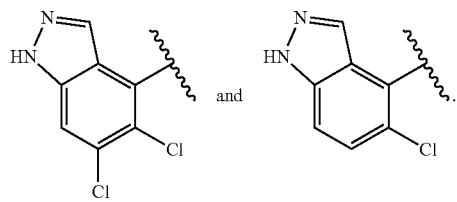

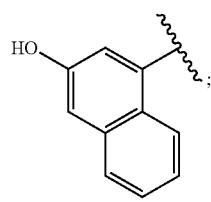 [SMILES: *c1cc(O)cc2ccccc12]

compounds of Formula (I) and pharmaceutically acceptable salts thereof wherein K is:

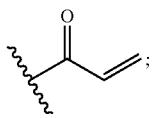 [SMILES: *C(=O)C=C];

compounds of Formula (I) and pharmaceutically acceptable salts thereof wherein W is:

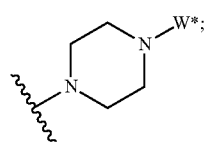;

compounds of Formula (I) and pharmaceutically acceptable salts thereof wherein J is:

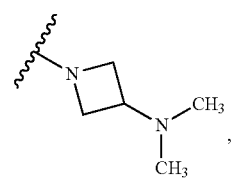

compounds of Formula (I) and pharmaceutically acceptable salts thereof wherein J is selected from:

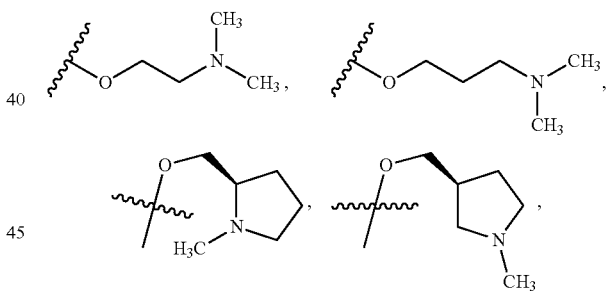

and/or compounds of Formula (I) and pharmaceutically acceptable salts thereof wherein $R^4$ is selected from the group consisting of:

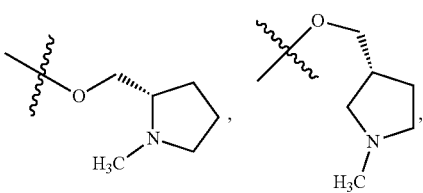

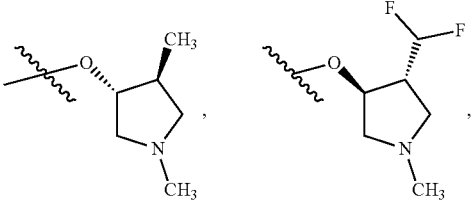

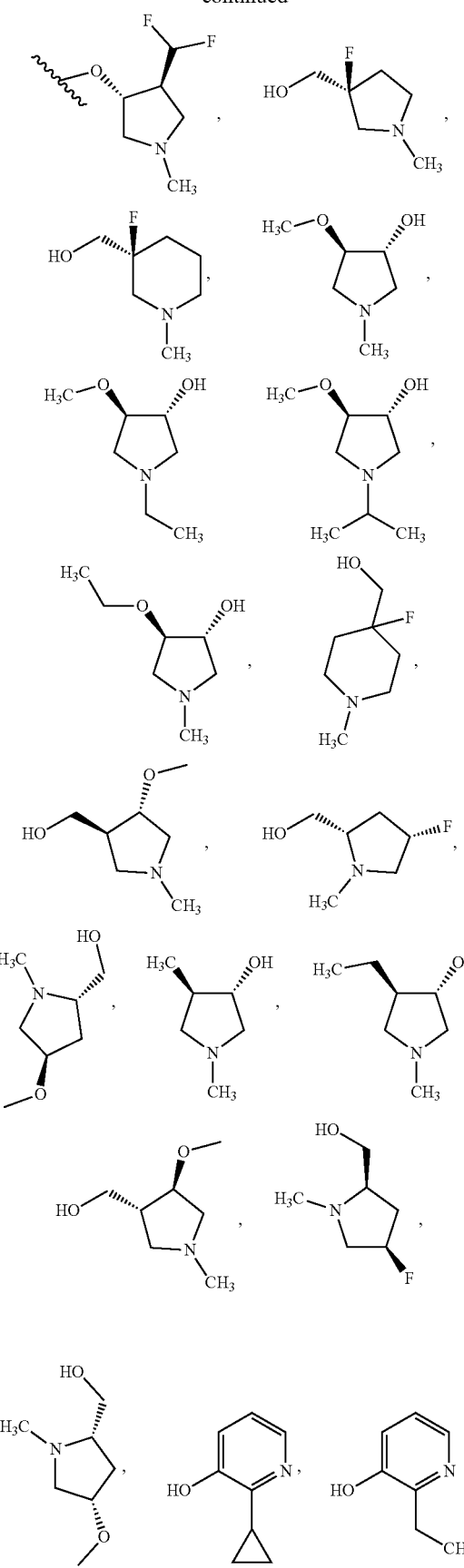
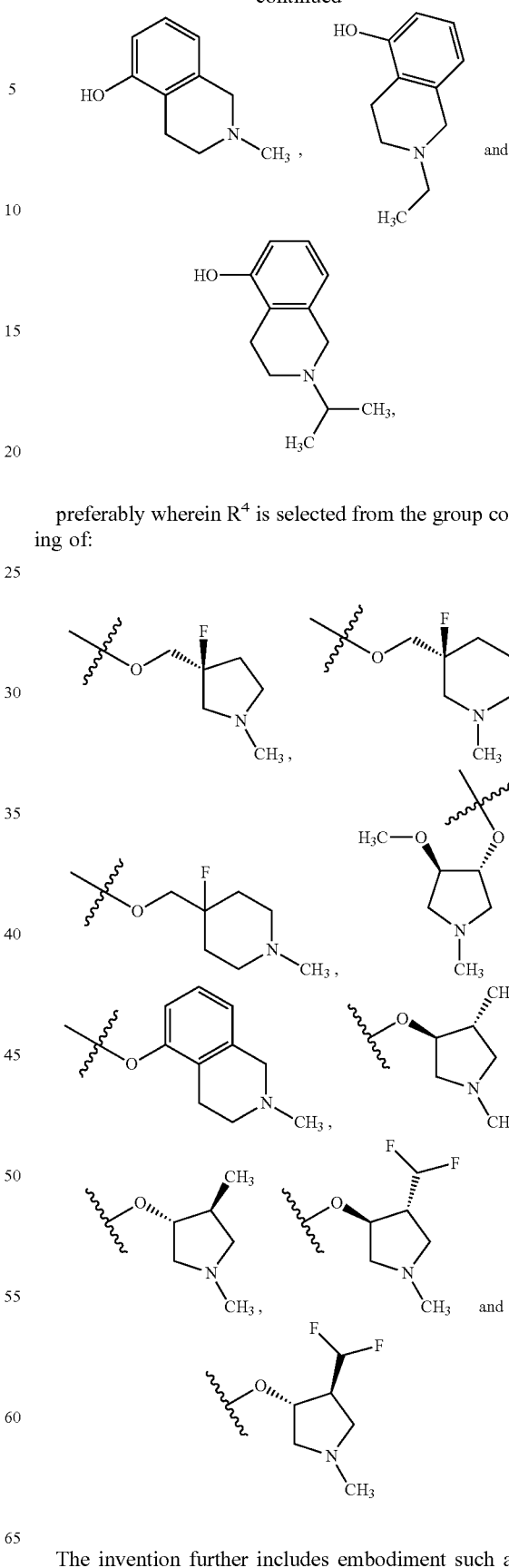
preferably wherein $R^4$ is selected from the group consisting of:
The invention further includes embodiment such as the compounds described in Formula (II):

Formula (II)

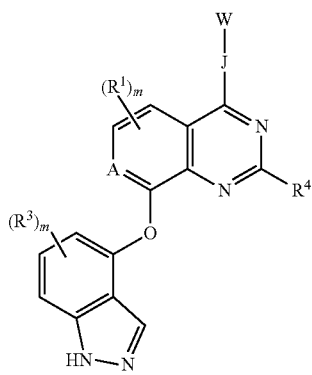

or a pharmaceutically acceptable salt thereof; wherein:
A is —C(H)— or nitrogen;
J is:

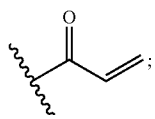

where W* represents the point of attachment to W, and where J is optionally substituted with 1 or more $R^2$;
W is:

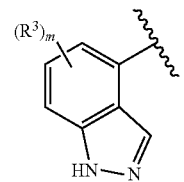

each $R^1$ is independently selected from the group consisting of $C_1$-$C_6$ alkyl, halogen, $C_1$-$C_6$ haloalkyl, cyano and $N(R^6)_2$;
$R^2$ is $C_1$-$C_6$ alkyl;
each $R^3$ is independently selected from the group consisting of $C_1$-$C_6$ alkyl, hydroxy, halogen, and $C_1$-$C_6$ halo-alkyl;
$R^4$ is —X—Y—Z where:
X is absent or is oxygen,
Y is absent or $C_1$-$C_6$ alkylenyl, and
Z is selected from H, heterocycle having 3-12 ring atoms and $C_3$-$C_6$ cycloalkyl,
where $R^4$ is optionally substituted with $R^7$;
each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;
each $R^7$ is independently $R^{7'}$ or $C_1$-$C_6$ alkyl-$R^{7'}$, where each $R^{7'}$ is independently selected from the group consisting of: $C_1$-$C_6$ alkyl and —N($R^6)_2$; and
each m is independently 0, 1, 2 or 3.

Formula (II) compounds or salts include those wherein

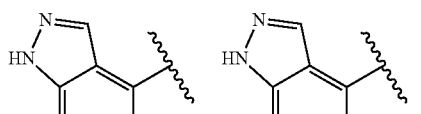

is selected from the group consisting of:

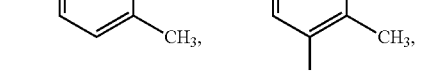
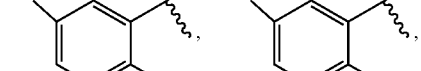
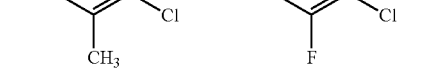

Formula (II) compounds or salts also include those wherein $R^4$ is selected from the group consisting of:

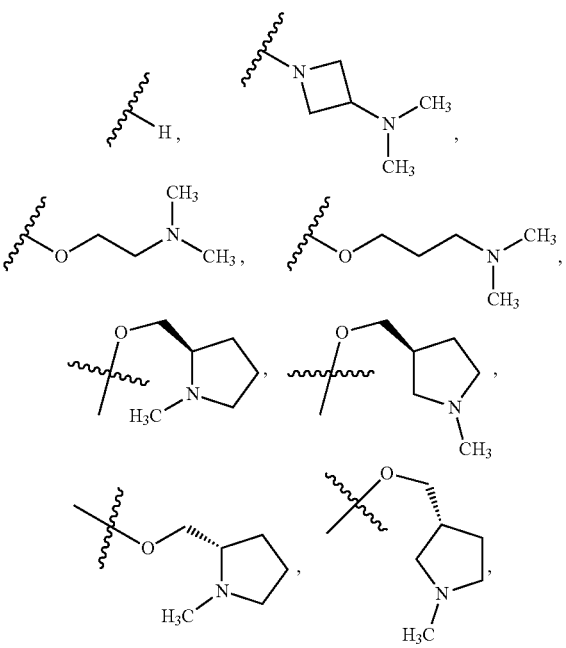

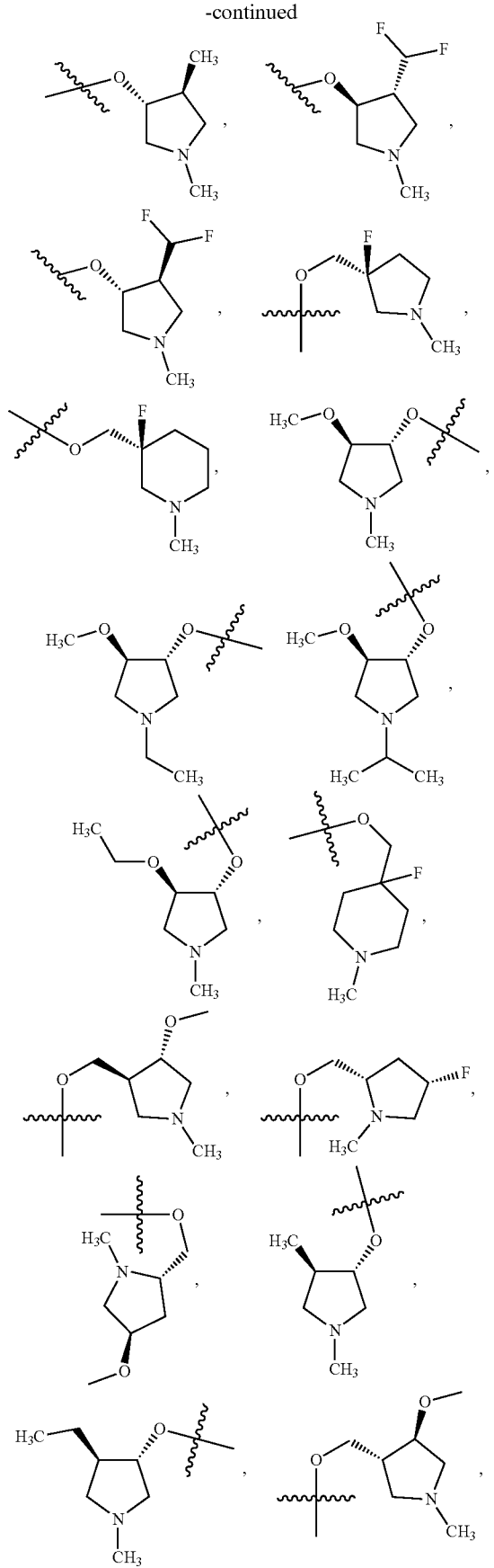
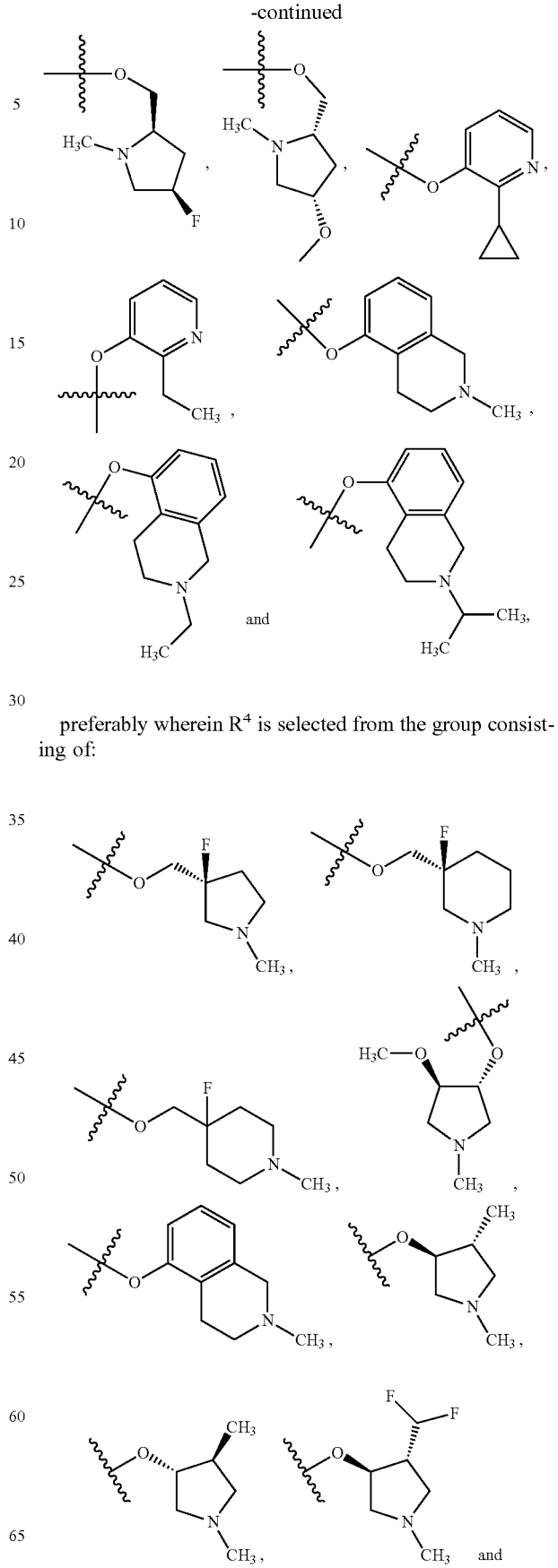
preferably wherein R[4] is selected from the group consisting of:

-continued

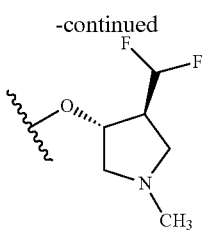

The invention further includes embodiment such as the compounds described in Formula (III):

Formula (III)

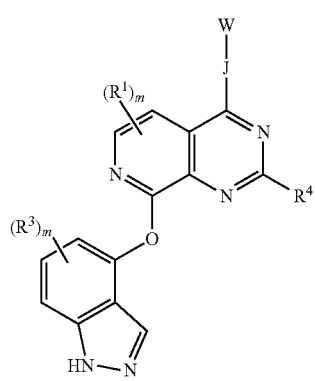

or a pharmaceutically acceptable salt thereof; wherein:
J is:

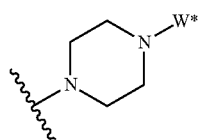

where W* represents the point of attachment to W, and where J is optionally substituted with 1 or more $R^2$;
W is selected from the group consisting of:

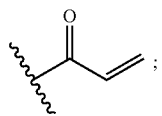 [SMILES: *C(=O)C=C]

each $R^1$ is independently selected from the group consisting of $C_1$-$C_6$ alkyl, halogen, $C_1$-$C_6$ haloalkyl, cyano and $N(R^6)_2$;
$R^2$ is $C_1$-$C_6$ alkyl;
each $R^3$ is independently selected from the group consisting of $C_1$-$C_6$ alkyl, hydroxy, halogen, and $C_1$-$C_6$ halo-alkyl;
$R^4$ is —X—Y—Z where:
X is absent or is oxygen,
Y is absent or $C_1$-$C_6$ alkylenyl, and
Z is selected from H, heterocycle having 3-12 ring atoms and $C_3$-$C_6$ cycloalkyl,
where $R^4$ is optionally substituted with $R^7$;
each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl and —$N(R^6)_2$; and
each m is independently 0, 1, 2 or 3.

Formula (III) compounds or salts include those wherein

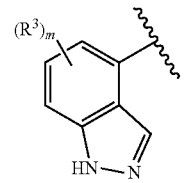

is selected from the group consisting of:

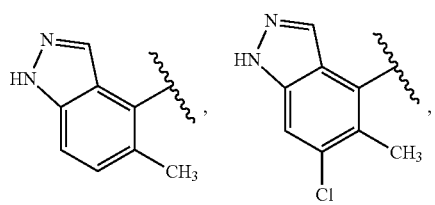

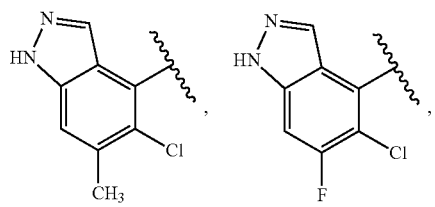

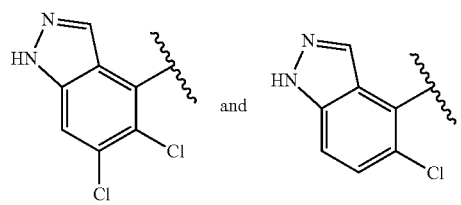

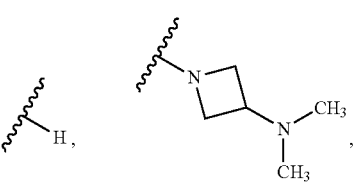 and 

Formula (III) compounds or salts also include those wherein $R^4$ is selected from the group consisting of:

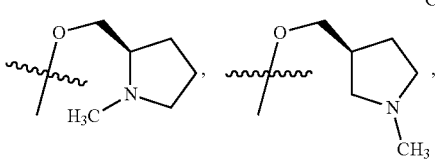

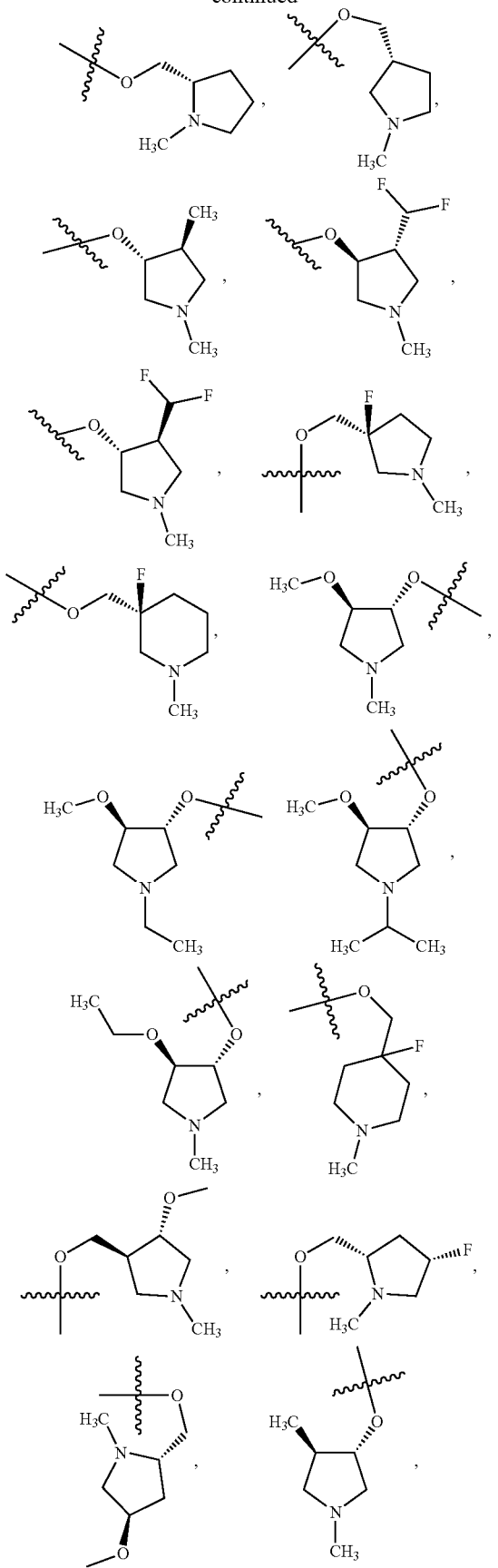
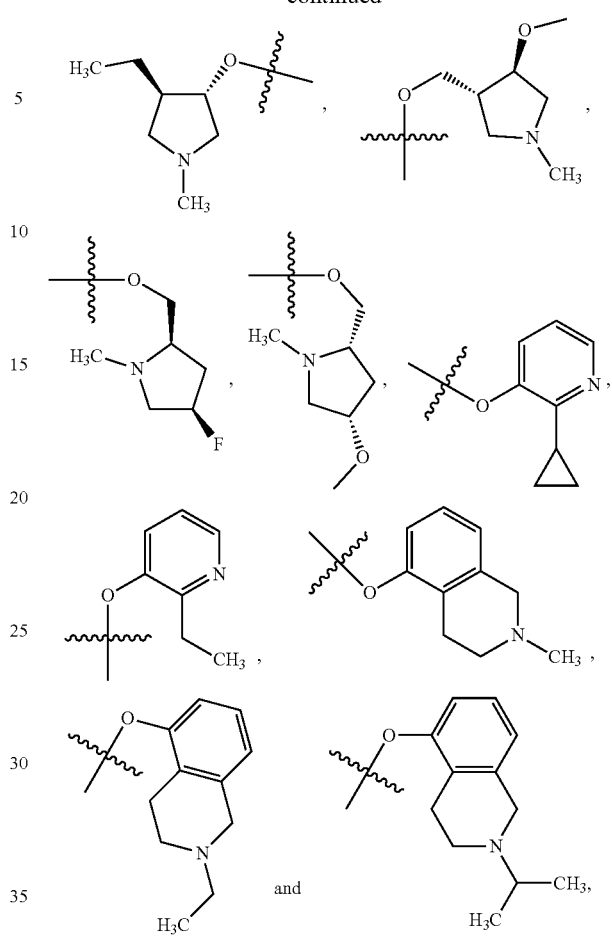
preferably wherein R[4] is selected from the group consisting of:
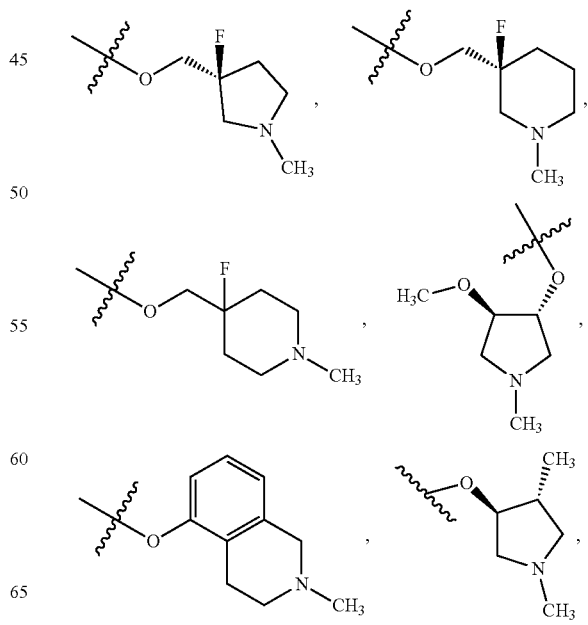

-continued

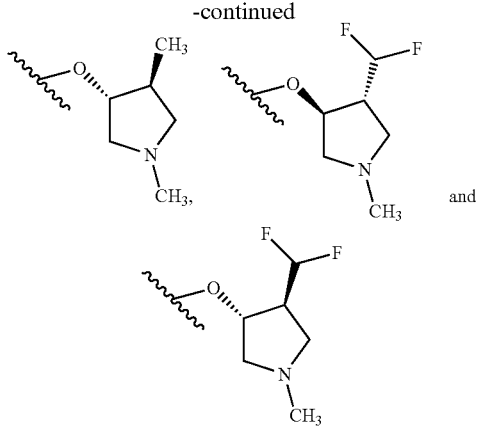

The invention still further includes embodiment such as the compounds described in Formula (IV):

Formula (IV)

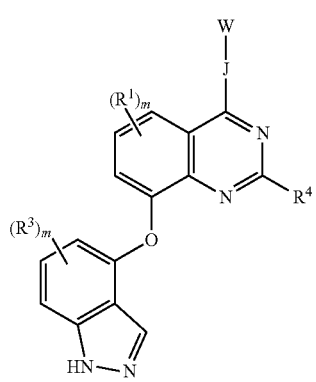

or a pharmaceutically acceptable salt thereof; wherein:
J is:

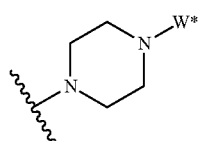

where W* represents the point of attachment to W, and where J is optionally substituted with 1 or more $R^2$;
W is selected from the group consisting of:

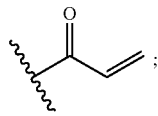 [SMILES: *C(=O)C=C]

each $R^1$ is independently selected from the group consisting of $C_1$-$C_6$ alkyl, halogen, $C_1$-$C_6$ haloalkyl, cyano and $N(R^6)_2$;
$R^2$ is $C_1$-$C_6$ alkyl;
each $R^3$ is independently selected from the group consisting of $C_1$-$C_6$ alkyl, hydroxy, halogen, and $C_1$-$C_6$ halo-alkyl;
$R^4$ is —X—Y—Z where:
X is absent or is oxygen,
Y is absent or $C_1$-$C_6$ alkylenyl, and
Z is selected from H, heterocycle having 3-12 ring atoms and $C_3$-$C_6$ cycloalkyl,
where $R^4$ is optionally substituted with $R^7$;
each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;
each $R^7$ is independently $R^{7'}$ or $C_1$-$C_6$ alkyl-$R^{7'}$, where each $R^{7'}$ is independently selected from the group consisting of: $C_1$-$C_6$ alkyl and —N($R^6)_2$; and
each m is independently is 0, 1, 2 or 3.

These Formula (IV) compounds or salts include those wherein

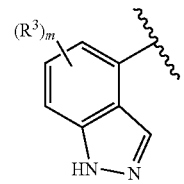

is selected from the group consisting of:

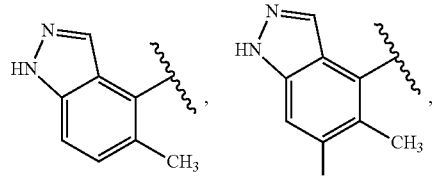

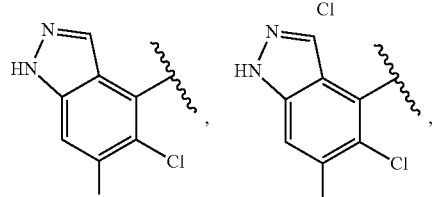

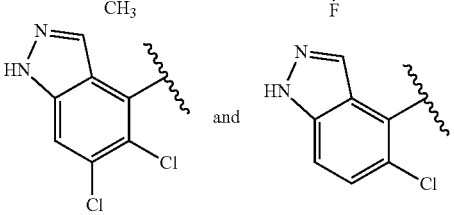

These Formula (IV) compounds or salts also include those wherein $R^4$ is selected from the group consisting of:
of:

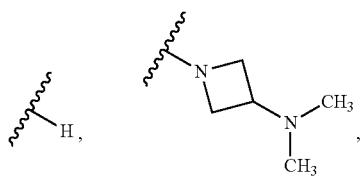

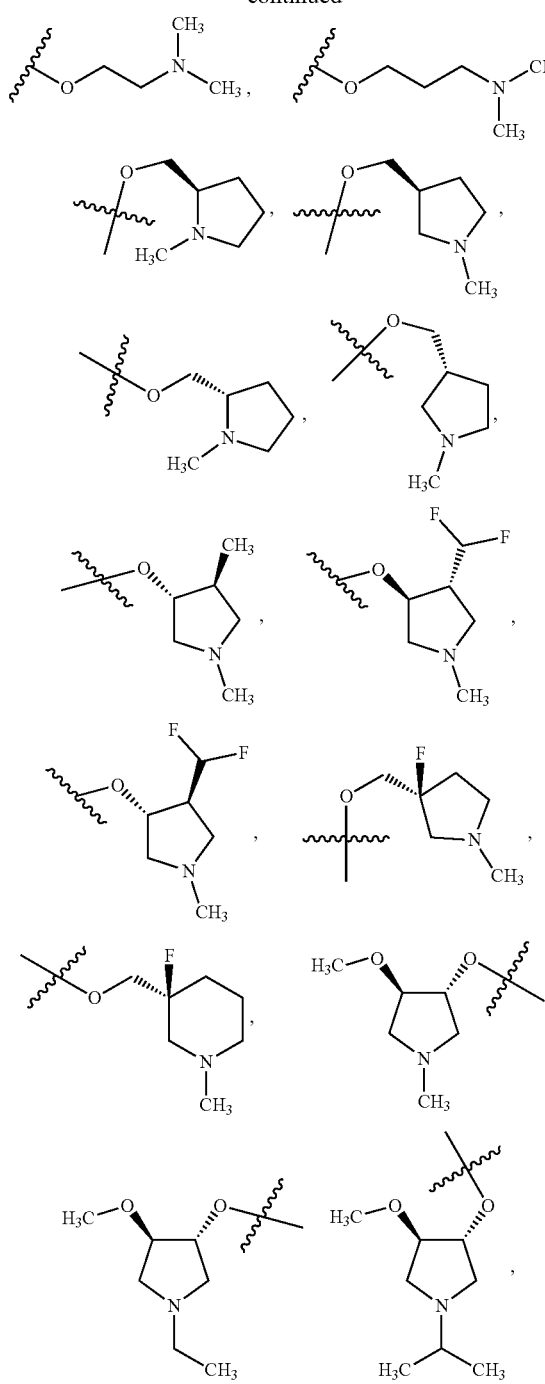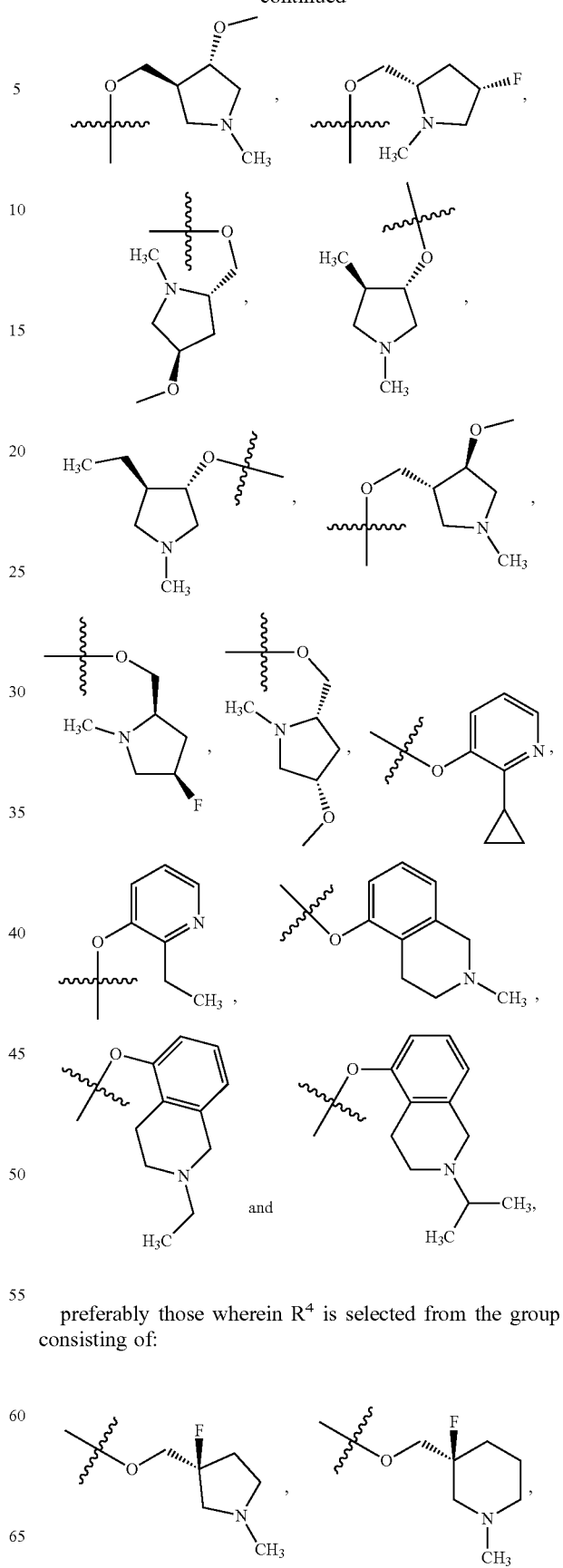
preferably those wherein $R^4$ is selected from the group consisting of:
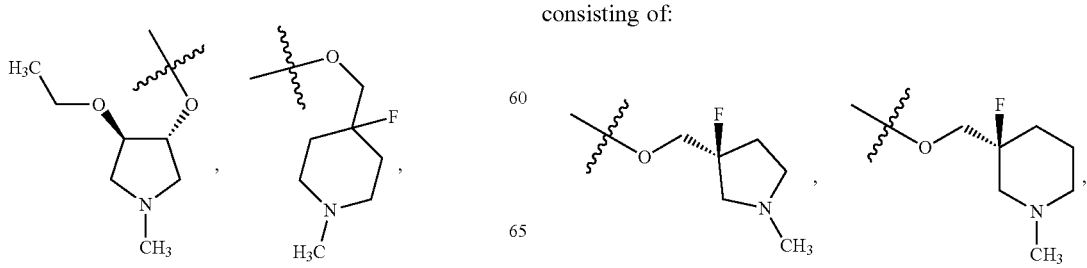

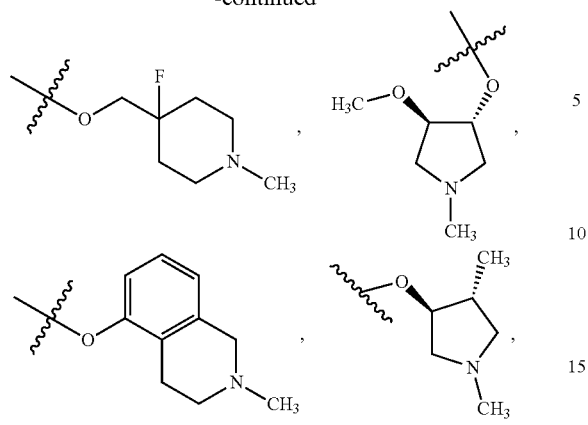
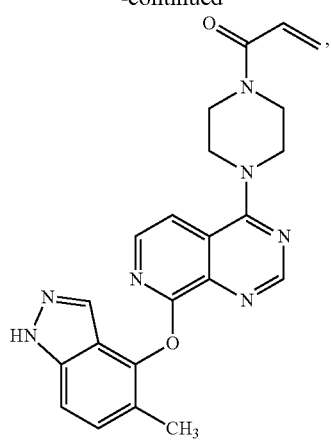
Moreover, embodiments of the invention include compounds selected from the group consisting of:
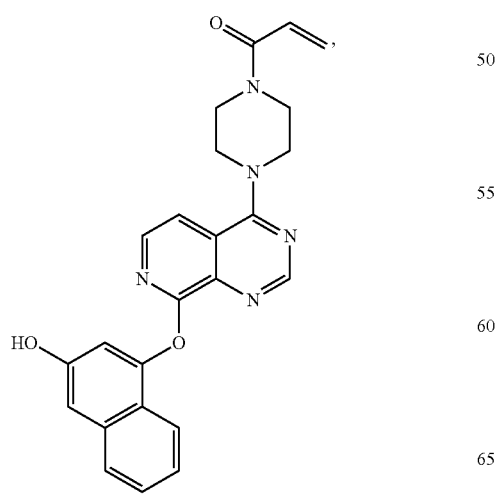

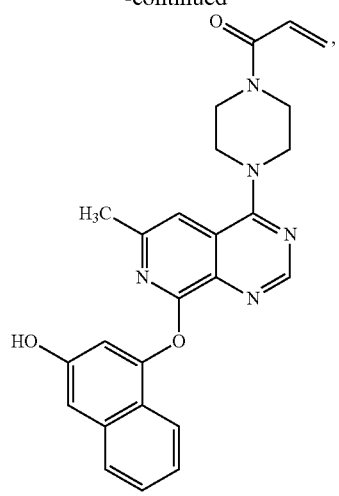
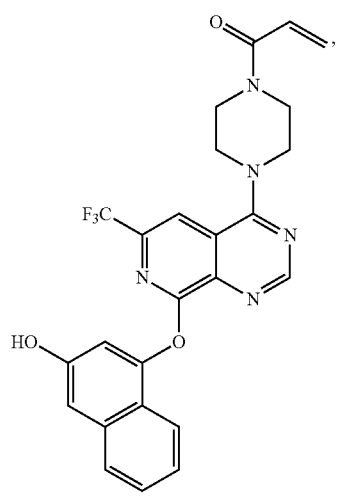
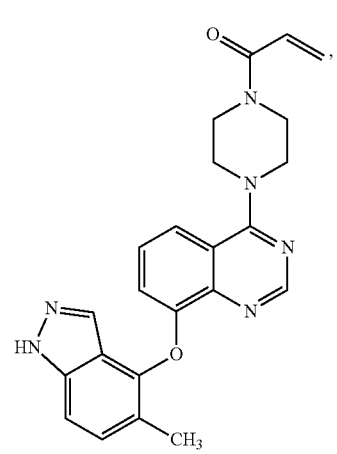
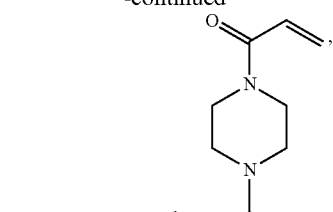
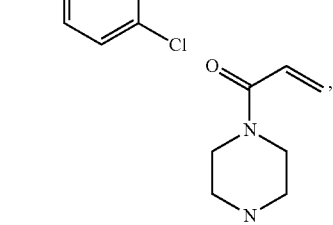
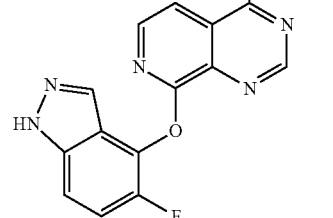
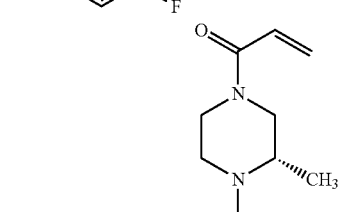
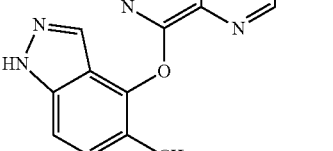

-continued
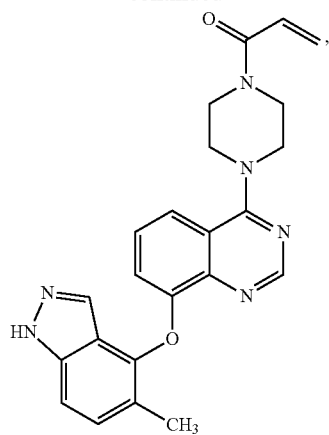
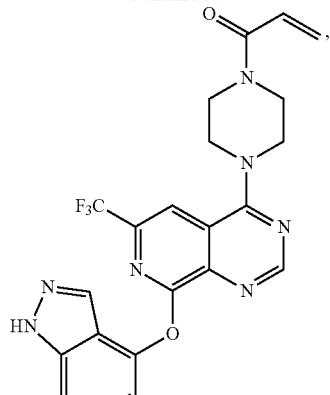
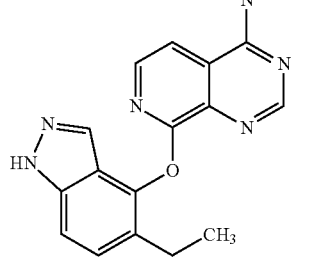
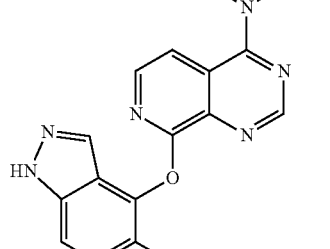
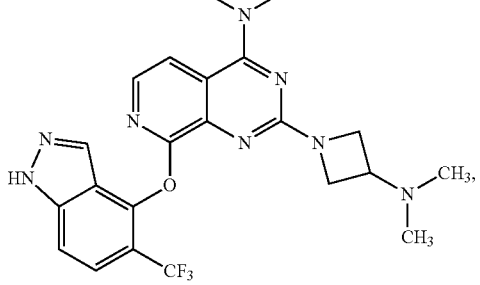

-continued
31
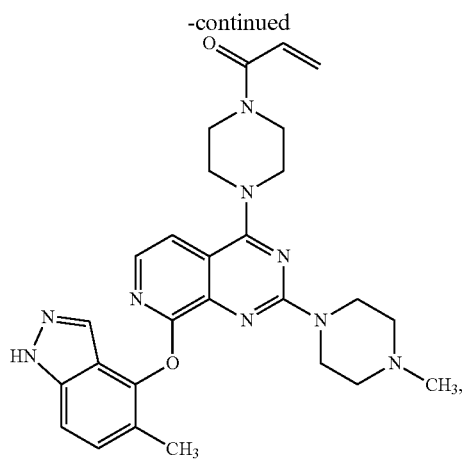
32
-continued
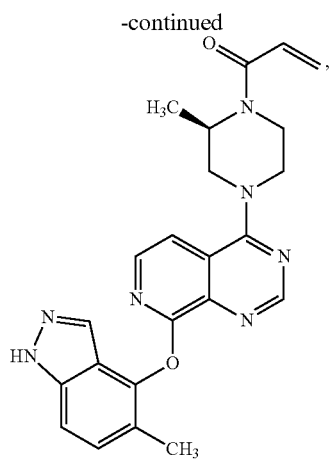
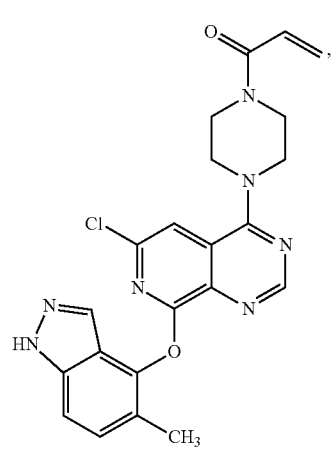
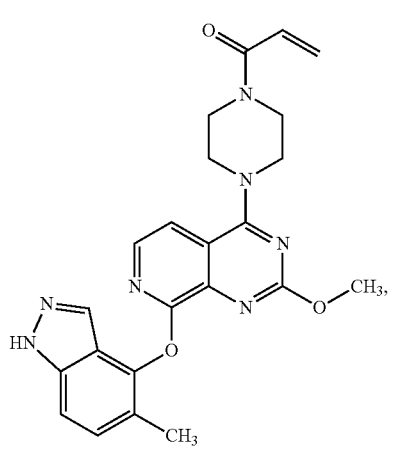
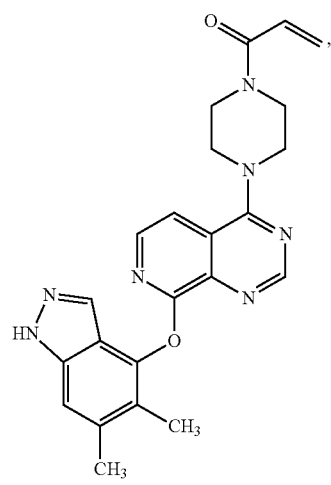
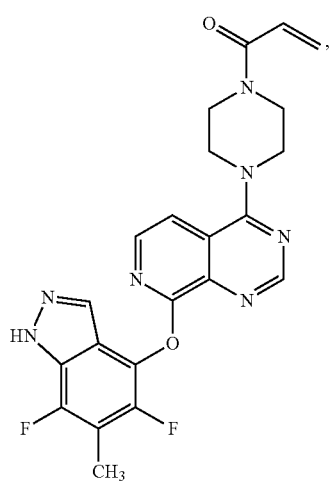

33
-continued
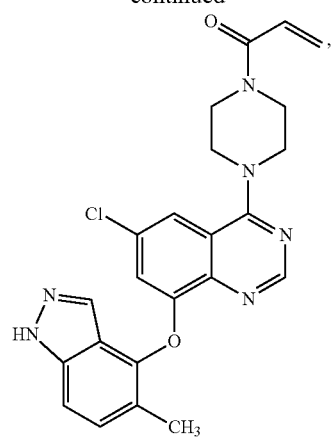
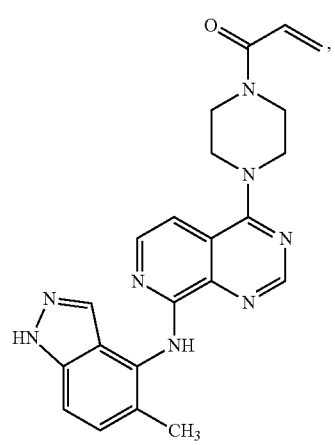
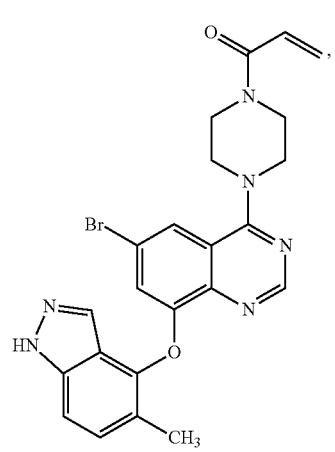
34
-continued
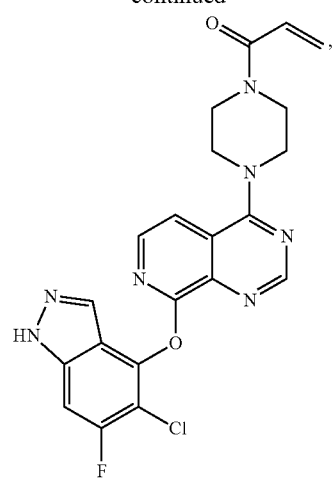
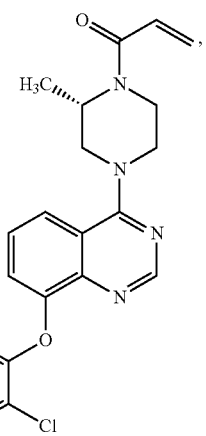
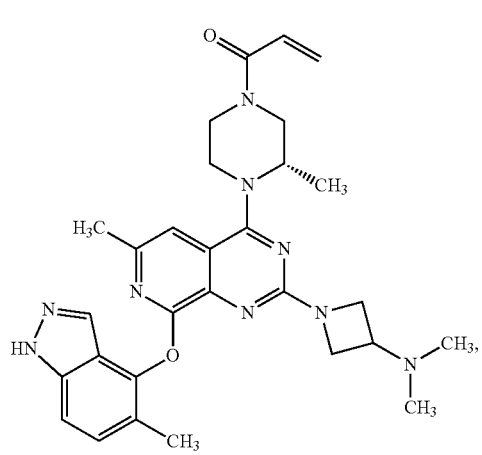

35
-continued
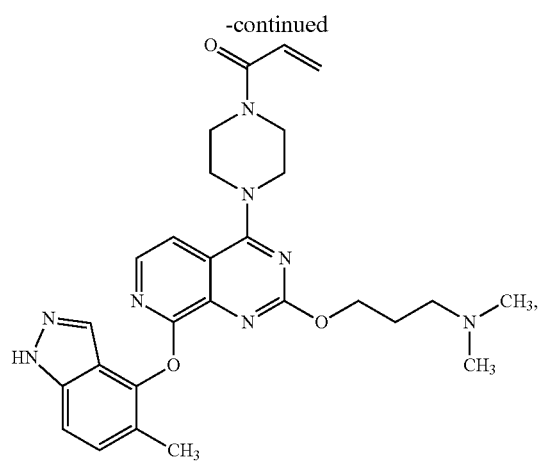
36
-continued
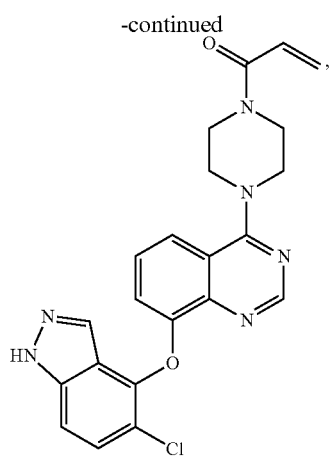
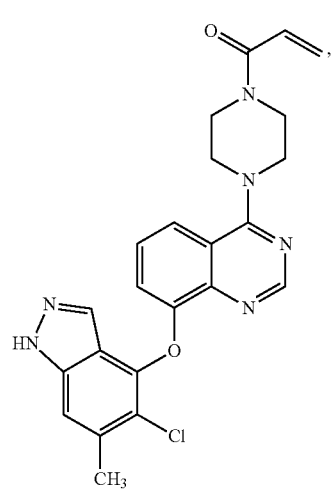
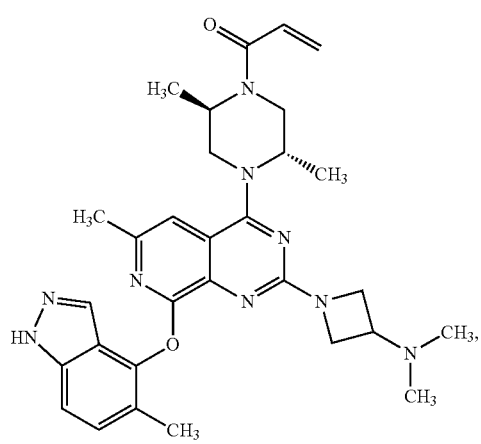
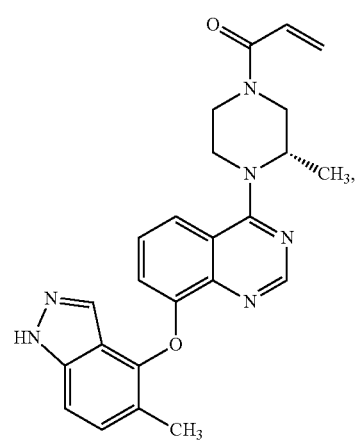
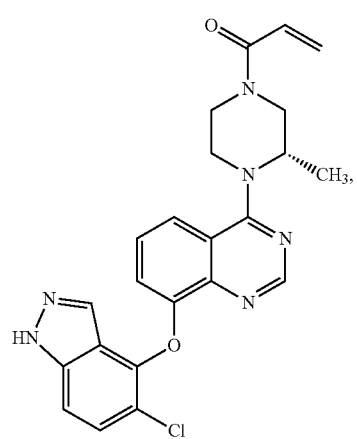

37
-continued
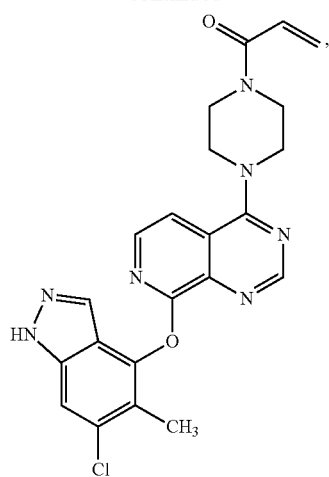
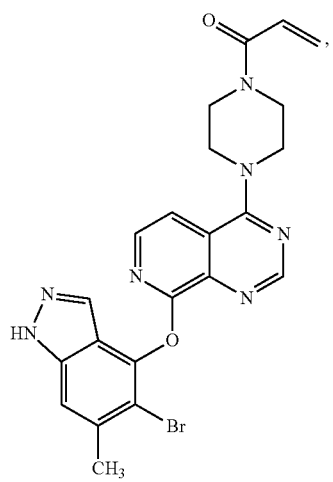
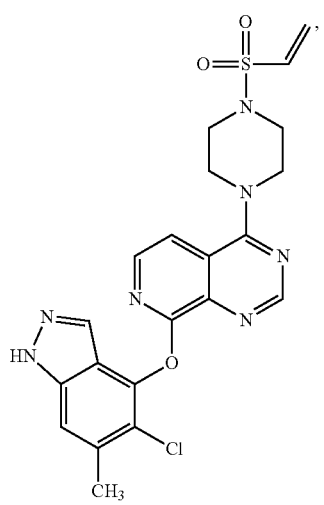
38
-continued
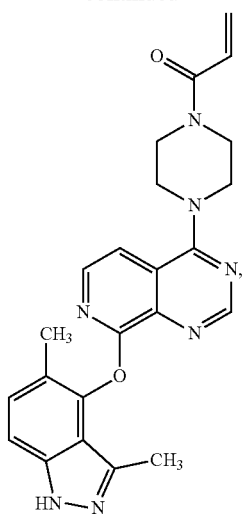
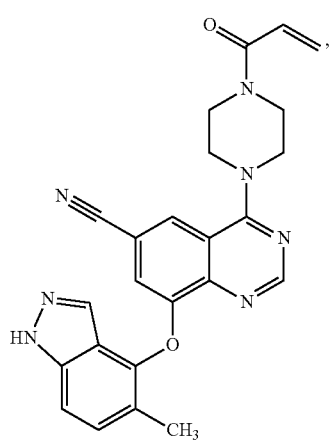
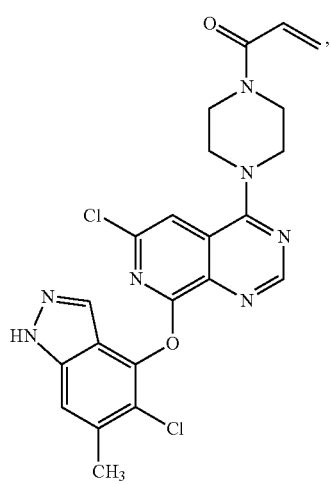

39
-continued
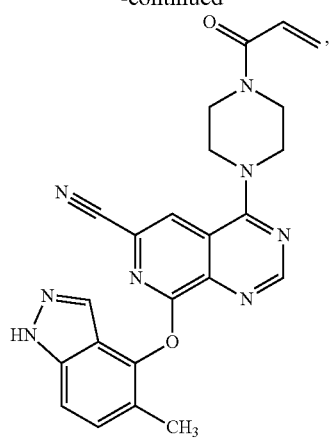
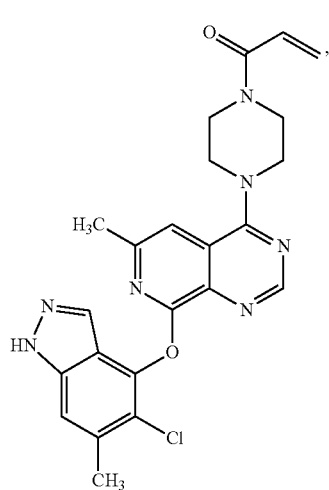
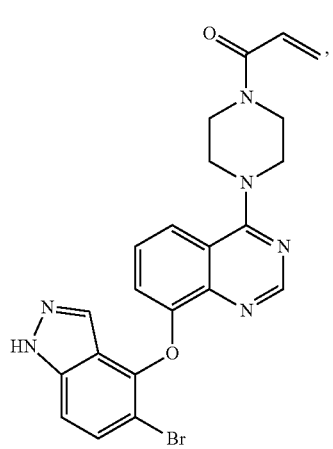
40
-continued
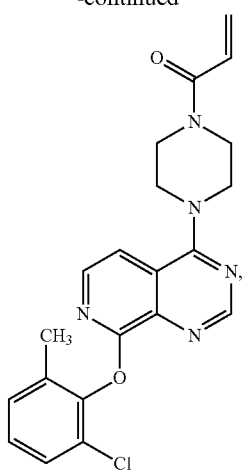
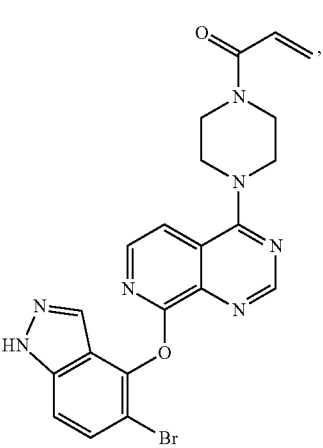
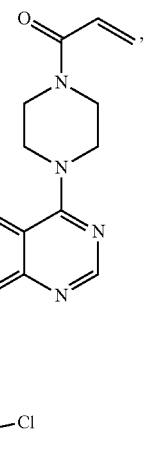

41
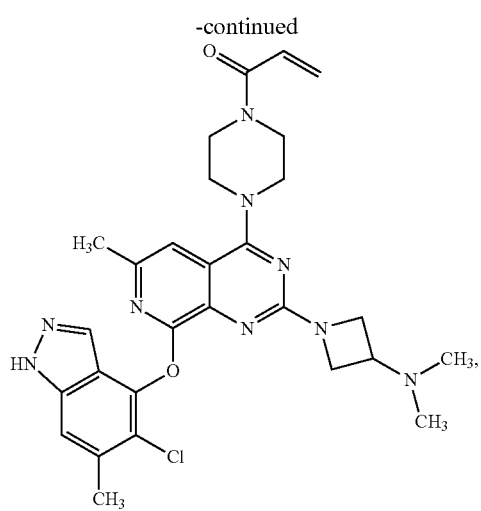
42
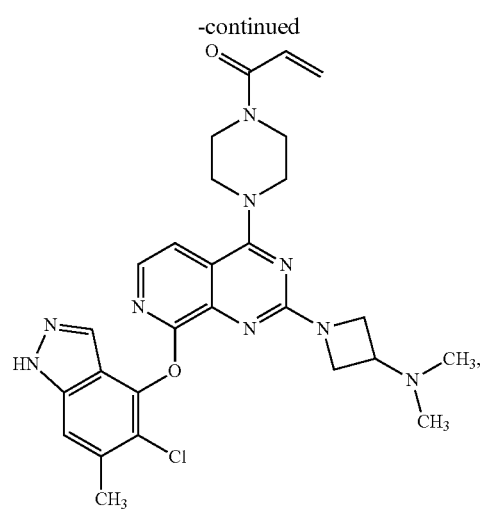
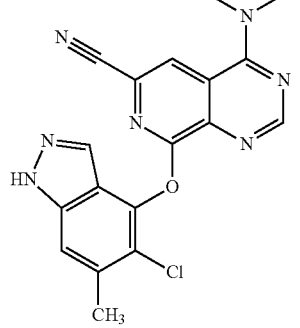
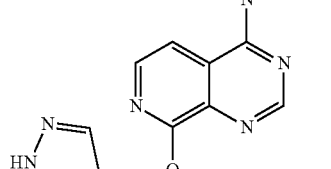

-continued
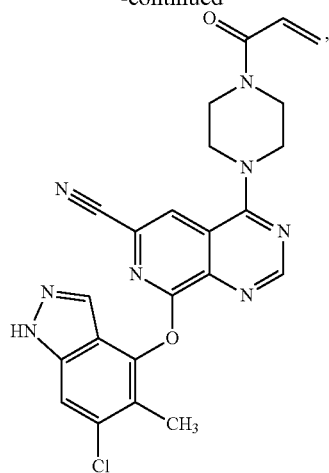
-continued
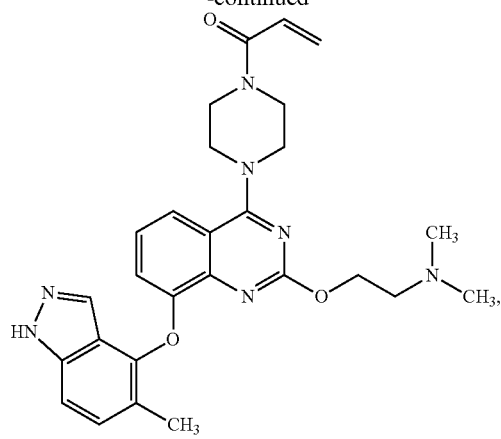
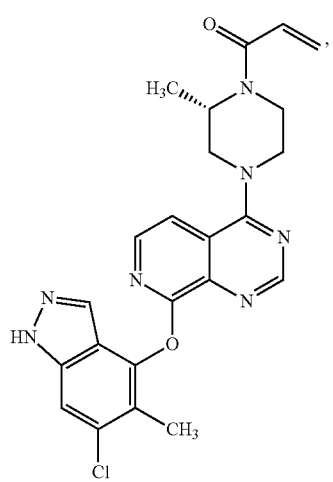
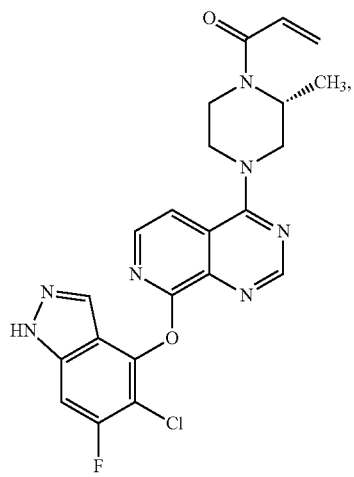
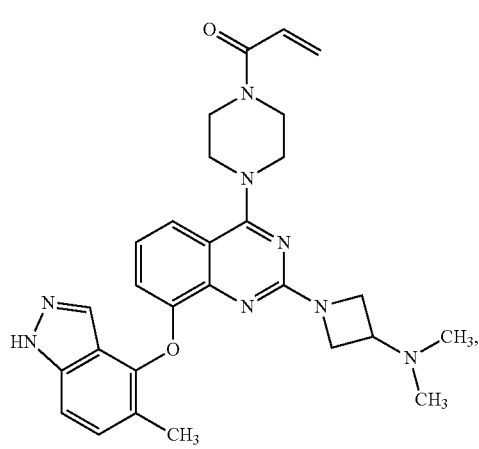

45
-continued
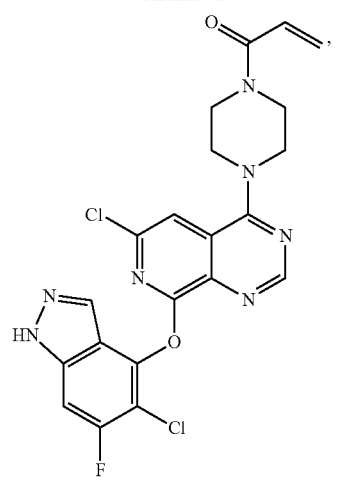
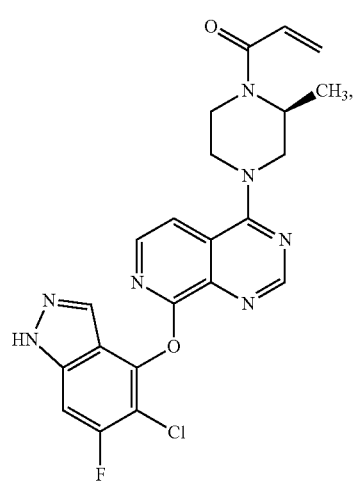
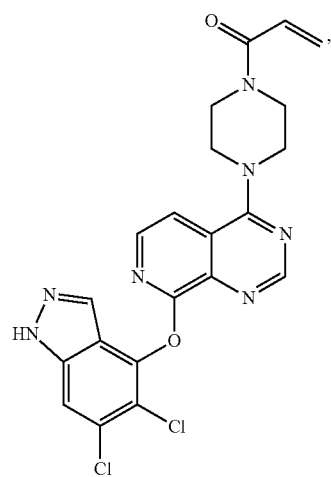
46
-continued
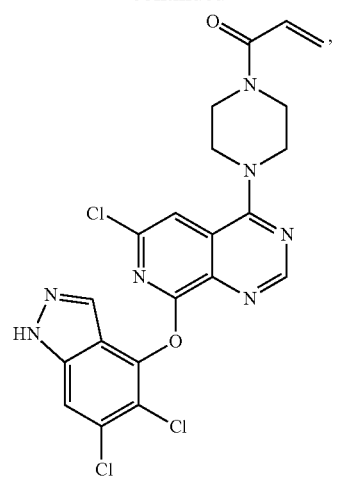
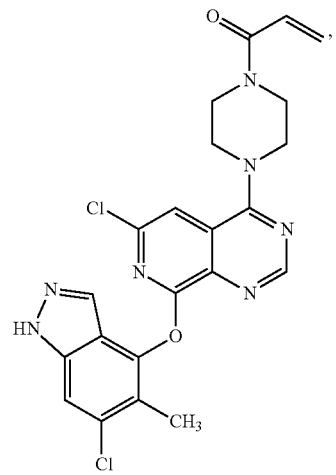
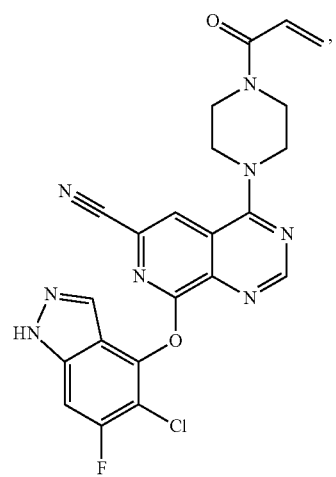

-continued
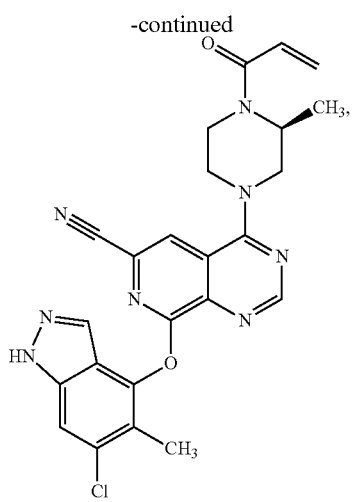
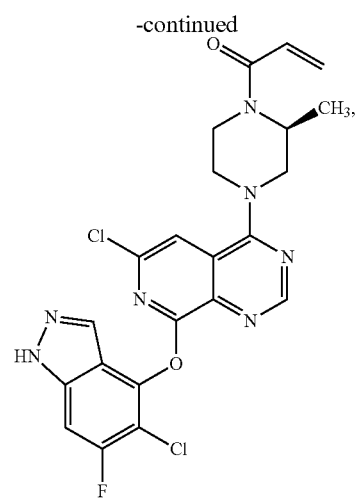
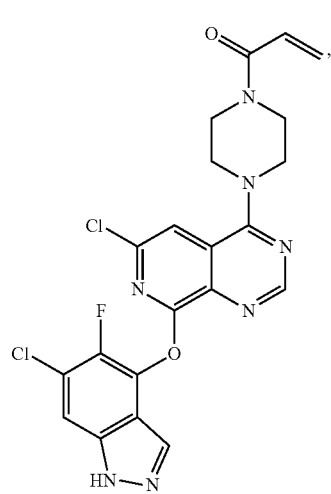
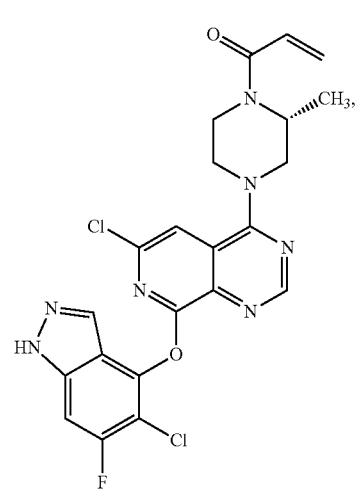
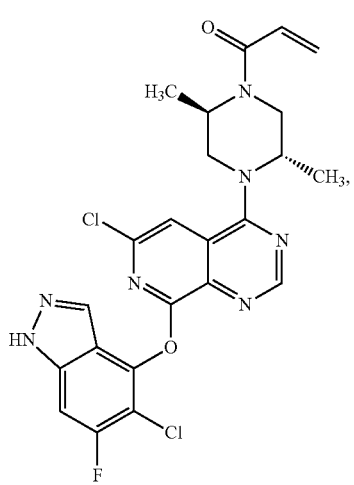
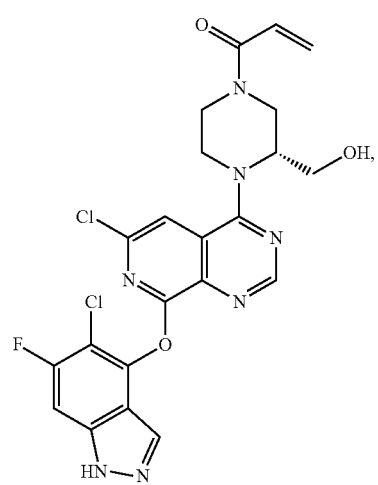

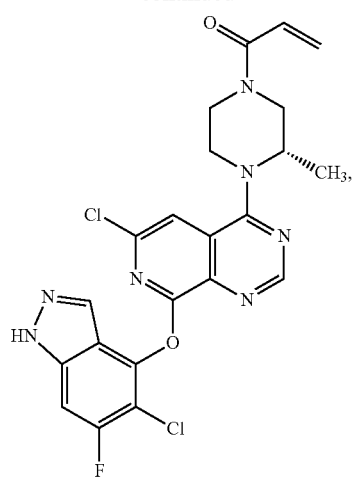
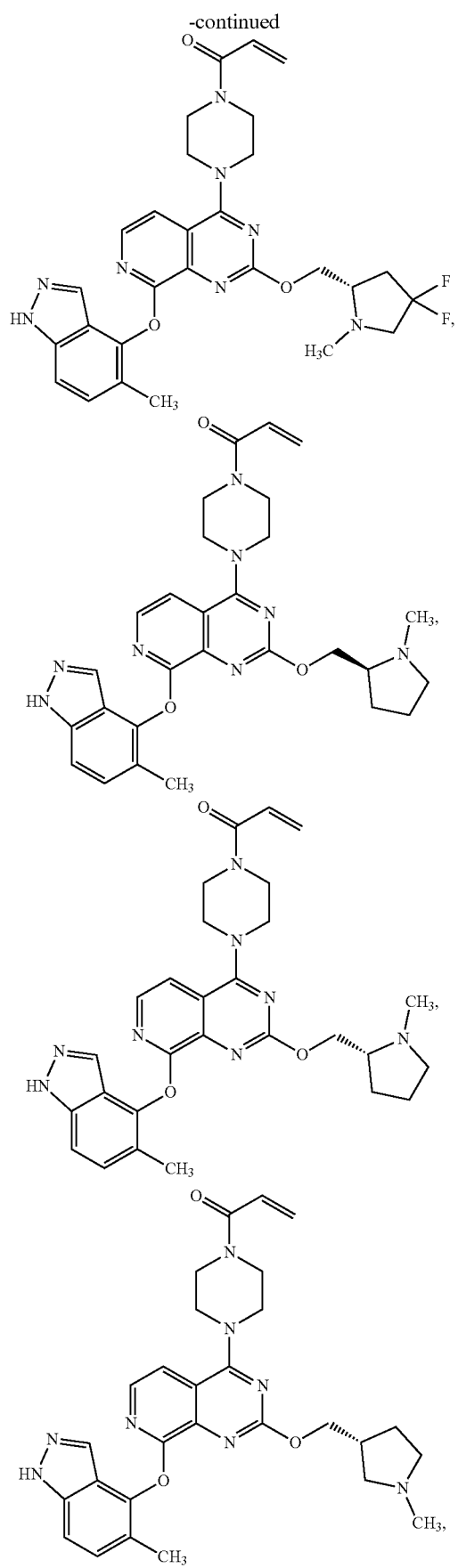

-continued

53
-continued
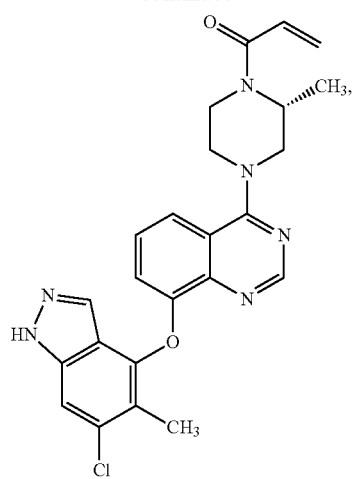
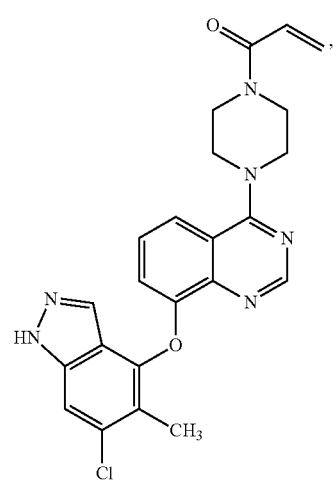
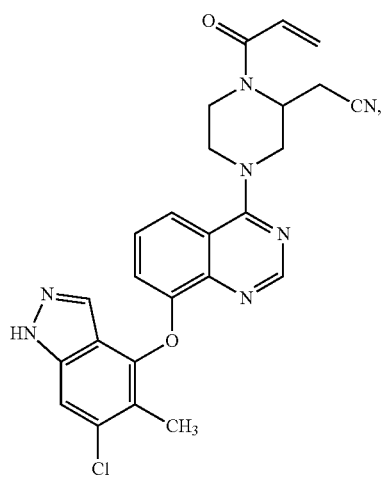
54
-continued
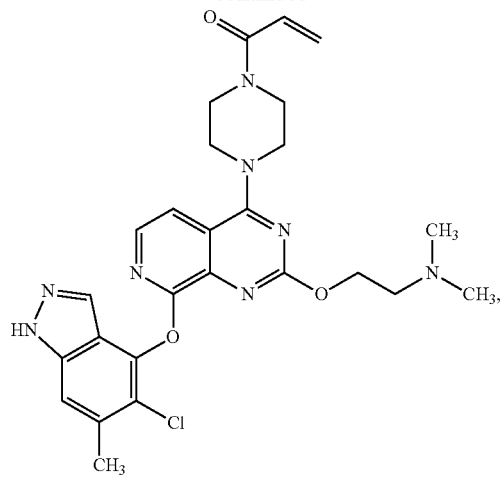
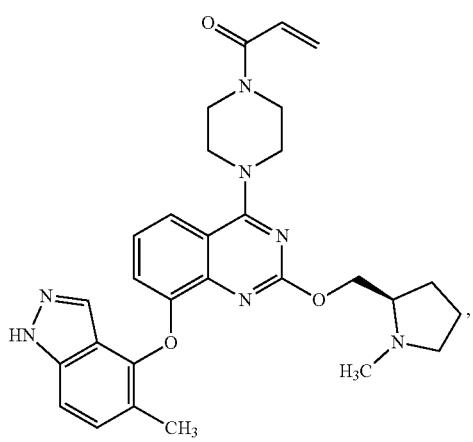
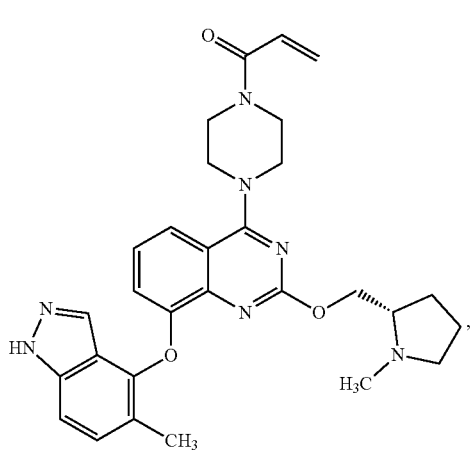

55
-continued
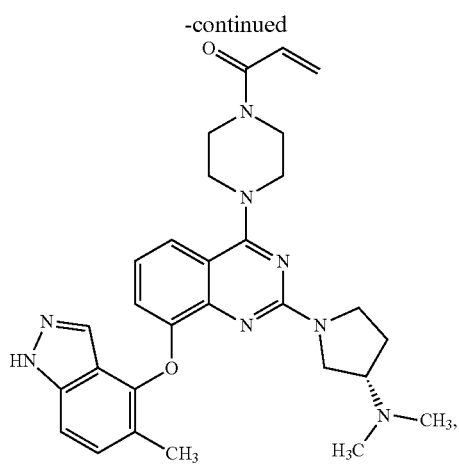
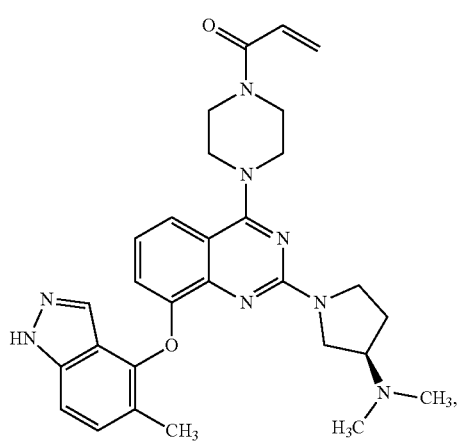
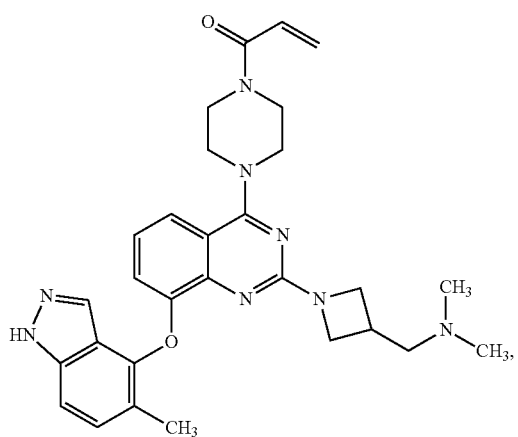
56
-continued
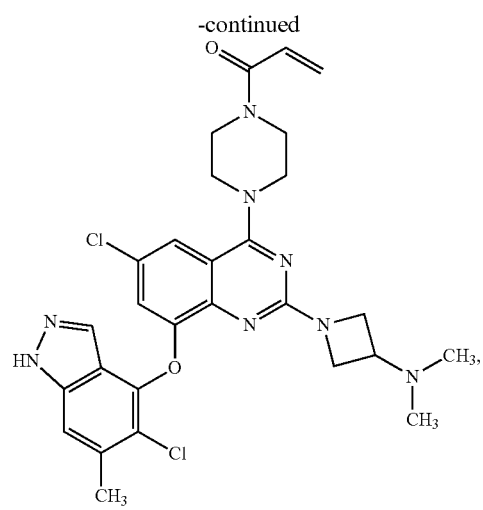
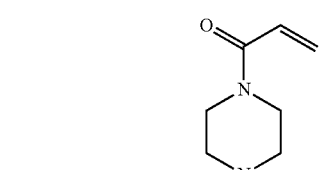
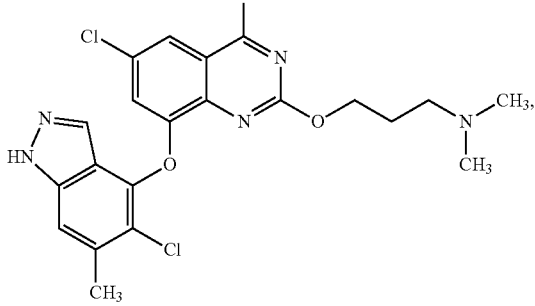
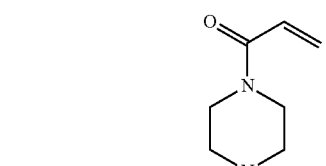
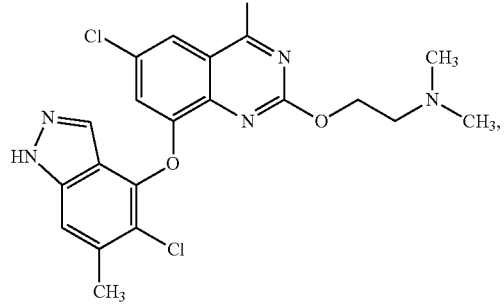

57
-continued
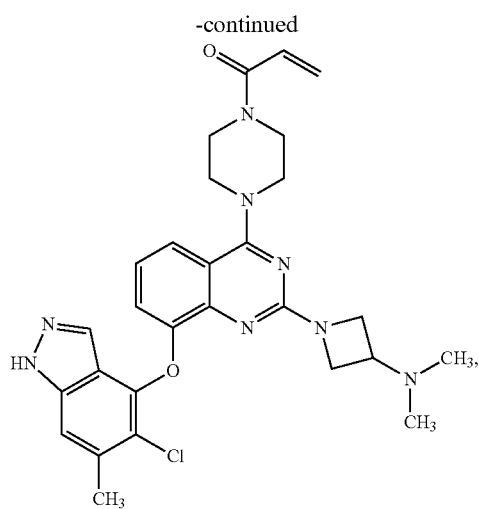
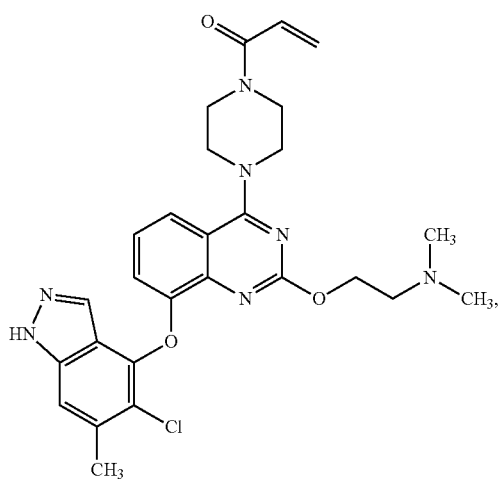
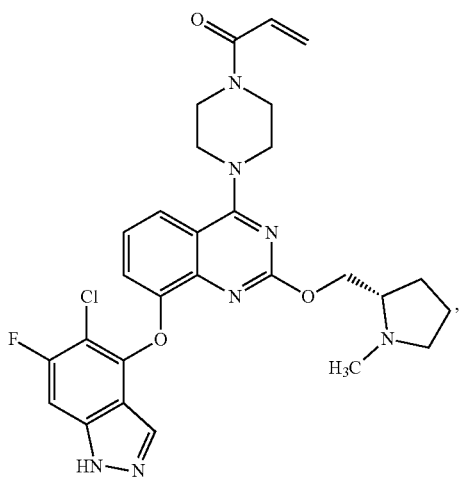
58
-continued
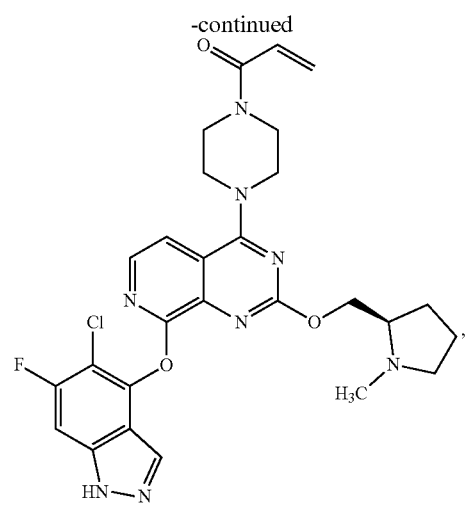
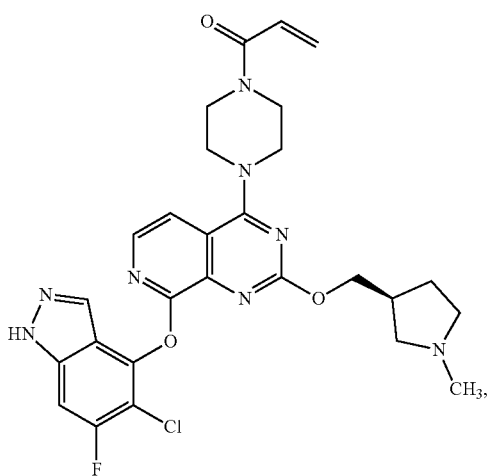
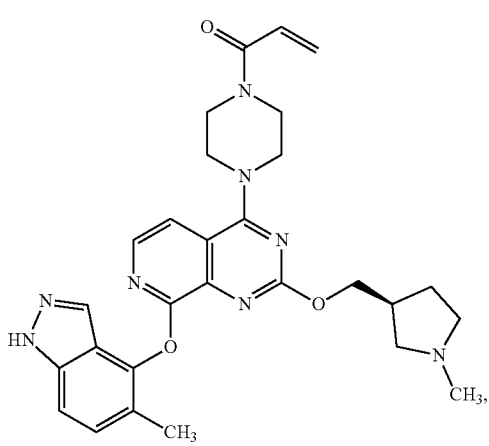

-continued

61
-continued
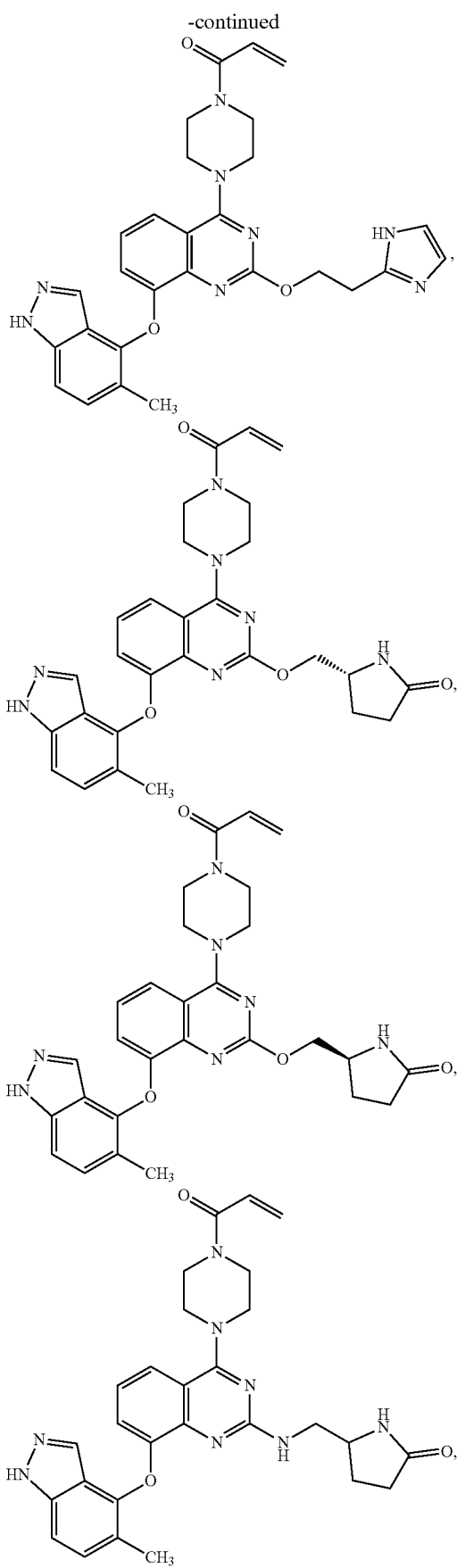
62
-continued
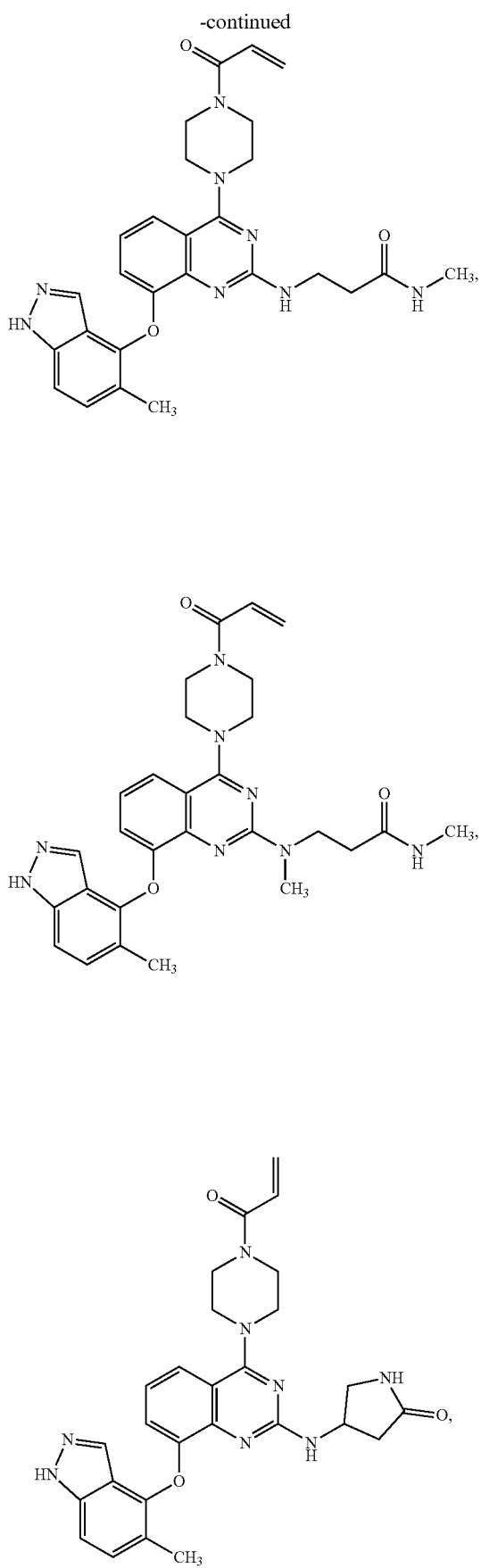

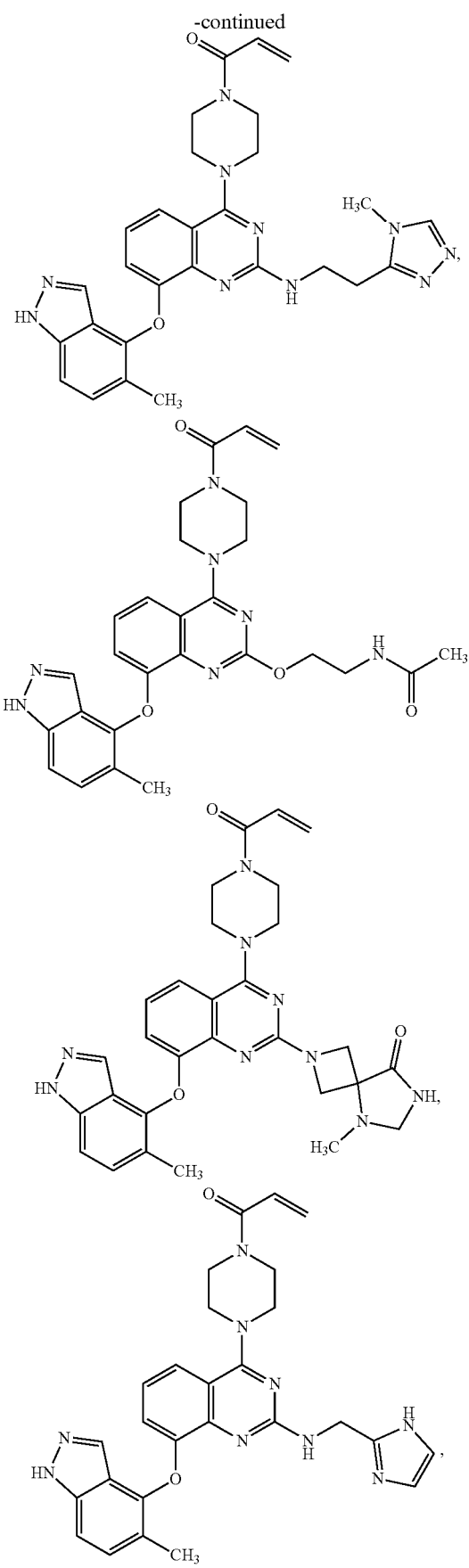
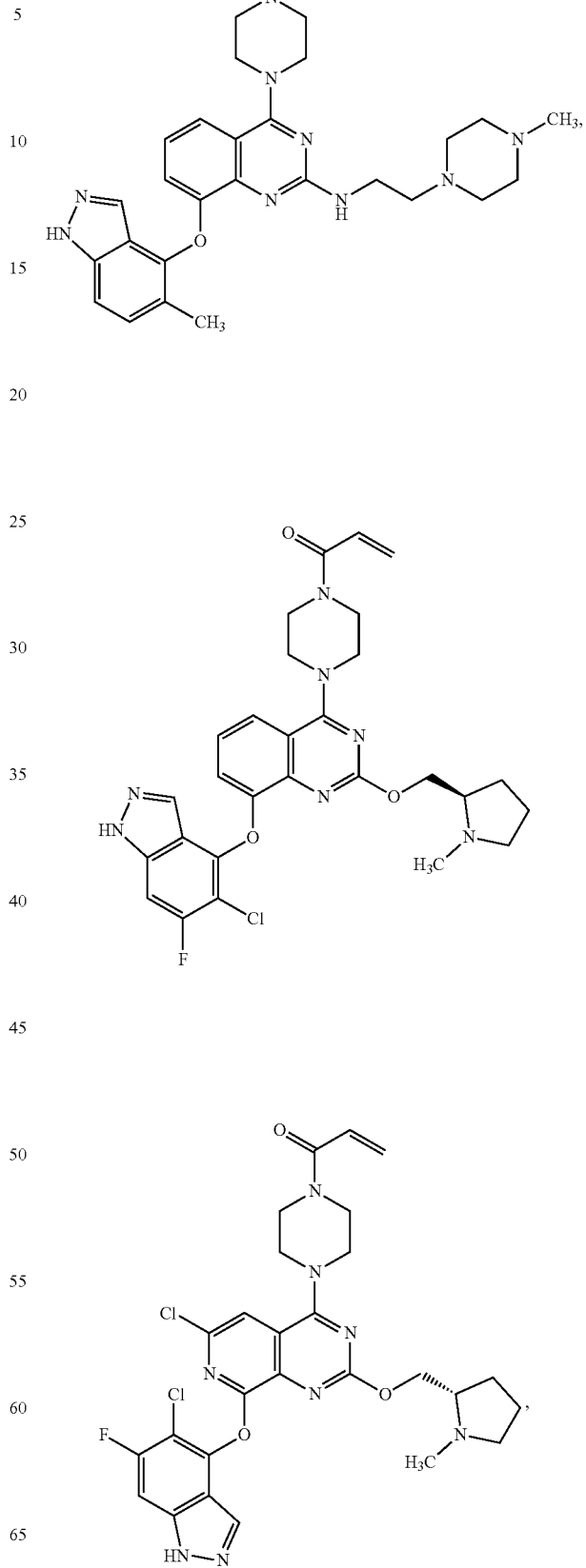

65
-continued
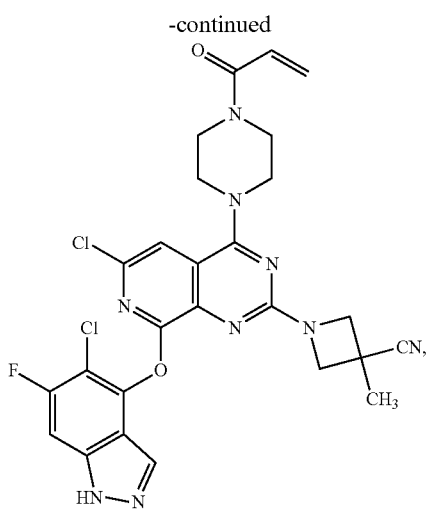
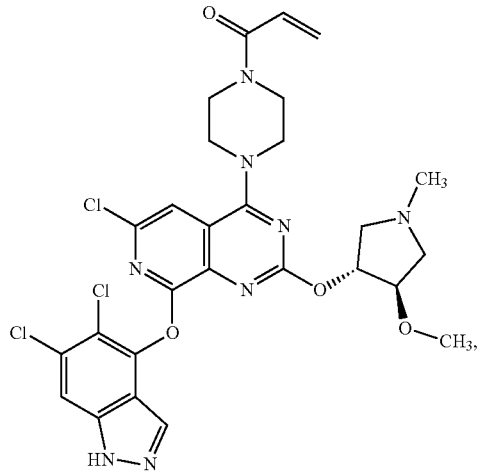
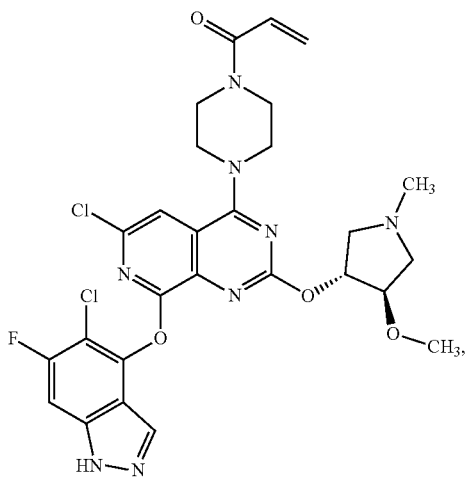
66
-continued
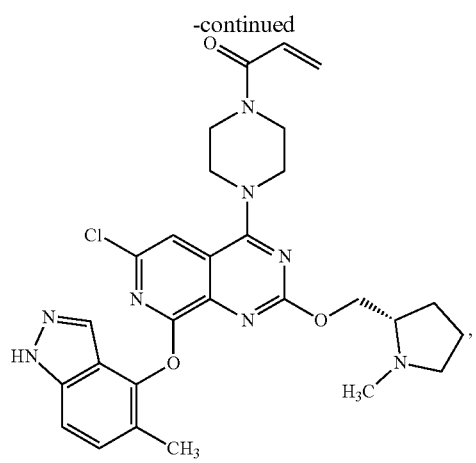
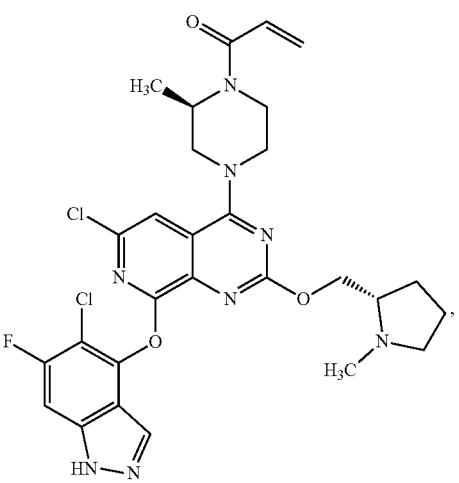
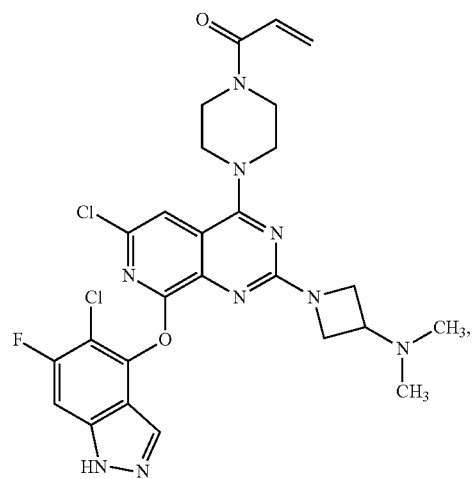

67
-continued
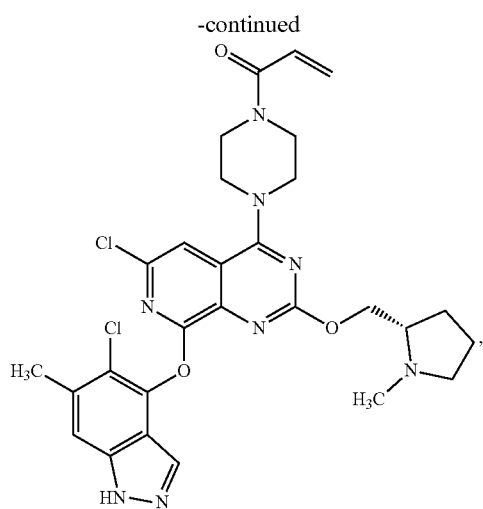
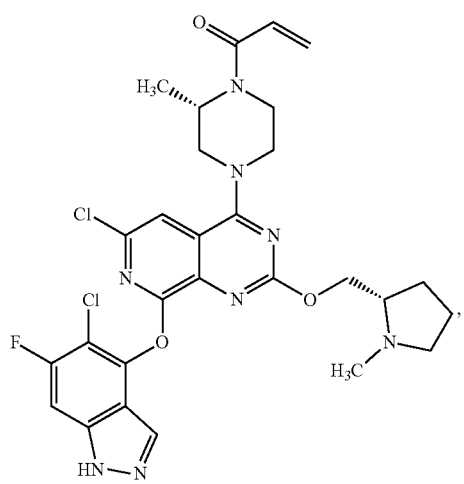
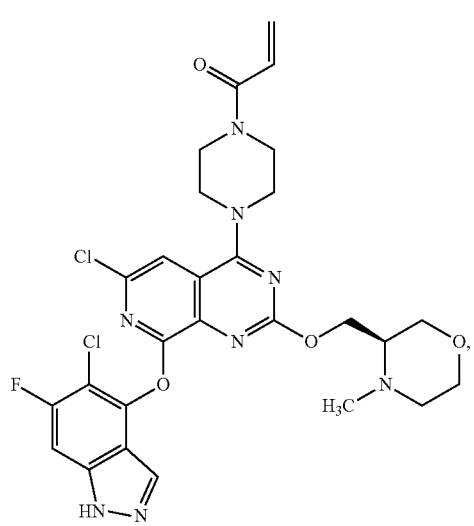
68
-continued
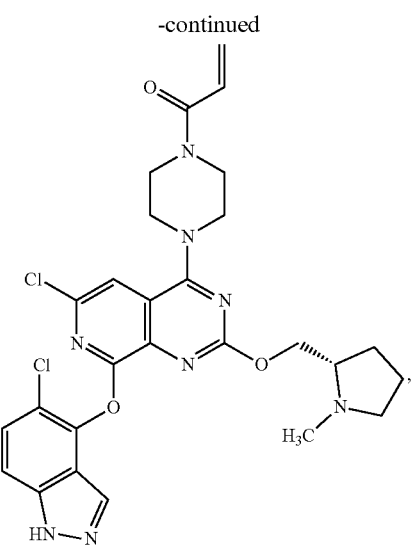
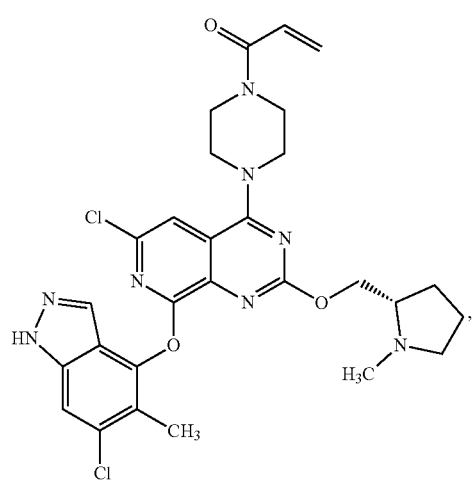
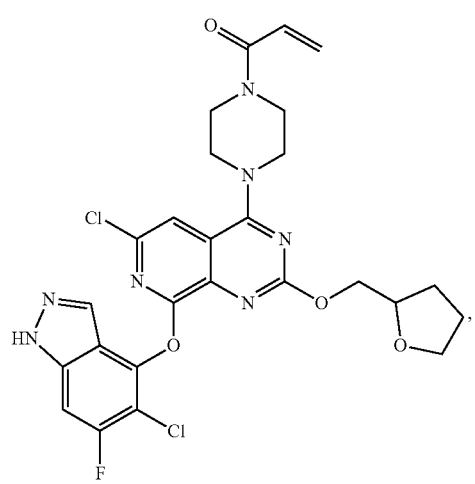

69
-continued
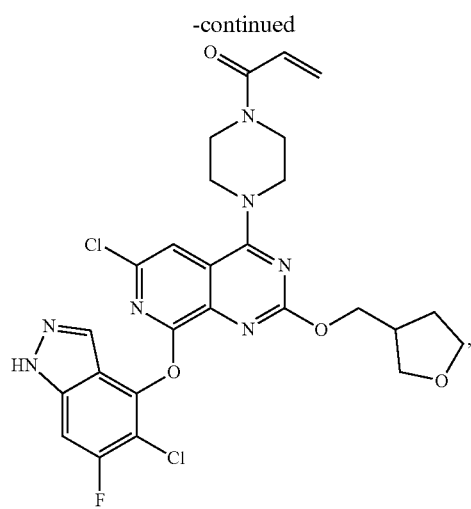
70
-continued
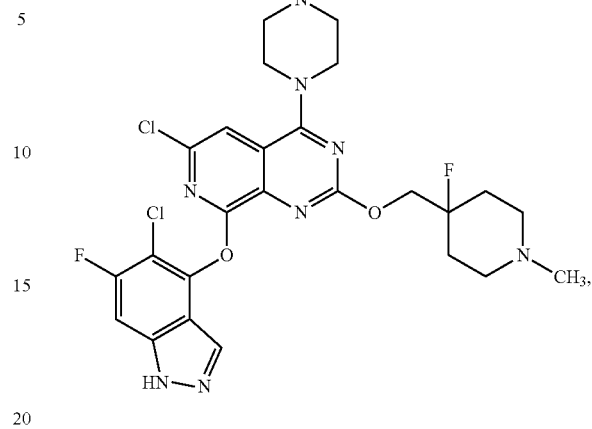
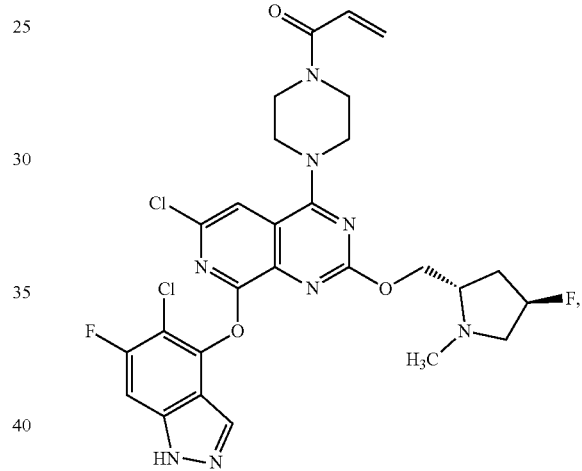
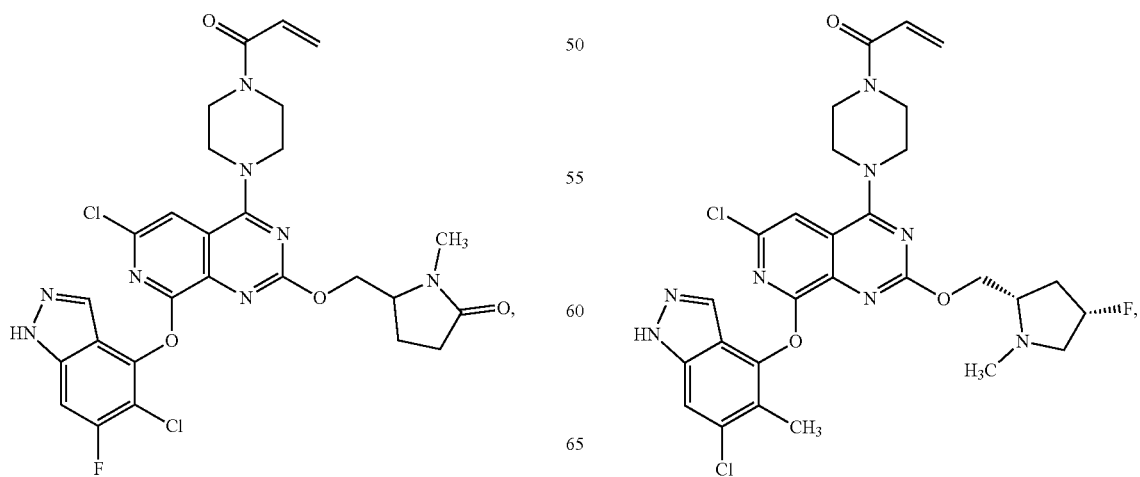

71
-continued
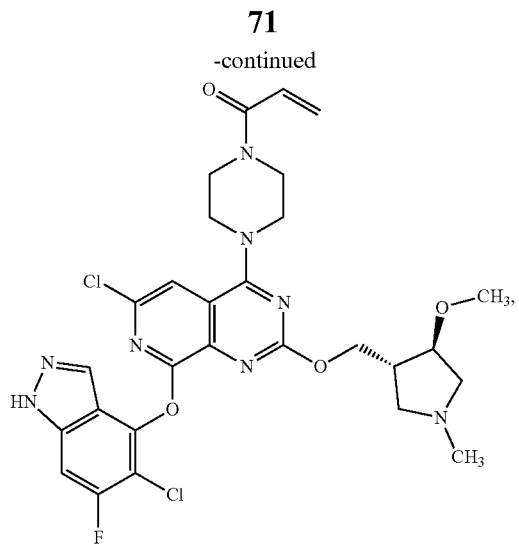
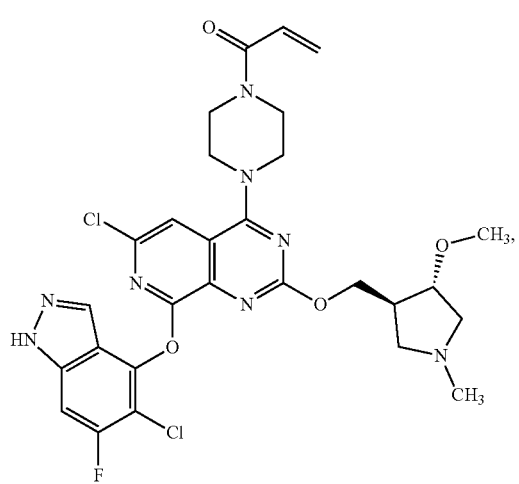
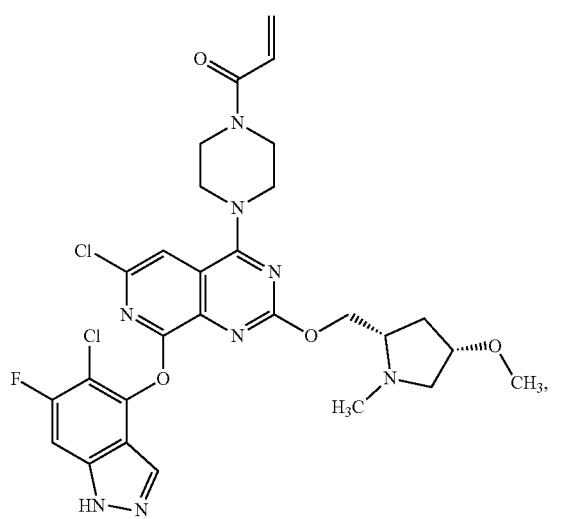
72
-continued
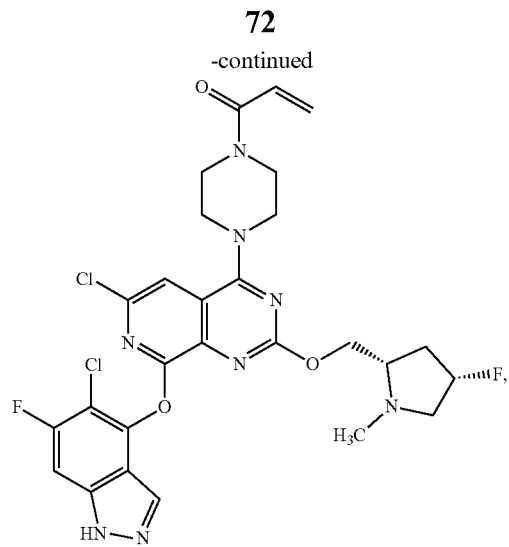
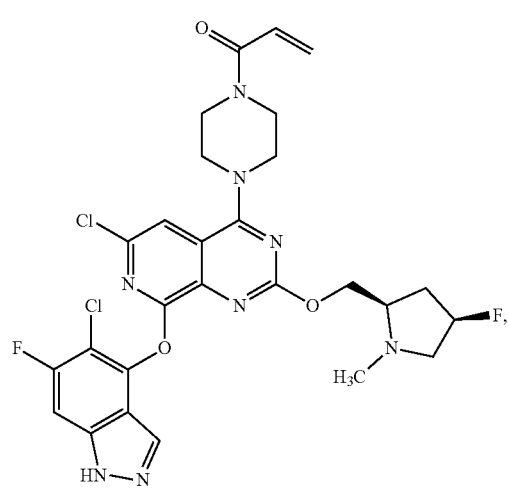
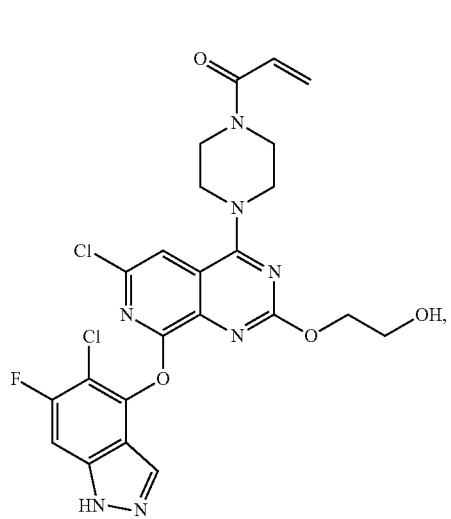

73
-continued
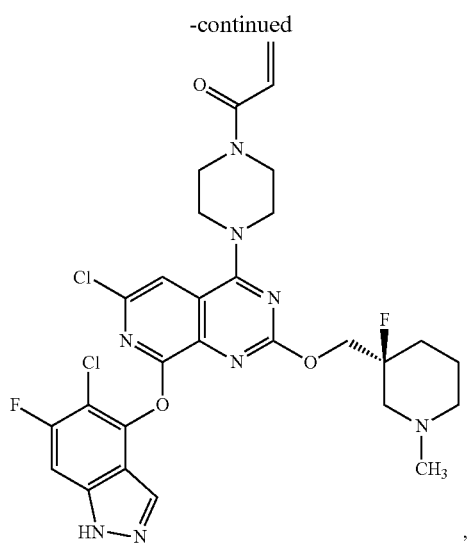
,
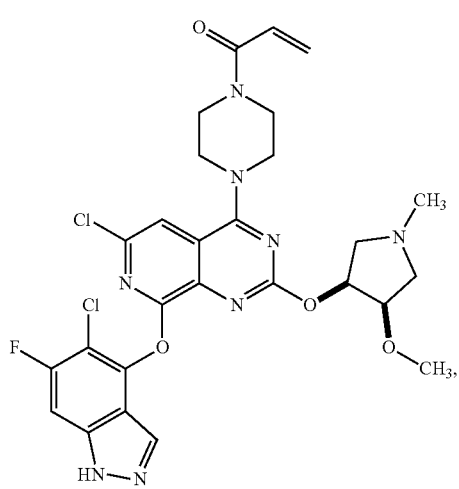
,
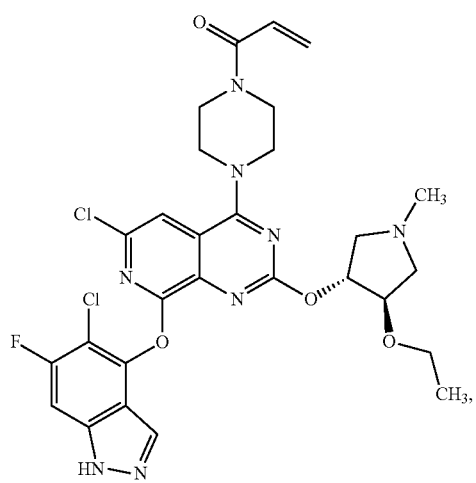
,
74
-continued
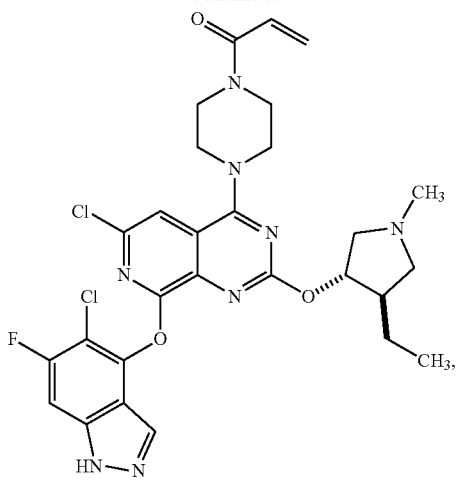
,
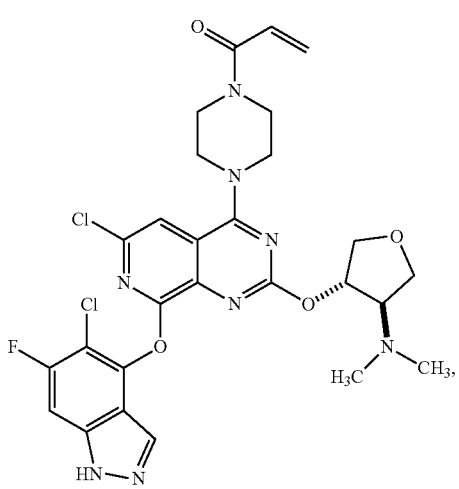
,
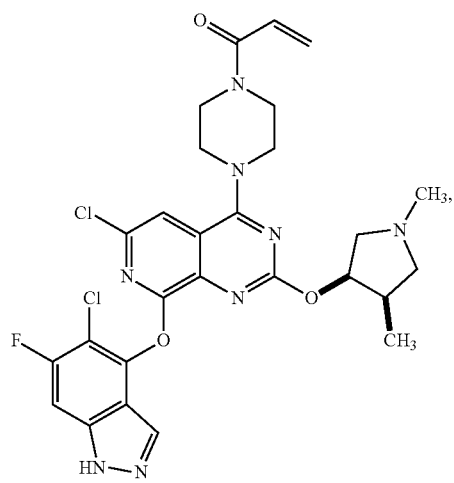
, 75
-continued
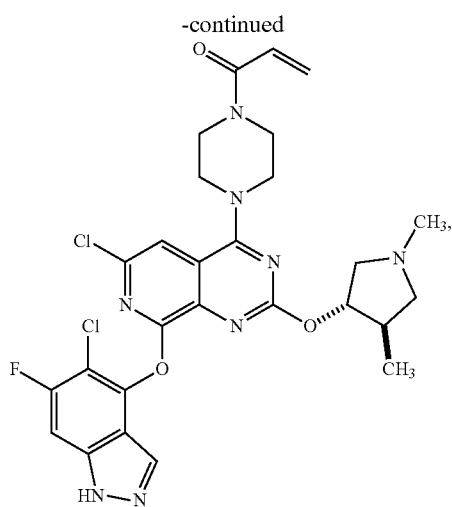
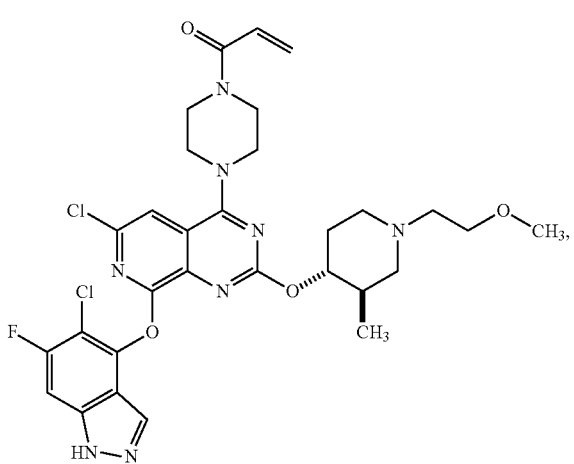
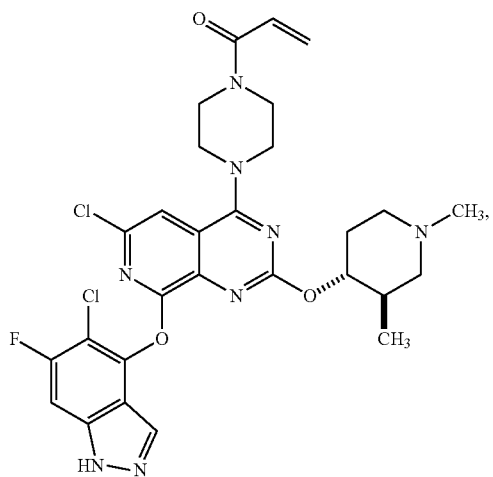
76
-continued
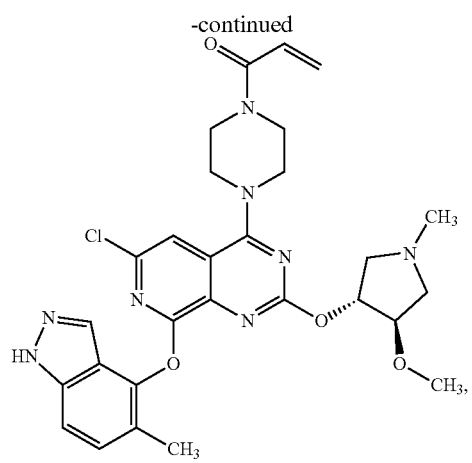
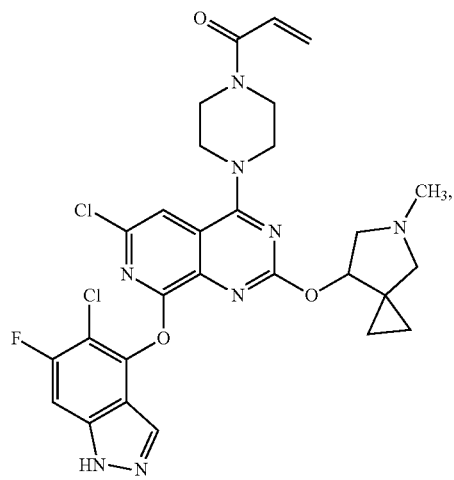
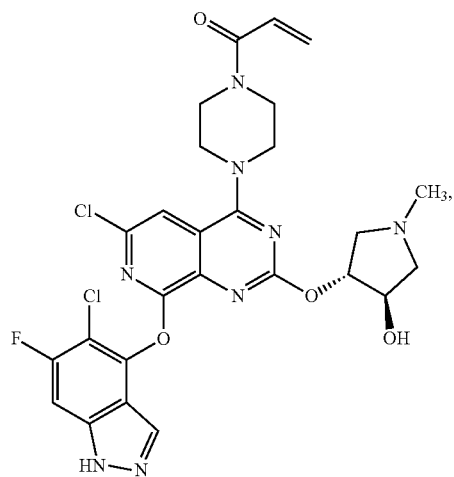

77
-continued
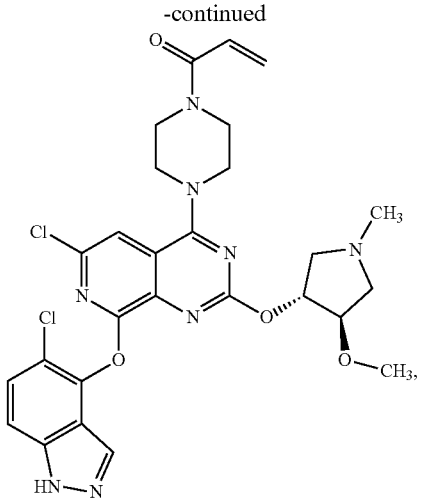
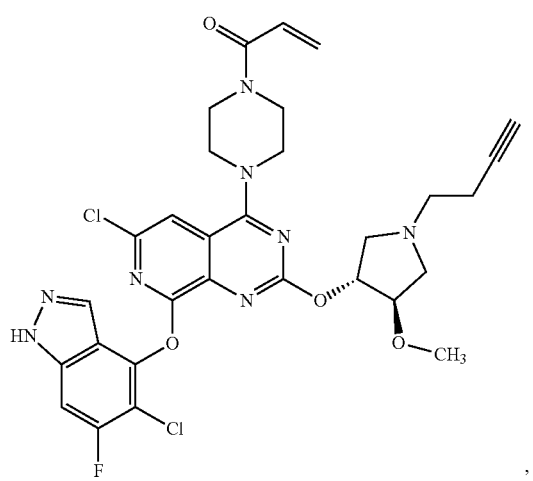
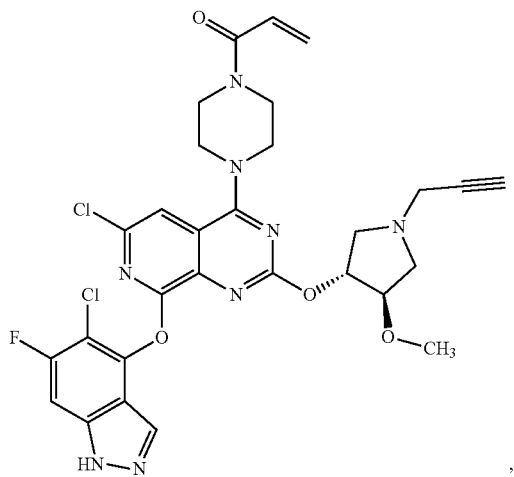
78
-continued
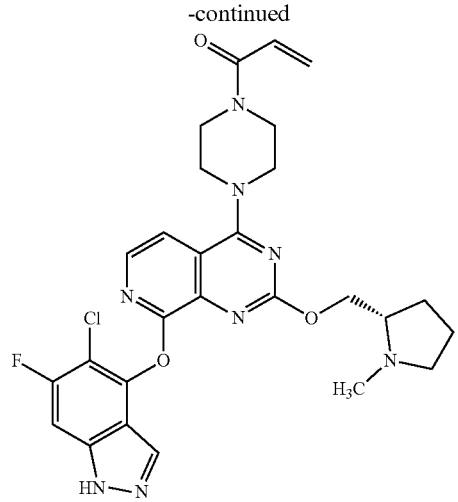
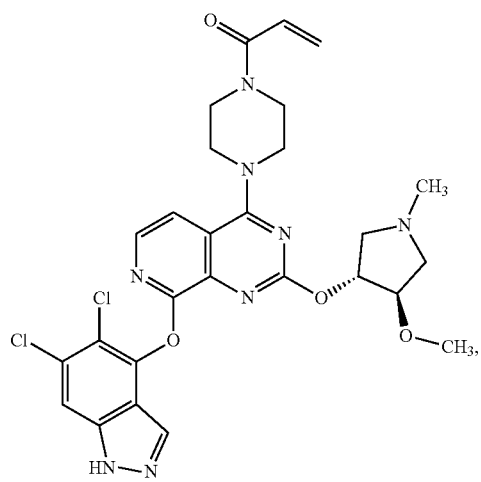
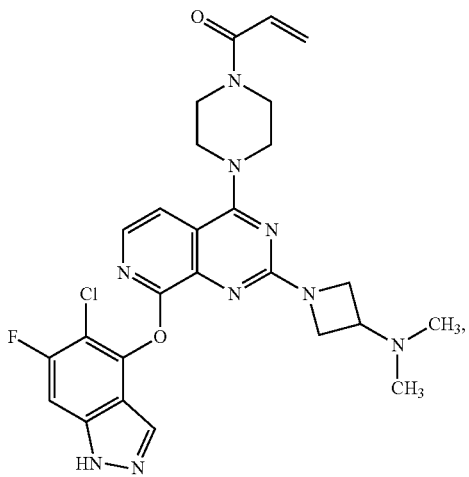

79
-continued
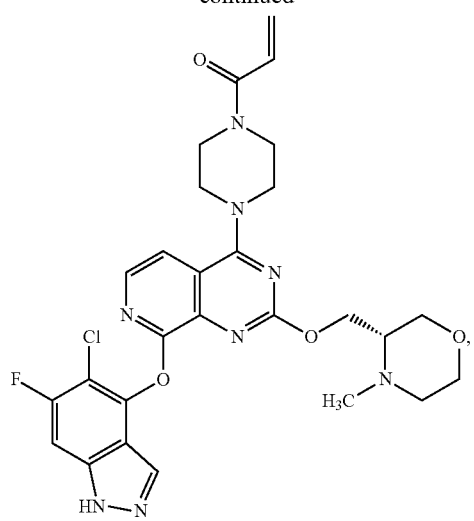
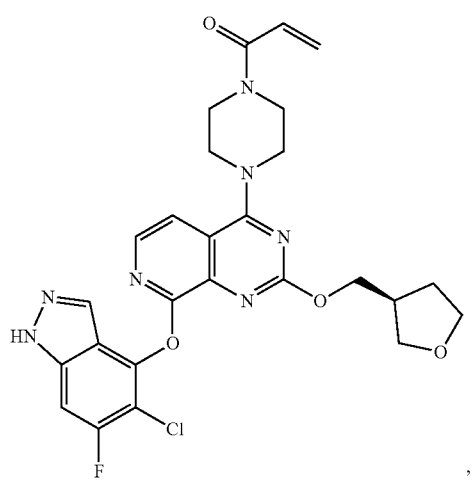
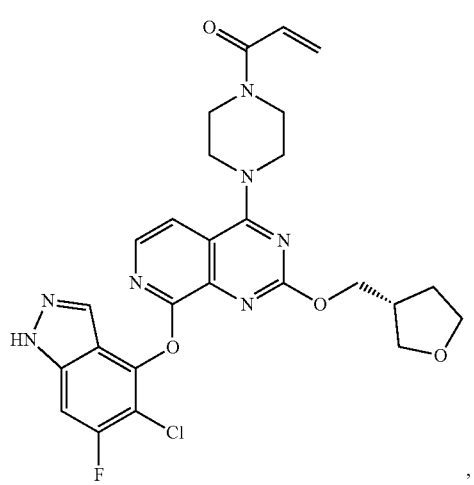
80
-continued
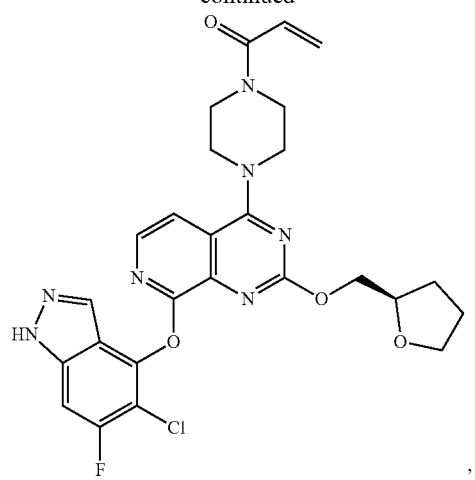
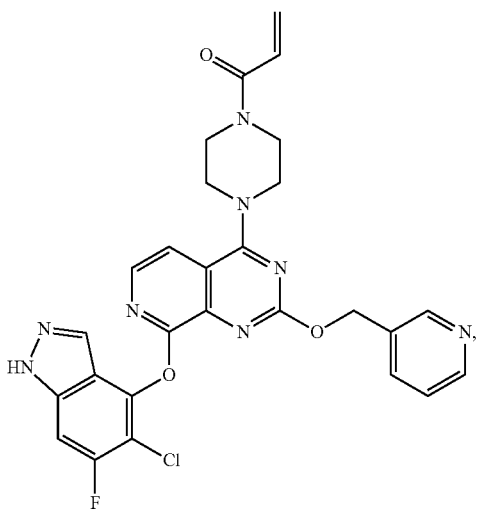
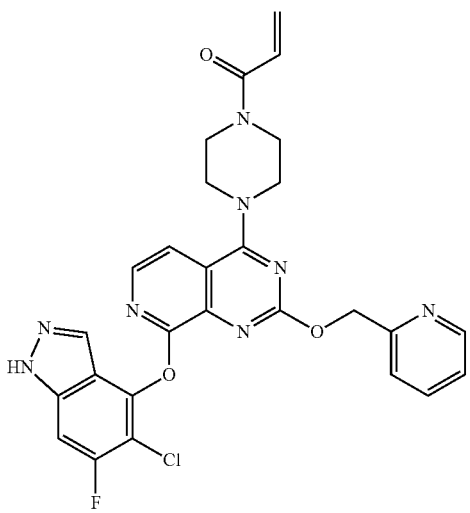

81
-continued
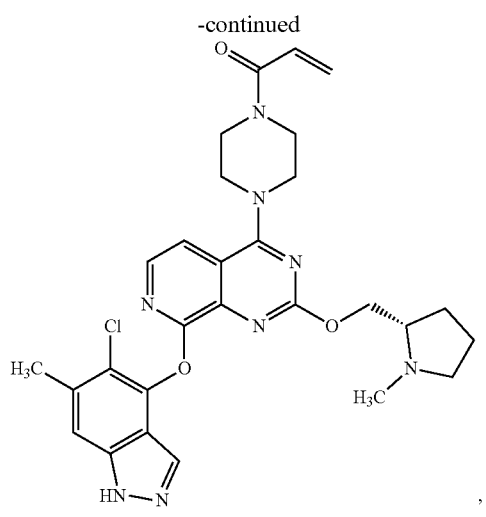
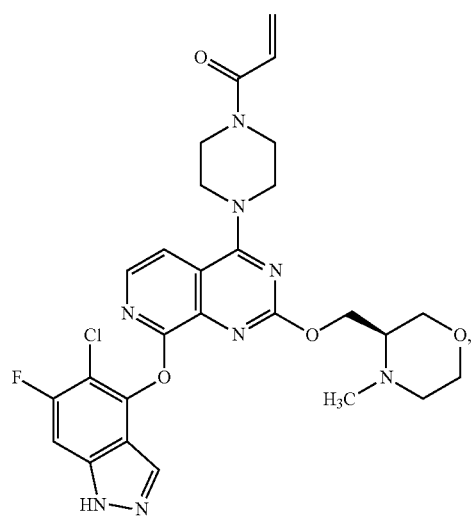
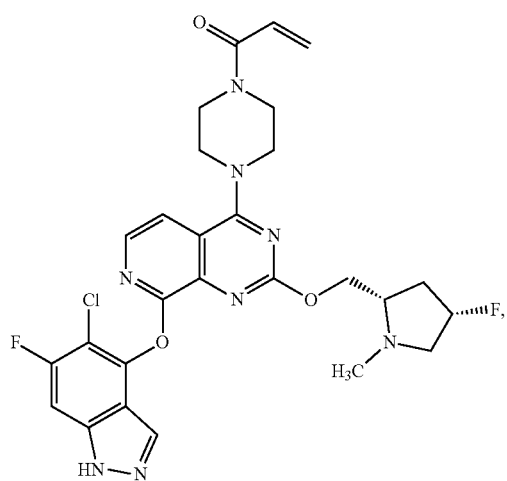
82
-continued
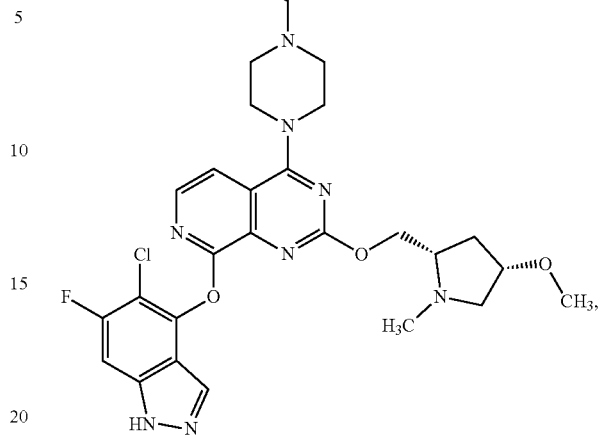
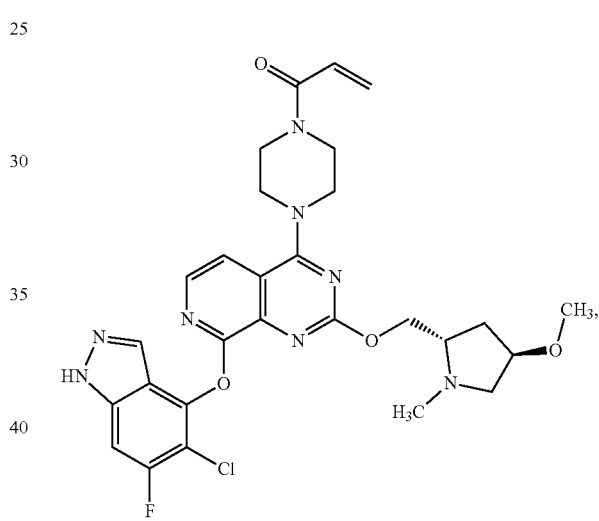
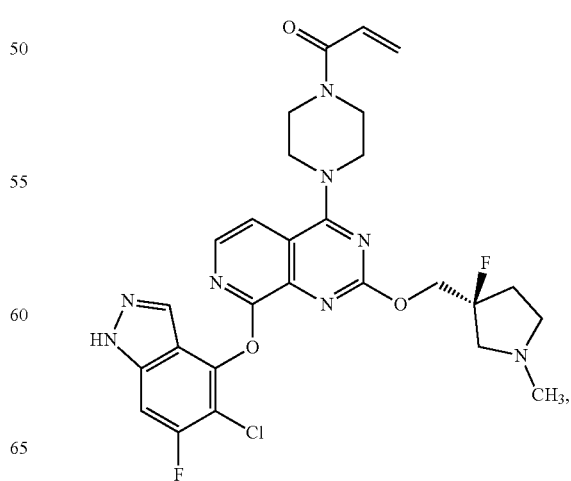

83
-continued
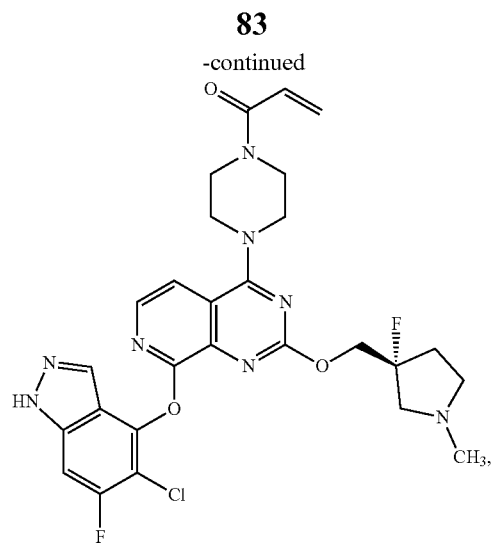
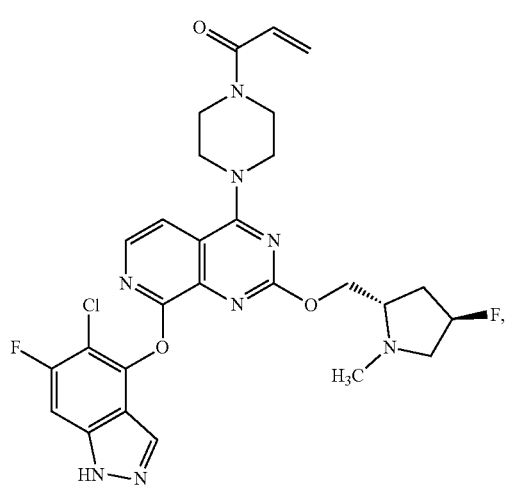
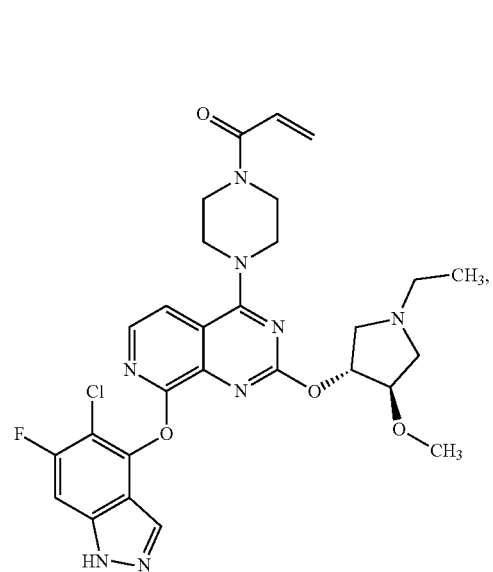
84
-continued
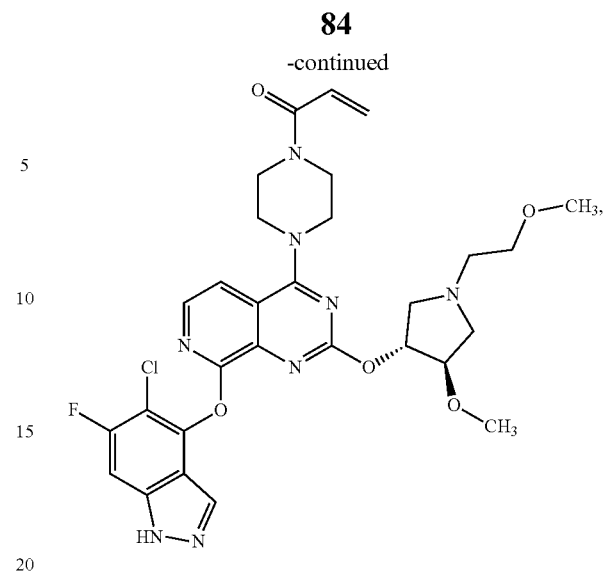
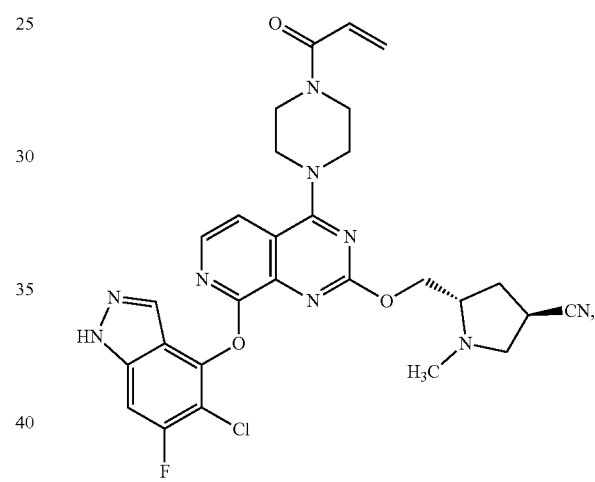
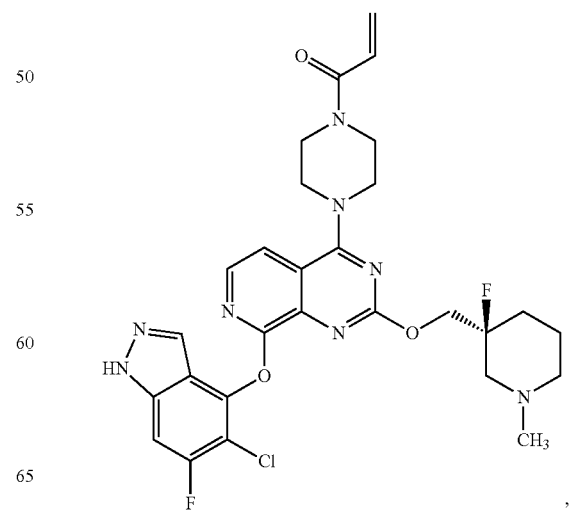

85
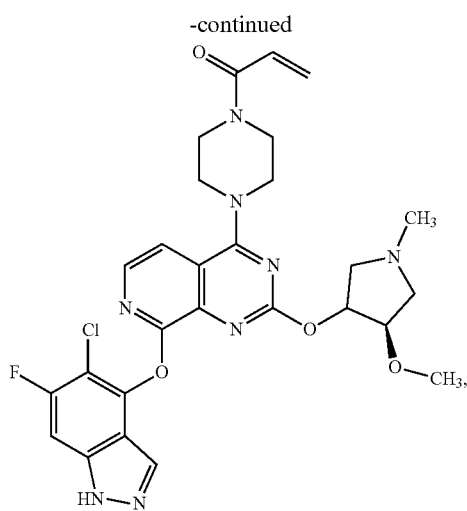
86
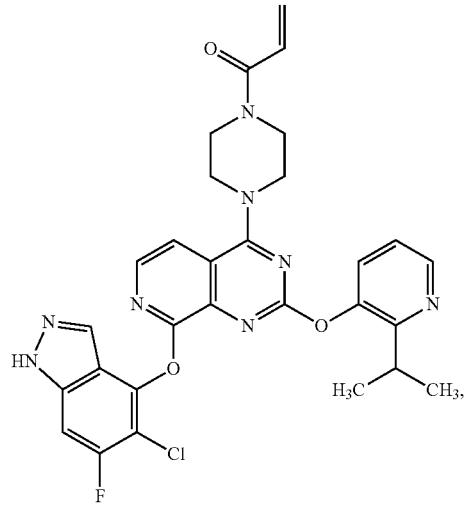
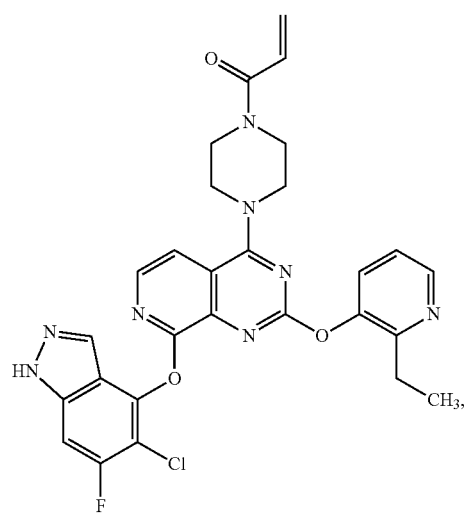
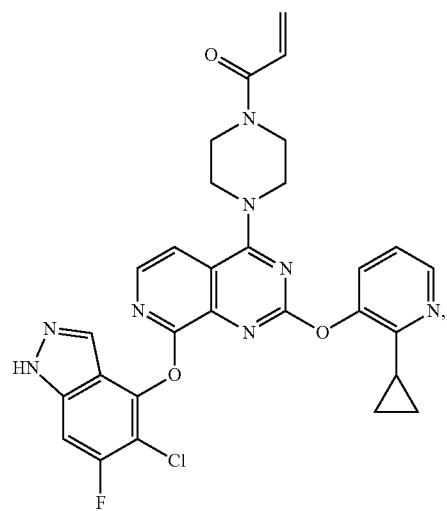
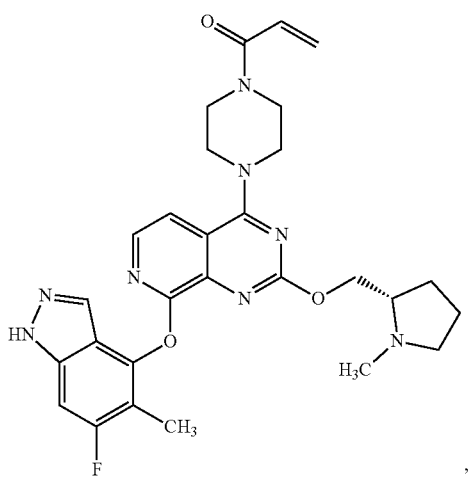
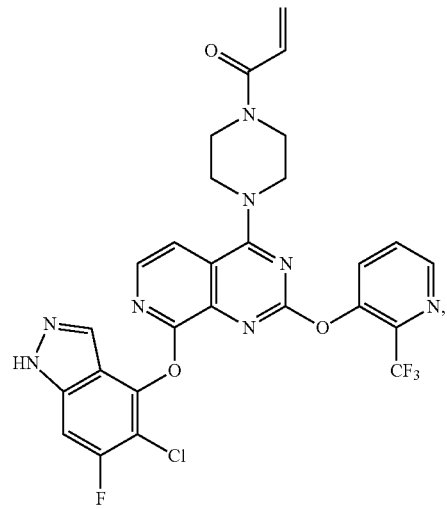

87
-continued
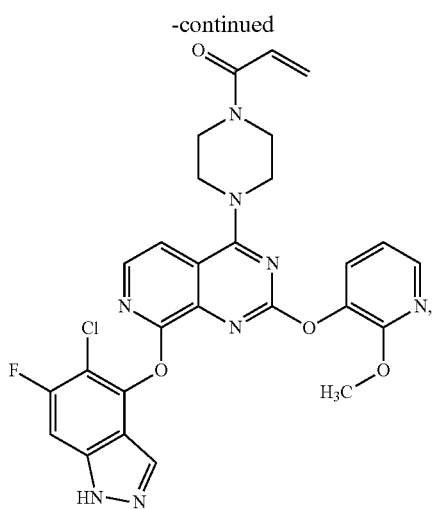
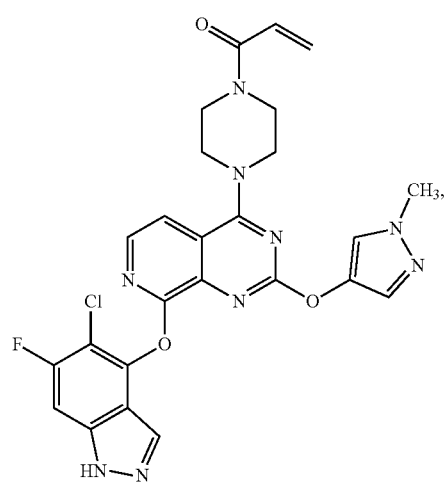
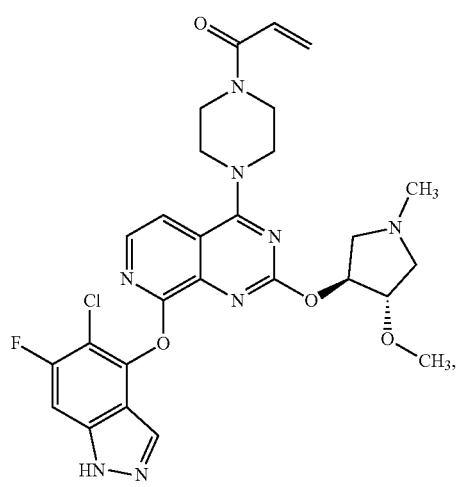
88
-continued
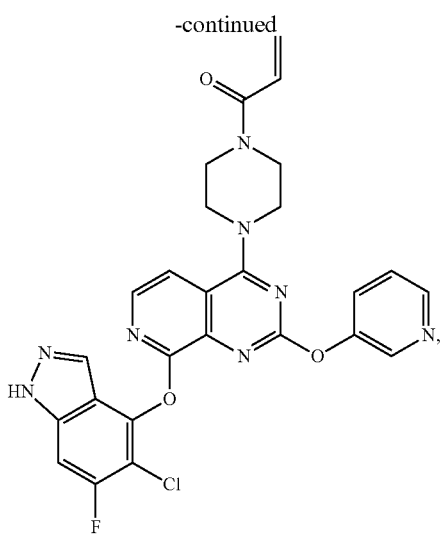
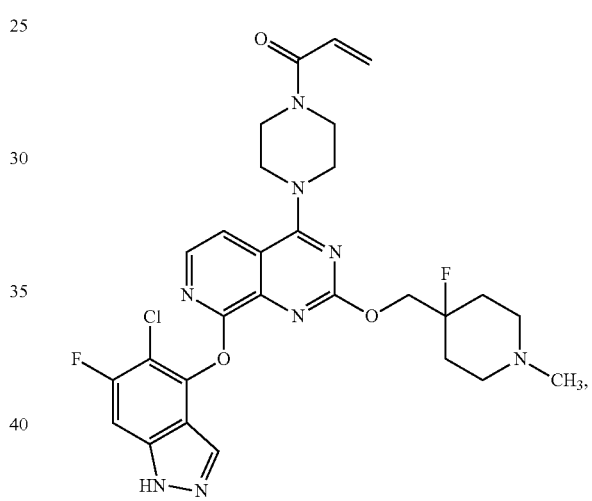
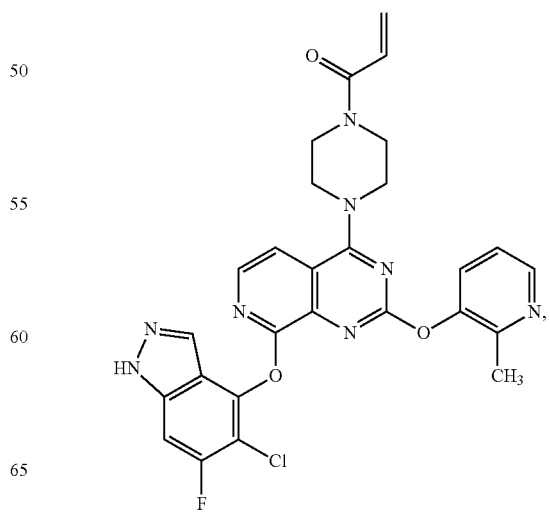

89
-continued
90
-continued
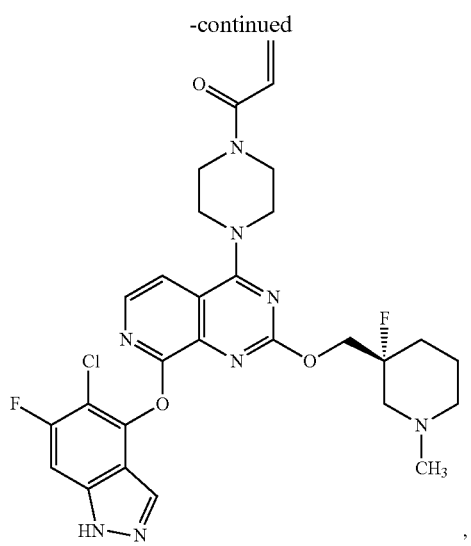
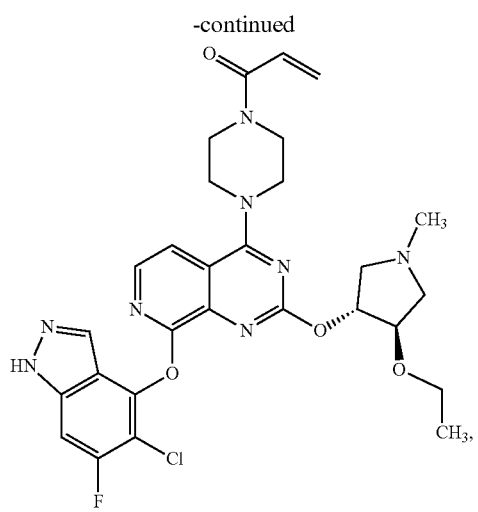
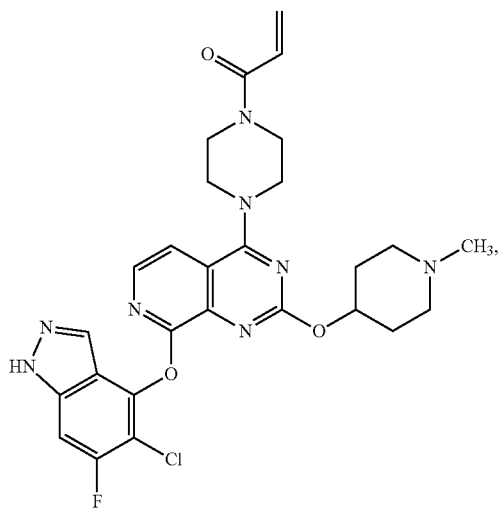
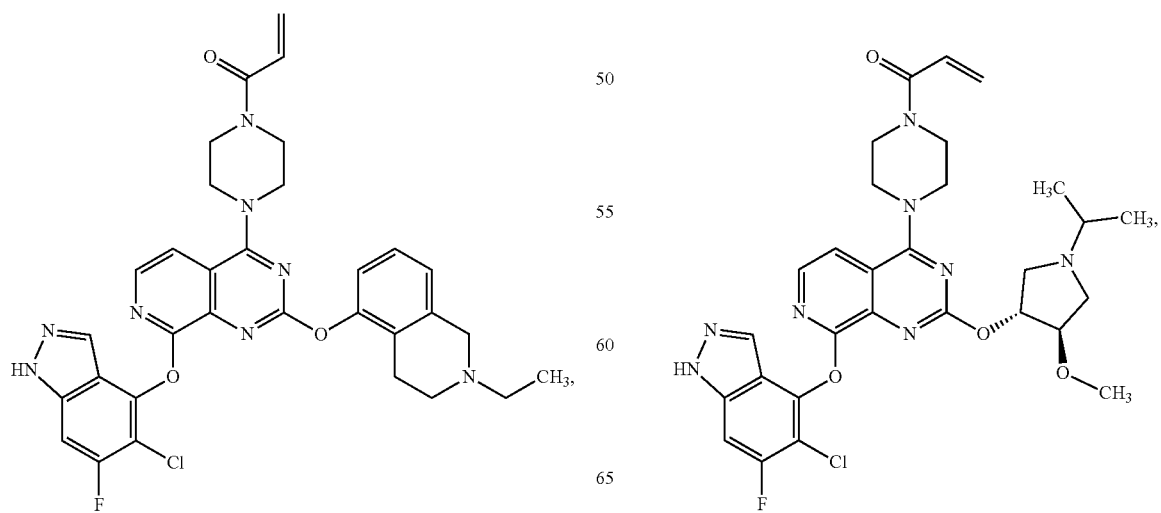

91
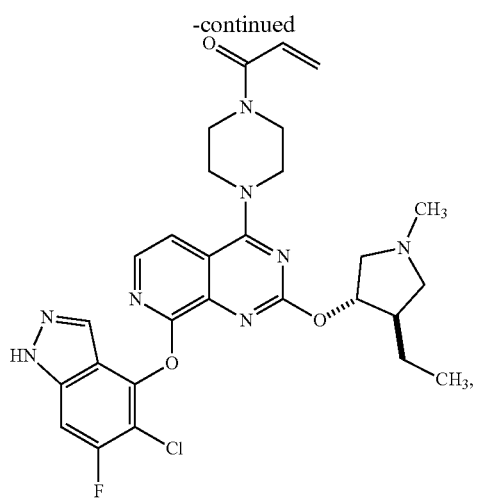
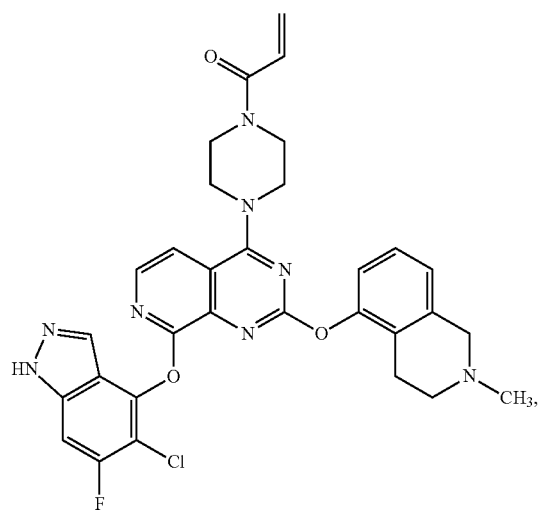
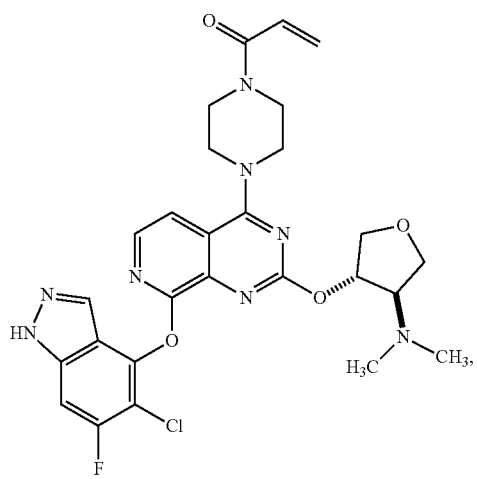
92
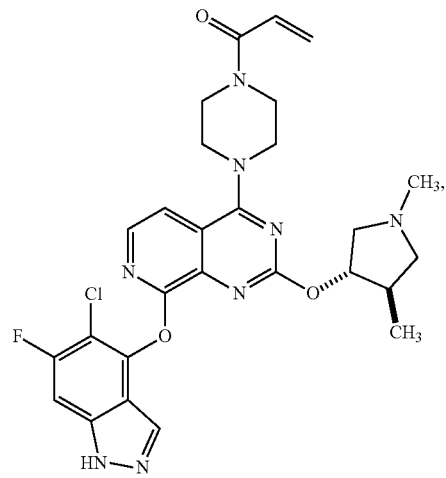
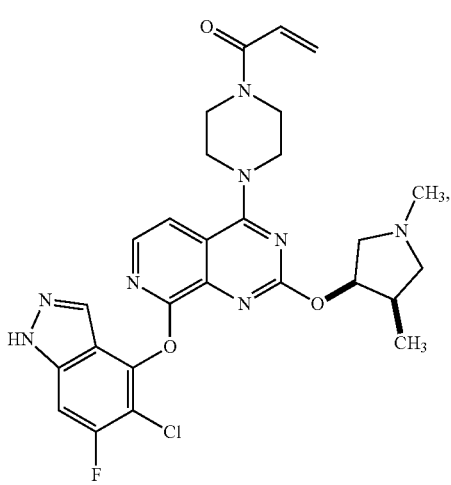
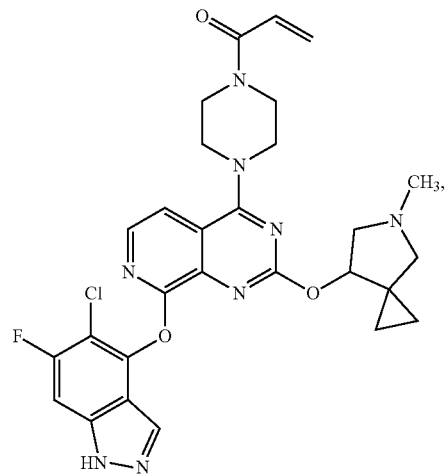

93
-continued
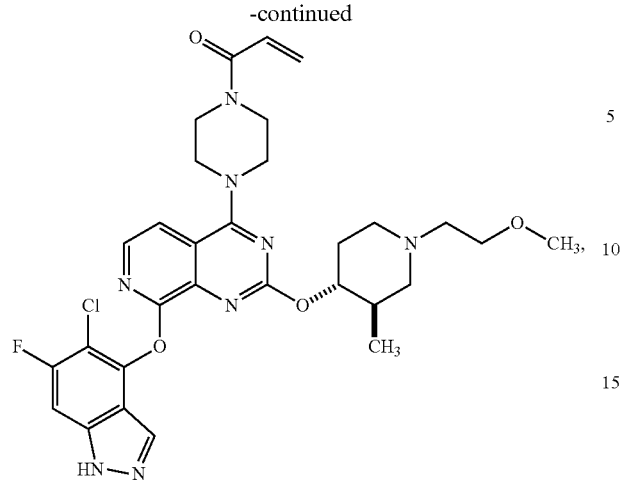
94
-continued
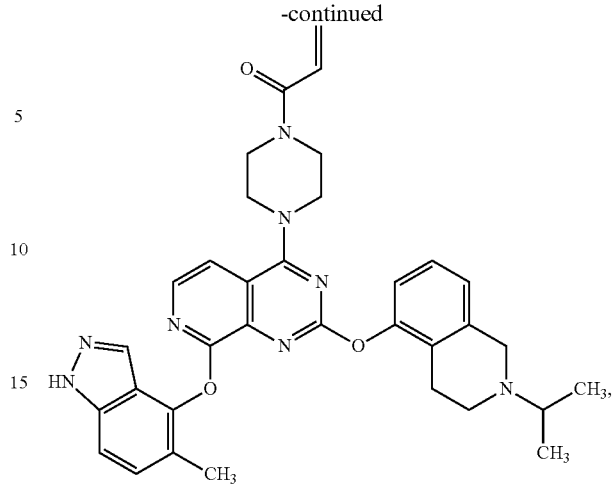
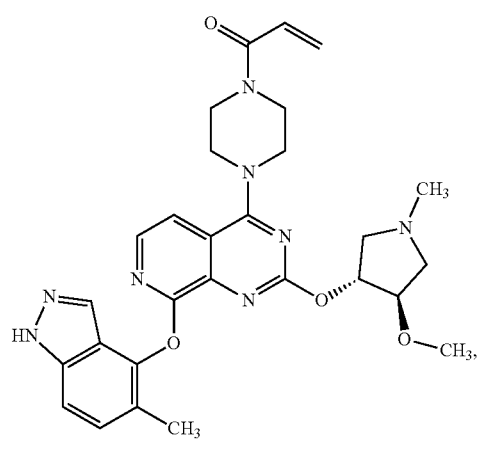
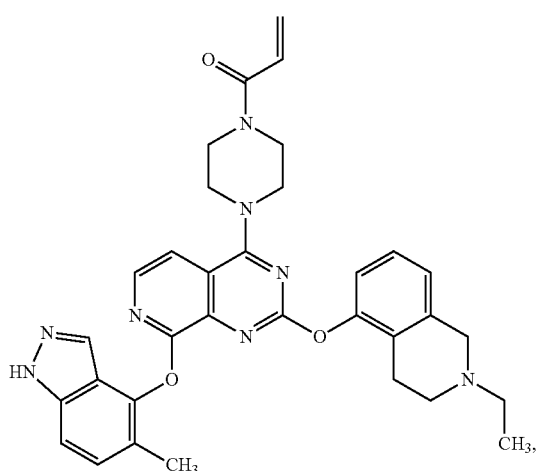
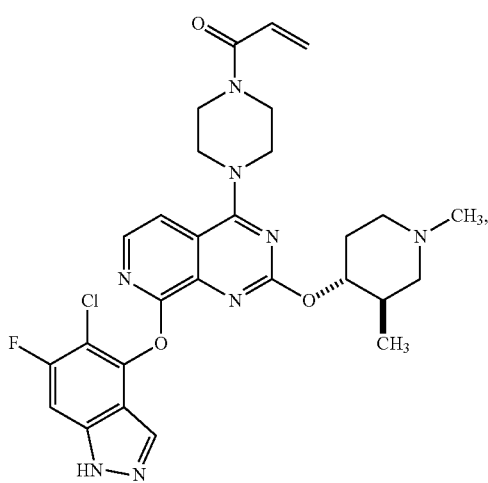
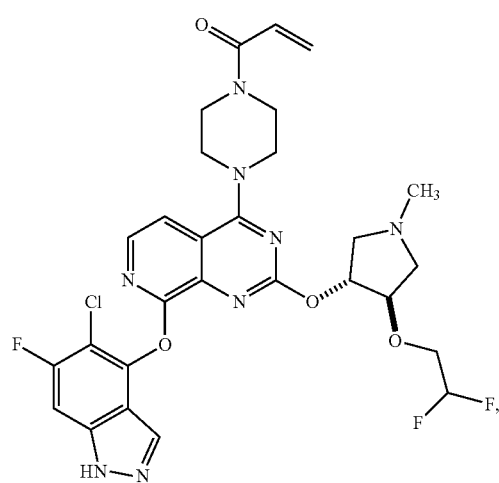

95
-continued
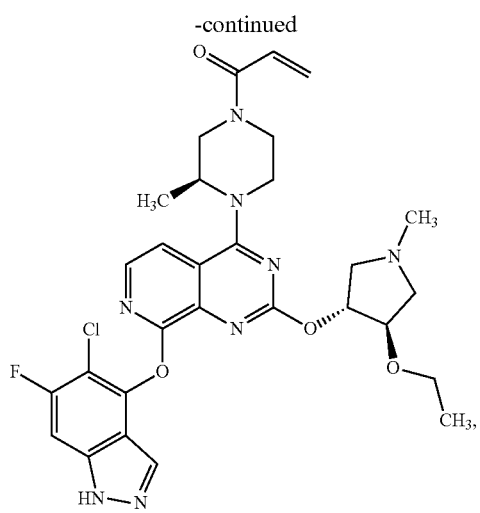
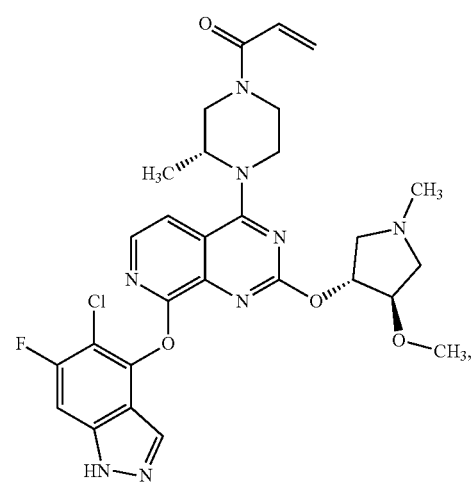
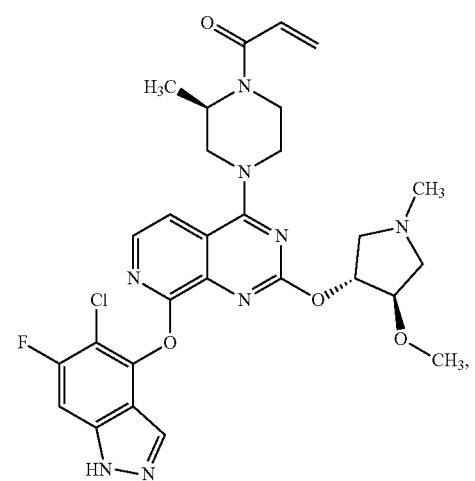
96
-continued
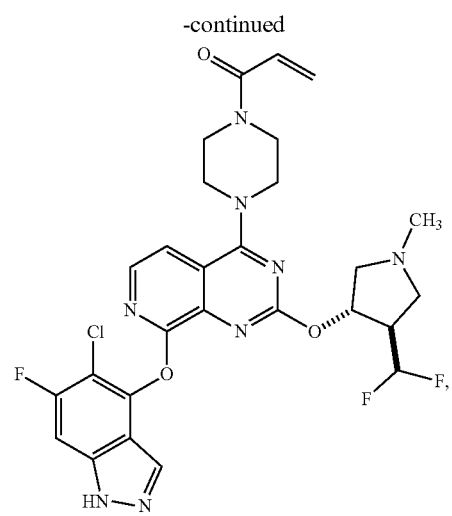
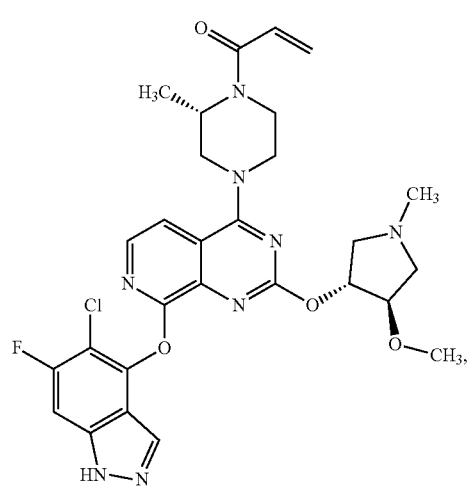
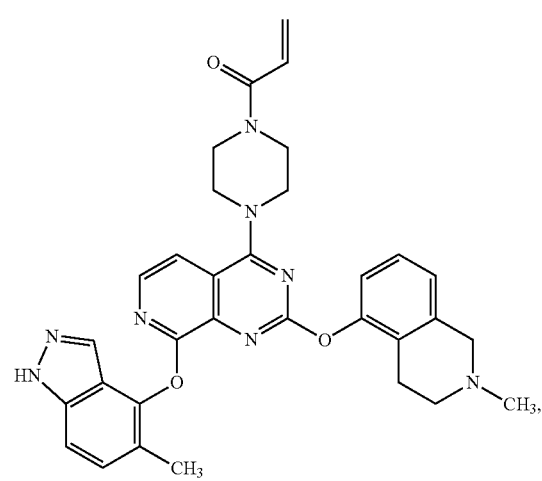

97
-continued
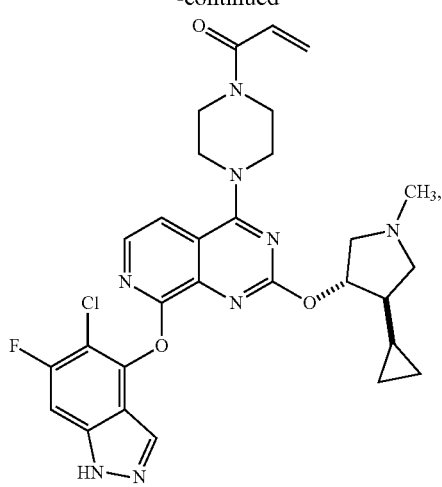
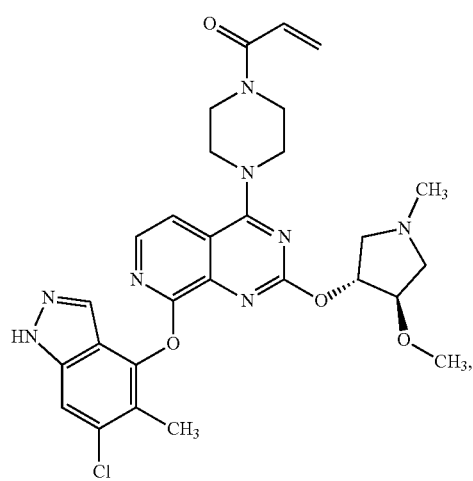
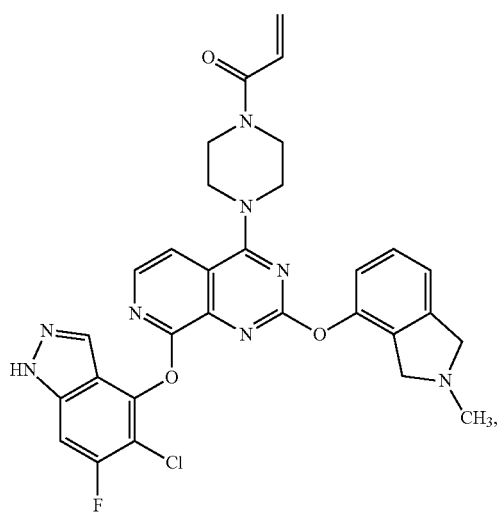
98
-continued
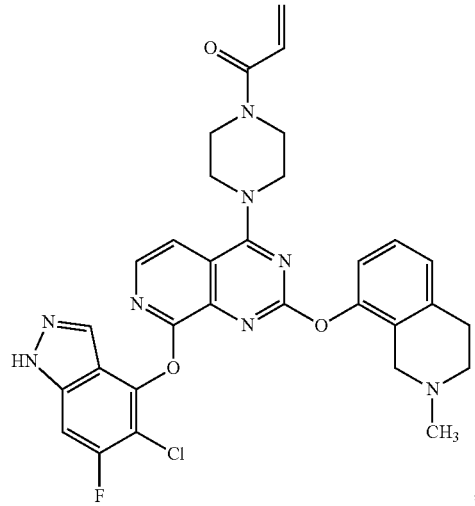
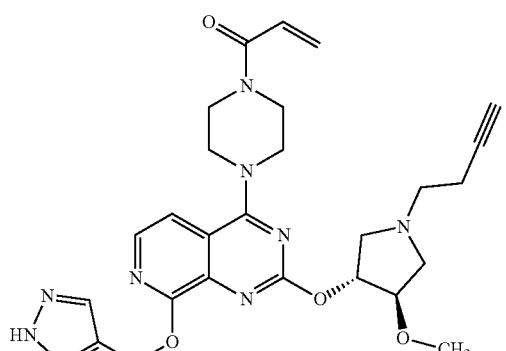
, 99
-continued
100
-continued
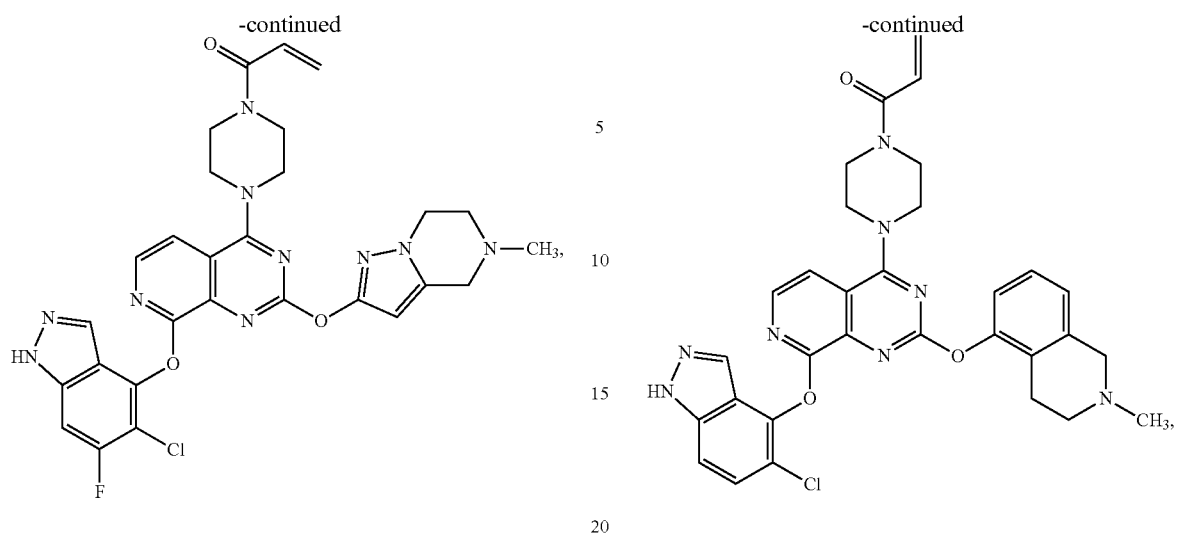

101
-continued
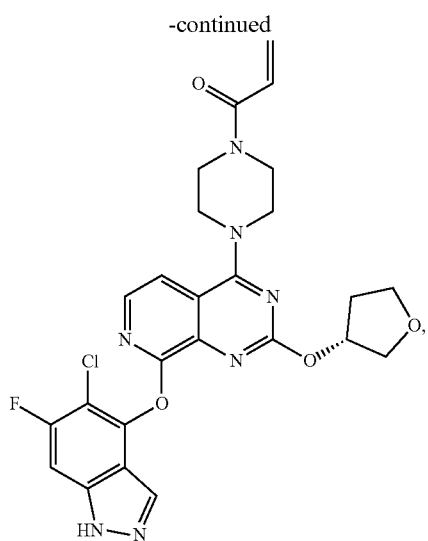
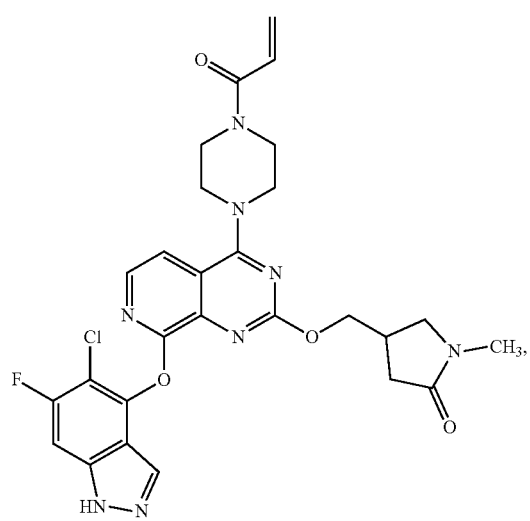
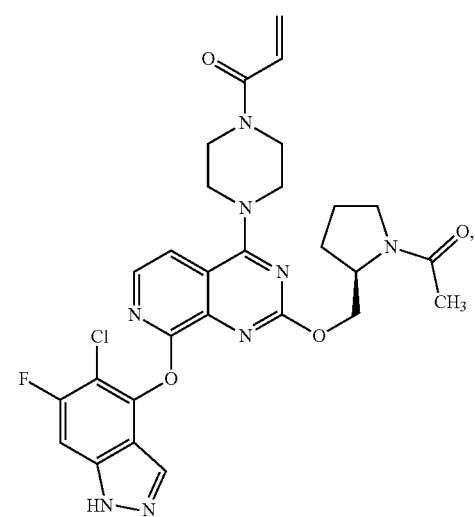
102
-continued
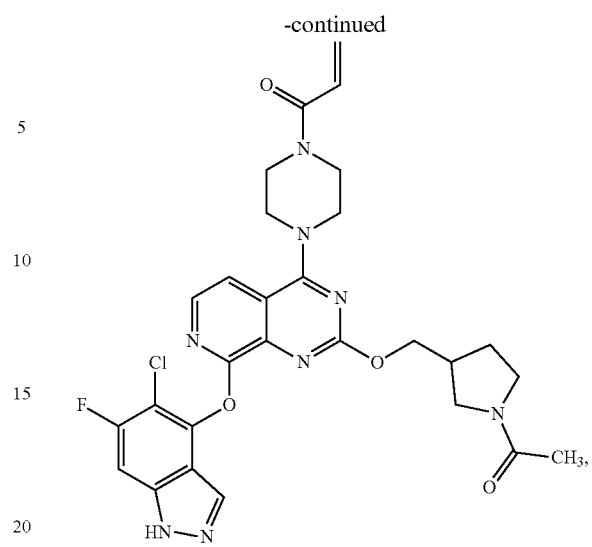
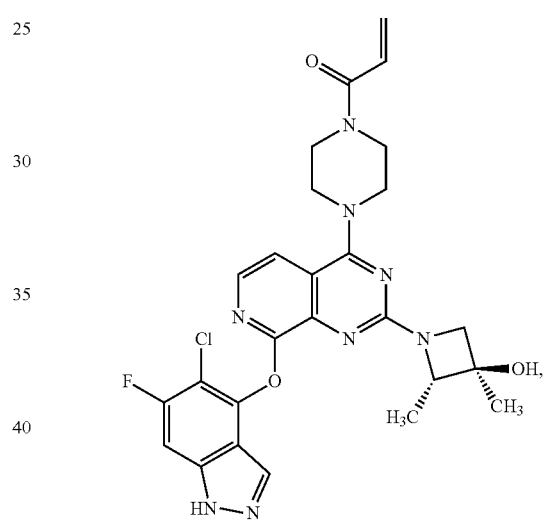
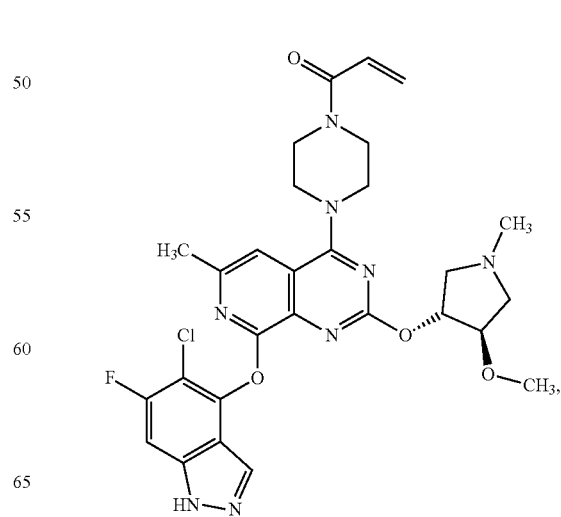

103
-continued
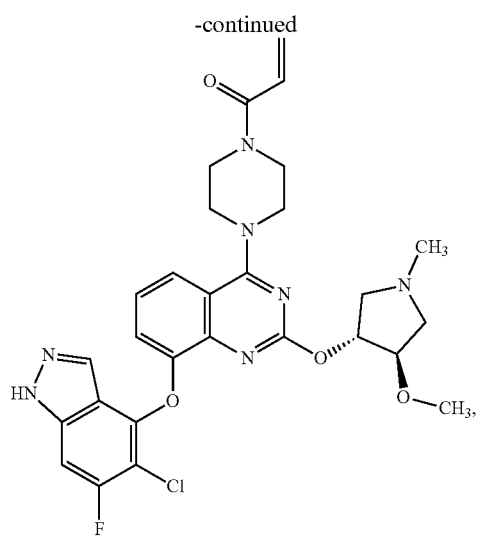
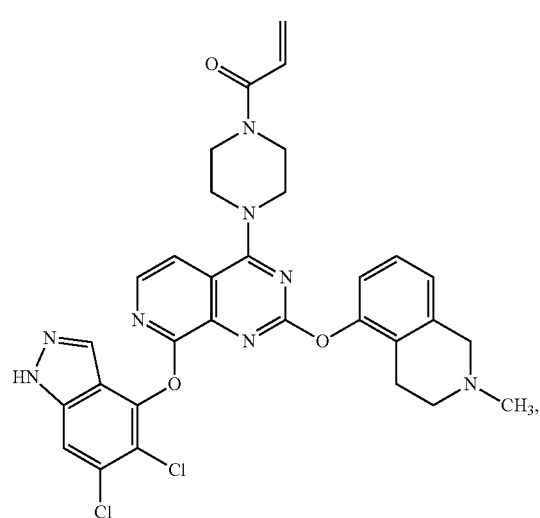
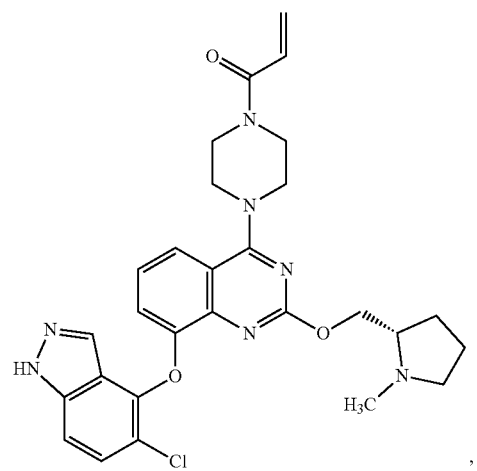
104
-continued
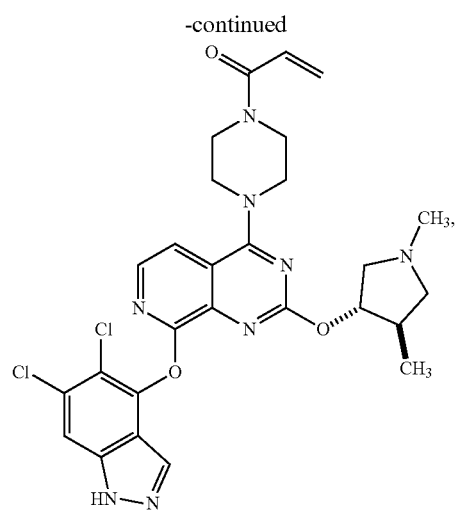
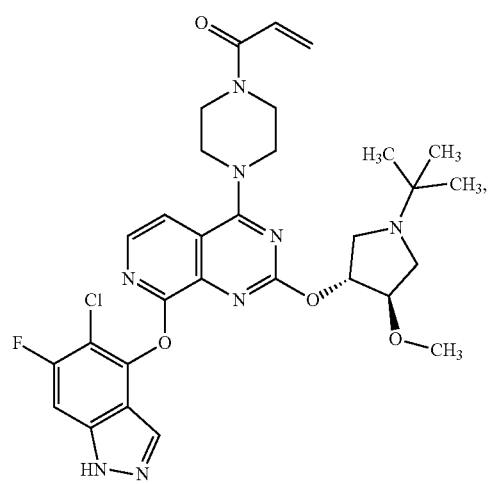
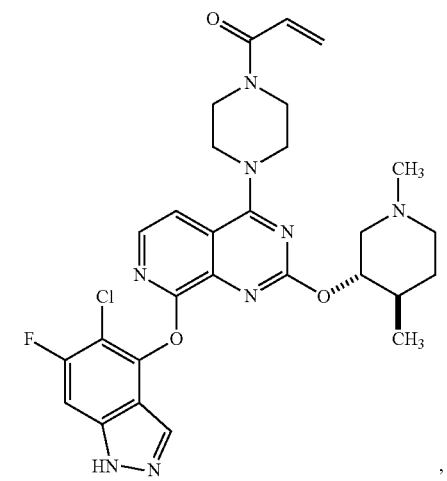

105
-continued
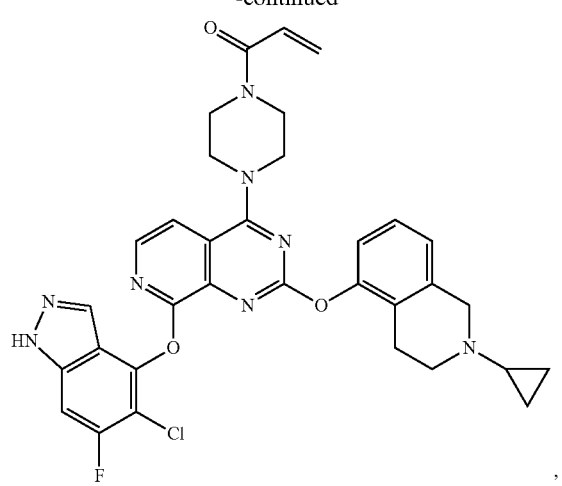
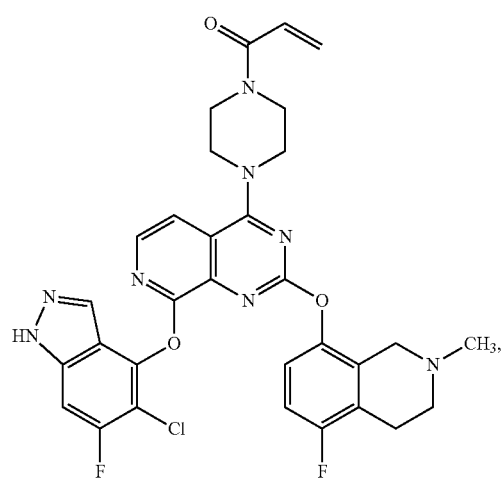
106
-continued
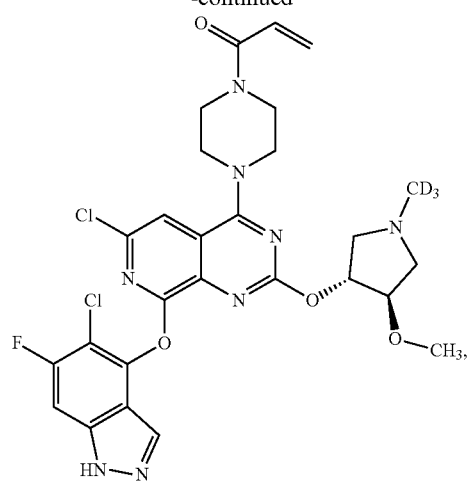
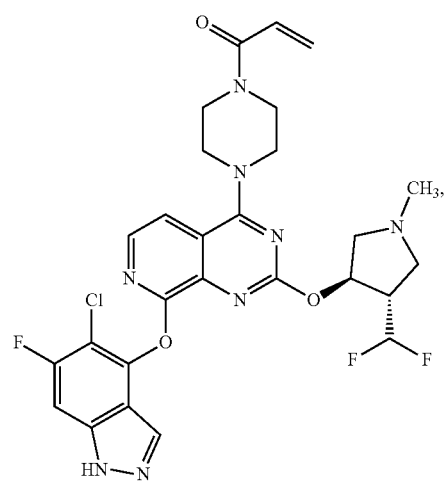
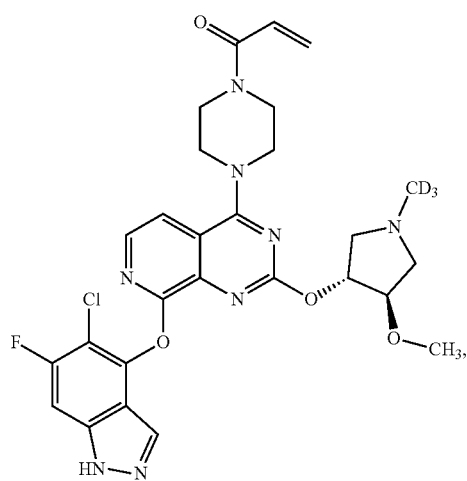
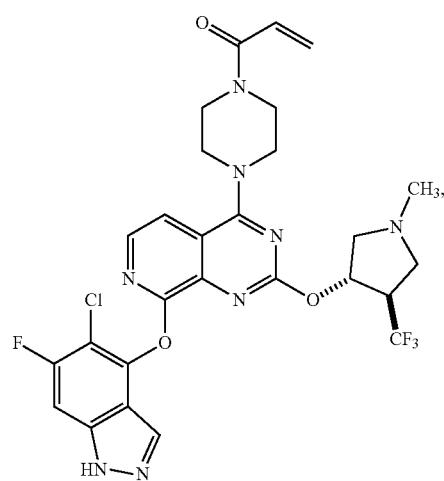

or a pharmaceutically acceptable salt thereof.

Embodiments of the invention preferentially include compounds selected from the group consisting of:

109
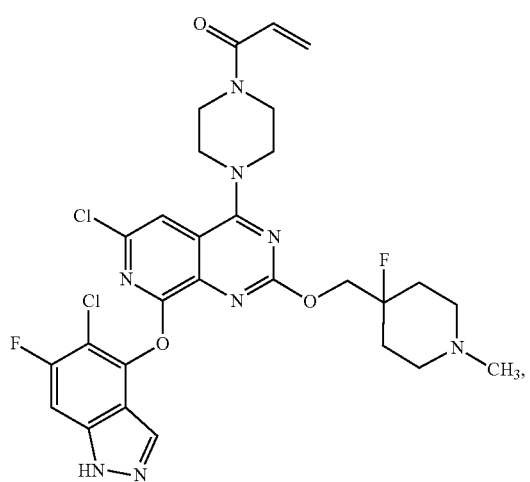
110
-continued
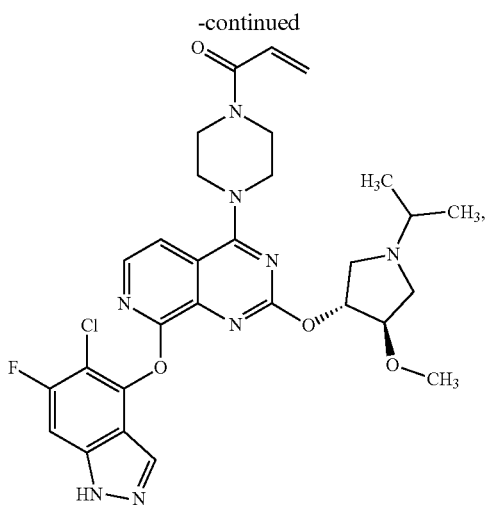
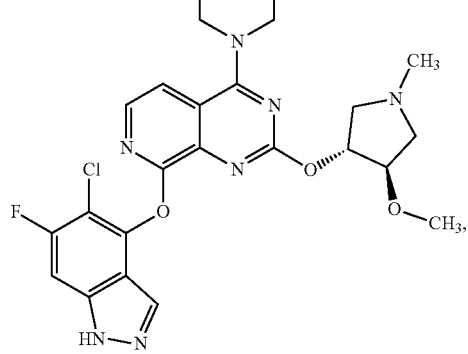
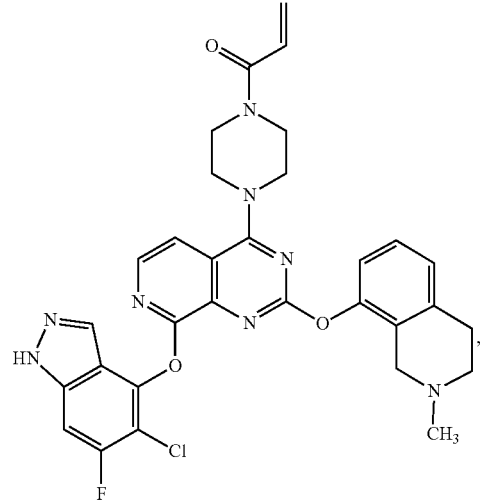
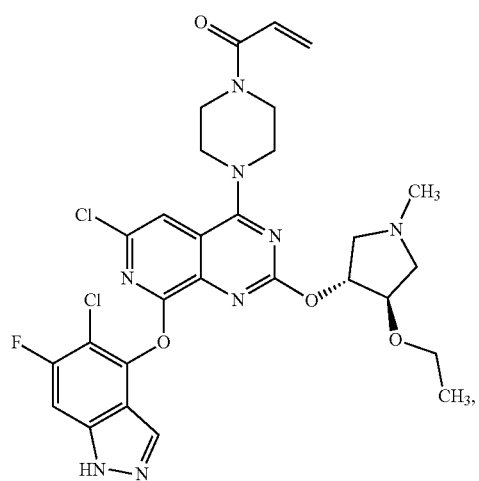
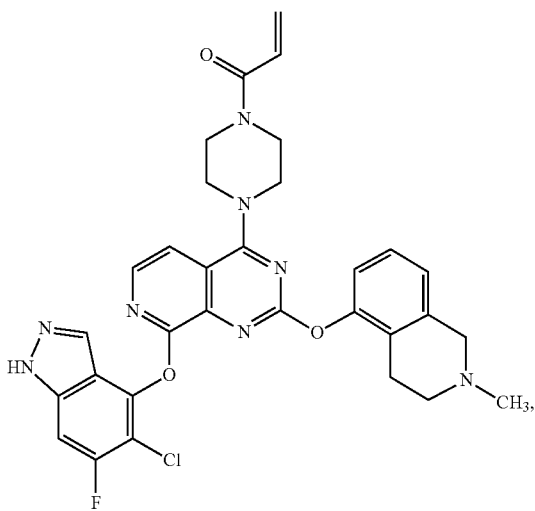

111
-continued
112
-continued
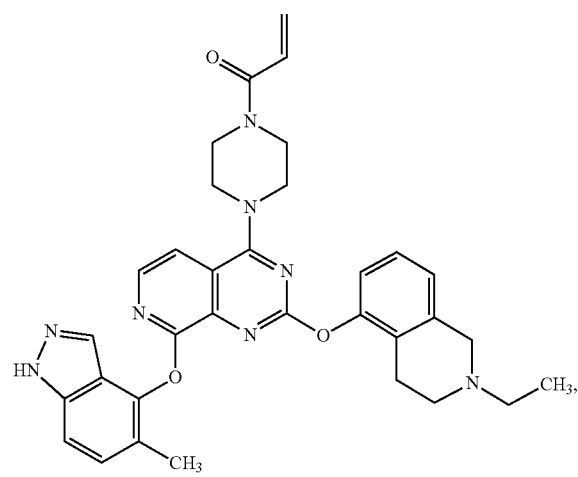
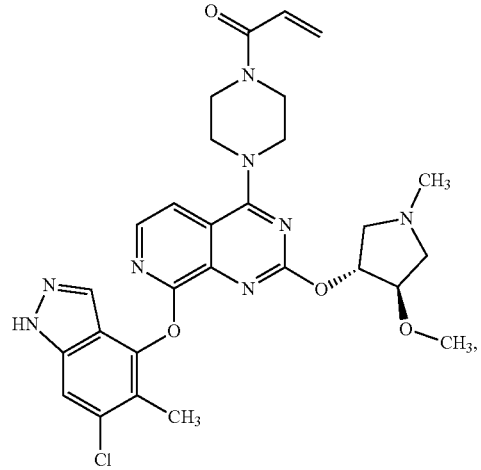
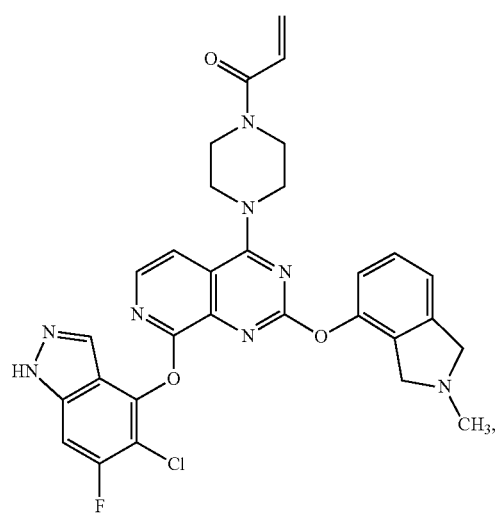
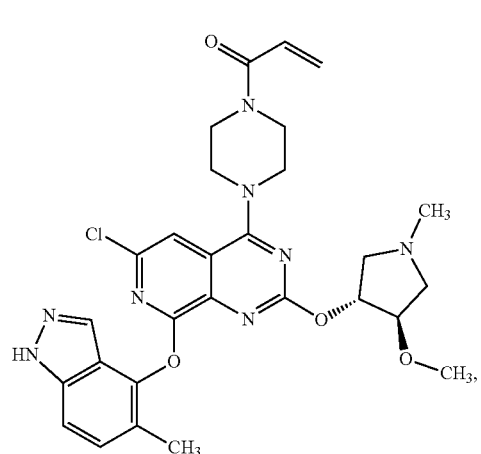
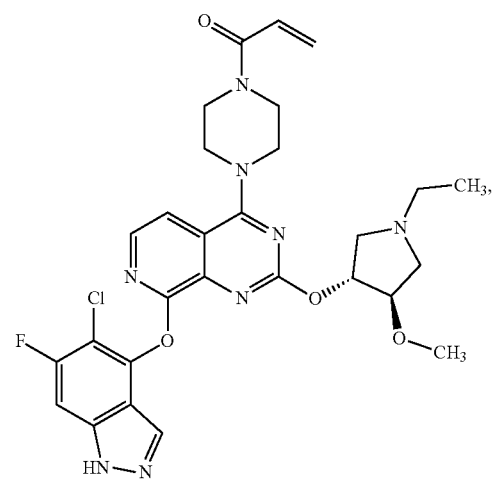
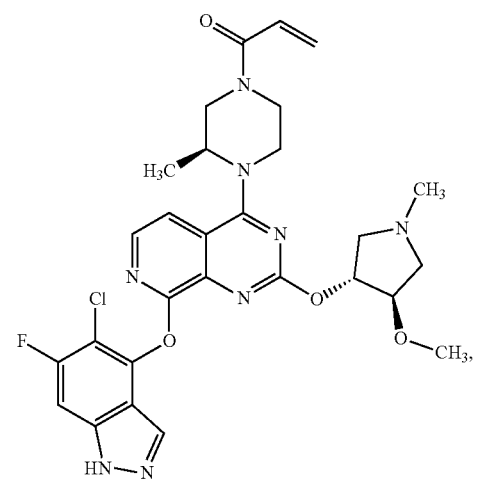

113
-continued
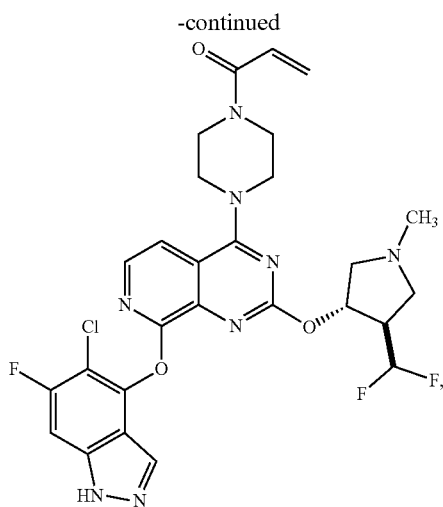
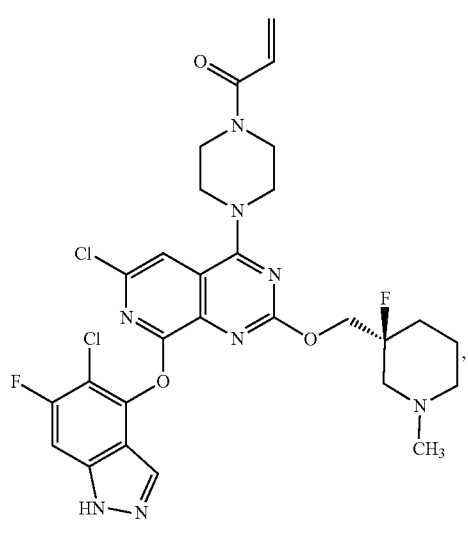
114
-continued
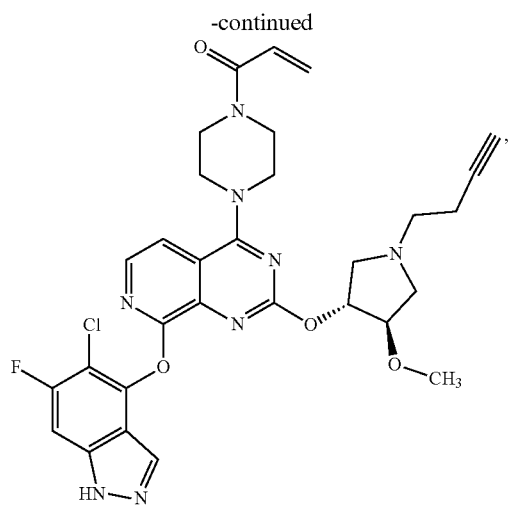
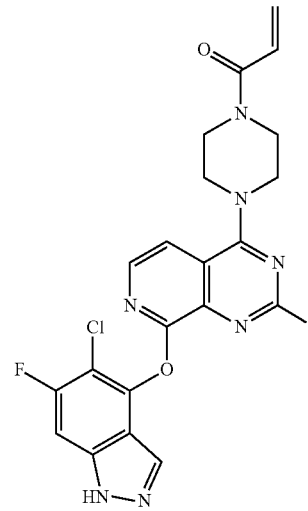
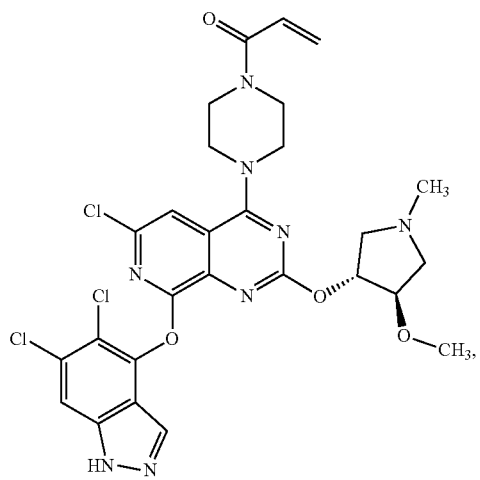

115
-continued
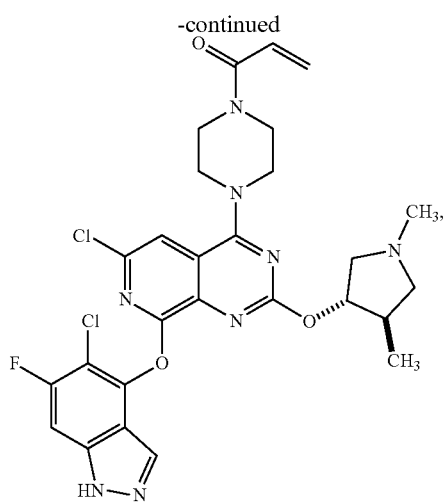
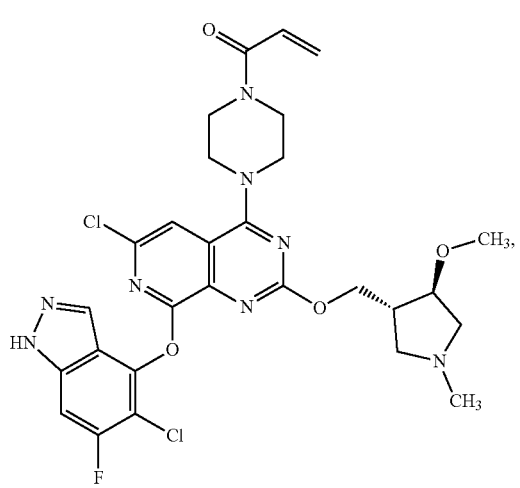
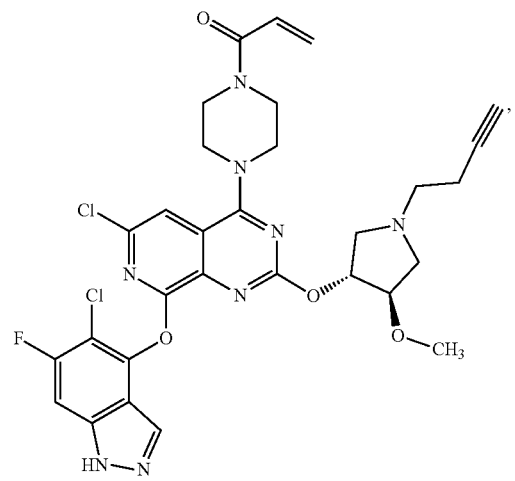
116
-continued
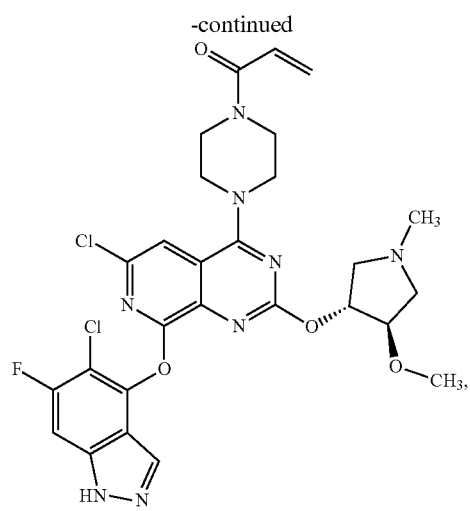
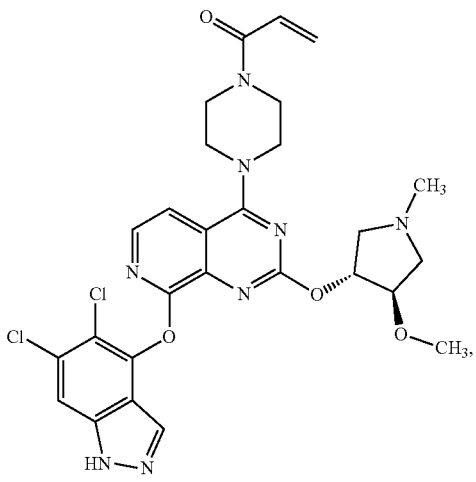
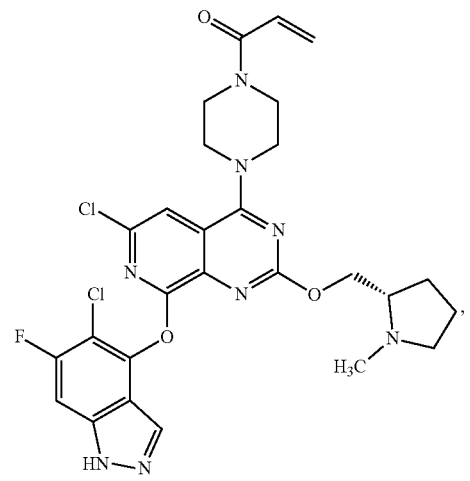

117
-continued
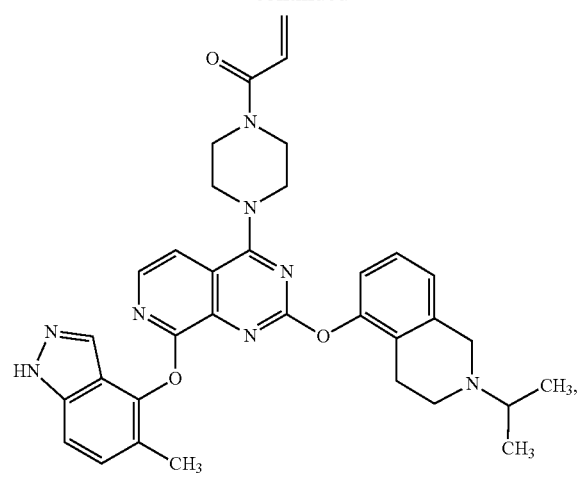
118
-continued
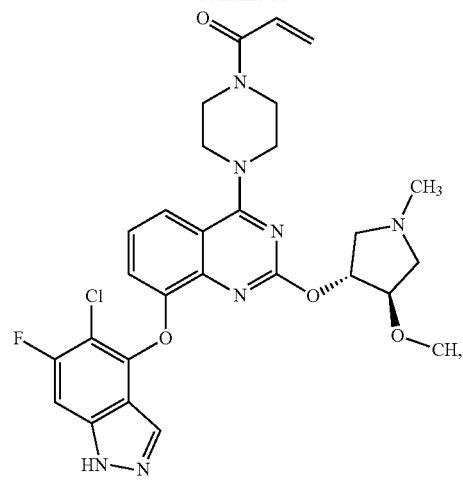
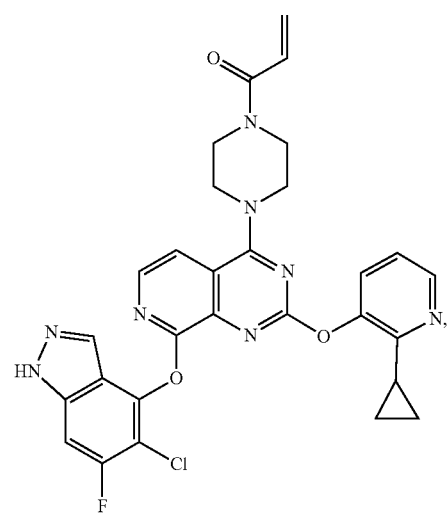
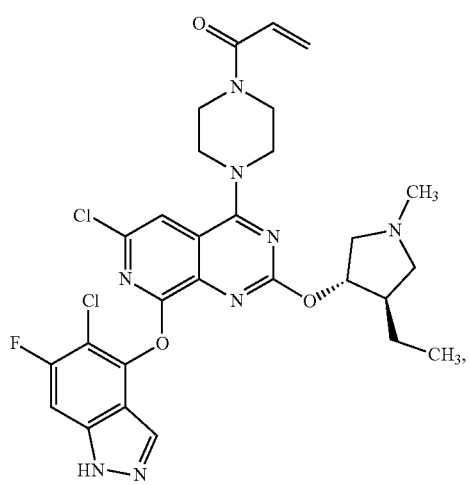
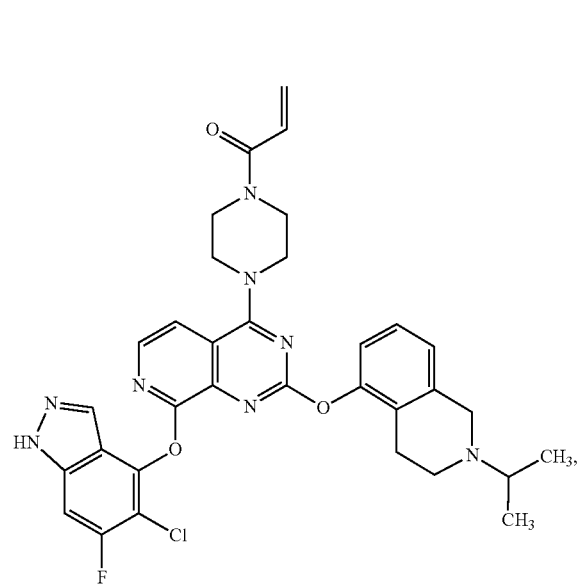
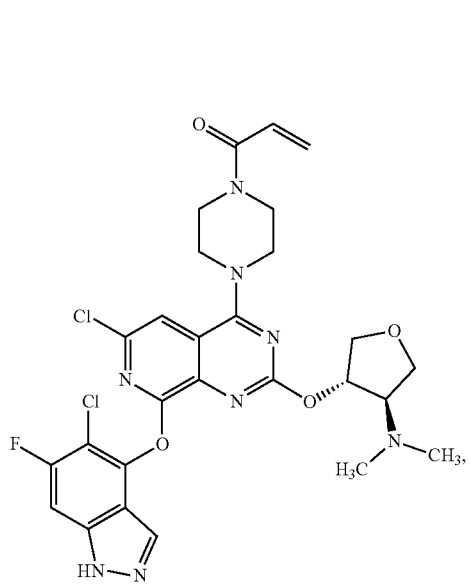

119
-continued
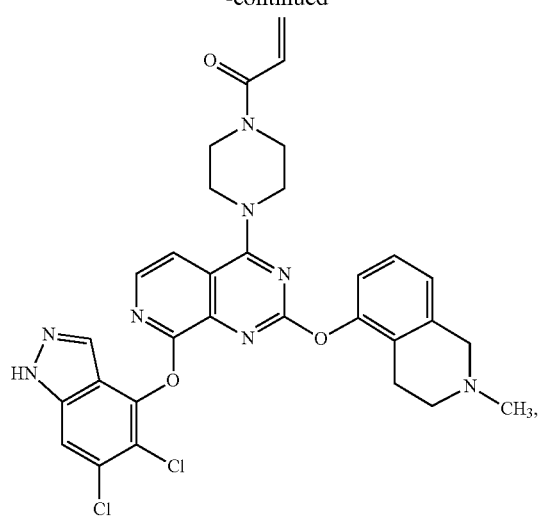
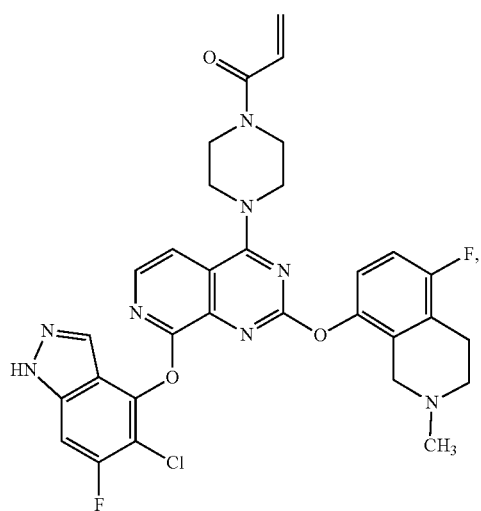
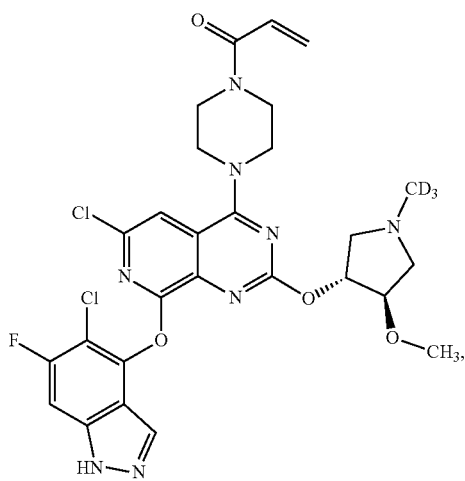
120
-continued
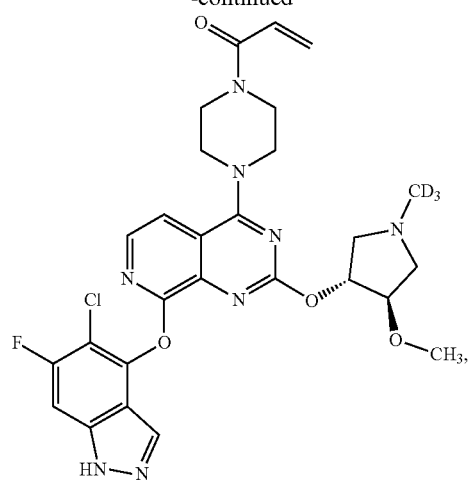
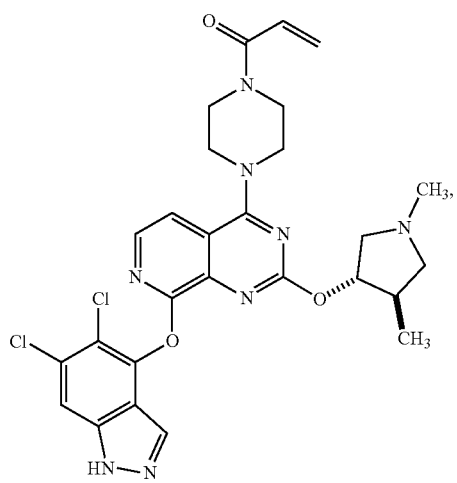
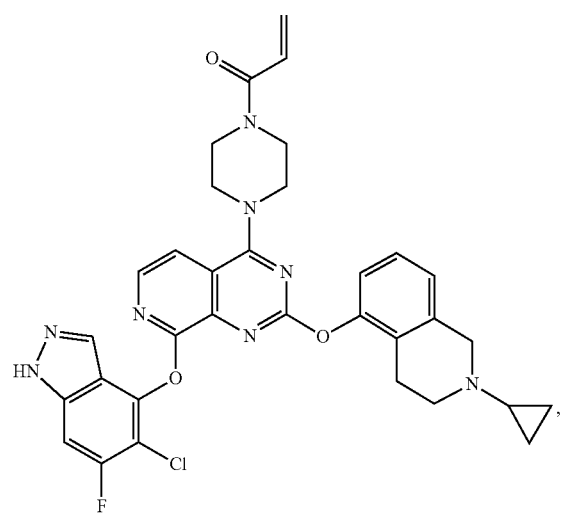

| 121 -continued | 122 -continued |
|---|---|
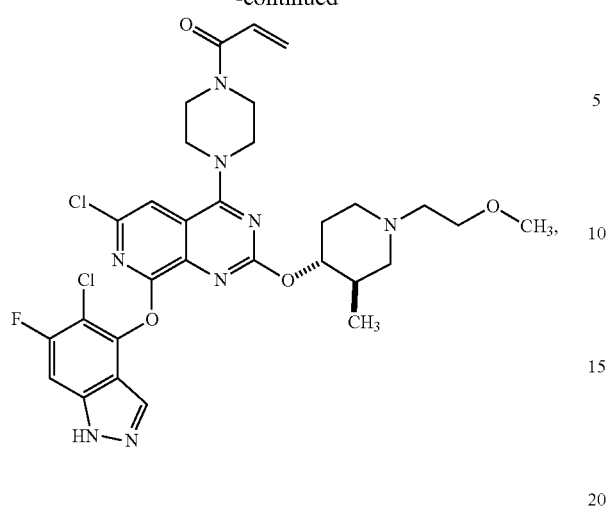
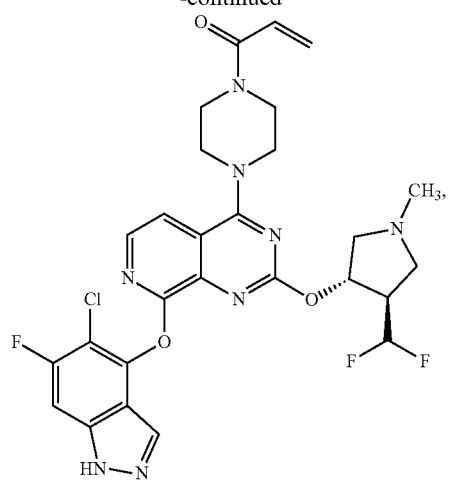
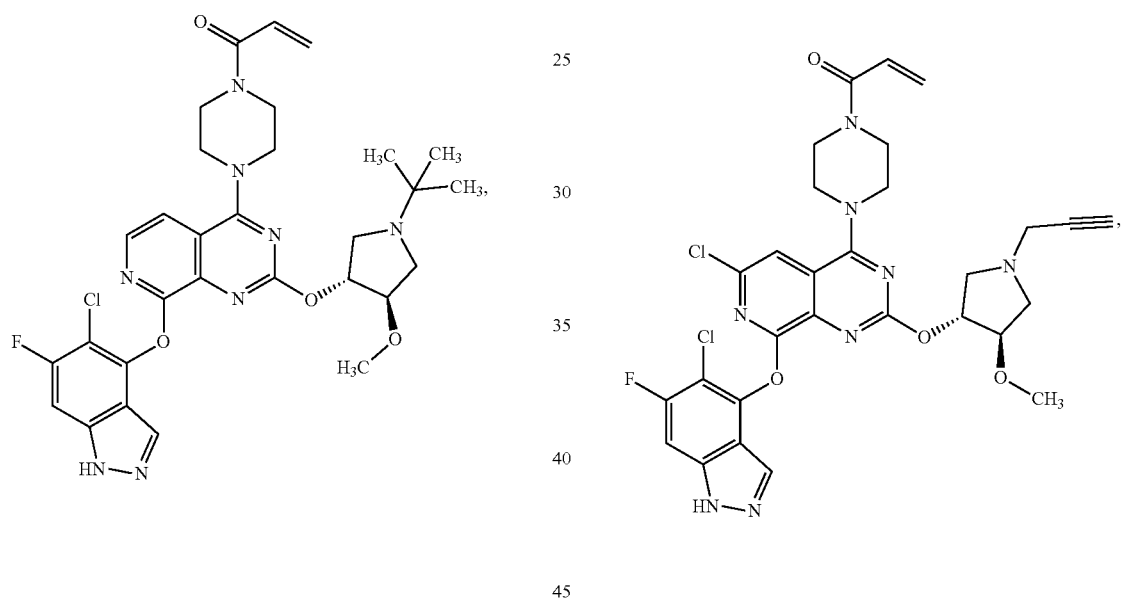
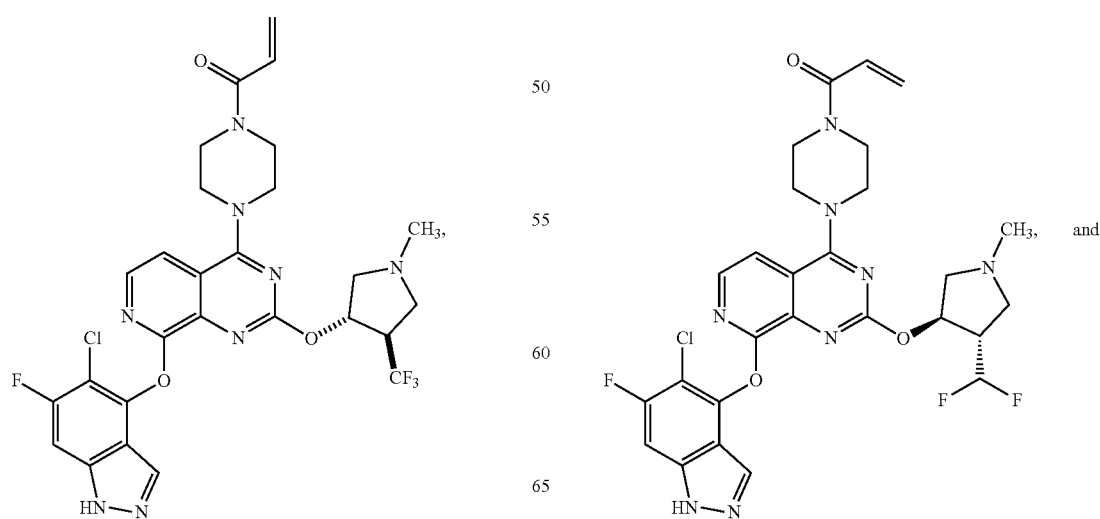

-continued

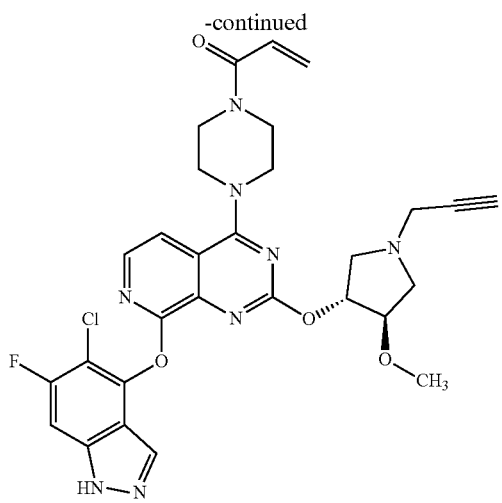

or a pharmaceutically acceptable salt thereof.

Additional embodiments of the invention include pharmaceutical composition comprising a therapeutically effective amount of a compound described herein or a pharmaceutically acceptable salt thereof, and a pharmaceutically acceptable excipient.

Additional embodiments of the invention also include methods for inhibiting KRAS activity in a cell by contacting the cell in which inhibition of KRAS activity is desired with a therapeutically effective amount of a compound described herein, or a pharmaceutically acceptable salt thereof, or a pharmaceutical composition containing said compound or pharmaceutically acceptable salt thereof.

Additional embodiments of the invention also include methods for treating cancer comprising administering to a patient having cancer a therapeutically effective amount of a compound or pharmaceutically acceptable salt thereof as described herein, alone, alone or in combination with one or more pharmaceutically acceptable carrier, excipient or diluent.

Embodiments further include such methods wherein the therapeutically effective amount of the administered compound or pharmaceutically acceptable salt thereof is between about 0.01 to 300 mg/kg per day; or is between about 0.1 to 100 mg/kg per day.

Additional embodiments of the invention also include methods for treating abnormal cell growth in a mammal comprising administering to the mammal a therapeutically effective amount of a compound as described herein or a pharmaceutically acceptable salt thereof. In certain such embodiments, the abnormal cell growth is cancer, and in certain of those embodiments the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. Such cancers may be KRAS associated cancers. Of particular interest are cancers such as lung cancer, colon cancer, pancreatic cancer, and ovarian cancer.

Embodiments of the invention also include the use a compound described herein, or use of a pharmaceutically acceptable salt thereof, for the preparation of a medicament useful in the treatment of abnormal cell growth in a mammal. In certain such embodiments, the abnormal cell growth is cancer, and in certain of those embodiments the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. Such cancers may be KRAS associated cancers.

Also related to cancer treatment, embodiments of the invention include methods for treating cancer in a patient in need thereof comprising: (a) determining that the cancer is associated with a KRAS mutation; and (b) administering to the patient a therapeutically effective amount of a compound or pharmaceutically acceptable salt as described herein, or a pharmaceutical composition thereof. In some embodiments the KRAS mutation is or incorporates a G12C mutation. In some embodiments the KRAS mutation is or incorporates a Ras mutation at codons 12, 13 and/or 61.

Definitions

Unless otherwise stated, the following terms used in the specification and claims have the meanings discussed below. Variables defined in this section, such as R, X, n and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("$(C_1$-$C_{20})$alkyl"), preferably 1 to 12 carbon atoms ("$(C_1$-$C_{12})$alkyl"), more preferably 1 to 8 carbon atoms ("$(C_1$-$C_8)$alkyl"), or 1 to 6 carbon atoms ("$(C_1$-$C_6)$alkyl"), or 1 to 4 carbon atoms ("$(C_1$-$C_4)$alkyl"). Examples of alkyl groups include methyl, ethyl, propyl, 2-propyl, n-butyl, iso-butyl, tert-butyl, pentyl, neopentyl, and the like.

Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^x$R$^y$, where R$^x$ and R$^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" for instance ($C_1$-$C_6$)haloalkyl, refers to an alkyl having one to six carbons and one or more halogen substituents, for instance —$CF_3$ and —$CHF_2$. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —NR$^x$R$^y$ group, wherein R$^x$ and R$^y$ are both hydrogen.

"($C_6$-$C_{12}$)aryl" refers to an all-carbon monocyclic or fused-ring polycyclic groups of 6 to 12 carbon atoms having a completely conjugated pi-electron system. Similarly, "($C_5$-$C_{12}$)aryl" refers to an all-carbon monocyclic or fused-ring polycyclic groups of 5 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —NR$^x$R$^y$, with R$^x$ and R$^y$ as defined above.

"($C_6$-$C_{12}$)aryl" also includes aryl rigs and ring systems as described above which additionally include fused thereto a carbocyclo or heterocycle, for instance:

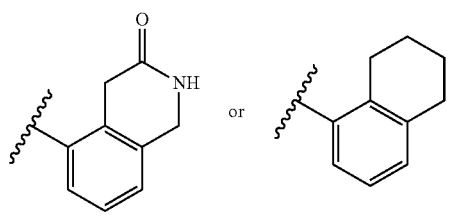 [SMILES: *c1cccc2c1CC(=O)NC2 ; *c1cccc2c1CCCC2]

"Cyano" refers to a —C≡N group. Cyano may be expressed as CN.

"($C_3$-$C_{10}$)cycloalkyl" refers to a 3 to 10 member all-carbon monocyclic ring, a 3 to 10 member all-carbon bicyclic ring, an all-carbon 5-member/6-member or 6-member/6-member fused bicyclic ring, a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system, and a bridged all-carbon ring system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^x$R$^y$, with R$^x$ and R$^y$ as defined above.

"G12C" refers to a mutation where the amino-acid at position-12 in wild-type KRAS has mutated from a glycine to a cysteine residue.

"Halogen" or the prefix "halo" refers to fluoro, chloro, bromo and iodo. Preferably halogen refers to fluoro or chloro.

"Heteroalkyl" refers to a straight chain or branched chain alkyl group of 1 to 20 carbon atoms, preferably 1 to 12 carbon atoms, more preferably 1 to 8 carbon atoms, or 1 to 6 carbon atoms, or 1 to 4 carbon atoms, wherein one, two or three of which carbon atoms are replaced by a heteroatom selected from NR$^x$, N, O, and S(O)$_n$ (where n is 0, 1 or 2). Typically the heteroatoms, of there are more than one heteroatoms, are not adjacent to one another.

Exemplary heteroalkyls include alkyl ethers, secondary and tertiary alkyl amines, amides, alkyl sulfides, and the like. The group may be a terminal group or a bridging group. As used herein, reference to the normal chain when used in the context of a bridging group refers to the direct chain of atoms linking the two terminal positions of the bridging group. As with "alkyl", typical substituent groups on "heteroalkyl" include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^x$R$^y$, where R$^x$ and R$^y$ are for example hydrogen, alkyl, cycloalkyl, aryl, carbonyl, acetyl, sulfonyl, trifluoromethanesulfonyl and, combined, a five- or six-member heteroalicyclic ring. "Heteroalkenyl" refers to a heteroalkyl possessing one or more carbon-carbon double bonds. "Heteroalkylene" refers to a di-valent form of heteroalkyl. "Heteroalkenylene" refers to a di-valent form of heteroalkenyl.

"Heteroaryl" refers to a monocyclic or fused ring group of 5 to 12 ring atoms containing one, two, three or four ring heteroatoms selected from NR$^x$, N, O, and S(O)$_n$ (where n is 0, 1 or 2) and, in addition, having a completely conjugated pi-electron system. Preferred heteroaryl groups include ($C_2$-$C_7$) heteroaryl in accordance with the definition above. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^x$R$^y$ with R$^x$ and R$^y$ as defined above. A pharmaceutically acceptable heteroaryl is one that is sufficiently stable to be attached to a compound of the invention, formulated into a pharmaceutical composition and subsequently administered to a patient in need thereof. Examples of typical monocyclic heteroaryl groups include, but are not limited to:

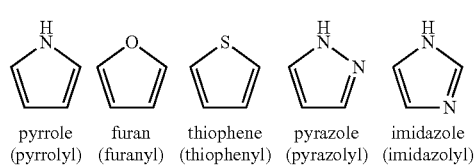

pyrrole  furan  thiophene  pyrazole  imidazole
(pyrrolyl) (furanyl) (thiophenyl) (pyrazolyl) (imidazolyl)

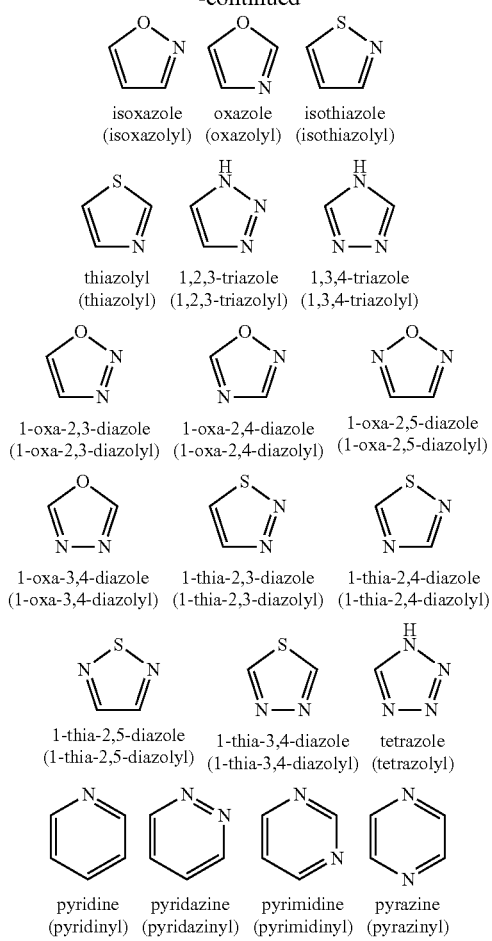
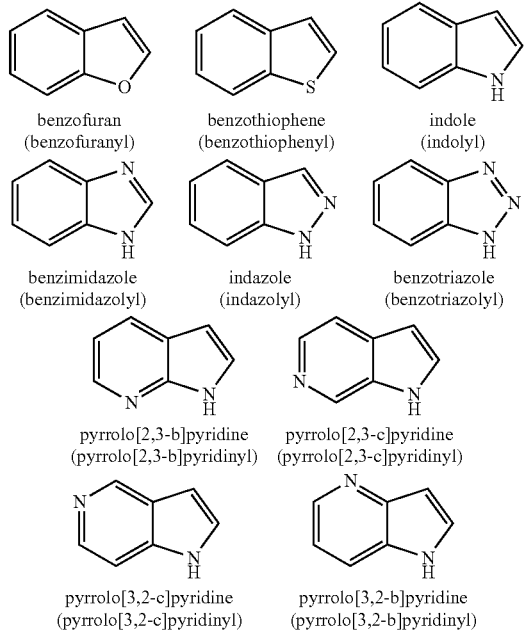
Examples of suitable fused ring heteroaryl groups include, but are not limited to:
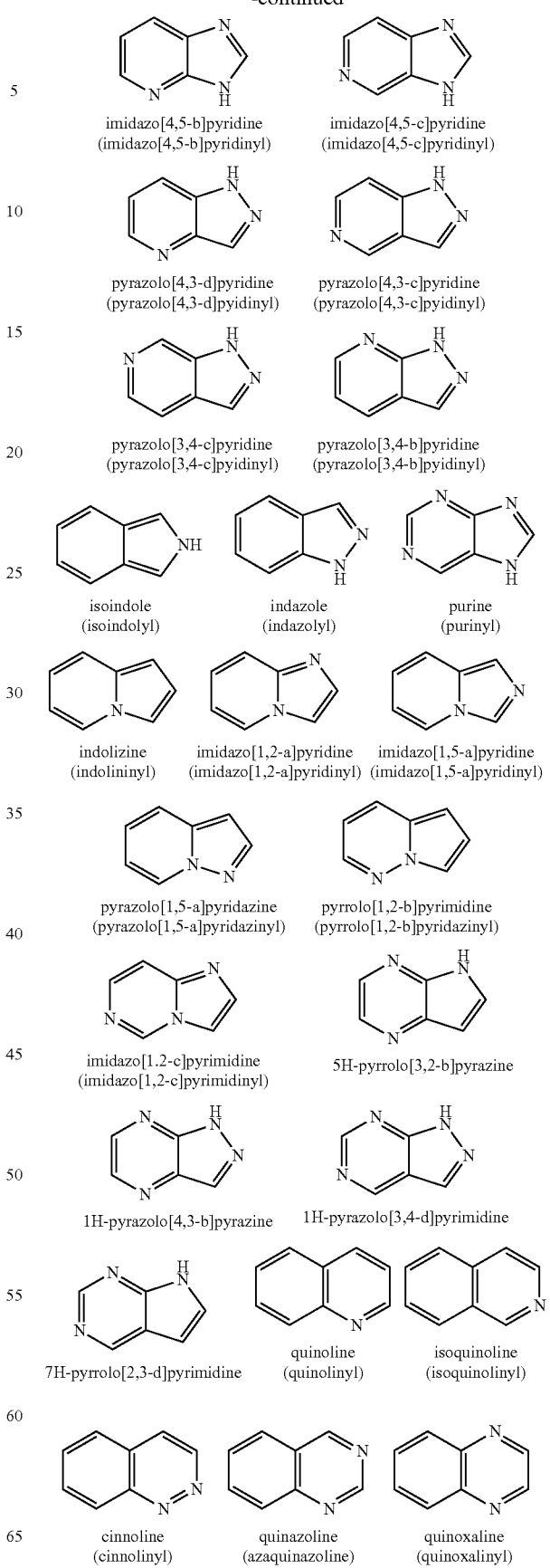

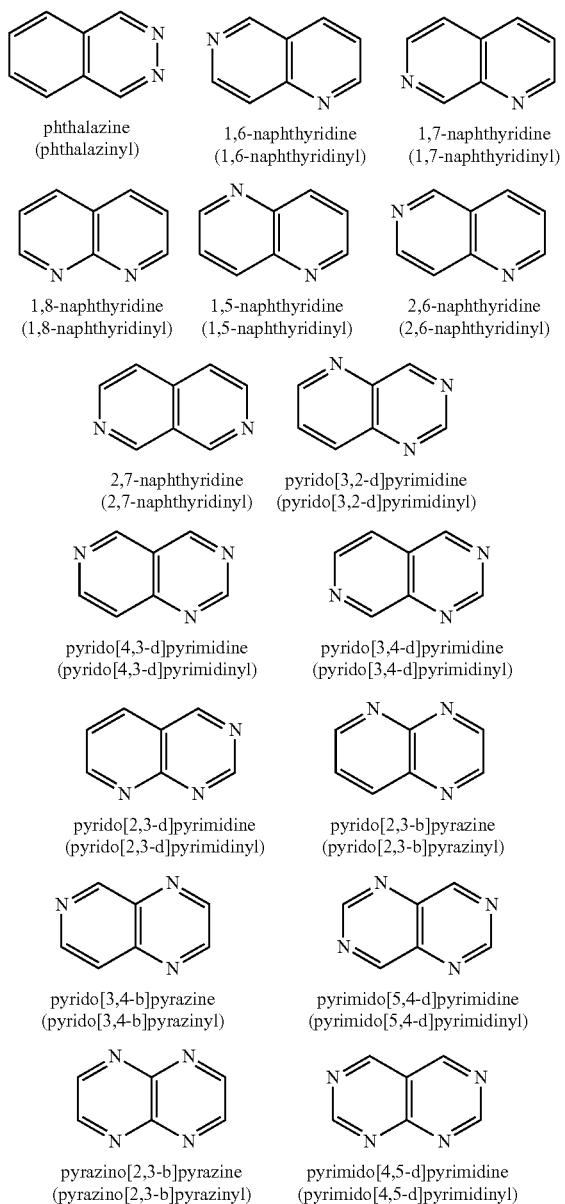

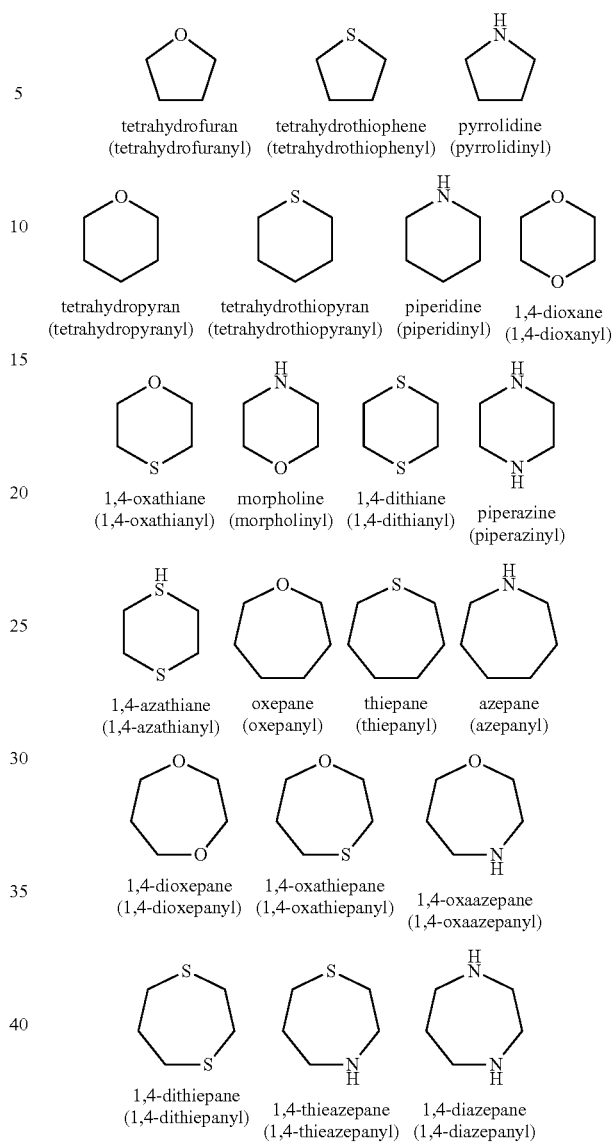

"Heterocyclyl" refers to a monocyclic, spirocyclic or fused ring system having 3 to 12 ring atoms containing one, two, three or four ring heteroatoms selected from N, O, and $S(O)_n$ (where n is 0, 1 or 2), and 1-9 carbon atoms The rings may also have one or more double bonds. However, the rings do not have a completely conjugated pi-electron system. Preferred heterocycles include ($C_2$-$C_6$) heterocycles in accordance with the definition above.

Examples of suitable saturated heterocyclic groups include, but are not limited to:

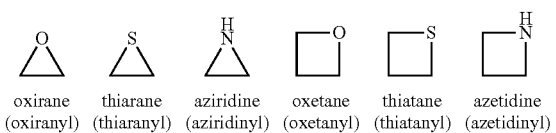

Examples of suitable partially unsaturated heterocyclic groups include, but are not limited to:

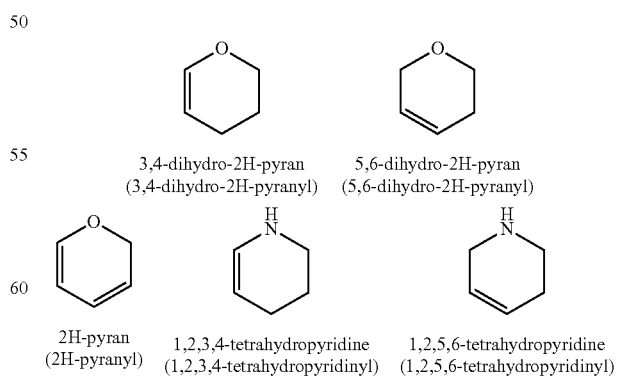

Examples of suitable fused heterocyclic groups include, but are not limited to:

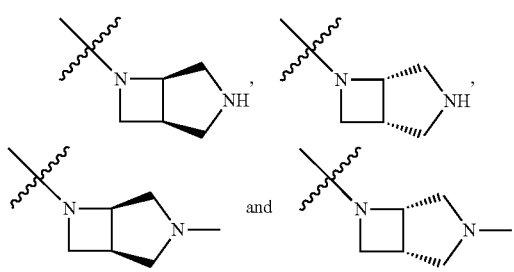

Examples of suitable semi-saturated fused heterocyclic groups include, but are not limited to:

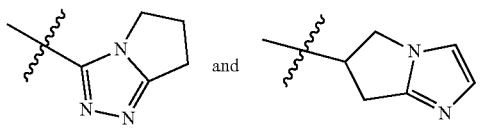 [SMILES: *c1nnc2n1CCC2 ; *C1Cc2nccn2C1]

Examples of suitable spirocyclic heterocyclic groups include, but are not limited to:

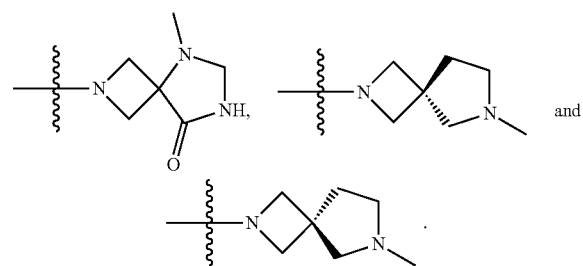

The heterocyclyl group is optionally substituted with one or two substituents independently selected from halo, lower alkyl, lower alkyl substituted with carboxy, ester hydroxy, mono or dialkylamino, or oxo. Moreover, the heterocycle may contain bridging, including bridging between non-adjacent carbons on the heterocycle, with the bridge containing 1-2 carbons and 0-1 heteroatoms selected from selected from $NR^x$, O, and $S(O)_n$ (where n is 0, 1 or 2).

"Hydroxy" or "hydroxyl" refers to an —OH group.

"In vitro" refers to procedures performed in an artificial environment such as, e.g., without limitation, in a test tube or culture medium.

"In vivo" refers to procedures performed within a living organism such as, without limitation, a mouse, rat or rabbit.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukariotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects: reducing the size of the tumor; inhibiting (that is, slowing to some extent, preferably stopping) tumor metastasis; inhibiting to some extent (that is, slowing to some extent, preferably stopping) tumor growth, and relieving to some extent (or, preferably, eliminating) one or more symptoms associated with the cancer.

"Treat", "treating" and "treatment" refer to a method of alleviating or abrogating a methyltransferase mediated cellular disorder and/or its attendant symptoms. With regard particularly to cancer, these terms simply mean that the life expectancy of an individual affected with a cancer will be increased or that one or more of the symptoms of the disease will be reduced.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds.

Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties. Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include: (i) where the compound contains a carboxylic acid functionality —(COOH), an ester thereof, for example, replacement of the hydrogen with $(C_1-C_8)$alkyl; (ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—$NH_2$ or —NHR where R≠H), an amide thereof, for example, replacement of one or both hydrogens with $(C_1-C_{10})$alkanoyl. Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration: The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001).

The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may include a bioadhesive agent, for example, chitosan or cyclodextrin.

The pressurized container, pump, spray, atomizer, or nebulizer contains a solution or suspension of the compound (s) of the invention comprising, for example, ethanol, aqueous ethanol, or a suitable alternative agent for dispersing, solubilizing, or extending release of the active, a propellant (s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The following abbreviations may be used herein: Ac (acetyl); AcCl (acetyl chloride); AcOH or HOAc (acetic acid); Ac$_2$O (acetic anhydride); aq. (aqueous); Boc or boc (tert-butoxycarbonyl); BOP ((benzotriazol-1-yloxy)tris(dimethylamino)phosphonium hexafluorophosphate); B$_2$pin$_2$ (bis(pinacolato)diboron); ca. (about or approximately); CDCl$_3$ (deuterated chloroform); CH$_2$Cl$_2$ and/or DCM (dichloromethane); DABCO (1,4-diazabicyclo[2,2,2]octane); DAST (Diethylaminosulfur trifluoride); DBU (1,8-diazabicyclo[5,4,0]undec-7-ene); DCE (dichloroethane); DEA (diethylamine); DIBAL or DIBAL-H (diisobutylaluminum hydride); DIC (diisopropylcarbodiimide); DIPEA or Hunig's base (N,N-diisopropylethylamine); DHP (dihydropyran); DMA (dimethylacetamide); DMF (dimethylformamide); DME (ethylene glycol); DMP (Dess-Martin Periodinane); DMAP (4-dimethylaminopyridine); DMSO (dimethylsulfoxide); DMSO-d$_6$ (deuterated dimethylsulfoxide); EDC or EDCI (1-ethyl-3-(3-dimethylaminopropyl)-carbodiimide); Et (ethyl); Et$_3$N or TEA (triethylamine); EtOH (ethanol); EtOAc (ethyl acetate); Et$_2$O (diethyl ether); g or gm (gram or grams); HATU (2-(7-aza-1H-benzotriazole-1-yl)-1,1,3,3-tetramethyluronium hexafluorophosphate); HBTU (o-(benzotriazole-1-yl)-1,1,3,3-tetramethyluronium hexafluorophosphate); HFIP (1,1,1,3,3,3-hexafluoro-2-propanol); HMPT (Tris(dimethylamino)phosphine); HPLC (high-performance liquid chromatography); HOBT (1-hydroxy benzotriazole); h or hr (hour or hours, as appropriate); iBu (isobutyl); IPA (iso-propyl alcohol); iPr (isopropyl); iPrOAc (isopropyl acetate); KHMDS (potassium bis(trimethylsilyl)amide); KOAc (potassium acetate); LAH (lithium aluminum hydride); LCMS (liquid chromatography-mass spectrometry); LDA (lithium diisopropylamide); LiHMDS (lithium bis(trimethylsilyl)amide); mCPBA (meta-chloroperoxybenzoic acid); Me (methyl); MeOH (methanol); MeOD (deuterated methanol); MeCN (acetonitrile); m or min (minute or minutes, as appropriate); mg (milligram or milligrams); Ms (methylsulfonyl); MsCl (methanesulfonyl chloride); N (normal); NBS (N-Bromosuccinimide); NCS (N-chlorosuccinimide); NFSI (N-Fluorodibenzenesulfonimide); NMR (nuclear magnetic resonance); nBu (n-butyl); nBuLi (n-butyl lithium); nPr (n-propyl); Pd/C (palladium on carbon); Pd$_2$(dba)$_3$ (tris(dibenzylideneacetone)dipalladium (0)); Pd(dppf)Cl$_2$ ([1,1'-bis(diphenylphosphino)ferrocene] dichloropalladium(II)); Pd[P(o-tol)$_3$]$_2$ (bis[tris(2-methylphenyl)phosphine]palladium); Ph (phenyl); PTSA or pTSA (p-Toluene sulfonic acid); PPTS: (pyridium p-toluenesulfonate); Rt (retention time); rt (room temperature); RuCl(p-cymene)[(R,R)-Ts-DPEN] ([N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium); s or sec (second or seconds, as appropriate); Selectfluor (N-Chloromethyl-N'-fluorotriethylenediammonium bis(tetrafluoroborate)); SEM (2-Trimethylsilylethoxymethoxy); SFC (supercritical fluid chromatography); Si-Thiol (silica 1-propanethiol); SK-CCO2-A (2-(dimethylaminomethyl)ferrocene-1-yl-palladium(II) chloride dinorbornylphosphine); T3P (propylphosphonic anhydride); TBAF (tetrabutyl ammonium fluoride); TBDM-SCl (t-butyl-dimethylsilyl chloride); TBME or MTBE (tert-butyl methyl ether); t-BuOH (2-methyl-2-propanol, tert-butanol or tert-butyl alcohol); tBu-Xphos (2-di-tert-butylphosphino-2',4',6'-triisopropylbiphenyl); TDA-1 (Tris [2-(2-methoxyethoxy)ethyl]amine or Tris(3,6-dioxaheptyl)amine); TEA, NEt₃ or Et₃N (triethylamine); TFA (trifluoroacetic acid); THF (tetrahydrofuran); THP (tetrahydropyran); TLC (thin layer chromatography); TMS (trimethylsilyl); TMSCl (trimethylsilyl chloride); TMSCF₃ (Trimethyl(trifluoromethyl)silane); Tos or tosyl (4-toluenesulfonyl); TOS-MIC (p-Toluenesulfonylmethyl isocyanide); UV (ultraviolet).

EXAMPLES

All of the reactions herein and the preparations of novel starting materials used herein are conventional and appropriate reagents and reaction conditions for their performance or preparation as well as procedures for isolating the desired products will be well-known to those skilled in the art with reference to literature precedents and the examples and preparations hereto.

General Synthetic Schemes

In a general synthetic process, compounds of the general structure represented by compound IX are prepared according to Method A:

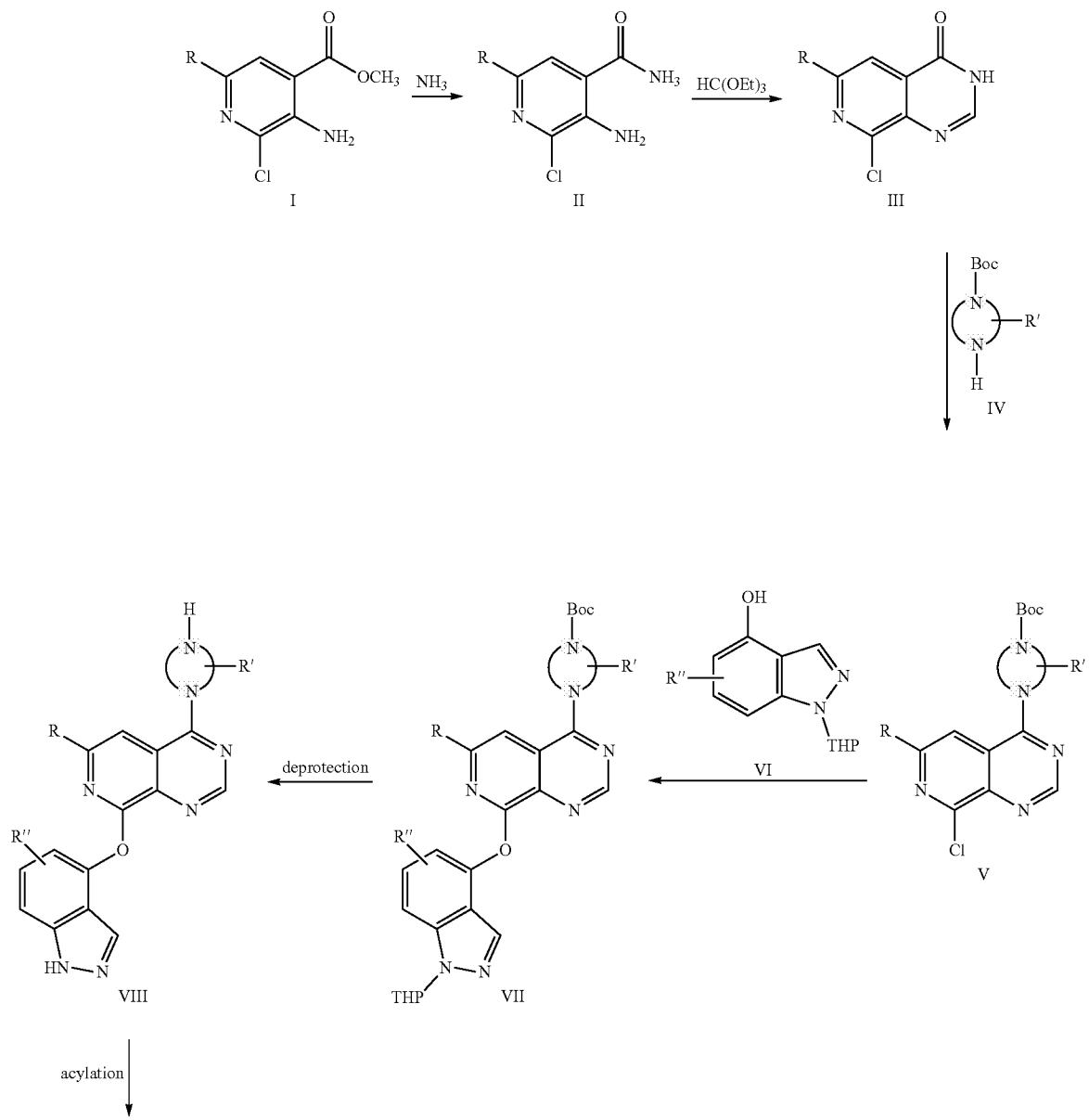

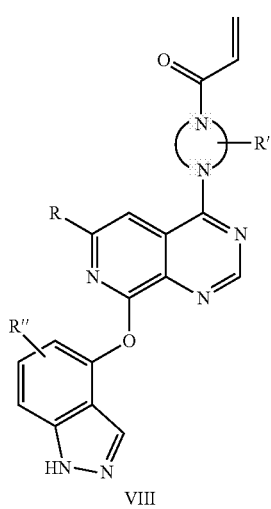

VIII

Compound I may be converted to the primary amide using ammonia in methanol and condensed with triethyl orthoformate to provide compound III. Compound III may be converted to compound V using amine IV in the presence of BOP reagent and DBU, or using POCl₃ instead of BOP reagent and DBU. Nucleophilic aromatic substitution of compound V may be accomplished using a competent nucleophile such as compound VI, in the presence of a base, such as $Cs_2CO_3$ and a solvent, such as DMA or DMSO to provide compound VII. Additives such as KF may be used if compound VI is a weak nucleophile. The protecting groups may be removed using an acid, such as TFA, followed by acylation with an acid chloride under Schotten-Baumann conditions to provide compound IX. R, R', and R" are as defined in the embodiments, schemes, examples and claims provided herein.

In a general synthetic process, compounds of the general structure represented by compound XIX and XX are prepared according to Method B:

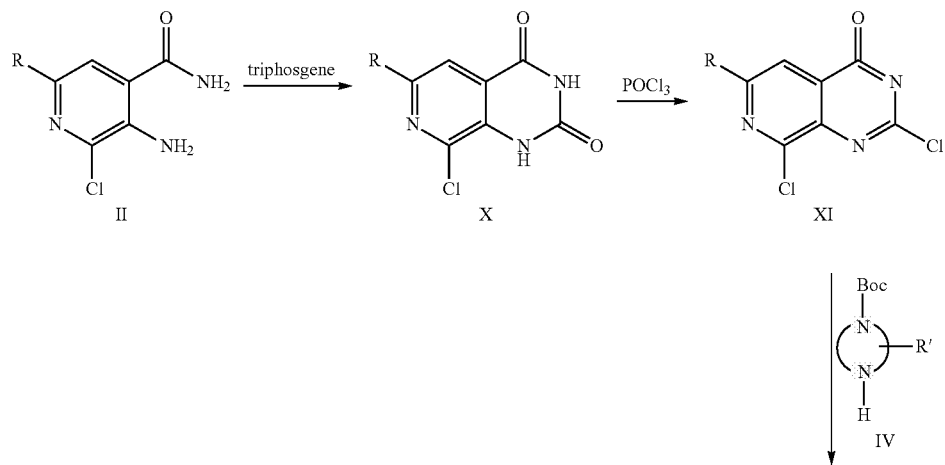

-continued

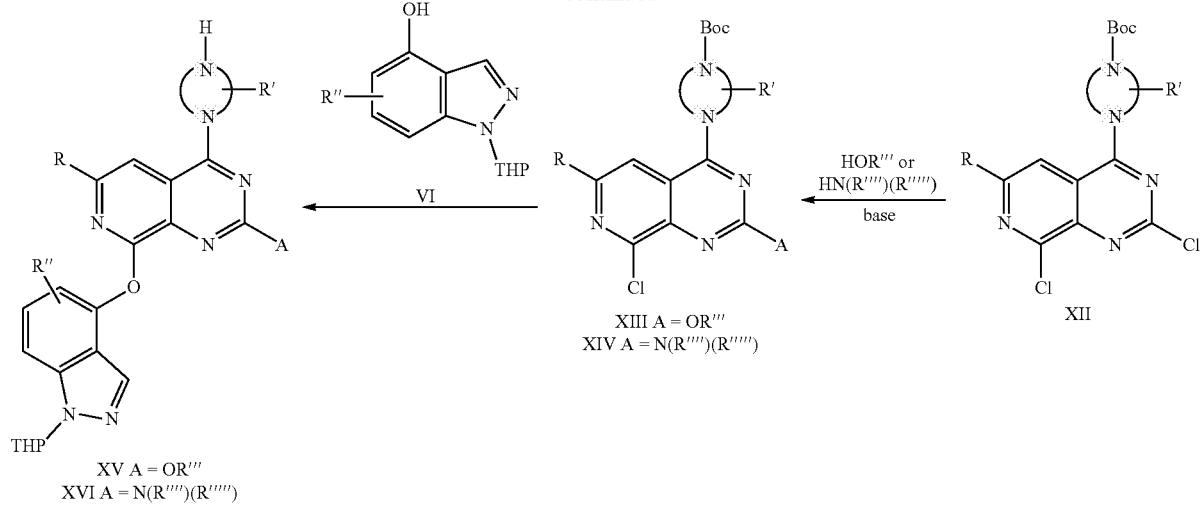

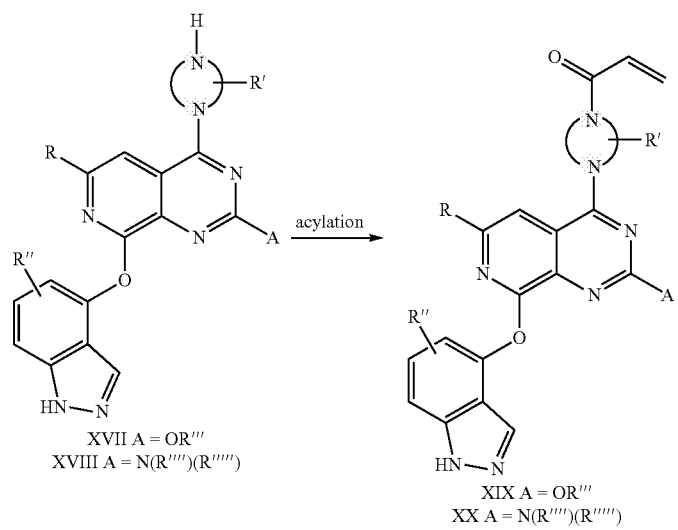

A primary amide II may be converted to a dione X using triphosgene. The dione X may be converted to a dichloride using POCl₃ and sequentially converted to the compound XII using amine IV under basic conditions. Compound XI may be converted to compound XIII or XIV using an oxygen or nitrogen nucleophile under basic conditions. Compound XIII or XIV may be converted to compound XV or XVI using a nucleophile VI under basic conditions. The protecting groups may then be removed using an acid, such as TFA, to give compound XVII or XVIII, followed by acylation with an acid chloride under Schotten-Baumann conditions to provide compound XIX or XX. R, R', and R'', R''', R'''', and R''''' are as defined in the embodiments, schemes, examples and claims provided herein.

In a general synthetic process, compounds of the general structure represented by compounds XXXIII and XXXIV are prepared according to Method C:

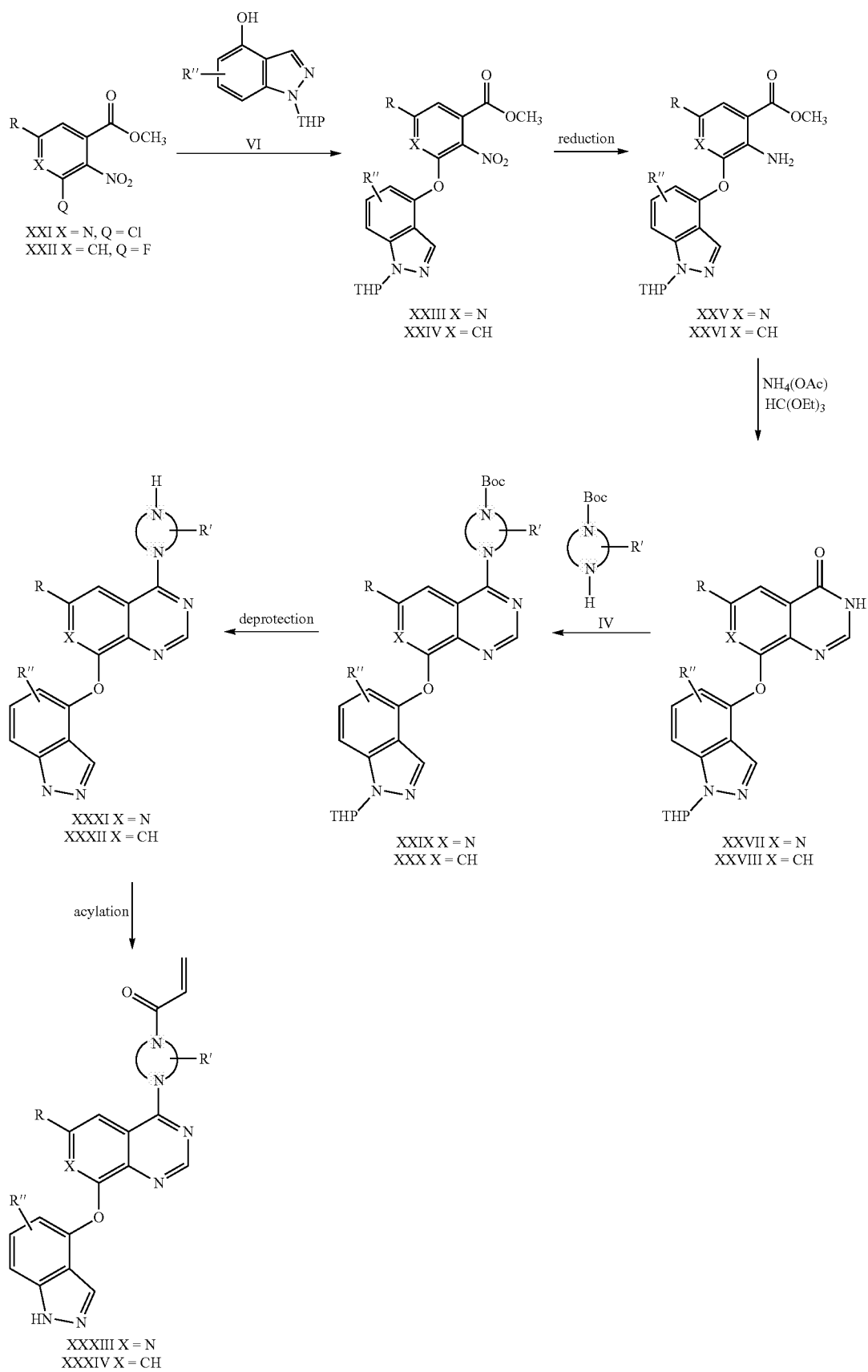

Compounds XXI or XXII may be converted to compound XXIII or XXIV using nucleophile VI under basic conditions. The nitro group may be reduced to provide compound XXV or XXVI, respectively. The compounds XXV and XXVI may be converted to the primary amide and condensed with triethyl orthoformate to give compound XXVII or XXVIII. Compound XXVII or XXVIII may be converted to compound XXIX or XXX using amine IV in the presence of BOP and DBU. The protecting groups may by removed using an acid, such as TFA, to give compound XXXI or XXXII, followed by acylation with an acid chloride under Schotten-Baumann conditions to provide compound XXXIII or XXXIV. R, R', and R", R'", R"", and R""' are as defined in the embodiments, schemes, examples and claims provided herein.

In a general synthetic process, compounds of the general structure represented by compounds LIII and LIV are prepared according to Method D:

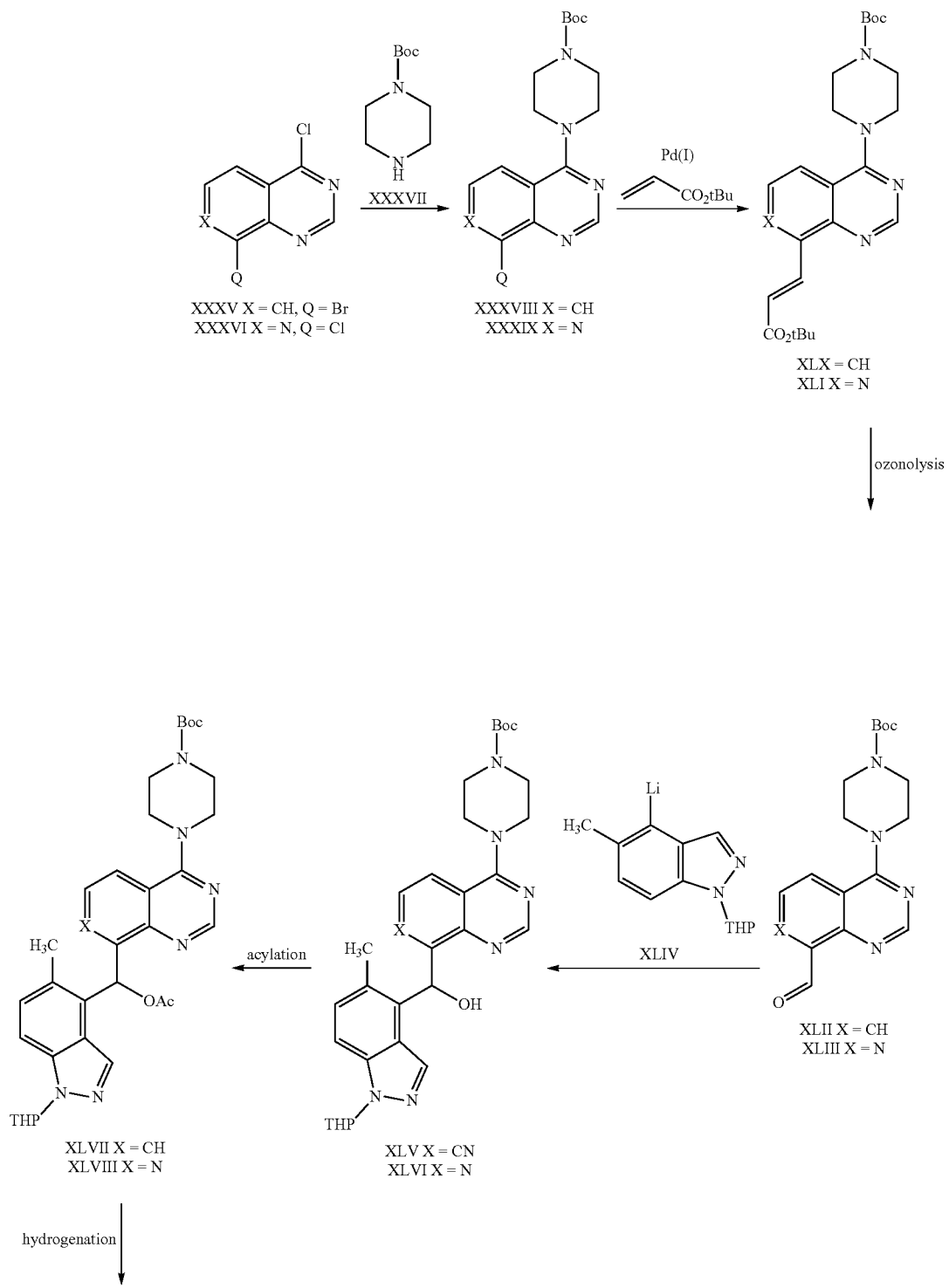

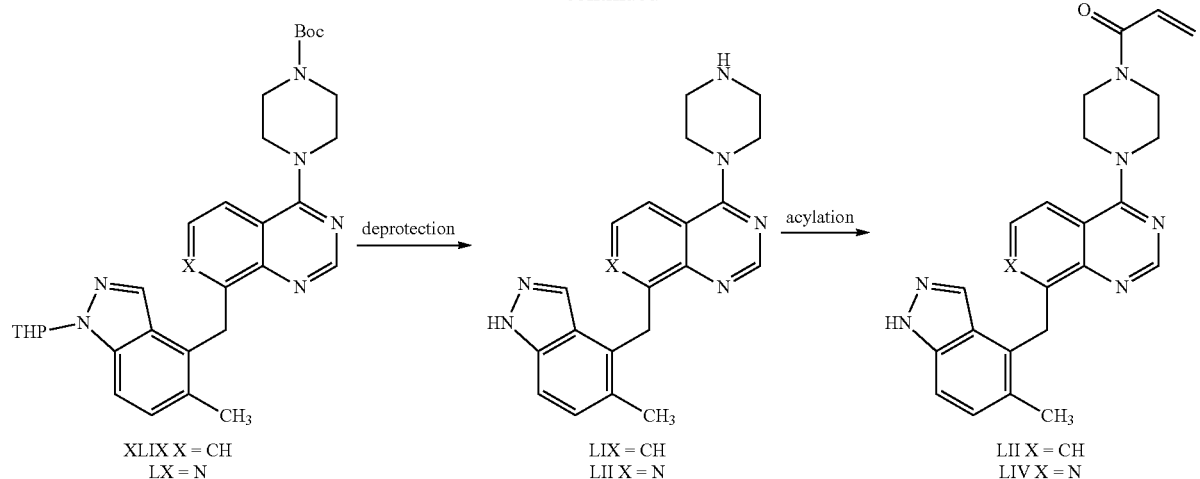

XLIX X = CH
L X = N

LI X = CH
LII X = N

LIII X = CH
LIV X = N

Compounds XXXV or XXXVI may be converted to compound XXXVIII or XXXIX using amine XXXVII under basic conditions. Compound XXXVIII or XXXIX may be converted to alkene XL or XLI using t-butyl acrylate, and a palladium catalyst, under basic conditions. Compound XL or XLI may be converted to aldehyde XLI or XLII using ozone. Addition of the aryl lithium species XLIV to aldehyde XLII or XLIII provides the secondary alcohol XLV or XLVI. Compound XLV or XLVI may be converted to compound XLVII or XLVIII using acetic anhydride in pyridine. Hydrogenolysis of compound XLVII or XLVIII using a Pd catalyst under a hydrogen atmosphere provides compound XLIX or L. The protecting groups may by removed using an acid, such as TFA, to give compound LI or LII, followed by acylation with an acid chloride under Schotten-Baumann conditions to provide compound LIII or LIV.

In a general synthetic process, compounds of the general structure represented by compounds XIX, XX, LXVII, and LXVIII are prepared according to Method E:

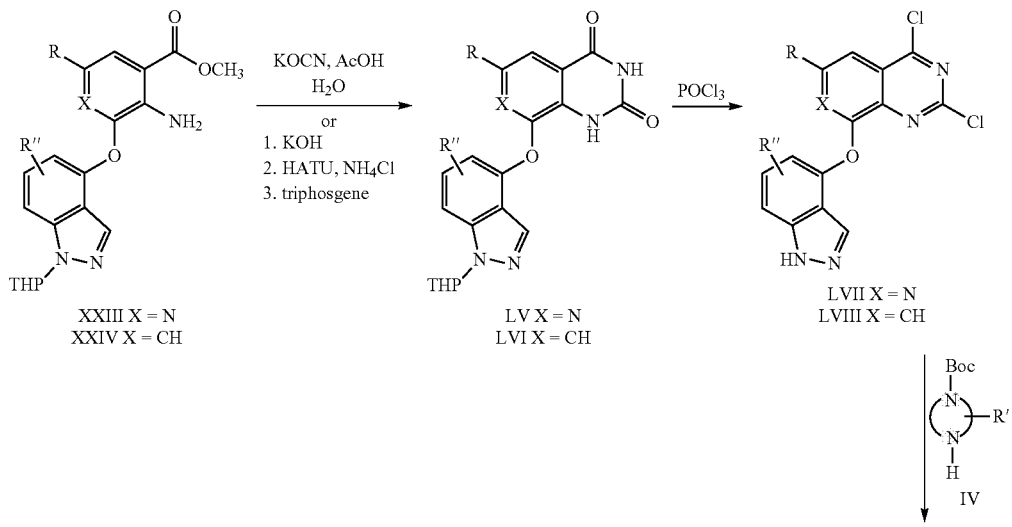

XXIII X = N
XXIV X = CH

LV X = N
LVI X = CH

LVII X = N
LVIII X = CH

IV

-continued

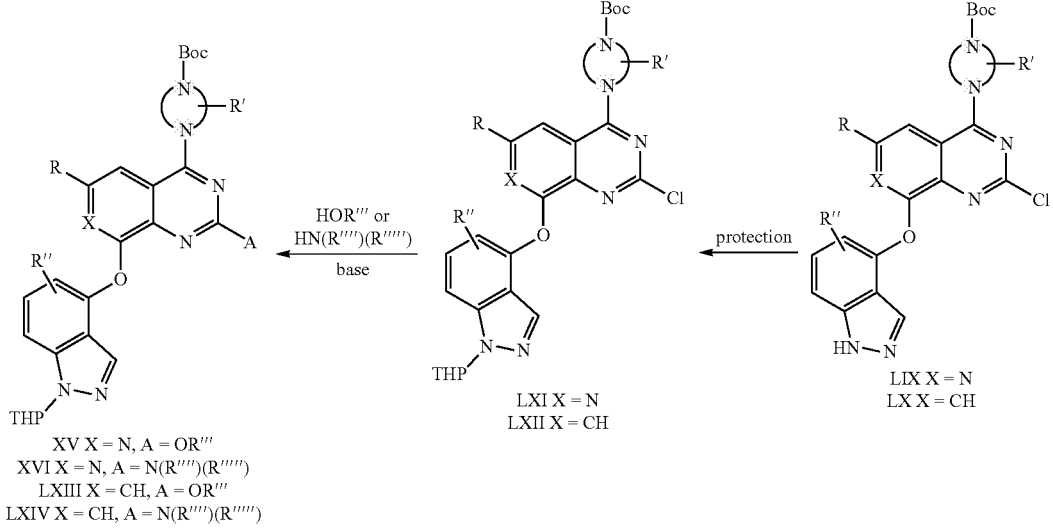

XV X = N, A = OR'''
XVI X = N, A = N(R'''')(R''''')
LXIII X = CH, A = OR'''
LXIV X = CH, A = N(R'''')(R''''')

LXI X = N
LXII X = CH

LIX X = N
LX X = CH deprotection ↓

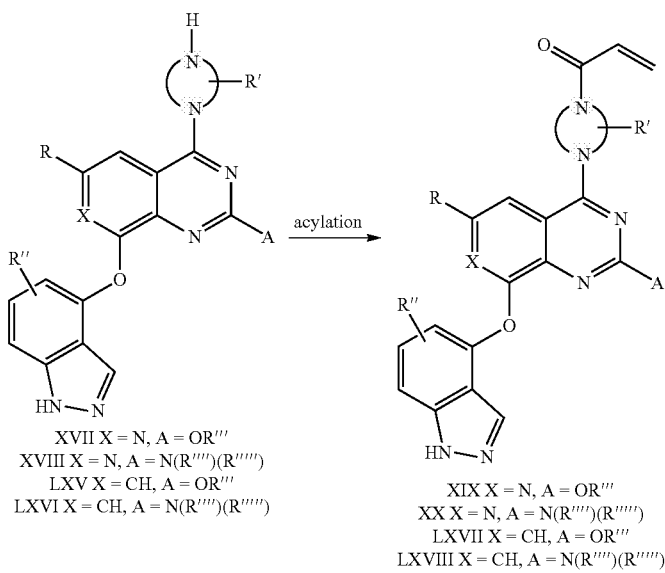

XVII X = N, A = OR'''
XVIII X = N, A = N(R'''')(R''''')
LXV X = CH, A = OR'''
LXVI X = CH, A = N(R'''')(R''''')

XIX X = N, A = OR'''
XX X = N, A = N(R'''')(R''''')
LXVII X = CH, A = OR'''
LXVIII X = CH, A = N(R'''')(R''''')

Compound XXIII or XXIV may be converted to compound LV or LVI using potassium cyanate in the presence of acetic acid. Alternatively, the ester may be hydrolyzed using KOH in methanol, and the resultant carboxylic acid converted to the primary amide using HATU and ammonium chloride, followed by cyclization using triphosgene to give compound LV or LVI. The dione LV or LVI may be converted to the dichloride LVII or LVIII using POCl₃. The aryl chloride LVII or LVIII may be substituted with an amine IV in the presence of DIEA to give compound LIX or LX. Nucleophilic aromatic substitution using a nitrogen or oxygen nucleophile in the presence of KF and DIEA, in a polar solvent such as DMSO, may provide compounds XV, XVI, LXIII, or LXIV. The protecting groups may be removed under acidic conditions and the resultant amine may be converted to compounds XIX, XX, LXVII, or LXVIII using an acid chloride under basic conditions. R, R', and R", R''', R'''', and R''''' are as defined in the embodiments, schemes, examples and claims provided herein.

In a general synthetic process, compounds of the general structure represented by compounds LXXVIII and LXXIX are prepared according to Method G

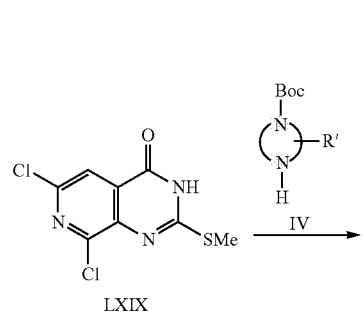
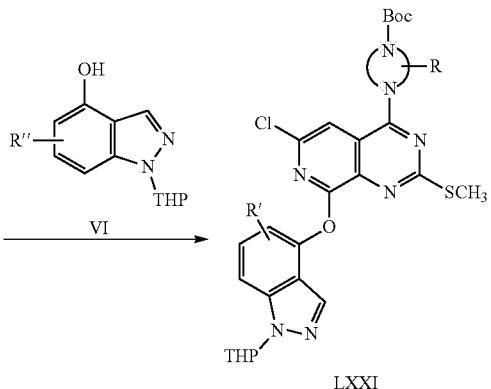
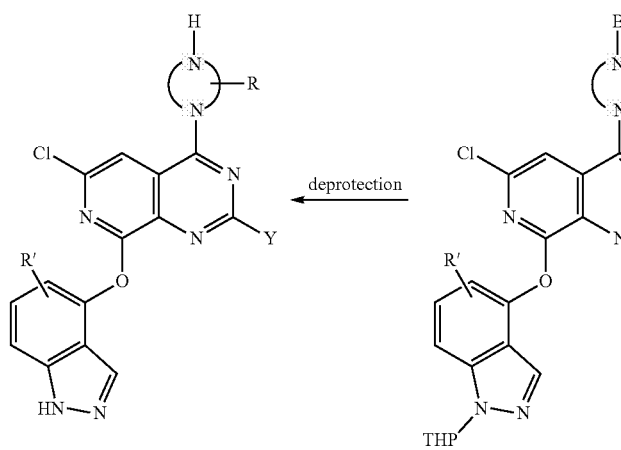
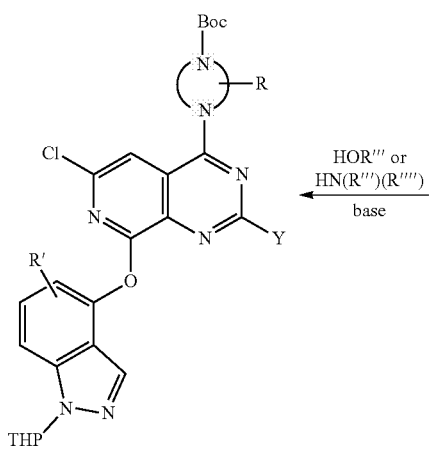
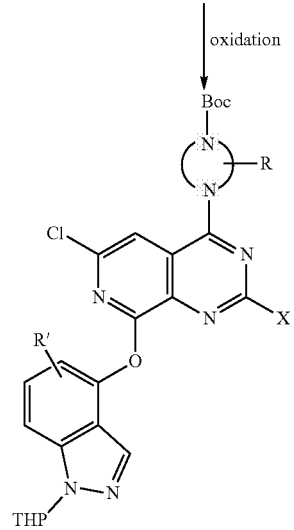
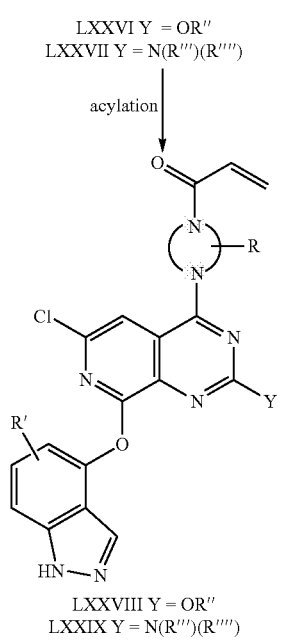

Compound LXIX may be converted to compound LXX in the presence of BOP reagent and DBU, or using POCl$_3$ instead of BOP reagent and DBU. Nucleophilic aromatic substitution with a compound such as VI can be accomplished in the presence of a base such as Cs$_2$CO$_3$ and a solvent such as DMA to provide a compound such as LXXI. Compound LXXI can be oxidized to the corresponding sulfone LXXII or sulfoxide LXXIII using m-CPBA in a solvent such as DCM. Nucleophic aromatic substitution with an alcohol can be accomplished in the presence of a base such as LHMDS in an appropriate solvent such as THF to provide compound LXXIV. The protecting groups may be removed under acidic conditions and the resultant amine may be converted to compound LXXVIII using an acid chloride under basic conditions. Alternatively nucleophic aromatic substitution of sulfone LXXII or sulfoxide LXXIII with an amine can be achieved in the presence of a base such as DIPEA in a solvent such as tBuOH. The protecting groups may be removed under acidic conditions and the resultant amine may be converted to compound LXXIX in the presence of an acid chloride under basic conditions. R, R', and R", R''', R'''', and R''''' are as defined in the embodiments, schemes, examples and claims provided herein.

In a general synthetic process, compounds of the general structure represented by compounds LXXXIV and LXXX are prepared according to Method H:

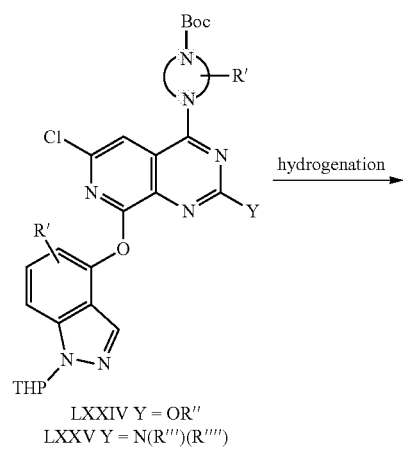

LXXIV Y = OR"
LXXV Y = N(R''')(R'''')

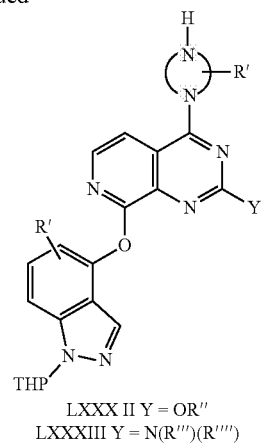

LXXXII Y = OR"
LXXXIII Y = N(R''')(R'''')

| acylation

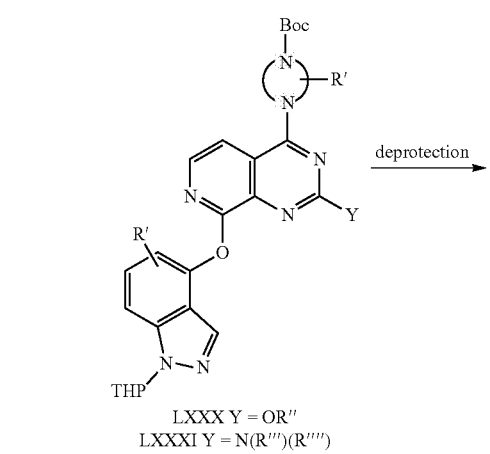

LXXX Y = OR"
LXXXI Y = N(R''')(R'''')

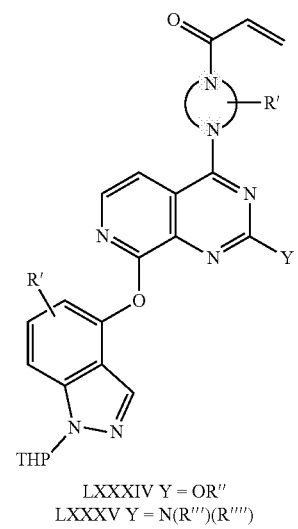

LXXXIV Y = OR"
LXXXV Y = N(R''')(R'''')

Compounds LXXIV and LXXV can be reduced in the presence of a catalyst such as palladium on carbon under an atmosphere of hydrogen to provide compounds LXXX and LXXXI, respectively. Compounds LXXX and LXXXI can be deprotected under acidic conditions and the resultant amines can be converted to the corresponding acrylamides LXXXIV and LXXXV in the presence of an acid chloride under basic conditions. R, R', and R", R''', R'''', and R''''' are as defined in the embodiments, schemes, examples and claims provided herein.

In a general synthetic process, compounds of the general structure represented by compound (VII) are prepared according to Method I:

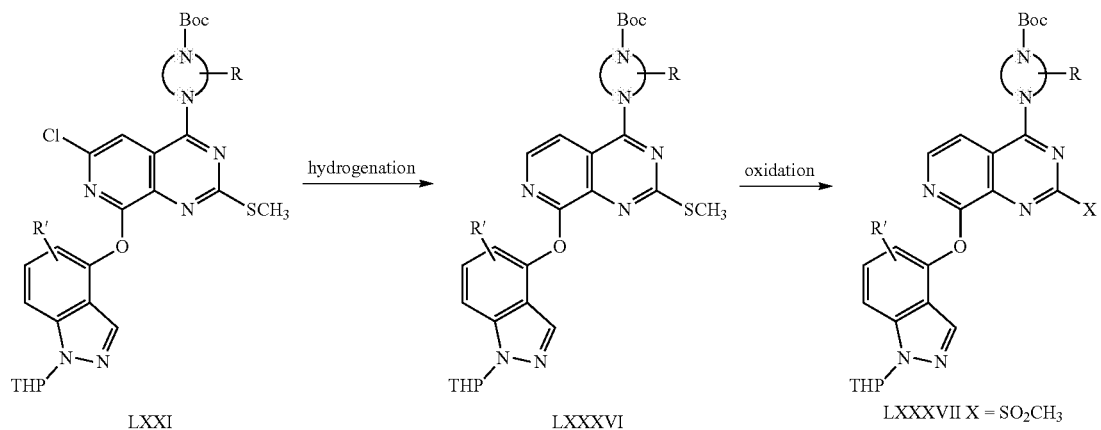

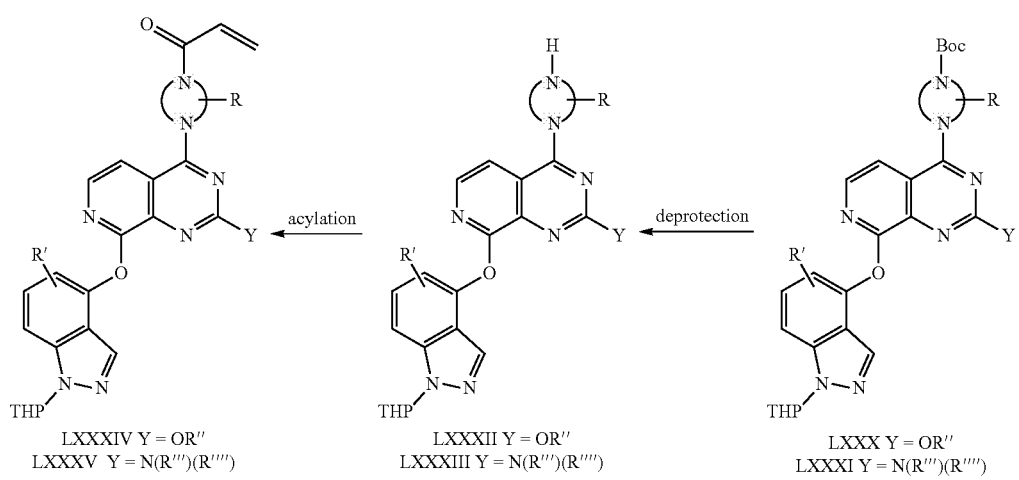

Compound LXXI can be hydrogenated in the presence of a catalyst such as PdCl(dppf) and a reductant such as NaBH4 to provide compound LXXXVI. Compound LXXXVI can be oxidized to a sulfone such as LXXXVII or a sulfoxide such as LXXXVIII in the presence of an oxidant such as m-CPBA in a solvent such as DCM. Nucleophic aromatic substitution of sulfone LXXXVII or sulfoxide LXXXVIII with an alcohol can be accomplished in the presence of an appropriate base such as LHMDS in a solvent such as THF to provide compound LXXX. The protecting groups may be removed under acidic conditions and the resultant amine may be converted to compound LXXXIV using an acid chloride under basic conditions. Alternatively nucleophic aromatic substitution of sulfone LXXXVII or sulfoxide LXXXVIII with an amine can be achieved in the presence of a base such as DIPEA in a solvent such as tBuOH to provide compound LXXXI. The protecting groups may be removed under acidic conditions and the resultant amine may be converted to compound LXXXV under in the presence of an acid chloride under basic conditions. R, R', and R'', R''', R'''', and R''''' are as defined in the embodiments, schemes, examples and claims provided herein.

In a general synthetic process, compounds of the general structure represented by compound (XCIII) are prepared according to Method K:

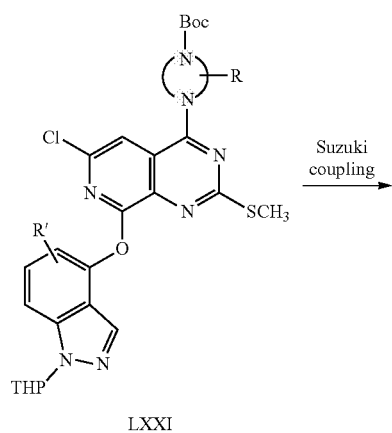
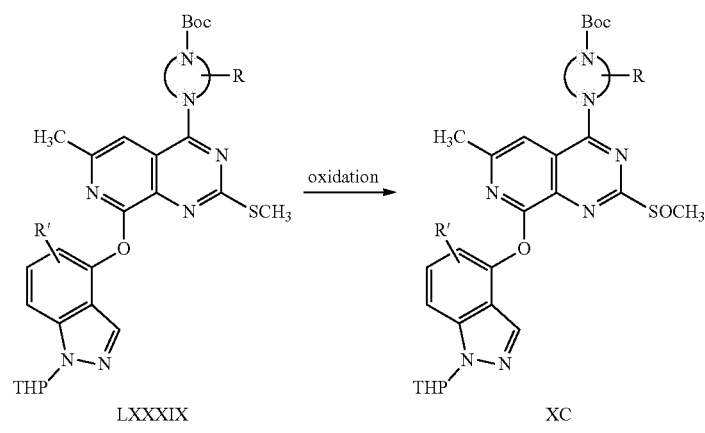

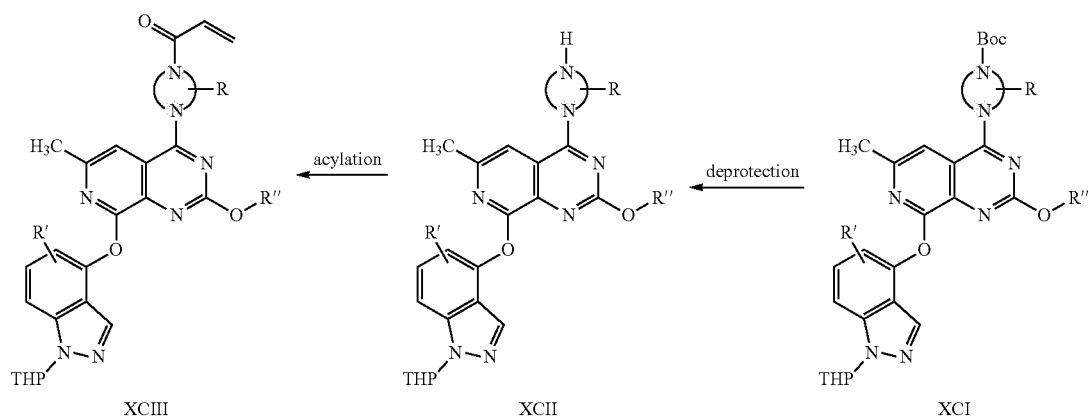

A compound such as LXXI can be converted to compound such as LXXXIX under standard Suzuki coupling conditions. A compound such as LXXXIX can be oxidized to a sulfoxide such as XC with an oxidant such as m-CPBA in a solvent such as DCM. Compound XC can be converted into compound XCI via nucleophilic aromatic substitution with an alcohol in the presence of an appropriate base such as LHMDS in a solvent such as THF. The protecting groups can be removed under acidic conditions and the amine may be converted to compound XCIII in the presence of an acid chloride under basic conditions. R, R', and R", R''' are as defined in the embodiments, schemes, examples and claims provided herein.

In a general synthetic process, compounds of the general structure represented by compound (LXVI) are prepared according to Method L:

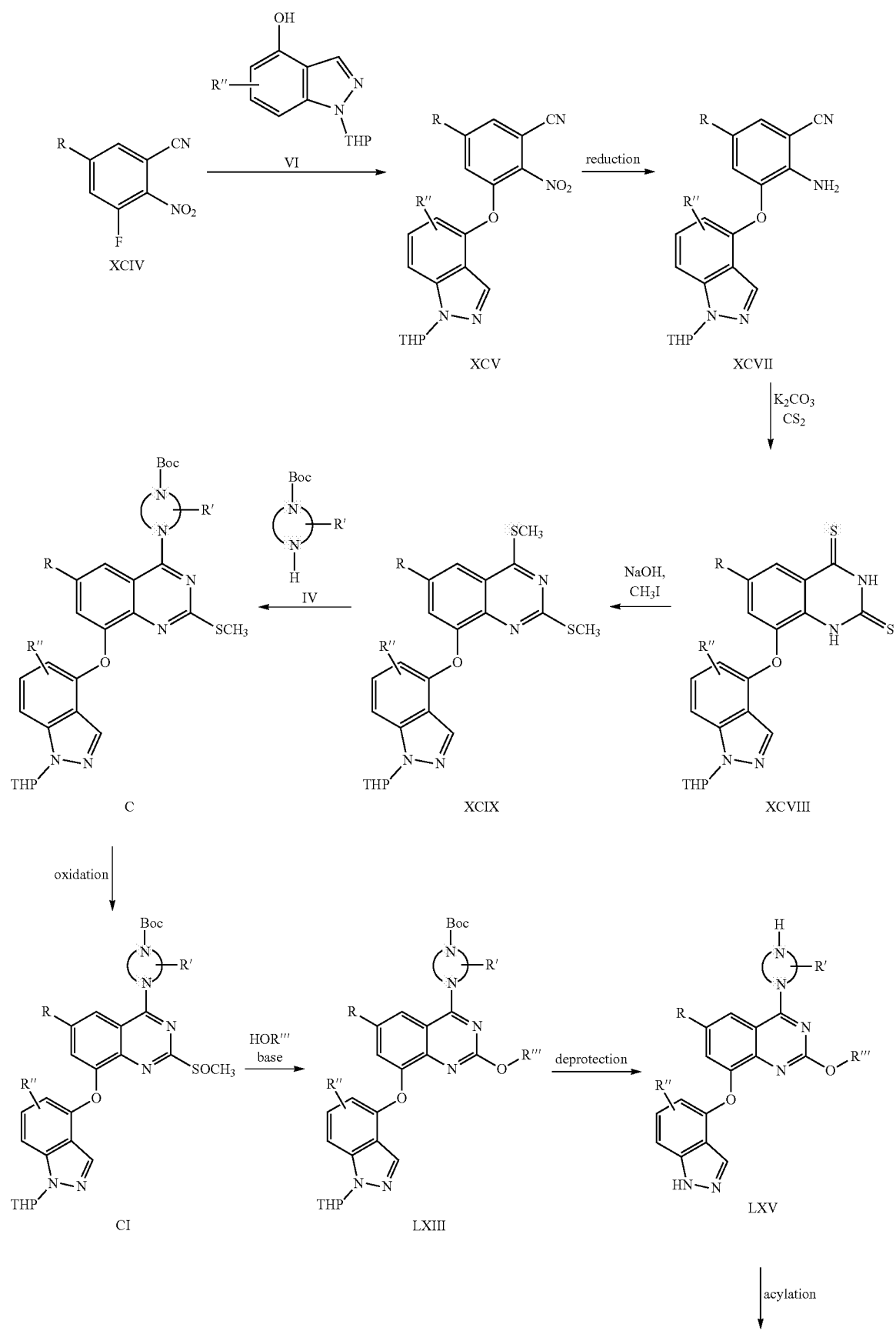

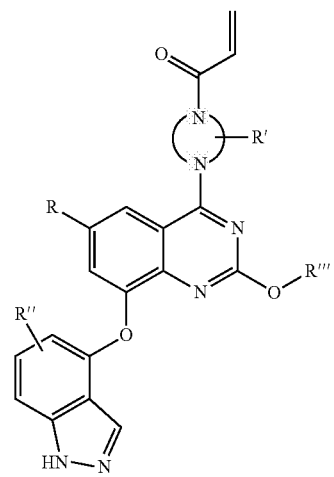

LXVI

Compounds XCIV be converted to compound XCV using nucleophile VI under basic conditions. The nitro group may be reduced to provide compound XCVI. The compounds XCVI may be converted to dithione XCVIII with $CS_2$ in the presence of a base such as $K_2CO_3$. Dithione XCVIII may be alkylated with methy iodide in the presence of a base such as NaOH. Nucleophilic aromatic substitution with an amine such as IV can be achieved at elevated temperatures in the presence of a base such as $K_2CO_3$ in a solvent such as DMA to provide compound C. A compound such as C can be oxidized to a sulfoxide such as CI with an oxidant such as m-CPBA in a solvent such as DCM. Compound CI can be converted into compound LXIII via nucleophilic aromatic substitution with an alcohol in the presence of an appropriate base such as LHMDS in a solvent such as THF. The protecting groups can be removed and the amine may be converted to compound LXVI in the presence of an acid chloride under basic conditions. R, R', and R", R''' are as defined in the embodiments, schemes, examples and claims provided herein.

Preparation of Key Synthetic Intermediates:

Preparation of tert-butyl 4-(8-chloropyrido[3,4-d]pyrimidin-4-yl)piperazine-1-carboxylate (4)

Step 1:

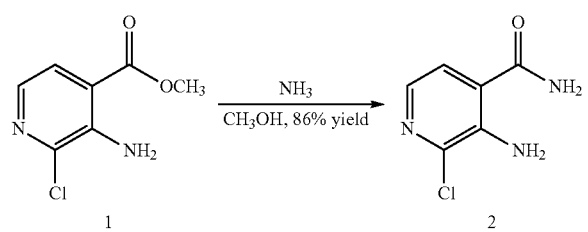

A mixture of methyl 3-amino-2-chloroisonicotinate (1) (180 g, 0.96 mol) and methanol (1.2 L) in an autoclave was purged with ammonia gas until saturation. The mixture was stirred at 30° C. for 48 hours. An aliquot of the crude reaction mixture was analyzed by LC-MS and showed that the reaction was finished. The mixture was concentrated and gave the give crude product which was triturated with EtOAc (200 mL), filtered, and the cake was collected and dried in a vacuum to afford 3-amino-2-chloropyridine-4-carboxamide (2) as a white solid (142 g, 86% yield). $^1$H NMR (400 MHz, DMSO-$d_6$) δ 8.19 (s, 1H), 7.68 (s, 1H), 7.62 (d, J=5.0 Hz, 1H), 7.51 (d, J=5.0 Hz, 1H), 6.77 (s, 2H). LCMS (ESI) m/z 172, 174 (M+H).

Step 2:

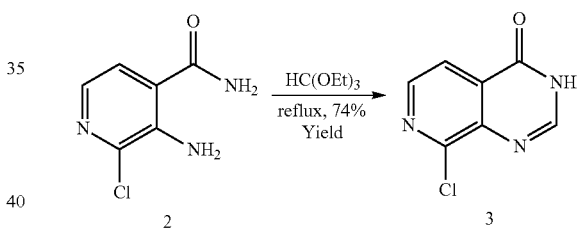

A mixture of 3-amino-2-chloroisonicotinamide (2) (140 g, 0.816 mol) in triethyl orthoformate (1.5 L) was heated at reflux for 16 h. The mixture was cooled to 25° C. and filtered. The cake was washed with EtOAc (2×100 mL), and dried which gave 8-chloropyrido[3,4-d]pyrimidin-4(3H)-one (3) as an off-white solid (110 g, 74% yield). $^1$H NMR (400 MHz, DMSO-$d_6$) δ 12.86 (s, 1H), 8.44 (d, J=5.1 Hz, 1H), 8.32 (s, 1H), 7.97 (d, J=5.1 Hz, 1H). LCMS (ESI) m/z 182, 184 (M+H).

Step 3

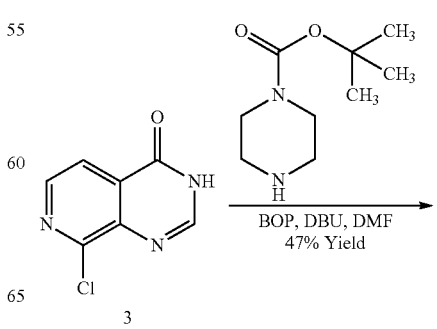

Step 2:

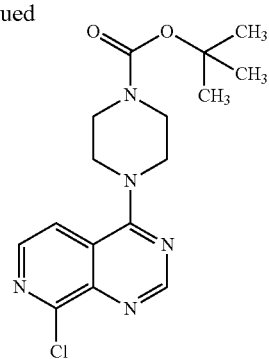
4

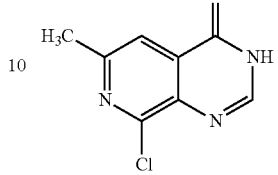

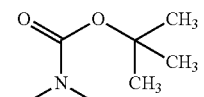
BOP, DBU, DMF
61% Yield

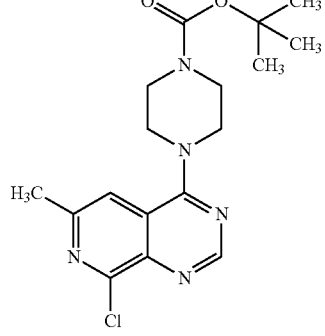
7

To a stirred suspension of 8-chloropyrido[3,4-d]pyrimidin-4(3H)-one (3) (110 g, 0.61 mol) in DMF (1.6 L) was added tert-butyl piperazine-1-carboxylate (135 g, 0.73 mol) and BOP (402 g, 0.91 mol), followed by DBU (184 g, 1.2 mol). The resulting solution was stirred at 25° C. for 6 hours. The crude reaction mixture was monitored by LCMS and showed most of the starting material was consumed. The mixture was diluted with ice water (7 L), and extracted with EtOAc (4×1.5 L). The combined organic layers were washed with water (3×3 L), brine (2 L), dried over $Na_2SO_4$, and concentrated which gave the crude product. The crude product was purified by silica gel chromatography and eluted with 5% methanol/DCM and gave tert-butyl 4-(8-chloropyrido[3,4-d]pyrimidin-4-yl)piperazine-1-carboxylate (4) as a light yellow solid (101 g, 47% yield). $^1$H NMR (400 MHz, $CDCl_3$) δ 8.89 (s, 1H), 8.34 (d, J=5.7 Hz, 1H), 7.58 (d, J=5.7 Hz, 1H), 4.13-3.79 (m, 4H), 3.66 (dd, J=6.2, 4.1 Hz, 4H), 1.50 (s, 9H). LCMS (ESI) m/z 350, 352 (M+H).

Preparation of tert-butyl 4-(8-chloro-6-methylpyrido[3,4-d]pyrimidin-4-yl)piperazine-1-carboxylate (7)

Step 1:

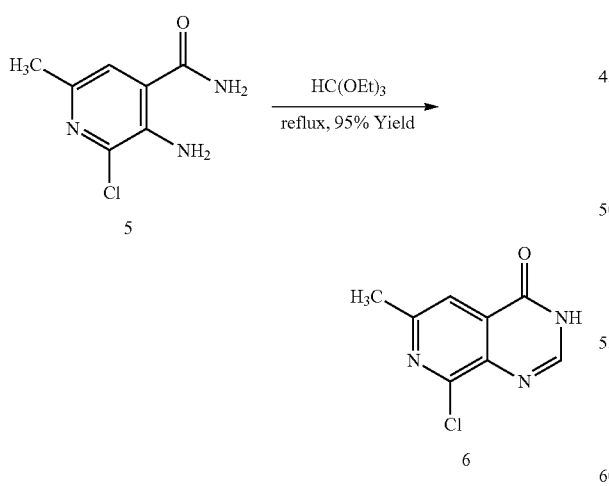

8-Chloro-6-methylpyrido[3,4-d]pyrimidin-4(3H)-one (6) (1.7 g, 95% yield) was prepared according to the procedure used to prepare 8-chloropyrido[3,4-d]pyrimidin-4(3H)-one (3). $^1$H NMR (400 MHz, DMSO-$d_6$) δ 12.73 (s, 1H), 8.24 (s, 1H), 7.83 (s, 3H), 2.57 (s, 3H). LCMS (ESI) m/z 196 (M+H).

Tert-butyl 4-(8-chloro-6-methylpyrido[3,4-d]pyrimidin-4-yl)piperazine-1-carboxylate (7) (1.7 g, 61% yield) was prepared according to the procedure used to prepare tert-butyl 4-(8-chloropyrido[3,4-d]pyrimidin-4-yl)piperazine-1-carboxylate (4). $^1$H NMR (400 MHz, DMSO-$d_6$) δ 8.84 (s, 1H), 7.40 (s, 1H), 3.90-3.77 (m, 4H), 3.65 (dd, J=6.2, 4.0 Hz, 4H), 2.68 (s, 3H), 1.50 (s, 9H). LCMS (ESI) m/z 364, 366 (M+H).

Preparation of 8-chloro-6-(trifluoromethyl)pyrido[3,4-d]pyrimidin-4(3H)-one (12)

Step 1:

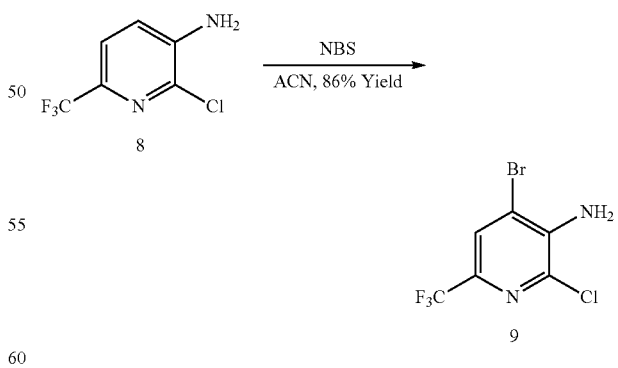

To a solution of 2-chloro-6-(trifluoromethyl)pyridin-3-amine (8) (5.0 g, 25 mmol) in acetonitrile (60 mL) was added NBS (5.0 g, 28 mmol). The mixture was stirred at reflux for 3 hours, concentrated and purified by silica gel chromatography and eluted with petroleum ether which gave 4-bromo-2-chloro-6-(trifluoromethyl)pyridin-3-amine (9) as a red semi-solid (6.0 g, 86% yield). ¹H NMR (400 MHz, CDCl₃) δ 7.68 (s, 1H), 4.93 (s, 2H). LCMS (ESI) m/z 275, 277 (M+H).

Step 2:

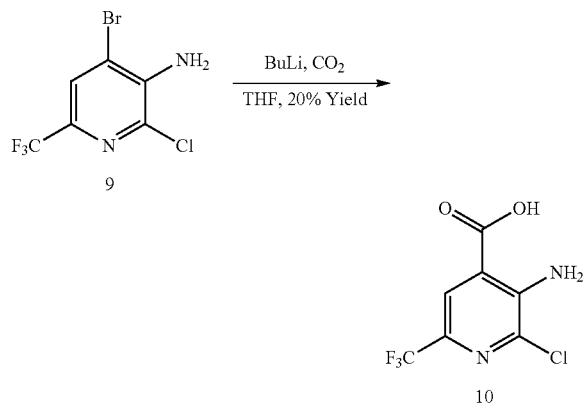

To a solution of 4-bromo-2-chloro-6-(trifluoromethyl)pyridin-3-amine (9) (17.7 g, 64.2 mmol) in THF (500 mL) was added BuLi (2.5 M in hexane, 116 mL, 289 mmol, 4.5 eq) at −78° C. under nitrogen. The resultant mixture was stirred at −75° C. for 30 minutes. Next, carbon dioxide gas was bubbled in the reaction mixture for 3 hours. The reaction was quenched with saturated NH₄Cl solution (100 mL), adjusted to pH 5 using 2 N HCl, and the aqeuous layer was extracted with EtOAc (3×200 mL). The combined EtOAc layers were washed with water (300 mL), dried over Na₂SO₄, filtered and concentrated which gave the crude product. A mixture of EtOAc and petroleum ether (petroleum ether:EtOAc=15:1, 20 mL) was added to the crude product and the mixture was allowed to stand overnight. A yellow solid was collected which gave 3-amino-2-chloro-6-(trifluoromethyl)pyridine-4-carboxylic acid (10) as a yellow solid (3.0 g, 20% yield). ¹H NMR (400 MHz, DMSO-d₆) δ 14.08 (s, 1H), 7.93 (s, 1H), 7.53 (s, 2H). LCMS (ESI) m/z 241, 243 (M+H).

Step 3:

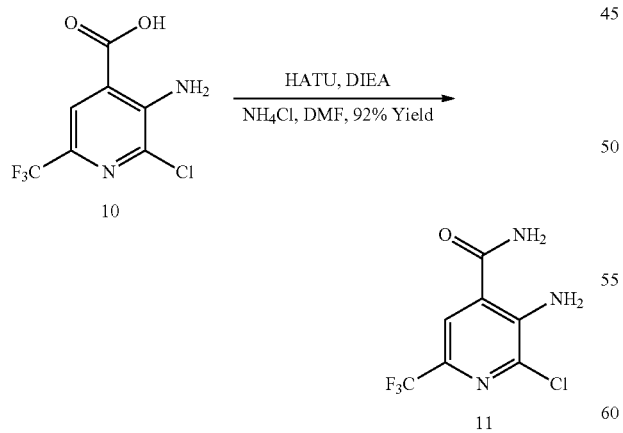

A mixture of 3-amino-2-chloro-6-(trifluoromethyl)pyridine-4-carboxylic acid (10) (2.5 g, 10 mmol), NH₄Cl (723 mg, 13.5 mmol), HATU (5.1 g, 13 mmol) and DIPEA (4.0 g, 31 mmol) in DMF (10 mL) was stirred at 25° C. under nitrogen for 3 hours. LCMS analysis showed the reaction was complete. The reaction was quenched with an aqueous LiCl solution, and extracted with EtOAc (2×100 mL). The combined EtOAc layers were washed with brine (20 mL), dried over Na₂SO₄, concentrated and purified by flash chromatography (EtOAc in petroleum ether) which gave 3-amino-2-chloro-6-(trifluoromethyl)pyridine-4-carboxamide (11) as a yellow solid (2.3 g, 92% yield). ¹H NMR (400 MHz, DMSO-d₆) δ 8.41 (s, 1H), 8.05 (s, 1H), 7.84 (s, 1H), 7.55 (s, 2H). LCMS (ESI) m/z 240, 242 (M+H).

Step 4:

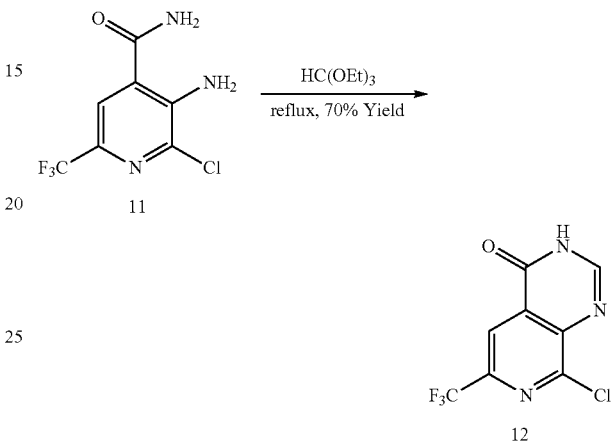

8-Chloro-6-(trifluoromethyl)pyrido[3,4-d]pyrimidin-4(3H)-one (12) (1.8 g, 70% yield) was prepared according to the procedure used to prepare 8-chloropyrido[3,4-d]pyrimidin-4(3H)-one (3). ¹H NMR (400 MHz, CDCl₃) δ 8.41 (s, 1H), 8.29 (s, 1H). LCMS (ESI) m/z 250, 252 (M+H).

Preparation of tert-butyl 4-(6,8-dichloropyrido[3,4-d]pyrimidin-4-yl)piperazine-1-carboxylate (16)

Step 1:

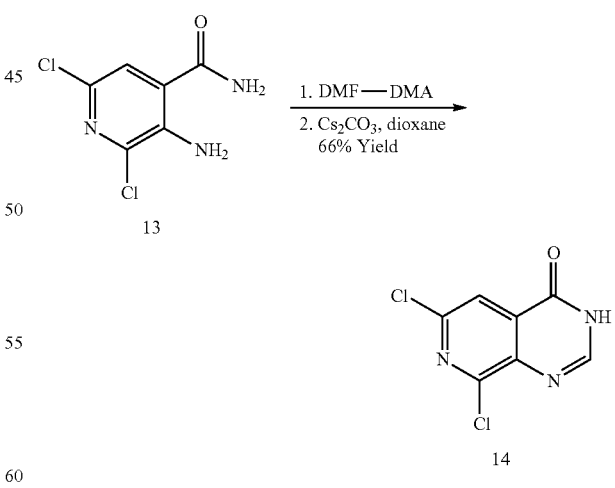

In a sealed tube, 3-amino-2, 6-dichloropyridine-4-carboxamide (13) (5 g, 0.024 mol) was added N, N-dimethylformamide dimethyl acetal (3.5 g, 0.03 mole) and the reaction mixture was heated at 100° C. for 15 minutes. LCMS and ¹H NMR showed that the starting material was consumed and 3-amino-2,6-dichloro-N-((dimethylamino)methylene)isonicotinamide was formed. To the crude reaction mixture was added 1,4-dioxane (30 mL) followed by the addition of cesium carbonate (15.8 g, 0.05 mol). The resultant reaction mixture was heated at 100° C. for 4 hours. TLC (40% EtOAc/hexane) and ¹H NMR showed that the reaction was done. The reaction mixture was concentrated under reduced pressure. The residue was diluted with ice cold water (15 mL) and acidified with 1 N HCl (pH=2-3). The solid obtained was filtered using a Buchner funnel and dried in a vacuum oven at 60° C. for 4 hours. The light yellow solid obtained was triturated with THF (30 mL), filtered under vacuum and dried in vacuum oven at 60° C. and gave 6,8-dichloropyrido[3,4-d]pyrimidin-4-ol (14) as light yellow solid (3.5 g, 66% yield). ¹H NMR (400 MHz, DMSO-d₆) δ 12.96 (s, 1H), 8.32 (s, 1H), 7.99 (s, 1H). LCMS (ESI) m/z 216 (M+H).

Step 2:

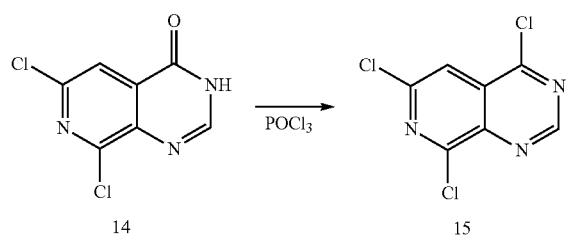

To 6, 8-dichloropyrido[3,4-d]pyrimidin-4-ol (14) (1.0 g, 4.0 mmol) was added POCl₃ (13 mL). The mixture was placed in an oil bath at 105° C. which eventually gave a brown solution upon stirring overnight. LCMS gave the product as the methyl ether (the LCMS solvent matrix was methanol). The crude reaction mixture was cooled to room temperature and the solvent was removed under reduced pressure. Toluene was added (10 mL) and the solvent was removed under reduced pressure. The process was repeated which gave 4,6,8-trichloropyrido[3,4-d]pyrimidine (15) as a black solid which was immediately used in the next step.

Step 3:

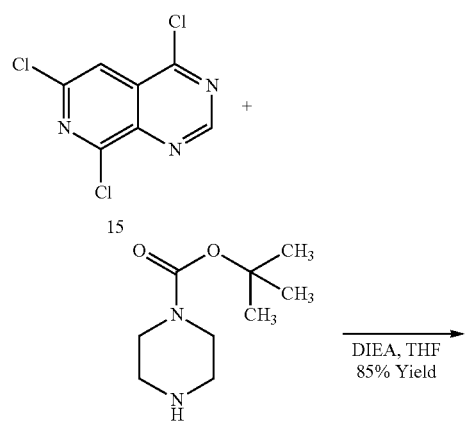

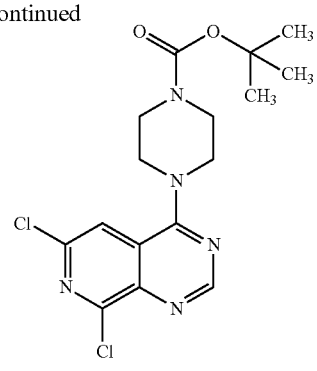

16

4,6,8-Trichloropyrido[3,4-d]pyrimidine (15) (1.1 g, 4.0 mmol) was dissolved in THF (13 mL) and sequentially treated with tert-butyl piperazine-1-carboxylate (1.6 g, 8.7 mmol) and DIEA (3.5 mL, 20 mmol). The resultant brown solution was stirred overnight at room temperature. LCMS gave only product. The reaction was added to 200 mL H₂O and extracted with EtOAc (2×150 mL). The combined organic extracts were washed with 10% NH₄Cl (200 mL), brine, dried over MgSO₄, filtered and concentrated which gave a brown oil. TLC (50% EtOAc/heptane) R_f 0.7. The crude product was dissolved in DCM and loaded onto a 25 g silica column (Biotage) and eluted with 10-50% EtOAc/heptane. The R_f 0.7 spot was isolated and gave tert-butyl 4-(6,8-dichloropyrido[3,4-d]pyrimidin-4-yl)piperazine-1-carboxylate (16) as a yellow solid (1.3 g, 85% yield). ¹H NMR (400 MHz, DMSO-d₆) δ 1.43 (s, 9H), 3.54 (br. s, 4H), 3.81-3.98 (m, 4H), 7.98 (s, 1H), 8.74 (s, 1H). LCMS (ESI) m/z 384 (M+H).

Preparation of tert-butyl 4-(2,8-dichloropyrido[3,4-d]pyrimidin-4-yl)piperazine-1-carboxylate (20)

Step 1:

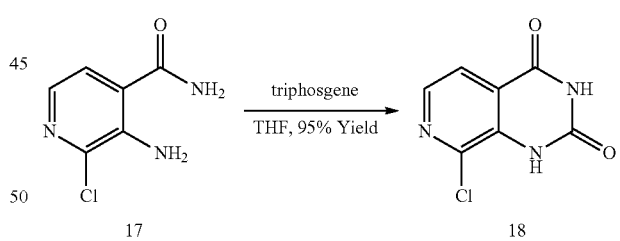

To a 2 L flask charged with a magnetic stir bar was added 3-amino-2-chloroisonicotinamide (17) (50 g, 292 mmol), THF (1 L) and triphosgene (43 g, 146 mmol). A reflux condenser was placed on the flask and the reaction was heated at 70° C. for 4 hours. A white precipitate formed. The reaction was cooled to room temperature and the THF was removed under reduced pressure. Ethyl acetate (1 L) was added and the precipitate was collected by filtration to provide a thick white solid. The filter cake was washed with hot EtOAc (3×1 L) and dried to give 8-chloropyrido[3,4-d]pyrimidine-2,4(1H,3H)-dione (18) as a white solid (55 g, 95% yield). ¹H NMR (400 MHz, DMSO-d₆) δ 11.76 (s, 1H), 10.98 (s, 1H), 8.19 (d, J=5.0 Hz, 1H), 7.79 (d, J=5.0 Hz, 1H). LCMS (ESI) m/z 198, 200 (M+H).

Step 2:

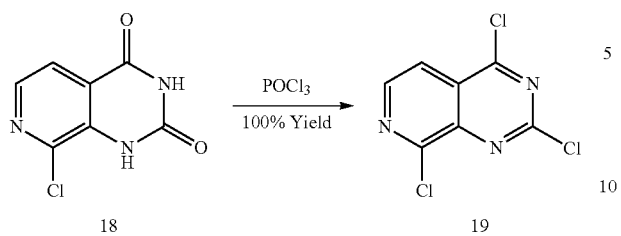

To a 1 L flask charged with a magnetic stir bar was added 8-chloropyrido[3,4-d]pyrimidine-2,4(1H,3H)-dione (18) (45 g, 228 mmol), diethylphenylamine (34.1 g, 228 mmol) and POCl₃ (600 mL). The mixture was heated at 120° C. for 16 hours. The mixture was concentrated and the residue was diluted with DCM (500 mL) and poured carefully into ice water. The product was extracted with DCM (3×500 mL). The combined organic layers were dried over anhydrous magnesium sulfate, filtered and concentrated which gave 2,4,8-trichloropyrido[3,4-d]pyrimidine (19) (crude 55 g). $^1$H NMR (400 MHz, CDCl₃) δ 8.62 (d, J=5.6 Hz, 1H), 7.97 (d, J=5.6 Hz, 1H). LCMS (ESI) m/z 234, 236 (M+H).

Step 3:

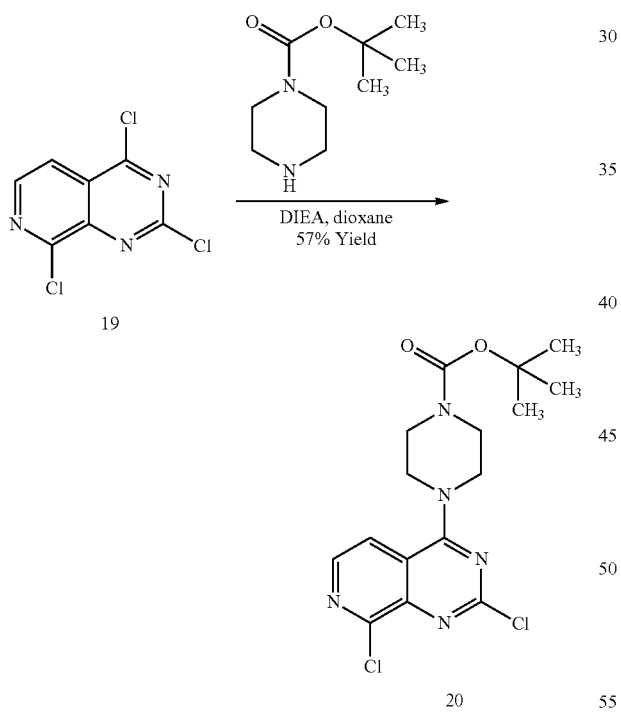

To a 500 mL round bottom charged with a magnetic stir bar was added 2,4,8-trichloropyrido[3,4-d]pyrimidine (19) (crude 55 g, 228 mmol), dioxane (400 mL), DIPEA (58.9 g, 457 mmol) and tert-butyl piperazine-1-carboxylate (38.2 g, 206 mmol). The mixture was heated at 80° C. for 3 hours. After cooling to room temperature, the reaction mixture was filtered and the residue was washed with DCM and gave tert-butyl 4-(2,8-dichloropyrido[3,4-d]pyrimidin-4-yl)piperazine-1-carboxylate (20) (50 g, 57% yield, two steps). $^1$H NMR (400 MHz, CDCl₃) δ 8.32 (d, J=5.7 Hz, 1H), 7.57 (d, J=5.7 Hz, 1H), 3.96-3.94 (m, 4H), 3.68-3.61 (m, 1H), 1.50 (s, 9H). LCMS (ESI) m/z 384, 386 (M+H).

Preparation of tert-butyl 4-[8-chloro-6-(trifluoromethyl)pyrido[3,4-d]pyrimidin-4-yl]piperazine-1-carboxylate (22)

Step 1:

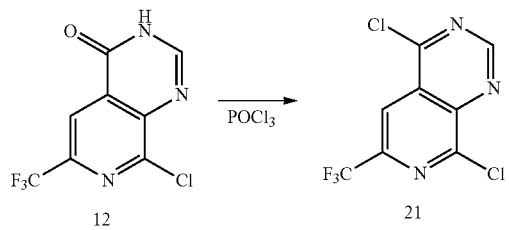

To a mixture of 8-chloro-6-(trifluoromethyl)pyrido[3,4-d]pyrimidin-4(3H)-one (12) (500 mg, 2 mmol) in POCl₃ (6 mL) was added N,N-dimethylaniline (0.5 mL), and the resultant mixture was stirred at 110° C. for 1 hour. TLC showed that 8-chloro-6-(trifluoromethyl)pyrido[3,4-d]pyrimidin-4(3H)-one (12) was consumed. The POCl₃ was removed under reduced pressure and the crude 4,8-dichloro-6-(trifluoromethyl)pyrido[3,4-d]pyrimidine (21) used in the next step.

Step 2:

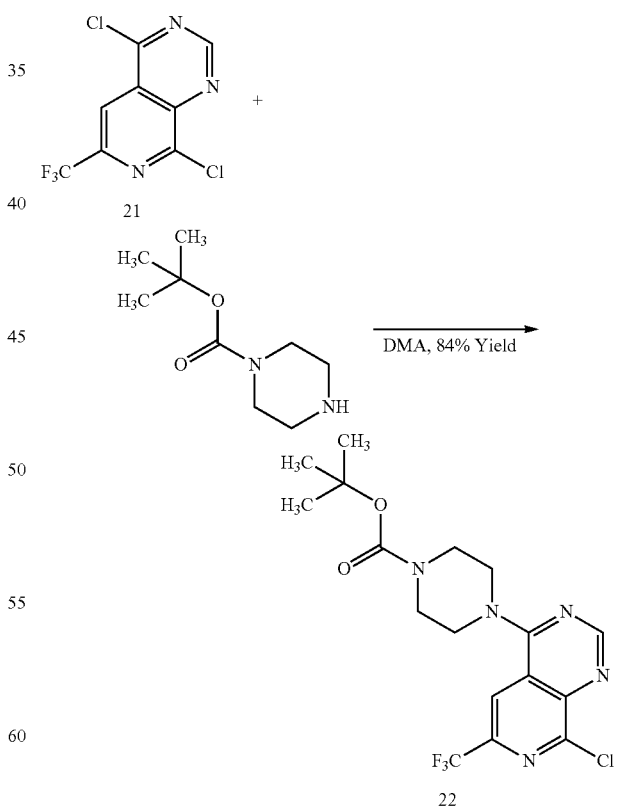

To a solution of 4,8-dichloro-6-(trifluoromethyl)pyrido[3,4-d]pyrimidine (21) (537 mg, 2 mmol) in DMA (2.5 mL) was added tert-butyl piperazine-1-carboxylate (933 mg, 5.0 mmol) at room temperature, and the resultant mixture was stirred at 60° C. for 1 hour. LCMS analysis showed the reaction was complete. The crude reaction mixture was cooled to room temperature and carefully diluted with saturated aqueous NaHCO₃ solution. The aqueous layer was extracted with EtOAc (3×50 mL), and the combined EtOAc layers were washed with brine, dried over Na₂SO₄, concentrated and purified using silica gel chromatography and eluted with 30% EtOAc in petroleum ether which gave tert-butyl 4-[8-chloro-6-(trifluoromethyl)pyrido[3,4-d]pyrimidin-4-yl]piperazine-1-carboxylate (22) as a yellow solid (700 mg, 84% yield). ¹H NMR (400 MHz, CDCl₃) δ 8.94 (s, 1H), 7.96 (s, 1H), 3.95 (m, 4H), 3.67 (m, 4H), 1.50 (s, 9H). LCMS (ESI) m/z 418, 420 (M+H).

Preparation of 5-methyl-1-(tetrahydro-2H-pyran-2-yl)-1H-indazol-4-ol (25)

Step 1:

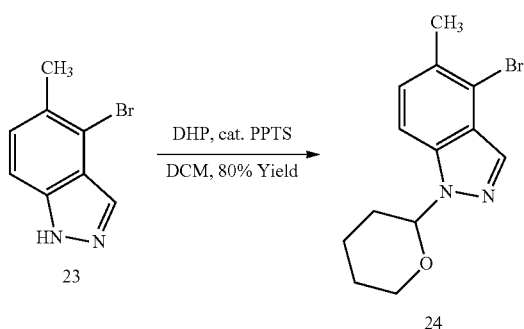 [SMILES: Cc1ccc2[nH]ncc2c1Br ; "DCM, 80% Yield" ; Cc1ccc2c(cnn2C2CCCCO2)c1Br]

This reaction was carried out in two parallel batches. To a stirred solution of 4-bromo-5-methyl-1H-indazole (23) (100 g, 474 mmol) in DCM (1 L) was added PPTS (12 g, 47 mmol) at 28° C., then DHP (120 g, 1.4 mol) was added in one portion at 28° C. After the addition, the resulting mixture was stirred at 30° C. for 18 hours. TLC (EtOAc/petroleum ether, 1:5) showed the starting material was consumed. The two batches were combined together for work-up. The reaction was quenched with H₂O (1.5 L) and the layers separated, and the aqueous layer extracted with DCM (14 The combined organic layers were washed with H₂O (14 brine (1 L), dried over Na₂SO₄ and concentrated to dryness. The residue was triturated with petroleum ether (300 mL) and gave 4-bromo-5-methyl-1-(tetrahydro-2H-pyran-2-yl)-1H-indazole (24) as an off-white solid (223 g, 80% yield). ¹H NMR (400 MHz, DMSO-d₆) δ 8.00 (s, 1H), 7.68 (d, J=8.5 Hz, 1H), 7.39 (d, J=8.5 Hz, 1H), 5.84 (dd, J=9.6, 2.5 Hz, 1H), 3.87 (d, J=12.4 Hz, 1H), 3.73 (ddd, J=11.5, 7.7, 6.0 Hz, 1H), 2.45 (s, 3H), 2.43-2.31 (m, 1H), 2.09-1.90 (m, 2H), 1.83-1.66 (m, 1H), 1.57 (dt, J=9.3, 3.9 Hz, 2H). LCMS (ESI) m/z 295, 297 (M+H).

Step 2:

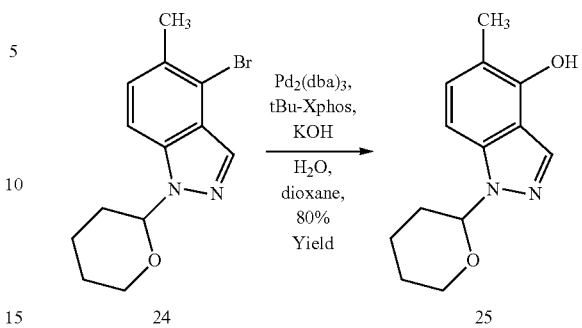

A solution of KOH (85.5 g, 1525 mmol) in H₂O (450 mL) was added to dioxane (1.8 L) at 29° C., followed by 4-bromo-5-methyl-1-(tetrahydro-2H-pyran-2-yl)-1H-indazole (24) (150 g, 508 mmol), Pd₂(dba)₃ (18.6 g, 20.3 mmol) and t-Bu-Xphos (17.3 g, 40.6 mmol). The resultant mixture was degassed and refilled with nitrogen three times. The resultant mixture was heated at 95° C. for 18 hours. TLC (petroleum ether/EtOAc=4:1) gave no starting material. The reaction mixture was cooled to 30° C. and evaporated to dryness. The residue was partitioned between MTBE (500 mL) and H₂O. The aqueous layer was extracted with MTBE (500 mL) and the combined organic layers were discarded. The aqueous phase was acidified to pH=2-3 using 2 N HCl and extracted with EtOAc (2×1 L). The combined organic layers were washed with H₂O (0.8 L) and brine (1 L), dried over Na₂SO₄ and evaporated to dryness. The residue was triturated with petroleum ether (500 mL) which gave 5-methyl-1-(tetrahydro-2H-pyran-2-yl)-1H-indazol-4-ol (25) as an off-white solid (95 g, 80% yield). ¹H NMR (400 MHz, CDCl₃) δ 8.02 (s, 1H), 7.13 (d, J=8.4 Hz, 1H), 7.04 (d, J=8.4 Hz, 1H), 5.65 (dd, J=9.6, 2.6 Hz, 1H), 4.11-3.98 (m, 1H), 3.73 (td, J=11.1, 2.7 Hz, 1H), 2.55 (dddd, J=13.6, 11.8, 9.8, 4.0 Hz, 1H), 2.30 (s, 3H), 2.19-2.09 (m, 1H), 2.08-1.95 (m, 1H), 1.81-1.67 (m, 2H), 1.66-1.55 (m, 1H). LCMS (ESI) m/z 233 (M+H).

Preparation of 3-methoxynaphthalen-1-ol (27)

Step 1:

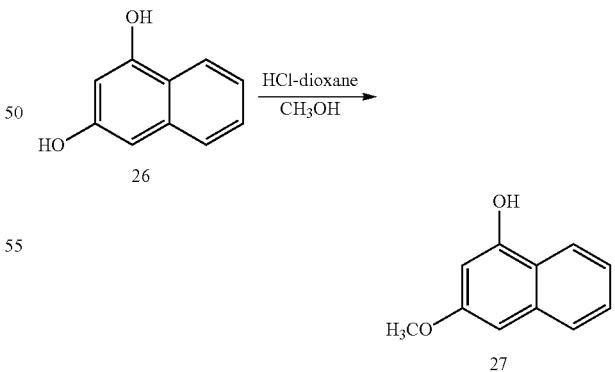

To a solution of naphthalene-1,3-diol (26) (25 g, 156 mmol) in methanol (200 mL), a solution of HCl in dioxane (100 mL of 4M HCl) was added and the resultant solution was stirred at 20° C. for 70 hours. LCMS analysis showed the reaction was complete, and the reaction mixture was concentrated under reduced pressure. The residue was purified by flash chromatography using silica gel and eluted with 10% EtOAc in heptane which gave 3-methoxynaphthalen-1-ol (27) as a yellow solid (13 g, 48% yield). $^1$H NMR (400 MHz, CDCl$_3$) δ 8.06 (d, J=8.3 Hz, 1H), 7.70 (d, J=8.2 Hz, 1H), 7.45 (ddd, J=8.2, 6.9, 1.2 Hz, 1H), 7.33 (ddd, J=8.1, 6.9, 1.2 Hz, 1H), 6.77 (d, J=2.1 Hz, 1H), 6.53 (d, J=2.2 Hz, 1H), 3.90 (s, 3H). LCMS (ESI) m/z 175 (M+H).

Preparation of 5-chloro-1-(tetrahydro-2H-pyran-2-yl)-1H-indazol-4-ol (30)

Step 1:

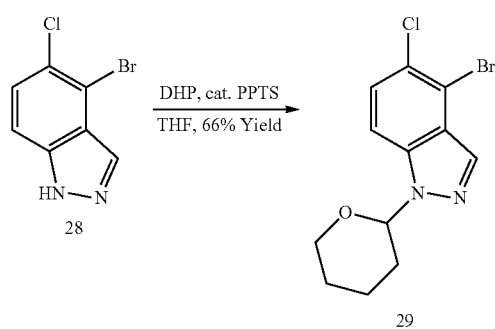 [SMILES: Clc1ccc2[nH]ncc2c1Br ; Clc1ccc2c(cnn2C2CCCCO2)c1Br]

To a solution of 4-bromo-5-chloro-1H-indazole (28) (950 mg, 4.10 mmol) in THF (50 mL) were added DHP (518 mg, 6.16 mmol) and PPTS (103 mg, 0.410 mmol). The mixture was stirred at 50° C. for 20 hours. Another 0.5 eq. DHP (173 mg, 2.05 mmol) was added and the resulting mixture was stirred at 50° C. for 16 hours. LCMS indicated the starting material was consumed and two regioisomers were formed. The solvent was removed under reduced pressure. The crude product was purified by silica column chromatography (20 g, 10% EtOAc/petroleum ether) and gave 4-bromo-5-chloro-1-(tetrahydro-2H-pyran-2-yl)-1H-indazole (29) as a white solid (850 mg, 66% yield). $^1$H NMR (400 MHz, DMSO-d$_6$) δ 8.11 (s, 1H), 7.84 (d, J=8.9 Hz, 1H), 7.61 (d, J=8.9 Hz, 1H), 5.93-5.88 (m, 1H), 3.87 (d, J=12.2 Hz, 1H), 3.77-3.72 (m, 1H), 2.37-2.32 (m, 1H), 2.01 (t, J=14.0 Hz, 2H), 1.73 (d, J=6.6 Hz, 1H), 1.58 (t, J=6.4 Hz, 2H). LCMS (ESI) m/z 315, 317 (M+H).

Step 2:

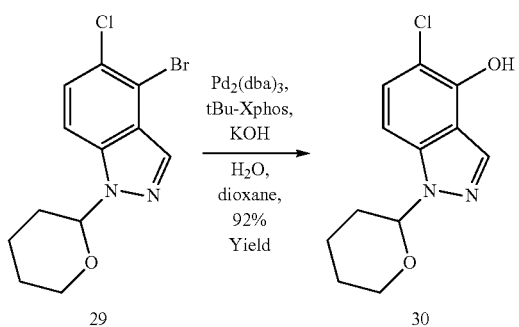 [SMILES: Clc1ccc2c(cnn2C2CCCCO2)c1Br ; Oc1c(Cl)ccc2c1cnn2C1CCCCO1]

5-Chloro-1-(tetrahydro-2H-pyran-2-yl)-1H-indazol-4-ol (30) (590 mg, 92% yield) was prepared according to the procedure used to prepare 5-methyl-1-(tetrahydro-2H-pyran-2-yl)-1H-indazol-4-ol (25). $^1$H NMR (400 MHz, DMSO-d$_6$) δ 10.72 (s, 1H), 8.23 (d, J=0.5 Hz, 1H), 7.31 (d, J=8.8 Hz, 1H), 7.16 (dd, J=8.8, 0.8 Hz, 1H), 5.76 (dd, J=9.7, 2.5 Hz, 1H), 3.91-3.83 (m, 1H), 3.76-3.69 (m, 1H), 2.42-2.29 (m, 1H), 2.05-1.99 (m, 1H), 1.94 (ddd, J=9.7, 6.1, 3.2 Hz, 1H), 1.74 (ddd, J=12.7, 10.6, 4.0 Hz, 1H), 1.61-1.52 (m, 2H). LCMS (ESI) m/z 253, 255 (M+H).

Preparation of 5-ethyl-1-(tetrahydro-2H-pyran-2-yl)-1H-indazol-4-ol (38)

Step 1:

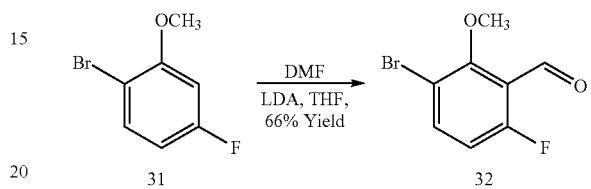

To a solution of 1-bromo-4-fluoro-2-methoxybenzene (31) (24 g, 2.44 mmol) in THF (200 mL) was added LDA (64.4 mL, 129 mmol, 2 M) dropwise at −78° C. and the mixture was stirred for 1 hour. DMF (10.3 g, 140 mmol) was added dropwise over 5 minutes, and the reaction mixture was stirred at −78° C. for another 45 minutes. The reaction was quenched by the addition of HCl (200 mL, 1 M), and the mixture was allowed to warm to 20° C. and then diluted with EtOAc (400 mL). The organic layer was washed with H$_2$O (200 mL) and brine (200 mL), dried over Na$_2$SO$_4$, filtered and concentrated. The crude product was purified by column chromatography on silica gel (1:10 EtOAc/petroleum ether) and gave 3-bromo-6-fluoro-2-methoxybenzaldehyde (32) as a yellow solid (18 g, 66% yield). $^1$H NMR (400 MHz, CDCl$_3$) δ 10.35 (s, 1H), 7.75 (dd, J=8.8, 4.0 Hz, 1H), 6.89 (t, J=6.0 Hz, 1H), 3.97 (s, 3H). LCMS (ESI) m/z 233, 235 (M+H).

Step 2:

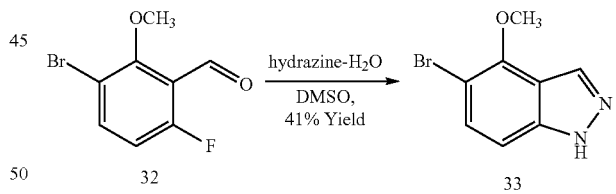

A mixture of 3-bromo-6-fluoro-2-methoxybenzaldehyde (32) (5 g, 22 mmol) and hydrazine hydrate (7 mL) in DMSO (150 mL) was heated at 130° C. for 16 hours. LCMS analysis showed mostly product. The mixture was diluted with EtOAc (400 mL) and washed with H$_2$O (3×200 mL). The organic layer was dried over Na$_2$SO$_4$, filtered and concentrated. The crude product was purified by silica gel chromatography (petroleum ether/EtOAc=10/3) and gave 5-bromo-4-methoxy-1H-indazole (33) as a yellow solid (2.0 g, 41% yield). $^1$H NMR (400 MHz, CDCl$_3$) δ 8.23 (s, 1H), 7.50 (d, J=12.0 Hz, 1H), 7.06 (d, J=8.0 Hz, 1H), 4.25 (s, 3H). LCMS (ESI) m/z 227, 229 (M+H).

Step 3:

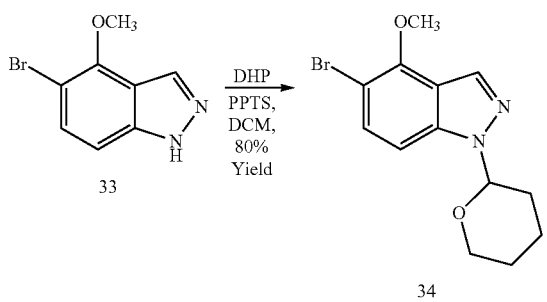

To a mixture of 5-bromo-4-methoxy-1H-indazole (33) (2 g, 8.8 mmol) and 3,4-dihydro-2H-pyran (1.5 g, 17.6 mmol) in DCM (40 mL) was added pyridinium toluene-4-sulphonate (221 mg, 0.88 mmol) and the mixture was stirred at 40° C. for 4 hours. The mixture was concentrated and the residue was purified by silica gel chromatography and eluted with petroleum ether/EtOAc (10/1) and gave 5-bromo-4-methoxy-1-(tetrahydro-2H-pyran-2-yl)-1H-indazole (34) as yellow oil (2.2 g, 80% yield). $^1$H NMR (400 MHz, CDCl$_3$) δ 8.29 (s, 1H), 7.37-7.30 (m, 2H), 5.67 (dd, J=8.0, 4.0 Hz, 1H), 4.17-4.15 (m, 1H), 3.82-3.76 (m, 1H), 2.29-2.25 (m, 1H), 2.20-2.15 (m, 1H), 2.08-2.05 (m, 1H), 1.78-1.69 (m, 3H). LCMS (ESI) m/z 331, 335 (M+Na).

Step 4:

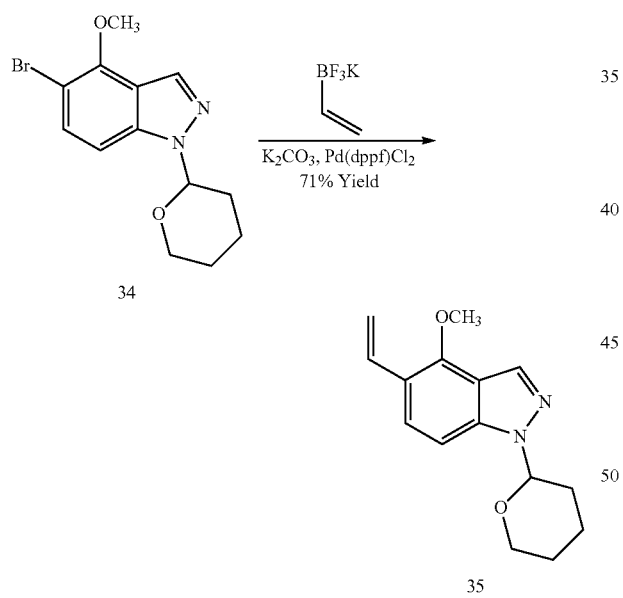

To a mixture of 5-bromo-4-methoxy-1-(tetrahydro-2H-pyran-2-yl)-1H-indazole (34) (2.2 g, 7.1 mmol), K$_2$CO$_3$ (1.95 g, 14.1 mmol) and potassium vinyltrifluoroborate (1.4 g, 11 mmol) in DMF (30 mL) was added Pd(dppf)Cl$_2$ (DCM complex) (577 mg, 0.71 mmol) and the mixture was stirred at 90° C. for 16 hours under nitrogen. LCMS gave mostly product. The mixture was concentrated and the residue was purified by silica gel chromatography and eluted with petroleum ether/EtOAc (1/5) and gave 5-ethenyl-4-methoxy-1-(tetrahydro-2H-pyran-2-yl)-1H-indazole (35) as yellow solid (1.3 g, 71% yield). $^1$H NMR (400 MHz, CDCl$_3$) δ 8.25 (d, J=0.7 Hz, 1H), 7.49 (d, J=8.0 Hz, 1H), 7.40 (d, J=12.0 Hz, 1H), 7.16 (dd, J=16.0, 12.0 Hz, 1H), 5.70-5.63 (m, 2H), 5.22 (dd, J=12.0, 1.2 Hz, 1H), 4.17-4.12 (m, 1H), 3.82-3.75 (m, 1H), 2.26-2.14 (m, 2H), 2.08-2.03 (m, 1H), 1.79-1.66 (m, 3H). LCMS (ESI) m/z 259 (M+H).

Step 5:

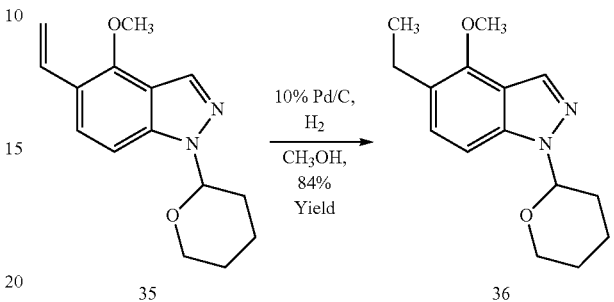

To a mixture of 5-ethenyl-4-methoxy-1-(tetrahydro-2H-pyran-2-yl)-1H-indazole (35) (1.3 g, 5.0 mmol) in methanol (40 mL) was added 10% Pd/C (130 mg) and the mixture was stirred at 20° C. for 4 hours under a hydrogen atmosphere. After filtration and concentration, 5-ethyl-4-methoxy-1-(tetrahydro-2H-pyran-2-yl)-1H-indazole (36) was obtained as yellow oil (1.1 g, 84% yield). $^1$H NMR (400 MHz, CDCl$_3$) δ 8.20 (d, J=0.7 Hz, 1H), 7.39 (dd, J=8.8, 0.9 Hz, 1H), 7.13 (d, J=8.0 Hz, 1H), 5.66 (dd, J=8.0, 4.0 Hz, 1H), 4.17-4.12 (m, 1H), 3.81-3.73 (m, 1H), 2.73-2.67 (m, 2H), 2.24-2.21 (m, 2H), 2.08-2.03 (m, 1H), 1.78-1.67 (m, 3H), 1.21 (t, J=8.0 Hz, 3H). LCMS (ESI) m/z 261 (M+H).

Step 6:

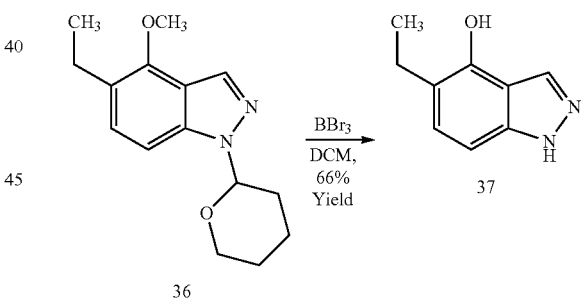

To a solution of 5-ethyl-4-methoxy-1-(tetrahydro-2H-pyran-2-yl)-1H-indazole (36) (1.1 g, 4.2 mmol) in DCM (5 mL) was added BBr$_3$ (10 mL, 1 M) at −78° C. and the mixture was stirred at 20° C. for 4 hours. To the mixture was added NaHCO$_3$ (sat. 30 mL) and the aqueous layer was extracted with DCM (3×30 mL). The combined organic layers were dried over Na$_2$SO$_4$, filtered, and concentrated. The crude product was purified by silica gel chromatography and eluted with petroleum ether/EtOAc (2/1) and gave 5-ethyl-1H-indazol-4-ol (37) as yellow oil (450 mg, 66% yield). $^1$H NMR (400 MHz, CDCl$_3$) δ 8.11 (s, 1H), 7.19 (d, J=8.0 Hz, 1H), 7.02 (d, J=8.0 Hz, 1H), 2.76-2.68 (m, 2H), 1.26 (t, J=8.0 Hz, 3H). LCMS (ESI) m/z 163 (M+H).

Step 7:

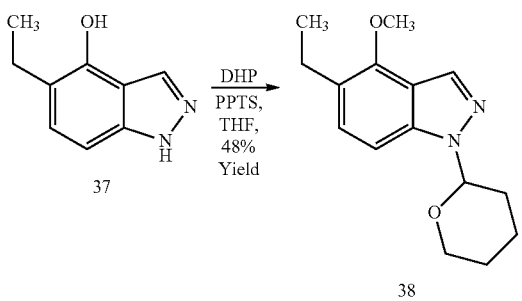

To a mixture of 5-ethyl-1H-indazol-4-ol (37) (440 mg, 2.7 mmol) and DHP (456 mg, 5.4 mmol) in THF (20 mL) was added PPTS (69 mg, 0.27 mmol) and the mixture was stirred at 70° C. for 16 hours. The mixture was concentrated and the residue was purified by silica gel chromatography and eluted with petroleum ether/EtOAc (7/3) and gave 5-ethyl-1-(tetrahydro-2H-pyran-2-yl)-1H-indazol-4-ol (38) as yellow oil (320 mg, 48% yield). $^1$H NMR (400 MHz, DMSO-d$_6$) δ 9.67 (s, 1H), 8.15 (s, 1H), 7.13 (d, J=8.0 Hz, 1H), 7.04 (d, J=8.0 Hz, 1H), 5.70 (dd, J=8.0, 4.0 Hz, 1H), 3.86-3.85 (m, 1H), 3.73-3.66 (m, 1H), 2.63 (q, J=8.0 Hz, 2H), 2.43-2.33 (m, 1H), 2.03-2.00 (m, 1H), 1.93-1.89 (m, 1H), 1.80-1.69 (m, 1H), 1.58-1.53 (m, 2H), 1.13 (t, J=8.0 Hz, 3H). LCMS (ESI) m/z 247 (M+H).

Preparation of 5-fluoro-1-(tetrahydro-2H-pyran-2-yl)-1H-indazol-4-ol (41)

Step 1:

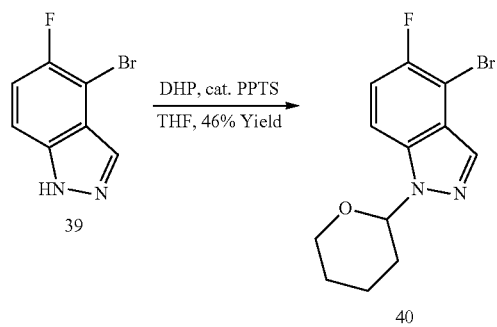 [SMILES: Fc1ccc2[nH]ncc2c1Br ; Fc1ccc2c(cnn2C2CCCCO2)c1Br]

4-Bromo-5-fluoro-1-(tetrahydro-2H-pyran-2-yl)-1H-indazole (40) (651 mg, 47% yield) was prepared according to the procedure used to prepare 4-bromo-5-methyl-1-(tetrahydro-2H-pyran-2-yl)-1H-indazole (24). $^1$H NMR (400 MHz, CDCl$_3$) δ 8.02 (d, J=0.9 Hz, 1H), 7.52 (ddd, J=9.0, 3.7, 0.9 Hz, 1H), 7.20 (t, J=8.8 Hz, 1H), 5.70 (dd, J=9.0, 2.8 Hz, 1H), 3.99 (ddt, J=11.8, 3.7, 1.6 Hz, 1H), 3.74 (ddd, J=11.6, 9.7, 3.3 Hz, 1H), 2.66-2.38 (m, 1H), 2.28-1.97 (m, 2H), 1.85-1.61 (m, 3H).

Step 2:

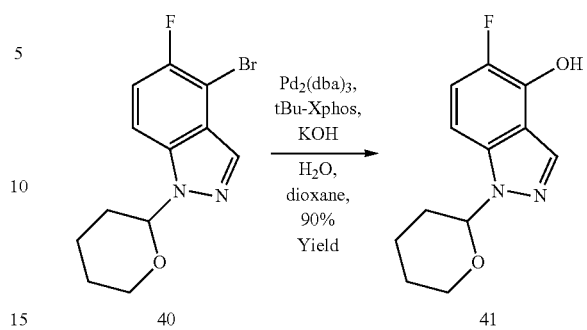

5-Fluoro-1-(tetrahydro-2H-pyran-2-yl)-1H-indazol-4-ol (41) (461 mg, 90% yield) was prepared according to the procedure used to prepare 5-methyl-1-(tetrahydro-2H-pyran-2-yl)-1H-indazol-4-ol (25). LCMS (ESI) m/z 267 (M+H).

Preparation of 5-chloro-6-methyl-1-(tetrahydro-2H-pyran-2-yl)-1H-indazol-4-ol (47)

Step 1:

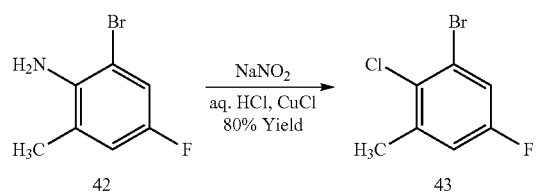

2-Bromo-4-fluoro-6-methylaniline (42) (5 g, 24.5 mmol) was added into the solution of concentrated HCl (30 mL) and H$_2$O (30 mL), which was stirred at 60-70° C. for 1 hour. The crude reaction mixture was cooled to 0-5° C. and NaNO$_2$ (2.0 g, 29 mmol) in H$_2$O (10 mL) was added and the reaction was stirred for 15 minutes. Next, the mixture was added to a solution of HCl (50 mL) and CuCl (3.6 g, 36.8 mmol) at 70-80° C. for 30 min. The crude reaction mixture was cooled to room temperature and extracted with DCM (3×100 mL). The combined organic layers were dried over Na$_2$SO$_4$, filtered and concentrated which gave 1-bromo-2-chloro-5-fluoro-3-methylbenzene (43) as a brown liquid (4.5 g, 80% yield). $^1$H NMR (400 MHz, CDCl$_3$) δ 7.23 (dd, J=7.8, 2.9 Hz, 1H), 6.97-6.91 (m, 1H), 2.43 (s, 3H). LCMS (ESI) m/z 216 (M+H).

Step 2:

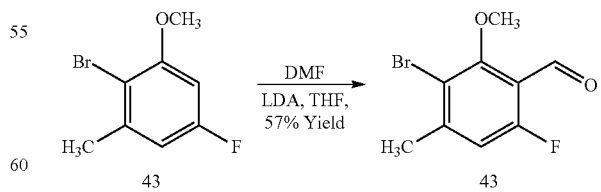

2-Bromo-3-chloro-6-fluoro-4-methylbenzaldehyde (44) (8.3 g, 57% yield) was prepared according to the procedure used to prepare 3-bromo-6-fluoro-2-methoxybenzaldehyde (32). $^1$H NMR (400 MHz, CDCl$_3$) δ 10.29 (s, 1H), 7.09 (d, J=10.6 Hz, 1H), 2.51 (s, 3H).

Step 3:

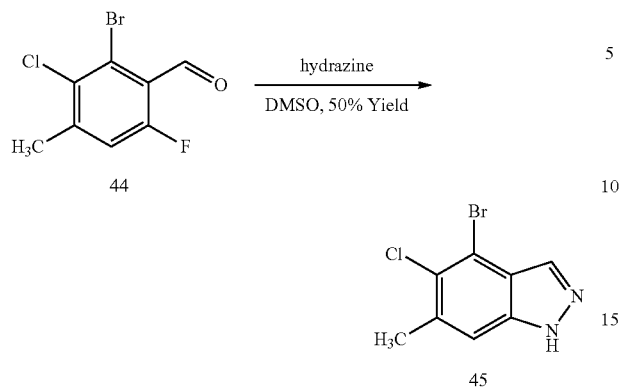

4-Bromo-5-chloro-6-methyl-1H-indazole (45) (108 mg, 50% yield) was prepared according to the procedure used to prepare 5-bromo-4-methoxy-1H-indazole (33). $^1$H NMR (400 MHz, CDCl$_3$) δ 8.02 (s, 1H), 7.33 (s, 1H), 2.56 (d, J=0.6 Hz, 3H). LCMS (ESI) m/z 245, 247 (M+H).

Step 4:

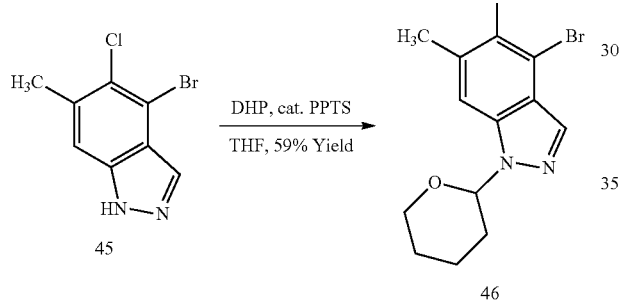

4-Bromo-5-chloro-6-methyl-1-(tetrahydro-2H-pyran-2-yl)-1H-indazole (46) (2.4 g, 59% yield) was prepared according to the procedure used to prepare 4-bromo-5-methyl-1-(tetrahydro-2H-pyran-2-yl)-1H-indazole (24) where the reaction was done in THF at 50° C. $^1$H NMR (400 MHz, CDCl$_3$) δ 7.94 (s, 1H), 7.43 (s, 1H), 5.66 (dd, J=9.0, 2.6 Hz, 1H), 3.99 (d, J=11.5 Hz, 1H), 3.80-3.64 (m, 1H), 2.56 (s, 3H), 2.54-2.46 (m, 1H), 2.15 (dd, J=8.1, 4.4 Hz, 1H), 2.11-2.03 (m, 1H), 1.79-1.64 (m, 3H). LCMS (ESI) m/z 329, 331 (M+H).

Step 5:

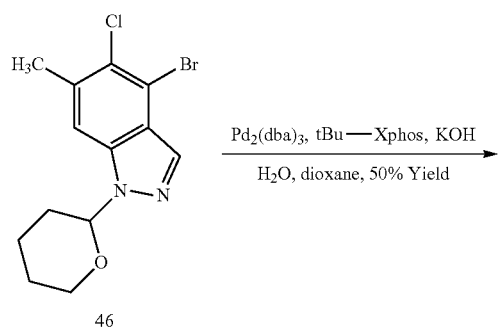

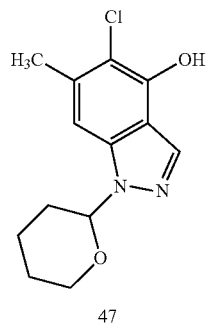

5-Chloro-6-methyl-1-(tetrahydro-2H-pyran-2-yl)-1H-indazol-4-ol (47) (373 mg, 50% yield) was prepared according to the procedure used to prepare 5-methyl-1-(tetrahydro-2H-pyran-2-yl)-1H-indazol-4-ol (25). $^1$H NMR (400 MHz, CDCl$_3$) δ 8.07 (s, 1H), 7.04 (s, 1H), 5.64 (dd, J=9.3, 2.7 Hz, 1H), 4.08-3.96 (m, 1H), 3.74 (d, J=2.8 Hz, 1H), 2.52 (d, J=3.9 Hz, 1H), 2.49 (d, J=0.5 Hz, 3H), 2.19-2.13 (m, 1H), 2.09-2.04 (m, 1H), 1.76 (t, J=9.4 Hz, 2H), 1.66 (s, 1H). LCMS (ESI) m/z 267, 269 (M+H).

Preparation of 5-bromo-6-methyl-1-(tetrahydro-2H-pyran-2-yl)-1H-indazol-4-ol (52)

Step 1:

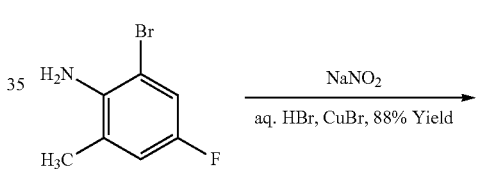

1,2-Dibromo-5-fluoro-3-methylbenzene (49) (13 g, 88% yield) was prepared according to the procedure used to prepare 1-bromo-2-chloro-5-fluoro-3-methylbenzene (43) except HBr and CuBr were used instead of HCl and CuCl, respectively. $^1$H NMR (400 MHz, DMSO-d$_6$) δ 7.60 (dd, J=8.2, 2.9 Hz, 1H), 7.35 (dd, J=9.3, 2.9 Hz, 1H), 2.44 (s, 3H).

Step 2:

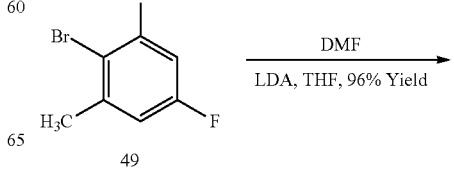

-continued

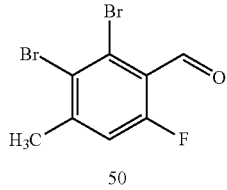

50

2,3-Dibromo-6-fluoro-4-methylbenzaldehyde (50) (13.5 g, 96% yield) was prepared according to the procedure used to prepare 3-bromo-6-fluoro-2-methoxybenzaldehyde (32). $^1$H NMR (400 MHz, DMSO-d$_6$) δ 10.11 (s, 1H), 7.55 (d, J=11.3 Hz, 1H), 2.52 (s, 3H).

Step 3:

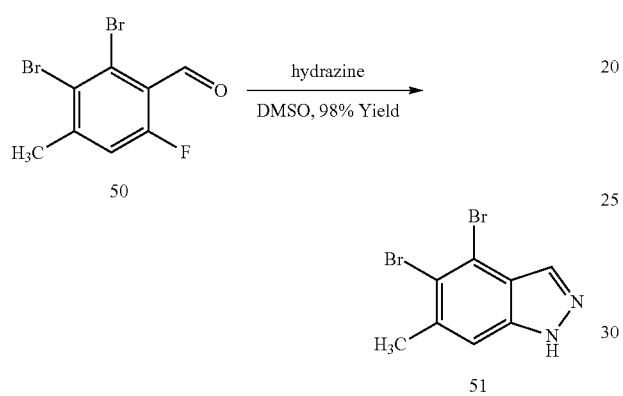

4,5-Dibromo-6-methyl-1H-indazole (51) (11.8 g, 98% yield) was prepared according to the procedure used to prepare 5-bromo-4-methoxy-1H-indazole (33). $^1$H NMR (400 MHz, DMSO-d$_6$) δ 12.93 (s, 1H), 7.98 (d, J=0.7 Hz, 1H), 7.58 (s, 1H), 2.55 (s, 3H). LCMS (ESI) m/z 289, 291 (M+H).

Step 4:

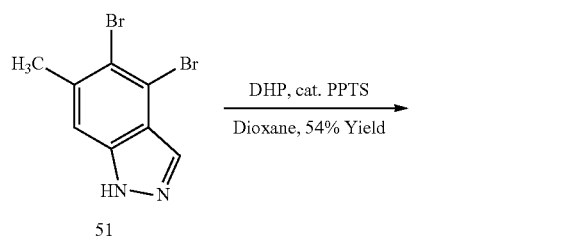

4,5-Dibromo-6-methyl-1-(tetrahydro-2H-pyran-2-yl)-1H-indazole (52) (8.2 g, 54% yield) was prepared according to the procedure used to prepare 4-bromo-5-methyl-1-(tetrahydro-2H-pyran-2-yl)-1H-indazole (24) except the reaction was done in dioxane at 90° C. $^1$H NMR (400 MHz, DMSO-d$_6$) δ 8.02 (d, J=1.3 Hz, 1H), 7.82 (s, 1H), 5.83 (d, J=9.4 Hz, 1H), 3.88 (d, J=11.3 Hz, 1H), 3.78-3.70 (m, 1H), 2.58 (d, J=0.9 Hz, 3H), 2.36 (ddd, J=13.2, 10.9, 6.6 Hz, 1H), 2.07-1.93 (m, 2H), 1.78-1.68 (m, 1H), 1.62-1.55 (m, 2H). LCMS (ESI) m/z 372, 374 (M+H).

Step 5:

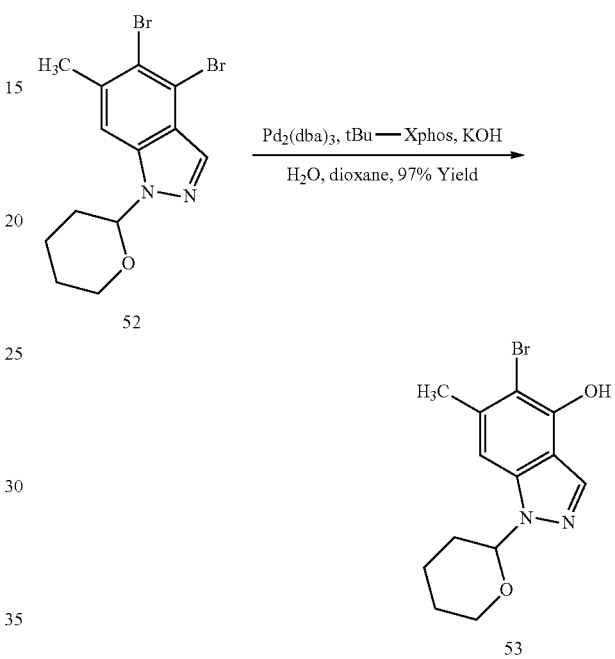

5-Bromo-6-methyl-1-(tetrahydro-2H-pyran-2-yl)-1H-indazol-4-ol (53) (2.2 g, 33% yield) was prepared according to the procedure used to prepare 5-methyl-1-(tetrahydro-2H-pyran-2-yl)-1H-indazol-4-ol (25). $^1$H NMR (400 MHz, DMSO-d$_6$) δ 10.73 (s, 1H), 8.19 (s, 1H), 7.17 (s, 1H), 5.71 (dd, J=9.7, 2.4 Hz, 1H), 3.87 (d, J=12.3 Hz, 1H), 3.75-3.65 (m, 1H), 2.44 (s, 3H), 2.39-2.32 (m, 1H), 2.06-1.98 (m, 1H), 1.92 (dd, J=13.1, 2.8 Hz, 1H), 1.78-1.67 (m, 1H), 1.56 (dd, J=10.2, 6.5 Hz, 2H). LCMS (ESI) m/z 311, 313 (M+H).

Preparation of 6-chloro-5-methyl-1-(tetrahydro-2H-pyran-2-yl)-1H-indazol-4-ol (61)

Step 1:

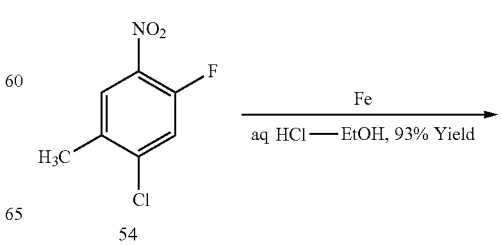

-continued

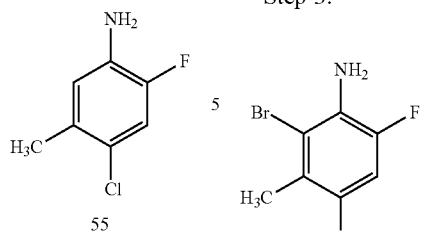

55

To a solution of 1-chloro-5-fluoro-2-methyl-4-nitrobenzene (54) (23.0 g, 121 mmol) in EtOH/H₂O (200 mL, 1:1) was added 12 M HCl (10.1 mL, 121 mmol). The mixture was heated at 80° C. and Fe (23.7 g, 425 mmol) was added slowly over a period of 30 minutes. The mixture was stirred at the same temperature for 1 hour. LCMS indicated the starting material was consumed and the desired product was formed. Then, the mixture was cooled to 25° C., diluted with EtOAc (300 mL) and acidified to pH=8-9 with saturated aqueous NaHCO₃. The layers were filtered, separated and the aqueous layer was extracted with EtOAc (2×300 mL). The combined organic layers were washed with brine, dried over Na₂SO₄, filtered and concentrated under reduced pressure and gave 4-chloro-2-fluoro-5-methylaniline (55) as a yellow solid (18.0 g, 93% yield). ¹H NMR (400 MHz, DMSO-d₆) δ 7.08 (d, J=11.1 Hz, 1H), 6.69 (d, J=9.6 Hz, 1H), 5.20 (s, 2H), 2.15 (s, 3H). LCMS (ESI) m/z 160, 162 (M+H).

Step 2:

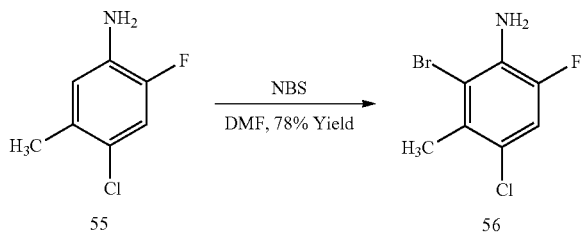

To a solution of 4-chloro-2-fluoro-5-methylaniline (55) (18.7 g, 117 mmol) in DMF (150 mL) was slowly added NBS (20.9 g, 117 mmol) at 0° C. Then the mixture was warmed up to 25° C. and stirred for 1 hour. LCMS indicated the starting material was consumed and the desired product was formed. The mixture was quenched with saturated aqueous NaHCO₃ and extracted with EtOAc (2×200 mL). The combined organic layers were washed with water, brine, dried over Na₂SO₄, filtered and concentrated under reduced pressure. The residue was purified by silica gel column chromatography (120 g, petroleum ether/EtOAc=98:2) and gave 2-bromo-4-chloro-6-fluoro-3-methylaniline (56) as a yellow solid (22.1 g, 79% yield). ¹H NMR (400 MHz, DMSO-d₆) δ 7.30 (d, J=10.9 Hz, 1H), 5.45 (s, 2H), 2.36 (d, J=1.0 Hz, 3H). LCMS (ESI) m/z 238, 240 (M+H).

Step 3:

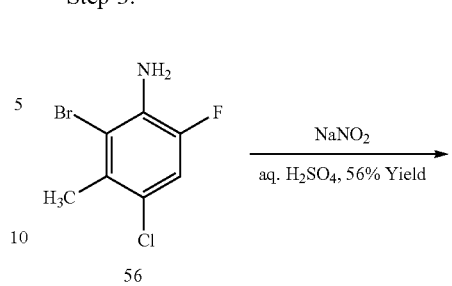

To a solution of concentrated H₂SO₄ (62 mL) in H₂O (250 mL) was added 2-bromo-4-chloro-6-fluoro-3-methylaniline (56) (22.1 g, 93 mmol), and the mixture was stirred at 25° C. for 10 minutes and cooled to 5° C. Next, NaNO₂ (7.1 g, 102 mmol) in H₂O (20 mL) was added drop-wise. The resulting mixture was stirred at 5° C. for 20 minutes and added to a solution of KI (62 g, 370 mmol) in H₂O (50 mL), which was stirred at 5° C. for 20 minutes and then warmed to 25° C. for 18 hour. TLC (petroleum ether) indicated the starting material was consumed. The mixture was quenched with water (150 mL) and extracted with EtOAc (2×500 mL). The combined organic layers were washed with saturated aqueous Na₂SO₃, brine, dried over Na₂SO₄, filtered and concentrated under reduced pressure. The residue was purified by silica gel column chromatography (120 g, petroleum ether) and gave 3-bromo-1-chloro-5-fluoro-4-iodo-2-methylbenzene (57) as a light yellow solid (18 g, 56% yield). ¹H NMR (400 MHz, DMSO-d₆) δ 7.60 (d, J=7.8 Hz, 1H), 2.56 (d, J=1.1 Hz, 3H).

Step 4:

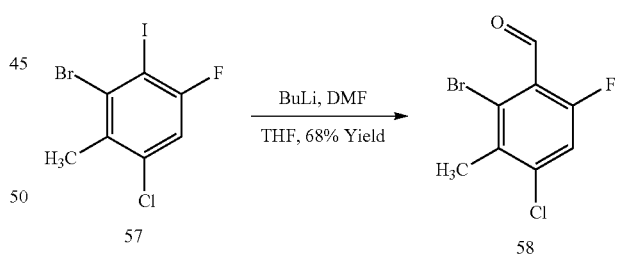

To a solution of 3-bromo-1-chloro-5-fluoro-4-iodo-2-methylbenzene (57) (17.5 g, 50.1 mmol) in THF (100 mL) was added drop-wise 2.5 M BuLi (20 mL, 50 mmol) at −100° C. The mixture was stirred at the same temperature for 30 minutes. Next, dry DMF (4.0 g, 55 mmol) was added and the mixture was stirred at −100° C. for 20 minutes. TLC (petroleum ether) indicated almost all of the starting material was consumed and the desired product was formed. The crude reaction mixture was quenched with 1 N HCl. Water was added to the mixture and the aqueous layer was extracted with EtOAc (2×150 mL). The combined organic layers were washed with H₂O, dried over Na₂SO₄, filtered and concentrated under reduced pressure. The crude product was purified by silica gel column chromatography (120 g, petroleum ether/EtOAc=97:3) and gave 2-bromo-4-chloro-6-fluoro-3-methylbenzaldehyde (58) as a yellow solid (8.6 g, 68% yield). ¹H NMR (400 MHz, DMSO-d₆) δ 10.18 (s, 1H), 7.75 (d, J=10.4 Hz, 1H), 2.52-2.50 (m, 3H). LCMS (ESI) m/z 251, 253 (M+H).

Step 5:

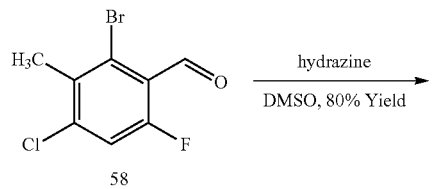

4-Bromo-6-chloro-5-methyl-1H-indazole (59) (6.7 g, 80% yield) was prepared according to the procedure used to prepare 5-bromo-4-methoxy-1H-indazole (33), except the reaction was done at 90° C. for 21 hours. ¹H NMR (400 MHz, DMSO-d₆) δ 13.43 (s, 1H), 8.00 (d, J=0.8 Hz, 1H), 7.73 (s, 1H), 2.53 (s, 3H). LCMS (ESI) m/z 245, 247 (M+H).

Step 6:

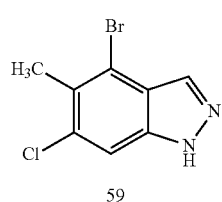

4-Bromo-6-chloro-5-methyl-1-(tetrahydro-2H-pyran-2-yl)-1H-indazole (60) (5.7 g, 73% yield) was prepared according to the procedure used to prepare 4-bromo-5-methyl-1-(tetrahydro-2H-pyran-2-yl)-1H-indazole (24) except the reaction was done in THF at 80° C. ¹H NMR (400 MHz, DMSO-d₆) δ 8.05 (s, 1H), 8.01 (s, 1H), 5.88 (dd, J=9.6, 2.4 Hz, 1H), 3.86 (d, J=12.1 Hz, 1H), 3.80-3.73 (m, 1H), 2.54 (s, 3H), 2.38-2.31 (m, 1H), 2.05-1.94 (m, 2H), 1.71 (dd, J=9.1, 3.3 Hz, 1H), 1.57 (dt, J=9.1, 4.6 Hz, 2H). LCMS (ESI) m/z 329, 331 (M+H).

Step 7:

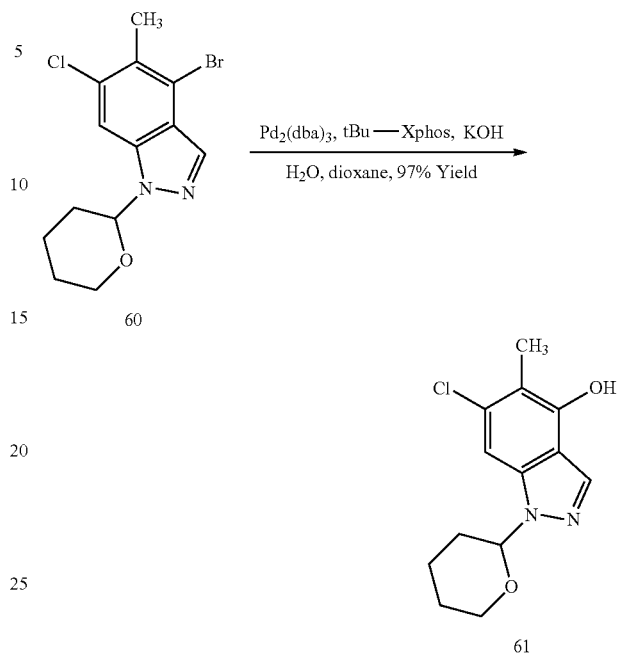

6-Chloro-5-methyl-1-(tetrahydro-2H-pyran-2-yl)-1H-indazol-4-ol (61) (5.2 g, 97% yield) was prepared according to the procedure used to prepare 5-methyl-1-(tetrahydro-2H-pyran-2-yl)-1H-indazol-4-ol (25). ¹H NMR (400 MHz, DMSO-d₆) δ 10.37 (s, 1H), 8.19 (s, 1H), 7.31 (s, 1H), 5.73 (dd, J=9.7, 2.4 Hz, 1H), 3.86 (d, J=11.2 Hz, 1H), 3.76-3.69 (m, 1H), 2.34 (dd, J=9.1, 3.0 Hz, 1H), 2.24 (s, 3H), 2.01 (dd, J=8.6, 4.4 Hz, 1H), 1.91 (dd, J=13.1, 2.8 Hz, 1H), 1.72 (s, 1H), 1.59-1.52 (m, 2H). LCMS (ESI) m/z 267, 269 (M+H).

Preparation of 5,6-dimethyl-1-(tetrahydro-2H-pyran-2-yl)-1H-indazol-4-ol (67)

Step 1:

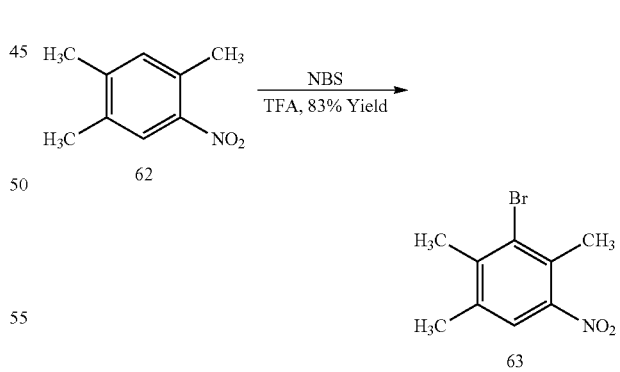

To a solution of 1,2,4-trimethyl-5-nitrobenzene (62) (2.0 g, 12.1 mmol) in trifluoroacetic acid (24 mL) was added NBS (1.2 g, 6.7 mmol) and iron (20 mg, 0.4 mmol). The reaction mixture was heated at 75° C. for 3 days, allowed to cool to room temperature and then the solvent was removed under reduced pressure. The resultant residue was dissolved in EtOAc and washed with aqueous saturated sodium bicarbonate, dried over magnesium sulfate, filtered, and concentrated under reduced pressure. The crude residue was purified over silica gel and eluted with 0-5% EtOAc/heptane and gave 3-bromo-1,2,4-trimethyl-5-nitrobenzene (63) as a white solid (1.4 g, 83% yield). ¹H NMR (400 MHz, CDCl₃) δ 7.55 (s, 1H), 2.57 (s, 3H), 2.47 (s, 3H), 2.39 (s, 3H).

Step 2:

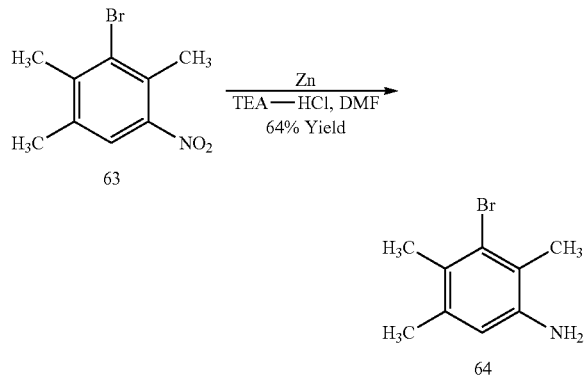

A suspension of 3-bromo-1,2,4-trimethyl-5-nitrobenzene (63) (3.0 g, 12.5 mmol), zinc dust (3.7 g, 56.1 mmol) and triethylamine HCl (9.4 g, 68.5 mmol) in DMF (42 mL) was heated at 105° C. overnight. The reaction mixture was allowed to cool to room temperature, and filtered through Celite. The filtrate was diluted with EtOAc and the organic layer was washed with brine (twice), dried over magnesium sulfate, filtered, and concentrated under reduced pressure. The crude product was purified by silica gel chromatography (ISCO 24 g silica) and eluted with EtOAc/heptane (0-40%) and gave 3-bromo-2,4,5-trimethylaniline (64) as brown oil which gave a brown solid upon standing (1.8 g, 66% yield). LCMS (ESI) m/z 214, 216 (M+H).

Step 3:

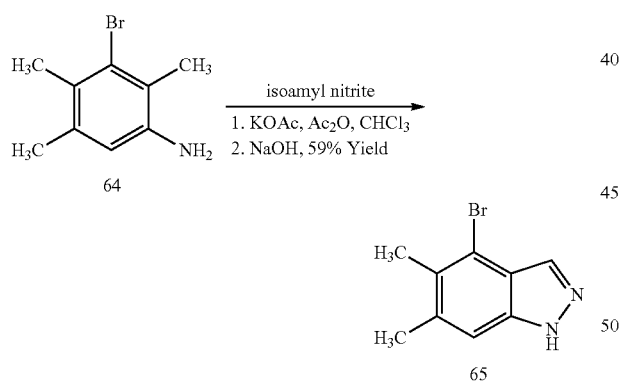

To a flask with a stir bar was added 3-bromo-2,4,5-trimethylaniline (64) (1.8 g, 8.3 mmol), potassium acetate (974 mg, 9.9 mmol) and chloroform (36 mL). This mixture was cooled to 0° C. with stirring. To the cooled mixture was added acetic anhydride (2.5 g, 25 mmol) drop-wise over 2 minutes. The reaction mixture was warmed to 25° C. and stirred for 1 hour. At this point, the reaction was heated at 60° C. Isoamylnitrite (1.9 g, 2.2 mL, 16 mmol) was added and the reaction was stirred overnight at 60° C. The crude reaction mixture was washed with saturated NaHCO₃. The solvent was removed under reduced pressure and the crude product was purified by silica gel chromatography (ISCO 40 g silica) and eluted with EtOAc/heptane (0-30%) and gave the N-acetyl indazole as an orange solid (1.5 g). The solid was dissolved in THF (8 mL) and water (5 mL) and cooled to 0° C. Next, 2 M NaOH (8.3 mL) was added and the reaction was stirred at 0° C. for 2 hours. The crude reaction mixture was diluted with EtOAc and water. The organic layer was washed with brine, dried over Na₂SO₄, filtered and concentrated under reduced pressure and dried overnight under house vacuum and gave 4-bromo-5,6-dimethyl-1H-indazole (65) as a brown solid (1.1 g, 59% yield). LCMS (APCI) m/z 225 (M+H).

Step 4:

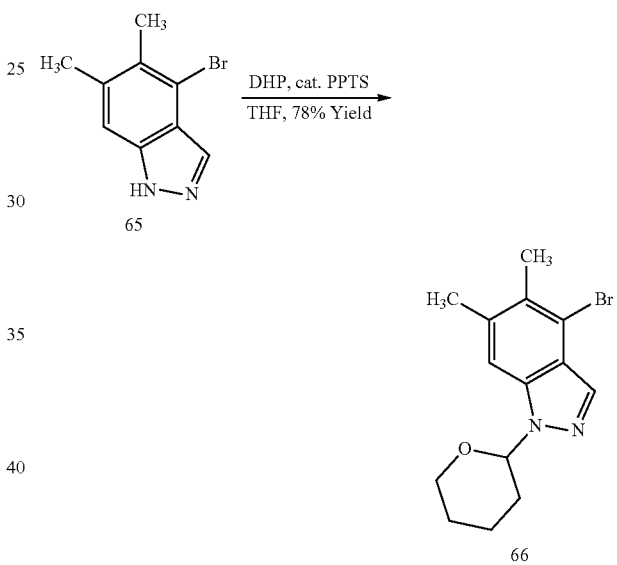

4-Bromo-5,6-dimethyl-1-(tetrahydro-2H-pyran-2-yl)-1H-indazole (66) (1.1 g, 76% yield) was prepared according to the procedure used to prepare 4-bromo-5-methyl-1-(tetrahydro-2H-pyran-2-yl)-1H-indazole (24) where the reaction was done in THF at 50° C.

Step 5:

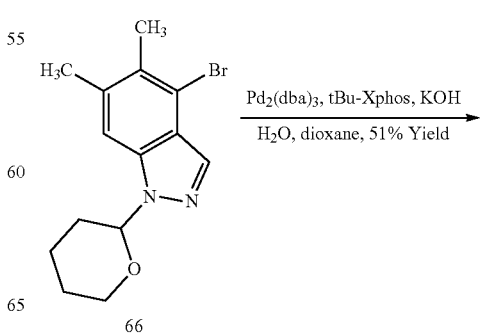

-continued

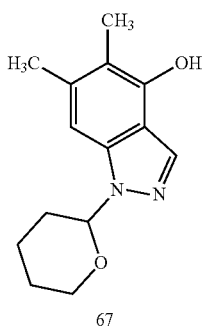

67

5,6-Dimethyl-1-(tetrahydro-2H-pyran-2-yl)-1H-indazol-4-ol (67) (463 mg, 51% yield) was prepared according to the procedure used to prepare 5-methyl-1-(tetrahydro-2H-pyran-2-yl)-1H-indazol-4-ol (25). LCMS (ESI) m/z 247 (M+H).

Preparation of 5-chloro-6-fluoro-1-(tetrahydro-2H-pyran-2-yl)-1H-indazol-4-ol (72)

Step 1:

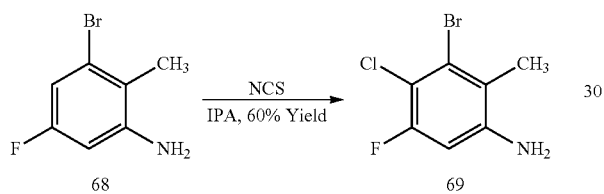

To a solution of 3-bromo-5-fluoro-2-methylbenzenamine (68) (10 g, 49 mmol) in IPA (70 mL) was added NCS (7.2 g, 54 mmol) and the dark solution stirred at 80° C. for 2 hours. The mixture was concentrated under reduced pressure and the crude product was purified by silica gel column chromatography using an ISCO cartridge (220 g) and eluted with EtOAc/heptane (15:85) and gave 3-bromo-4-chloro-5-fluoro-2-methylaniline (69) as yellow solid (5.7 g, 49% yield). $^1$H NMR (400 MHz, DMSO-$d_6$) δ 6.62 (d, J=11.6 Hz, 1H), 5.66 (br. s, 2H), 2.18 (d, J=0.9 Hz, 3H). LCMS (ESI) m/z 237.

Step 2:

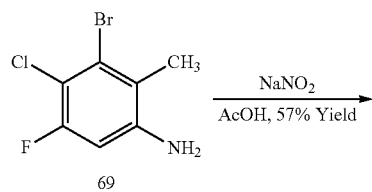

To a solution of 3-bromo-4-chloro-5-fluoro-2-methylaniline (69) (4 g, 16.8 mmol) in AcOH (20 mL), was added NaNO$_2$ (1.5 g, 22 mmol). The reaction was stirred at room temperature for 7 hours. LCMS analysis showed the reaction complete. The mixture was concentrated under reduced pressure and the crude product was purified by silica gel flash chromatography and eluted with EtOAc/petroleum ether (20:80) and gave 4-bromo-5-chloro-6-fluoro-1H-indazole (70) as yellow solid (2.4 g, 57% yield). $^1$H NMR (400 MHz, DMSO-$d_6$) ppm 13.68 (br. s, 1H), 8.10 (s, 1H), 7.69 (dd, J=0.9, 9.1 Hz, 1H). LCMS (ESI) m/z 249 (M+H).

Step 3:

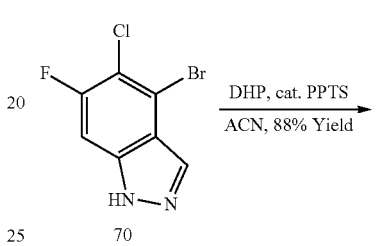

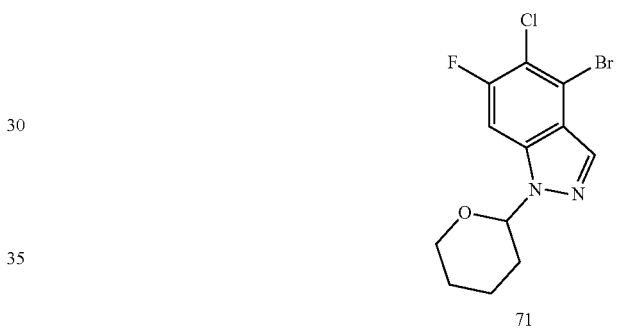

4-Bromo-5-chloro-6-fluoro-1-(tetrahydro-2H-pyran-2-yl)-1H-indazole (71) (819 mg, 88% yield) was prepared according to the procedure used to prepare 4-bromo-5-methyl-1-(tetrahydro-2H-pyran-2-yl)-1H-indazole (24), except acetonitrile was used as the solvent. $^1$H NMR (400 MHz, CDCl$_3$) δ 7.98 (d, J=0.6 Hz, 1H), 7.40 (dd, J=0.9, 8.6 Hz, 1H), 5.65 (dd, J=2.6, 8.9 Hz, 1H), 4.06-3.94 (m, 1H), 3.85-3.65 (m, 1H), 2.57-2.35 (m, 1H), 2.23-1.99 (m, 2H), 1.86-1.62 (m, 3H). LCMS (ESI) m/z 333 (M+H).

Step 4:

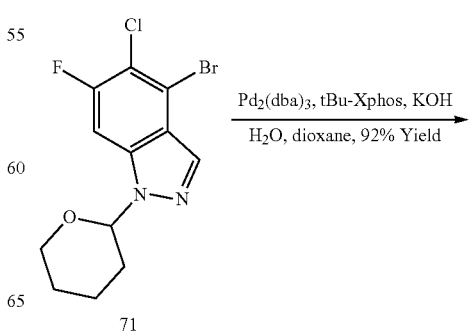

-continued

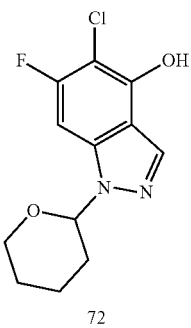

72

5-Chloro-6-fluoro-1-(tetrahydro-2H-pyran-2-yl)-1H-indazol-4-ol (72) (612 mg, 92% yield) was prepared according to the procedure used to prepare 5-methyl-1-(tetrahydro-2H-pyran-2-yl)-1H-indazol-4-ol (25). $^1$H NMR (400 MHz, CDCl$_3$) δ 8.07 (s, 1H), 6.99 (dd, J=0.7, 8.8 Hz, 1H), 5.60 (dd, J=2.6, 9.2 Hz, 1H), 4.08-3.98 (m, 1H), 3.81-3.68 (m, 1H), 2.58-2.43 (m, 1H), 2.21-2.07 (m, 2H), 1.85-1.60 (m, 3H). LCMS (ESI) m/z 187 [M-THP+H].

Preparation of 3,5-dimethyl-1-(tetrahydro-2H-pyran-2-yl)-1H-indazol-4-ol (76)

Step 1:

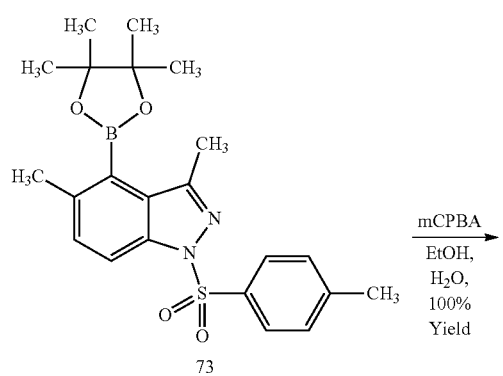

To a solution of 3,5-dimethyl-1-[(4-methylphenyl)sulfonyl]-4-(4,4,5,5-tetramethyl-1,3,2-dioxaborolan-2-yl)-1H-indazole (73) (450 mg, 1.1 mmol) in EtOH (12 mL) was added mCPBA (273 mg, 1.6 mmol) and water (6 mL). The reaction was stirred at 20° C. for 3 hours. LCMS analysis showed the reaction was finished. The crude reaction mixture was diluted with EtOAc (30 mL), washed with saturated NaHCO$_3$ and brine, dried over Na$_2$SO$_4$, filtered and concentrated. The crude product was purified over silica gel which was eluted with 0-90% EtOAc/petroleum ether and gave 3,5-dimethyl-1-[(4-methylphenyl)sulfonyl]-1H-indazol-4-ol (74) as a yellow solid (370 mg, 100% yield). $^1$H NMR (400 MHz, DMSO-d$_6$) δ 9.45 (s, 1H), 7.71 (d, J=8.4 Hz, 2H), 7.41 (d, J=8.4 Hz, 1H), 7.35 (d, J=8.1 Hz, 2H), 7.30 (d, J=8.4 Hz, 1H), 2.53 (s, 3H), 2.31 (s, 3H), 2.23 (s, 3H). LCMS (ESI) m/z 317 (M+H).

Step 2:

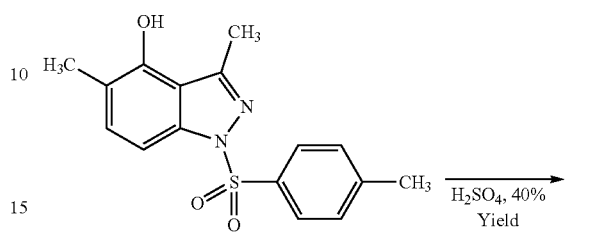

A mixture of 3,5-dimethyl-1-[(4-methylphenyl)sulfonyl]-1H-indazol-4-ol (74) (400 mg, 1.3 mmol) in H$_2$SO$_4$ (70%, 10 mL) was stirred at room temperature for 48 hours. LCMS analysis showed the desired compound was observed, and some starting material remained. The crude reaction mixture was diluted with ice water and adjusted to pH 6 with a solution of NaOH. The aqueous layer was extracted with EtOAc (5×30 mL), and the combined organic layers were washed with water, dried over Na$_2$SO$_4$, filtered and concentrated. The crude product was purified over silica gel and eluted with 0-55% EtOAc/petroleum ether and gave 3,5-dimethyl-1H-indazol-4-ol (75) as a yellow solid (90 mg, 40% yield). $^1$H NMR (400 MHz, DMSO-d$_6$) δ 12.23 (s, 1H), 8.70 (s, 1H), 6.96 (s, 1H), 6.77 (d, J=8.3 Hz, 1H), 2.56 (s, 3H), 2.21 (s, 3H). LCMS (ESI) m/z 163 (M+H).

Step 3:

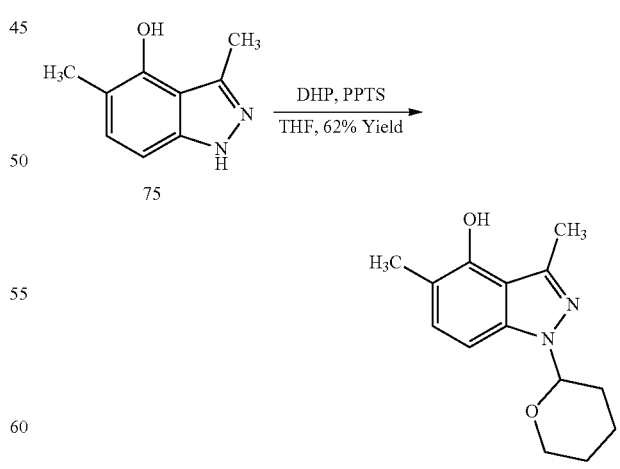

3,5-Dimethyl-1-(tetrahydro-2H-pyran-2-yl)-1H-indazol-4-ol (76) (80 mg, 61% yield) was prepared according to the procedure used to prepare 4-bromo-5-methyl-1-(tetrahydro- 2H-pyran-2-yl)-1H-indazole (24) except the reaction was done in THF at reflux. LCMS (ESI) m/z 247 (M+H).

Preparation of 5,7-difluoro-6-methyl-1-(tetrahydro-2H-pyran-2-yl)-1H-indazol-4-ol (84)

Step 1:

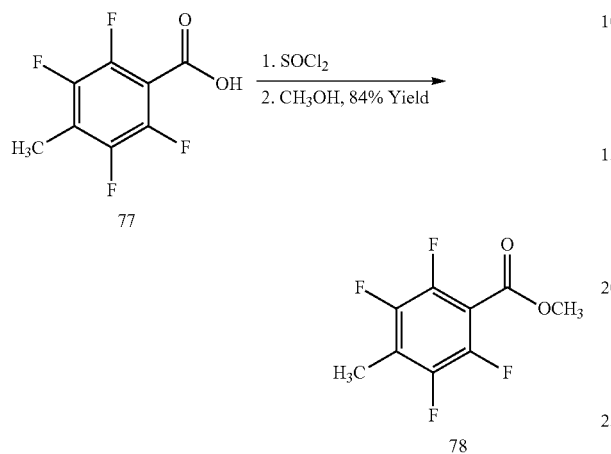

A mixture of 2,3,5,6-tetrafluoro-4-methylbenzoic acid (77) (2.0 g, 9.6 mmol) in SOCl₂ (10 mL) was stirred at reflux for 2 hours. The crude reaction mixture was concentrated and the solvent removed under reduced pressure. The crude product was dissolved in methanol (30 mL) and the reaction was stirred at room temperature for 1 hour. The crude reaction mixture was concentrated and the crude product was purified using silica gel flash chromatography and eluted with 5% EtOAc/petroleum ether which gave methyl 2,3,5,6-tetrafluoro-4-methylbenzoate (78) as a colorless oil (1.8 g, 84% yield). ¹H NMR (400 MHz, CDCl₃) δ 3.97 (s, 3H), 2.32 (t, J=2.1 Hz, 3H).

Step 2:

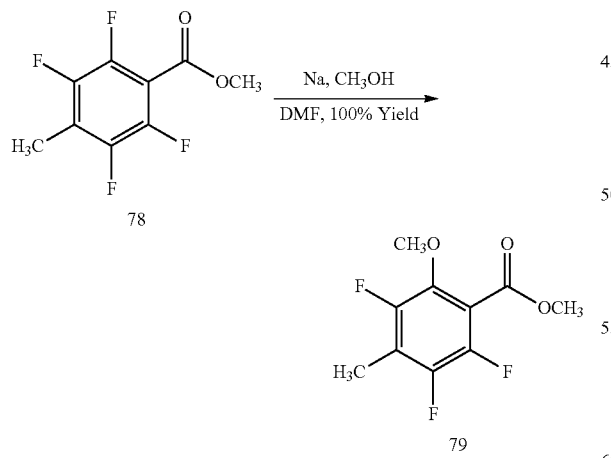

To a solution of sodium (146 mg, 6.4 mmol) in dry methanol (2 mL) was added methyl 2,3,5,6-tetrafluoro-4-methylbenzoate (78) (940 mg, 4.2 mmol) and DMF (5 mL). The resulting mixture was stirred at room temperature for 1 hour. TLC showed the starting material was consumed. The reaction was quenched with 1 N HCl at 0° C., and the aqueous layer was extracted with EtOAc (2×30 mL). The combined organic extracts were washed with brine, dried over Na₂SO₄, filtered and concentrated and gave methyl 2,3,5-trifluoro-6-methoxy-4-methylbenzoate (79) as a colorless oil (991 mg, 100% yield). ¹H NMR (400 MHz, CDCl₃) δ 3.95 (s, 3H), 3.93 (d, J=1.4 Hz, 3H), 2.26 (t, J=2.2 Hz, 3H). LCMS (ESI) m/z 235 (M+H).

Step 3:

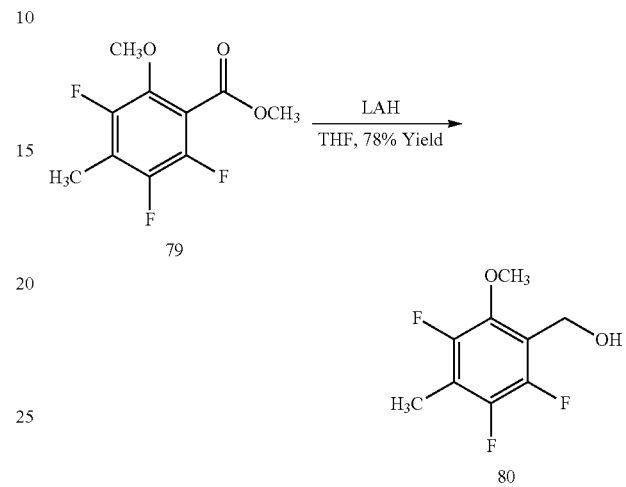

To a solution of methyl 2,3,5-trifluoro-6-methoxy-4-methylbenzoate (79) (996 mg, 4.2 mmol) in dry THF (10 mL) was added LiAlH₄ (323 mg, 8.5 mmol) at −10° C. The resulting mixture was stirred at −10° C. for 30 minutes. TLC showed all starting material was consumed. The reaction was quenched with 1 N HCl at 0° C., and the aqueous layer was extracted with EtOAc (2×20 mL). The combined EtOAc layers were concentrated and the crude product was purified using silica gel flash chromatography which was eluted with 12% EtOAc/petroleum ether and gave (2,3,5-trifluoro-6-methoxy-4-methylphenyl)methanol (80) as a white solid (680 mg, 78% yield). ¹H NMR (400 MHz, CDCl₃) δ 4.75 (d, J=1.8 Hz, 2H), 3.97 (d, J=1.8 Hz, 3H), 2.24 (t, J=2.2 Hz, 3H). LCMS (ESI) m/z 189 (M−OH).

Step 4:

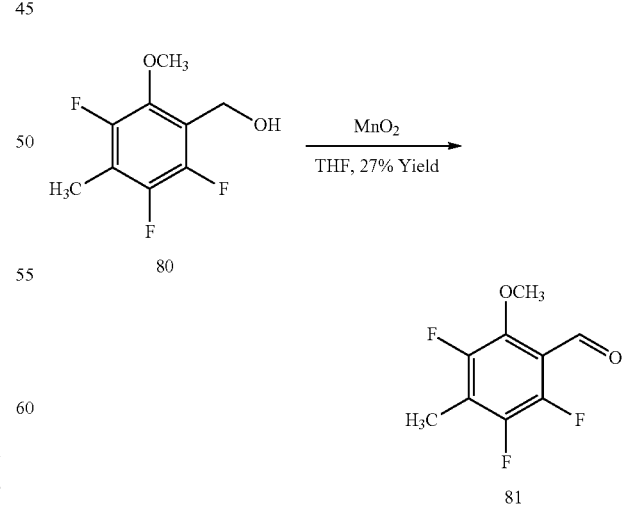

To a mixture of (2,3,5-trifluoro-6-methoxy-4-methylphenyl)methanol (80) (680 mg, 3.3 mmol) in THF (30 mL) was added MnO$_2$ (2.9 g, 33 mmol), and the resulting mixture was stirred at 48° C. overnight. The reaction mixture was filtered through Celite, and the filtrate was concentrated and purified using silica gel flash chromatography and eluted with 2% EtOAc/petroleum ether and gave 2,3,5-trifluoro-6-methoxy-4-methylbenzaldehyde (81) as a white solid (180 mg, 27% yield). $^1$H NMR (400 MHz, CDCl$_3$) δ 10.31 (s, 1H), 4.02 (d, J=2.0 Hz, 3H), 2.31 (t, J=2.3 Hz, 3H). LCMS (ESI) m/z 205 (M+H).

Step 5:

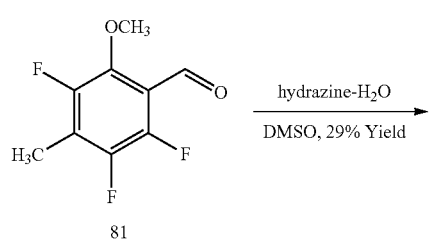

5,7-Difluoro-4-methoxy-6-methyl-1H-indazole (82) (512 mg, 29% yield) was prepared according to the procedure used to prepare 5-bromo-4-methoxy-H-indazole (33). $^1$H NMR (400 MHz, DMSO-d$_6$) δ 13.62 (s, 1H), 8.32 (d, J=1.9 Hz, 1H), 4.09 (s, 3H), 2.27 (t, J=2.2 Hz, 3H). LCMS (ESI) m/z 199 (M+H).

Step 6:

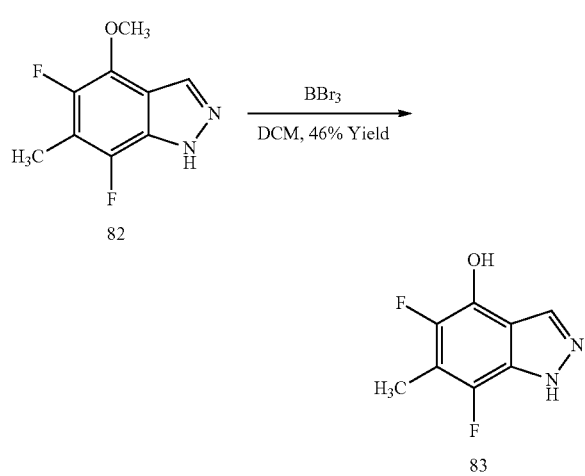

To 5,7-difluoro-4-methoxy-6-methyl-1H-indazole (82) (650 mg, 3.3 mmol) was added BBr$_3$ in DCM (5 mL) at −40° C. The crude reaction mixture was stirred at room temperature for 1 hour. TLC showed all of the starting material was consumed. The reaction was quenched with saturated NaHCO$_3$ solution at 0° C. The aqueous layer was extracted with EtOAc (3×50 mL), and the combined organic layers were washed with water (50 mL), dried over Na$_2$SO$_4$, filtered and concentrated. The crude product was purified using silica gel flash chromatography and eluted with 30% EtOAc/petroleum ether and gave 5,7-difluoro-6-methyl-1H-indazol-4-ol (83) as a red solid (279 mg, 46% yield). $^1$H NMR (400 MHz, DMSO-d$_6$) δ 13.40 (s, 1H), 10.13 (s, 1H), 8.20-8.15 (m, 1H), 2.26 (t, J=2.1 Hz, 3H). LCMS (ESI) m/z 185 (M+H).

Step 7:

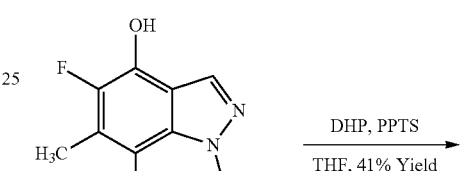

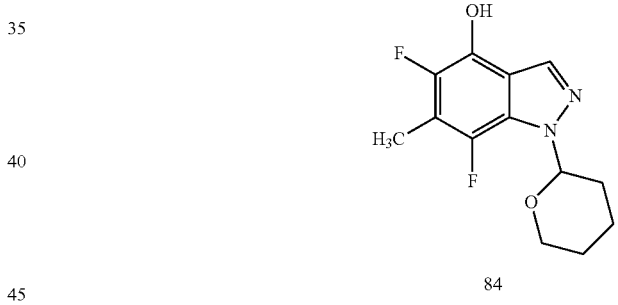

5,7-Difluoro-6-methyl-1-(tetrahydro-2H-pyran-2-yl)-1H-indazol-4-ol (84) (160 mg, 41% yield) was prepared according to the procedure used to prepare 4-bromo-5-methyl-1-(tetrahydro-2H-pyran-2-yl)-1H-indazole (24) except the reaction was done in THF at reflux. $^1$H NMR (400 MHz, DMSO-d$_6$) δ 10.31 (s, 1H), 8.20 (d, J=2.0 Hz, 1H), 5.75 (dd, J=9.8, 1.8 Hz, 1H), 3.89 (d, J=12.0 Hz, 1H), 3.62 (ddd, J=11.5, 8.3, 4.6 Hz, 1H), 2.38 (dt, J=14.4, 6.4 Hz, 1H), 2.26 (t, J=2.4 Hz, 3H), 2.01 (m, 2H), 1.71 (m, 1H), 1.54 (dd, J=11.0, 7.3 Hz, 2H). LCMS (ESI) m/z 291 (M+Na).

Preparation of Examples

The following examples were prepared according to Method A:

201

Preparation of 1-(4-{8-[(5-methyl-1H-indazol-4-yl)oxy]pyrido[3,4-d]pyrimidin-4-yl}piperazin-1-yl)prop-2-en-1-one (Example-1A)

Step 1:

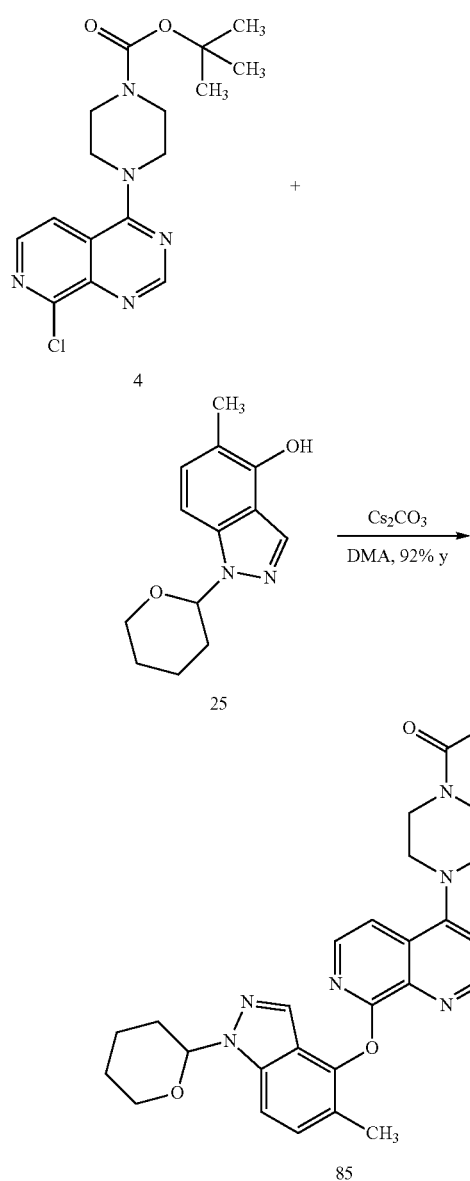

To a vial was added 5-methyl-1-(tetrahydro-2H-pyran-2-yl)-1H-indazol-4-ol phenol (25) (398 mg, 1.74 mmol), tert-butyl 4-(8-chloropyrido[3,4-d]pyrimidin-4-yl)piperazine-1-carboxylate (4) (500 mg, 1.43 mmol), cesium carbonate (931 mg, 2.86 mmol) and DMA (3.6 mL). The mixture was degassed, purged with nitrogen and placed in a sand bath at 90° C. After 4.5 hours, LCMS gave mostly product and no aryl chloride. The reaction was cooled to room temperature and added drop-wise to water (50 mL). Tert-butyl 4-(8-{[5-methyl-1-(tetrahydro-2H-pyran-2-yl)-1H-indazol-4-yl]oxy}pyrido[3,4-d]pyrimidin-4-yl)piperazine-1-carboxylate

202

(85) was collected as a white solid (720 mg, 92% yield). $^1$H NMR (400 MHz, DMSO-d$_6$) δ 1.37-1.49 (m, 9H), 1.53-1.64 (m, 2H), 1.68-1.83 (m, 1H), 1.88-2.09 (m, 2H), 2.17 (s, 3H), 2.29-2.44 (m, 1H), 3.57 (br. s, 4H), 3.69-3.80 (m, 1H), 3.80-3.87 (m, 4H), 3.89-3.91 (m, 1H), 5.83-5.86 (m, 1H), 7.38 (d, J=8.8 Hz, 1H), 7.50-7.61 (m, 2H), 7.65 (s, 1H), 7.87 (d, J=5.9 Hz, 1H), 8.82 (s, 1H). LCMS (ESI) m/z 545 (M+H).

Step 2:

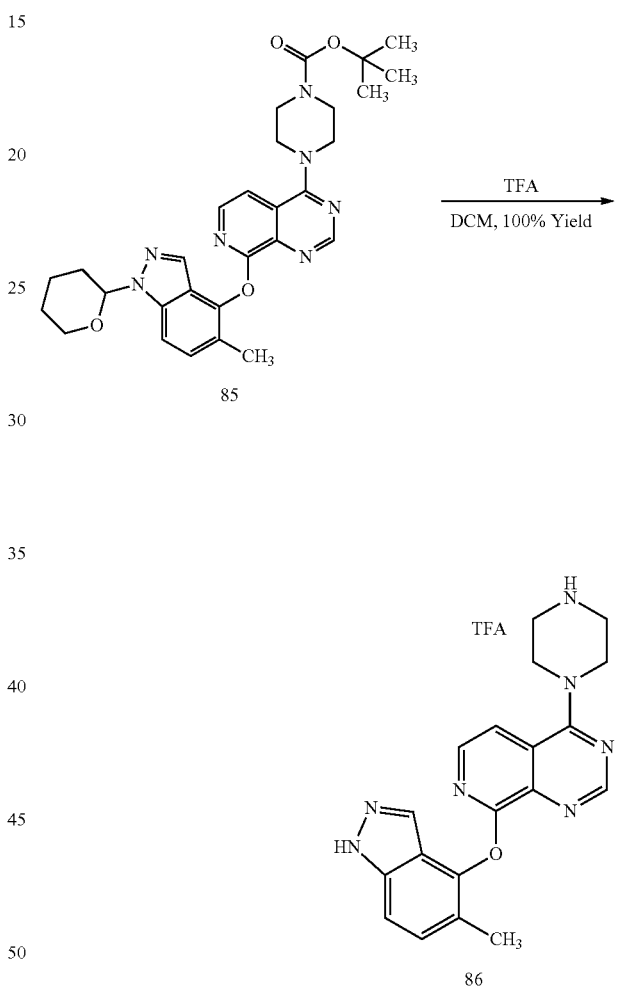

To a solution of tert-butyl 4-(8-{[5-methyl-1-(tetrahydro-2H-pyran-2-yl)-1H-indazol-4-yl]oxy}pyrido[3,4-d]pyrimidin-4-yl)piperazine-1-carboxylate (85) (1.1 g, 2.0 mmol) in DCM (10 mL) was added TFA (2 mL). The mixture was stirred at room temperature for 4 hours. LCMS indicated the starting material was consumed and the desired product was formed. The solvent was removed under reduced pressure and gave 8-[(5-methyl-1H-indazol-4-yl)oxy]-4-(piperazin-1-yl)pyrido[3,4-d]pyrimidine (86) as a brown oil (730 mg, 100% yield). LCMS (ESI) m/z 362 (M+H).

Step 3:

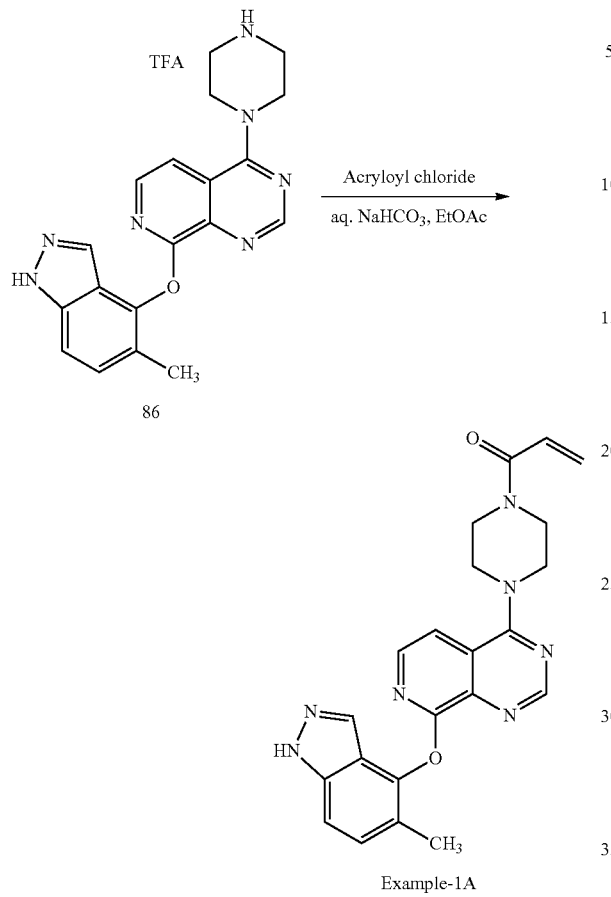

Preparation of tert-butyl 4-(6-cyano-8-{[5-methyl-1-(tetrahydro-2H-pyran-2-yl)-1H-indazol-4-yl]oxy}pyrido[3,4-d]pyrimidin-4-yl)piperazine-1-carboxylate (88)

Step 1:

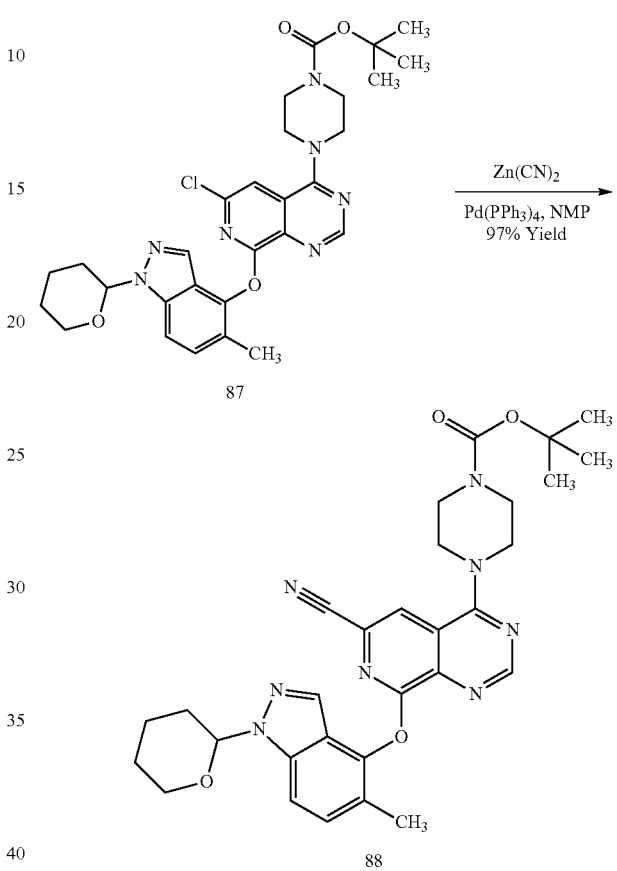

To a stirred solution of 8-[(5-methyl-1H-indazol-4-yl)oxy]-4-(piperazin-1-yl)pyrido[3,4-d]pyrimidine (86) (500 mg, 1.38 mmol) in saturated aqueous NaHCO$_3$ (50 mL) and EtOAc (50 mL) was added a solution of acryloyl chloride (125 mg, 1.38 mmol) in EtOAc (20 mL). After the addition, the mixture was stirred at room temperature for 30 minutes. LCMS indicated the starting material was consumed and the desired product was formed. The organic layer was separated. The aqueous layer was extracted with EtOAc (2×80 mL). The combined organic layers were dried over Na$_2$SO$_4$, filtered and concentrated under reduced pressure. The crude product was purified by silica gel column chromatography using a Biotage C18 column (30 g) and eluted using 25-40% acetonitrile/H$_2$O (0.1% NH$_3$) gradient at 25 mL/min, and gave 1-(4-{8-[(5-methyl-1H-indazol-4-yl)oxy]pyrido[3,4-d]pyrimidin-4-yl}piperazin-1-yl)prop-2-en-1-one (Example-1A) as a yellow solid (202 mg, 35% yield). $^1$H NMR (400 MHz, CDCl$_3$) δ 8.98 (s, 1H), 7.96 (d, J=5.9 Hz, 1H), 7.75 (s, 1H), 7.34 (s, 2H), 7.31 (d, J=5.9 Hz, 1H), 6.62 (dd, J=16.8, 10.5 Hz, 1H), 6.39 (dd, J=16.8, 1.7 Hz, 1H), 5.80 (dd, J=10.5, 1.7 Hz, 1H), 3.90 (s, 4H), 3.80 (s, 4H), 2.31 (s, 3H). LCMS (ESI) m/z 416 (M+H).

The intermediates detailed in the following preparation afford Examples-18A, -19A, -27A, -28A, -32A, and -33A according to Method A. However, these examples fall outside of the synthetic scope of preceding examples due to the nitrile inclusion and, thus, this preparation is included here for completeness. Subsequent chemistry to afford final examples is similar to the Method A examples, with minimal additions or changes that one skilled in the art can appreciate.

A mixture of tert-butyl 4-(6-chloro-8-{[5-methyl-1-(tetrahydro-2H-pyran-2-yl)-1H-indazol-4-yl]oxy}pyrido[3,4-d]pyrimidin-4-yl)piperazine-1-carboxylate (87) (100 mg, 0.17 mmol, prepared using method A), Zn(CN)$_2$ (40 mg, 0.34 mmol), dppf (19 mg, 0.034 mmol), and Pd$_2$(dba)$_3$ (16 mg, 0.017 mmol) in NMP (10 mL) was heated at 150° C. in microwave for 1.5 hours under nitrogen. LCMS of the crude reaction mixture indicated that the starting material was consumed and the desired product was formed. After cooling, water (50 mL) was added and the aqueous layer was extracted with EtOAc (3×60 mL). The combined organic layers were washed with brine, dried over Na$_2$SO$_4$, filtered and concentrated under reduced pressure. The crude product was purified using silica gel (4 g) and eluted with 4% methanol/DCM and gave tert-butyl 4-(6-cyano-8-{[5-methyl-1-(tetrahydro-2H-pyran-2-yl)-1H-indazol-4-yl]oxy}pyrido[3,4-d]pyrimidin-4-yl)piperazine-1-carboxylate (88) as a yellow solid (95 mg, 97% yield). $^1$H NMR (400 MHz, DMSO-d$_6$) δ 8.89 (s, 1H), 8.26 (s, 1H), 7.76 (s, 1H), 7.63 (d, J=8.6 Hz, 1H), 7.42 (d, J=8.6 Hz, 1H), 5.87 (dd, J=9.7, 2.0 Hz, 1H), 4.01-3.93 (m, 4H), 3.89 (s, 1H), 3.77 (d, J=12.4, 5.8 Hz, 1H), 3.57 (m, 4H), 2.42-2.35 (m, 1H), 2.16 (s, 3H), 2.01 (d, J=13.8 Hz, 2H), 1.74 (d, J=7.5 Hz, 1H), 1.59 (s, 2H), 1.44 (s, 9H). LCMS (ESI) m/z 571 (M+H).

The intermediates detailed in the following preparation afford example 38A according to method A. However, this example falls outside of the synthetic scope of the preceding examples due to the deprotection step and, thus, this preparation is included here for completeness. Subsequent chemistry to afford final examples is similar to the Method A examples, with minimal additions or changes that one skilled in the art can appreciate.

Preparation of 1-[(3R)-4-{6-chloro-8-[(5-chloro-6-fluoro-1H-indazol-4-yl)oxy]pyrido[3,4-d]pyrimidin-4-yl}-3-(hydroxymethyl)piperazin-1-yl]prop-2-en-1-one (Example-38A)

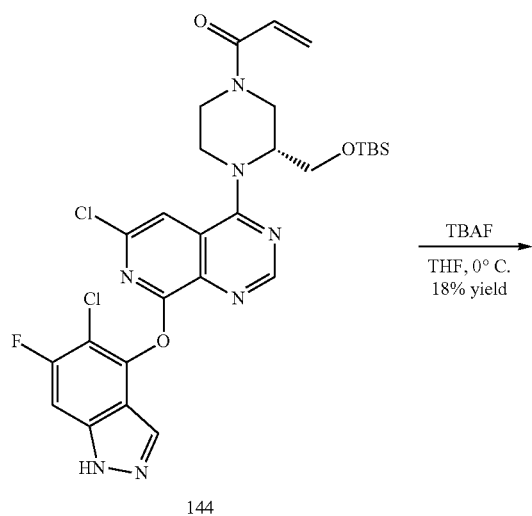

To a solution of 1-[(3R)-3-({[tert-butyl(dimethyl)silyl]oxy}methyl)-4-{8-[(5-chloro-6-fluoro-1H-indazol-4-yl)oxy]pyrido[3,4-d]pyrimidin-4-yl}piperazin-1-yl]prop-2-en-1-one (144) (300 mg, 0.474 mmol) in THF (20 mL) was added a solution of TBAF (1.0 M in THF, 0.95 mL, 0.95 mmol) slowly at 0° C. After addition the reaction was stirred for another 2 h at 0-5° C. LCMS analysis showed the completion of the reaction. Saturated aq. NaHCO₃ (50 mL) was added. The mixture was extracted with EtOAc (50 mL). The organic layer was washed with brine, dried over Na₂SO₄, and concentrated. The crude residue was purified by prep-HPLC using an Xbridge 150×19 mm, 5 μm column and eluted with 28-33% acetonitrile/H₂O (0.05% NH₄OH), at 20 mL/min to provide 1-[(3R)-4-{6-chloro-8-[(5-chloro-6-fluoro-1H-indazol-4-yl)oxy]pyrido[3,4-d]pyrimidin-4-yl}-3-(hydroxymethyl)piperazin-1-yl]prop-2-en-1-one (Example-38A) (45 mg, 18% yield). $^1$H NMR (400 MHz, DMSO-$d_6$) δ 13.62 (s, 1H), 8.80 (s, 1H), 8.12-7.86 (m, 2H), 7.65 (dd, J=8.8, 1.1 Hz, 1H), 6.82 (ddd, J=26.0, 16.5, 10.7 Hz, 1H), 6.17 (d, J=17.8 Hz, 1H), 5.74 (dd, J=10.4, 2.3 Hz, 1H), 5.12 (d, J=31.4 Hz, 1H), 4.76 (d, J=23.6 Hz, 1H), 4.39 (t, J=15.8 Hz, 1H), 4.30 (d, J=13.5 Hz, 1H), 4.14 (d, J=14.1 Hz, 1H), 3.75 (ddd, J=11.2, 8.5, 4.9 Hz, 1H), 3.67-3.48 (m, 2H), 3.12 (d, J=14.2 Hz, 1H), 2.97 (t, J=11.6 Hz, 1H). LCMS (ESI) m/z 518 (M+H).

The intermediates detailed in the following preparation afford Example 41A according to method A. However, this example falls outside of the synthetic scope of the preceding examples due to the animation and, thus, this preparation is included here for completeness. Subsequent chemistry to afford final examples is similar to the Method A examples, with minimal additions or changes that one skilled in the art can appreciate.

Preparation of tert-butyl 4-(6-amino-8-{[5-methyl-1-(tetrahydro-2H-pyran-2-yl)-1H-indazol-4-yl]oxy}pyrido[3,4-d]pyrimidin-4-yl)piperazine-1-carboxylate (146)

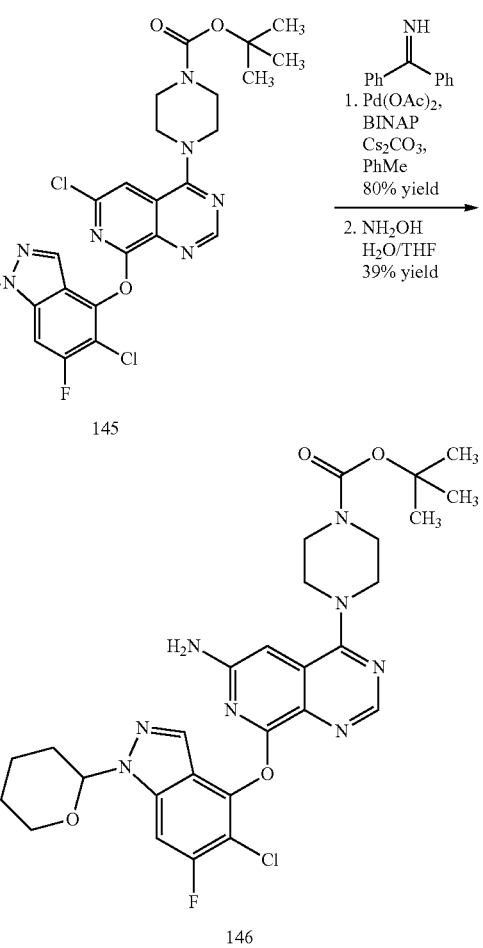

Step 1:

To tert-butyl 4-(6-chloro-8-{[5-chloro-6-fluoro-1-(tetrahydro-2H-pyran-2-yl)-1H-indazol-4-yl]oxy}pyrido[3,4-d]pyrimidin-4-yl)piperazine-1-carboxylate (145) (300 mg, 0.485 mmol), $Cs_2CO_3$ (484 mg, 1.46 mmol), (+/−) BINAP (31.5 mg, 0.0485 mmol), and $Pd(OAc)_2$ (5.73 mg, 0.0243 mmol) in toluene (9.7 mL) was added benzophenone imine (237 mg, 1.31 mmol). The resultant brown solution was degassed and purged with nitrogen (3×) and placed into a preheated oil bath at 100° C. The crude reaction mixture was heated at 100° C. for 24 h. The reaction was analyzed by LCMS, which showed conversion to the product. The crude reaction mixture was diluted with EtOAc (20 mL) and 50% brine. The layers were separated and the aqueous layer was extracted with EtOAc (2×20 mL). The combined organics were washed with brine, dried over $MgSO_4$, filtered and concentrated. The crude product was and purified by chromatography (25 g $SiO_2$, Biotage, 10-50% EtOAc/heptane) to provide tert-butyl 4-(6-[(diphenylmethylidene)amino]-8-{[5-methyl-1-(tetrahydro-2H-pyran-2-yl)-1H-indazol-4-yl]oxy}pyrido[3,4-d]pyrimidin-4-yl)piperazine-1-carboxylate (295 mg, 80% yield). $^1$H NMR (400 MHz, DMSO-$d_6$) 1.43 (s, 9H), 1.58 (br. s, 2H), 1.66-1.79 (m, 1H), 1.95-2.06 (m, 2H), 2.29-2.41 (m, 1H), 3.41 (s, 8H), 3.72-3.81 (m, 1H), 3.88 (d, J=11.4 Hz, 1H), 5.88 (dd, J=9.6, 2.1 Hz, 1H), 6.62 (s, 1H), 6.99 (dd, J=7.7, 1.6 Hz, 2H), 7.24-7.35 (m, 3H), 7.39-7.47 (m, 2H), 7.50-7.61 (m, 3H), 7.88 (d, J=9.2 Hz, 1H), 7.93 (s, 1H), 8.65 (s, 1H).

Step 2:

To a solution of tert-butyl 4-(6-[(diphenylmethylidene)amino]-8-{[5-methyl-1-(tetrahydro-2H-pyran-2-yl)-1H-indazol-4-yl]oxy}pyrido[3,4-d]pyrimidin-4-yl)piperazine-1-carboxylate (275 mg, 0.36 mmol) in MeOH (1.8 mL) and THF (1.8 mL) was added 50% $NH_2OH$ in $H_2O$ (0.21 mL, 3.6 mmol). After 24 h the reaction was analyzed by LCMS analysis, which showed clean conversion to product. The crude reaction mixture was added dropwise to 60 mL $H_2O$. A yellow gum formed. The mixture was diluted with EtOAc (40 mL) and the layers separated. The aqueous layer was extracted with EtOAc (40 mL) and the combined organic layers were washed with saturated $NaHCO_3$, brine, dried over $MgSO_4$, filtered and concentrated. The crude product was purified over (Biotage, 10 g $SiO_2$, 5-60% EtOAc/heptane) to provide tert-butyl 4-(6-amino-8-{[5-methyl-1-(tetrahydro-2H-pyran-2-yl)-1H-indazol-4-yl]oxy}pyrido[3,4-d]pyrimidin-4-yl)piperazine-1-carboxylate (146) (84 mg, 39% yield) as a white solid. $^1$H NMR (400 MHz, DMSO-$d_6$) 1.44 (s, 9H), 1.58 (br. s, 2H), 1.68-1.79 (m, 1H), 1.99-2.09 (m, 2H), 2.27-2.41 (m, 1H), 3.55 (br. s, 4H), 3.62 (d, J=3.7 Hz, 4H), 3.72-3.82 (m, 1H), 3.85-3.93 (m, 1H), 5.86 (dd, J=9.8, 1.9 Hz, 1H), 6.11 (s, 2H), 6.45 (s, 1H), 7.84 (d, J=9.3 Hz, 1H), 7.88 (s, 1H), 8.44 (s, 1H).

Examples in the following table were prepared according to Method A and the procedure used to prepare 1-(4-{8-[(5-methyl-1H-indazol-4-yl)oxy]pyrido[3,4-d]pyrimidin-4-yl}piperazin-1-yl)prop-2-en-1-one (Example-1A), tert-butyl 4-(6-cyano-8-{[5-methyl-1-(tetrahydro-2H-pyran-2-yl)-1H-indazol-4-yl]oxy}pyrido[3,4-d]pyrimidin-4-yl)piperazine-1-carboxylate (88), and tert-butyl 4-(6-amino-8-{[5-methyl-1-(tetrahydro-2H-pyran-2-yl)-1H-indazol-4-yl]oxy}pyrido[3,4-d]pyrimidin-4-yl)piperazine-1-carboxylate (146). The following examples were made with non-critical changes or substitutions to the exemplified procedure used to prepare Example-1A, 88, and 146 that someone who is skilled in the art would be able to realize.

| Example | Structure | Compound Name | LCMS m/z | $^1$H NMR |
|---|---|---|---|---|
| 2A | 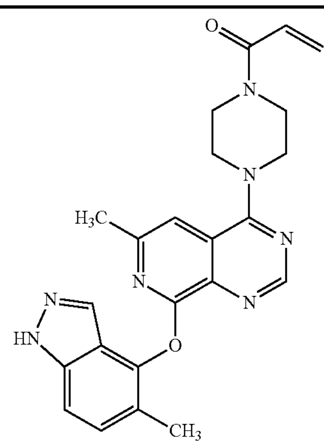 | 1-(4-{6-methyl-8-[(5-methyl-1H-indazol-4-yl)oxy]pyrido[3,4-d]pyrimidin-4-yl}piperazin-1-yl)prop-2-en-1-one | 430 (M + H) | $^1$H NMR (400 MHz, CDCl$_3$) δ 8.92 (s, 1H), 7.70 (s, 1H), 7.31 (s, 2H), 7.11 (s, 1H), 6.63 (dd, J = 16.8, 10.5 Hz, 1H), 6.39 (dd, J = 16.8, 1.8 Hz, 1H), 5.80 (dd, J = 10.5, 1.8 Hz, 1H), 3.87 (m, 8H), 2.33 (s, 3H), 2.31 (s, 3H). |

-continued

| Example | Structure | Compound Name | LCMS m/z | ¹H NMR |
|---|---|---|---|---|
| 3A | 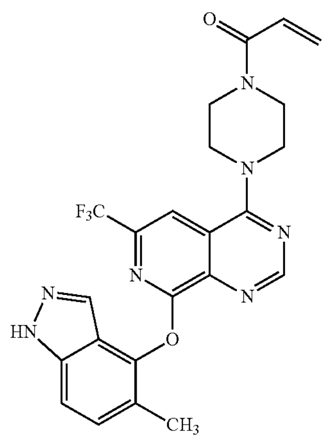 [SMILES: C=CC(=O)N1CCN(c2ncnc3c(Oc4c(C)ccc5[nH]ncc45)nc(C(F)(F)F)cc23)CC1] | 1-(4-{8-[(5-methyl-1H-indazol-4-yl)oxy]-6-(trifluoromethyl)pyrido[3,4-d]pyrimidin-4-yl}piperazin-1-yl)prop-2-en-1-one | 484 (M + H) | ¹H NMR (400 MHz, DMSO-d₆) δ 13.16 (s, 1H), 8.91 (s, 1H), 7.93 (s, 1H), 7.65 (s, 1H), 7.41 (d, J = 8.4 Hz, 1H), 7.33 (d, J = 8.5 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.03 (s, 4H), 3.81 (d, J = 31.9 Hz, 4H), 2.19 (s, 3H). |
| 4A | 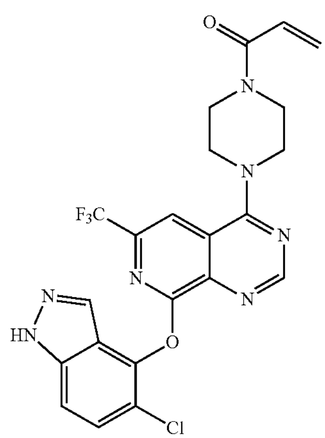 [SMILES: C=CC(=O)N1CCN(c2ncnc3c(Oc4c(Cl)ccc5[nH]ncc45)nc(C(F)(F)F)cc23)CC1] | 1-(4-{8-[(5-chloro-1H-indazol-4-yl)oxy]-6-(trifluoromethyl)pyrimido[3,4-d]pyrimidin-4-yl}piperazin-1-yl)prop-2-en-1-one | 504 (M + H) | ¹H NMR (400 MHz, DMSO-d₆) δ 13.49 (s, 1H), 8.91 (s, 1H), 7.99 (s, 1H), 7.84 (s, 1H), 7.54 (d, J = 2.8 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.04 (s, 4H), 3.70-3.90 (m, 4H). |
| 5A | 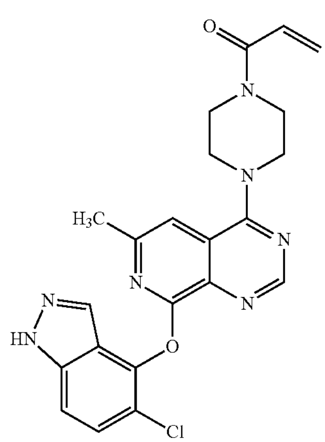 [SMILES: C=CC(=O)N1CCN(c2ncnc3c(Oc4c(Cl)ccc5[nH]ncc45)nc(C)cc23)CC1] | 1-(4-{8-[(5-chloro-1H-indazol-4-yl)oxy]-6-methylpyrido[3,4-d]pyrimidin-4-yl}piperazin-1-yl)prop-2-en-1-one | 450 (M + H) | ¹H NMR (400 MHz, DMSO-d₆) δ 13.43 (s, 1H), 8.77 (s, 1H), 7.75 (s, 1H), 7.50 (s, 2H), 7.45 (s, 1H), 6.85 (dd, J = 16.7, 10.5 Hz, 1H), 6.18 (dd, J = 16.7, 2.3 Hz, 1H), 5.75 (dd, J = 10.4, 2.3 Hz, 1H), 3.88 (d, J = 3.2 Hz, 4H), 3.90-3.70 (m, 4H), 2.28 (s, 3H). |

-continued

| Example | Structure | Compound Name | LCMS m/z | ¹H NMR |
|---|---|---|---|---|
| 6A | 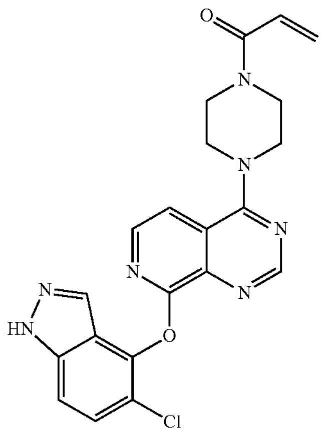 [SMILES: C=CC(=O)N1CCN(c2ncnc3c(Oc4c(Cl)ccc5[nH]ncc45)nccc23)CC1] | 1-(4-{8-[(5-chloro-1H-indazol-4-yl)oxy]pyrido[3,4-d]pyrimidin-4-yl}piperazin-1-yl)prop-2-en-1-one | 436 (M + H) | ¹H NMR (400 MHz, DMSO-d$_6$) δ 13.45 (s, 1H), 8.84 (s, 1H), 7.91 (d, J = 5.9 Hz, 1H), 7.79 (d, J = 1.5 Hz, 1H), 7.63 (d, J = 5.9 Hz, 1H), 7.56-7.37 (m, 2H), 6.84 (dd, J = 16.7, 10.5 Hz, 1H), 6.18 (dd, J = 16.7, 2.4 Hz, 1H), 5.75 (dd, J = 10.4, 2.4 Hz, 1H), 4.06-3.83 (m, 4H), 3.81 (d, J = 26.8 Hz, 4H). |
| 7A | 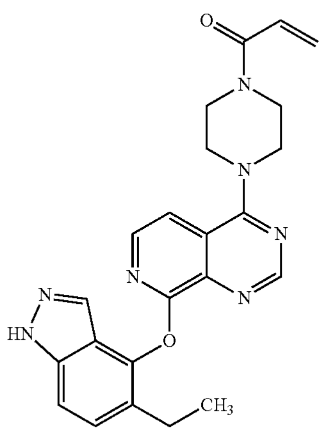 [SMILES: C=CC(=O)N1CCN(c2ncnc3c(Oc4c(CC)ccc5[nH]ncc45)nccc23)CC1] | 1-(4-{8-[(5-ethyl-1H-indazol-4-yl)oxy]pyrido[3,4-d]pyrimidin-4-yl}piperazin-1-yl)prop-2-en-1-one | 430 (M + H) | ¹H NMR (400 MHz, DMSO-d$_6$) δ 13.12 (s, 1H), 8.84 (s, 1H), 7.89 (d, J = 5.9 Hz, 1H), 7.58-7.54 (m, 2H), 7.41 (d, J = 8.6 Hz, 1H), 7.34 (d, J = 8.5 Hz, 1H), 6.84 (dd, J = 16.7, 10.5, 1H), 6.18 (dd, J = 16.7, 2.3 Hz, 1H), 5.75 (dd, J = 10.4, 2.3 Hz, 1H), 3.92 (s, 4H), 3.90-3.70 (m, 4H), 2.57 (dd, J = 15.1, 7.6 Hz, 2H), 1.10 (t, J = 7.5 Hz, 3H). |
| 8A | 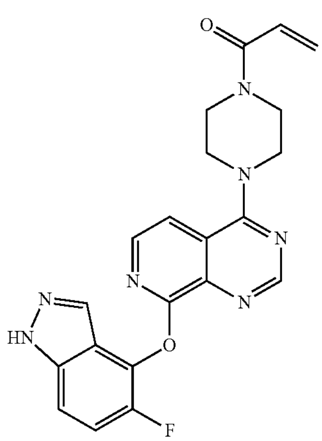 [SMILES: C=CC(=O)N1CCN(c2ncnc3c(Oc4c(F)ccc5[nH]ncc45)nccc23)CC1] | 1-(4-{8-[(5-fluoro-1H-indazol-4-yl)oxy]pyrido[3,4-d]pyrimidin-4-yl}piperazin-1-yl)prop-2-en-1-one | 420 (M + H) | ¹H NMR (700 MHz, DMSO-d$_6$) δ 13.37 (s, 1H), 8.82 (s, 1H), 7.93 (d, J = 5.8 Hz, 1H), 7.87 (s, 1H), 7.63 (d, J = 5.8 Hz, 1H), 7.49 (dd, J = 9.0, 3.3 Hz, 1H), 7.43 (t, J = 9.7 Hz, 1H), 6.83 (dd, J = 16.7, 10.4 Hz, 1H), 6.17 (dd, J = 16.6, 2.3 Hz, 1H), 5.74 (dd, J = 10.4, 2.3 Hz, 1H), 3.92 (s, 4H), 3.83 (s, 2H), 3.76 (s, 2H). |

| Example | Structure | Compound Name | LCMS m/z | ¹H NMR |
|---------|-----------|---------------|----------|--------|
| 9A | 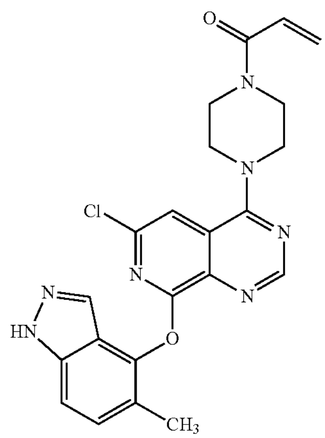 [SMILES: C=CC(=O)N1CCN(c2ncnc3c(Oc4c(C)ccc5[nH]ncc45)nc(Cl)cc23)CC1] | 1-(4-{6-chloro-8-[(5-methyl-1H-indazol-4-yl)oxy]pyrido[3,4-d]pyrimidin-4-yl}piperazin-1-yl)prop-2-en-1-one | 450 (M + H) | ¹H NMR (400 MHz, DMSO-d₆) δ 2.19 (s, 3H), 3.76 (s, 2H), 3.83 (m, 2H), 3.93 (br. s, 4H), 5.76 (dd, J = 16.6, 2.0 Hz, 1H), 6.18 (dd, J = 16.6, 2.3 Hz, 1H), 6.83 (dd, J = 16.8, 10.4 Hz, 1H), 7.33 (d, J = 8.6 Hz, 1H), 7.42 (d, J = 8.5 Hz, 1H), 7.61 (s, 1H), 7.67 (s, 1H), 8.81 (s, 1H), 13.19 (s, 1H). |
| 10A | 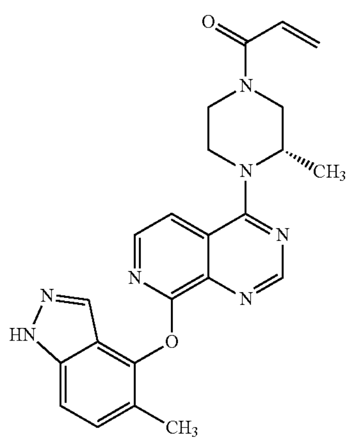 [SMILES: C=CC(=O)N1CCN(c2ncnc3c(Oc4c(C)ccc5[nH]ncc45)nccc23)[C@@H](C)C1] | 1-[(3S)-3-methyl-4-{8-[(5-methyl-1H-indazol-4-yl)oxy]pyrido[3,4-d]pyrimidin-4-yl}piperazin-1-yl]prop-2-en-1-one | 430 (M + H) | ¹H NMR (400 MHz, MeOD) δ 8.80 (s, 1H), 7.88 (d, J = 5.9 Hz, 1H), 7.65 (s, 1H), 7.51 (d, J = 5.9 Hz, 1H), 7.39 (dd, J = 18.5, 8.4 Hz, 2H), 6.83 (dd, J = 36.7, 13.8 Hz, 1H), 6.30 (d, J = 17.9 Hz, 1H), 5.82 (d, J = 9.7 Hz, 1H), 4.97 (s, 1H), 4.65-4.36 (m, 2H), 4.15-4.10 (m, 1H), 3.85-3.50 (m, 2H), 3.24-3.10 (m, 1H), 2.26 (s, 3H), 1.44 (d, J = 6.7 Hz, 3H). |
| 11A | 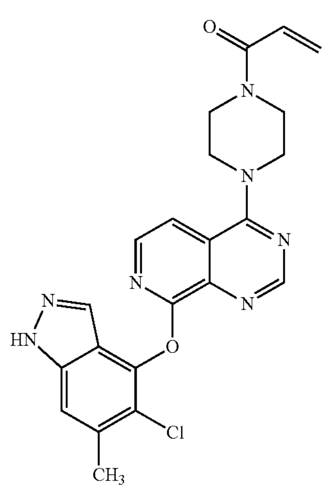 [SMILES: C=CC(=O)N1CCN(c2ncnc3c(Oc4c(Cl)c(C)cc5[nH]ncc45)nccc23)CC1] | 1-(4-{8-[(5-chloro-6-methyl-1H-indazol-4-yl)oxy]pyrido[3,4-d]pyrimidin-4-yl}piperazin-1-yl)prop-2-en-1-one | 450 (M + H) | ¹H NMR (400 MHz, MeOD) δ 8.80 (s, 1H), 7.90 (d, J = 5.9 Hz, 1H), 7.76 (d, J = 0.8 Hz, 1H), 7.62 (d, J = 5.9 Hz, 1H), 7.46 (s, 1H), 6.82 (dd, J = 16.8, 10.6 Hz, 1H), 6.28 (dd, J = 16.8, 1.9 Hz, 1H), 5.81 (dd, J = 10.6, 1.9 Hz, 1H), 4.10-4.00 (m, 4H), 3.92 (s, 4H), 2.55 (s, 3H). |

| Example | Structure | Compound Name | LCMS m/z | ¹H NMR |
|---------|-----------|---------------|----------|--------|
| 12A | 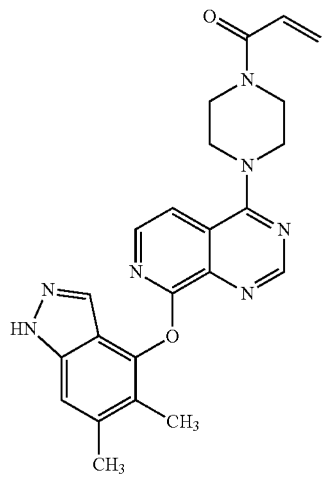 [SMILES: C=CC(=O)N1CCN(c2ncnc3c(Oc4c(C)c(C)cc5[nH]ncc45)nccc23)CC1] | 1-(4-{8-[(5,6-dimethyl-1H-indazol-4-yl)oxy]pyrido[3,4-d]pyrimidin-4-yl}piperazin-1-yl)prop-2-en-1-one | 430 (M + H) | ¹H NMR (400 MHz, DMSO-d₆) δ 12.96 (s, 1H), 8.83 (s, 1H), 7.87 (d, J = 5.9 Hz, 1H), 7.46-7.61 (m, 2H), 7.28 (s, 1H), 6.84 (dd, J = 16.8, 10.5 Hz, 1H), 6.17 (dd, J = 16.7, 2.4 Hz, 1H), 5.74 (dd, J = 10.4, 2.3 Hz, 1H), 3.91 (br. s, 4H), 3.83 (br. s, 2H), 3.77 (br. s, 2H), 2.41 (s, 3H), 2.07 (s, 3H). |
| 13A | 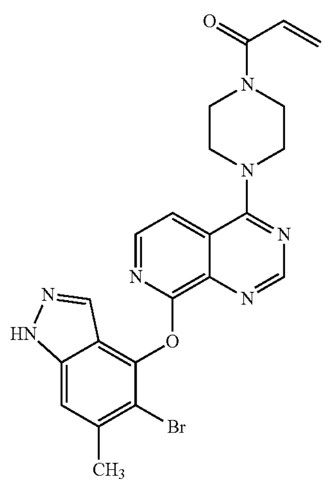 [SMILES: C=CC(=O)N1CCN(c2ncnc3c(Oc4c(Br)c(C)cc5[nH]ncc45)nccc23)CC1] | 1-(4-{8-[(5-bromo-6-methyl-1H-indazol-4-yl)oxy]pyrido[3,4-d]pyrimidin-4-yl}piperazin-1-yl)prop-2-en-1-one | 494/496 (M + H) | ¹H NMR (400 MHz, DMSO-d₆) δ 13.30 (s, 1H), 8.84 (s, 1H), 7.90 (d, J = 5.9 Hz, 1H), 7.69 (s, 1H), 7.61 (d, J = 5.9 Hz, 1H), 7.50 (s, 1H), 6.87-6.81 (m, 1H), 6.18 (dd, J = 16.7, 2.3 Hz, 1H), 5.75 (dd, J = 10.4, 2.3 Hz, 1H), 3.92 (s, 4H), 3.85-3.75 (m, 4H), 2.54 (s, 3H). |
| 14A | 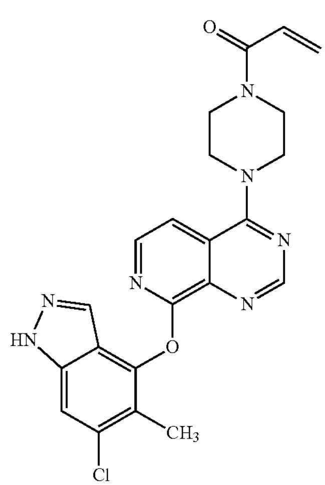 [SMILES: C=CC(=O)N1CCN(c2ncnc3c(Oc4c(C)c(Cl)cc5[nH]ncc45)nccc23)CC1] | 1-(4-{8-[(6-chloro-5-methyl-1H-indazol-4-yl)oxy]pyrido[3,4-d]pyrimidin-4-yl}piperazin-1-yl)prop-2-en-1-one | 450 (M + H) | ¹H NMR (400 MHz, DMSO-d₆) δ 13.29 (s, 1H), 8.84 (s, 1H), 7.90 (d, J = 5.8 Hz, 1H), 7.65 (d, J = 9.1 Hz, 2H), 7.60 (d, J = 5.9 Hz, 1H), 6.84 (dd, J = 16.7, 10.4 Hz, 1H), 6.20 (d, J = 2.1 Hz, 1H), 5.75 (dd, J = 10.4, 2.1 Hz, 1H), 3.92 (s, 4H), 3.85-3.75 (m, 4H), 2.19 (s, 3H). |

| Example | Structure | Compound Name | LCMS m/z | $^1$H NMR |
|---|---|---|---|---|
| 15A | 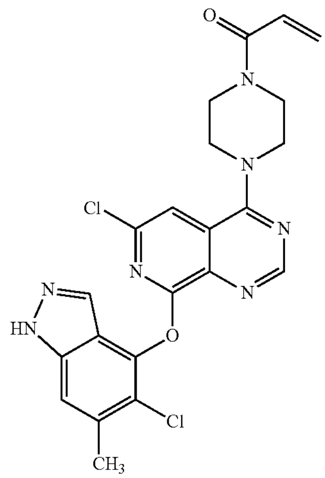 [SMILES: C=CC(=O)N1CCN(c2ncnc3c(Oc4c(Cl)c(C)cc5[nH]ncc45)nc(Cl)cc23)CC1] | 1-(4-{6-chloro-8-[(5-chloro-6-methyl-1H-indazol-4-yl)oxy]pyrido[3,4-d]pyrimidin-4-yl}piperazin-1-yl)prop-2-en-1-one | 484 (M + H) | $^1$H NMR (400 MHz, DMSO-d$_6$) δ 2.51 (s, 3H), 3.66-3.88 (m, 5H), 3.94 (br. s, 4H), 5.72 (dd, J = 10.6, 2.6 Hz, 1H), 6.18 (dd, J = 16.7, 2.3 Hz, 1H), 6.83 (dd, J = 16.8, 10.5 Hz, 1H), 7.53 (s, 1H), 7.67 (s, 1H), 7.80 (s, 1H), 8.68-8.88 (m, 1H), 13.36 (s, 1H). |
| 16A | 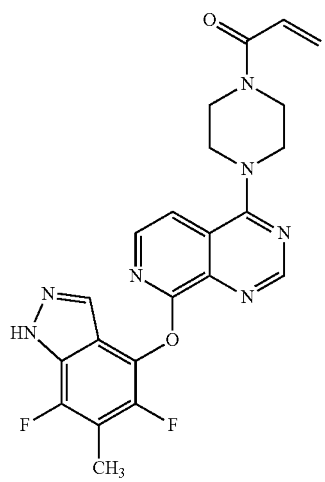 [SMILES: C=CC(=O)N1CCN(c2ncnc3c(Oc4c(F)c(C)c(F)c5[nH]ncc45)nccc23)CC1] | 1-(4-{8-[(5,7-difluoro-6-methyl-1H-indazol-4-yl)oxy]pyrido[3,4-d]pyrimidin-4-yl}piperazin-1-yl)prop-2-en-1-one | 452 (M + H) | $^1$H NMR (400 MHz, DMSO-d$_6$) δ 13.85 (s, 1H), 8.83 (s, 1H), 7.97 (s, 1H), 7.93 (d, J = 5.9 Hz, 1H), 7.63 (d, J = 5.9 Hz, 1H), 6.84 (dd, J = 16.7, 10.4 Hz, 1H), 6.18 (dd, J = 16.7, 2.3 Hz, 1H), 5.75 (dd, J = 10.4, 2.3 Hz, 1H), 3.95-3.90 (m, 4H), 3.85-3.80 (m, 4H), 2.34 (s, 3H). |
| 17A | 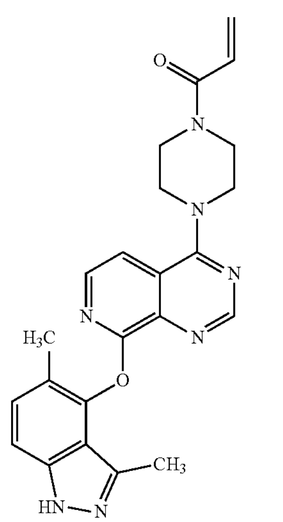 [SMILES: C=CC(=O)N1CCN(c2ncnc3c(Oc4c(C)ccc5[nH]nc(C)c45)nccc23)CC1] | 1-(4-{8-[(3,5-dimethyl-1H-indazol-4-yl)oxy]pyrido[3,4-d]pyrimidin-4-yl}piperazin-1-yl)prop-2-en-1-one | 430 (M + H) | $^1$H NMR (400 MHz, MeOD) δ 8.81 (s, 1H), 7.90 (d, J = 5.9 Hz, 1H), 7.58 (d, J = 6.0 Hz, 1H), 7.32 (s, 2H), 6.81 (dd, J = 16.8, 10.6 Hz, 1H), 6.28 (dd, J = 16.8, 1.6 Hz, 1H), 5.81 (dd, J = 10.6, 1.6 Hz, 1H), 4.10-4.00 (m, 4H), 3.91 (s, 4H), 2.18 (d, J = 14.3 Hz, 6H). |

-continued

| Example | Structure | Compound Name | LCMS m/z | ¹H NMR |
|---|---|---|---|---|
| 18A | 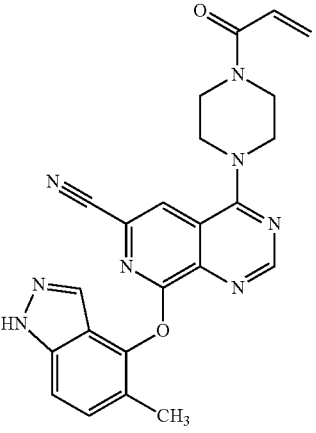 | 4-(4-acryloylpiperazin-1-yl)-8-[(5-methyl-1H-indazol-4-yl)oxy]pyrido[3,4-d]pyrimidine-6-carbonitrile | 441 (M + H) | ¹H NMR (400 MHz, DMSO-$d_6$) δ 13.21 (s, 1H), 8.91 (s, 1H), 8.28 (s, 1H), 7.69 (s, 1H), 7.43 (d, J = 8.4 Hz, 1H), 7.34 (d, J = 8.5 Hz, 1H), 6.84 (dd, J = 16.7, 10.5 Hz, 1H), 6.18 (dd, J = 16.7, 2.3 Hz, 1H), 5.75 (dd, J = 10.4, 2.3 Hz, 1H), 4.05-4.00 (m, 4H), 3.85-3.80 (m, 4H), 2.19 (s, 3H). |
| 19A | 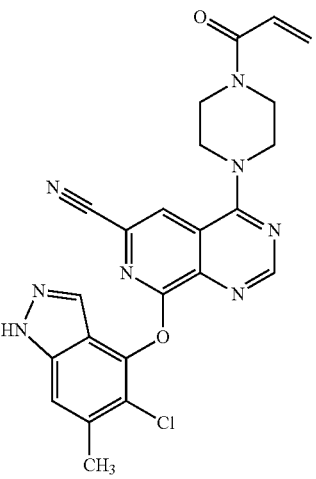 [SMILES: C=CC(=O)N1CCN(c2ncnc3c(Oc4c(Cl)c(C)cc5[nH]ncc45)nc(C#N)cc23)CC1] | 4-(4-acryloylpiperazin-1-yl)-8-[(5-chloro-6-methyl-1H-indazol-4-yl)oxy]pyrido[3,4-d]pyrimidine-6-carbonitrile | 475 (M + H) | ¹H NMR (400 MHz, DMSO-$d_6$) δ 2.53 (s, 3H), 3.67-3.89 (m, 4H), 4.04 (br. s, 4H), 5.75 (dd, J = 10.6, 2.0 Hz, 1H), 6.18 (dd, J = 16.7, 2.4 Hz, 1H), 6.83 (dd, J = 16.8, 10.5 Hz, 1H), 7.54 (s, 1H), 7.81 (s, 1H), 8.34 (s, 1H), 8.91 (s, 1H) 13.37 (s, 1H). |
| 20A | 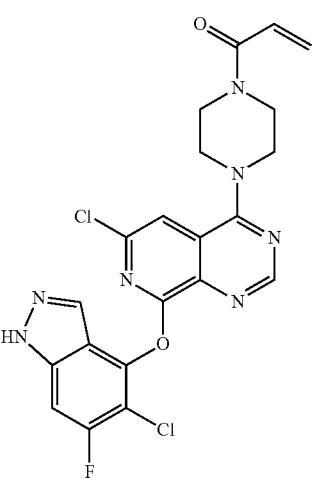 [SMILES: C=CC(=O)N1CCN(c2ncnc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]pyrido[3,4-d]pyrimidin-4-yl}piperazin-1-yl)prop-2-en-1-one | 488 (M + H) | ¹H NMR (400 MHz, DMSO-$d_6$) δ 3.70-3.88 (m, 4H), 3.96 (br. s, 4H), 5.74 (dd, J = 10.5, 2.3, 1H), 6.18 (dd, J = 16.7, 2.3 Hz, 1H), 6.83 (dd, J = 16.7, 10.4 Hz, 1H), 7.64 (d, J = 8.8 Hz, 1H), 7.72 (s, 1H), 7.93 (s, 1H), 8.81 (s, 1H), 13.62 (br. s, 1H). |

-continued

| Example | Structure | Compound Name | LCMS m/z | ¹H NMR |
|---|---|---|---|---|
| 21A | 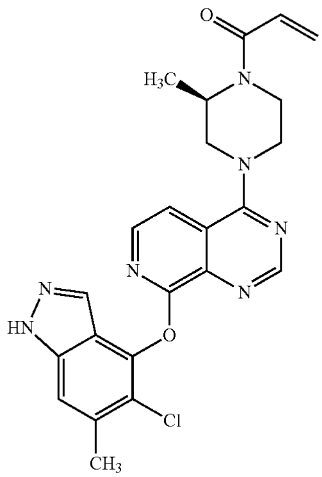 [SMILES: C=CC(=O)N1CCN(c2ncnc3c(Oc4c(Cl)c(C)cc5[nH]ncc45)nccc23)C[C@H]1C] | 1-[(2R)-4-{8-[(5-chloro-6-methyl-1H-indazol-4-yl)oxy]pyrido[3,4-d]pyrimidin-4-yl}-2-methylpiperazin-1-yl]prop-2-en-1-one | 464 (M + H) | ¹H NMR (400 MHz, DMSO-d₆) δ 13.29 (s, 1H), 8.82 (s, 1H), 7.90 (d, J = 6.0 Hz, 1H), 7.73 (s, 1H), 7.63 (d, J = 5.9 Hz, 1H), 7.49 (s, 1H), 6.81 (dd, J = 16.7, 10.5 Hz, 1H), 6.17 (d, J = 16.5 Hz, 1H), 5.73 (d, J = 9.7 Hz, 1H), 4.69-4.52 (m, 1H), 4.35-4.25 (m, 1H), 4.25-3.98 (m, 2H), 3.75-3.69 (m, 1H), 3.59-3.41 (m, 2H), 2.53 (s, 3H), 1.23 (d, J = 6.4 Hz, 3H). |
| 22A | 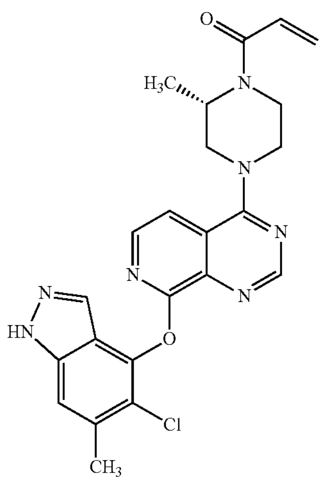 [SMILES: C=CC(=O)N1CCN(c2ncnc3c(Oc4c(Cl)c(C)cc5[nH]ncc45)nccc23)C[C@@H]1C] | 1-[(2S)-4-{8-[(5-chloro-6-methyl-1H-indazol-4-yl)oxy]pyrido[3,4-d]pyrimdin-4-yl}-2-methylpiperazin-1-yl]prop-2-en-1-one | 464 (M + H) | ¹H NMR (400 MHz, DMSO-d₆) δ 13.30 (s, 1H), 8.82 (s, 1H), 7.91 (d, J = 5.9 Hz, 1H), 7.73 (s, 1H), 7.63 (d, J = 5.9 Hz, 1H), 7.49 (s, 1H), 6.82 (dd, J = 16.7, 10.5 Hz, 1H), 6.17 (d, J = 16.4 Hz, 1H), 5.73 (d, J = 10.6 Hz, 1H), 4.75-4.49 (m, 1H), 4.37-4.29 (m, 1H), 4.23-3.99 (m, 2H), 3.77-3.71 (m, 1H), 3.59-3.43 (m, 2H), 2.51 (s, 3H), 1.24 (s, 3H). |
| 23A | 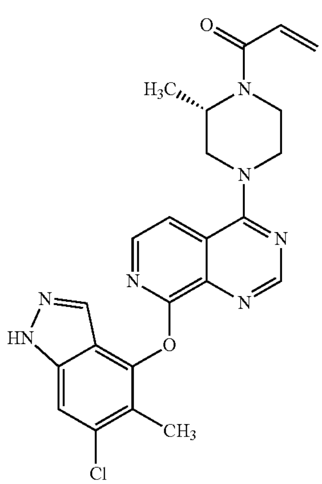 [SMILES: C=CC(=O)N1CCN(c2ncnc3c(Oc4c(C)c(Cl)cc5[nH]ncc45)nccc23)C[C@@H]1C] | 1-[(2S)-4-{8-[(6-chloro-5-methyl-1H-indazol-4-yl)oxy]pyrido[3,4-d]pyrimidin-4-yl}-2-methylpiperazin-1-yl]prop-2-en-1-one | 464 (M + H) | ¹H NMR (400 MHz, DMSO-d₆) δ 13.28 (s, 1H), 8.81 (d, J = 10.3 Hz, 1H), 7.91 (d, J = 5.9 Hz, 1H), 7.61-7.67 (m, 3H), 6.82 (dd, J = 16.6, 10.5 Hz, 1H), 6.17 (d, J = 16.6 Hz, 1H), 5.73 (d, J = 10.6 Hz, 1H), 4.70-4.53 (m, 1H), 4.21 (m, 3H), 3.74 (dd, J = 13.4, 3.9 Hz, 1H), 3.50 (s, 2H), 2.19 (s, 3H), 1.24 (br. s, 3H). |

| Example | Structure | Compound Name | LCMS m/z | ¹H NMR |
|---|---|---|---|---|
| 24A | 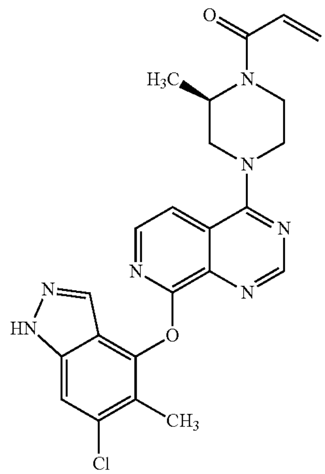 [SMILES: C=CC(=O)N1CCN(c2ncnc3c(Oc4c(C)c(Cl)cc5[nH]ncc45)nccc23)C[C@H]1C] | 1-[(2R)-4-{8-[(6-chloro-5-methyl-1H-indazol-4-yl)oxy]pyrido[3,4-d]pyrimidin-4-yl}-2-methylpiperazin-1-yl]prop-2-en-1-one | 464 (M + H) | ¹H NMR (400 MHz, DMSO-d₆) δ 13.28 (s, 1H), 8.81 (d, J = 10.4 Hz, 1H), 7.90 (d, J = 5.9 Hz, 1H), 7.64 (dd, J = 13.6, 9.8 Hz, 3H), 6.82 (dd, J = 16.6, 10.5 Hz, 1H), 6.17 (d, J = 16.6 Hz, 1H), 5.73 (d, J = 10.2 Hz, 1H), 4.70-5.53 (m, 1H), 4.21 (m, 3H), 3.74 (dd, J = 13.5, 3.9 Hz, 1H), 3.51 (s, 2H), 2.18 (d, J = 10.2 Hz, 3H), 1.25 (br. s, 3H). |
| 25A | 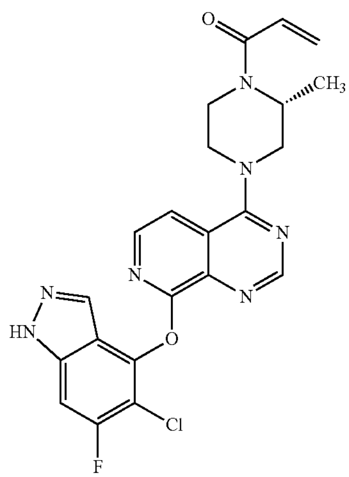 [SMILES: C=CC(=O)N1CCN(c2ncnc3c(Oc4c(Cl)c(F)cc5[nH]ncc45)nccc23)C[C@H]1C] | 1-[(2R)-4-{8-[(5-chloro-6-fluoro-1H-indazol-4-yl)oxy]pyrido[3,4-d]pyrimidin-4-yl}-2-methylpiperazin-1-yl]prop-2-en-1-one | 468 (M + H) | ¹H NMR (400 MHz, DMSO-d₆) δ 8.80 (s, 1H), 7.94 (d, J = 5.9 Hz, 1H), 7.85 (s, 1H), 7.68 (d, J = 5.9 Hz, 1H), 7.60 (d, J = 8.9 Hz, 1H), 6.81 (dd, J = 16.6, 10.4 Hz, 1H), 6.17 (d, J = 16.8 Hz, 1H), 5.78-5.70 (d, J = 16.8 Hz, 1H), 4.76-4.47 (m, 1H), 4.39-4.30 (m, 1H), 4.28-4.06 (m, 2H), 3.80-3.72 (m, 1H), 3.62-3.45 (m, 2H), 1.19 (br. s, 3H). |
| 26A | 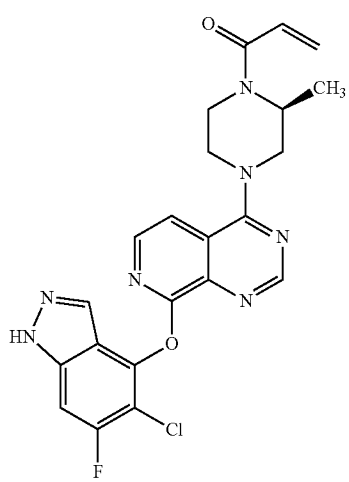 [SMILES: C=CC(=O)N1CCN(c2ncnc3c(Oc4c(Cl)c(F)cc5[nH]ncc45)nccc23)C[C@@H]1C] | 1-[(2S)-4-{8-[(5-chloro-6-fluoro-1H-indazol-4-yl)oxy]pyrido[3,4-d]pyrimidin-4-yl}-2-methylpiperazin-1-yl]prop-2-en-1-one | 468 (M + H) | ¹H NMR (400 MHz, DMSO-d₆) δ 13.56 (s, 1H), 8.82 (s, 1H), 7.94 (d, J = 5.9 Hz, 1H), 7.85 (s, 1H), 7.68 (d, J = 5.9 Hz, 1H), 7.60 (d, J = 8.8, 1H), 6.81 (dd, J = 16.7, 10.5 Hz, 1H), 6.17 (d, J = 15.8, Hz, 1H), 5.73 (d, J = 10.1 Hz, 1H), 4.73-4.47 (m, 1H), 4.37-4.30 (m, 1H), 4.23-3.98 (m, 2H), 3.79-3.72 (m, 1H), 3.63-3.42 (m, 2H), 1.23 (br. s, 3H). |

-continued

| Example | Structure | Compound Name | LCMS m/z | ¹H NMR |
|---------|-----------|---------------|----------|--------|
| 27A | 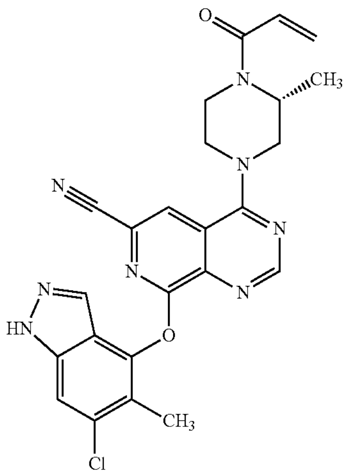 [SMILES: C=CC(=O)N1CCN(c2ncnc3c(Oc4c(C)c(Cl)cc5[nH]ncc45)nc(C#N)cc23)C[C@H]1C] | 4-[(3R)-4-acryloyl-3-methylpiperazin-1-yl]-8-[(6-chloro-5-methyl-1H-indazol-4-yl)oxy]pyrido[3,4-d]pyrimidine-6-carbonitrile | 489 (M + H) | ¹H NMR (400 MHz, DMSO-d₆) δ 13.35 (s, 1H), 8.89 (s, 1H), 8.34 (s, 1H), 7.76 (s, 1H), 7.69 (s, 1H), 6.80 (dd, J = 16.6, 10.4 Hz, 1H), 6.17 (d, J = 16.8 Hz, 1H), 5.74 (d, J = 10.0 Hz, 1H), 4.65-4.53 (m, 1H), 4.44-4.35 (m, 1H), 4.22 (m, 1H), 4.03 (m, 1H), 3.92 (m, J = 10.8 Hz, 1H), 3.71 (m, 2H), 2.22 (s, 3H), 1.23 (br. s, 3H). |
| 28A | 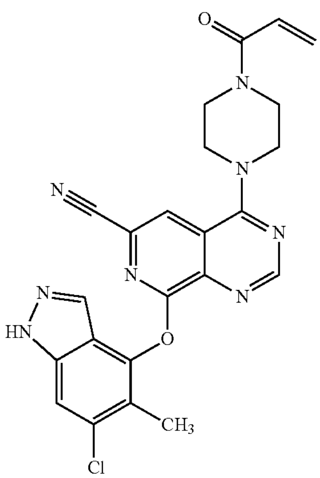 [SMILES: C=CC(=O)N1CCN(c2ncnc3c(Oc4c(C)c(Cl)cc5[nH]ncc45)nc(C#N)cc23)CC1] | 4-(4-acryloylpiperazin-1-yl)-8-[(6-chloro-5-methyl-1H-indazol-4-yl)oxy]pyrido[3,4-d]pyrimidine-6-carbonitrile | 475 (M + H) | ¹H NMR (400 MHz, DMSO-d₆) δ 13.35 (s, 1H), 8.91 (s, 1H), 8.33 (s, 1H), 7.75 (s, 1H), 7.69 (s, 1H), 6.87-6.80 (m, 1H), 6.19 (dd, J = 16.7, 2.3 Hz, 1H), 5.76 (dd, J = 10.4, 2.3 Hz, 1H), 4.02 (m, 4H), 3.81 (m, 4H), 2.22 (s, 3H). |
| 29A | 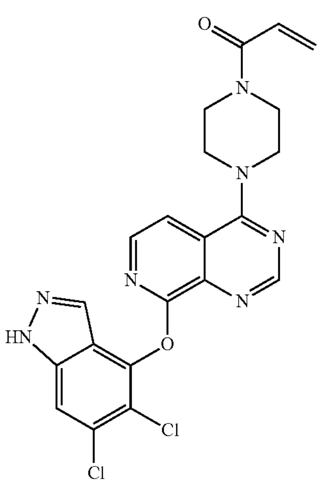 | 1-(4-{8-[(5,6-dichloro-1H-indazol-4-yl)oxy]pyrido[3,4-d]pyrimidin-4-yl}piperazin-1-yl)prop-2-en-1-one | 479 (M + H) | ¹H NMR (400 MHz, CD₃OD) δ 8.87 (s, 1H), 8.23 (s, 1H), 7.92 (s, 1H), 7.42-7.53 (m, 1H), 6.72-6.89 (m, 1H), 6.29 (dd, J = 16.8, 2.0 Hz, 1H), 5.76-5.87 (m, 1H), 4.11-4.23 (m, 4H), 3.92 (br. s, 4H). |

| Example | Structure | Compound Name | LCMS m/z | ¹H NMR |
|---|---|---|---|---|
| 30A | 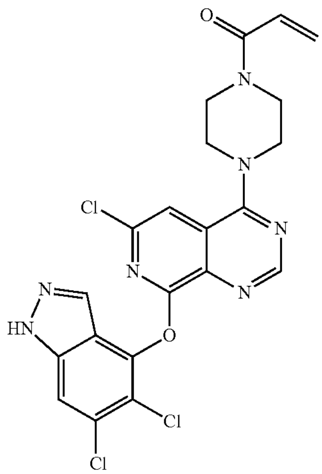 [SMILES: C=CC(=O)N1CCN(c2ncnc3c(Oc4c(Cl)c(Cl)cc5[nH]ncc45)nc(Cl)cc23)CC1] | 1-(4-{6-chloro-8-[(5,6-dichloro-1H-indazol-4-yl)oxy]pyrido[3,4-d]pyrimidin-4-yl}piperazin-1-yl)prop-2-en-1-one | 504 (M + H) | ¹H NMR (400 MHz, DMSO-d₆) δ 8.78-8.84 (m, 1H), 7.90 (s, 1H), 7.93 (s, 1H), 7.71 (s, 1H), 6.83 (dd, J = 16.7, 10.4 Hz, 1H), 6.18 (dd, J = 16.8, 2.3 Hz, 1H), 5.68-5.80 (m, 1H), 3.95 (br. s, 4H), 3.83 (br. s, 2H), 3.76 (br. s, 2H). |
| 31A | 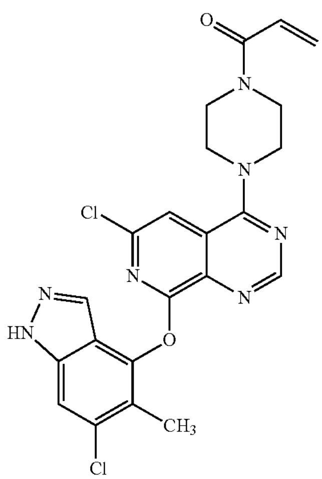 [SMILES: C=CC(=O)N1CCN(c2ncnc3c(Oc4c(C)c(Cl)cc5[nH]ncc45)nc(Cl)cc23)CC1] | 1-(4-{6-chloro-8-[(6-chloro-5-methyl-1H-indazol-4-yl)oxy]pyrido[3,4-d]pyrimidin-4-yl}piperazin-1-yl)prop-2-en-1-one | 484 (M + H) | ¹H NMR (400 MHz, DMSO-d₆) δ 13.34 (s, 1H), 8.81 (s, 1H), 7.74 (s, 1H), 7.66 (d, J = 10.8 Hz, 2H), 6.83 (dd, J = 16.7, 10.4 Hz, 1H), 6.18 (dd, J = 16.7, 2.4 Hz, 1H), 5.74 (dd, J = 10.4, 2.4 Hz, 1H), 3.94 (dd, J = 6.9, 3.6 Hz, 4H), 3.80 (dd, J = 30.3, 5.2 Hz, 4H), 2.22 (s, 3H). |
| 32A | 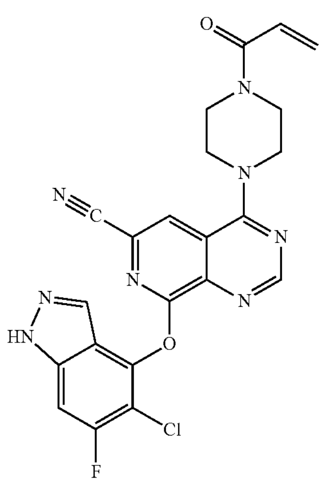 | 4-(4-acryloylpiperazin-1-yl)-8-[(5-chloro-6-fluoro-1H-indazol-4-yl)oxy]pyrido[3,4-d]pyrimidine-6-carbonitrile | 470 (M + H) | ¹H NMR (400 MHz, DMSO-d₆) δ 8.83 (s, 1H), 7.92 (d, J = 5.9 Hz, 1H), 7.86 (s, 2H), 7.65 (d, J = 5.9 Hz, 1H), 6.84 (dd, J = 16.7, 10.4 Hz, 1H), 6.17 (dd, J = 16.8, 2.3 Hz, 1H), 5.70-5.77 (m, 1H), 3.93 (br. s, 4H), 3.84 (br. s, 2H), 3.77 (br. s, 2H). |

-continued

| Example | Structure | Compound Name | LCMS m/z | ¹H NMR |
|---|---|---|---|---|
| 33A | 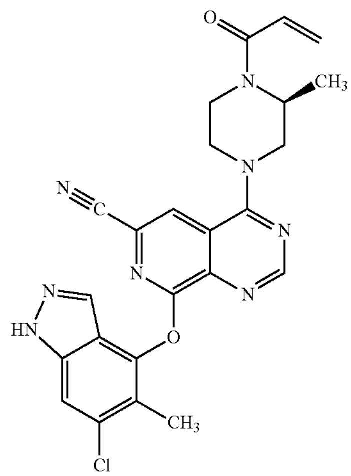 [SMILES: C=CC(=O)N1CCN(c2ncnc3c(Oc4c(C)c(Cl)cc5[nH]ncc45)nc(C#N)cc23)C[C@@H]1C] | 4-[(3S)-4-acryloyl-3-methylpiperazin-1-yl]-8-[(6-chloro-5-methyl-1H-indazol-4-yl)oxy]pyrido[3,4-d]pyrimidine-6-carbonitrile | 489 (M + H) | ¹H NMR (400 MHz, DMSO-d₆) δ 13.35 (s, 1H), 8.89 (s, 1H), 8.35 (s, 1H), 7.75 (s, 1H), 7.68 (s, 1H), 6.80 (dd, J = 16.7, 10.4 Hz, 1H), 6.17 (d, J = 16.6 Hz, 1H), 5.74 (d, J = 10.5 Hz, 1H), 4.58 (d, J = 48.7 Hz, 1H), 4.43-4.34 (m, 1H), 4.22 (s, 1H), 4.03 (s, 1H), 3.92 (d, J = 13.4 Hz, 2H), 3.85-3.51 (m, 3H), 1.23 (s, 3H). |
| 34A | 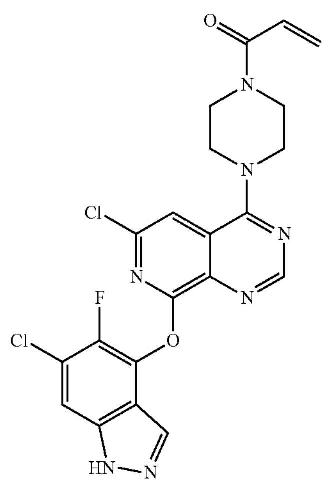 [SMILES: C=CC(=O)N1CCN(c2ncnc3c(Oc4c(F)c(Cl)cc5[nH]ncc45)nc(Cl)cc23)CC1] | 1-(4-{6-chloro-8-[(6-chloro-5-fluoro-1H-indazol-4-yl)oxy]pyrido[3,4-d]pyrimidin-4-yl}piperazin-1-yl)prop-2-en-1-one | 488 (M + H) | ¹H NMR (400 MHz, DMSO-d₆) δ 13.10 (br. s, 1H), 8.34 (s, 1H), 7.53 (s, 1H), 7.35 (d, J = 4.6 Hz, 1H), 7.26 (s, 1H), 6.36 (dd, J = 16.7, 10.4 Hz, 1H), 5.71 (dd, J = 16.7, 2.4 Hz, 1H), 5.24-5.31 (m, 1H), 3.46-3.52 (m, 4H), 3.37 (br. s, 2H), 3.30 (br. s, 2H). |
| 35A | 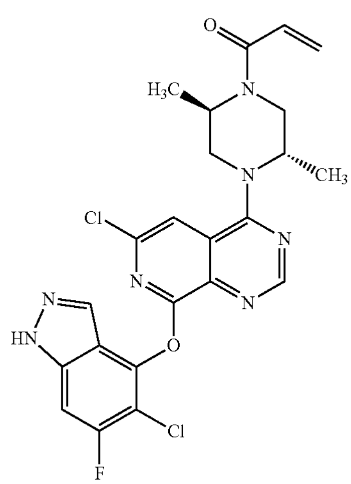 [SMILES: C=CC(=O)N1C[C@H](C)N(c2ncnc3c(Oc4c(Cl)c(F)cc5[nH]ncc45)nc(Cl)cc23)C[C@H]1C] | 1-[(2R,5S)-4-{6-chloro-8-[(5-chloro-6-fluoro-1H-indazol-4-yl)oxy]pyrido[3,4-d]pyrimidin-4-yl}-2,5-dimethylpiperazin-1-yl]prop-2-en-1-one | 516, 518 (M + H) | ¹H NMR (400 MHz, DMSO-d₆) δ 13.63 (s, 1H), 8.83 (s, 1H), 7.95 (s, 1H), 7.65 (dd, J = 8.9, 1.0 Hz, 1H), 7.61 (d, J = 2.5 Hz, 1H), 6.82 (ddd, J = 16.6, 13.4, 10.4 Hz, 1H), 6.18 (dd, J = 16.7, 2.4 Hz, 1H), 5.74 (ddd, J = 10.5, 4.6, 2.4 Hz, 1H), 4.88-4.68 (m, 1.5H), 4.45 (s, 0.5H), 4.19-4.04 (m, 1.5H), 3.94-3.78 (m, 2H), 3.49 (dd, J = 13.8, 3.9 Hz, 0.5H), 1.28 (t, J = 7.0 Hz, 3H), 1.19 (d, J = 6.7 Hz, 1.5H), 1.12 (d, J = 6.8 Hz, 1.5H). |

| Example | Structure | Compound Name | LCMS m/z | ¹H NMR |
|---|---|---|---|---|
| 36A | 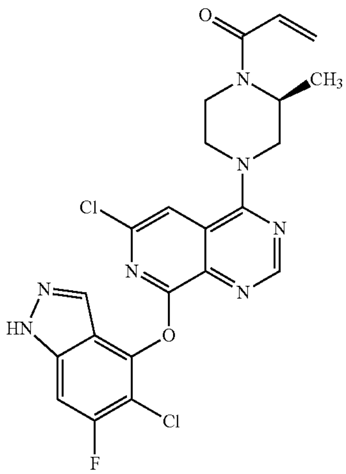 [SMILES: C=CC(=O)N1CCN(c2ncnc3c(Oc4c(Cl)c(F)cc5[nH]ncc45)nc(Cl)cc23)C[C@@H]1C] | 1-[(2S)-4-{6-chloro-8-[(5-chloro-6-fluoro-1H-indazol-4-yl)oxy]pyrido[3,4-d]pyrimidin-4-yl}-2-methylpiperazin-1-yl]prop-2-en-1-one | 502, 504 (M + H) | ¹H NMR (400 MHz, DMSO-d₆) δ 13.62 (s, 1H), 8.80 (s, 1H), 7.94 (s, 1H), 7.74 (s, 1H), 7.65 (dd, J = 8.8, 1.1 Hz, 1H), 6.80 (dd, J = 16.6, 10.4 Hz, 1H), 6.17 (d, J = 16.6 Hz, 1H), 5.73 (d, J = 10.4 Hz, 1H), 4.59 (d, J = 60.1 Hz, 1H), 4.42-4.28 (m, 1H), 4.24-3.93 (m, 2H), 3.87-3.47 (m, 3H), 1.23 (s, 3H). |
| 37A | 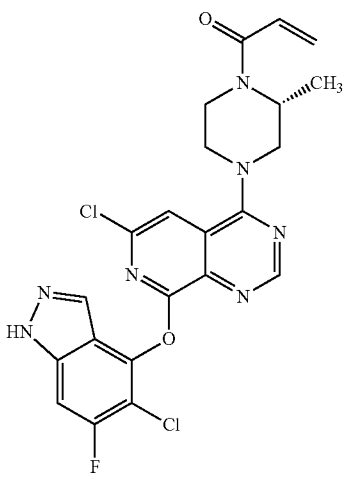 [SMILES: C=CC(=O)N1CCN(c2ncnc3c(Oc4c(Cl)c(F)cc5[nH]ncc45)nc(Cl)cc23)C[C@H]1C] | 1-[(2R)-4-{6-chloro-8-[(5-chloro-6-fluoro-1H-indazol-4-yl)oxy]pyrido[3,4-d]pyrimidin-4-yl}-2-methylpiperazin-1-yl]prop-2-en-1-one | 502, 504 (M + H) | ¹H NMR (400 MHz, DMSO-d₆) δ 13.64 (s, 1H), 8.79 (s, 1H), 7.94 (s, 1H), 7.74 (s, 1H), 7.64 (dd, J = 8.9, 1.0 Hz, 1H), 6.80 (dd, J = 16.6, 10.5 Hz, 1H), 6.17 (d, J = 16.6 Hz, 1H), 5.73 (d, J = 10.4 Hz, 1H), 4.59 (d, J = 60.2 Hz, 1H), 4.33 (d, J = 10.9 Hz, 1H), 4.20-3.94 (m, 2H), 3.87-3.47 (m, 3H), 1.23 (s, 3H). |
| 39A | 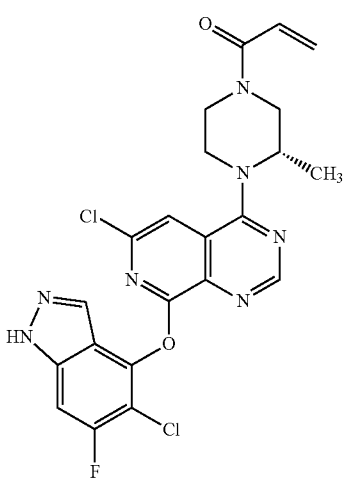 [SMILES: C=CC(=O)N1CCN(c2ncnc3c(Oc4c(Cl)c(F)cc5[nH]ncc45)nc(Cl)cc23)[C@@H](C)C1] | 1-[(3S)-4-{6-chloro-8-[(5-chloro-6-fluoro-1H-indazol-4-yl)oxy]pyrido[3,4-d]pyrimidin-4-yl}-3-methylpiperazin-1-yl]prop-2-en-1-one | 502, 504 (M + H) | ¹H NMR (400 MHz, DMSO-d₆) δ 13.63 (s, 1H), 8.82 (s, 1H), 7.94 (s, 1H), 7.65 (dd, J = 8.9, 1.1 Hz, 1H), 7.62 (d, J = 3.0 Hz, 1H), 6.95-6.75 (m, 1H), 6.19 (dd, J = 16.5, 5.8 Hz, 1H), 5.75 (dd, J = 10.4, 2.4 Hz, 1H), 4.93-4.72 (m, 1H), 4.46-3.92 (m, 3H), 3.76-3.37 (m, 2H), 3.27-2.95 (m, 1H), 1.31 (d, J = 5.7 Hz, 3H). |

| Example | Structure | Compound Name | LCMS m/z | ¹H NMR |
|---|---|---|---|---|
| 40A | 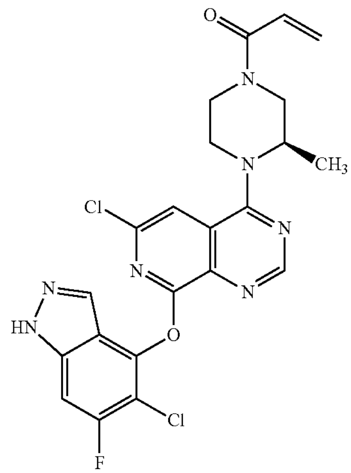 [SMILES: C=CC(=O)N1CCN(c2ncnc3c(Oc4c(Cl)c(F)cc5[nH]ncc45)nc(Cl)cc23)[C@H](C)C1] | 1-[(3R)-4-{6-chloro-8-[(5-chloro-6-fluoro-1H-indazol-4-yl)oxy]pyrido[3,4-d]pyrimidin-4-yl}-3-methylpiperazin-1-yl]prop-2-en-1-one | 502, 504 (M + H) | ¹H NMR (400 MHz, DMSO-d$_6$) δ 13.65 (s, 1H), 8.82 (s, 1H), 7.94 (s, 1H), 7.65 (d, J = 8.9 Hz, 1H), 7.61 (d, J = 3.0 Hz, 1H), 6.85 (td, J = 15.5, 10.5 Hz, 1H), 6.20 (dt, J = 16.8, 4.4 Hz, 1H), 5.75 (dd, J = 10.4, 2.4 Hz, 1H), 4.93-4.74 (m, 1H), 4.45-4.17 (m, 2H), 4.07 (dd, J = 53.1, 13.6 Hz, 1H), 3.81-3.38 (m, 2H), 3.27-2.99 (m, 1H), 1.30 (d, J = 5.0 Hz,). |
| 41A | 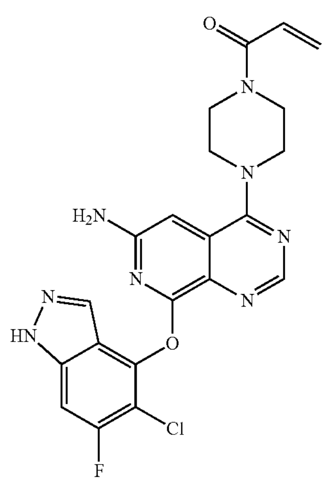 [SMILES: C=CC(=O)N1CCN(c2ncnc3c(Oc4c(Cl)c(F)cc5[nH]ncc45)nc(N)cc23)CC1] | 1-(4-{6-amino-8-[(5-chloro-6-fluoro-1H-indazol-4-yl)oxy]pyrido[3,4-d]pyrimidin-4-yl}piperazin-1-yl)prop-2-en-1-one | 469 (M + H) | ¹H NMR (400 MHz, DMSO-d$_6$) δ 3.70 (m, 4H), 3.75-3.80 (m, 4H), 5.74 (dd, J = 10.4, 2.3 Hz, 1H), 6.11 (s, 2H), 6.17 (dd, J = 16.7, 2.4 Hz, 1H), 6.47 (s, 1H), 6.86 (dd, J = 16.7, 10.4 Hz, 1H), 7.54 (d, J = 8.9 Hz, 1H), 7.79 (s, 1H), 8.46 (s, 1H), 13.50 (br. s, 1H). |

The intermediates detailed in the following preparation afford Examples-1, -2, and -6 according to Method A. However, these examples fall outside of the synthetic scope of the preceding examples due to the phenol deprotection and, thus, the preparation is included here for completeness. Subsequent chemistry to afford the final examples is similar to the Method A examples, with minimal additions or changes that one skilled in the art can appreciate.

Preparation of 1-(4-{8-[(3-hydroxynaphthalen-1-yl)oxy]-6-(trifluoromethyl)pyrido[3,4-d]pyrimidin-4-yl}piperazin-1-yl)prop-2-en-1-one (Example-1)

Step 1:

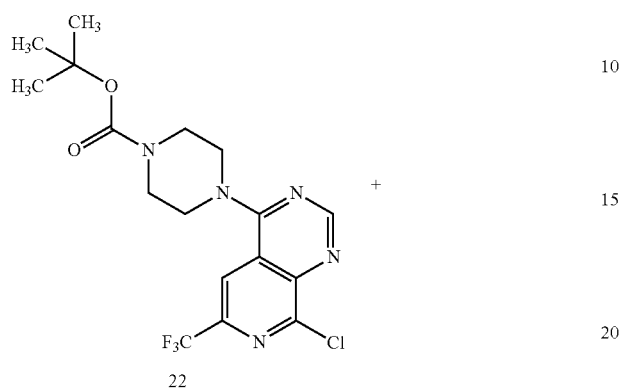

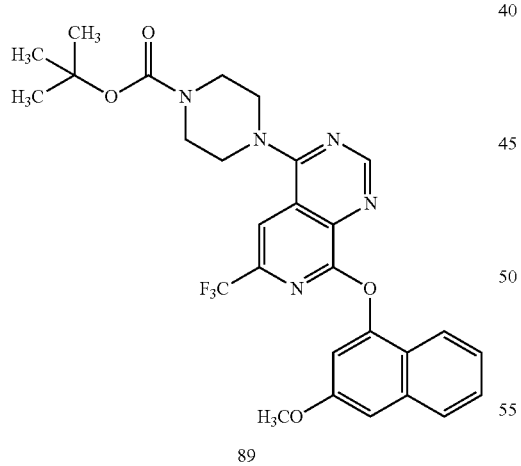

Tert-butyl 4-{8-[(3-methoxynaphthalen-1-yl)oxy]-6-(trifluoromethyl)pyrido[3,4-d]pyrimidin-4-yl}piperazine-1-carboxylate (89) (400 mg, 75% yield) was prepared according to the procedure used to prepare tert-butyl 4-(8-{[5-methyl-1-(tetrahydro-2H-pyran-2-yl)-1H-indazol-4-yl]oxy}pyrido[3,4-d]pyrimidin-4-yl)piperazine-1-carboxylate (85) except the solvent was replaced with DMSO and the reaction was heated at 60° C. for 1 hour. LCMS ESI m/z 556 (M+H).

Step 2:

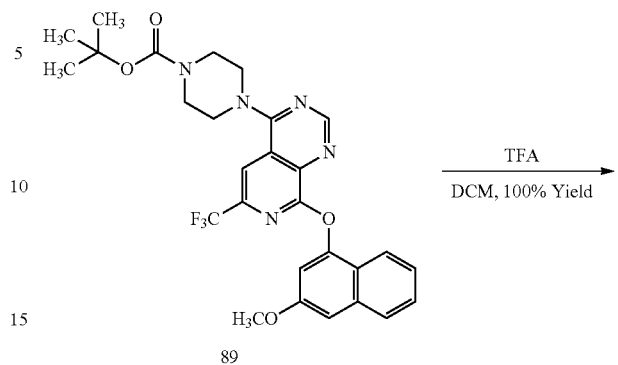

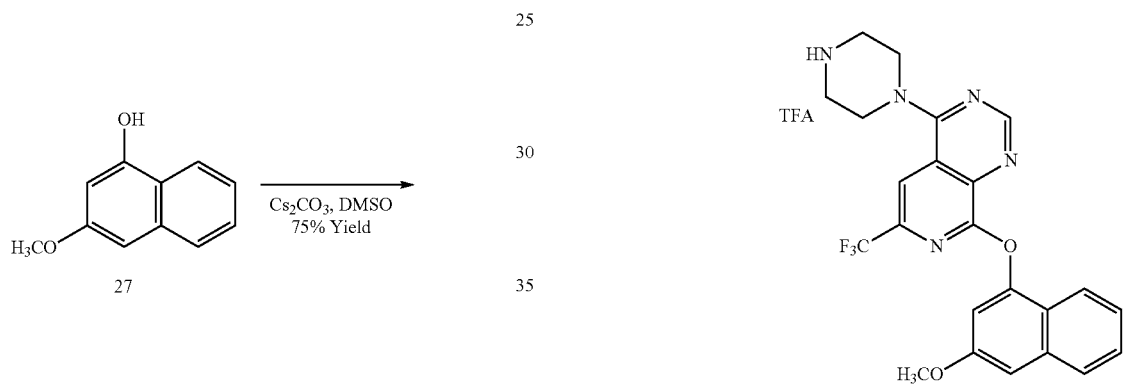

8-[(3-Methoxynaphthalen-1-yl)oxy]-4-(piperazin-1-yl)-6-(trifluoromethyl)pyrido[3,4-d]pyrimidine (90) (328 mg, 100% yield) was prepared according to the procedure used to prepare 8-[(5-methyl-1H-indazol-4-yl)oxy]-4-(piperazin-1-yl)pyrido[3,4-d]pyrimidine (86). LCMS ESI m/z 456 (M+H).

Step 3:

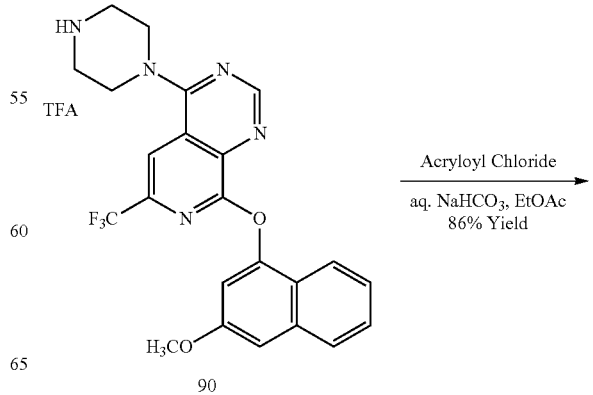

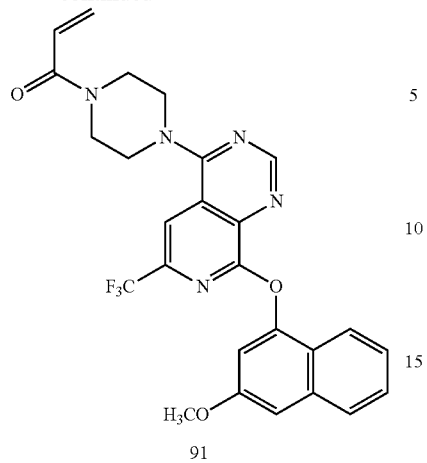

91

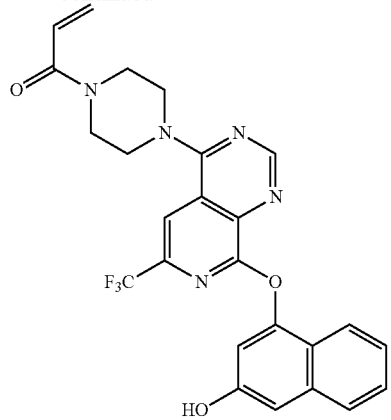

Example-1

1-(4-{8-[(3-Methoxynaphthalen-1-yl)oxy]-6-(trifluoromethyl)pyrido[3,4-d]pyrimidin-4-yl}piperazin-1-yl)prop-2-en-1-one (91) (316 mg, 86% yield) was prepared according to the procedure used to prepare 1-(4-{8-[(5-methyl-1H-indazol-4-yl)oxy]pyrido[3,4-d]pyrimidin-4-yl}piperazin-1-yl)prop-2-en-1-one (Example-1A). The product was purified by silica gel flash chromatography which was eluted with 3% methanol in DCM. ¹H NMR (400 MHz, CDCl₃) δ 9.06 (s, 1H), 7.86 (d, J=8.4 Hz, 1H), 7.79 (d, J=8.2 Hz, 1H), 7.70 (s, 1H), 7.46 (t, J=7.4 Hz, 1H), 7.29 (d, J=7.9 Hz, 1H), 7.14 (d, J=7.5 Hz, 2H), 6.60 (dd, J=16.8, 10.5 Hz, 1H), 6.42 (m, 1H), 5.85 (m, 1H), 4.09 (s, 4H), 3.96-3.87 (m, 7H). LCMS (ESI) m/z 510 (M+H).

Step 4:

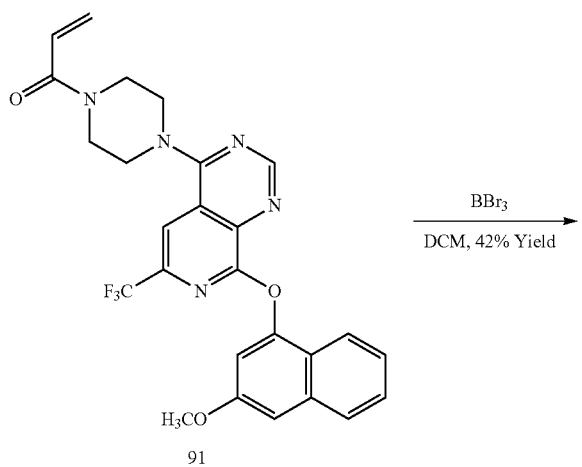

91

To a solution of BBr₃ in DCM (5 mL) was added 1-(4-(8-((3-methoxynaphthalen-1-yl)oxy)-6-(trifluoromethyl)pyrido[3,4-d]pyrimidin-4-yl)piperazin-1-yl)prop-2-en-1-one (91) (100 mg, 0.20 mmol) at −60° C., and the resultant mixture was stirred at 0° C. for 1 hour. The reaction was quenched with aqueous saturated NaHCO₃ solution, and extracted with EtOAc (2×50 mL). The combined EtOAc layers were washed with brine, dried over Na₂SO₄, filtered and concentrated. The crude was purified by prep-HPLC using a Gemini-C18 column (100×21.2 mm, 5 μm) and eluted with a 40-50% acetonitrile/H₂O (0.1% formic acid) gradient and gave 1-(4-{8-[(3-hydroxynaphthalen-1-yl)oxy]-6-(trifluoromethyl)pyrido[3,4-d]pyrimidin-4-yl}piperazin-1-yl) prop-2-en-1-one (Example-1) as a light yellow solid (42 mg, 42% yield). ¹H NMR (400 MHz, DMSO-d₆) δ 10.09 (s, 1H), 8.91 (s, 1H), 7.96 (s, 1H), 7.75 (dd, J=29.0, 8.3 Hz, 2H), 7.44 (t, J=7.4 Hz, 1H), 7.24 (t, J=7.5 Hz, 1H), 7.11 (s, 1H), 7.02 (d, J=1.9 Hz, 1H), 6.83 (dd, J=16.7, 10.4 Hz, 1H), 6.18 (dd, J=16.7, 2.1 Hz, 1H), 5.75 (dd, J=10.5, 2.0 Hz, 1H), 4.03 (s, 4H), 3.81 (d, J=32.9 Hz, 4H). LCMS (ESI) m/z 496 (M+H).

1-(4-{8-[(3-Hydroxynaphthalen-1-yl)oxy]-6-methyl-pyrido[3,4-d]pyrimidin-4-yl}piperazin-1-yl)prop-2-en-1-one (Example-2) was Prepared According to the Procedure Used to Prepare 1-(4-{8-[(3-hydroxynaphthalen-1-yl)oxy]-6-(trifluoromethyl)pyrido[3,4-d]pyrimidin-4-yl}piperazin-1-yl)prop-2-en-1-one (Example-1)

| Example | Structure | Compound Name | LCMS m/z | $^1$H NMR |
|---|---|---|---|---|
| 2 | 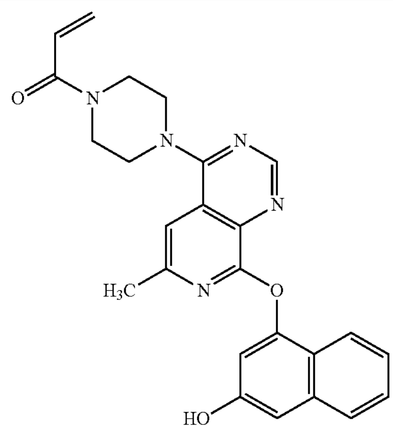 [SMILES: C=CC(=O)N1CCN(c2ncnc3c(Oc4cc(O)cc5ccccc45)nc(C)cc23)CC1] | 1-(4-{8-[(3-Hydroxynaphthalen-1-yl)oxy]-6-methylpyrido[3,4-d]pyrimidin-4-yl}piperazin-1-yl)prop-2-en-1-one | 442 (M + H) | $^1$H NMR (400 MHz, DMSO-d$_6$) δ 9.93 (s, 1H), 8.77 (s, 1H), 7.74 (dd, J = 19.9, 8.4 Hz, 2H), 7.43 (dd, J = 8.7, 5.3 Hz, 2H), 7.25-7.19 (m, 1H), 7.06 (d, J = 2.0 Hz, 1H), 6.91 (d, J = 2.2 Hz, 1H), 6.85 (dd, J = 16.7, 10.5 Hz, 1H), 6.18 (dd, J = 16.7, 2.3 Hz, 1H), 5.75 (dd, J = 10.4, 2.3 Hz, 1H), 3.88 (s, 4H), 3.88-3.74 (m, 4H), 2.32 (s, 3H). |
| 6 | 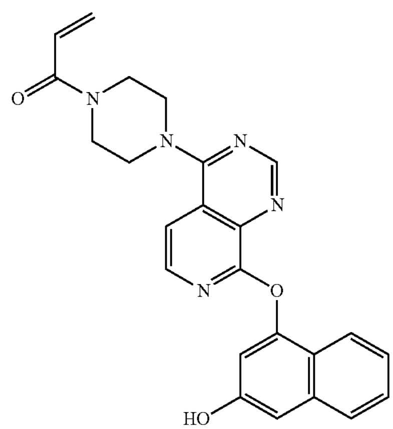 [SMILES: C=CC(=O)N1CCN(c2ncnc3c(Oc4cc(O)cc5ccccc45)nccc23)CC1] | 1-(4-{8-[(3-Hydroxynaphthalen-1-yl)oxy]pyrido[3,4-d]pyrimidin-4-yl}piperazin-1-yl)prop-2-en-1-one | 428 (M + H) | $^1$H NMR (400 MHz, DMSO-d$_6$) δ 9.95 (s, 1H), 8.84 (s, 1H), 7.92 (d, J = 5.9 Hz, 1H), 7.77 (d, J = 8.3 Hz, 1H), 7.64 (d, J = 8.4 Hz, 1H), 7.59 (d, J = 5.9 Hz, 1H), 7.42 (t, J = 7.1 Hz, 1H), 7.20 (t, J = 7.2 Hz, 1H), 7.09 (d, J = 2.1 Hz, 1H), 6.94 (d, J = 2.2 Hz, 1H), 6.84 (dd, J = 16.7, 10.4, Hz, 1H), 6.18 (dd, J = 16.7, 2.3 Hz, 1H), 5.75 (dd, J = 10.4, 2.3 Hz, 1H), 3.91 (d, J = 2.7 Hz, 4H), 3.84-3.77 (m, 4H). |

The intermediates detailed in the following preparation afford Example-3 according to Method A. However, Example-3 was synthesized in a parallel library format and, thus, its preparation is included for completeness.

Preparation of 1-{4-[8-(2-Chloro-6-methylphenoxy)pyrido[3,4-d]pyrimidin-4-yl]piperazin-1-yl}prop-2-en-1-one (Example-3)

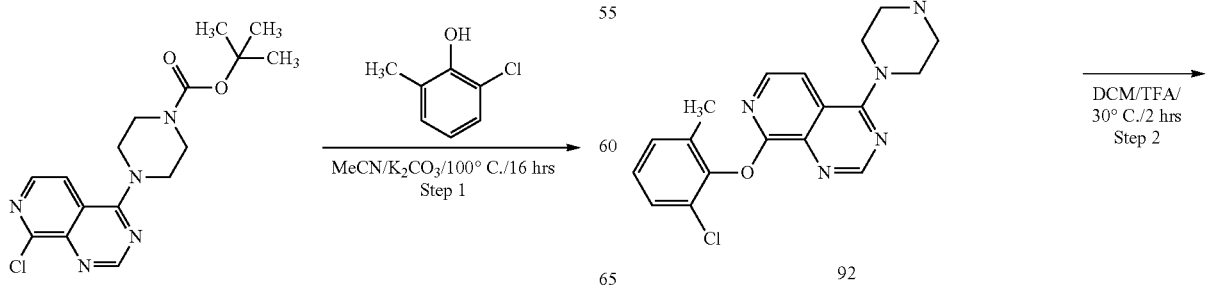

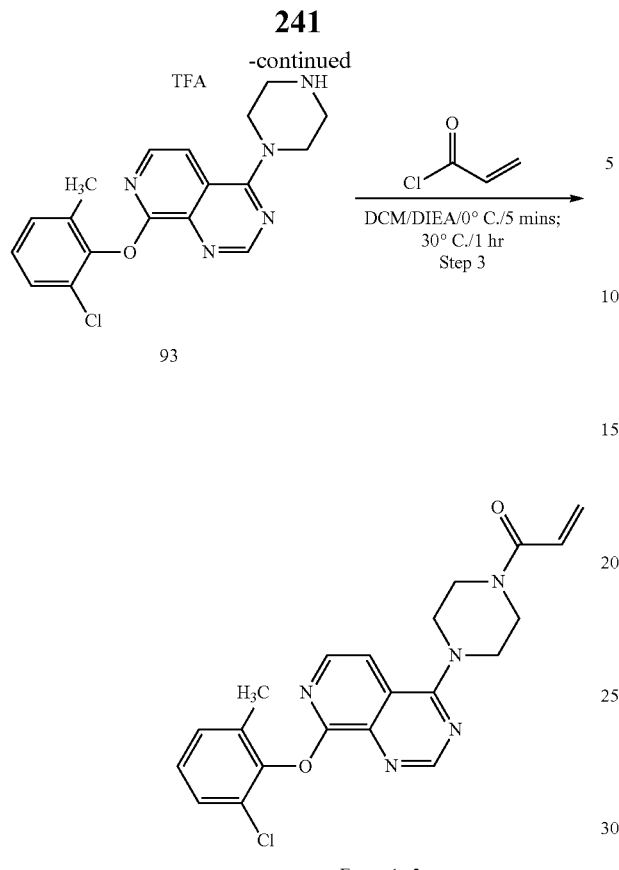

Example-3

Step 1:

A solution of tert-butyl 4-(8-chloropyrido[3,4-d]pyrimidin-4-yl)piperazine-1-carboxylate in acetonitrile (4) (1.0 mL, 0.15 M) was added to 2-chloro-6-methylphenol (180 µmol) followed by the addition of K₂CO₃ (300 µmol). The reaction vessel was sealed and heated at 100° C. for 16 hours. The solvent was removed and the crude product (92) was purified by prep TLC.

Step 2:

A solution of DCM and TFA (7:1 V/V, 1.6 mL) was added to tert-butyl 4-[8-(2-chloro-6-methylphenoxy)pyrido[3,4-d]pyrimidin-4-yl]piperazine-1-carboxylate (92) (100 µmol) and the reaction was stirred for 2 hours. The solvent was removed under reduced pressure.

Step 3:

A 0.1 M solution of acryloyl chloride in DCM was prepared and 1.0 mL of the solution was added to a solution of 8-(2-chloro-6-methylphenoxy)-4-(piperazin-1-yl)pyrido[3,4-d]pyrimidine (93) (100 µmol) and DIEA (300 µmol) in DCM (1.0 mL) at 0° C. The reaction was heated for 1 hour at 30° C. and monitored by LCMS until the reaction was finished. The solvent was removed under reduced pressure and the crude product was purified by prep-HPLC using an Agela Durashell C18 column (150×25 mm, 5 µm) and eluted with a 26-66% acetonitrile/water (0.05 M NH₄OH) gradient at 35 mL/minute and gave 1-{4-[8-(2-chloro-6-methylphenoxy)pyrido[3,4-d]pyrimidin-4-yl]piperazin-1-yl}prop-2-en-1-one (Example-3). LCMS (ESI) m/z 410 (M+H).

The following examples were prepared according to general Method B:

Preparation of 1-(4-{2-methoxy-8-[(5-methyl-1H-indazol-4-yl)oxy]pyrido[3,4-d]pyrimidin-4-yl}piperazin-1-yl)prop-2-en-1-one (Example-1B)

Step 1:

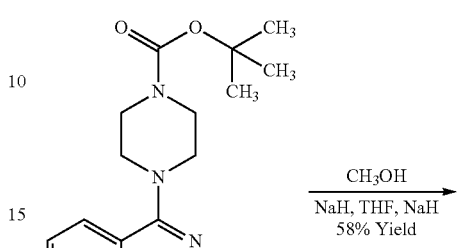

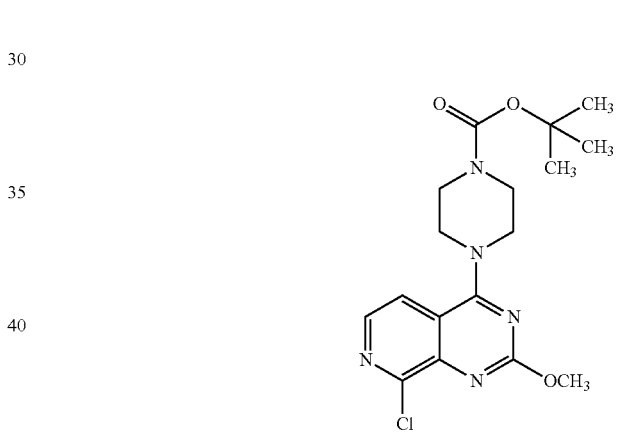

To a mixture of NaH (60% in oil, 48 mg, 1.2 mmol) in THF (6 mL) was added methanol (70 mg, 2.2 mmol). The solution was stirred at room temperature for 30 minutes followed by the addition of tert-butyl 4-(2,8-dichloropyrido[3,4-d]pyrimidin-4-yl)piperazine-1-carboxylate (20) (421 mg, 1.1 mmol). The crude reaction mixture was stirred at room temperature for 16 hours. LCMS gave ~80% of desired product. The solvent was removed under reduced pressure and the crude product was diluted with EtOAc (5 mL) and water (4 mL). The layers were separated and the aqueous layer was extracted with EtOAc (2×8 mL). The combined organic layers were dried over Na₂SO₄, filtered and concentrated. The crude product was purified using prep-TLC which was eluted with petroleum ether/EtOAc (2:1) and gave tert-butyl 4-(8-chloro-2-methoxypyrido[3,4-d]pyrimidin-4-yl)piperazine-1-carboxylate (94) as a yellow solid (244 mg, 58% yield). LCMS (ESI) m/z 380 (M+H).

Step 2:

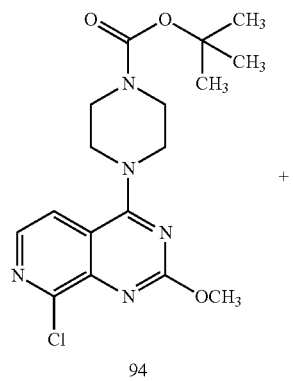

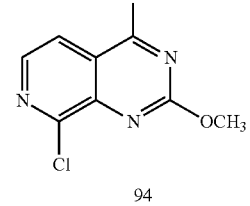

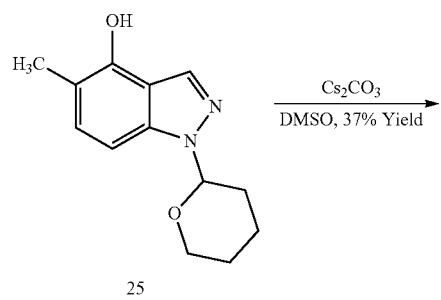

Tert-butyl 4-(2-methoxy-8-{[5-methyl-1-(tetrahydro-2H-pyran-2-yl)-1H-indazol-4-yl]oxy}pyrido[3,4-d]pyrimidin-4-yl)piperazine-1-carboxylate (95) (138 mg, 37% yield) was prepared according to the procedure used to prepare 4-(8-{[5-methyl-1-(tetrahydro-2H-pyran-2-yl)-1H-indazol-4-yl]oxy}pyrido[3,4-d]pyrimidin-4-yl)piperazine-1-carboxylate (85) except the reaction was done in DMSO at 135° C. for 2 hours. LCMS (ESI) m/z 576 (M+H).

Step 3:

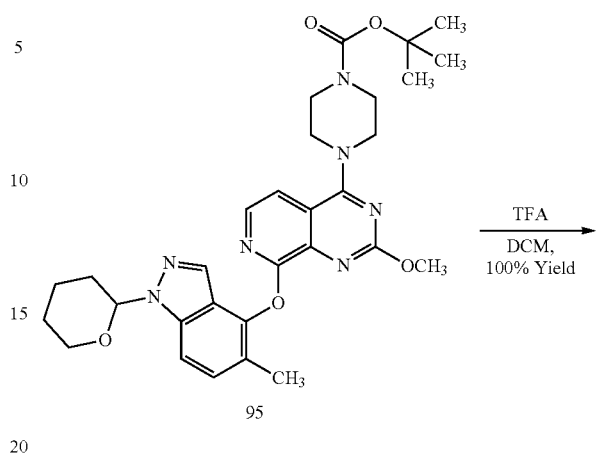

2-Methoxy-8-[(5-methyl-1H-indazol-4-yl)oxy]-4-(piperazin-1-yl)pyrido[3,4-d]pyrimidine (95) was prepared according to the procedure used to prepare 8-[(5-methyl-1H-indazol-4-yl)oxy]-4-(piperazin-1-yl)pyrido[3,4-d]pyrimidine (86). The solvent was removed and the crude product was used in the next step. LCMS (ESI) m/z 392 (M+H).

Step 4:

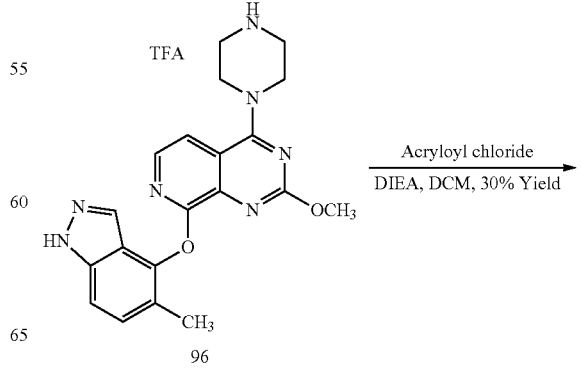

245
-continued

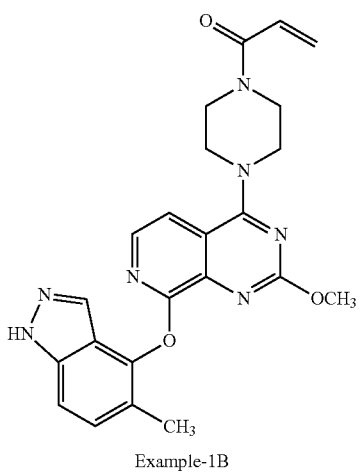

Example-1B 1-(4-{2-Methoxy-8-[(5-methyl-1H-indazol-4-yl)oxy] pyrido[3,4-d]pyrimidin-4-yl}piperazin-1-yl)prop-2-en-1-one (Example-1B) (32 mg, 30% yield) was prepared according to the procedure used to prepare 1-{4-[8-(2-chloro-6-methylphenoxy)pyrido[3,4-d]pyrimidin-4-yl]piperazin-1-yl}prop-2-en-1-one (Example-3). The crude product was purified by prep-HPLC using a YMC-Actus Triart C18 column (150×30 mm, 5 μm) and eluted with 30-50% acetonitrile/water (0.05% ammonia). $^1$H NMR (400 MHz, DMSO-$d_6$) δ 13.10 (s, 1H), 7.73 (d, J=5.8 Hz, 1H), 7.49-7.63 (m, 2H), 7.24-7.43 (m, 2H), 6.84 (dd, J=16.7, 10.4 Hz, 1H), 6.18 (dd, J=16.6, 2.3 Hz, 1H), 5.75 (dd, J=10.3, 2.3 Hz, 1H), 3.98 (s, 3H), 3.72-3.94 (m, 8H), 2.12-2.25 (m, 3H). LCMS (ESI) m/z 446 (M+H).

Preparation of 1-(4-{2-[3-(dimethylamino)azetidin-1-yl]-8-[(5-methyl-1H-indazol-4-yl)oxy]pyrido[3,4-d]pyrimidin-4-yl}piperazin-1-yl)prop-2-en-1-one (Example-2B)

Step 1:

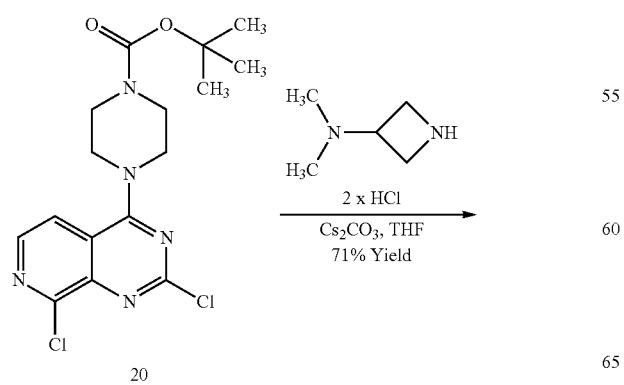

246
-continued

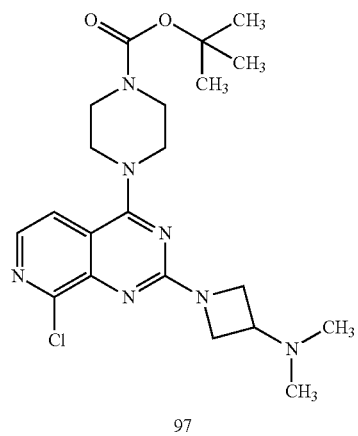

97

Tert-butyl 4-{8-chloro-2-[3-(dimethylamino)azetidin-1-yl]pyrido[3,4-d]pyrimidin-4-yl}piperazine-1-carboxylate (97) (224 mg, 71% yield) was prepared according to the procedure used to prepare tert-butyl 4-(8-chloro-2-methoxypyrido[3,4-d]pyrimidin-4-yl)piperazine-1-carboxylate (94) except the base was replaced with $Cs_2CO_3$. LCMS (ESI) m/z 450 (M+H).

Step 2:

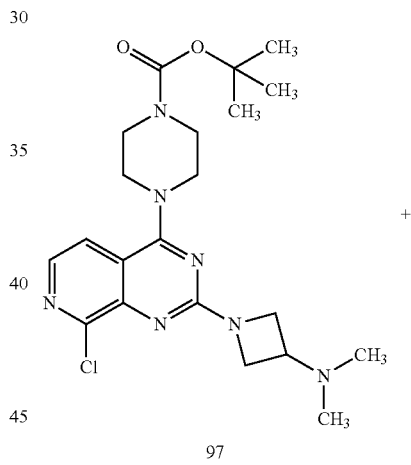

97

+

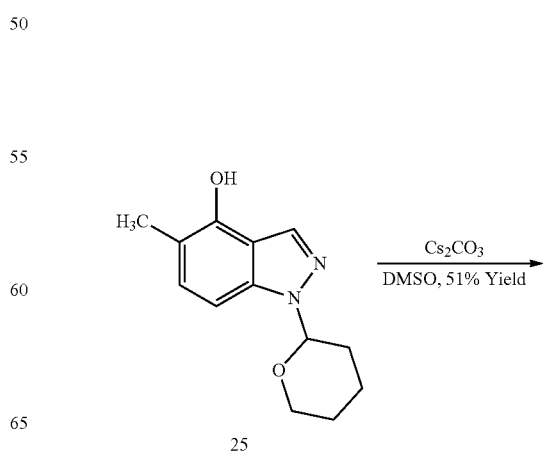

247

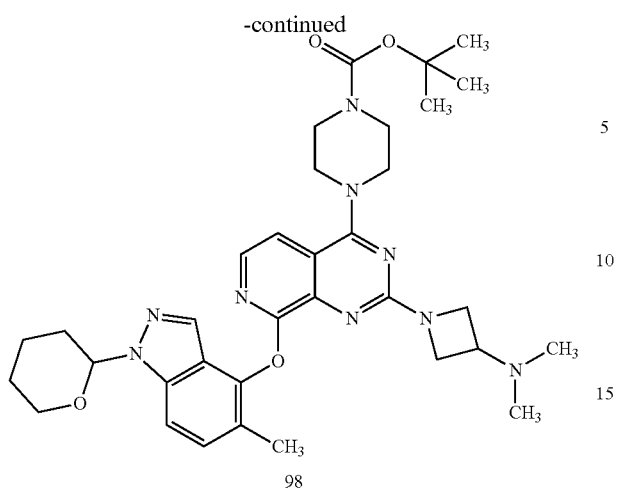

98

Tert-butyl 4-(2-[3-(dimethylamino)azetidin-1-yl]-8-{[5-methyl-1-(tetrahydro-2H-pyran-2-yl)-1H-indazol-4-yl]oxy}pyrido[3,4-d]pyrimidin-4-yl)piperazine-1-carboxylate (98) (163 mg, 51% yield) was prepared according to the procedure used to prepare 4-(8-{[5-methyl-1-(tetrahydro-2H-pyran-2-yl)-1H-indazol-4-yl]oxy}pyrido[3,4-d]pyrimidin-4-yl)piperazine-1-carboxylate (85) except the reaction was done in DMSO at 135° C. for 2 hours in a microwave. $^1$H NMR (400 MHz, CDCl$_3$) δ 7.71 (s, 1H), 7.55 (d, J=5.8 Hz, 1H), 7.33-7.39 (m, 1H), 7.27-7.31 (m, 1H), 7.09 (d, J=5.8 Hz, 1H), 5.68 (dd, J=9.4, 2.6 Hz, 1H), 4.20-4.32 (m, 2H), 3.99-4.11 (m, 3H), 3.56-3.80 (m, 9H), 3.12-3.27 (m, 1H), 2.44-2.66 (m, 1H), 2.29 (s, 3H), 2.23 (s, 6H), 2.11-2.19 (m, 1H), 2.01-2.10 (m, 1H), 1.70-1.80 (m, 2H), 1.64-1.69 (m, 1H), 1.46-1.54 (m, 9H). LCMS (ESI) m/z 644 (M+H).

Step 3:

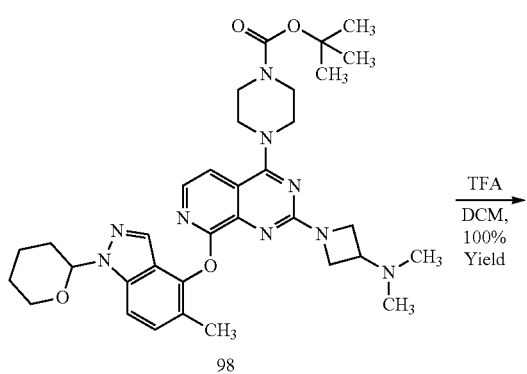

98

$\xrightarrow{\text{TFA}}{\text{DCM, 100% Yield}}$

248

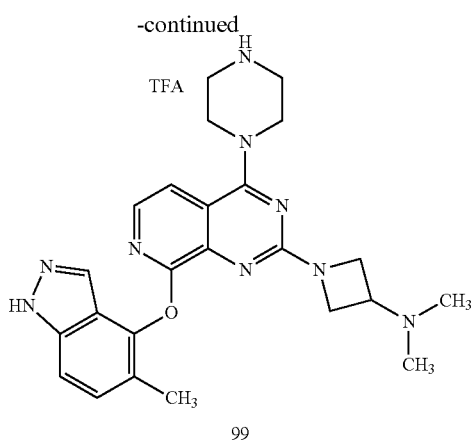

99

N,N-Dimethyl-1-{8-[(5-methyl-1H-indazol-4-yl)oxy]-4-(piperazin-1-yl)pyrido[3,4-d]pyrimidin-2-yl}azetidin-3-amine (99) was prepared according to the procedure used to prepare 8-[(5-methyl-1H-indazol-4-yl)oxy]-4-(piperazin-1-yl)pyrido[3,4-d]pyrimidine (86). LCMS (ESI) m/z 460 (M+H).

Step 4:

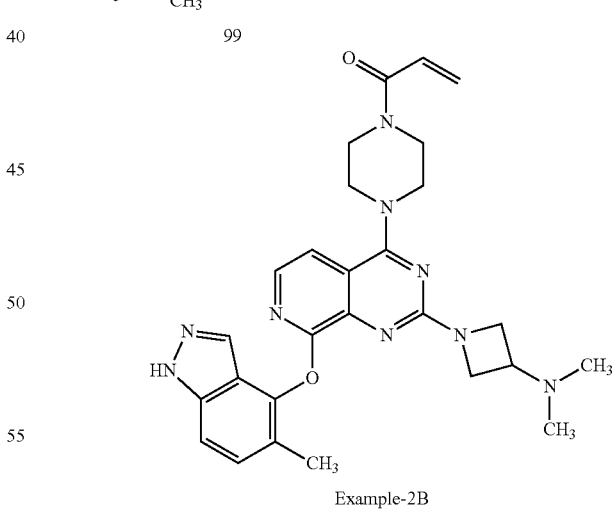

Example-2B 1-(4-{2-[3-(Dimethylamino)azetidin-1-yl]-8-[(5-methyl-1H-indazol-4-yl)oxy]pyrido[3,4-d]pyrimidin-4-yl}piperazin-1-yl)prop-2-en-1-one (Example-2B) (24 mg, 26% yield) was prepared according to the procedure used to prepare 1-{4-[8-(2-chloro-6-methylphenoxy)pyrido[3,4-d]pyrimidin-4-yl]piperazin-1-yl}prop-2-en-1-one (Example-3). $^1$H NMR (400 MHz, DMSO-d$_6$) δ 13.09 (s, 1H), 7.48-7.62 (m, 2H), 7.24-7.41 (m, 3H), 6.85 (dd, J=16.8, 10.5 Hz, 1H), 6.17 (dd, J=16.7, 2.4 Hz, 1H), 5.76 (d, J=2.3 Hz, 1H), 5.70-5.79 (m, 1H), 5.73 (d, J=2.3 Hz, 1H), 4.14 (dd, J=8.9, 7.4 Hz, 2H), 3.90 (dd, J=9.2, 5.1 Hz, 2H), 3.68-3.86 (m, 8H), 3.08-3.22 (m, 1H), 2.08-2.20 (m, 9H). LCMS (ESI) m/z 514 (M+H).

The examples in the following table were prepared using method B and the procedures used to prepare 1-(4-{2-methoxy-8-[(5-methyl-1H-indazol-4-yl)oxy]pyrido[3,4-d]pyrimidin-4-yl}piperazin-1-yl)prop-2-en-1-one Example-1B (ethers) or 1-(4-{2-[3-(dimethylamino)azetidin-1-yl]-8-[(5-methyl-1H-indazol-4-yl)oxy]pyrido[3,4-d]pyrimidin-4-yl}piperazin-1-yl)prop-2-en-1-one Example-2B (amines). The following examples were made with non-critical changes or substitutions to the exemplified procedure used to prepare Example-1B or Example-2B that someone who is skilled in the art would be able to realize.

| Example | Structure | Compound Name | LCMS m/z | ¹H NMR |
|---|---|---|---|---|
| 3B | 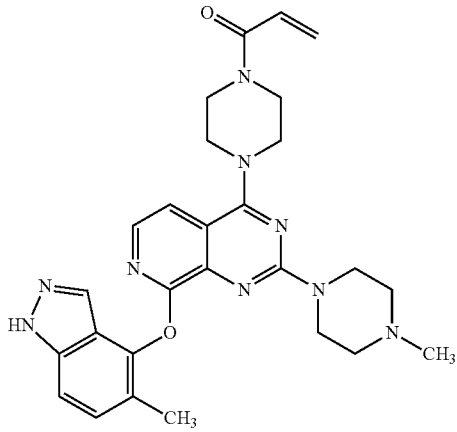 [SMILES: C=CC(=O)N1CCN(c2nc(N3CCN(C)CC3)nc3c(Oc4c(C)ccc5[nH]ncc45)nccc23)CC1] | 1-(4-{8-[(5-methyl-1H-indazol-4-yl)oxy]-2-(4-methylpiperazin-1-yl)pyrido[3,4-d]pyrimidin-4-yl}piperazin-1-yl)prop-2-en-1-one | 514 (M + H) | ¹H NMR (400 MHz, DMSO-d$_6$) δ 13.08 (br. s, 1H), 7.45-7.59 (m, 2H), 7.23-7.42 (m, 3H), 6.83 (dd, J = 16.7, 10.5 Hz, 1H), 6.11-6.23 (m, 1H), 5.68-5.81 (m, 1H), 3.66-3.93 (m, 12H), 3.17 (s, 1H), 2.33-2.44 (m, 4H), 2.12-2.27 (m, 6H). |
| 4B | 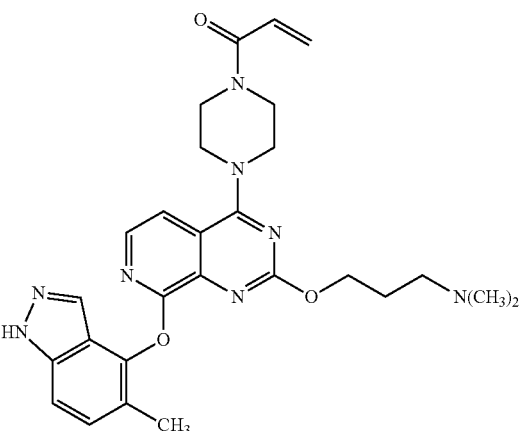 | 1-(4-{2-[3-(dimethylamino)propoxy]-8-[(5-methyl-1H-indazol-4-yl)oxy]pyrido[3,4-d]pyrimidin-4-yl}piperazin-1-yl)prop-2-en-1-one | 446 (M + H) | ¹H NMR (400 MHz, CD$_3$OD) δ 7.71-7.75 (m, 1H), 7.55-7.74 (m, 3H), 7.40-7.43 (m, 1H), 6.77-6.90 (m, 1H), 6.31 (dd, J = 16.8, 2.0 Hz, 1H), 5.84 (dd, J = 10.8, 1.8 Hz, 1H), 4.62 (s, 2H), 4.08 (br. s, 4H), 3.95 (br. s, 4H), 3.00-3.16 (m, 2H), 2.66 (br. s, 6H), 2.28 (s, 3H), 2.20 (br. s, 2H). |
| 5B | 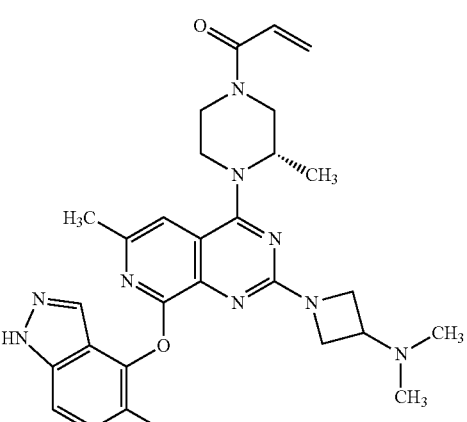 | 1-[(3S)-4-{2-[3-(dimethylamino)azetidin-1-yl]-6-methyl-8-[(5-methyl-1H-indazol-4-yl)oxy]pyrido[3,4-d]pyrimidin-4-yl}-3-methylpiperazin-1-yl]prop-2-en-1-one | 542 (M + H) | ¹H NMR (400 MHz, DMSO-d$_6$) δ 13.07 (s, 1H), 7.53 (s, 1H), 7.32 (d, J = 8.4 Hz, 1H), 7.27 (d, J = 8.4 Hz, 1H), 7.12 (s, 1H), 6.92-6.78 (m, 1H), 6.18 (m, 1H), 5.74 (dd, J = 10.4, 2.2 Hz, 1H), 4.59 (s, 1H), 4.13 (d, J = 7.0 Hz, 2H), 4.00-3.95 (m, 4H), 3.60 (d, J = 10.7 Hz, 1H), 3.46 (m, 2H), 3.21 (d, J = 14.8 Hz, 1H), 3.10 (m, 1H), 2.20-2.10 (m, 12H), 1.24 (d, J = 5.8 Hz, 3H). |

-continued

| Example | Structure | Compound Name | LCMS m/z | ¹H NMR |
|---------|-----------|---------------|----------|--------|
| 6B | 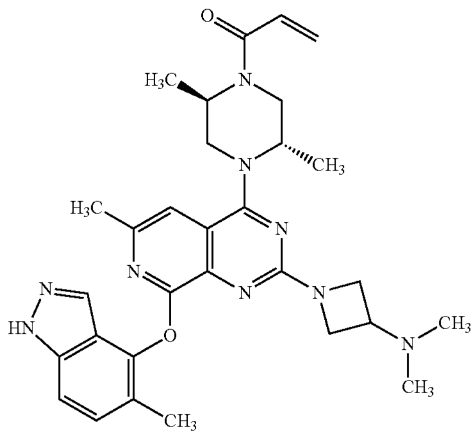 [SMILES: C=CC(=O)N1C[C@H](C)N(c2nc(N3CC(N(C)C)C3)nc3c(Oc4c(C)ccc5[nH]ncc45)nc(C)cc23)C[C@H]1C] | 1-[(2R,5S)-4-{2-[3-(Dimethylamino)azetidin-1-yl]-6-methyl-8-[(5-methyl-1H-indazol-4-yl)oxy]pyrido[3,4-d]pyrimidin-4-yl}-2,5-dimethylpiperazin-1-yl]prop-2-en-1-one | 556 (M + H) | ¹H NMR (400 MHz, DMSO-d₆) δ 13.06 (s, 1H), 7.53 (s, 1H), 7.32 (d, J = 8.5 Hz, 1H), 7.27 (d, J = 8.4 Hz, 1H), 7.12 (s, 1H), 6.83 (td, J = 16.7, 10.5 Hz, 1H), 6.17 (dd, J = 16.7, 2.3 Hz, 1H), 5.76-5.70 (m, 1H), 4.68 (d, J = 35.3 Hz, 2H), 4.09 (m, 3H), 3.97 (d, J = 13.8 Hz, 1H), 3.86-3.79 (m, 3H), 3.68 (d, J = 13.3 Hz, 1H), 3.11 (dd, J = 11.5, 6.0 Hz, 1H), 2.17 (s, 3H), 2.16 (s, 3H), 2.11 (s, 6H), 1.24 (d, J = 4.7 Hz, 6H). |
| 7B | 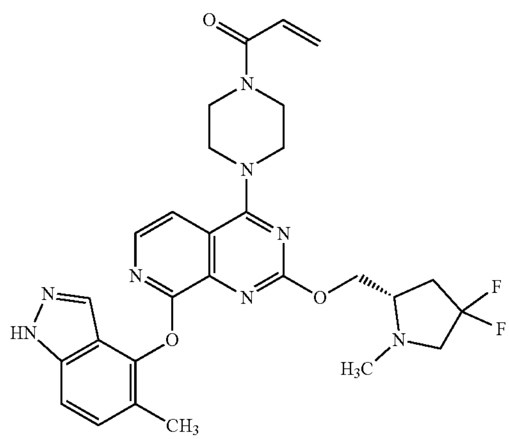 [SMILES: C=CC(=O)N1CCN(c2nc(OC[C@@H]3CC(F)(F)CN3C)nc3c(Oc4c(C)ccc5[nH]ncc45)nccc23)CC1] | 1-[4-(2-{[(2S)-4,4-difluoro-1-methylpyrrolidin-2-yl]methoxy}-8-[(5-methyl-1H-indazol-4-yl)oxy]pyrido[3,4-d]pyrimidin-4-yl)piperazin-1-yl]prop-2-en-1-one | 565 (M + H) | ¹H NMR (400 MHz, DMSO-d₆) δ 13.07 (s, 1H), 7.72 (d, J = 5.8 Hz, 1H), 7.56 (s, 1H), 7.53 (d, J = 5.9 Hz, 1H), 7.36 (d, J = 8.6 Hz, 1H), 7.29 (d, J = 8.5 Hz, 1H), 6.83 (dd, J = 16.7, 10.4 Hz, 1H), 6.175 (dd, J₁ = 16 Hz, J₂ = 2.3 Hz, 1H), 5.75 (dd, J₁ = 12.8 Hz, J = 4.0 Hz, 1H), 4.59-4.35 (m, 2H), 4.01-3.88 (m, 4H), 3.87-3.69 (m, 4H), 3.41-3.35 (m, 1H), 3.10-2.88 (m, 1H), 2.72-2.61 (m, 1H), 2.61-2.53 (m, 1H), 2.39 (s, 3H), 2.35-2.20 (m, 1H), 2.17 (s, 3H). |
| 8B | 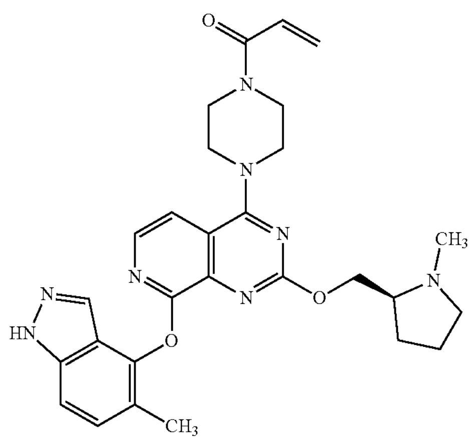 [SMILES: C=CC(=O)N1CCN(c2nc(OC[C@@H]3CCCN3C)nc3c(Oc4c(C)ccc5[nH]ncc45)nccc23)CC1] | 1-[4-(8-[(5-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 529 (M + H) | ¹H NMR (600 MHz, DMSO-d₆) δ 13.10 (s, 1H), 7.71 (d, J = 5.8 Hz, 1H), 7.56 (s, 1H), 7.53 (d, J = 5.8 Hz, 1H), 7.36 (d, J = 8.4 Hz, 1H), 7.30 (d, J = 8.5 Hz, 1H), 6.83 (dd, J = 16.7, 10.4 Hz, 1H), 6.18 (dd, J = 16.8, 2.3 Hz, 1H), 5.75 (dd, J = 10.6, 2.2 Hz, 1H), 4.43 (dd, J = 10.9, 4.7 Hz, 1H), 4.26 (dd, J = 10.9, 6.3 Hz, 1H), 3.95-3.85 (m, 4H), 3.86-3.75 (m, 4H), 3.01-2.92 (m, 1H), 2.69-2.60 (m, 1H), 2.39 (s, 3H), 2.26-2.14 (m, 4H), 2.03-1.93 (m, 1H), 1.80-1.59 (m, 3H). |

| Example | Structure | Compound Name | LCMS m/z | ¹H NMR |
|---|---|---|---|---|
| 9B | 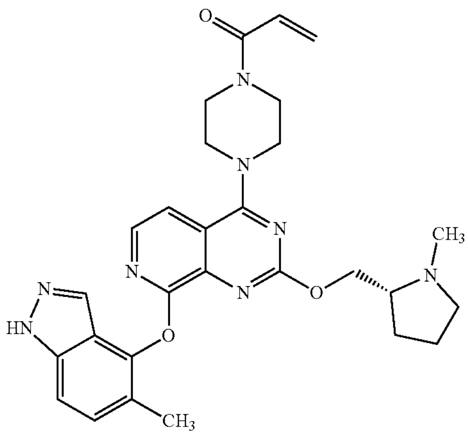 [SMILES: C=CC(=O)N1CCN(c2nc(OC[C@H]3CCCN3C)nc3c(Oc4c(C)ccc5[nH]ncc45)nccc23)CC1] | 1-[4-(8-[(5-methyl-1H-indazol-4-yl)oxy]-2-{[(2R)-1-methylpyrrolidin-2-yl]methoxy}pyrido[3,4-d]pyrimidin-4-yl)piperazin-1-yl]prop-2-en-1-one | 529 (M + H) | ¹H NMR (400 MHz, DMSO-d₆) δ 13.10 (s, 1H), 7.71 (d, J = 5.75 Hz, 1H), 7.47-7.61 (m, 2H), 7.24-7.41 (m, 2H), 6.83 (dd, J = 16.7, 10.4 Hz, 1H), 6.18 (dd, J = 16.7, 2.4 Hz, 1H), 5.67-5.82 (m, 1H), 4.42 (dd, J = 10.8, 4.6 Hz, 1H), 4.23 (dd, J = 10.8, 6.4 Hz, 1H), 3.86-3.93 (m, 4H), 3.84 (br. s, 2H), 3.77 (br. s, 2H), 2.94 (dt, J = 6.3, 3.3 Hz, 1H), 2.60 (dd, J = 6.2, 4.6 Hz, 1H), 2.37 (s, 3H), 2.10-2.25 (m, 4H), 1.89-2.02 (m, 1H), 1.57-1.74 (m, 3H). |
| 10B | 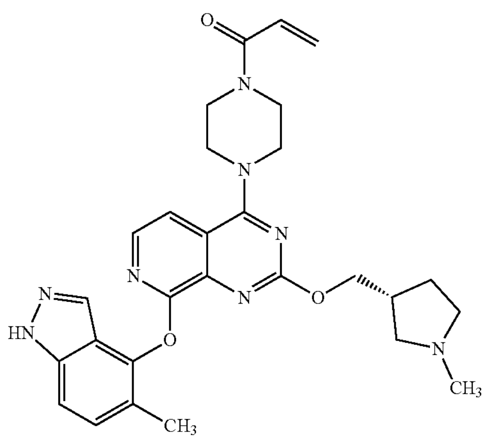 [SMILES: C=CC(=O)N1CCN(c2nc(OC[C@@H]3CCN(C)C3)nc3c(Oc4c(C)ccc5[nH]ncc45)nccc23)CC1] | 1-[4-(8-[(5-methyl-1H-indazol-4-yl)oxy]-2-{[(3R)-1-methylpyrrolidin-3-yl]methoxy}pyrido[3,4-d]pyrimidin-4-yl)piperazin-1-yl]prop-2-en-1-one | 529 (M + H) | ¹H NMR (400 MHz, DMSO-d₆) δ 13.09 (s, 1H), 7.72 (d, J = 5.8 Hz, 1H), 7.48-7.59 (m, 2H), 7.23-7.41 (m, 2H), 6.83 (dd, J = 16.7, 10.4 Hz, 1H), 6.17 (dd, J = 16.6, 2.3 Hz, 1H), 5.67-5.80 (m, 1H), 4.26 (dd, J = 7.0, 2.5 Hz, 2H), 3.80-3.91 (m, 6H), 3.76 (br. s, 2H), 2.54-2.63 (m, 2H), 2.41 (br. s, 3H), 2.26 (s, 3H), 2.17 (s, 3H), 1.91-2.00 (m, 1H), 1.47-1.61 (m, 1H). |
| 11B | 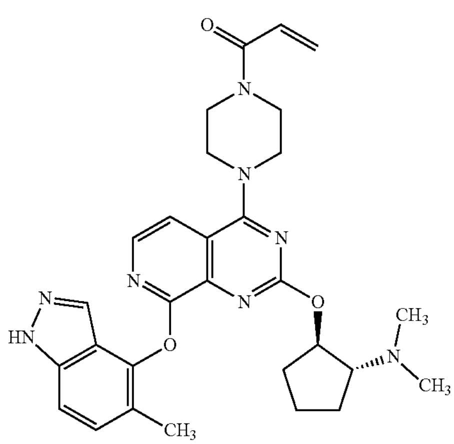 [SMILES: C=CC(=O)N1CCN(c2nc(O[C@@H]3CCC[C@H]3N(C)C)nc3c(Oc4c(C)ccc5[nH]ncc45)nccc23)CC1] | 1-[4-(2-{[(1R,2R)-2-(dimethylamino)cyclopentyl]oxy}-8-[(5-methyl-1H-indazol-4-yl)oxy]pyrido[3,4-d]pyrimidin-4-yl)piperazin-1-yl]prop-2-en-1-one | 543 (M + H) | ¹H NMR (400 MHz, CD₃OD) δ 8.52 (s, 1H), 7.79 (d, J = 5.9 Hz, 1H), 7.74 (s, 1H), 7.62 (d, J = 5.9 Hz, 1H), 7.47 (d, J = 8.6 Hz, 1H), 7.41 (d, J = 8.6 Hz, 1H), 6.81 (dd, J = 16.8, 10.6 Hz, 1H), 6.29 (dd, J = 16.8, 1.9 Hz, 1H), 5.82 (dd, J = 10.6, 2.0 Hz, 1H), 5.46 (dt, J = 8.0, 5.2 Hz, 1H), 4.19-4.02 (m, 4H), 4.00-3.71 (m, 5H), 2.74 (s, 6H), 2.33 (dd, J = 13.9, 7.4 Hz, 1H), 2.28 (s, 3H), 2.24-2.15 (m, 1H), 2.13-1.98 (m, 1H), 1.98-1.80 (m, 3H). |

255 / 256

-continued

| Example | Structure | Compound Name | LCMS m/z | $^1$H NMR |
|---|---|---|---|---|
| 12B | 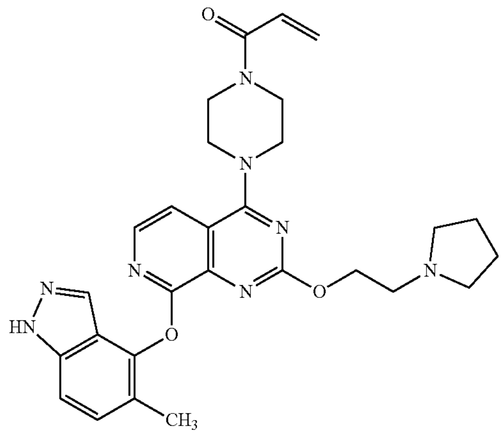 [SMILES: C=CC(=O)N1CCN(c2nc(OCCN3CCCC3)nc3c(Oc4c(C)ccc5[nH]ncc45)nccc23)CC1] | 1-(4-{8-[(5-methyl-1H-indazol-4-yl)oxy]-2-[2-(pyrrolidin-1-yl)ethoxy]pyrido[3,4-d]pyrimidin-4-yl}piperazin-1-yl)prop-2-en-1-one | 529 (M + H) | $^1$H NMR (400 MHz, DMSO-d$_6$) δ 13.13 (s, 1H), 7.75 (d, J = 5.8 Hz, 1H), 7.62-7.52 (m, 2H), 7.37 (d, J = 8.5 Hz, 1H), 7.30 (d, J = 8.5 Hz, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 4.68 (t, J = 4.9 Hz, 2H), 3.99-3.74 (m, 8H), 3.48 (s, 2H), 3.23 (br. s, 4H), 2.17 (s, 3H), 1.85 (s, 4H). |
| 13B | 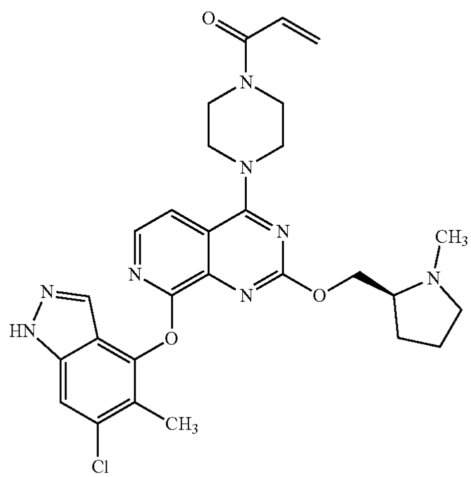 [SMILES: C=CC(=O)N1CCN(c2nc(OC[C@@H]3CCCN3C)nc3c(Oc4c(C)c(Cl)cc5[nH]ncc45)nccc23)CC1] | 1-[4-(8-[(6-chloro-5-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 563 (M + H) | $^1$H NMR (600 MHz, DMSO-d$_6$) δ 13.27 (s, 1H), 7.27 (t, J = 4.5 Hz, 1H), 7.61 (s, 1H), 7.58-7.53 (m, 2H), 6.81 (ddd, J = 14.4, 10.4, 3.6 Hz, 1H), 6.17 (d, J = 16.7 Hz, 1H), 5.75 (d, J = 10.7 Hz, 1H), 4.40 (dd, J = 10.9, 4.6 Hz, 1H), 4.22 (dd, J = 10.8, 6.3 Hz, 1H), 3.91 (d, J = 5.6 Hz, 4H), 3.80 (d, J = 40.3 Hz, 4H), 3.00-2.88 (m, 1H), 2.64-2.57 (m, 1H), 2.36 (s, 3H), 2.24-2.14 (m, 4H), 1.95 (dt, J = 12.0, 7.8 Hz, 1H), 1.75-1.59 (m, 3H). |

The following examples were prepared according to general Method C:

Preparation of methyl 3-nitro-2-{[1-(tetrahydro-2H-pyran-2-yl)-5-(trifluoromethyl)-1H-indazol-4-yl]oxy}pyridine-4-carboxylate (102)

Step 1:

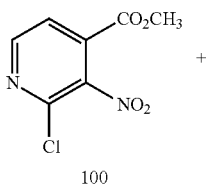

100

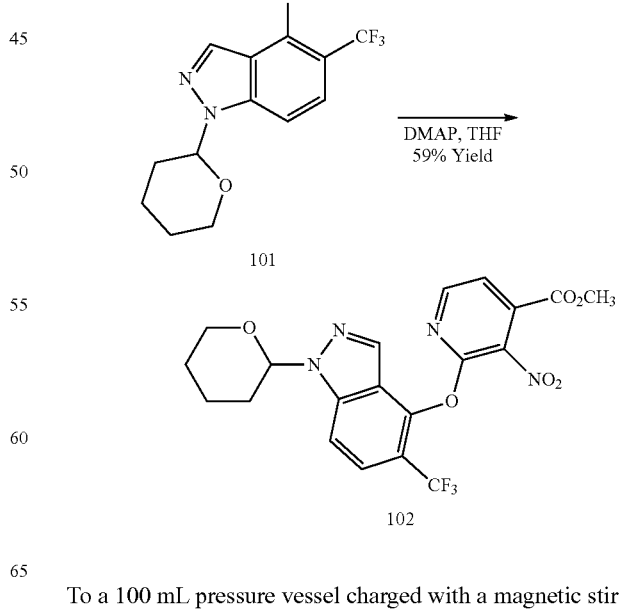

To a 100 mL pressure vessel charged with a magnetic stir bar was added methyl 2-chloro-3-nitropyridine-4-carboxylate (100) (605 mg, 2.8 mmol), 1-(tetrahydro-2H-pyran-2-yl)-5-(trifluoromethyl)-1H-indazol-4-ol (101) (800 mg, 2.8 mmol), DMAP (854 mg, 7.0 mmol) and THF (11.2 mL). The flask was sealed and heated at 70° C. After 3 hours the reaction was checked by LCMS, which showed good conversion to the desired product. The crude reaction mixture was diluted with EtOAc and the organic layer was washed with water, brine, dried over anhydrous magnesium sulfate, filtered and concentrated. The crude product was purified over 10 g of silica gel (Biotage column) which was eluted with 25% EtOAc/heptanes and gave methyl 3-nitro-2-{[1-(tetrahydro-2H-pyran-2-yl)-5-(trifluoromethyl)-1H-indazol-4-yl]oxy}pyridine-4-carboxylate (102) as a pinkish solid (764 mg, 59% yield). $^1$H NMR (400 MHz, CDCl$_3$) δ 8.22 (d, J=5.1 Hz, 1H), 7.77 (d, J=0.8 Hz, 1H), 7.67 (d, J=8.9 Hz, 1H), 7.62 (d, J=8.9 Hz, 1H), 7.58 (d, J=5.1 Hz, 1H), 5.76 (dd, J=9.0, 2.7 Hz, 1H), 4.16-3.88 (m, 4H), 3.87-3.64 (m, 1H), 2.63-2.33 (m, 1H), 2.26-2.04 (m, 2H), 1.90-1.66 (m, 3H).

Preparation of methyl 2-{[5-chloro-6-methyl-1-(tetrahydro-2H-pyran-2-yl)-1H-indazol-4-yl]oxy}-6-methyl-3-nitropyridine-4-carboxylate (104)

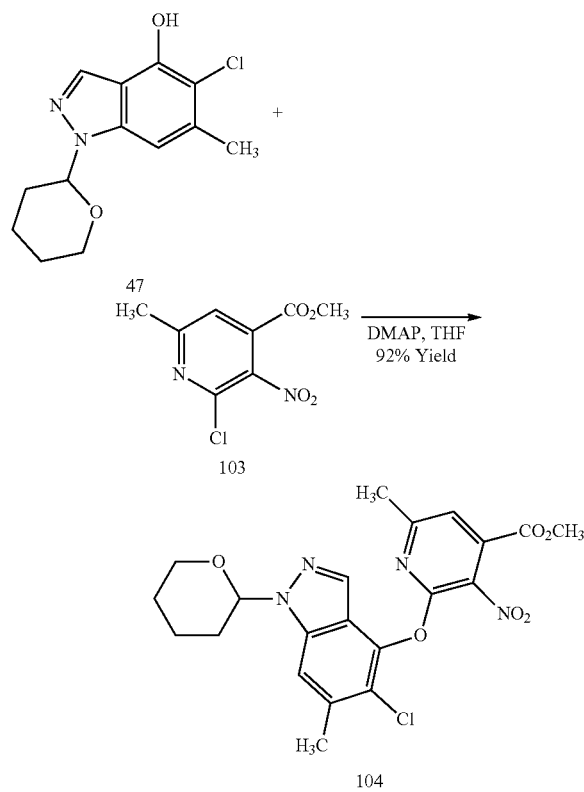

A mixture of methyl 2-chloro-6-methyl-3-nitropyridine-4-carboxylate (103) (340 mg, 1.5 mmol), 5-chloro-6-methyl-1-(tetrahydro-2H-pyran-2-yl)-1H-indazol-4-ol (47) (393 mg, 1.47 mmol) and DMAP (450 mg, 3.7 mmol) in tetrahydrofuran (10 mL) was stirred at 70° C. overnight. The crude reaction mixture was diluted with EtOAc, and sequentially washed with water and brine. The organic layer was dried over sodium sulfate and concentrated. The crude product was purified over silica gel (ISCO 40 g cartridge) and eluted with 0-100% EtOAc/heptane and gave methyl 2-{[5-chloro-6-methyl-1-(tetrahydro-2H-pyran-2-yl)-1H-indazol-4-yl]oxy}-6-methyl-3-nitropyridine-4-carboxylate (104) as a cream solid (627 mg, 92% yield). $^1$H NMR (400 MHz, CDCl$_3$) δ 7.78 (d, J=0.6 Hz, 1H), 7.42 (s, 1H), 7.39-7.32 (m, 1H), 5.70 (dd, J=2.6, 9.4 Hz, 1H), 4.10-4.03 (m, 1H), 3.97 (s, 3H), 3.86-3.71 (m, 1H), 2.55 (s, 3H), 2.35 (s, 3H), 2.21-2.07 (m, 2H), 1.85-1.63 (m, 4H). LCMS (ESI) m/z 461 (M+H).

Preparation of 1-(4-{8-[(5-methyl-1H-indazol-4-yl)oxy]quinazolin-4-yl}piperazin-1-yl)prop-2-en-1-one (Example-1C)

Step 1:

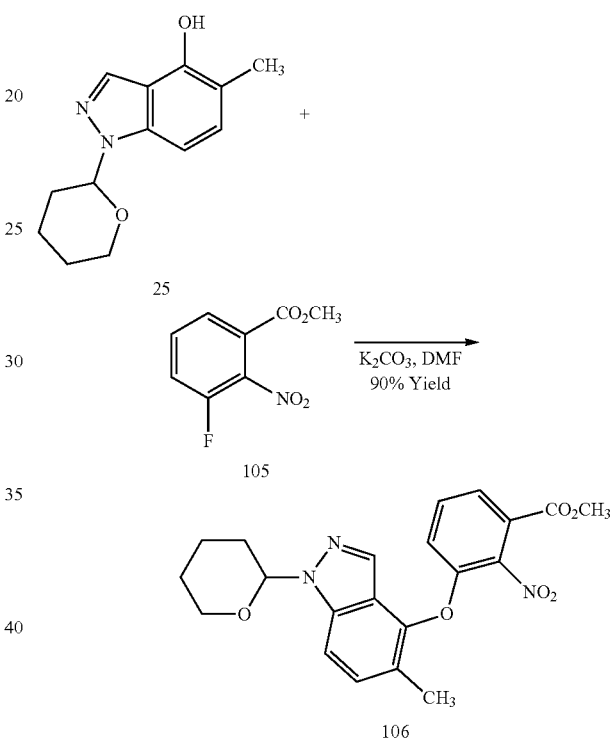

To a solution of methyl 3-fluoro-2-nitrobenzoate (105) (2 g, 10 mmol) in DMF (60 mL) was added 5-methyl-1-(tetrahydro-2H-pyran-2-yl)-1H-indazol-4-ol (25) (2.33 g, 10 mmol) and K$_2$CO$_3$ (2.78 g, 20.1 mmol). The reaction was stirred at 60° C. for 16 hours. LCMS analysis showed the reaction was done. Water (100 mL) was added and the mixture was extracted with EtOAc (2×100 mL). The combined organic layers were washed with brine, dried over Na$_2$SO$_4$, filtered and evaporated. The crude product was purified by silica gel chromatography and eluted with petroleum ether/EtOAc (1/1) and gave methyl 3-{[5-methyl-1-(tetrahydro-2H-pyran-2-yl)-1H-indazol-4-yl]oxy}-2-nitrobenzoate (106) (3.9 g, 90% yield). $^1$H NMR (400 MHz, CDCl$_3$) δ 7.77-7.64 (m, 2H), 7.44 (d, J=8.5 Hz, 1H), 7.38-7.24 (m, 2H), 6.83-6.75 (m, 1H), 5.70 (dd, J=9.5, 2.5 Hz, 1H), 4.04 (d, J=11.1 Hz, 1H), 3.95 (s, 3H), 3.77 (dd, J=14.7, 6.9 Hz, 1H), 2.52 (td, J=13.3, 3.9 Hz, 1H), 2.32-2.24 (m, 3H), 2.20-2.04 (m, 2H), 1.83-1.61 (m, 3H). LCMS (ESI) m/z 412 (M+H).

Step 2:

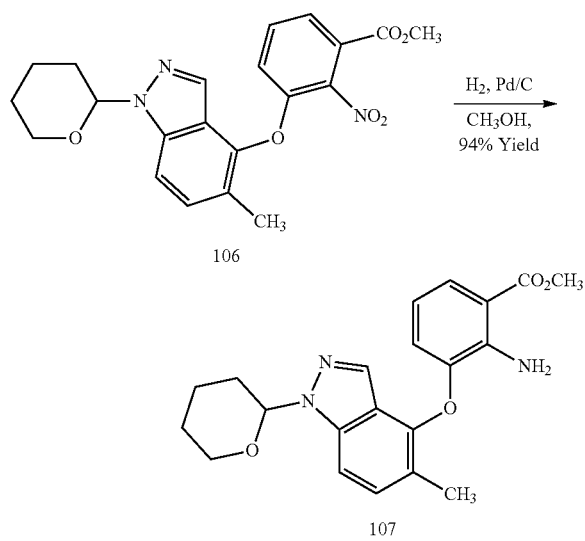

To a solution of methyl 3-{[5-methyl-1-(tetrahydro-2H-pyran-2-yl)-1H-indazol-4-yl]oxy}-2-nitrobenzoate (106) (4 g, 9.7 mmol) in methanol (60 mL) was added 10% Pd/C (500 mg) under a hydrogen atmosphere. The reaction was stirred at 25° C. for 16 hours. LCMS analysis showed the reaction was done. The crude reaction mixture was filtered and the filtrate was concentrated and gave 8-((5-methyl-1-(tetrahydro-2H-pyran-2-yl)-1H-indazol-4-yl)oxy)quinazolin-4(3H)-one (107) (3.5 g, 94% yield). $^1$H NMR (400 MHz, CDCl$_3$) δ 7.64-7.50 (m, 2H), 7.35 (d, J=8.5 Hz, 1H), 7.29 (s, 1H), 6.52 (d, J=7.8 Hz, 1H), 6.40 (t, J=8.0 Hz, 1H), 5.68 (dd, J=9.4, 2.6 Hz, 1H), 4.08-4.00 (m, 1H), 3.91 (s, 3H), 3.74 (td, J=11.0, 2.9 Hz, 1H), 2.61-2.47 (m, 1H), 2.29 (s, 3H), 2.19-2.10 (m, 1H), 2.10-2.05 (m, 1H), 1.83-1.60 (m, 3H). LCMS (ESI) m/z 382 (M+H).

Step 3:

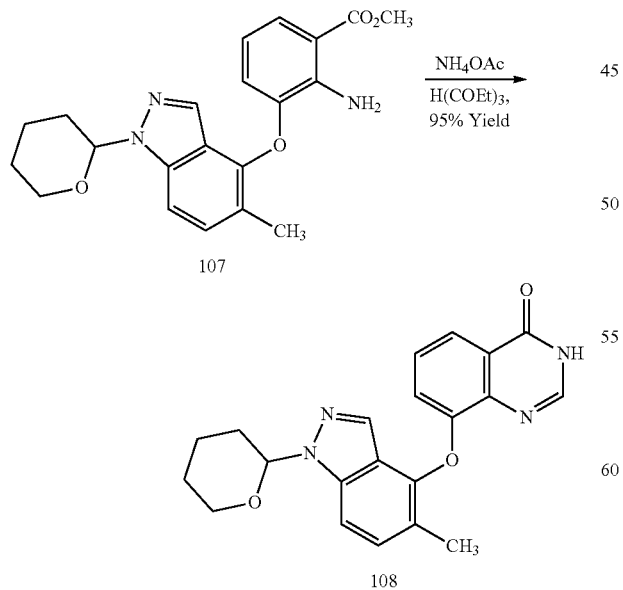

To a solution of 8-((5-methyl-1-(tetrahydro-2H-pyran-2-yl)-1H-indazol-4-yl)oxy)quinazolin-4(3H)-one (107) (1.5 g, 3.9 mmol) in triethoxy methane (30 mL) was added NH$_4$OAc (3.0 g, 39 mmol) in a sealed tube. The reaction was heated at reflux and stirred for 2 days. LCMS analysis showed the reaction was done. The crude reaction mixture was concentrated to dryness. The crude product was purified by silica gel column chromatography and eluted with DCM/methanol (4/1) and gave 8-((5-methyl-1-(tetrahydro-2H-pyran-2-yl)-1H-indazol-4-yl)oxy)quinazolin-4(3H)-one (108) (1.4 g, 95% yield). $^1$H NMR (400 MHz, CDCl$_3$) δ 8.40 (s, 1H), 7.96 (d, J=7.4 Hz, 1H), 7.63 (s, 1H), 7.42 (d, J=8.5 Hz, 1H), 7.30 (dd, J=14.5, 8.3 Hz, 2H), 6.83 (d, J=8.0 Hz, 1H), 5.70 (dd, J=9.5, 2.3 Hz, 1H), 4.11-4.01 (m, 1H), 3.77 (dd, J=15.1, 6.7 Hz, 1H), 2.61-2.45 (m, 1H), 2.30 (s, 3H), 2.11 (m, 2H), 1.84-1.57 (m, 3H). LCMS (ESI) m/z 377 (M+H).

Step 4:

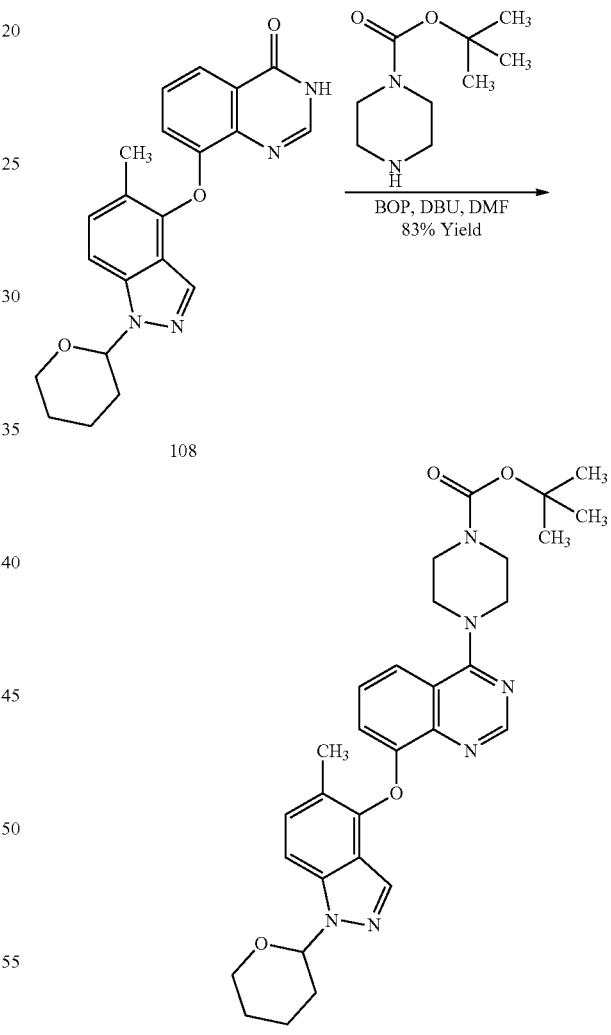

To a solution of 8-((5-methyl-1-(tetrahydro-2H-pyran-2-yl)-1H-indazol-4-yl)oxy)quinazolin-4(3H)-one (108) (400 mg, 1.06 mmol) in DMF (30 mL) was added tert-butyl piperazine-1-carboxylate (396 mg, 2.1 mmol), DBU (485 mg, 3.2 mmol) and BOP (705 mg, 1.6 mmol). The crude reaction mixture was stirred at 25° C. for 4 hours. LCMS analysis showed the reaction was done. The crude reaction mixture was diluted with water (50 mL) and extracted with EtOAc (2×50 mL). The combined organic layers were washed with brine, dried over Na₂SO₄, filtered and evaporated. The crude product was purified by silica gel column chromatography and eluted with petroleum ether/EtOAc (1/1) and gave 4-(8-((5-methyl-1-(tetrahydro-2H-pyran-2-yl)-1H-indazol-4-yl)oxy)quinazolin-4-yl)piperazine-1-carboxylate (109) (480 mg, 83% yield). ¹H NMR (400 MHz, CDCl₃) δ 8.93 (s, 1H), 7.63 (s, 1H), 7.51 (d, J=8.4 Hz, 1H), 7.41 (d, J=8.5 Hz, 1H), 7.32 (d, J=8.6 Hz, 1H), 7.20 (t, J=8.2 Hz, 1H), 6.70 (d, J=7.8 Hz, 1H), 5.70 (dd, J=9.6, 2.4 Hz, 1H), 4.07 (d, J=10.5 Hz, 1H), 3.77 (m, 5H), 3.67 (m, 4H), 2.63-2.47 (m, 1H), 2.31 (s, 3H), 2.20-2.06 (m, 2H), 1.74 (m, 3H), 1.51 (s, 9H). LCMS (ESI) m/z 545 (M+H).

Step 5:

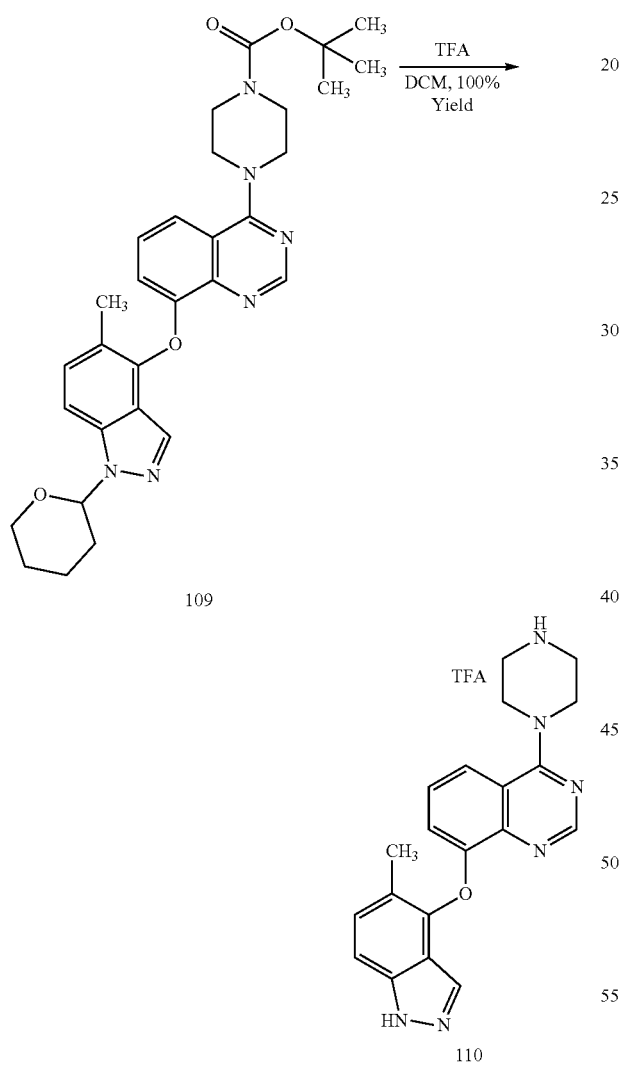

A solution of tert-butyl 4-(8-((5-methyl-1-(tetrahydro-2H-pyran-2-yl)-1H-indazol-4-yl)oxy)quinazolin-4-yl)piperazine-1-carboxylate (109) (480 mg, 0.88 mmol) in 25% TFA/DCM (30 mL) was stirred at 25° C. for 3 hours. LCMS analysis showed the reaction was done. The crude reaction mixture was concentrated to dryness and gave 8-((5-methyl-1H-indazol-4-yl)oxy)-4-(piperazin-1-yl)quinazoline (110) (390 mg, 100% yield). LCMS (ESI) m/z 361 (M+H).

Step 6:

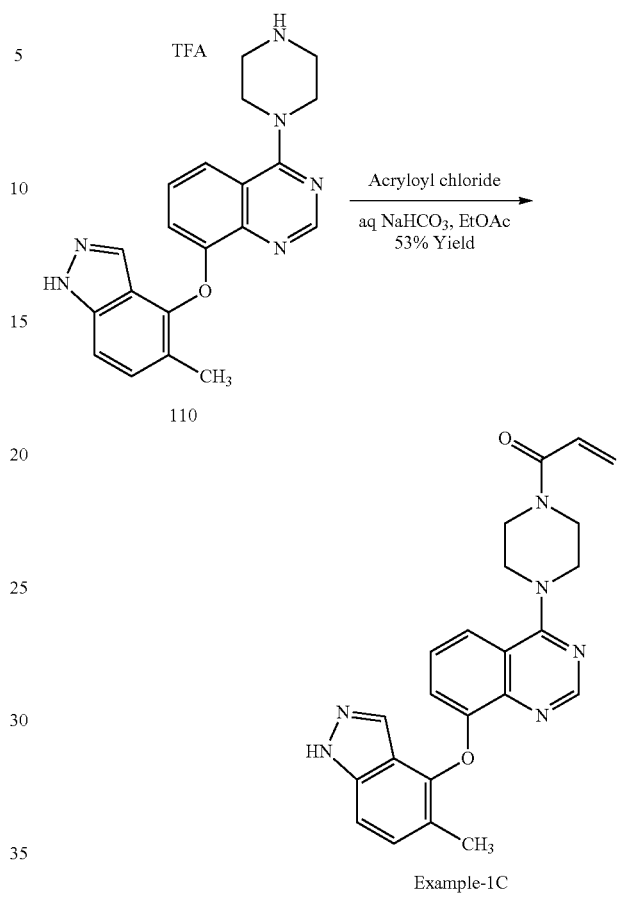

To a solution of 8-((5-methyl-1H-indazol-4-yl)oxy)-4-(piperazin-1-yl)quinazoline (110) (300 mg, 0.83 mmol) in EtOAc (20 mL) was added a saturated NaHCO₃ solution (20 mL). A solution of acryloyl chloride (113 mg, 1.25 mmol) in EtOAc (5 mL) was added dropwise. After the addition, the reaction was stirred for another 30 minutes. LCMS analysis showed the reaction was done. The crude reaction mixture was extracted with EtOAc (2×50 mL) and the combined organic layers were dried over Na₂SO₄ and evaporated. The crude product was purified by silica gel column chromatography and eluted with EtOAc/methanol (9/1) and gave 1-(4-{8-[(5-methyl-1H-indazol-4-yl)oxy]quinazolin-4-yl}piperazin-1-yl)prop-2-en-1-one (Example-1C) (184 mg, 53% yield). ¹H NMR (400 MHz, DMSO-d₆) δ 13.15 (s, 1H), 8.72 (s, 1H), 7.74 (d, J=8.2 Hz, 1H), 7.52-7.23 (m, 4H), 6.85 (dd, J=16.4, 9.7 Hz, 2H), 6.17 (dd, J=16.7, 2.3 Hz, 1H), 5.74 (dd, J=10.4, 2.3 Hz, 1H), 3.81 (d, J=5.4 Hz, 8H), 2.25 (s, 3H). LCMS (ESI) m/z 415 (M+H).

The intermediates detailed in the following preparation afford Example 12C according to method C. However, this example falls outside of the synthetic scope of the preceding examples due to halogenation, thus, the preparation is included here for completeness. Subsequent chemistry to afford final examples is similar to the Method C examples, with minimal additions or changes that one skilled in the art can appreciate.

263

Preparation of methyl 2-amino-5-chloro-3-{[1-(tetrahydro-2H-pyran-2-yl)-1H-indazol-4-yl]oxy}benzoate (111)

264

Preparation of methyl 2-amino-5-bromo-3-{[5-methyl-1-(tetrahydro-2H-pyran-2-yl)-1H-indazol-4-yl]oxy}benzoate (112)

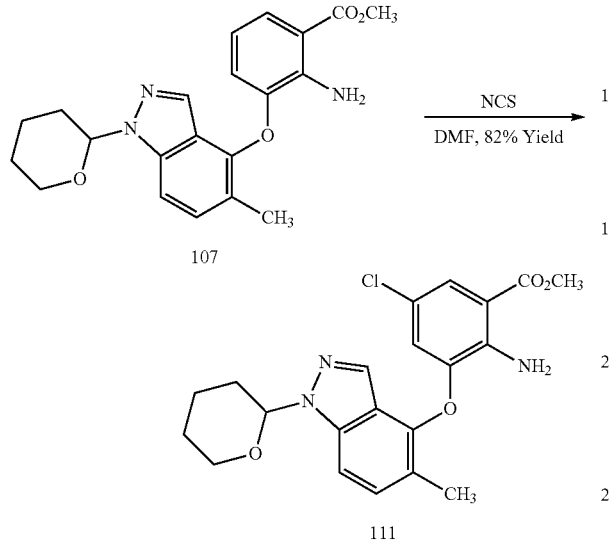

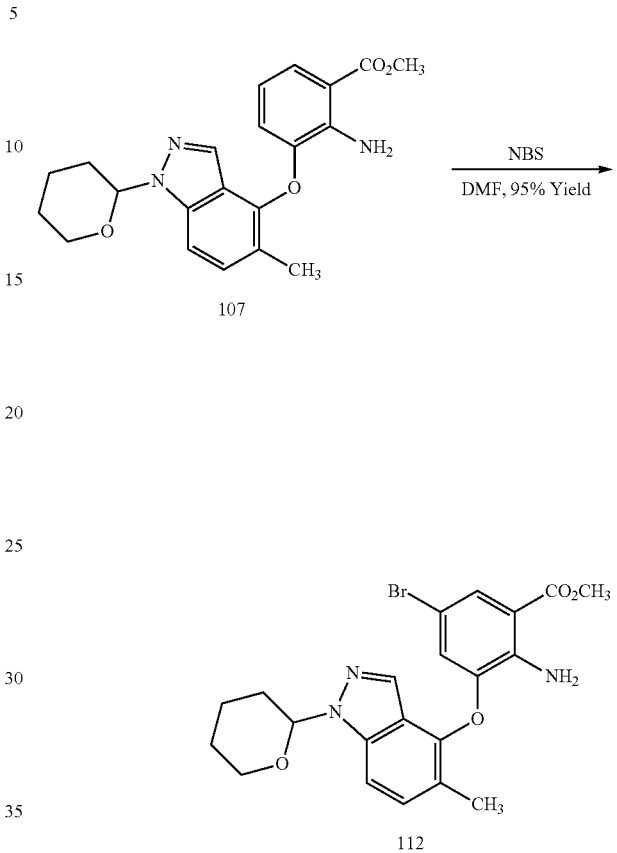

To a solution of 8-((5-methyl-1-(tetrahydro-2H-pyran-2-yl)-1H-indazol-4-yl)oxy)quinazolin-4(3H)-one (107) (300 mg, 0.79 mmol) in DMF (1.5 mL) was added NCS (110 mg, 0.83 mmol). The crude reaction mixture was stirred at 50° C. for 3 hours. The solvent was removed under reduced pressure and the crude product was triturated with acetonitrile and gave a white solid (212 mg). The filtrate was concentrated and purified by prep-HPLC using an Xbridge 150×30 mm, 10 μm column and eluted with 58-100% acetonitrile/$H_2O$ (0.05% $NH_4OH$), at 25 mL/min and another 53 mg of product was collected. Altogether, methyl 2-amino-5-chloro-3-{[1-(tetrahydro-2H-pyran-2-yl)-1H-indazol-4-yl]oxy}benzoate (111) was collected as a white solid (265 mg, 82% yield). $^1$H NMR (400 MHz, CDCl$_3$) δ 7.64 (s, 1H), 7.56 (d, J=2.3 Hz, 1H), 7.41 (d, J=8.5 Hz, 1H), 7.30 (d, J=8.8 Hz, 1H), 6.43 (d, J=2.3 Hz, 1H), 6.24 (br. s, 2H), 5.71 (dd, J=2.6, 9.4 Hz, 1H), 4.06 (br. d, J=10.0 Hz, 1H), 3.92 (s, 3H), 3.82-3.72 (m, 1H), 2.62-2.47 (m, 1H), 2.28 (s, 3H), 2.22-2.06 (m, 2H), 1.82-1.64 (m, 3H). LCMS (ESI) m/z 416 (M+H).

The intermediates detailed in the following preparation afford Example 13C according to method C. However, this example falls outside of the synthetic scope of the preceding examples due to halogenation, thus, the preparation is included here for completeness. Subsequent chemistry to afford final examples is similar to the Method C examples, with minimal additions or changes that one skilled in the art can appreciate.

Methyl 2-amino-5-bromo-3-{[5-methyl-1-(tetrahydro-2H-pyran-2-yl)-1H-indazol-4-yl]oxy}benzoate (112) (690 mg, 95% yield) was prepared according to the procedure used to prepare methyl 2-amino-5-chloro-3-{[1-(tetrahydro-2H-pyran-2-yl)-1H-indazol-4-yl]oxy}benzoate (111). $^1$H NMR (400 MHz, CDCl$_3$) δ 7.71 (d, J=2.3 Hz, 1H), 7.64 (d, J=0.8 Hz, 1H), 7.41 (d, J=8.5 Hz, 1H), 7.30 (d, J=8.5 Hz, 1H), 6.54 (d, J=2.3 Hz, 1H), 6.27 (br. s, 2H), 5.71 (dd, J=2.6, 9.4 Hz, 1H), 4.10-4.02 (m, 1H), 3.94-3.90 (m, 3H), 3.81-3.72 (m, 1H), 2.63-2.48 (m, 1H), 2.32-2.25 (m, 3H), 2.22-2.06 (m, 2H), 1.84-1.63 (m, 3H). LCMS (ESI) m/z 460, 462 (M+H).

The intermediates detailed in the following preparation afford Example 14C according to method C. However, this example falls outside of the synthetic scope of the preceding examples due to cyanation, thus, the preparation is included here for completeness. Subsequent chemistry to afford final examples is similar to the Method C examples, with minimal additions or changes that one skilled in the art can appreciate.

Preparation of tert-butyl 4-(6-cyano-8-{[5-methyl-1-(tetrahydro-2H-pyran-2-yl)-1H-indazol-4-yl]oxy}quinazolin-4-yl)piperazine-1-carboxylate (114)

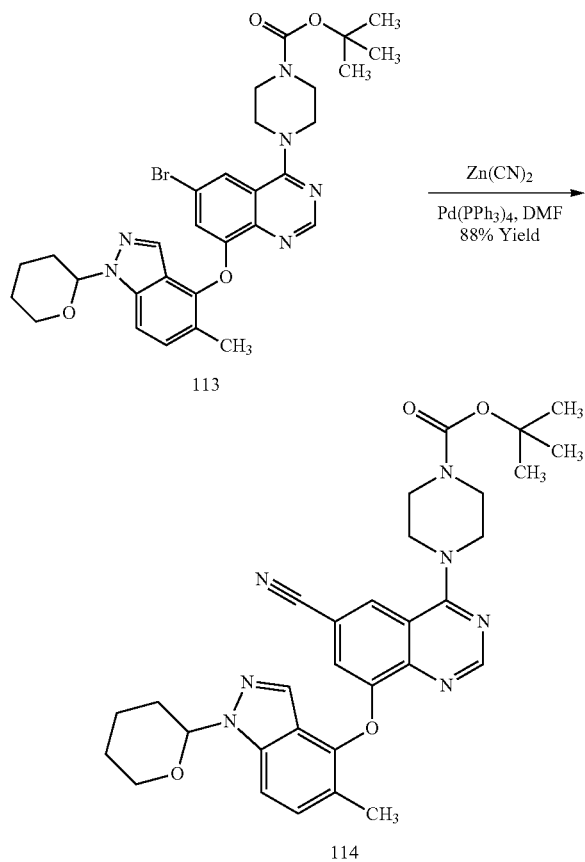

A mixture of tert-butyl 4-(6-bromo-8-{[5-methyl-1-(tetrahydro-2H-pyran-2-yl)-1H-indazol-4-yl]oxy}quinazolin-4-yl)piperazine-1-carboxylate (113, prepared according to Method C) (217 mg, 0.35 mmol), Zn(CN)$_2$ (65 mg, 0.56 mmol), Pd(PPh$_3$)$_4$ (40 mg, 0.035 mmol) in DMF (6 mL), under nitrogen, was stirred at 120° C. under microwave for 5 hours. LCMS gave complete conversion to the desired product. The crude reaction mixture was cooled to room temperature and diluted with water (20 mL). The aqueous layer was extracted with EtOAc (3×10 mL) and the combined organic layers were concentrated and the crude product was purified over silica gel which was eluted with 10-50% EtOAc and gave tert-butyl 4-(6-cyano-8-{[5-methyl-1-(tetrahydro-2H-pyran-2-yl)-1H-indazol-4-yl]oxy}quinazolin-4-yl)piperazine-1-carboxylate (114) as a white solid (214 mg, 88% yield). TLC (50% EtOAc/petroleum ether) R$_f$ 0.4; $^1$H NMR (400 MHz, CDCl$_3$) δ 8.96 (s, 1H), 7.85 (d, J=1.5 Hz, 1H), 7.69 (s, 1H), 7.50 (d, J=8.5 Hz, 1H), 7.36 (d, J=8.5 Hz, 1H), 6.72 (d, J=1.5 Hz, 1H), 5.74 (dd, J=2.4, 9.4 Hz, 1H), 4.09 (br. d, J=10.5 Hz, 1H), 3.87 (br. d, J=5.3 Hz, 4H), 3.82-3.75 (m, 1H), 3.73-3.64 (m, 4H), 2.64-2.48 (m, 1H), 2.29 (s, 3H), 2.21-2.10 (m, 2H), 1.85-1.74 (m, 2H), 1.73-1.65 (m, 1H), 1.52 (s, 9H). LCMS (ESI) m/z 570 (M+H).

The following examples were prepared using method C and the procedure used to prepare 1-(4-{8-[(5-methyl-1H-indazol-4-yl)oxy]quinazolin-4-yl}piperazin-1-yl)prop-2-en-1-one (Example-1C). The following examples were made with non-critical changes or substitutions to the exemplified procedure used to prepare Example-1C that someone who is skilled in the art would be able to realize.

| Example | Structure | Compound Name | LCMS m/z | $^1$H NMR |
|---|---|---|---|---|
| 2C | 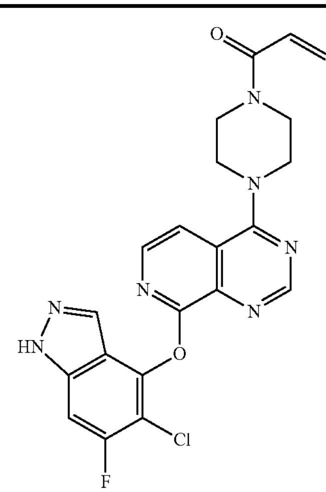 | 1-(4-{8-[(5-chloro-6-fluoro-1H-indazol-4-yl)oxy]pyrido[3,4-d]pyrimidin-4-yl}piperazin-1-yl)prop-2-en-1-one | 454 (M + H) | $^1$H NMR (400 MHz, DMSO-d$_6$) δ 13.55 (s, 1H), 8.83 (s, 1H), 7.93 (d, J = 4.0 Hz, 1H), 7.86 (s, 1H), 7.67 (d, J = 5.9 Hz, 1H), 7.60 (dd, J = 8.9, 0.8 Hz, 1H), 6.83 (dt, J = 16.7, 10.7 Hz, 1H), 6.21-6.14 (m, 1H), 5.77-5.72 (m, 1H), 3.98-3.89 (m, 4H), 3.85-3.75 (m, 4H). |

| Example | Structure | Compound Name | LCMS m/z | ¹H NMR |
|---|---|---|---|---|
| 3C | 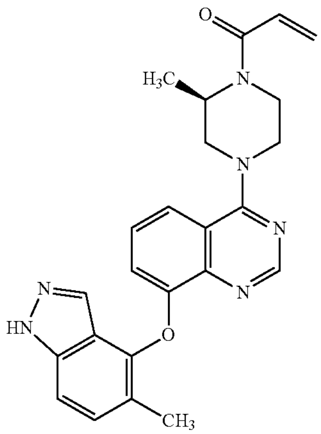 [SMILES: C=CC(=O)N1CCN(c2ncnc3c(Oc4c(C)ccc5[nH]ncc45)cccc23)C[C@H]1C] | 1-[(2R)-2-methyl-4-{8-[(5-methyl-1H-indazol-4-yl)oxy]quinazolin-4-yl}piperazin-1-yl]prop-2-en-1-one | 429 (M + H) | ¹H NMR (400 MHz, DMSO-d₆) δ 13.16 (br. s, 1H), 8.71 (s, 1H), 7.77 (d, J = 8.3 Hz, 1H), 7.43-7.26 (m, 4H), 6.93-6.77 (m, 2H), 6.17 (br. d, J = 16.3 Hz, 1H), 5.74 (br. d, J = 10.8 Hz, 1H), 4.87-4.41 (m, 1H), 4.39-3.98 (m, 3H), 3.83-3.39 (m, 3H), 2.26 (s, 3H), 1.27 (br. s, 3H). |
| 4C | 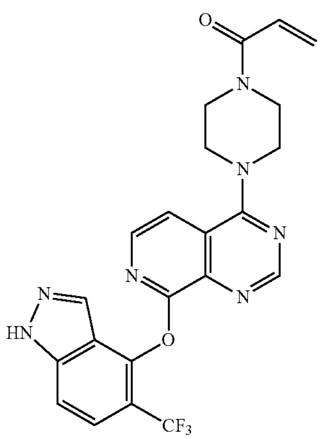 [SMILES: C=CC(=O)N1CCN(c2ncnc3c(Oc4c(C(F)(F)F)ccc5[nH]ncc45)nccc23)CC1] | 1-[4-(8-{[5-(trifluoromethyl)-1H-indazol-4-yl]oxy}pyrido[3,4-d]pyrimidin-4-yl)piperazin-1-yl]prop-2-en-1-one | NA | ¹H NMR (400 MHz, DMSO-d₆) δ 13.62 (s, 1H), 8.84 (s, 1H), 7.92 (d, J = 5.8 Hz, 1H), 7.80-7.68 (m, 2H), 7.68-7.60 (m, 2H), 6.85 (dd, J = 16.7, 10.4 Hz, 1H), 6.18 (dd, J = 16.7, 2.4 Hz, 1H), 5.75 (dd, J = 10.4, 2.4 Hz, 1H), 3.95-3.90 (m, 4H), 3.85 (br. s, 2H), 3.77 (br. s, 2H). |
| 5C | 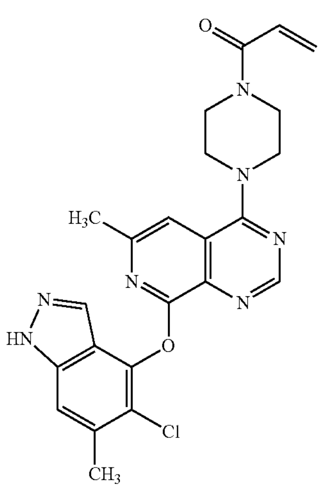 [SMILES: C=CC(=O)N1CCN(c2ncnc3c(Oc4c(Cl)c(C)cc5[nH]ncc45)nc(C)cc23)CC1] | 1-(4-{8-[(5-chloro-6-methyl-1H-indazol-4-yl)oxy]-6-methylpyrido[3,4-d]pyrimidin-4-yl}piperazin-1-yl)prop-2-en-1-one | 464 (M + H) | ¹H NMR (400 MHz, DMSO-d₆) δ 13.14-12.89 (m, 1H), 8.75 (s, 1H), 7.56 (s, 1H), 7.43 (br. s, 2H), 6.90-6.63 (m, 1H), 6.15 (d, J = 16.8 Hz, 1H), 5.72 (d, J = 10.5 Hz, 1H), 3.91 (br. s, 4H), 3.81 (br. s, 4H), 2.52 (s, 3H), 2.29 (s, 3H). |

-continued

| Example | Structure | Compound Name | LCMS m/z | ¹H NMR |
|---|---|---|---|---|
| 6C | 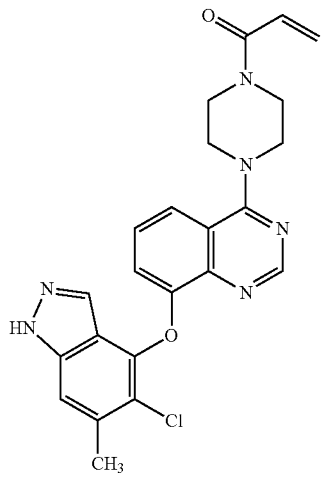 [SMILES: C=CC(=O)N1CCN(c2ncnc3c(Oc4c(Cl)c(C)cc5[nH]ncc45)cccc23)CC1] | 1-(4-{8-[(5-chloro-6-methyl-1H-indazol-4-yl)oxy]quinazolin-4-yl}piperazin-1-yl)prop-2-en-1-one | 449 (M + H) | ¹H NMR (400 MHz, DMSO-d₆) δ 13.25 (s, 1H), 8.66 (s, 1H), 7.84 (d, J = 8.4 Hz, 1H), 7.53-7.33 (m, 2H), 7.10 (s, 1H), 7.09-7.03 (m, 1H), 6.85 (dd, J = 16.7, 10.5 Hz, 1H), 6.17 (dd, J = 16.7, 1.9 Hz, 1H), 5.88-5.58 (m, 1H), 3.90-3.70 (m, 8H), 2.52 (s, 3H). |
| 7C | 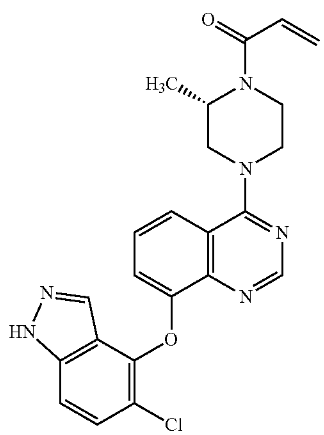 [SMILES: C=CC(=O)N1CCN(c2ncnc3c(Oc4c(Cl)ccc5[nH]ncc45)cccc23)C[C@@H]1C] | 1-[(2S)-4-{8-[(5-chloro-1H-indazol-4-yl)oxy]quinazolin-4-yl}-2-methylpiperazin-1-yl]prop-2-en-1-one | 449 (M + H) | ¹H NMR (400 MHz, DMSO-d₆) δ 8.59 (s, 1H), 7.83 (s, 1H), 7.55-7.40 (m, 3H), 7.14 (s, 2H), 6.83-6.70 (m, 1H), 6.21-6.08 (m, 1H), 5.78-5.66 (m, 1H), 4.74-4.42 (m, 1H), 4.35-3.91 (m, 3H), 3.74-3.69 (m, 1H), 3.67-3.59 (m, 1H), 3.49-3.24 (m, 1H), 1.20 (br. s, 3H). |
| 8C | 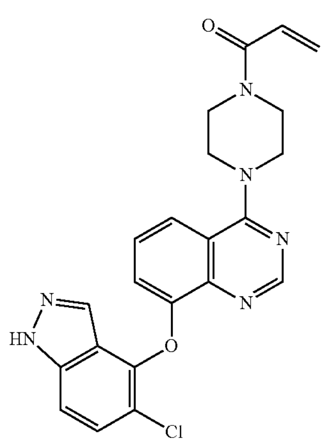 [SMILES: C=CC(=O)N1CCN(c2ncnc3c(Oc4c(Cl)ccc5[nH]ncc45)cccc23)CC1] | 1-(4-{8-[(5-chloro-1H-indazol-4-yl)oxy]quinazolin-4-yl}piperazin-1-yl)prop-2-en-1-one | 435 (M + H) | ¹H NMR (400 MHz, DMSO-d₆) δ 13.47-13.36 (m, 1H), 8.68-8.59 (m, 1H), 7.88-7.81 (m, 1H), 7.53-7.41 (m, 3H), 7.18-7.11 (m, 2H), 6.89-6.80 (m, 1H), 6.21-6.14 (m, 1H), 5.76-5.71 (m, 1H), 3.83 (br. s, 8H). |

| Example | Structure | Compound Name | LCMS m/z | ¹H NMR |
|---|---|---|---|---|
| 9C | 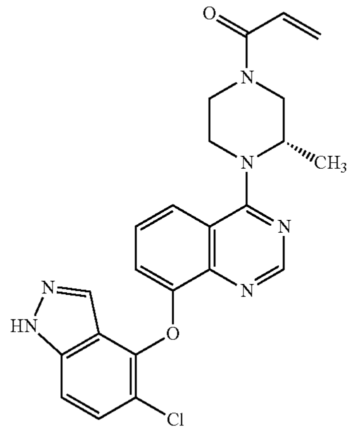 [SMILES: C=CC(=O)N1CCN(c2ncnc3c(Oc4c(Cl)ccc5[nH]ncc45)cccc23)[C@@H](C)C1] | 1-[(3S)-4-{8-[(5-chloro-1H-indazol-4-yl)oxy]quinazolin-4-yl}-3-methylpiperazin-1-yl]prop-2-en-1-one | 449 (M + H) | ¹H NMR (400 MHz, DMSO-d₆) δ 13.41 (br. s, 1H), 8.65 (s, 1H), 7.85-7.71 (m, 1H), 7.56-7.39 (m, 3H), 7.22-7.09 (m, 2H), 6.95-6.77 (m, 1H), 6.24-6.09 (m, 1H), 5.79-5.69 (m, 1H), 4.79-4.63 (m, 1H), 4.49-4.22 (m, 1H), 4.18-3.92 (m, 2H), 3.66-3.40 (m, 2H), 3.24-3.02 (m, 1H), 1.28-1.22 (m, 3H). |
| 10C | 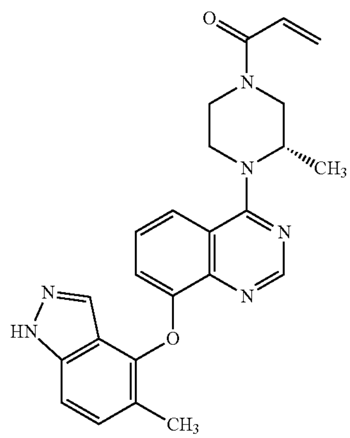 [SMILES: C=CC(=O)N1CCN(c2ncnc3c(Oc4c(C)ccc5[nH]ncc45)cccc23)[C@@H](C)C1] | 1-[(3S)-3-methyl-4-{8-[(5-methyl-1H-indazol-4-yl)oxy]quinazolin-4-yl}piperazin-1-yl]prop-2-en-1-one | 429 (M + H) | ¹H NMR (400 MHz, DMSO-d₆) δ 13.15 (s, 1H), 8.72 (s, 1H), 7.67 (d, J = 7.9 Hz, 1H), 7.42-7.28 (m, 4H), 6.94-6.78 (m, 2H), 6.19 (br. dd, J = 7.1, 16.5 Hz, 1H), 5.79-5.69 (m, 1H), 4.69 (br. s, 1H), 4.46-4.23 (m, 1H), 4.17-3.95 (m, 2H), 3.66-3.44 (m, 2H), 3.23-3.01 (m, 1H), 2.26 (s, 3H), 1.29-1.25 (m, 3H). |
| 11C | 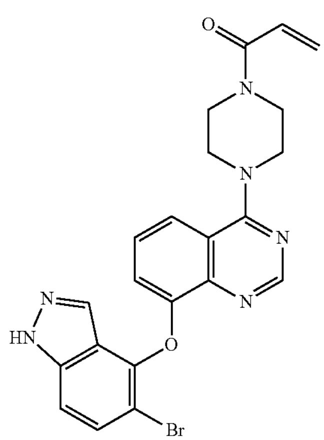 [SMILES: C=CC(=O)N1CCN(c2ncnc3c(Oc4c(Br)ccc5[nH]ncc45)cccc23)CC1] | 1-(4-(8-((5-bromo-1H-indazol-4-yl)oxy)quinazolin-4-yl)piperazin-1-yl)prop-2-en-1-one | 479/481 (M + H) | ¹H NMR (400 MHz, DMSO-d₆) δ 13.41 (s, 1H), 8.67 (s, 1H), 7.84 (d, J = 8.1 Hz, 1H), 7.62 (d, J = 8.8 Hz, 1H), 7.44 (t, J = 8.1 Hz, 1H), 7.38 (d, J = 9.0 Hz, 1H), 7.14 (s, 1H), 7.10 (d, J = 7.5 Hz, 1H), 6.85 (dd, J = 16.7, 10.4 Hz, 1H), 6.17 (dd, J = 16.7, 2.4 Hz, 1H), 5.74 (dd, J = 10.4, 2.3 Hz, 1H), 3.81 (m, 8H). |

-continued

| Example | Structure | Compound Name | LCMS m/z | ¹H NMR |
|---|---|---|---|---|
| 12C | 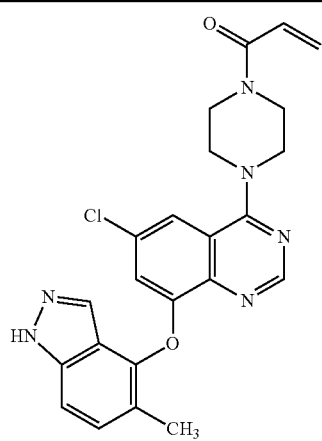 | 1-(4-{6-chloro-8-[(5-methyl-1H-indazol-4-yl)oxy]quinazolin-4-yl}piperazin-1-yl)prop-2-en-1-one | 449 (M + H) | ¹H NMR (400 MHz, DMSO-d$_6$) δ 13.25 (br. s, 1H), 8.73 (s, 1H), 7.70 (s, 1H), 7.49 (s, 1H), 7.46-7.31 (m, 2H), 6.83 (br. dd, J = 10.3, 6.3 Hz, 1H), 6.68 (s, 1H), 6.17 (br. d, J = 16.8 Hz, 1H), 5.74 (br. d, J = 10.3 Hz, 1H), 3.95-3.66 (m, 8H), 2.24 (s, 3H). |
| 13C | 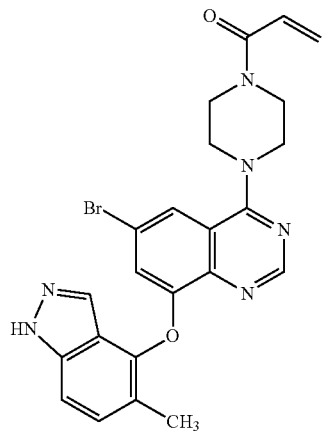 [SMILES: C=CC(=O)N1CCN(c2ncnc3c(Oc4c(C)ccc5[nH]ncc45)cc(Br)cc23)CC1] | 1-(4-{6-bromo-8-[(5-methyl-1H-indazol-4-yl)oxy]quinazolin-4-yl}piperazin-1-yl)prop-2-en-1-one | 493/495 (M + H) | ¹H NMR (400 MHz, DMSO-d$_6$) δ 13.27 (br. s, 1H), 8.74 (s, 1H), 7.83 (d, J = 2.0 Hz, 1H), 7.49 (s, 1H), 7.44-7.39 (m, 1H), 7.38-7.34 (m, 1H), 6.89-6.75 (m, 2H), 6.17 (dd, J = 2.4, 16.7 Hz, 1H), 5.78-5.69 (m, 1H), 3.93-3.70 (m, 8H), 2.23 (s, 3H). |
| 14C | 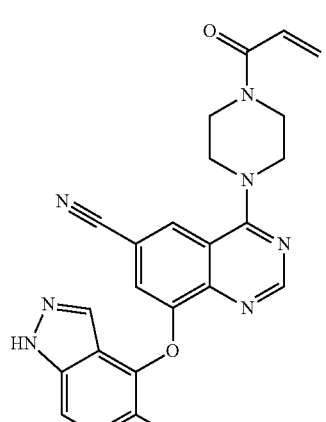 | 1-(4-{8-[(5-methyl-1H-indazol-4-yl)oxy]pyrido[3,4-d]pyrimidin-4-yl}piperazin-1-yl)prop-2-en-1-one | 440 (M + H) | ¹H NMR (600 MHz, DMSO-d$_6$) δ 13.24 (br. s, 1H), 8.77 (s, 1H), 8.24 (d, J = 1.3 Hz, 1H), 7.46 (s, 1H), 7.44-7.39 (m, 1H), 7.38-7.33 (m, 1H), 6.99 (d, J = 1.3 Hz, 1H), 6.84 (dd, J = 10.4, 16.7 Hz, 1H), 6.18 (dd, J = 2.4, 16.7 Hz, 1H), 5.79-5.70 (m, 1H), 3.95 (br. s, 4H), 3.88-3.72 (m, 4H), 2.25 (s, 3H). |

| Example | Structure | Compound Name | LCMS m/z | ¹H NMR |
|---------|-----------|---------------|----------|--------|
| 15C | 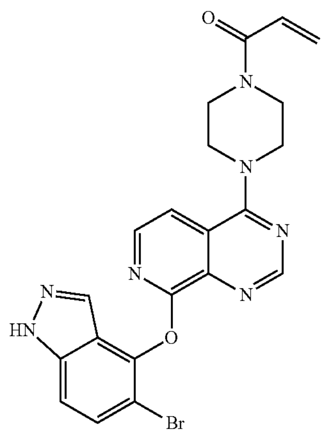 [SMILES: C=CC(=O)N1CCN(c2ncnc3c(Oc4c(Br)ccc5[nH]ncc45)nccc23)CC1] | 1-(4-{8-[(5-bromo-1H-indazol-4-yl)oxy]pyrido[3,4-d]pyrimidin-4-yl}piperazin-1-yl)prop-2-en-1-one | 480/482 (M + H) | ¹H NMR (400 MHz, DMSO-d₆) δ 13.43 (br. s, 1H), 8.83 (s, 1H), 7.90 (d, J = 5.9 Hz, 1H), 7.75 (s, 1H), 7.65-7.58 (m, 2H), 7.46 (d, J = 8.8 Hz, 1H), 6.83 (dd, J = 10.5, 16.7 Hz, 1H), 6.17 (dd, J = 2.2, 16.7 Hz, 1H), 5.74 (d, J = 1.0 Hz, 1H), 3.92 (br. s, 4H), 3.80 (br. d, J = 1.0 Hz, 4H). |
| 16C | 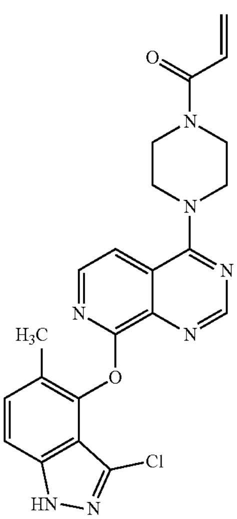 [SMILES: C=CC(=O)N1CCN(c2ncnc3c(Oc4c(C)ccc5[nH]nc(Cl)c45)nccc23)CC1] | 1-(4-{8-[(3-chloro-5-methyl-1H-indazol-4-yl)oxy]pyrido[3,4-d]pyrimidin-4-yl}piperazin-1-yl)prop-2-en-1-one | 450 (M + H) | ¹H NMR (400 MHz, DMSO-d₆) δ 13.32 (s, 1H), 8.84 (s, 1H), 7.88 (d, J = 5.9 Hz, 1H), 7.56 (d, J = 5.9 Hz, 1H), 7.40 (s, 2H), 6.84 (dd, J = 16.7, 10.4 Hz, 1H), 6.18 (dd, J = 10.4, 2.3 Hz, 1H), 5.75 (dd, J = 10.4, 2.3 Hz, 1H), 4.00-3.67 (m, 8H), 2.17 (s, 3H). |
| 17C | 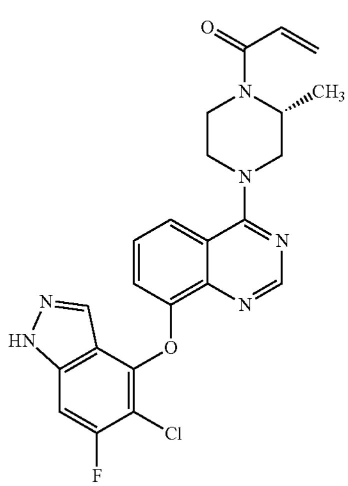 [SMILES: C=CC(=O)N1CCN(c2ncnc3c(Oc4c(Cl)c(F)cc5[nH]ncc45)cccc23)C[C@H]1C] | 1-[(2R)-4-{8-[(5-chloro-6-fluoro-1H-indazol-4-yl)oxy]quinazolin-4-yl}-2-methylpiperazin-1-yl]prop-2-en-1-one | 467 (M + H) | ¹H NMR (400 MHz, DMSO-d₆) δ 13.41 (s, 1H), 8.57 (s, 1H), 7.96 (dd, J = 8.4, 1.2 Hz, 1H), 7.53 (t, J = 8.1 Hz, 1H), 7.43 (dd, J = 13.4, 8.1 Hz, 2H), 6.87 (d, J = 1.4 Hz, 1H), 6.81 (dd, J = 16.7, 10.5 Hz, 1H), 6.16 (dd, J = 16.8, 2.3 Hz, 1H), 5.72 (dd, J = 10.4, 2.4 Hz, 1H), 4.76-4.45 (m, 1H), 4.31 (d, J = 12.9 Hz, 1H), 4.21-4.01 (m, 2H), 3.64 (dd, J = 13.4, 3.9 Hz, 1H), 3.47-3.35 (m, 2H), 1.23 (s, 3H). |

-continued

| Example | Structure | Compound Name | LCMS m/z | ¹H NMR |
|---|---|---|---|---|
| 18C | 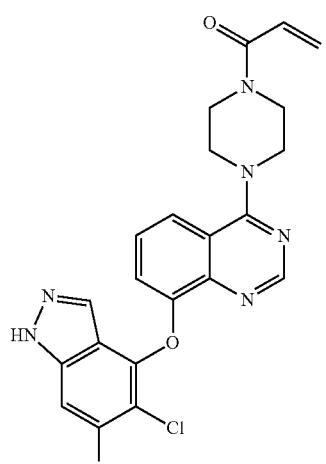 | 1-(4-{8-[(5-chloro-6-fluoro-1H-indazol-4-yl)oxy]quinazolin-4-yl}piperazin-1-yl)prop-2-en-1-one | 453 (M + H) | ¹H NMR (400 MHz, DMSO-d₆) δ 13.42 (s, 1H), 8.59 (s, 1H), 7.94 (d, J = 8.2 Hz, 1H), 7.51 (d, J = 8.2 Hz, 1H), 7.43 (dd, J = 8.3, 3.5 Hz, 2H), 6.85 (dd, J = 21.7, 15.4 Hz, 2H), 6.17 (dd, J = 16.7, 2.4 Hz, 1H), 5.74 (dd, J = 10.4, 2.4 Hz, 1H), 3.84-3.78 (m, 8H). |
| 19C | 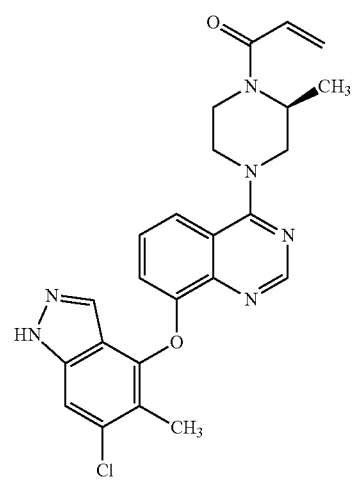 [SMILES: C=CC(=O)N1CCN(c2ncnc3c(Oc4c(C)c(Cl)cc5[nH]ncc45)cccc23)C[C@@H]1C] | 1-[(2S)-4-{8-[(5-chloro-6-methyl-1H-indazol-4-yl)oxy]quinazolin-4-yl}-2-methylpiperazin-1-yl]prop-2-en-1-one | 463 (M + H) | ¹H NMR (400 MHz, DMSO-d₆) δ 13.25 (s, 1H), 8.66 (s, 1H), 7.83 (d, J = 8.1 Hz, 1H), 7.56 (s, 1H), 7.43 (t, J = 8.1 Hz, 1H), 7.17 (s, 1H), 7.06 (d, J = 7.2 Hz, 1H), 6.82 (dd, J = 16.7, 10.5 Hz, 1H), 6.16 (dd, J = 16.5 Hz, 1H), 5.72 (dd, 1H), 4.62 (m, 1H), 4.29 (m, J = 12.4 Hz, 1H), 4.12 (m, J = 13.1 Hz, 2H), 3.80-3.55 (m, 2H), 2.32 (s, 3H), 1.30-1.14 (m, 1H). |
| 20C | 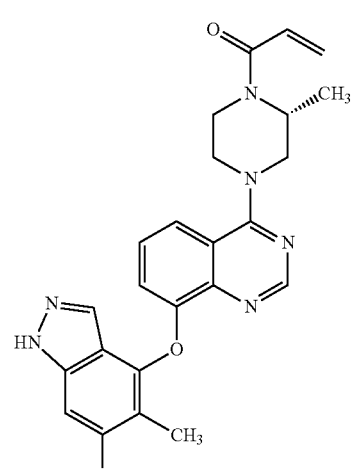 | 1-[(2R)-4-{8-[(5-chloro-6-methyl-1H-indazol-4-yl)oxy]quinazolin-4-yl}-2-methylpiperazin-1-yl]prop-2-en-1-one | 463 (M + H) | ¹H NMR (400 MHz, DMSO-d₆) δ 13.25 (s, 1H), 8.66 (s, 1H), 7.83 (d, J = 8.4 Hz, 1H), 7.56 (s, 1H), 7.43 (t, J = 8.2 Hz, 1H), 7.17 (s, 1H), 7.06 (d, J = 7.7 Hz, 1H), 6.82 (dd, J = 16.7, 10.5 Hz, 1H), 6.16 (d, J = 17.9 Hz, 1H), 5.73 (d, J = 11.8 Hz, 1H) 4.79-4.44 (m, 1H), 4.29 (d, J = 12.9 Hz, 2H), 4.18-4.03 (m, 2H), 3.84-3.54 (m, 2H), 1.24 (s, 3H). |

| Example | Structure | Compound Name | LCMS m/z | ¹H NMR |
|---|---|---|---|---|
| 21C | 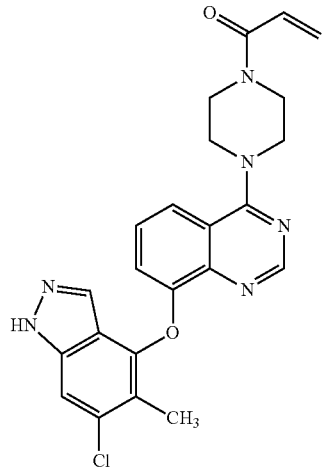 [SMILES: C=CC(=O)N1CCN(c2ncnc3c(Oc4c(C)c(Cl)cc5[nH]ncc45)cccc23)CC1] | 1-(4-{8-[(5-chloro-6-methyl-1H-indazol-4-yl)oxy]quinazolin-4-yl}piperazin-1-yl)prop-2-en-1-one | 449 (M + H) | ¹H NMR (400 MHz, DMSO-$d_6$) δ 13.25 (s, 1H), 8.68 (s, 1H), 7.81 (d, J = 8.3 Hz, 1H), 7.56 (s, 1H), 7.42 (t, J = 8.1 Hz, 1H), 7.19 (s, 1H), 7.05 (d, J = 7.7 Hz, 1H), 6.85 (dd, J = 16.7, 10.4 Hz, 1H), 6.17 (dd, J = 16.7, 2.4 Hz, 1H), 5.74 (dd, J = 10.4, 2.3 Hz, 1H), 3.82 (m, 8H), 2.32 (s, 3H). |
| 22C | 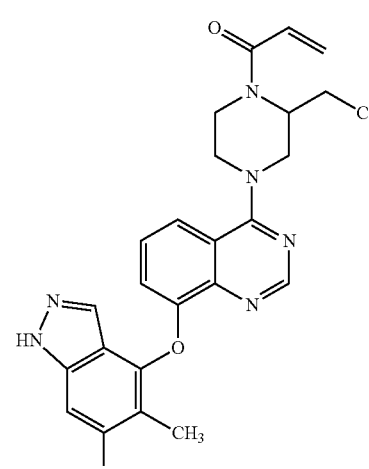 | (1-acryloyl-4-{8-[(5-chloro-6-mehtyl-1H-indazol-4-yl)oxy]quinazolin-4-yl}piperazin-2-yl)acetonitrile | 488 (M + H) | ¹H NMR (400 MHz, DMSO-$d_6$) δ 13.26 (s, 1H), 8.71 (s, 1H), 7.85 (d, J = 8.4 Hz, 1H), 7.58 (s, 1H), 7.43 (t, J = 8.1 Hz, 1H), 7.21 (s, 1H), 7.05 (d, J = 7.7 Hz, 1H), 7.00-6.78 (m, 1H), 6.20 (dd, J = 16.6, 2.3 Hz, 1H), 5.79 (d, J = 10.5 Hz, 1H), 5.14-4.79 (m, 1H), 4.33-4.16 (m, 2H), 3.66-2.95 (m, 6H), 2.31 (s, 3H). |

The intermediates detailed in the following preparation afford Example-4 according to method A. However, this example fall outside of the synthetic scope of the preceding examples due to sulfone formation, thus, the preparation is included here for completeness. Subsequent chemistry to afford final examples is similar to the Method A examples, with minimal additions or changes that one skilled in the art can appreciate.

Preparation of 8-[(5-chloro-6-methyl-1H-indazol-4-yl)oxy]-4-[4-(ethenylsulfonyl)piperazin-1-yl]pyrido[3,4-d]pyrimidine (Example-4)

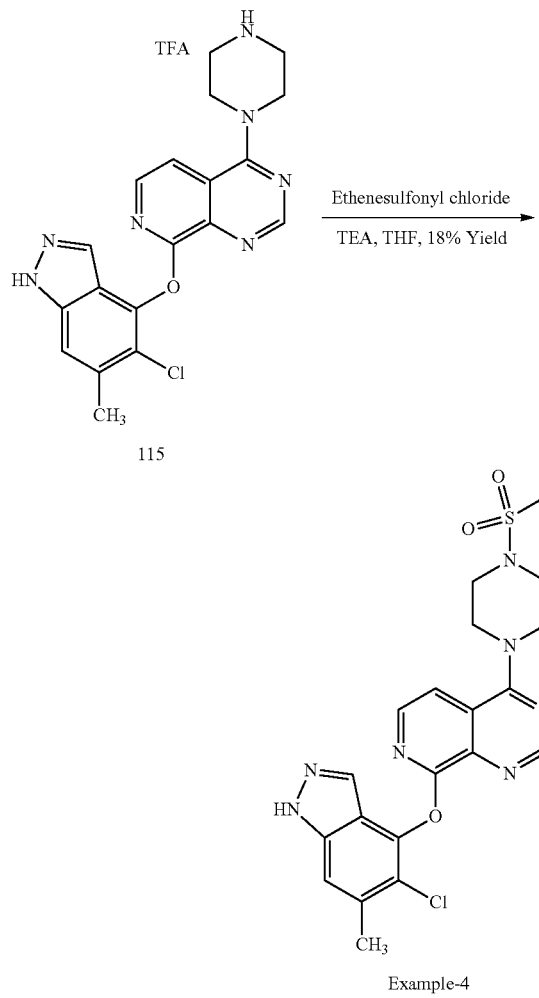

Example-4

To a stirred solution of 8-[(5-chloro-6-methyl-1H-indazol-4-yl)oxy]-4-(piperazin-1-yl)pyrido[3,4-d]pyrimidine (115) (145 mg, 0.37 mmol) in THF (50 mL) and Et$_3$N (432 mg, 4.27 mmol) was added a solution of ethenesulfonyl chloride (46.4 mg, 0.37 mmol) in THF (20 mL) at 0-5° C. After the addition, the mixture was stirred at the same temperature for 15 minutes. LCMS analysis showed the reaction was complete. The crude reaction mixture was poured into water (60 mL) and extracted with EtOAc (3×50 mL). The combined organic layers were dried over Na$_2$SO$_4$, and concentrated which gave the crude product. The crude product was purified by pre-HPLC using a Gemini-C18, 100×21.2 mm, 5 µm column and eluted using a 40-50% acetonitrile-H$_2$O (0.05% NH$_3$) gradient, and gave 8-[(5-chloro-6-methyl-1H-indazol-4-yl)oxy]-4-[4-(ethenylsulfonyl)piperazin-1-yl]pyrido[3,4-d]pyrimidine (Example-4) as a white powder (32 mg, 18% yield). $^1$H NMR (400 MHz, DMSO-d$_6$) δ 13.30 (s, 1H), 8.86 (s, 1H), 7.91 (d, J=5.9 Hz, 1H), 7.72 (s, 1H), 7.56 (d, J=5.9 Hz, 1H), 7.49 (s, 1H), 6.88 (dd, J=16.5, 10.0 Hz, 1H), 6.20 (dd, J=22.4, 13.3 Hz, 2H), 3.95-3.90 (m, 4H), 3.30-3.26 (m, 4H), 2.51 (s, 3H). LCMS (ESI) m/z 486, 488 (M+H).

The intermediates detailed in the following preparation afford Example-5 in via a route analogous to method A. However, this example fall outside of the synthetic scope of the preceding examples due the biarylamine formation, thus, this preparation is included here for completeness.

Preparation of 1-(4-{8-[(5-methyl-1H-indazol-4-yl)amino]pyrido[3,4-d]pyrimidin-4-yl}piperazin-1-yl)prop-2-en-1-one (Example-5)

Step 1:

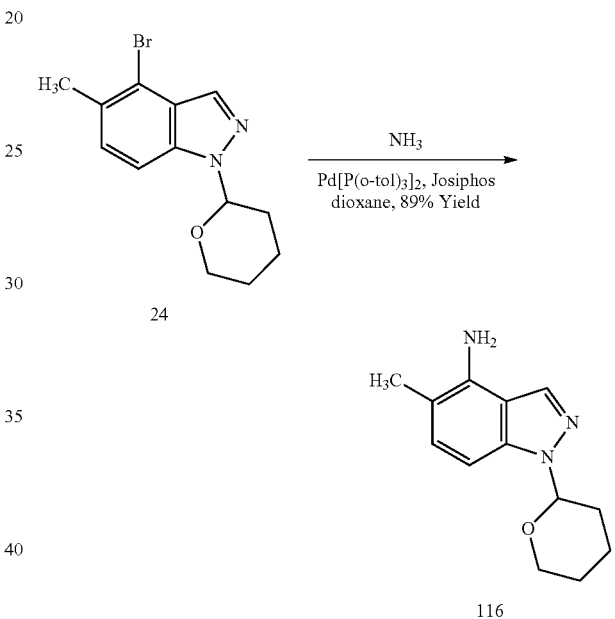

A 2.5×10$^{-3}$ M stock solution of the catalyst (4.1 mL) containing Pd[P(o-tol)$_3$]$_2$(7.3 mg) and CyPF-t-Bu (1-dicyclohexylphosphino-2-di-t-butylphosphinoethylferrocene) (5.6 mg) was added to a mixture of NaO-t-Bu (300 mg, 1.0 mmol) in THF (2.0 M) and 4-bromo-5-methyl-1-(tetrahydro-2H-pyran-2-yl)-1H-indazole (24) (300 mg, 1.0 mmol) in microwave vial under nitrogen. Ammonia (10.2 mL of a 0.5 M solution in dioxane) was added via a gas-tight syringe. The vial was sealed with a Teflon-lined cap and kept at 100° C. overnight. The crude reaction mixture was diluted with EtOAc and water. The aqueous layer was extracted with EtOAc. The combined organic phases were washed with brine and concentrated under reduced pressure. The crude product was purified using silica gel (ISCO 12 g column) which was eluted with a 0-65% EtOAc/heptane gradient and gave 5-methyl-1-(tetrahydro-2H-pyran-2-yl)-1H-indazol-4-amine (116) as light brown solid (209 mg, 89% yield). $^1$H NMR (400 MHz, DMSO-d$_6$) δ 8.14 (s, 1H), 6.97 (d, J=8.3 Hz, 1H), 6.70 (d, J=8.3 Hz, 1H), 5.62 (dd, J=9.7, 2.4 Hz, 1H), 5.50 (s, 2H), 3.87 (d, J=12.2 Hz, 1H), 3.68 (ddd, J=11.4, 7.7, 6.0 Hz, 1H), 2.30-2.45 (m, 1H), 2.12 (s, 3H), 1.95-2.07 (m, 1H), 1.84-1.95 (m, 1H), 1.64-1.79 (m, 1H), 1.50-1.60 (m, 2H). LCMS (APCI) m/z 232 (M+H).

Step 2:

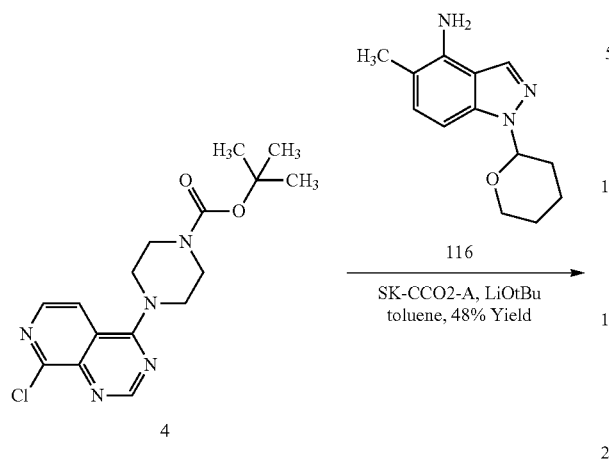

Step 3:

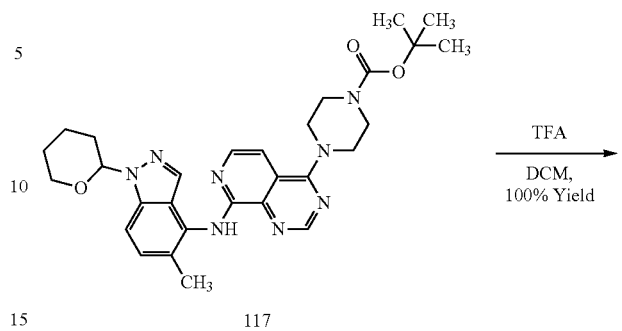

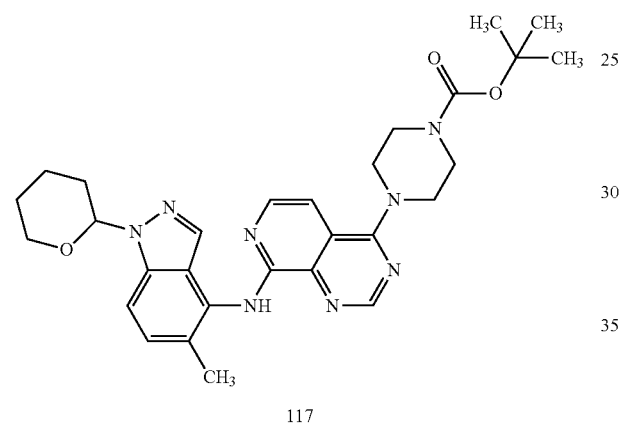

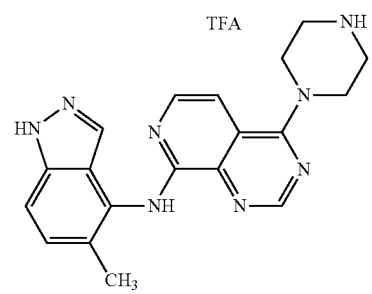

To a flask with 5-methyl-1-(tetrahydro-2H-pyran-2-yl)-1H-indazol-4-amine (116) (195 mg, 0.6 mmol), tert-butyl 4-(8-chloropyrido[3,4-d]pyrimidin-4-yl)piperazine-1-carboxylate (4) (129 mg, 0.6 mmol) and SK-CCO2-A (24 mg, 0.04 mmol, cas 614753-51-4) in toluene (10 mL) under nitrogen was added a solution of LiO-tBu (134 mg, 1.7 mmol) in THF (1.0 M). The brown solution was purged with nitrogen for three minutes and stirred at 100° C. for 18 hours and 115° C. for two more hours. The crude reaction mixture was cooled to room temperature and diluted with EtOAc and aqueous NH₄Cl. The aqueous layer was extracted with EtOAc and the combined organic layers were concentrated under reduced pressure. The crude product was purified using silica gel (ISCO 24 g column) which was eluted with a 5-10% isopropanol/EtOAc gradient and gave tert-butyl 4-(8-((5-methyl-1-(tetrahydro-2H-pyran-2-yl)-1H-indazol-4-yl)amino)pyrido[3,4-d]pyrimidin-4-yl)piperazine-1-carboxylate (117) (145 mg, 48% yield). LCMS (ESI) m/z 545 (M+H).

N-(5-Methyl-1H-indazol-4-yl)-4-(piperazin-1-yl)pyrido[3,4-d]pyrimidin-8-amine (118) (97 mg, 100% yield) was prepared according to the procedure used to prepare 8-[(5-methyl-1H-indazol-4-yl)oxy]-4-(piperazin-1-yl)pyrido[3,4-d]pyrimidine (86). LCMS (ESI) m/z 361 (M+H).

Step 4:

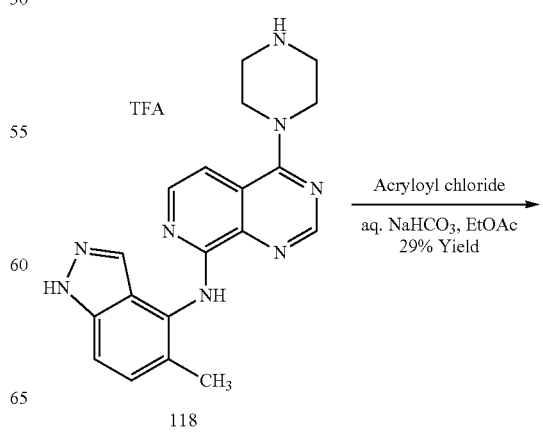

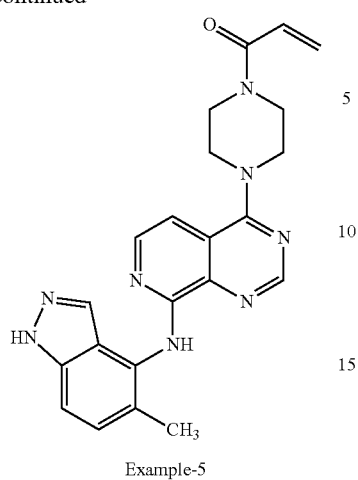

Example-5

1-(4-{8-[(5-Methyl-1H-indazol-4-yl)amino]pyrido[3,4-d]pyrimidin-4-yl}piperazin-1-yl)prop-2-en-1-one (Example-5) (32 mg, 29% yield) was prepared according to the procedure used to prepare 1-(4-{8-[(5-methyl-1H-indazol-4-yl)oxy]pyrido[3,4-d]pyrimidin-4-yl}piperazin-1-yl)prop-2-en-1-one (Example-1A). The crude product was purified using SFC (ZymorSPHER HADP column with methanol). $^1$H NMR (700 MHz, DMSO-d$_6$) δ 12.89 (br. s, 1H), 9.16 (s, 1H), 8.77 (s, 1H), 7.82 (d, J=5.9 Hz, 1H), 7.70 (s, 1H), 7.33 (d, J=8.4 Hz, 1H), 7.26 (d, J=8.4 Hz, 1H), 7.05 (d, J=5.72 Hz, 1H), 6.83 (dd, J=16.7, 10.3 Hz, 1H), 6.17 (dd, J=16.7, 2.2 Hz, 1H), 5.71-5.75 (m, 1H), 3.86 (br. s, 4H), 3.81 (br. s, 2H), 3.76 (br. s, 2H), 2.28 (s, 3H). LCMS (APCI) m/z 415 (M+H).

The following examples were prepared according to general method D:

Preparation of 1-(4-{8-[(5-methyl-1H-indazol-4-yl)methyl]quinazolin-4-yl}piperazin-1-yl)prop-2-en-1-one (Example-1D)

Step 1:

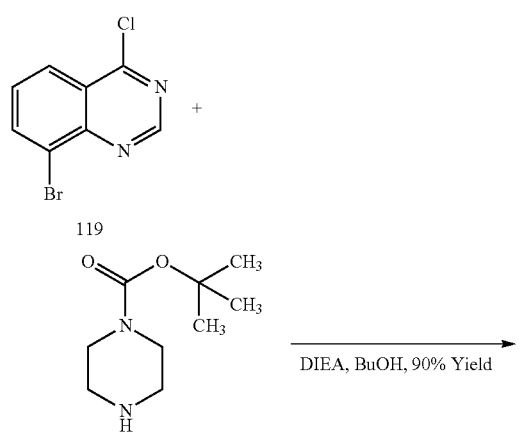

DIEA, BuOH, 90% Yield

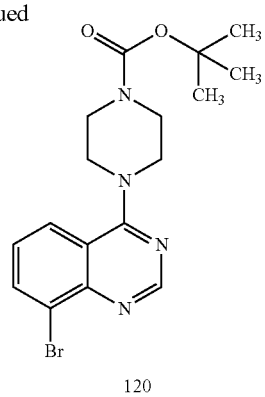

120

A mixture of 8-bromo-4-chloroquinazoline (119) (2 g, 8 mmol), tert-butyl piperazine-1-carboxylate (1.7 g, 90 mmol) and DIPEA (2.0 g, 16 mmol) in 25 mL BuOH was heated at 90° C. for 6 hours. The solvent was removed under reduced pressure and the crude product was purified by silica gel flash chromatography, which was eluted with 0-30% EtOAc/petroleum ether and gave tert-butyl 4-(8-bromoquinazoline-4-yl)piperazine-1-carboxylate (120) as a white solid (3.0 g, 90% yield). $^1$H NMR (400 MHz, CDCl$_3$) δ 8.87 (s, 1H), 8.07 (d, J=7.5 Hz, 1H), 7.84 (d, J=8.3 Hz, 1H), 7.34 (t, J=8.0 Hz, 1H), 3.80-3.72 (m, 4H), 3.68-3.62 (m, 4H), 1.50 (s, 9H). LCMS (ESI) m/z 393, 395 (M+H).

Step 2:

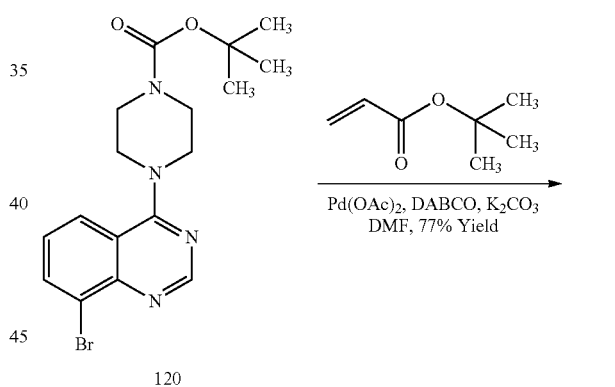

Pd(OAc)$_2$, DABCO, K$_2$CO$_3$
DMF, 77% Yield

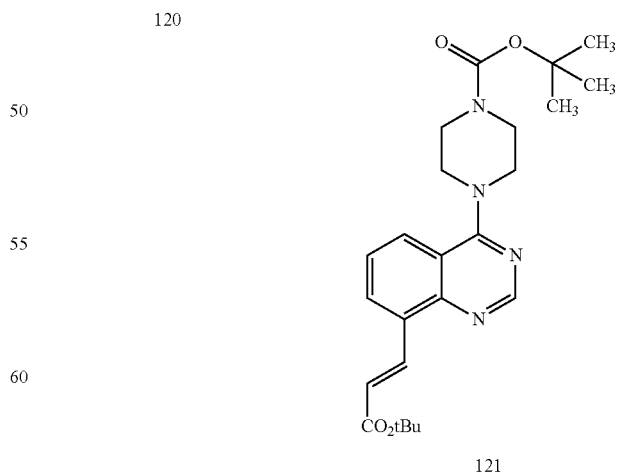

121

A mixture of tert-butyl 4-(8-bromoquinazoline-4-yl)piperazine-1-carboxylate (120) (1.0 g, 2.5 mmol), tert-butyl acrylate (489 mg, 3.81 mmol), Pd(OAc)$_2$ (57 mg, 0.25 mmol), DABCO (57 mg, 0.51 mmol) and K$_2$CO$_3$ (351 mg, 2.54 mmol) in dry DMF (12 mL) was heated at 120° C. for 16 hours under an atmosphere of nitrogen. LCMS analysis showed the reaction was complete. The crude reaction mixture was concentrated and diluted with H$_2$O (50 mL). The aqueous layer was extracted with EtOAc (3×40 mL) and the combined organic layers were washed with H$_2$O (2×50 mL), brine (50 mL), dried over Na$_2$SO$_4$, filtered and concentrated. The crude product was purified by silica gel flash chromatography and eluted with 0-35% EtOAc/petroleum ether and gave tert-butyl 4-{8-[(1E)-3-tert-butoxy-3-oxoprop-1-en-1-yl]quinazolin-4-yl}piperazine-1-carboxylate (121) as an off-white solid (850 mg, 77% yield). $^1$H NMR (400 MHz, CDCl$_3$) δ 8.82 (s, 1H), 8.61 (d, J=16.2 Hz, 1H), 7.98 (d, J=7.2 Hz, 1H), 7.89 (d, J=8.3 Hz, 1H), 7.47 (t, J=7.9 Hz, 1H), 6.68 (d, J=16.2 Hz, 1H), 3.83-3.71 (m, 4H), 3.70-3.58 (m, 4H), 1.57 (s, 9H), 1.50 (s, 9H). LCMS (ESI) m/z 441 (M+H).

Step 3:

which was eluted with 0-40% EtOAc/petroleum ether, and gave tert-butyl 4-(8-formylquinazolin-4-yl)piperazine-1-carboxylate (122) as a white solid (448 mg, 82% yield). $^1$H NMR (400 MHz, CDCl$_3$) δ 11.26 (s, 1H), 8.84 (s, 1H), 8.35 (dd, J=7.3, 1.3 Hz, 1H), 8.13 (dd, J=8.3, 1.3 Hz, 1H), 7.59 (t, J=8.0 Hz, 1H), 3.91-3.75 (m, 4H), 3.73-3.55 (m, 4H), 1.50 (s, 9H). LCMS (ESI) m/z 343 (M+H).

Step 4:

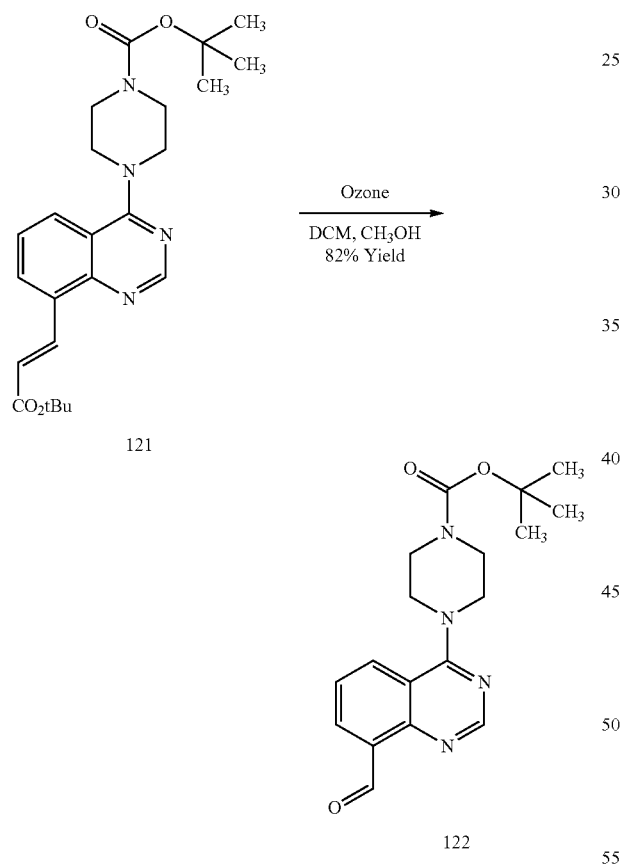

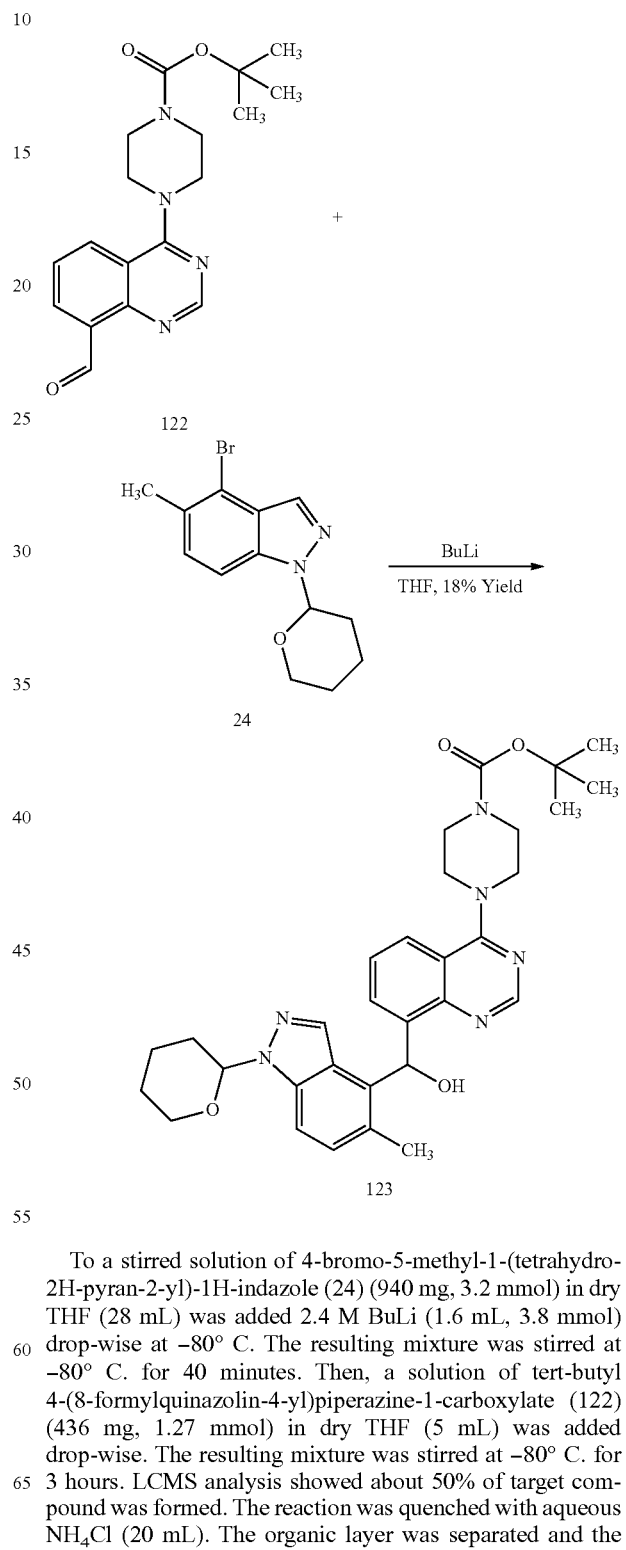

To a stirred solution of tert-butyl 4-{8-[(1E)-3-tert-butoxy-3-oxoprop-1-en-1-yl]quinazolin-4-yl}piperazine-1-carbonylate (121) (700 mg, 1.59 mmol) in DCM (35 mL) and methanol (35 mL) was bubbled ozone gas at −50° C. After about 30 minutes, the LCMS trace showed the starting material was consumed. Nitrogen gas was bubbled into the crude reaction mixture with stirring for about 20 minutes, followed by the addition of PPh$_3$ (625 mg, 2.4 mmol). The resulting mixture was stirred for 1 hour at room temperature. The crude reaction mixture was concentrated and the crude product was purified by silica gel flash chromatography, To a stirred solution of 4-bromo-5-methyl-1-(tetrahydro-2H-pyran-2-yl)-1H-indazole (24) (940 mg, 3.2 mmol) in dry THF (28 mL) was added 2.4 M BuLi (1.6 mL, 3.8 mmol) drop-wise at −80° C. The resulting mixture was stirred at −80° C. for 40 minutes. Then, a solution of tert-butyl 4-(8-formylquinazolin-4-yl)piperazine-1-carboxylate (122) (436 mg, 1.27 mmol) in dry THF (5 mL) was added drop-wise. The resulting mixture was stirred at −80° C. for 3 hours. LCMS analysis showed about 50% of target compound was formed. The reaction was quenched with aqueous NH$_4$Cl (20 mL). The organic layer was separated and the aqueous layer was extracted with EtOAc (2×30 mL). The combined organic layers were washed with brine (40 mL), dried over Na₂SO₄, filtered and concentrated. The crude product was purified by silica gel flash chromatography, which was eluted with 0-60% EtOAc/petroleum ether, and gave tert-butyl 4-(8-{hydroxy[5-methyl-1-(tetrahydro-2H-pyran-2-yl)-1H-indazol-4-yl]methyl}quinazolin-4-yl)piperazine-1-carboxylate (123) as a white solid (330 mg, 18% yield). ¹H NMR (400 MHz, CDCl₃) δ 8.83 (s, 1H), 8.18 (d, J=15.0 Hz, 1H), 7.76 (d, J=8.2 Hz, 1H), 7.58-7.45 (m, 1H), 7.28 (d, J=3.5 Hz, 1H), 7.17 (t, J=7.6 Hz, 1H), 7.04 (s, 1H), 6.90-6.75 (m, 1H), 6.37 (br. s, 1H), 5.80-5.62 (m, 1H), 4.17-3.96 (m, 2H), 3.90-3.70 (m, 5H), 3.69-3.56 (m, 4H), 2.66-2.48 (m, 1H), 2.34 (s, 3H), 2.20-2.05 (m, 2H), 1.82-1.73 (m, 2H), 1.50 (s, 9H). LCMS (ESI) m/z 559 (M+H).

Step 5:

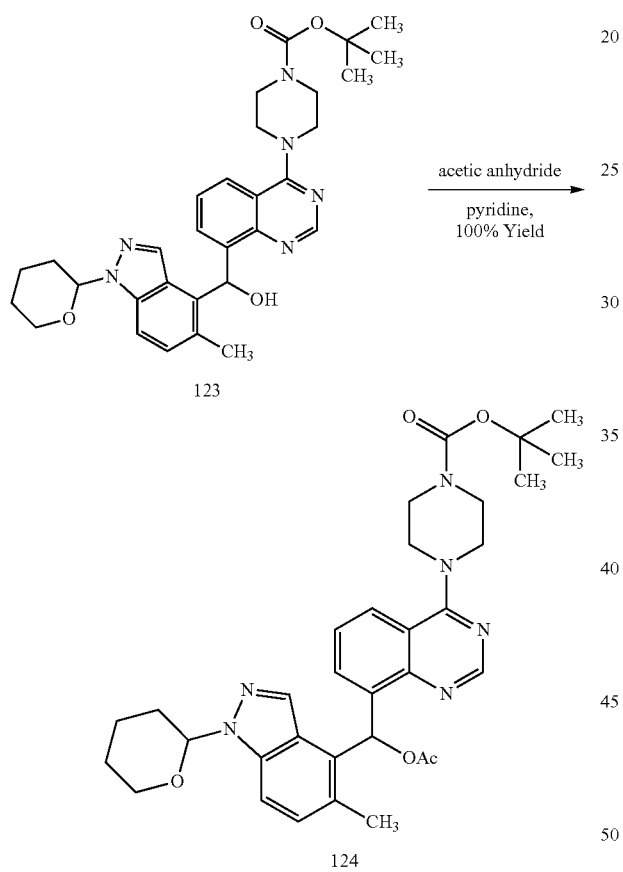

A solution of tert-butyl 4-(8-(hydroxy(5-methyl-1-(tetrahydro-2H-pyran-2-yl)-1H-indazol-4-yl)methylquinazolin-4-yl)piperazine-1-carboxylate (123) (120 mg, 0.22 mmol) and Ac₂O (84 mg, 1.1 mmol) in pyridine (8 mL) was stirred at 80° C. for 5 hours. LCMS analysis showed the reaction was complete. The solvent was removed under reduced pressure and gave tert-butyl 4-(8-{(acetyloxy)[5-methyl-1-(tetrahydro-2H-pyran-2-yl)-1H-indazol-4-yl]methyl}quinazolin-4-yl)piperazine-1-carboxylate (124) as an oil which was used in the next step without further purification (129 mg, 100% yield). LCMS (ESI) m/z 601 (M+H).

Step 6:

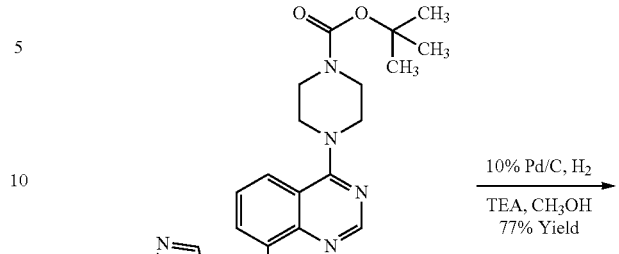

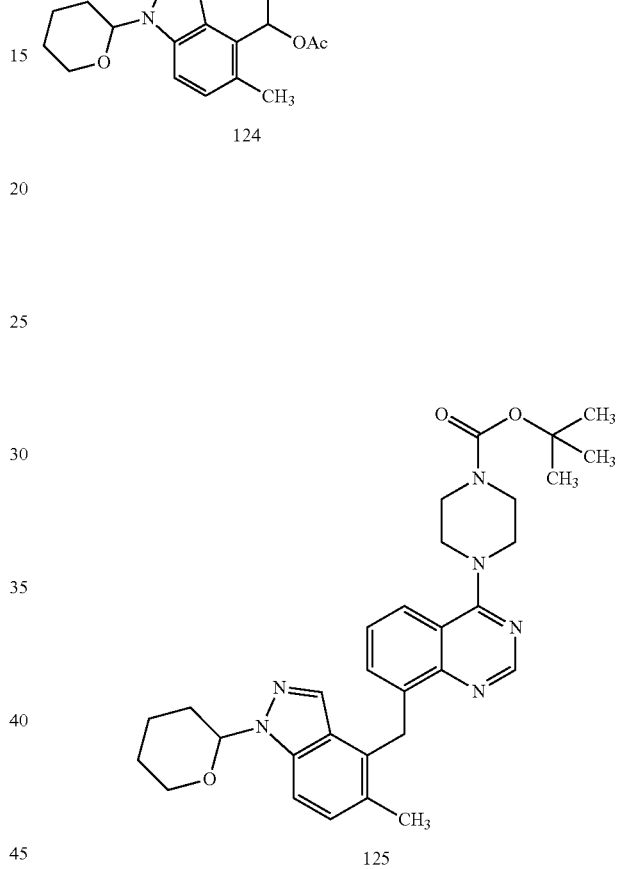

A mixture of tert-butyl 4-(8-{(acetyloxy)[5-methyl-1-(tetrahydro-2H-pyran-2-yl)-1H-indazol-4-yl]methyl}quinazolin-4-yl)piperazine-1-carboxylate (124) (129 mg, 0.22 mmol), Et₃N (65 mg, 0.64 mmol) and 10% Pd/C (30 mg) in methanol (25 mL) was stirred under a hydrogen atmosphere for 5 hours. LCMS analysis showed the reaction was complete. The crude reaction mixture was filtered. The filtrate was concentrated and the crude product was purified by silica gel flash chromatography, which was eluted with 0-30% EtOAc/petroleum ether and gave tert-butyl 4-(8-{[5-methyl-1-(tetrahydro-2H-pyran-2-yl)-1H-indazol-4-yl]methyl}quinazolin-4-yl)piperazine-1-carboxylate (125) as a colorless gum (90 mg, 77% yield). LCMS (ESI) m/z 543 (M+H).

Step 7:

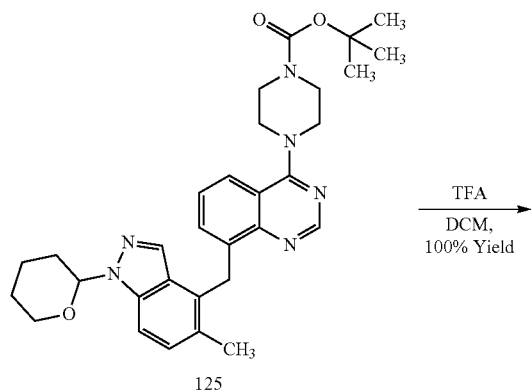

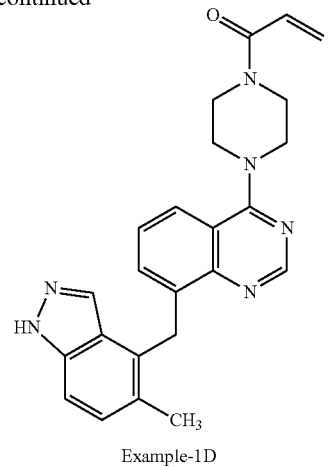

Example-1D 1-(4-{8-[(5-Methyl-1H-indazol-4-yl)methyl]quinazolin-4-yl}piperazin-1-yl)prop-2-en-1-one (Example-1D) (40 mg, 61% yield) was prepared according to the procedure used to prepare 1-(4-{8-[(5-methyl-1H-indazol-4-yl)oxy]pyrido[3,4-d]pyrimidin-4-yl}piperazin-1-yl)prop-2-en-1-one (Example-1A). The crude product was purified by pre-HPLC using a Gemini-C18, 100×21.2 mm, 5 μm column and eluted with 15-25% acetonitrile/H₂O (0.1% formic acid). ¹H NMR (400 MHz, MeOD) δ 8.79 (s, 1H), 7.91 (d, J=8.3 Hz, 1H), 7.80 (s, 1H), 7.39 (s, 1H), 7.31 (d, J=8.4 Hz, 2H), 7.03 (d, J=7.4 Hz, 1H), 6.82 (dd, J=16.8, 10.7 Hz, 1H), 6.26 (d, J=16.8 Hz, 1H), 5.80 (d, J=10.7 Hz, 1H), 4.84 (s, 2H), 3.89 (s, 8H), 2.31 (s, 3H). LCMS (ESI) m/z 413 (M+H).

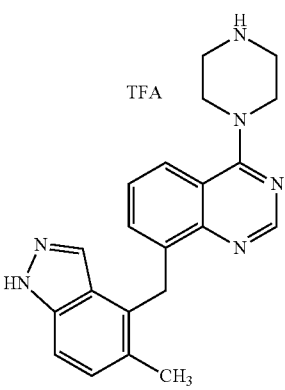

8-[(5-Methyl-1H-indazol-4-yl)methyl]-4-(piperazin-1-yl)quinazoline (126) (59 mg, 100% yield) was prepared according to the procedure used to prepare 8-[(5-methyl-1H-indazol-4-yl)oxy]-4-(piperazin-1-yl)pyrido[3,4-d]pyrimidine (86).

Step 8:

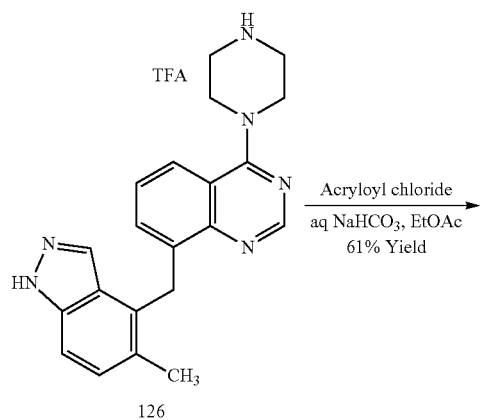

Preparation of 1-(4-{8-[(5-methyl-1H-indazol-4-yl)methyl]pyrido[3,4-d]pyrimidin-4-yl}piperazin-1-yl)prop-2-en-1-one (Example-2D)

Step 1:

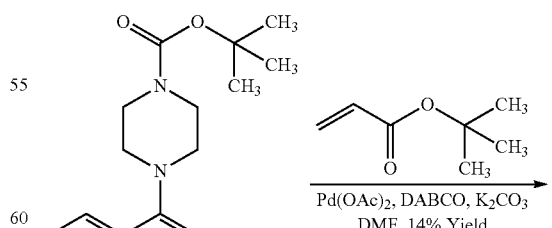

-continued

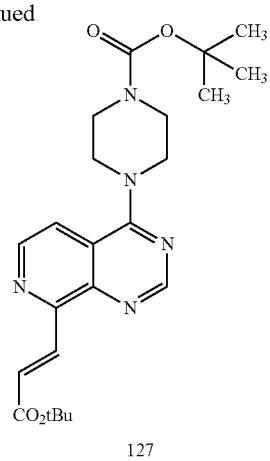

127

Tert-butyl 4-{8-[(1E)-3-tert-butoxy-3-oxoprop-1-en-1-yl]pyrido[3,4-d]pyrimidin-4-yl}piperazine-1-carboxylate (127) (880 mg, 14% yield) was prepared according to the procedure used to prepare tert-butyl 4-{8-[(1E)-3-tert-butoxy-3-oxoprop-1-en-1-yl]quinazolin-4-yl}piperazine-1-carboxylate (121). $^1$H NMR (400 MHz, CDCl$_3$) δ 8.83 (s, 1H), 8.74 (d, J=5.6 Hz, 1H), 8.60 (d, J=5.6 Hz, 1H), 7.60 (d, J=15.8 Hz, 1H), 7.20 (d, J=15.8 Hz, 1H), 3.84 (m, 4H), 3.66 (m, 4H), 1.56 (s, 9H), 1.50 (s, 9H). LCMS (ESI) m/z 442 (M+H).

Step 2:

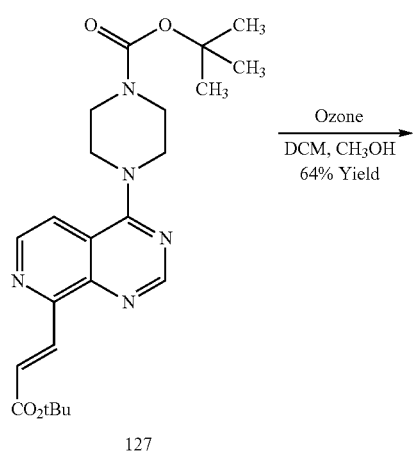

Tert-butyl 4-(8-formylpyrido[3,4-d]pyrimidin-4-yl)piperazine-1-carboxylate (128) (630 mg, 64% yield) was prepared according to the procedure used to prepare tert-butyl 4-(8-formylquinazolin-4-yl)piperazine-1-carboxylate (122). $^1$H NMR (400 MHz, DMSO-d$_6$) δ 11.05 (s, 1H), 8.80 (s, 1H), 8.77 (d, J=5.5 Hz, 1H), 8.19 (d, J=5.5 Hz, 1H), 3.95 (m, 4H), 3.57 (m, 4H), 1.44 (s, 9H). LCMS (ESI) m/z 344 (M+H).

Step 3:

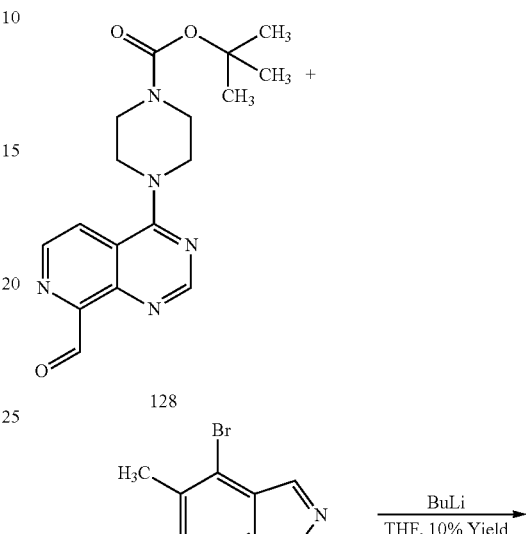

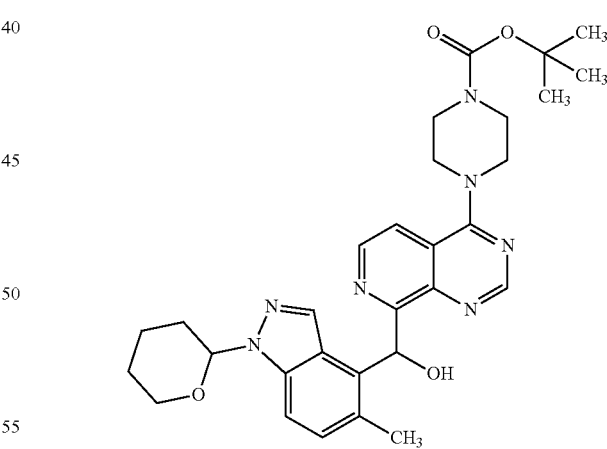

129

Tert-butyl 4-(8-{hydroxy[5-methyl-1-(tetrahydro-2H-pyran-2-yl)-1H-indazol-4-yl]methyl}pyrido[3,4-d]pyrimidin-4-yl)piperazine-1-carboxylate (129) (200 mg, 10% yield) was prepared according to the procedure used to prepare tert-butyl 4-(8-{hydroxy[5-methyl-1-(tetrahydro-2H-pyran-2-yl)-1H-indazol-4-yl]methyl}quinazolin-4-yl)piperazine-1-carboxylate (123). LCMS (ESI) m/z 560 (M+H).

Step 4:

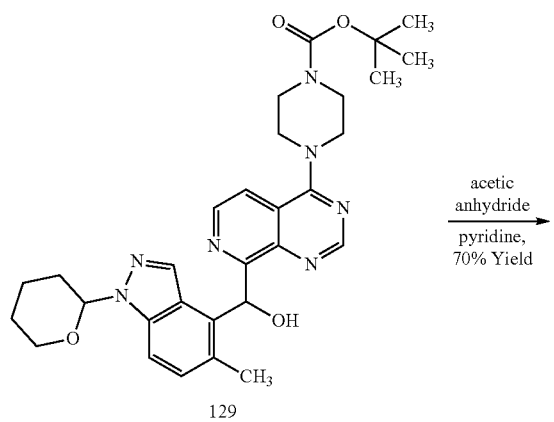

129 acetic anhydride
⟶
pyridine, 70% Yield

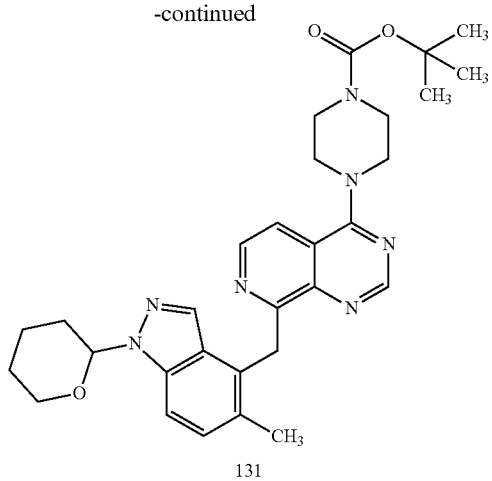

131

Tert-butyl 4-(8-{[5-methyl-1-(tetrahydro-2H-pyran-2-yl)-1H-indazol-4-yl]methyl}pyrido[3,4-d]pyrimidin-4-yl)piperazine-1-carboxylate (131) (28 mg, 26% yield) was prepared according to the procedure used to prepare tert-butyl 4-(8-{[5-methyl-1-(tetrahydro-2H-pyran-2-yl)-1H-indazol-4-yl]methyl}quinazolin-4-yl)piperazine-1-carboxylate (125). $^1$H NMR (400 MHz, CDCl$_3$) δ 8.87 (s, 1H), 8.42 (t, J=5.2 Hz, 1H), 8.04 (d, J=5.3 Hz, 1H), 7.45 (t, J=5.9 Hz, 1H), 7.35 (d, J=8.5 Hz, 1H), 7.25 (s, 1H), 5.63 (dd, J=9.4, 2.2 Hz, 1H), 5.10 (m, 2H), 4.00-3.98 (m, 1H), 3.82 (m, 4H), 3.70 (m, 5H), 2.60-2.47 (m, 4H), 2.13-2.09 (m, 1H), 1.72-1.63 (m, 4H), 1.47 (s, 9H). LCMS (ESI) m/z 544 (M+H).

Step 6:

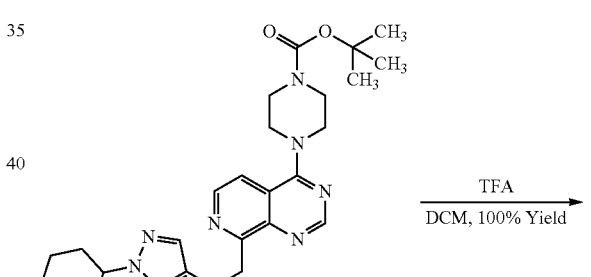

131

TFA
⟶
DCM, 100% Yield

130

Tert-butyl 4-(8-{(acetyloxy)[5-methyl-1-(tetrahydro-2H-pyran-2-yl)-1H-indazol-4-yl]methyl}pyrido[3,4-d]pyrimidin-4-yl)piperazine-1-carboxylate (130) (130 mg, 70% yield) was prepared according to the procedure used to prepare tert-butyl 4-(8-{(acetyloxy)[5-methyl-1-(tetrahydro-2H-pyran-2-yl)-1H-indazol-4-yl]methyl}quinazolin-4-yl)piperazine-1-carboxylate (124). $^1$H NMR (400 MHz, CDCl$_3$) δ 8.72 (d, J=10.1 Hz, 1H), 8.57 (m, 1H), 8.45 (d, J=6.1 Hz, 1H), 8.31 (d, J=14.1 Hz, 1H), 7.52-7.46 (m, 1H), 7.41-7.34 (m, 1H), 7.22 (d, J=8.6 Hz, 1H), 5.60 (m, 1H), 3.74 (m, 10H), 2.86 (d, J=10.3 Hz, 3H), 2.60-2.52 (m, 1H), 2.21 (d, J=6.9 Hz, 3H), 2.17-2.13 (m, 2H), 1.73-1.64 (m, 3H), 1.48 (s, 9H). LCMS (ESI) m/z 602 (M+H).

Step 5:

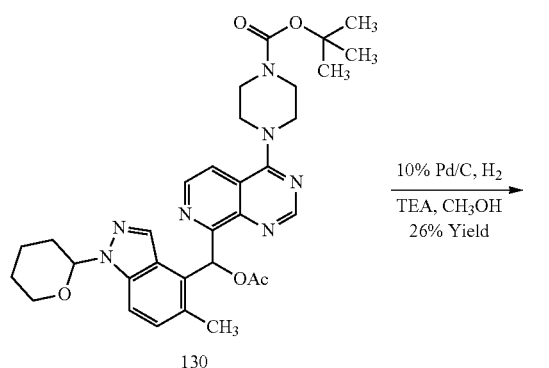

130

10% Pd/C, H$_2$
⟶
TEA, CH$_3$OH
26% Yield

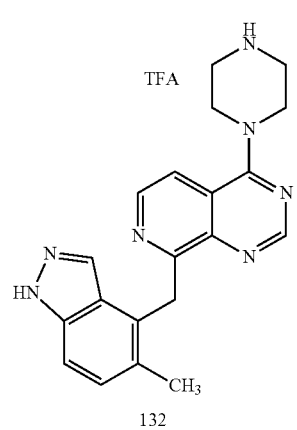

TFA

132

8-[(5-Methyl-1H-indazol-4-yl)methyl]-4-(piperazin-1-yl)pyrido[3,4-d]pyrimidine (132) (19 mg, 100% yield) was prepared according to the procedure used to prepare 8-[(5-methyl-1H-indazol-4-yl)oxy]-4-(piperazin-1-yl)pyrido[3,4-d]pyrimidine (86). LCMS (ESI) m/z 360 (M+H).

Step 7:

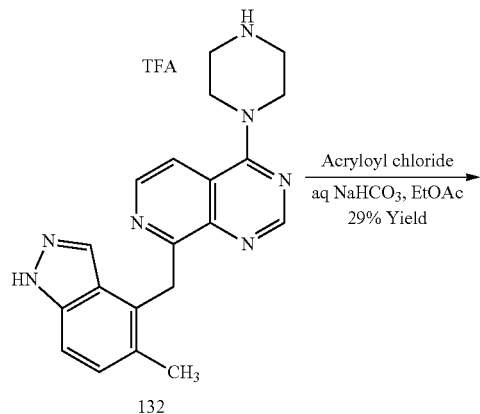

1-(4-{8-[(5-Methyl-1H-indazol-4-yl)methyl]pyrido[3,4-d]pyrimidin-4-yl}piperazin-1-yl)prop-2-en-1-one (Example-2D) (6 mg, 19% yield) was prepared according to the procedure used to prepare 1-(4-{8-[(5-methyl-1H-indazol-4-yl)oxy]pyrido[3,4-d]pyrimidin-4-yl}piperazin-1-yl)prop-2-en-1-one (Example-1A). $^1$H NMR (400 MHz, MeOD) δ 8.80 (s, 1H), 8.35 (d, J=5.8 Hz, 1H), 7.85 (s, 1H), 7.75 (dd, J=5.6, 3.1 Hz, 1H), 7.28 (dd, J=25.2, 8.5 Hz, 2H), 6.80 (dd, J=16.8, 10.6 Hz, 1H), 6.26 (dd, J=16.8, 1.8 Hz, 1H), 5.79 (dd, J=10.6, 1.8 Hz, 1H), 5.06 (s, 2H), 3.90 (m, 8H), 2.46 (s, 3H). LCMS (ESI) m/z 413 (M+H).

The following examples were prepared according to general method E:

Preparation of 1-(4-{8-[(5-chloro-6-methyl-1H-indazol-4-yl)oxy]-2-[3-(dimethylamino)azetidin-1-yl]-6-methylpyrido[3,4-d]pyrimidin-4-yl}piperazin-1-yl)prop-2-en-1-oneol (Example-1E)

Step 1:

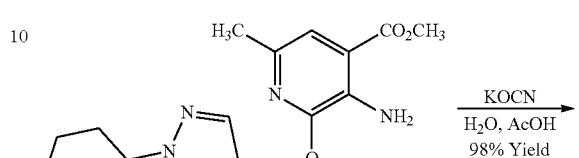

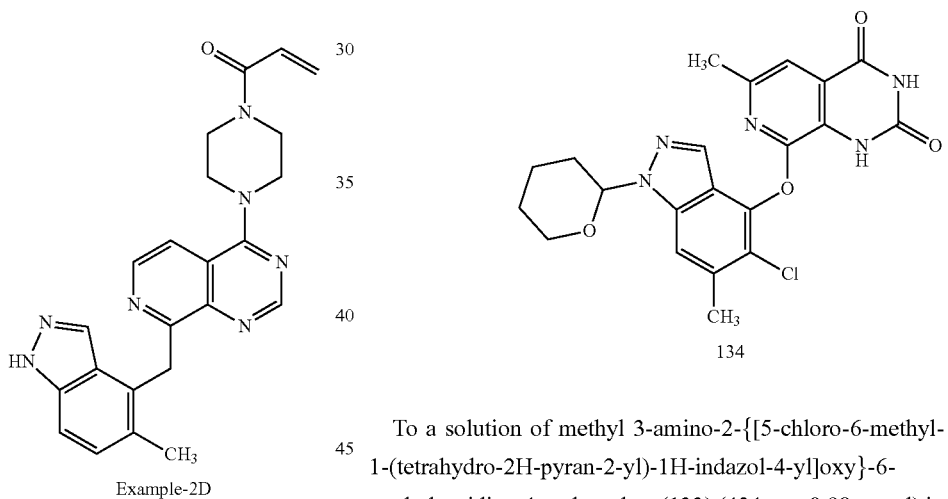

To a solution of methyl 3-amino-2-{[5-chloro-6-methyl-1-(tetrahydro-2H-pyran-2-yl)-1H-indazol-4-yl]oxy}-6-methylpyridine-4-carboxylate (133) (424 mg, 0.98 mmol) in AcOH (15 mL) at 80° C. was added KOCN (904 mg, 11.1 mmol) in water (1 mL) and the yellow solution stirred at 80° C. for 30 minutes. After 30 minutes, LCMS gave starting material and product. Additional solid KOCN, in 11 mmol aliquots, was added every 30 minutes until all of the starting material was consumed. The reaction mixture was cooled and diluted with water to give a suspension. The solid was filtered, washed with water and dried. The solid was dissolved in a mixture of diethyl ether and DCM, concentrate and slurried in water. The mixture was filtered and dried to give 8-{[5-chloro-6-methyl-1-(tetrahydro-2H-pyran-2-yl)-1H-indazol-4-yl]oxy}-6-methylpyrido[3,4-d]pyrimidine-2,4(1H,3H)-dione (134) as a cream solid (426 mg, 98% yield). LCMS (ESI) m/z 442 (M+H).

Step 2:

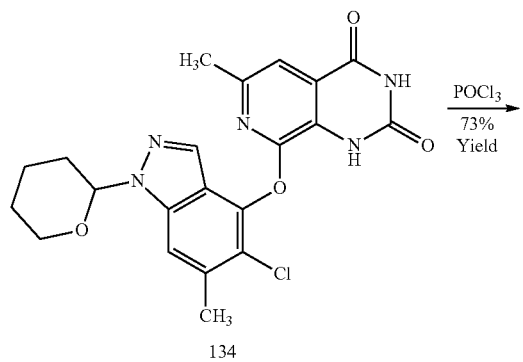

134

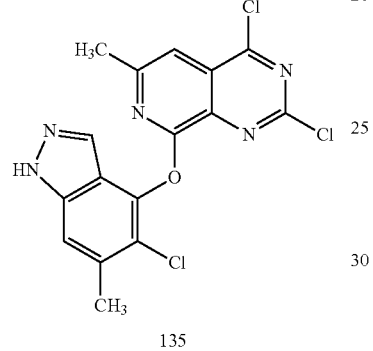

135

A solution of 8-{[5-chloro-6-methyl-1-(tetrahydro-2H-pyran-2-yl)-1H-indazol-4-yl]oxy}-6-methylpyrido[3,4-d]pyrimidine-2,4(1H,3H)-dione (134) (426 mg, 0.96 mmol) in POCl$_3$ (6 mL) and dimethylaniline (0.05 mL) was stirred at 100° C. for 6 hours. The crude reaction mixture was concentrated and azeotroped with toluene. Ice was added to the crude product and the mixture basified with sodium bicarbonate. The crude product was extracted into DCM, dried over sodium sulfate and concentrated which gave 2,4-dichloro-8-[(5-chloro-6-methyl-1H-indazol-4-yl)oxy]-6-methylpyrido[3,4-d]pyrimidine (135) as a brown foam (278 mg, 73% yield). LCMS (ESI) m/z 393 (M+H).

Step 3:

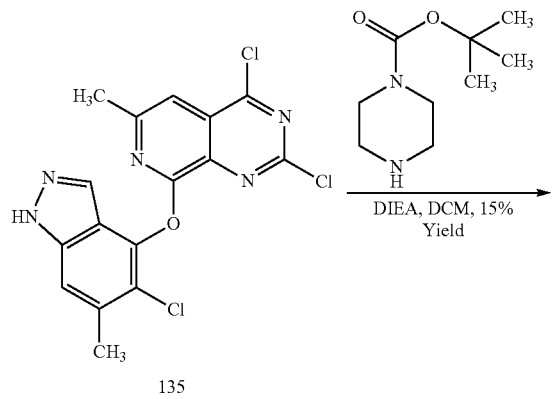

135

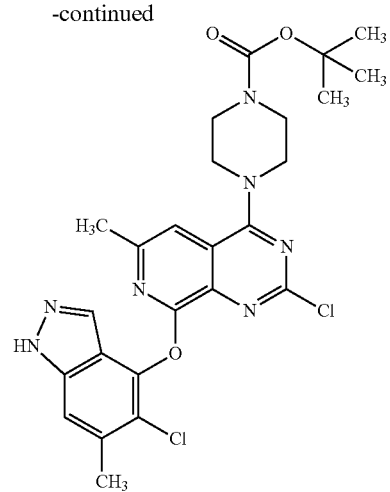

136

A solution of 2,4-dichloro-8-[(5-chloro-6-methyl-1H-indazol-4-yl)oxy]-6-methylpyrido[3,4-d]pyrimidine (278 mg, 0.70 mmol), tert-butyl piperazine-1-carboxylate (135) (157 mg, 0.84 mmol) and diisopropylethylamine (273 mg, 2.11 mmol) in DCM (10 mL) was stirred overnight. The crude reaction mixture was concentrated and purified using silica gel chromatography (12 g ISCO cartridge) and eluted with EtOAc/heptane (0-100%) and gave tert-butyl 4-{2-chloro-8-[(5-chloro-6-methyl-1H-indazol-4-yl)oxy]-6-methyl-pyrido[3,4-d]pyrimidin-4-yl}piperazine-1-carboxylate (136) as a brown solid (57 mg, 15% yield). $^1$H NMR (400 MHz, CDCl$_3$) δ 7.81 (s, 1H), 7.34 (s, 1H), 7.11 (s, 1H), 3.91 (br. s, 4H), 3.75-3.62 (m, 4H), 2.53 (s, 3H), 2.32 (s, 3H), 1.49 (s, 9H). LCMS (ESI) m/z 544 (M+H).

Step 4:

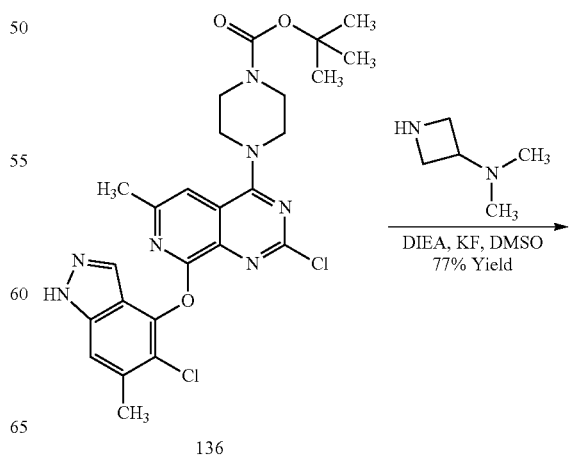

136

301

-continued

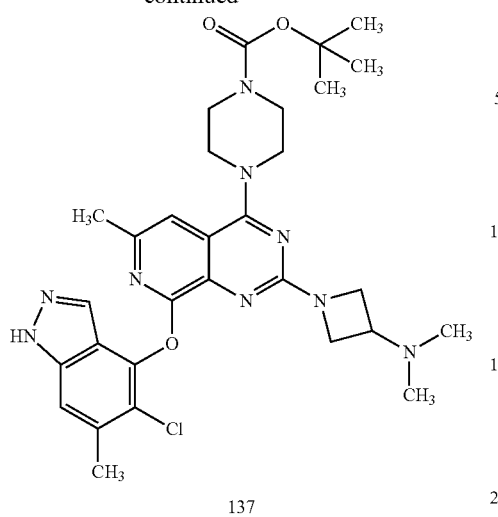

137

A mixture of tert-butyl 4-{2-chloro-8-[(5-chloro-6-methyl-1H-indazol-4-yl)oxy]-6-methylpyrido[3,4-d]pyrimidin-4-yl}piperazine-1-carboxylate (136) (57 mg, 0.10 mmol), N,N-dimethylazetidin-3-amine dihydrochloride (109 mg, 0.63 mmol), DIEA (0.13 mL, 0.73 mmol) and KF (12 mg, 0.21 mmol) in DMSO (2 mL) was stirred at 115° C. for 5 hours. The crude reaction mixture was cooled to room temperature and diluted with EtOAc and wash with water (2×) and brine. The organic layer was dried over sodium sulfate and concentrate which gave tert-butyl 4-{8-[(5-chloro-6-methyl-1H-indazol-4-yl)oxy]-2-[3-(dimethylamino)azetidin-1-yl]-6-methylpyrido[3,4-d]pyrimidin-4-yl}piperazine-1-carboxylate (137) as brown foam (49 mg, 77% yield). LCMS (ESI) m/z 608 (M+H).

Step 5:

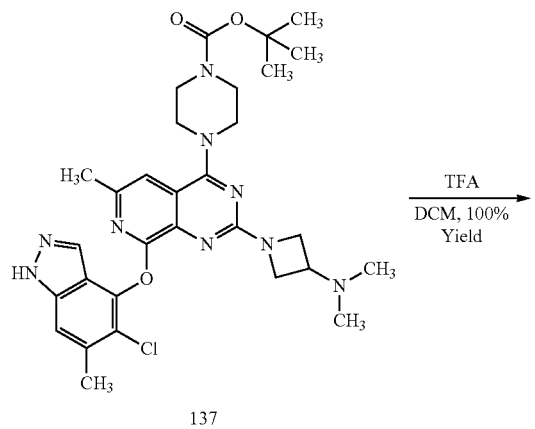

137

302

-continued

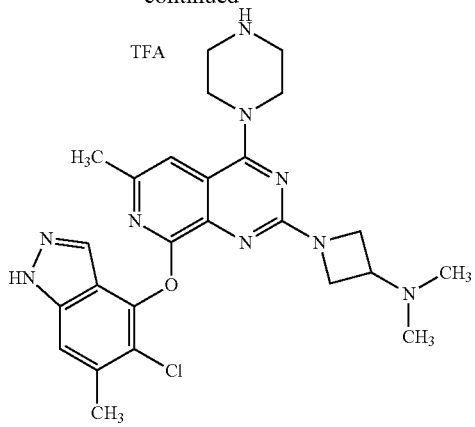

138

1-{8-[(5-Chloro-6-methyl-1H-indazol-4-yl)oxy]-6-methyl-4-(piperazin-1-yl)pyrido[3,4-d]pyrimidin-2-yl}-N,N-dimethylazetidin-3-amine (138) (87 mg, 100% yield) was prepared according to the procedure used to prepare 8-[(5-methyl-1H-indazol-4-yl)oxy]-4-(piperazin-1-yl)pyrido[3,4-d]pyrimidine (86). LCMS (ESI) m/z 508 (M+H).

Step 6:

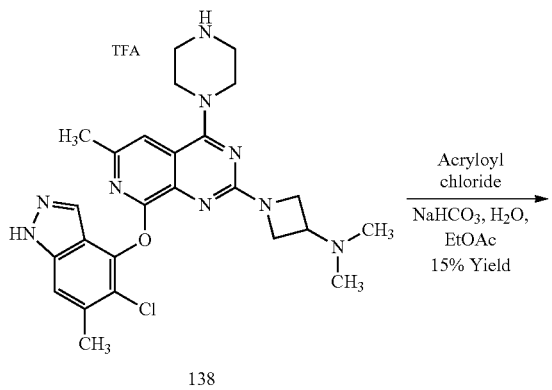

138

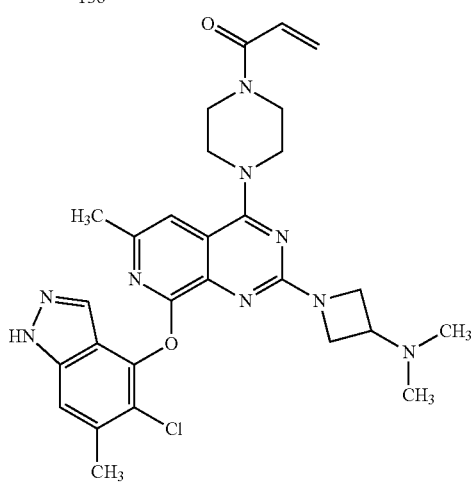

Example-1E 1-(4-{8-[(5-Chloro-6-methyl-1H-indazol-4-yl)oxy]-2-[3-(dimethylamino)azetidin-1-yl]-6-methylpyrido[3,4-d]pyrimidin-4-yl}piperazin-1-yl)prop-2-en-1-one (Example-1E)

(7 mg, 15% yield) was prepared according to the procedure used to prepare 1-(4-{8-[(5-methyl-1H-indazol-4-yl)oxy]pyrido[3,4-d]pyrimidin-4-yl}piperazin-1-yl)prop-2-en-1-one (Example-1A). LCMS (ESI) m/z 562 (M+H).

The examples in the following table were prepared using Method E and the procedure used to prepare 1-(4-{8-[(5-Chloro-6-methyl-1H-indazol-4-yl)oxy]-2-[3-(dimethylamino)azetidin-1-yl]-6-methylpyrido[3,4-d]pyrimidin-4-yl}piperazin-1-yl)prop-2-en-1-one (Example-1E). The following examples were made with non-critical changes or substitutions to the exemplified procedure used to prepare Example-1E that someone who is skilled in the art would be able to realize.

| Example | Structure | Compound Name | LCMS m/z | $^1$H NMR |
|---|---|---|---|---|
| 2E | 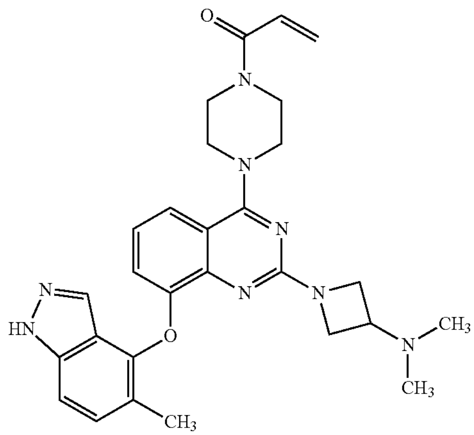 [SMILES: C=CC(=O)N1CCN(c2nc(N3CC(N(C)C)C3)nc3c(Oc4c(C)ccc5[nH]ncc45)cccc23)CC1] | 1-(4-{2-[3-(dimethylamino)azetidin-1-yl]-8-[(5-methyl-1H-indazol-4-yl)oxy]quinazolin-4-yl}piperazin-1-yl)prop-2-en-1-one | 513 (M + H) | $^1$H NMR (400 MHz, DMSO-d$_6$) δ 13.04 (s, 1H), 7.57 (d, J = 8.0 Hz, 1H), 7.32-7.22 (m, 3H), 7.06-6.92 (m, 1H), 7.06-6.92 (m, 1H), 6.85 (dd, J = 10.4, 16.7 Hz, 1H), 6.17 (dd, J = 2.4, 16.7 Hz, 1H), 5.73 (dd, J = 2.3, 10.3 Hz, 1H), 3.97 (br. s, 2H), 3.83-3.64 (m, 10H), 3.16-3.00 (m, 1H), 2.30 (s, 3H), 2.10 (br. s, 6H). |
| 3E | 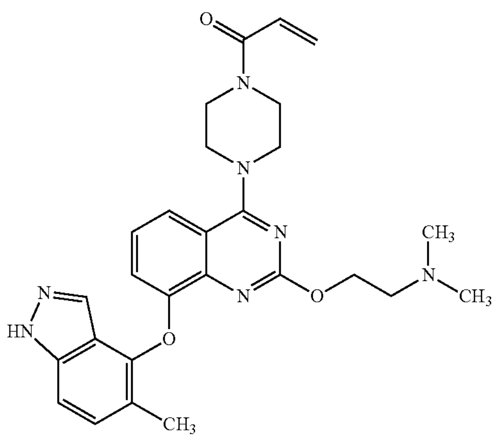 [SMILES: C=CC(=O)N1CCN(c2nc(OCCN(C)C)nc3c(Oc4c(C)ccc5[nH]ncc45)cccc23)CC1] | 1-(4-{2-[2-(dimethylamino)ethoxy]-8-[(5-methyl-1H-indazol-4-yl)oxy]quinazolin-4-yl}piperazin-1-yl)prop-2-en-1-one | 502 (M + H) | $^1$H NMR (400 MHz, DMSO-d$_6$) δ 13.03 (s, 1H), 7.76 (d, J = 7.3 Hz, 1H), 7.31-7.16 (m, 4H), 7.07 (s, 1H), 6.84 (dd, J = 10.5, 16.7 Hz, 1H), 6.17 (dd, J = 2.3, 16.8 Hz, 1H), 5.78-5.68 (m, 1H), 4.13 (t, J = 5.9 Hz, 2H), 3.86-3.70 (m, 8H), 2.43 (t, J = 5.8 Hz, 2H), 2.33 (s, 3H), 2.11 (s, 6H). |
| 4E | 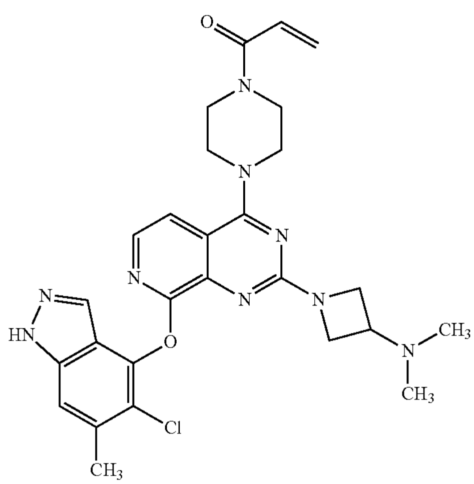 [SMILES: C=CC(=O)N1CCN(c2nc(N3CC(N(C)C)C3)nc3c(Oc4c(Cl)c(C)cc5[nH]ncc45)nccc23)CC1] | 1-(4-{8-[(5-chloro-6-methyl-1H-indazol-4-yl)oxy]-2-[3-(dimethylamino)azetidin-1-yl]pyrido[3,4-d]pyrimidin-4-yl}piperazin-1-yl)prop-2-en-1-one | 548 (M + H) | $^1$H NMR (400 MHz, CD$_3$OD) δ 7.72 (s, 1H), 7.52 (d, J = 5.8 Hz, 1H), 7.42 (d, J = 5.7 Hz, 2H), 6.81 (dd, J = 16.8, 10.6 Hz, 1H), 6.26 (dd, J = 16.8, 1.9 Hz, 1H), 5.80 (dd, J = 10.6, 1.9 Hz, 1H), 4.31 (dd, J = 9.7, 7.2 Hz, 2H), 4.07 (dd, J = 9.8, 5.2 Hz, 2H), 3.88 (m, 8H), 2.54 (s, 3H), 2.28 (s, 6H). |

-continued

| Example | Structure | Compound Name | LCMS m/z | ¹H NMR |
|---------|-----------|---------------|----------|--------|
| 5E | 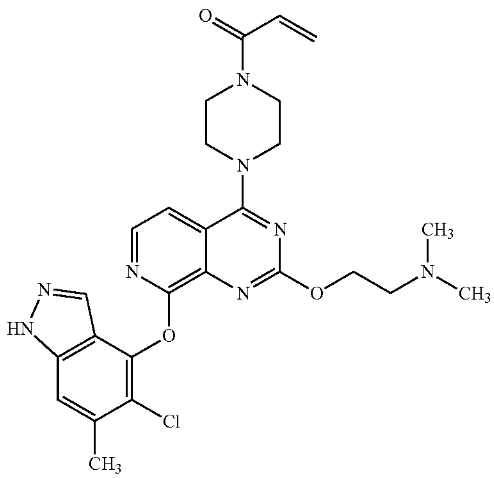 [SMILES: C=CC(=O)N1CCN(c2nc(OCCN(C)C)nc3c(Oc4c(Cl)c(C)cc5[nH]ncc45)nccc23)CC1] | 1-(4-{8-[(5-chloro-6-methyl-1H-indazol-4-yl)oxy]-2-[2-(dimethylamino)ethoxy]pyrido[3,4-d]pyrimidin-4-yl}piperazin-1-yl)prop-2-en-1-one | 537 (M + H) | ¹H NMR (400 MHz, DMSO-$d_6$) δ 13.27 (s, 1H), 7.74 (d, J = 5.8 Hz, 1H), 7.66 (s, 1H), 7.58 (d, J = 5.9 Hz, 1H), 7.46 (s, 1H), 6.83 (dd, J = 16.7, 10.5 Hz, 1H), 6.18 (dd, J = 16.7, 2.3 Hz, 1H), 5.75 (dd, J = 10.4, 2.3 Hz, 1H), 4.46 (t, J = 5.8 Hz, 2H), 3.97-3.70 (m, 8H), 2.72-2.64 (m, 2H), 2.49 (s, 6H), 2.25 (s, 3H). |
| 6E | 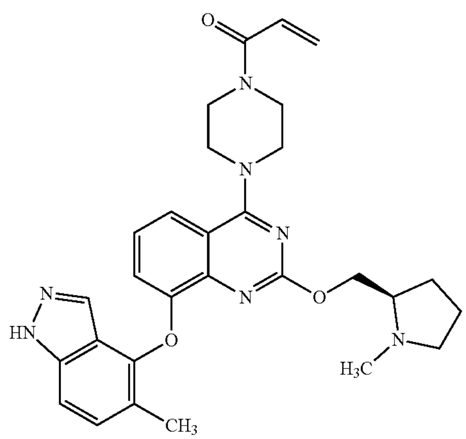 [SMILES: C=CC(=O)N1CCN(c2nc(OC[C@H]3CCCN3C)nc3c(Oc4c(C)ccc5[nH]ncc45)cccc23)CC1] | 1-[4-(8-[(5-methyl-1H-indazol-4-yl)oxy]-2-{[(2R)-1-methylpyrrolidin-2-yl]methoxy}quinazolin-4-yl)piperazin-1-yl]prop-2-en-1-one | 528 (M + H) | ¹H NMR (400 MHz, CD$_3$OD) δ = 7.75 (d, J = 7.5 Hz, 1H), 7.39-7.29 (m, 3H), 7.23 (t, J = 8.2 Hz, 1H), 6.96 (d, J = 7.0 Hz, 1H), 6.89-6.80 (m, 1H), 6.33-6.25 (m, 1H), 5.85-5.79 (m, 1H), 4.39-4.29 (m, 2H), 3.98-3.88 (m, 8H), 3.11-3.04 (m, 1H), 2.76-2.67 (m, 1H), 2.47 (s, 3H), 2.37 (s, 3H), 2.35-2.29 (m, 1H), 2.11-2.01 (m, 1H), 1.86-1.78 (m, 2H), 1.76-1.66 (m 1H). |
| 7E | 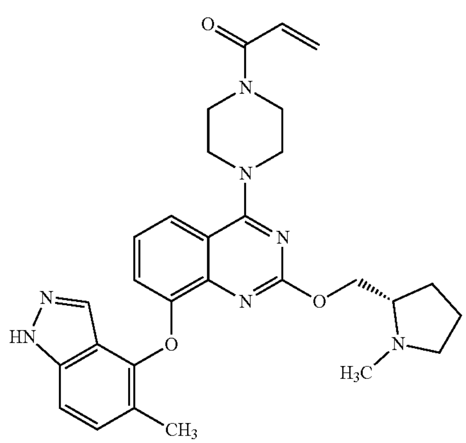 [SMILES: C=CC(=O)N1CCN(c2nc(OC[C@@H]3CCCN3C)nc3c(Oc4c(C)ccc5[nH]ncc45)cccc23)CC1] | 1-[4-(8-[(5-methyl-1H-indazol-4-yl)oxy]-2-{[(2S)-1-methylpyrrolidin-2-yl]methoxy}quinazolin-4-yl)piperazin-1-yl]prop-2-en-1-one | 528 (M + H) | ¹H NMR (400 MHz, CD$_3$OD) δ = 7.78 (d, J = 7.5 Hz, 1H), 7.50 (s, 1H), 7.42 (s, 2H), 7.25 (t, J = 8.2 Hz, 1H), 6.92-6.76 (m, 2H), 6.30 (dd, J = 2.0, 16.8 Hz, 1H), 5.83 (dd, J = 1.8, 10.5 Hz, 1H), 4.76 (br. d, J = 13.1 Hz, 1H), 4.54 (dd, J = 6.0, 13.1 Hz, 1H), 4.06-3.90 (m, 8H), 3.51 (br. s, 2H), 2.92 (br. s, 1H), 2.83 (s, 3H), 2.36 (s, 3H), 2.33-2.23 (m, 1H), 2.11-1.92 (m, 3H). |

-continued

| Example | Structure | Compound Name | LCMS m/z | ¹H NMR |
|---|---|---|---|---|
| 8E | 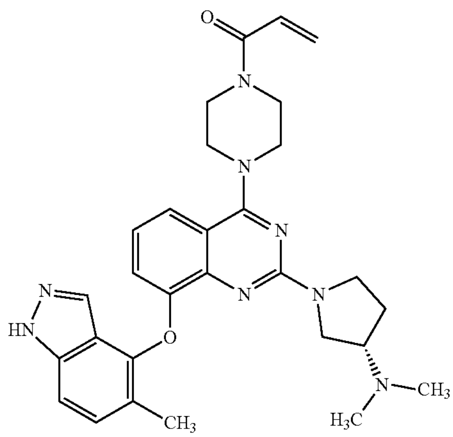 [SMILES: C=CC(=O)N1CCN(c2nc(N3CC[C@H](N(C)C)C3)nc3c(Oc4c(C)ccc5[nH]ncc45)cccc23)CC1] | 1-(4-{2-[(3S)-2-(dimethylamino)pyrrolidin-1-yl]-8-[(5-methyl-1H-indazol-4-yl)oxy]quinazolin-4-yl}piperazin-1-yl)prop-2-en-1-one | 527 (M + H) | ¹H NMR (400 MHz, CD₃OD) δ = 7.60 (dd, J = 1.2, 8.3 Hz, 1H), 7.36-7.26 (m, 3H), 7.05-6.98 (m, 1H), 6.94 (br. d, J = 6.5 Hz, 1H), 6.84 (dd, J = 10.6, 16.8 Hz, 1H), 6.27 (dd, J = 1.9, 16.8 Hz, 1H), 5.87-5.73 (m, 1H), 3.94-3.73 (m, 10H), 3.50 (br. d, J = 6.2 Hz, 1H), 3.26 (br. s, 1H), 2.84 (br. s, 1H), 2.39 (s, 3H), 2.33 (s, 6H), 2.27-2.19 (m, 1H), 1.90-1.79 (m, 1H). |
| 9E | 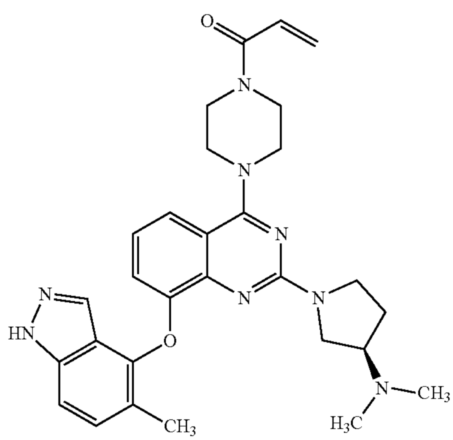 [SMILES: C=CC(=O)N1CCN(c2nc(N3CC[C@@H](N(C)C)C3)nc3c(Oc4c(C)ccc5[nH]ncc45)cccc23)CC1] | 1-(4-{2-[(3R)-3-(dimethylamino)pyrrolidin-1-yl]-8-[(5-methyl-1H-indazol-4-yl)oxy]quinazolin-4-yl}piperazin-1-yl)prop-2-en-1-one | 527 (M + H) | ¹H NMR (400 MHz, CD₃OD) δ = 7.60 (dd, J = 1.3, 8.3 Hz, 1H), 7.38-7.25 (m, 3H), 7.05-6.98 (m, 1H), 6.97-6.90 (m, 1H), 6.84 (dd, J = 10.6, 16.8 Hz, 1H), 6.27 (dd, J = 2.0, 16.8 Hz, 1H), 5.85-5.75 (m, 1H), 3.95-3.73 (m, 10H), 3.56-3.46 (m, 1H), 3.28 (br. s, 1H), 2.90 (br. s, 1H), 2.39 (s, 3H), 2.36 (s, 6H), 2.29-2.21 (m, 1H), 1.94-1.81 (m, 1H). |
| 10E | 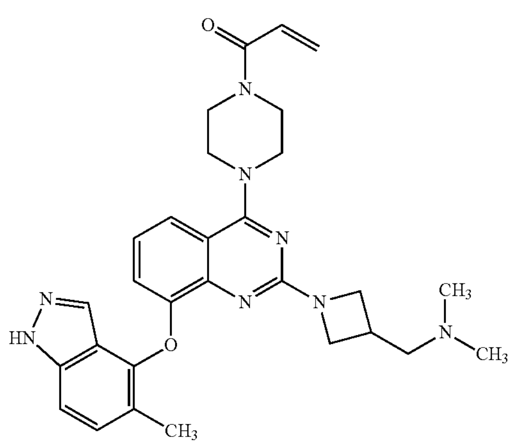 [SMILES: C=CC(=O)N1CCN(c2nc(N3CC(CN(C)C)C3)nc3c(Oc4c(C)ccc5[nH]ncc45)cccc23)CC1] | 1-[4-(2-{3-[(dimethylamino)methyl]azetidin-1-yl}-8-[(5-methyl-1H-indazol-4-yl)oxy]quinazolin-4-yl)piperazin-1-yl]prop-2-en-1-one | 527 (M + H) | ¹H NMR (400 MHz, CD₃OD) δ = 7.54 (d, J = 7.5 Hz, 1H), 7.46 (s, 1H), 7.38-7.31 (m, 2H), 6.95 (t, J = 8.0 Hz, 1H), 6.87-6.78 (m, J = 10.8, 16.8 Hz, 1H), 6.67 (d, J = 7.8 Hz, 1H), 6.26 (dd, J = 1.8, 16.8 Hz, 1H), 5.79 (dd, J = 1.9, 10.7 Hz, 1H), 4.31 (t, J = 8.5 Hz, 2H), 3.92-3.82 (m, 6H), 3.81-3.74 (m, 4H), 2.99-2.86 (m, 1H), 2.66 (d, J = 7.3 Hz, 2H), 2.32 (s, 3H), 2.28 (s, 6H). |

-continued

| Example | Structure | Compound Name | LCMS m/z | ¹H NMR |
|---|---|---|---|---|
| 11E | 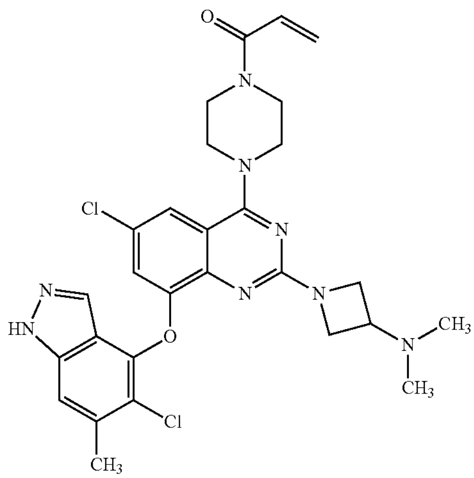 [SMILES: C=CC(=O)N1CCN(c2nc(N3CC(N(C)C)C3)nc3c(Oc4c(Cl)c(C)cc5[nH]ncc45)cc(Cl)cc23)CC1] | 1-(4-{6-chloro-8-[(5-chloro-6-methyl-1H-indazol-4-yl)oxy]-2-[3-(dimethylamino)azetidin-1-yl]quinazolin-4-yl}piperazin-1-yl)prop-2-en-1-one | 581 (M + H) | ¹H NMR (400 MHz, CD₃OD) δ = 7.60-7.56 (m, 1H), 7.55-7.51 (m, 1H), 7.43-7.38 (m, 1H), 6.87-6.79 (m, 1H), 6.78-6.76 (m, 1H), 6.30-6.22 (m, 1H), 5.82-5.76 (m, 1H), 4.24-4.16 (m, 2H), 3.99-3.92 (m, 2H), 3.90-3.84 (m, 4H), 3.82-3.74 (m, 4H), 3.38-3.34 (m, 1H), 2.57 (s, 3H), 2.32 (s, 6H). |
| 12E | 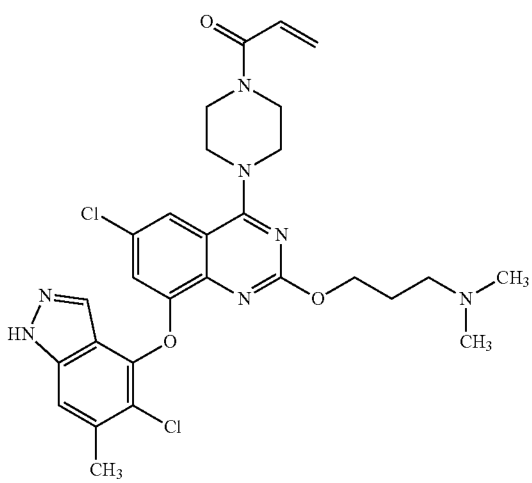 [SMILES: C=CC(=O)N1CCN(c2nc(OCCCN(C)C)nc3c(Oc4c(Cl)c(C)cc5[nH]ncc45)cc(Cl)cc23)CC1] | 1-(4-{6-chloro-8-[(5-chloro-6-methyl-1H-indazol-4-yl)oxy]-2-[3-(dimethylamino)propoxy]quinazolin-4-yl}piperazin-1-yl)prop-2-en-1-one | 584 (M + H) | ¹H NMR (400 MHz, CD₃OD) δ = 8.60-8.46 (m, 1H), 7.75 (d, J = 2.0 Hz, 1H), 7.54 (s, 1H), 7.48-7.43 (m, 1H), 6.86 (d, J = 2.0 Hz, 1H), 6.84-6.77 (m, 1H), 6.33-6.25 (m, 1H), 5.86-5.78 (m, 1H), 4.43 (s, 2H), 4.01-3.86 (m, 8H), 3.20-3.12 (m, 2H), 2.78 (s, 6H), 2.58 (s, 3H), 2.19-2.09 (m, 2H). |
| 13E | 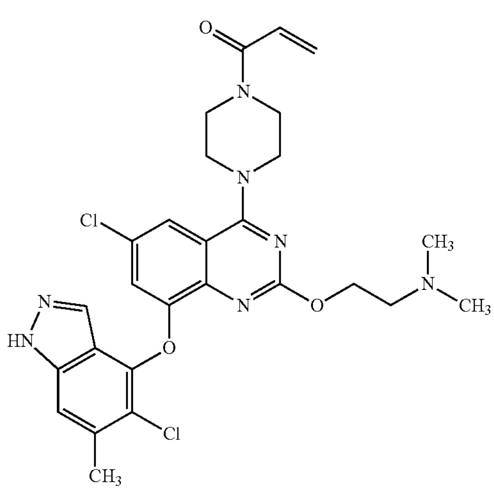 [SMILES: C=CC(=O)N1CCN(c2nc(OCCN(C)C)nc3c(Oc4c(Cl)c(C)cc5[nH]ncc45)cc(Cl)cc23)CC1] | 1-(4-{6-chloro-8-[(5-chloro-6-methyl-1H-indazol-4-yl)oxy]-2-[2-(dimethylamino)ethoxy]quinazolin-4-yl}piperazin-1-yl)prop-2-en-1-one | 570 (M + H) | ¹H NMR (400 MHz, CD₃OD) δ = 7.79-7.71 (m, 1H), 7.44-7.37 (m, 2H), 7.06-6.99 (m, 1H), 6.86-6.76 (m, 1H), 6.30-6.22 (m, 1H), 5.83-5.76 (m, 1H), 4.39-4.33 (m, 2H), 3.90 (br. d, J = 5.3 Hz, 8H), 2.84-2.76 (m, 2H), 2.56 (s, 3H), 2.40 (s, 6H). |

| Example | Structure | Compound Name | LCMS m/z | ¹H NMR |
|---|---|---|---|---|
| 14E | 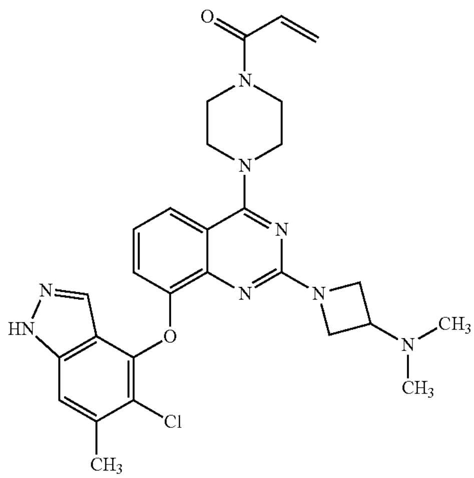 | 1-(4-{8-[(5-chloro-6-methyl-1H-indazol-4-yl)oxy]-2-[3-(dimethylamino)azetidin-1-yl]quinazolin-4-yl}piperazin-1-yl)prop-2-en-1-one | 547 (M + H) | ¹H NMR (400 MHz, CD₃OD) δ = 7.65 (dd, J = 1.3, 8.3 Hz, 1H), 7.34 (d, J = 3.4 Hz, 2H), 7.10-7.03 (m, 1H), 6.95 (dd, J = 1.2, 7.8 Hz, 1H), 6.84 (dd, J = 10.5, 16.9 Hz, 1H), 6.28 (dd, J = 2.0, 16.8 Hz, 1H), 5.84-5.77 (m, 1H), 4.21-4.13 (m, 2H), 3.93-3.86 (m, 6H), 3.81 (br. s, 4H), 3.25-3.18 (m, 1H), 2.57 (d, J = 0.7 Hz, 3H), 2.23 (s, 6H). |
| 15E | 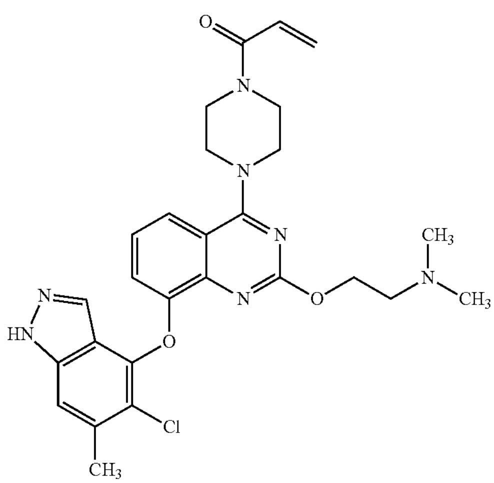 [SMILES: C=CC(=O)N1CCN(c2nc(OCCN(C)C)nc3c(Oc4c(Cl)c(C)cc5[nH]ncc45)cccc23)CC1] | 1-(4-{8-[(5-chloro-6-methyl-1H-indazol-4-yl)oxy]-2-[2-(dimethylamino)ethoxy]quinazolin-4-yl}piperazin-1-yl)prop-2-en-1-one | 536 (M + H) | ¹H NMR (400 MHz, CD₃OD) δ = 7.84 (dd, J = 1.3, 8.2 Hz, 1H), 7.36-7.26 (m, 3H), 7.13 (d, J = 0.9 Hz, 1H), 6.83 (dd, J = 10.5, 16.8 Hz, 1H), 6.28 (dd, J = 2.0, 16.8 Hz, 1H), 5.81 (dd, J = 2.0, 10.6 Hz, 1H), 4.26 (t, J = 5.6 Hz, 2H), 3.91 (s, 8H), 2.61-2.58 (m, 2H), 2.57 (d, J = 0.7 Hz, 3H), 2.27 (s, 6H). |
| 16E | 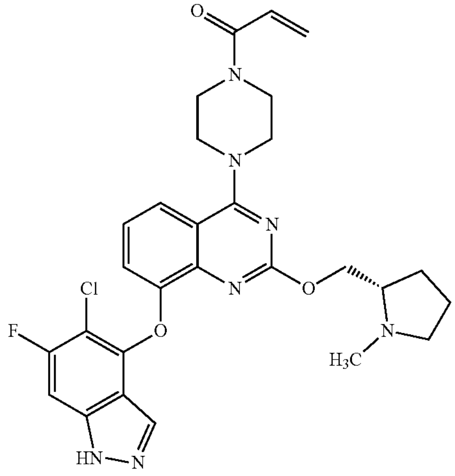 [SMILES: C=CC(=O)N1CCN(c2nc(OC[C@@H]3CCCN3C)nc3c(Oc4c(Cl)c(F)cc5[nH]ncc45)cccc23)CC1] | 1-[4-(8-[(5-chloro-6-fluoro-1H-indazol-4-yl)oxy]-2-{[(2S)-1-methylpyrrolidin-2-yl]methoxy}quinazolin-4-yl)piperazin-1-yl]prop-2-en-1-one | 566 (M + H) | ¹H NMR (400 MHz, DMSO-d₆) δ 7.92 (d, J = 8.4 Hz, 1H), 7.67 (d, J = 7.3 Hz, 1H), 7.40 (t, J = 8.1 Hz, 1H), 7.33 (d, J = 8.8 Hz, 1H), 6.82 (dd, J = 16.7, 10.4 Hz, 1H), 6.76 (s, 1H), 6.16 (dd, J = 16.7, 2.4 Hz, 1H), 5.74 (dd, J = 10.5, 2.4 Hz, 1H), 3.89-3.61 (m, 10H), 2.87 (dt, J = 9.0, 4.4 Hz, 1H), 2.27 (t, J = 6.9 Hz, 1H), 2.16 (s, 3H), 2.06 (q, J = 8.7 Hz, 1H), 1.85-1.69 (m, 1H), 1.65-1.53 (m, 2H), 1.43-1.30 (m, 1H). |

-continued

| Example | Structure | Compound Name | LCMS m/z | ¹H NMR |
|---|---|---|---|---|
| 17E | 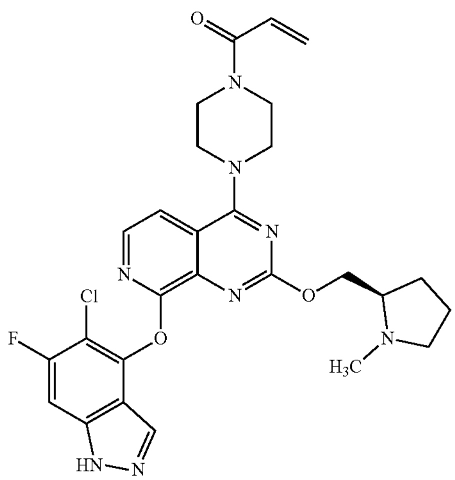 [SMILES: C=CC(=O)N1CCN(c2nc(OC[C@H]3CCCN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(2R)-1-methylpyrrolidin-2-yl]methoxy}pyrido[3,4-d]pyrimidin-4-yl)piperazin-1-yl]prop-2-en-1-one | 566 (M + H) | ¹H NMR (400 MHz, DMSO-d₆) δ 13.52 (s, 1H), 7.77 (d, J = 5.8 Hz, 1H), 7.75 (s, 1H), 7.63 (d, J = 5.9 Hz, 1H), 7.56 (dd, J = 8.9, 1.1 Hz, 1H), 6.83 (dd, J = 16.7, 10.4 Hz, 1H), 6.17 (dd, J = 16.7, 2.4 Hz, 1H), 5.74 (dd, J = 10.4, 2.4 Hz, 1H), 4.37 (dd, J = 10.8, 4.7 Hz, 1H), 4.19 (dd, J = 10.8, 6.3 Hz, 1H), 3.97-3.71 (m, 8H), 3.02-2.88 (m, 1H), 2.63-2.54 (m, 1H), 2.36 (s, 3H), 2.18 (q, J = 8.4 Hz, 1H), 2.00-1.89 (m, 1H), 1.75-1.55 (m, 3H). |
| 18E | 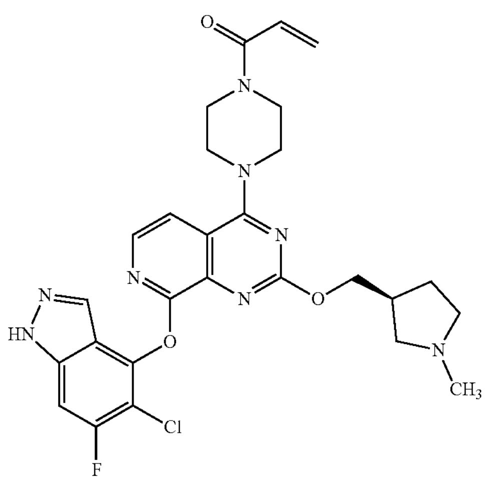 [SMILES: C=CC(=O)N1CCN(c2nc(OC[C@H]3CCN(C)C3)nc3c(Oc4c(Cl)c(F)cc5[nH]ncc45)nccc23)CC1] | 1-[4-(8-[(5-chloro-6-fluoro-1H-indazol-4-yl)oxy]-2-{[(3S)-1-methylpyrrolidin-3-yl]methoxy}pyrido[3,4-d]pyrimidin-4-yl)piperazin-1-yl]prop-2-en-1-one | 567 (M + H) | ¹H NMR (400 MHz, DMSO-d₆) δ 13.54 (s, 1H), 7.79 (d, J = 5.8 Hz, 1H), 7.74 (s, 1H), 7.64 (d, J = 5.8 Hz, 1H), 7.56 (d, J = 9.2 Hz, 1H), 6.83 (dd, J = 16.7, 10.4 Hz, 1H), 6.18 (dd, J = 16.7, 2.3 Hz, 1H), 5.75 (dd, J = 10.5, 2.3 Hz, 1H), 4.19 (m, 2H), 3.99-3.73 (m, 8H), 2.54 (m, 1H), 2.40-2.30 (m, 2H), 2.23 (s, 3H), 2.07-1.85 (m, 2H), 1.55-1.40 (m, 2H). |
| 19E | 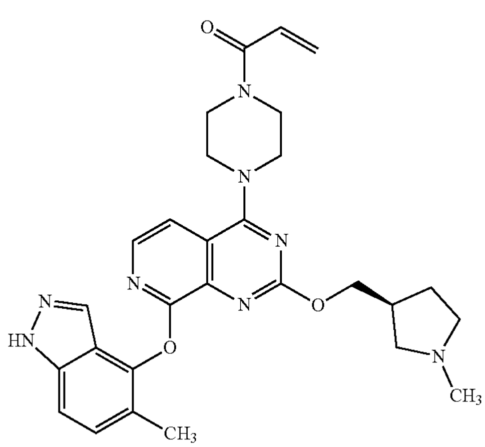 [SMILES: C=CC(=O)N1CCN(c2nc(OC[C@H]3CCN(C)C3)nc3c(Oc4c(C)ccc5[nH]ncc45)nccc23)CC1] | 1-[4-(8-[(5-methyl-1H-indazol-4-yl)oxy]-2-{[(3S)-1-methylpyrrolidin-3-yl]methoxy}pyrido[3,4-d]pyrimidin-4-yl)piperazin-1-yl]prop-2-en-1-one | 529 (M + H) | ¹H NMR (400 MHz, DMSO-d₆) δ 13.12 (s, 1H), 7.72 (d, J = 5.8 Hz, 1H), 7.57 (s, 1H), 7.53 (d, J = 5.9 Hz, 1H), 7.36 (d, J = 8.6 Hz, 1H), 7.29 (d, J = 8.5 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.32-4.24 (m, 2H), 3.91-3.87 (m, 4H), 3.84 (s, 2H), 3.76 (s, 2H), 2.74-2.62 (m, 3H), 2.55 (dd, J = 9.3, 5.8 Hz, 2H), 2.33 (s, 3H), 2.17 (s, 3H), 1.99 (d, J = 8.9, 4.7 Hz, 1H), 1.63-1.53 (m, 1H). |

-continued

| Example | Structure | Compound Name | LCMS m/z | ¹H NMR |
|---|---|---|---|---|
| 20E | 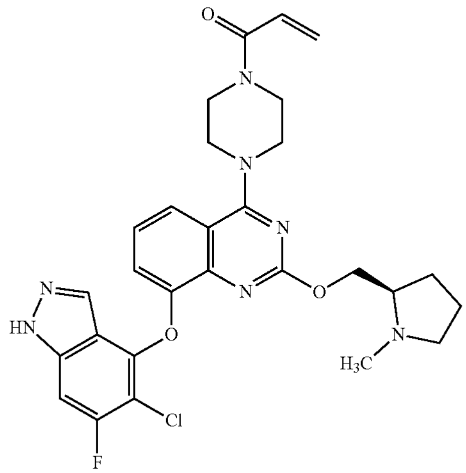 [SMILES: C=CC(=O)N1CCN(c2nc(OC[C@H]3CCCN3C)nc3c(Oc4c(Cl)c(F)cc5[nH]ncc45)cccc23)CC1] | 1-[4-(8-[(5-chloro-6-fluoro-1H-indazol-4-yl)oxy]-2-{[(2R)-1-methylpyrrolidin-2-yl]methoxy}quinazolin-4-yl)piperazin-1-yl]prop-2-en-1-one | 566 (M + H) | ¹H NMR (400 MHz, DMSO-d₆) δ 13.34 (s, 1H), 7.93 (d, J = 8.5 Hz, 1H), 7.79-7.62 (m, 1H), 7.42 (t, J = 8.1 Hz, 1H), 7.36-7.27 (m, 1H), 6.82 (dd, J = 16.7, 10.4 Hz, 1H), 6.76 (d, J = 1.0 Hz, 1H), 6.16 (dd, J = 16.7, 2.4 Hz, 1H), 5.74 (dd, J = 10.4, 2.4 Hz, 1H), 3.82-3.74 (m, 9H), 3.69-3.59 (m, 1H), 2.87 (dt, J = 9.2, 4.5 Hz, 1H), 2.30-2.21 (m, 1H), 2.16 (s, 3H), 2.06 (q, J = 8.7 Hz, 1H), 1.76 (dq, J = 12.2, 8.2 Hz, 1H), 1.59 (pd, J = 6.8, 6.0, 4.2 Hz, 2H), 1.35 (dq, J = 13.6, 7.0 Hz, 1H). |
| 21E | 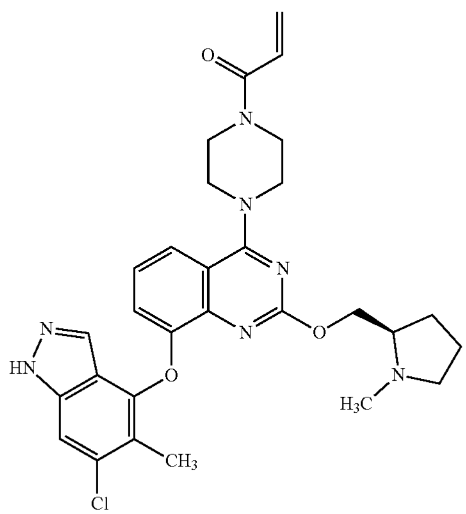 [SMILES: C=CC(=O)N1CCN(c2nc(OC[C@H]3CCCN3C)nc3c(Oc4c(C)c(Cl)cc5[nH]ncc45)cccc23)CC1] | 1-[4-(8-[(6-chloro-5-methyl-1H-indazol-4-yl)oxy]-2-{[(2R)-1-methylpyrrolidin-2-yl]methoxy}quinazolin-4-yl)piperazin-1-yl]prop-2-en-1-one | 562 (M + H) | ¹H NMR (400 MHz, DMSO-d₆) δ 13.13 (s, 1H), 8.15 (s, 1H), 7.82 (dd, J = 8.2, 1.5 Hz, 1H), 7.45 (s, 1H), 7.38 (d, J = 7.7 Hz, 1H), 7.32 (t, J = 7.9 Hz, 1H), 6.92 (s, 1H), 6.83 (dd, J = 16.7, 10.4 Hz, 1H), 6.17 (dd, J = 16.7, 2.4 Hz, 1H), 5.74 (dd, J = 10.4, 2.4 Hz, 1H), 3.99-3.91 (m, 1H), 3.92-3.70 (m, 8H), 2.96 (s, 1H), 2.40 (s, 4H), 2.28 (s, 3H), 2.21 (s, 1H), 1.91-1.77 (m, 1H), 1.70-1.60 (m, 2H), 1.55-1.43 (m, 1H). |
| 22E | 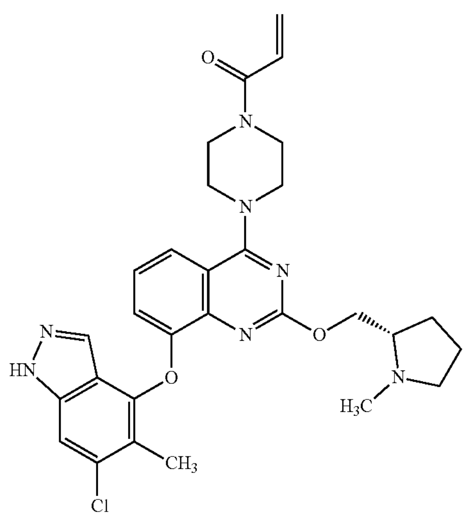 [SMILES: C=CC(=O)N1CCN(c2nc(OC[C@@H]3CCCN3C)nc3c(Oc4c(C)c(Cl)cc5[nH]ncc45)cccc23)CC1] | 1-[4-(8-[(6-chloro-5-methyl-1H-indazol-4-yl)oxy]-2-{[(2S)-1-methylpyrrolidin-2-yl]methoxy}quinazolin-4-yl)piperazin-1-yl]prop-2-en-1-one | 562 (M + H) | ¹H NMR (400 MHz, DMSO-d₆) δ 13.13 (s, 1H), 8.20 (s, 1H), 7.82 (dd, J = 8.4, 1.4 Hz, 1H), 7.44 (s, 1H), 7.39 (d, J = 7.6 Hz, 1H), 7.32 (t, J = 8.0 Hz, 1H), 6.93 (s, 1H), 6.83 (dd, J = 16.7, 10.5 Hz, 1H), 6.16 (dd, J = 16.7, 2.4 Hz, 1H), 5.73 (dd, J = 10.4, 2.4 Hz, 1H), 3.99-3.89 (m, 1H), 3.87-3.69 (m, 8H), 2.91 (dq, J = 9.4, 4.6 Hz, 1H), 2.40 (s, 4H), 2.23 (d, J = 5.1 Hz, 3H), 2.13 (p, J = 8.4 Hz, 1H), 1.90-1.76 (m, 1H), 1.69-1.56 (m, 2H), 1.53-1.41 (m, 1H). |

The examples in the table were prepared in parallel library format using Method E and the procedure used to prepare 1-(4-{8-[(5-Chloro-6-methyl-1H-indazol-4-yl)oxy]-2-[3-(dimethylamino)azetidin-1-yl]-6-methylpyrido[3,4-d]pyrimidin-4-yl}piperazin-1-yl)prop-2-en-1-one (Example-1E). The following examples were made with non-critical changes or substitutions to the exemplified procedure used to prepare Example-1E that someone who is skilled in the art would be able to realize.

| | | | |
|---|---|---|---|
| 1F | | 1-[4-(2-{[(4-methyl-1H-imidazol-2-yl)methyl]amino}-8-[(5-methyl-1H-indazol-4-yl)oxy]quinazolin-4-yl)piperazin-1-yl]prop-2-en-1-one | 524 (M + H) |
| 2F | | 1-[4-(8-[(5-methyl-1H-indazol-4-yl)oxy]-2-{[(4-methyl-4H-1,2,4-triazol-3-yl)methyl]amino}quinazolin-4-yl)piperazin-1-yl]prop-2-en-1-one | 525 (M + H) |
| 3F | | 1-[4-(8-[(5-methyl-1H-indazol-4-yl)oxy]-2-{[1-(4-methyl-4H-1,2,4-triazol-3-yl)ethyl]amino}quinazolin-4-yl)piperazin-1-yl]prop-2-en-1-one | 539 (M + H) |

-continued
| | | | |
|---|---|---|---|
| 4F | 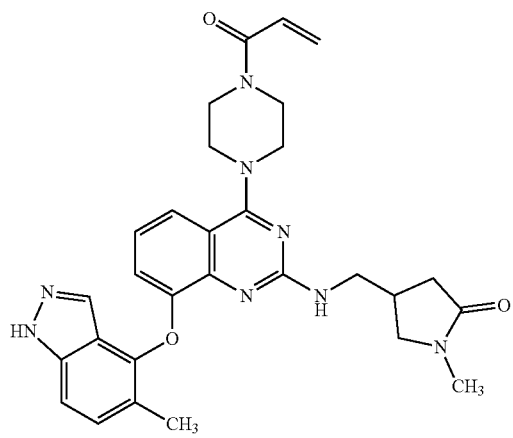 [SMILES: C=CC(=O)N1CCN(c2nc(NCC3CC(=O)N(C)C3)nc3c(Oc4c(C)ccc5[nH]ncc45)cccc23)CC1] | 4-[({4-(4-acryloylpiperazin-1-yl)-8-[(5-methyl-1H-indazol-4-yl)oxy]quinazolin-2-yl}amino)methyl]-1-methylpyrrolidin-2-one | 541 (M + H) |
| 5F | 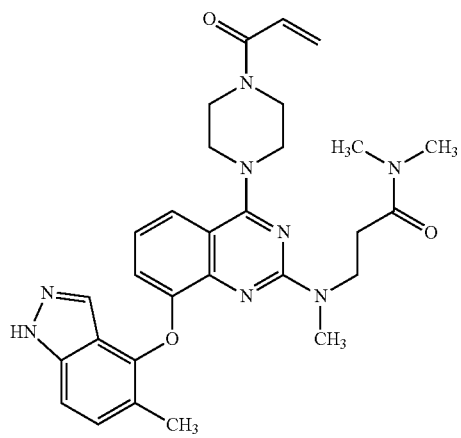 [SMILES: C=CC(=O)N1CCN(c2nc(N(C)CCC(=O)N(C)C)nc3c(Oc4c(C)ccc5[nH]ncc45)cccc23)CC1] | $N^3$-{4-(4-acryloylpiperazin-1-yl)-8-[(5-methyl-1H-indazol-4-yl)oxy]quinazolin-2-yl}-N,N,$N^3$-trimethyl-β-alaninamide | 543 (M + H) |
| 6F | 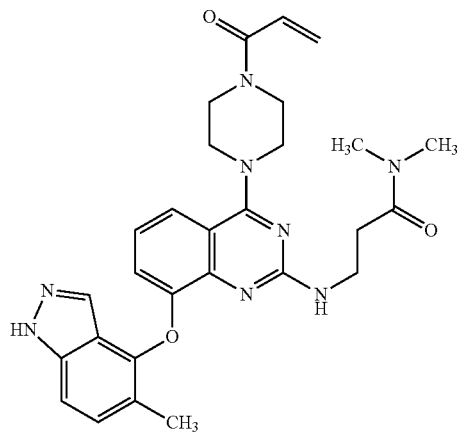 [SMILES: C=CC(=O)N1CCN(c2nc(NCCC(=O)N(C)C)nc3c(Oc4c(C)ccc5[nH]ncc45)cccc23)CC1] | $N^3$-{4-(4-acryloylpiperazin-1-yl)-8-[(5-methyl-1H-indazol-4-yl)oxy]quinazolin-2-yl}-N,N-dimethyl-β-alaninamide | 529 (M + H) |

| | | | |
|---|---|---|---|
| 7F | 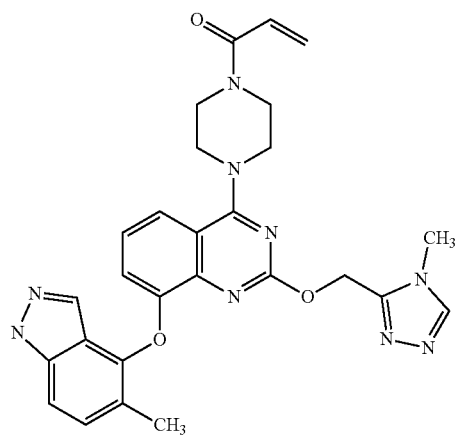 [SMILES: C=CC(=O)N1CCN(c2nc(OCc3nncn3C)nc3c(Oc4c(C)ccc5[nH]ncc45)cccc23)CC1] | 1-(4-{8-[(5-methyl-1H-indazol-4-yl)oxy]-2-[(4-methyl-4H-1,2,4-triazol-3-yl)methoxy]quinazolin-4-yl}piperazin-1-yl)prop-2-en-1-one | 526 (M + H) |
| 8F | 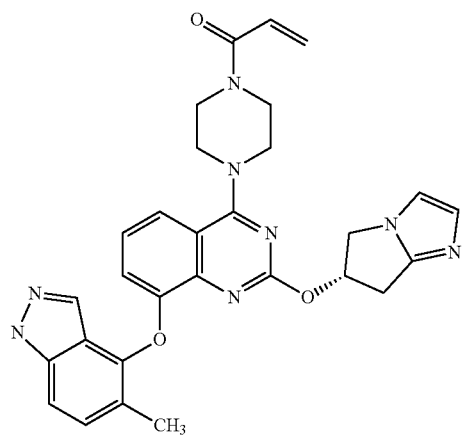 [SMILES: C=CC(=O)N1CCN(c2nc(O[C@H]3Cc4nccn4C3)nc3c(Oc4c(C)ccc5[nH]ncc45)cccc23)CC1] | 1-(4-{2-[(6S)-6,7-dihydro-5H-pyrrolo[1,2-a]imidazol-6-yloxy]-8-[(5-methyl-1H-indazol-4-yl)oxy]quinazolin-4-yl}piperazin-1-yl)prop-2-en-1-one | 537 (M + H) |
| 9F | 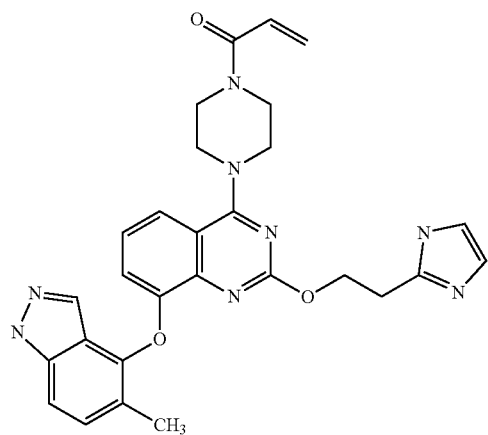 [SMILES: C=CC(=O)N1CCN(c2nc(OCCc3ncc[nH]3)nc3c(Oc4c(C)ccc5[nH]ncc45)cccc23)CC1] | 1-(4-{2-[2-(1H-imidazol-2-yl)ethoxy]-8-[(5-methyl-1H-indazol-4-yl)oxy]quinazolin-4-yl}piperazin-1-yl)prop-2-en-1-one | 525 (M + H) |

| | | | |
|---|---|---|---|
| 10F | 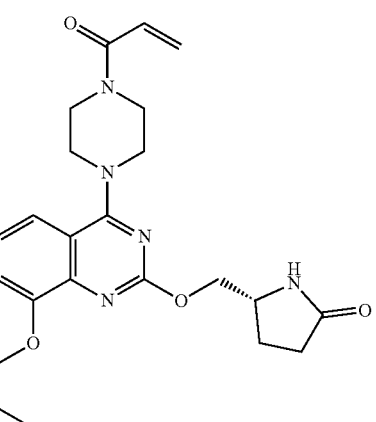 | (5R)-5-[({4-(4-acryloylpiperazin-1-yl)-8-[(5-methyl-1H-indazol-4-yl)oxy]quinazolin-2-yl}oxy)methyl]pyrrolidin-2-one | 528 (M + H) |
| 11F | 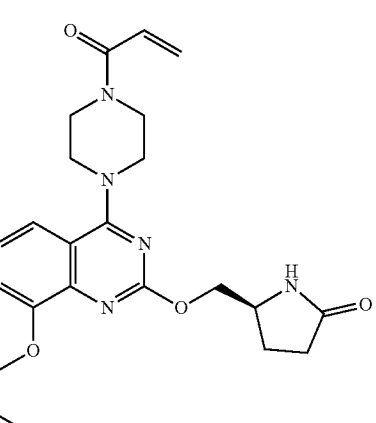 | (5S)-5-[({4-(4-acryloylpiperazin-1-yl)-8-[(5-methyl-1H-indazol-4-yl)oxy]quinazolin-2-yl}oxy)methyl]pyrrolidin-2-one | 528 (M + H) |
| 12F | 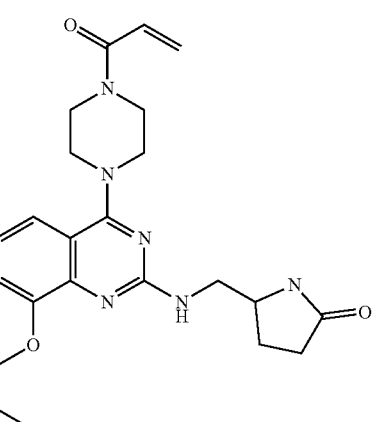 | 5-[({4-(4-acryloylpiperazin-1-yl)-8-[(5-methyl-1H-indazol-4-yl)oxy]quinazolin-2-yl}amino)methyl]pyrrolidin-2-one | 527 (M + H) |

| | | | |
|---|---|---|---|
| 13F | 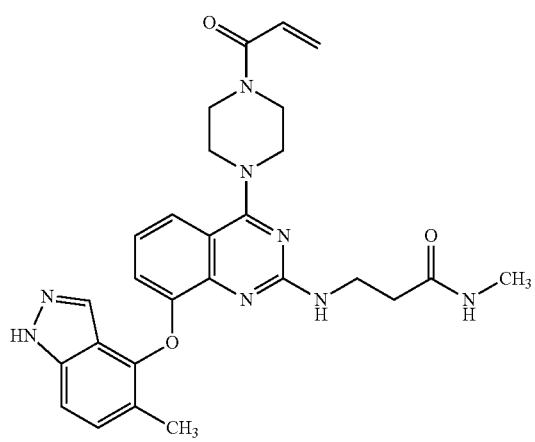 [SMILES: C=CC(=O)N1CCN(c2nc(NCCC(=O)NC)nc3c(Oc4c(C)ccc5[nH]ncc45)cccc23)CC1] | $N^3$-{4-(4-acryloylpiperazin-1-yl)-8-[(5-methyl-1H-indazol-4-yl)oxy]quinazolin-2-yl}-N-methyl-β-alaninamide | 515 (M + H) |
| 14F | 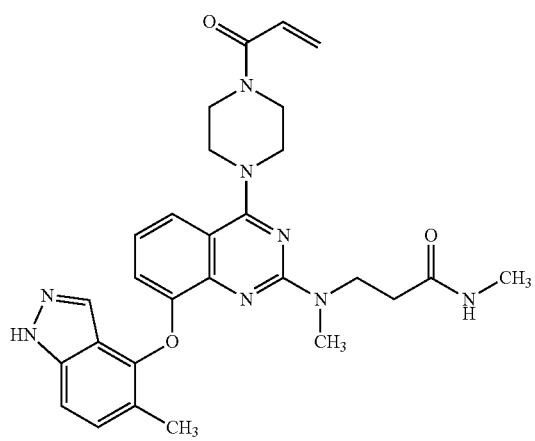 [SMILES: C=CC(=O)N1CCN(c2nc(N(C)CCC(=O)NC)nc3c(Oc4c(C)ccc5[nH]ncc45)cccc23)CC1] | $N^3$-{4-(4-acryloylpiperazin-1-yl)-8-[(5-methyl-1H-indazol-4-yl)oxy]quinazolin-2-yl}-N,$N^3$-dimethyl-β-alaninamide | 529 (M + H) |
| 15F | 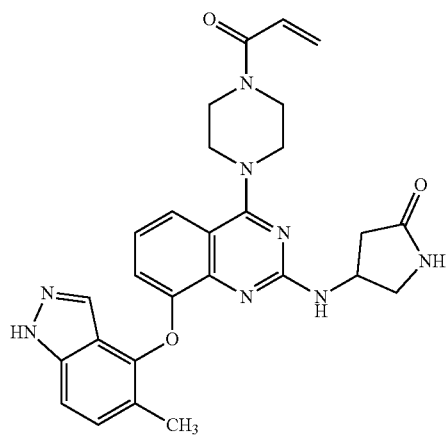 [SMILES: C=CC(=O)N1CCN(c2nc(NC3CNC(=O)C3)nc3c(Oc4c(C)ccc5[nH]ncc45)cccc23)CC1] | 4-({4-(4-acryloylpiperazin-1-yl)-8-[(5-methyl-1H-indazol-4-yl)oxy]quinazolin-2-yl}amino)pyrrolidin-2-one | 513 (M + H) |

| | | | |
|---|---|---|---|
| 16F | 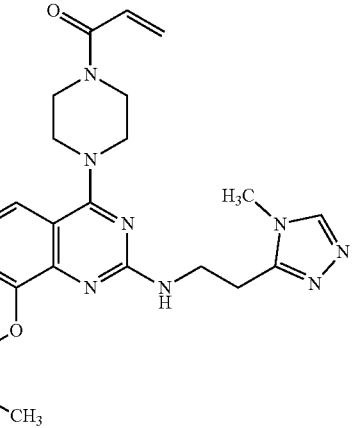 | 1-[4-(8-[(5-methyl-1H-indazol-4-yl)oxy]-2-{[2-(4-methyl-4H-1,2,4-triazol-3-yl)ethyl]amino}quinazolin-4-yl)piperazin-1-yl]prop-2-en-1-one | 539 (M + H) |
| 17F | 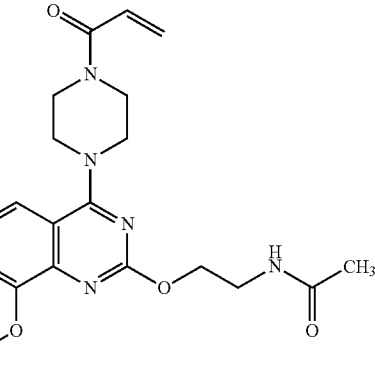 | N-[2-({4-(4-acryloylpiperazin-1-yl)-8-[(5-methyl-1H-indazol-4-yl)oxy]quinazolin-2-yl}oxy)ethyl]acetamide | 516 (M + H) |
| 18F | 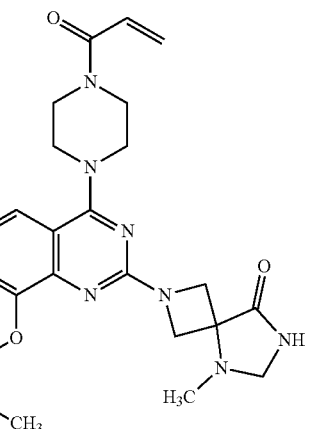 | 2-{4-(4-acryloylpiperazin-1-yl)-8-[(5-methyl-1H-indazol-4-yl)oxy]quinazolin-2-yl}-5-methyl-2,5,7-triazaspiro[3.4]octan-8-one | 554 (M + H) |

-continued
| | | | |
|---|---|---|---|
| 19F | 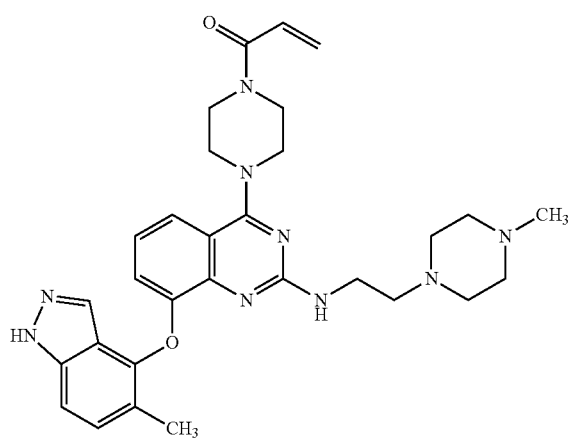 [SMILES: C=CC(=O)N1CCN(c2nc(NCCN3CCN(C)CC3)nc3c(Oc4c(C)ccc5[nH]ncc45)cccc23)CC1] | 1-[4-(8-[(5-methyl-1H-indazol-4-yl)oxy]-2-{[2-(4-methylpiperazin-1-yl)ethyl]amino}quinazolin-4-yl)piperazin-1-yl]prop-2-en-1-one | 556 (M + H) |
| 20F | 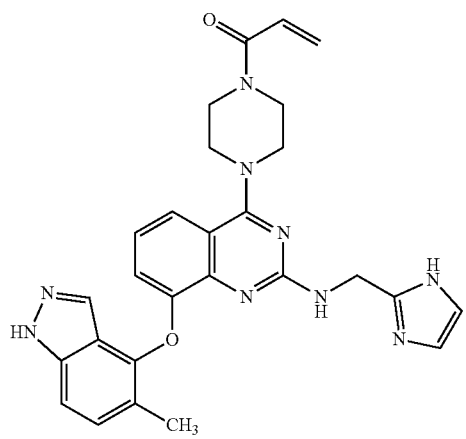 [SMILES: C=CC(=O)N1CCN(c2nc(NCc3ncc[nH]3)nc3c(Oc4c(C)ccc5[nH]ncc45)cccc23)CC1] | 1-(4-{2-[(1H-imidazol-2-ylmethyl)amino]-8-[(5-methyl-1H-indazol-4-yl)oxy]quinazolin-4-yl}piperazin-1-yl)prop-2-en-1-one | 510 (M + H) |
| 21F | 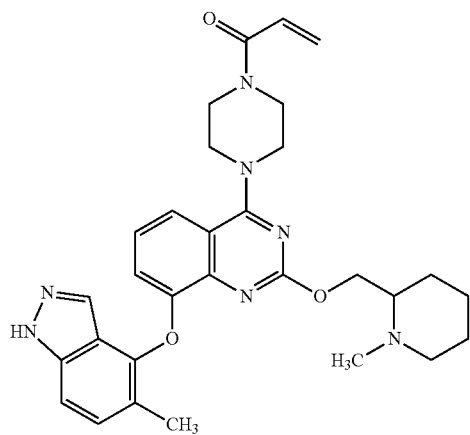 [SMILES: C=CC(=O)N1CCN(c2nc(OCC3CCCCN3C)nc3c(Oc4c(C)ccc5[nH]ncc45)cccc23)CC1] | 1-(4-{8-[(5-methyl-1H-indazol-4-yl)oxy]-2-[(1-methylpiperidin-2-yl)methoxy]quinazolin-4-yl}piperazin-1-yl)prop-2-en-1-one | 542 (M + H) |

| | | | |
|---|---|---|---|
| 22F | 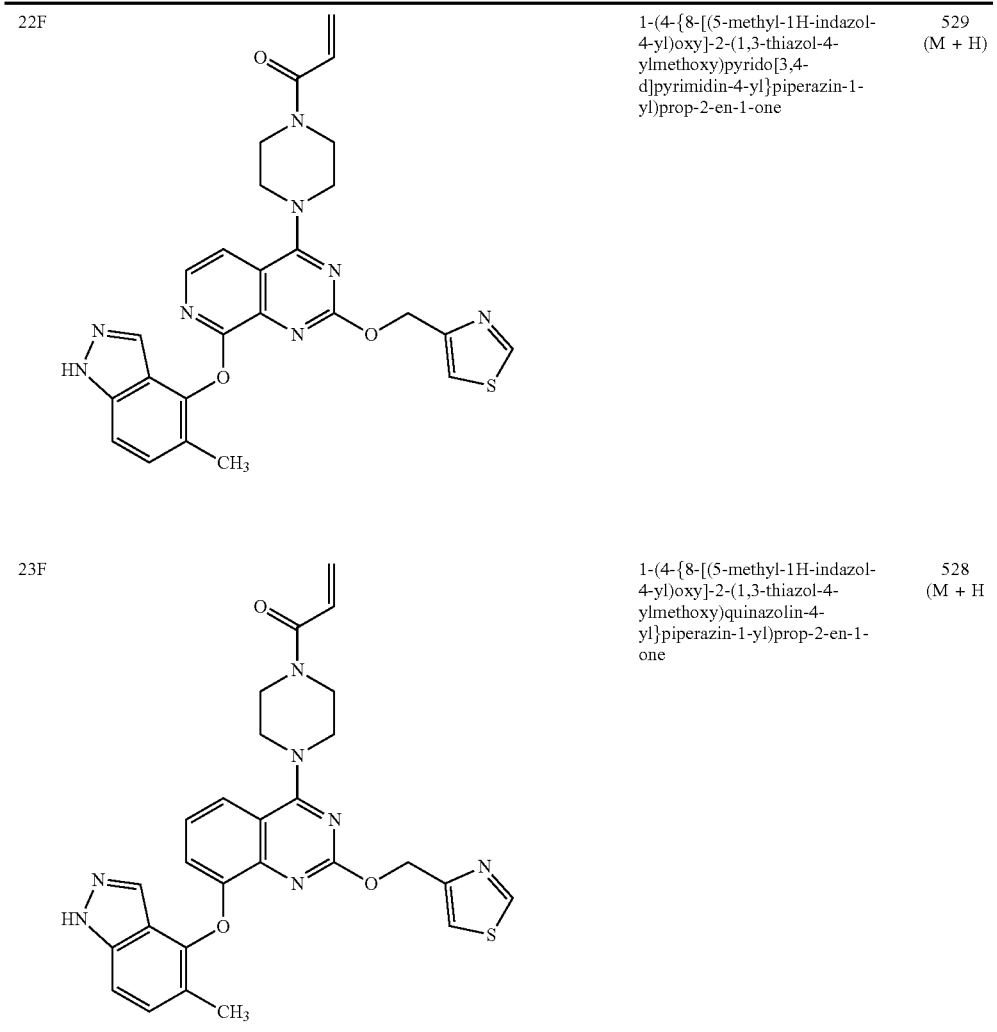 | 1-(4-{8-[(5-methyl-1H-indazol-4-yl)oxy]-2-(1,3-thiazol-4-ylmethoxy)pyrido[3,4-d]pyrimidin-4-yl}piperazin-1-yl)prop-2-en-1-one | 529 (M + H) |
| 23F | | 1-(4-{8-[(5-methyl-1H-indazol-4-yl)oxy]-2-(1,3-thiazol-4-ylmethoxy)quinazolin-4-yl}piperazin-1-yl)prop-2-en-1-one | 528 (M + H |

Preparation of Additional Intermediates:

Preparation of 3-chloro-5-methyl-1-(tetrahydro-2H-pyran-2-yl)-1H-indazol-4-ol (139)

Step 1:

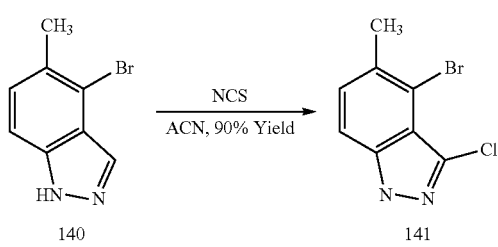

To a solution of 4-bromo-5-methyl-1H-indazole (140) (3.0 g, 14.2 mmol) in acetonitrile (50 mL) was added NCS (2.1 g, 15.6 mmol) in small portions. After the addition, the reaction was heated at 65° C. for 6 hours. LCMS gave only product. The crude reaction mixture was cooled to room temperature and EtOAc (100 mL) was added. The organic layer was washed with a 1 N NaOH solution (20 mL) and brine (50 mL), dried over sodium sulfate and concentrated under reduced pressure which gave 4-bromo-3-chloro-5-methyl-1H-indazole (141) (3.3 g, 90% yield). $^1$H NMR (400 MHz, DMSO-$d_6$) δ 13.56 (s, 1H), 7.55 (d, J=8.5 Hz, 1H), 7.44 (d, J=8.5 Hz, 1H), 2.57 (s, 3H). LCMS (ESI) m/z 245/247 (M+H).

Step 2:

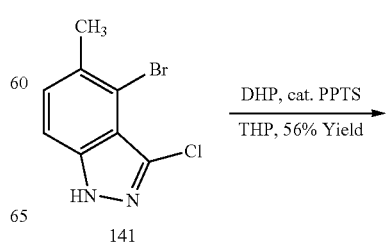

-continued

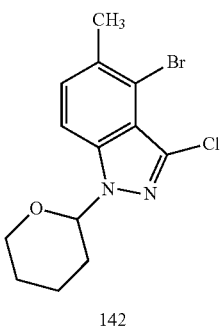

142

4-Bromo-3-chloro-5-methyl-1-(tetrahydro-2H-pyran-2-yl)-1H-indazole (142) (2.5 g, 56% yield) was prepared according to the procedure used to prepare 4-bromo-5-methyl-1-(tetrahydro-2H-pyran-2-yl)-1H-indazole (24). $^1$H NMR (400 MHz, CDCl$_3$) δ 7.43 (d, J=8.6 Hz, 1H), 7.27 (d, J=7.3 Hz, 1H), 5.63 (dd, J=8.9, 2.9 Hz, 1H), 4.01-3.96 (m, 1H), 3.77-3.66 (m, 1H), 2.56-2.47 (m, 1H), 2.19-2.13 (m, 1H), 2.08-2.02 (m, 1H), 1.81-1.62 (m, 3H). LCMS (ESI) m/z 352/354 (M+Na).

Step 3:

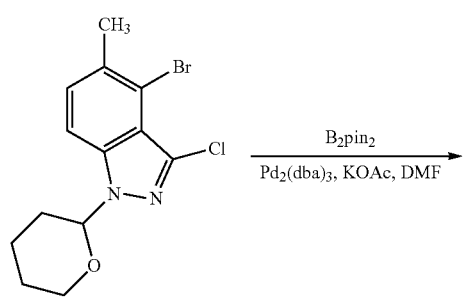

142

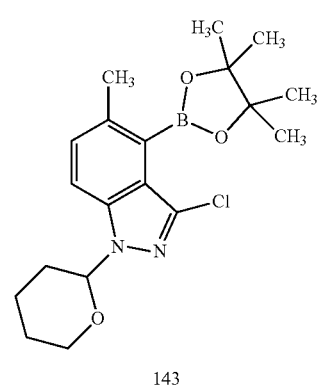

143

To a stirred solution of 4-bromo-3-chloro-5-methyl-1-(tetrahydro-2H-pyran-2-yl)-1H-indazole (142) (1.9 g, 5.8 mmol) in DMF (60 mL) was added 4,4,4',4',5,5,5',5'-octamethyl-2,2'-bi(1,3,2-dioxaborolane) (2.2 g, 8.6 mmol), KOAc (1.7 g, 17.3 mmol) and Pd(dppf)Cl$_2$ (422 mg, 0.58 mmol) under a nitrogen atmosphere. The crude reaction mixture was stirred at 105° C. for 6 hours. LCMS analysis showed conversion to product. After cooling, water (50 mL) was added and the mixture was extracted with EtOAc (2×50 mL). The organic layers were combined, washed with brine, dried over sodium sulfate and concentrated under reduced pressure. The crude product was purified by silica gel chromatography and eluted with EtOAc/petroleum (1/9) and gave 3-chloro-5-methyl-1-(tetrahydro-2H-pyran-2-yl)-4-(4,4,5,5-tetramethyl-1,3,2-dioxaborolan-2-yl)-1H-indazole (143) (1.3 g, 60% yield). LCMS (ESI) m/z 377 (M+H).

Step 4:

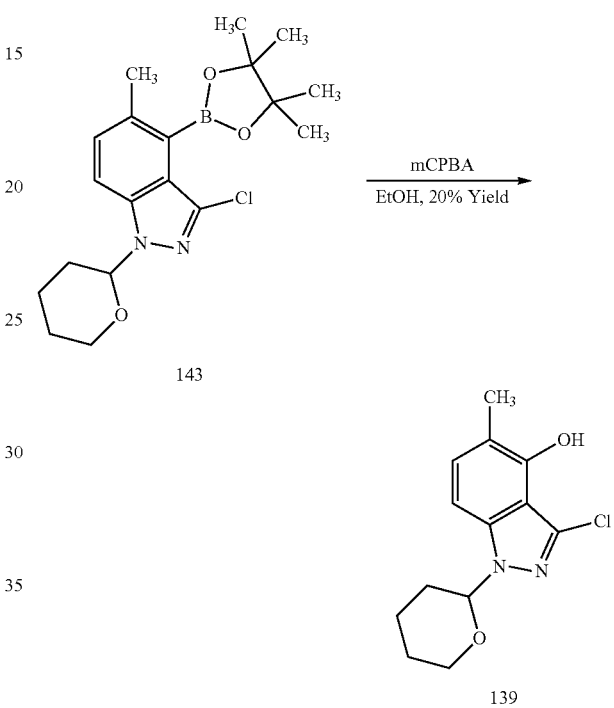

To a solution of 3-chloro-5-methyl-1-(tetrahydro-2H-pyran-2-yl)-4-(4,4,5,5-tetramethyl-1,3,2-dioxaborolan-2-yl)-1H-indazole (143) (1.3 g, 3.4 mmol) in EtOH (30 mL) was added mCPBA (893 mg, 5.2 mmol) and H$_2$O (15 mL). The reaction was stirred at 20° C. for 16 hours. LCMS gave mostly product. The crude reaction mixture was diluted with a 10% solution of NaHCO$_3$ (10 mL) and the aqueous layer was extracted with EtOAc (2×50 mL). The combined organic layers were washed with brine, dried over sodium sulfate and concentrated under reduced pressure. The crude product was purified by silica gel column chromatography which was eluted with EtOAc/petroleum ether (1/5) and gave 3-chloro-5-methyl-1-(tetrahydro-2H-pyran-2-yl)-1H-indazol-4-ol (139) (180 mg, 80% purity, 20% yield). $^1$H NMR (400 MHz, DMSO-d$_6$) δ 9.18 (s, 1H), 7.18 (d, J=8.6 Hz, 1H), 7.09 (d, J=8.5 Hz, 1H), 5.69 (dd, J=9.7, 2.5 Hz, 1H), 3.92-3.81 (m, 1H), 3.76-3.63 (m, 1H), 2.35-2.26 (m, 1H), 2.25 (d, J=9.9 Hz, 3H), 2.03-1.96 (m, 1H), 1.96-1.88 (m, 1H), 1.79-1.65 (m, 1H), 1.60-1.49 (m, 2H). LCMS (ESI) m/z 267 (M+H) and 289 (M+Na).

Preparation of 5,6-dichloro-1-(tetrahydro-2H-pyran-2-yl)-1H-indazol-4-ol (163)

Step 1:

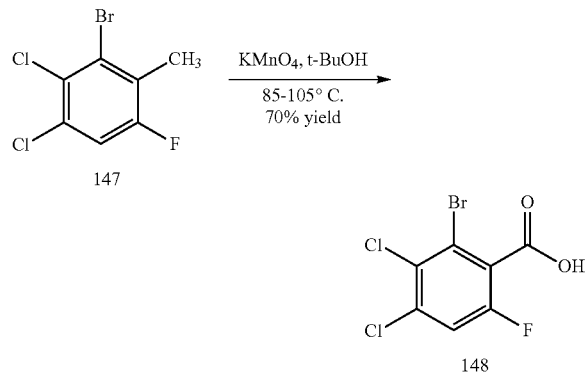

To a mixture of 3-bromo-1,2-dichloro-5-fluoro-4-methylbenzene (147) (4.7 g, 18.3 mmol) in 1:1 water-tBuOH (45 mL), was added KMnO₄ (8.7 g, 54.8 mmol) at 80° C. The mixture was heated at 90° C. overnight. An additional 4.5 g of KMnO₄ was added and stirred at 105° C. overnight. The mixture was diluted with EtOH and filtered through a celite pad. The filtrate was concentrated in vacuo to give a white solid that was diluted with ether/water. The aqueous layer was dried using a lyophilizer and gave a white solid (4.9 g). The white solid was suspended in EtOAc/EtOH and the insoluble material was removed by filtration. The filtrate was gave 3.7 g (70% yield) of 2-bromo-3,4-dichloro-6-fluorobenzoic acid (148) as white solid. $^1$H NMR (400 MHz, DMSO-d₆) δ 7.53 (d, J=7.8 Hz, 1H).

Step 2:

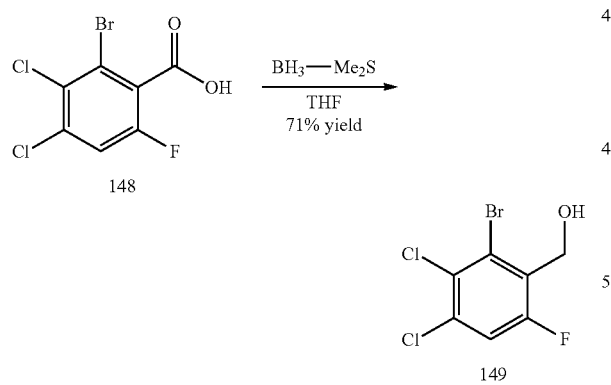

A solution of 2-bromo-3,4-dichloro-6-fluorobenzoic acid (148) (2.2 g, 7.8 mmol) in THF (11 mL) under N₂ was cooled to 0° C. The mixture was treated dropwise with a solution of BH₃·SMe₂ in THF (2.0 M in THF, 112 mL, 24.1 mmol). The generation of gas was observed. After addition was complete, the mixture was stirred at 0° C. for an additional 1.5 h and then heated to 70° C. for 18 hr. The crude reaction mixture was analyzed by LCMS, which indicated formation of the desired product. The reaction was cooled with an ice bath and then carefully quenched with EtOH. The mixture was filtered to remove insoluble material and then concentrated. The residue was partitioned between EtOAc (130 mL) and acidic water (130 mL). The organic layer was washed with sat. NH₄Cl solution, dried over Na₂SO₄ and concentrated to give a pale solid, which was purified by column chromatography (SiO₂, ISCO, 0-30% EtOAc/heptane) to provide 1.5 g of (2-bromo-3,4-dichloro-6-fluorophenyl)methanol (149) (71% yield) as a pale solid. $^1$H NMR (400 MHz, CDCl₃) δ 7.29 (d, J=8.7 Hz, 1H), 4.87 (d, J=2.3 Hz, 2H).

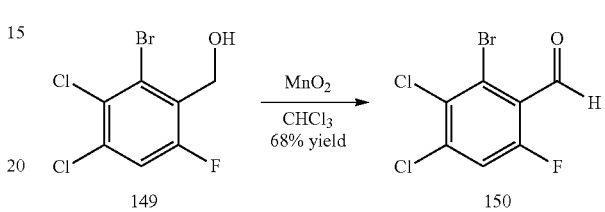

Step 3:

To a solution of (2-bromo-3,4-dichloro-6-fluorophenyl)methanol (149) (315 mg, 1.15 mmol) in CHCl₃ (12 mL) was added MnO₂ (700 mg, 8.05 mmol) portionwise. Then the mixture was heated to reflux for 20 h. LCMS analysis showed consumption of the starting material. The mixture was filtered through celite. The black filtrate was concentrated to afford a crude residue, which was purified by column chromatography (SiO₂, ISCO, 0-10% EtOAc/heptane) to provide 215 mg of 2-bromo-3,4-dichloro-6-fluorobenzaldehyde (150) (68% yield) as white solid. $^1$H NMR (400 MHz, CDCl₃) δ 10.27 (s, 1H), 7.38 (d, J=9.7 Hz, 1H).

Step 4:

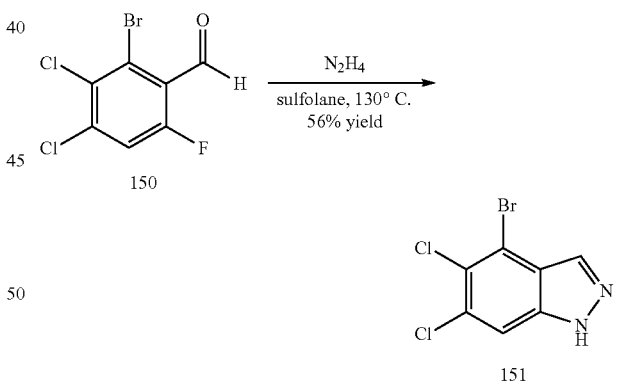

To a vial containing 2-bromo-3,4-dichloro-6-fluorobenzaldehyde (150) (761 mg, 2.80 mmol) was added anhydrous hydrazine (628 mg, 19.6 mmol) and sulfolane (14 mL). The solution was heated to 130° C. for 20 h. The reaction was cooled to room temperature and then diluted with EtOAc. The mixture was washed with water (2×). The organic layer was dried over Na₂SO₄, filtered, and concentrated. The residue was purified by chromatography (SiO₂, ISCO, 5-50% EtOAc/heptane) to provide 448 mg of 4-bromo-5,6-dichloro-1H-indazole (151) (56% yield) as white solid. $^1$H NMR (400 MHz, DMSO-d₆) δ 13.72 (br. s, 1H), 8.11 (s, 1H), 7.95 (d, J=0.9 Hz, 1H). LCMS (ESI) m/z 265 (M+H).

Step 5:

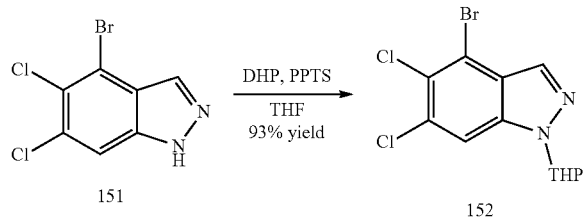

To a solution of 4-bromo-5,6-dichloro-1H-indazole (151) (123 mg, 0.46 mmol) in THF (5 mL) was added PPTS (8.1 mg, 0.03 mmol) and DHP (156 mg, 1.85 mmol). The reaction mixture was stirred at 50° C. for 5 h. LCMS analysis showed complete consumption of the starting material with conversion to the product. The mixture was concentrated and the residue was portioned between EtOAc and water. The organic layer was washed with brine, concentrated, and purified by column chromatography (SiO$_2$, ISCO, 0-25% EtOAc/heptane) to give 150 mg of 4-bromo-5,6-dichloro-1-(tetrahydro-2H-pyran-2-yl)-1H-indazole (152) (93% yield) as white solid. LCMS (ESI) m/z 265 (M-THP).

Step 6:

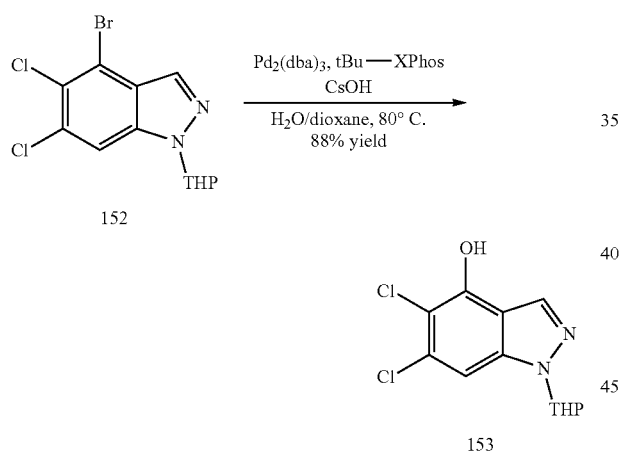

4-bromo-5,6-dichloro-1-(tetrahydro-2H-pyran-2-yl)-1H-indazole (152) (423 mg, 1.21 mmol) and CsOH (543 mg, 3.63 mmol) were dissolved in dioxane/water and was added to the catalyst Pd$_2$(dba)$_3$ (55.3 mg) and ligand tBu-XPhos (51.3 mg). The reaction mixture was degassed with a stream of N$_2$ and heated to 80° C. for 2.5 h. LCMS analysis showed that the starting material was consumed with formation of the desired product. The reaction mixture was partitioned between EtOAc and aqueous NH$_4$Cl solution. The aqueous phase was adjusted to slight acidity with 2N HCl and then extracted with EtOAc. The combined organics were dried over Na$_2$SO$_4$ and concentrated. The residue was purified by chromatography (SiO$_2$, ISCO, 10-90% EtOAc/heptane) and gave 307 mg of 5,6-dichloro-1-(tetrahydro-2H-pyran-2-yl)-1H-indazol-4-ol (153) (88% yield, ~80% purity) as a brown solid, which was taken on without further purification. LCMS (ESI) m/z 203 (M-THP).

Preparation of 6-chloro-5-fluoro-1-(tetrahydro-2H-pyran-2-yl)-1H-indazol-4-ol (157)

Step 1:

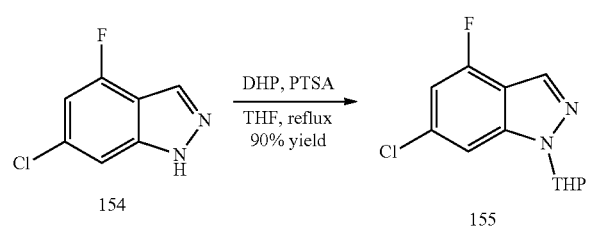

To a mixture or 6-chloro-4-fluoro-1H-indazole (154) (606 mg, 3.55 mmol) and PTSA monohydrate (67.6 mg, 0.36 mmol) in THF was added DHP (359 mg, 0.39 mL, 4.26 mmol) and the mixture was stirred at reflux for 2 h. LCMS analysis showed conversion to the desired product. The mixture was diluted with EtOAc and washed with water. The organic layer was dried over Na$_2$SO$_4$ and concentrated. The crude oil was purified by chromatography (ISCO, SiO$_2$, 0-100% DCM/heptanes) to provide 816 mg of 6-chloro-4-fluoro-1-(tetrahydro-2H-pyran-2-yl)-1H-indazole (155) (90% yield) as a colorless oil that slowly crystallized. LCMS (ESI) m/z 171 (M-THP).

Step 2:

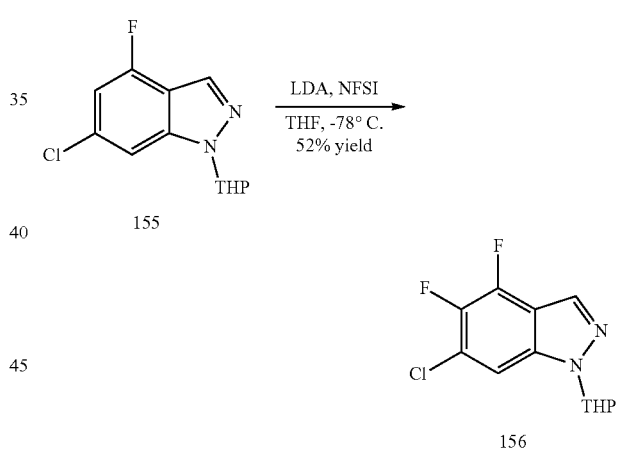

A solution of LDA (1.0 M in THF, 1.5 mL, 1.5 mmol) was added to a solution of 6-chloro-4-fluoro-1-(tetrahydro-2H-pyran-2-yl)-1H-indazole (155) (273 mg, 1.07 mmol) in THF (10.7 mL) at −70° C. The resultant light yellow reaction mixture was stirred at the same temperature for 1 h. A solution of NFSI (473 mg, 1.5 mmol) in THF (1.5 mL) was added dropwise. LCMS analysis indicated formation of the desired product with some remaining starting material. The mixture was quenched with saturated aqueous NH$_4$Cl and the mixture was extracted with EtOAc. The organic layer was washed with brine, dried over Na$_2$SO$_4$, filtered and concentrated. The crude product was purified by chromatography (SiO$_2$, ISCO, 0-20% EtOAc/heptane) to provide 6-chloro-4,5-difluoro-1-(tetrahydro-2H-pyran-2-yl)-1H-indazole (156) (152 mg, 52% yield). $^1$H NMR (400 MHz, CDCl$_3$) δ 8.07-8.11 (m, 1H), 7.49 (dt, J=4.9, 1.2 Hz, 1H), 5.66 (dd, J=8.9, 2.6 Hz, 1H), 3.97-4.02 (m, 1H), 3.73-3.79

(m, 1H), 2.42-2.52 (m, 1H), 2.07-2.17 (m, 2H), 1.68-1.79 (m, 3H). LCMS (ESI) m/z 189 (M-THP).

Step 3:

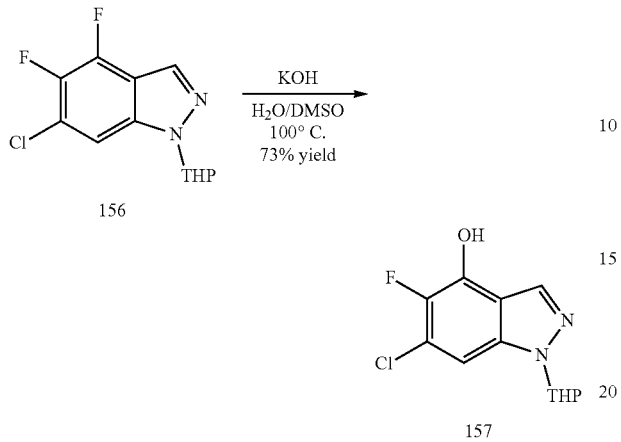

A mixture of 6-chloro-4,5-difluoro-1-(tetrahydro-2H-pyran-2-yl)-1H-indazole (156) (151 mg, 0.554 mmol), water (40 µL, 2.22 mmol) and KOH (124 mg, 2.22 mmol) in DMSO (1.85 mL) was stirred at 100° C. for 3.5 h. LCMS analysis showed consumption of the starting material and formation of the desired product. EtOAc and water were added and the layers were separated. The aqueous phase was adjusted to slight acidity with 2 N HCl. The aqueous layer was extracted with EtOAc. The combined organics were dried over Na₂SO₄, filtered, and concentrated. The residue was purified by chromatography (SiO₂, ISCO, 5-65% EtOAc/heptane) to provide 6-chloro-5-fluoro-1-(tetrahydro-2H-pyran-2-yl)-1H-indazol-4-ol (157) (110 mg, 73% yield) as a white solid. ¹H NMR (400 MHz, DMSO-d₆) δ 11.06 (s, 1H), 8.20 (s, 1H), 7.40 (d, J=4.77 Hz, 1H), 5.76 (dd, J=9.66, 2.45 Hz, 1H), 3.79-3.89 (m, 1H), 3.67-3.78 (m, 1H), 2.26-2.40 (m, 1H), 2.01 (d, J=5.01 Hz, 1H), 1.88-1.96 (m, 1H), 1.63-1.77 (m, 1H), 1.50-1.60 (m, 2H). LCMS (ESI) m/z 187 (M-THP).

Preparation of [(2S,4R)-4-fluoro-1-methylpyrrolidin-2-yl]methanol (161)

Step 1:

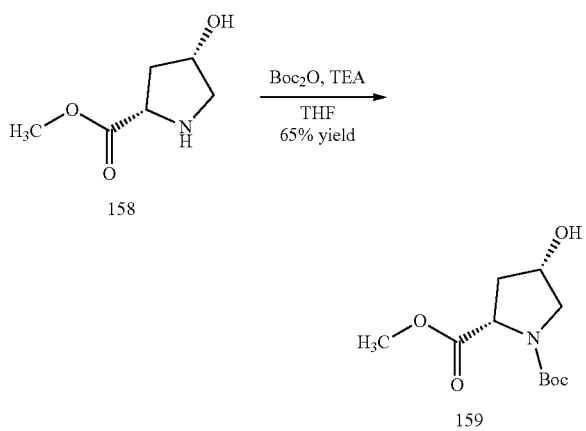

To methyl (4S)-4-hydroxy-L-prolinate (19 g, 10 mmol) and TEA (17.2 g, 170 mmol) in THF (400 mL) was added (Boc)₂O (31.4 g, 7.58 mmol) at 0° C. for 0.5 h. The mixture was stirred at room temperature for 16 h. LCMS analysis showed consumption of the starting material. The mixture was transferred to a separatory funnel, diluted with 500 mL EtOAc, and washed with H₂O (3×300 mL). The combined organics were dried over Na₂SO₄, filtered and concentrated to provide 1-tert-butyl 2-methyl (2S,4S)-4-hydroxypyrrolidine-1,2-dicarboxylate (159) (21 g, 65% yield), which was taken on without further purification. ¹H NMR (400 MHz, DMSO-d₆) δ 4.98 (dd, J=18.7, 3.5 Hz, 1H), 4.21 (ddd, J=13.9, 8.9, 4.6 Hz, 2H), 3.62 (d, J=12.4 Hz, 3H), 3.53-3.42 (m, 1H), 3.10 (dd, J=10.5, 4.3 Hz, 1H), 2.40-2.25 (m, 1H), 1.82 (dt, J=12.8, 4.7 Hz, 1H), 1.36 (d, J=26.6 Hz, 9H). LCMS (ESI) m/z 190 (M-tBu).

Step 2:

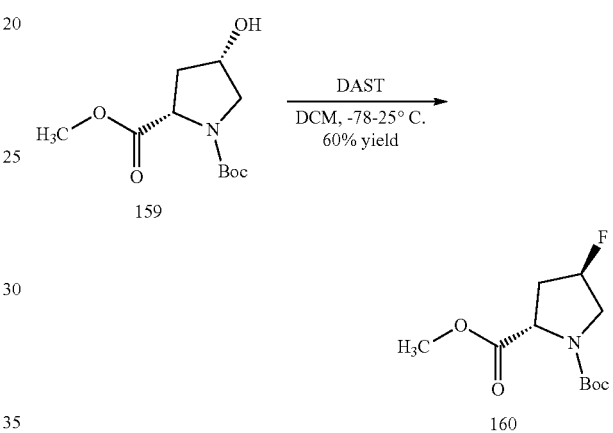

To a solution of 1-tert-butyl 2-methyl (2S,4S)-4-hydroxypyrrolidine-1,2-dicarboxylate (159) (16.4 g, 20 mmol) in DCM (400 mL) was added DAST (32.3 g, 201 mmol) at −78° C. The reaction was stirred for 1 h and then warmed to room temperature and stirred for an additional 24 h. LCMS analysis showed conversion to the desired product. The reaction was quenched by addition of saturated aqueous NaHCO₃ (300 mL). The mixture was extracted with EtOAc (3×300 mL). The combined organics were dried over anhydrous Na₂SO₄, filtered, and concentrated. Purification by flash chromatography (SiO₂, 0-10% EtOAc/petroleum ether) to provide 1-tert-butyl 2-methyl (2S,4R)-4-fluoropyrrolidine-1,2-dicarboxylate (160) (10 g, 70% yield) as a colorless oil. LCMS (ESI) m/z 192 (M-tBu).

Step 3:

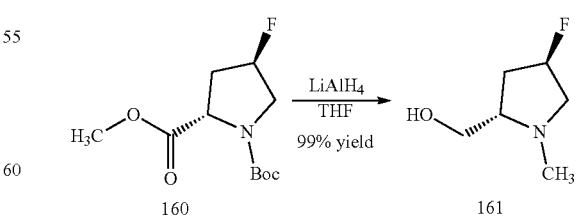

To a solution of 1-tert-butyl 2-methyl (2S,4R)-4-fluoropyrrolidine-1,2-dicarboxylate (160) (6.92 g, 28 mmol) in THF (100 mL) was added LiAlH₄ (3.19 mg, 84 mmol) and the mixture was stirred at room temperature for 16 h. LCMS analysis showed formation of the desired product. The mixture was dried over Na$_2$SO$_4$.10H$_2$O and stirred for 1 h. The mixture was filtered and concentrated to provide [(2S,4R)-4-fluoro-1-methylpyrrolidin-2-yl]methanol (161) as a colorless oil (3.7 g, 99% yield), which was taken on without further purification. LCMS (ESI) m/z 134 (M+H).

Preparation of [(2S,4R)-4-fluoro-1-methylpyrrolidin-2-yl]methanol (163)

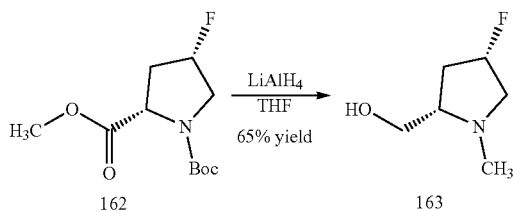

To a solution of 1-tert-butyl 2-methyl (2S,4S)-4-fluoro-pyrrolidine-1,2-dicarboxylate (162) (8.8 g, 36 mmol) in THF (400 mL) was added LiAlH$_4$ (4.05 g, 107 mmol) portion-wise at 20° C. under an N$_2$ atmosphere. After stirring for 2 h, H$_2$O (4.1 mL) and saturated aqueous NaHCO$_3$ (8.2 mL) were added dropwise to quench the reaction. EtOAc (500 mL) was added and the mixture was filtered. The filtrate was dried over Na$_2$SO$_4$, filtered, and concentrated. The crude residue was purified by flash chromatography (SiO$_2$, 9:1 DCM/MeOH) to provide [(2S,4S)-4-fluoro-1-methylpyrrolidin-2-yl]methanol (163) (3.1 g, 65% yield). $^1$H NMR (400 MHz, DMSO-d$_6$) δ 5.20-4.98 (m, 1H), 4.48 (m, 1H), 3.48 (m, 1H), 3.38-3.27 (m, 1H), 3.10 (m, 1H), 2.34-2.27 (m, 1H), 2.26 (s, 3H), 2.25-2.19 (m, 1H), 1.77-1.61 (m, 1H). LCMS (ESI) m/z 134 (M+H).

Preparation of [(2S,4R)-4-methoxy-1-methylpyrrolidin-2-yl]methanol (166)

Step 1:

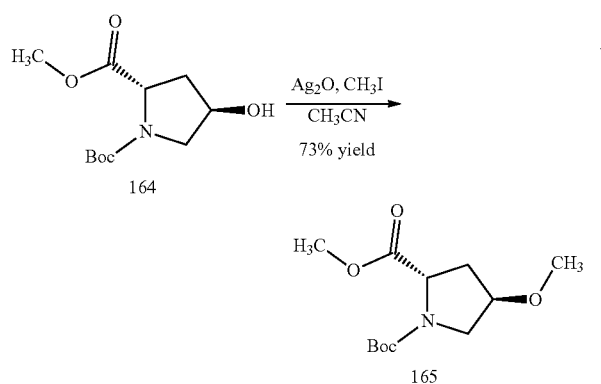

To a solution of 1-tert-butyl 2-methyl (2S,4R)-4-hydroxy-pyrrolidine-1,2-dicarboxylate (164) (6 g, 24.5 mmol) in CH$_3$CN (120 mL) was added Ag$_2$O (17.0 g, 73.4 mmol) and CH$_3$I (27.76 g, 196 mmol). The mixture was stirred at 20° C. for 16 h. LCMS analysis showed formation of the desired product with some remaining starting material. Additional CH$_3$I (6.94 g, 49 mmol) was added and the reaction was stirred at 20° C. for an additional 16 h. LCMS analysis showed consumption of the starting material. The mixture was filtered. The filtrate was concentrated to dryness and purified by flash chromatography (SiO$_2$, 8:1 petroleum ether/EtOAc) to afford 1-tert-butyl 2-methyl (2S,4R)-4-hydroxypyrrolidine-1,2-dicarboxylate (165) as colorless oil (4.6 g, 73% yield). LCMS (ESI) m/z 282 (M+Na).

Step 2:

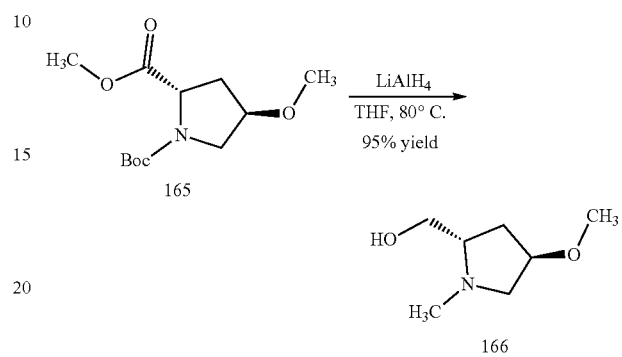

To a solution of 1-tert-butyl 2-methyl (2S,4R)-4-hydroxy-pyrrolidine-1,2-dicarboxylate (165) (1.6 g, 6.2 mmol) in THF (30 mL) was added LiAlH$_4$ (703 mg, 18.5 mmol) and the mixture was stirred at 80° C. for 3 h. LCMS analysis showed formation of the desired product. The reaction was cooled to room temperature. Na$_2$SO$_4$.10H$_2$O was added and the mixture was stirred for 10 min. The mixture was filtered to afford [(2S,4R)-4-methoxy-1-methylpyrrolidin-2-yl]methanol (166) (0.85 g, 95% yield) as a colorless oil. $^1$H NMR (400 MHz, DMSO-d$_6$) δ 4.38 (s, 1H), 3.81-3.74 (m, 1H), 3.40 (d, J=10.8 Hz, 1H), 3.27-3.21 (m, 2H), 3.16 (s, 3H), 2.38-2.30 (m, 1H), 2.25 (s, 3H), 2.08 (dd, J=9.5, 6.0 Hz, 1H), 1.73 (m, 2H). LCMS (ESI) m/z 146 (M+H).

Preparation of [(2S,4S)-4-methoxy-1-methylpyrrolidin-2-yl]methanol (169)

Step 1:

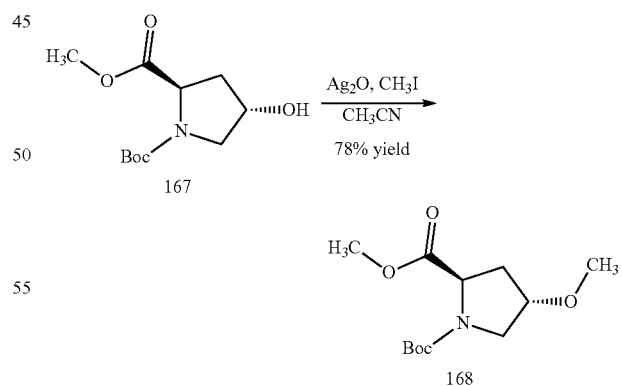

To a solution of 1-tert-butyl 2-methyl (2R,4S)-4-hydroxy-pyrrolidine-1,2-dicarboxylate (167) (3 g, 12.23 mmol) in CH$_3$CN (80 mL) was added Ag$_2$O (8.5 g, 36.7 mmol) and CH$_3$I (17.4 g, 122 mmol) and the mixture was stirred at 20° C. for 16 h. LCMS analysis showed remaining starting material. More Ag$_2$O (4 g) and CH$_3$I (9 g) was added and the reaction was stirred at 20° C. for an additional 16 h. LCMS analysis showed consumption of the starting material. The mixture was filtered and concentrated to dryness. The residue was purified by flash chromatography (SiO$_2$, 1:1 petroleum ether/EtOAc) to afford 1-tert-butyl 2-methyl (2R,4S)-4-methoxypyrrolidine-1,2-dicarboxylate (168) as colorless oil (2.5 g, 79% yield). $^1$H NMR (400 MHz, DMSO-d$_6$) δ 4.21 (dd, J=9.2, 4.0 Hz, 1H), 3.92-3.86 (m, 1H), 3.59 (d, J=11.5 Hz, 3H), 3.48 (dd, J=11.4, 5.6 Hz, 1H), 3.21 (dd, J=11.4, 3.1 Hz, 1H), 3.13 (t, J=3.8 Hz, 3H), 2.33 (d, J=14.0 Hz, 1H), 1.98 (dd, J=13.8, 4.1 Hz, 1H), 1.34 (d, J=26.9 Hz, 9H). LCMS (ESI) m/z 282 (M+Na).

Step 2:

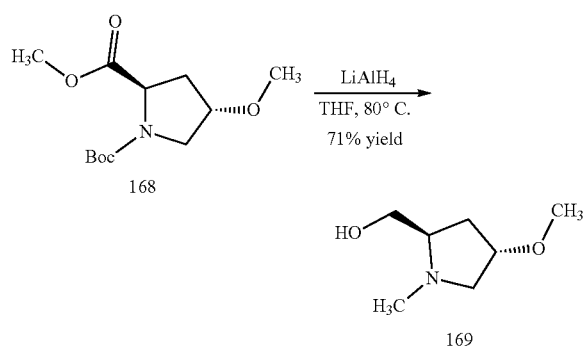

To a solution of 1-tert-butyl 2-methyl (2R,4S)-4-methoxypyrrolidine-1,2-dicarboxylate (168) (2 g, 7.71 mmol) in THF (80 mL) was added LiAlH$_4$ (879 mg, 23.1 mmol) and the mixture was stirred at 80° C. for 3 h. LCMS analysis showed conversion to the product. After cooling to 20° C., Na$_2$SO$_4$.10H$_2$O was added and the mixture was stirred for 10 min. The mixture was filtered and concentrated to afford [(2R,4S)-4-methoxy-1-methylpyrrolidin-2-yl]methanol (169) as a colorless oil (1.1 g, 79% yield), which was taken on without further purification. $^1$H NMR (400 MHz, DMSO-d$_6$) δ 4.40-4.32 (m, 1H), 3.75 (dt, J=9.3, 4.7 Hz, 1H), 3.44 (td, J=6.0, 2.9 Hz, 1H), 3.35-3.23 (m, 1H), 3.13 (s, 3H), 2.98 (d, J=10.5 Hz, 1H), 2.21 (s, 3H), 2.19-2.09 (m, 3H), 1.47 (dd, J=6.2, 2.4 Hz, 1H). LCMS (ESI) m/z 146 (M+H).

Preparation of (3R,5S)-5-(hydroxymethyl)-1-methylpyrrolidine-3-carbonitrile (173)

Step 1:

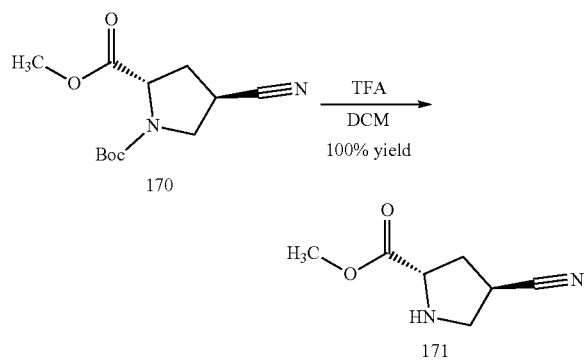

To a solution of 1-tert-butyl 2-methyl (2S,4R)-4-cyanopyrrolidine-1,2-dicarboxylate (170) (2 g, 7.86 mmol) in DCM (10 mL) was added TFA (5 mL) and the mixture was stirred at 20° C. for 2 h. LCMS analysis showed formation of the product. The mixture was concentrated to afford the methyl (4R)-4-cyano-L-prolinate (171) as a colorless oil (2.11 g, 100% yield). LCMS (ESI) m/z 155 (M+H).

Step 2:

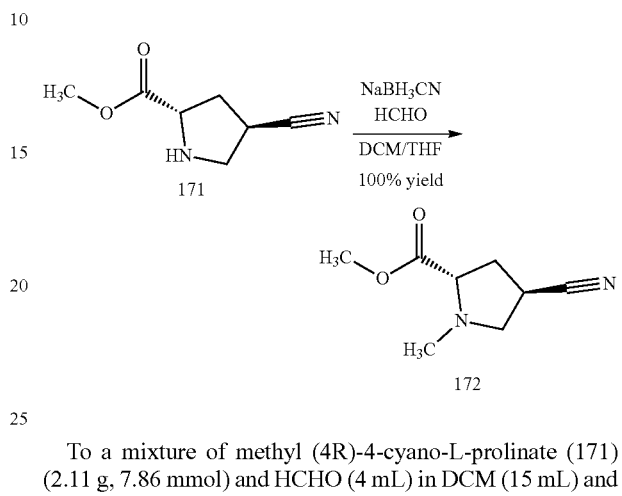

To a mixture of methyl (4R)-4-cyano-L-prolinate (171) (2.11 g, 7.86 mmol) and HCHO (4 mL) in DCM (15 mL) and THF (5 mL) was added NaBH$_3$CN (990 mg, 15.7 mmol) and the mixture was stirred at 25° C. for 16 h. LCMS analysis showed formation of the product. H$_2$O (50 mL) was added and the mixture was extracted with DCM (3×100 mL). The combined organics were washed with brine (10 mL), dried over Na$_2$SO$_4$, filtered, and concentrated to provide methyl (4R)-4-cyano-1-methyl-L-prolinate (172) as yellow oil (1.32 g, 100% yield). $^1$H NMR (400 MHz, DMSO-d$_6$) δ 3.66 (s, 3H), 3.32-3.21 (m, 3H), 2.58 (t, J=8.0 Hz, 1H), 2.34-2.27 (m, 5H). LCMS (ESI) m/z 169 (M+H).

Step 3:

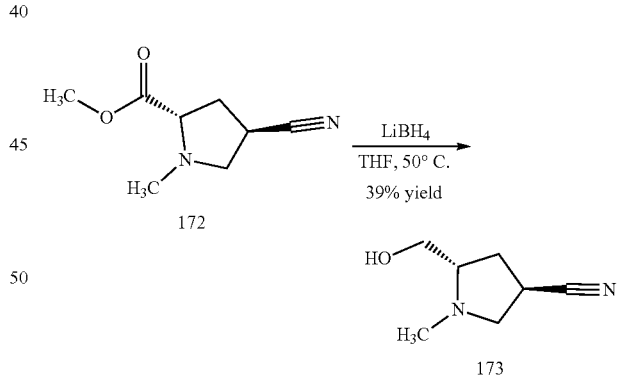

To a solution of methyl (4R)-4-cyano-1-methyl-L-prolinate (172) (1.32 g, 8.56 mmol) in THF (20 mL) was added LiBH$_4$ (377 mg, 17.1 mmol) and the mixture was stirred at 50° C. for 16 h. LCMS analysis showed consumption of the starting material and formation of the product. H$_2$O (10 mL) was added and the resultant mixture was stirred for 10 min. The mixture was extracted with EtOAc (3×20 mL). The combined organics were dried over Na$_2$SO$_4$, filtered and concentrated to provide (3R,5S)-5-(hydroxymethyl)-1-methylpyrrolidine-3-carbonitrile (173) as colorless oil (472 mg, 39% yield), which was taken on without further purification. LCMS (ESI) m/z 141 (M+H).

Preparation of [(3S)-3-fluoro-1-methylpyrrolidin-3-yl]methanol (177)

Step 1:

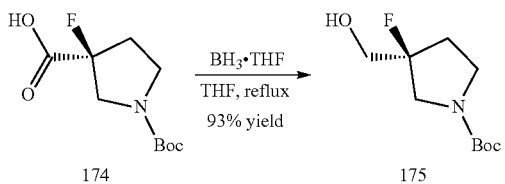 [SMILES: CC(C)(C)OC(=O)N1CC[C@@](F)(C(=O)O)C1 ; CC(C)(C)OC(=O)N1CC[C@@](F)(CO)C1 ; "BH3·THF"]

A solution of (3S)-1-(tert-butoxycarbonyl)-3-fluoropyrrolidine-3-carboxylic acid (174) (WO2013072813) (1.25 g, 5.38 mmol) in dry THF (18 mL) was treated dropwise with a solution of $BH_3$ (1.0 M in THF, 17.2 mL) under an atmosphere of $N_2$. After addition the mixture was heated to reflux for 16 h. LCMS analysis showed formation of the desired product with complete consumption of the starting material. The reaction was cooled to 25° C. and MeOH (10 mL) was added dropwise. The mixture was stirred for 2 h, cooled to 0° C., and then treated with 0.5 M HCl (3 mL). The solution was stirred for 0.5 h. Saturated aqueous $NaHCO_3$ was added to adjust the reaction mixture to pH>7. The mixture was concentrated to remove MeOH. The residue was diluted with $H_2O$ (30 mL) and then extracted with EtOAc (3×20 mL). The combined organics were washed with brine (30 mL), dried over $Na_2SO_4$, and concentrated. The crude residue was purified by flash chromatography ($SiO_2$, 10-70% EtOAc/petroleum ether) to afford tert-butyl (3S)-3-fluoro-3-(hydroxymethylpyrrolidine-1-carboxylate (175) (1.1 g, 93% yield) as a colorless oil. $^1H$ NMR (400 MHz, DMSO-$d_6$) δ 5.19 (t, J=5.9 Hz, 1H), 3.67-3.51 (m, 2H), 3.50-3.40 (m, 2H), 3.39-3.25 (m, 2H), 2.12-1.90 (m, 2H), 1.40 (s, 9H). LCMS (ESI) m/z 242 (M+Na).

Step 2:

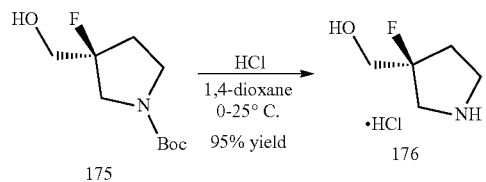 [SMILES: CC(C)(C)OC(=O)N1CC[C@@](F)(CO)C1 ; Cl ; OC[C@]1(F)CCNC1 ; Cl]

To a stirred solution of (3S)-3-fluoro-3-(hydroxymethyl)pyrrolidine-1-carboxylate (175) (1.09 g, 5.0 mmol) in 1,4-dioxane (4 mL) was added HCl (4 M in 1,4-dioxane, 8 mL) at 0-10° C. The resulting mixture was stirred at 25° C. for 16 h. LCMS analysis showed consumption of the starting material. The solvent was removed under reduced pressure to afford (3S)-3-fluoro-3-(hydroxymethyl)pyrrolidinium chloride (176) (740 mg, 95% yield) as a white solid. $^1H$ NMR (400 MHz, DMSO-$d_6$) δ 9.75 (s, 2H), 5.47 (s, 1H), 3.78-3.55 (m, 2H), 3.47-3.18 (m, 4H), 2.21-1.98 (m, 2H). LCMS (ESI) m/z 120 (M+H).

Step 3:

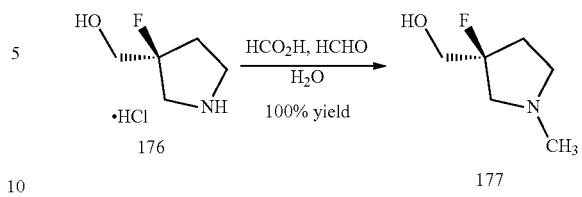

A mixture of (3S)-3-fluoro-3-(hydroxymethyl)pyrrolidinium chloride (176) (740 mg, 4.76 mmol), aqueous formaldehyde (5 mL), and formic acid (10 mL) in a sealed tube was heated to 100° C. for 48 h. LCMS analysis showed complete consumption of the starting material with formation of the desired product. The reaction was concentrated to dryness. Concentrated HCl (5 mL) was added to the residue. The resultant mixture was stirred for 2 h and then concentrated to dryness. $H_2O$ (15 mL) was added to the residue. The mixture was carefully basified with solid $K_2CO_3$ and then extracted with EtOAc (3×30 mL). The combined organics were dried over $Na_2SO_4$ and concentrated. The crude product was purified by flash chromatography ($SiO_2$, 0-15% MeOH/DCM) to afford [(3S)-3-fluoro-1-methylpyrrolidin-3-yl]methanol (177) (630 mg, yield 100% yield) as a light yellow oil. $^1H$ NMR (400 MHz, DMSO-$d_6$) δ 5.09 (s, 1H), 3.52-3.25 (m, 2H), 2.67-2.62 (m, 1H), 2.62-2.59 (m, 1H), 2.58-2.51 (m, 1H), 2.41-2.28 (m, 1H), 2.22 (s, 3H), 1.98-1.73 (m, 2H). LCMS (ESI) m/z 134 (M+H).

Preparation of [(3R)-3-fluoro-1-methylpyrrolidin-3-yl]nethanol (181)

Step 1:

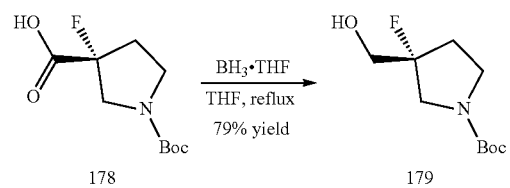 [SMILES: CC(C)(C)OC(=O)N1CC[C@](F)(C(=O)O)C1 ; CC(C)(C)OC(=O)N1CC[C@](F)(CO)C1 ; "BH3·THF"]

A solution of (3R)-1-(tert-butoxycarbonyl)-3-fluoropyrrolidine-3-carboxylic acid (178) (WO2013072813) (1.79 g, 7.65 mmol) in dry THF (24 mL) was treated dropwise with a solution of $BH_3$ (1.0 M in THF, 30 mL) under an atmosphere of $N_2$. After addition the mixture was heated to reflux for 16 h. LCMS analysis showed formation of the desired product with complete consumption of the starting material. The reaction was cooled to 25° C. and MeOH (10 mL) was added dropwise. The mixture was stirred for 2 h, cooled to 0° C., and then treated with 0.5 M HCl (3 mL). The solution was stirred for 0.5 h. Saturated aqueous $NaHCO_3$ was added to adjust the reaction mixture to pH>7. The mixture was concentrated to remove MeOH. The residue was diluted with $H_2O$ (30 mL) and then extracted with EtOAc (3×20 mL). The combined organics were washed with brine (30 mL), dried over $Na_2SO_4$, and concentrated. The crude residue was purified by flash chromatography ($SiO_2$, 10-70% EtOAc/petroleum ether) to afford tert-butyl (3R)-3-fluoro-3-(hydroxymethyl)pyrrolidine-1-carboxylate (179) (1.33 g, 79% yield) as a colorless oil. $^1H$ NMR (400 MHz, DMSO-$d_6$) δ 5.19 (t, J=5.9 Hz, 1H), 3.64-3.52 (m, 2H), 3.50-3.40 (m, 2H), 3.38-3.34 (m, 1H), 3.32-3.10 (m, 1H), 2.11-1.90 (m, 2H), 1.40 (s, 9H). LCMS (ESI) m/z 242 (M+Na).

Step 2:

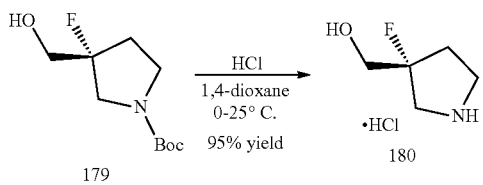 [SMILES: CC(C)(C)OC(=O)N1CC[C@](F)(CO)C1 ; Cl ; OC[C@@]1(F)CCNC1 ; Cl]

To a stirred solution of (3R)-3-fluoro-3-(hydroxymethyl)pyrrolidine-1-carboxylate (179) (1.33 g, 6.061 mmol) in 1,4-dioxane (5 mL) was added HCl (4 M in 1,4-dioxane, 10 mL) at 0-10° C. The resulting mixture was stirred at 25° C. for 16 h. LCMS analysis showed consumption of the starting material. The solvent was removed under reduced pressure to afford (3R)-3-fluoro-3-(hydroxymethyl)pyrrolidinium chloride (180) (892 mg, 95% yield) as a white solid. $^1$H NMR (400 MHz, DMSO-$d_6$) δ 9.63 (s, 2H), 5.45 (s, 1H), 3.74-3.53 (m, 2H), 3.42-3.24 (m, 4H), 2.18-1.99 (m, 2H). LCMS (ESI) m/z 120 (M+H).

Step 3:

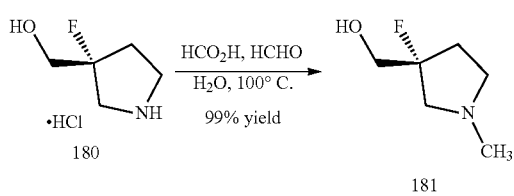

A mixture of (3R)-3-fluoro-3-(hydroxymethyl)pyrrolidinium chloride (180) (892 mg, 5.73 mmol), aqueous formaldehyde (5 mL), and formic acid (10 mL) in a sealed tube was heated to 100° C. for 48 h. LCMS analysis showed complete consumption of the starting material with formation of the desired product. The reaction was concentrated to dryness. Concentrated HCl (5 mL) was added to the residue. The resultant mixture was stirred for 2 h and then concentrated to dryness, and H$_2$O (15 mL) was added to the residue. The mixture was carefully basified with solid K$_2$CO$_3$ and then extracted with EtOAc (3×30 mL). The combined organics were dried over Na$_2$SO$_4$ and concentrated. The crude product was purified by flash chromatography (SiO$_2$, 0-15% MeOH/DCM) to afford [(3R)-3-fluoro-1-methylpyrrolidin-3-yl]methanol (181) (630 mg, 100% yield) as a light yellow oil. $^1$H NMR (400 MHz, DMSO-$d_6$) δ 5.09 (s, 1H), 3.57-3.28 (m, 2H), 2.84-2.52 (m, 3H), 2.42-2.30 (m, 1H), 2.22 (s, 3H), 1.99-1.66 (m, 2H). LCMS (ESI) m/z 134 (M+H).

Preparation of [(3R)-3-fluoro-1-methylpiperidin-3-yl]methanol (184)

Step 1:

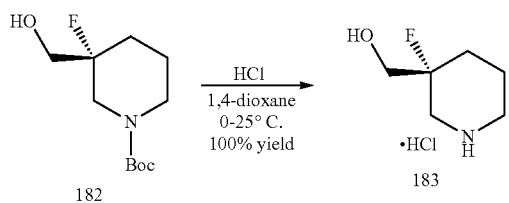 [SMILES: CC(C)(C)OC(=O)N1CCC[C@](F)(CO)C1 ; Cl ; OC[C@@]1(F)CCCNC1 ; Cl]

To a stirred solution of tert-butyl (3R)-3-fluoro-3-(hydroxymethyl)piperidine-1-carboxylate (182) (500 mg, 2.14 mmol) in DCM (3 mL) was added HCl (4M 1,4-dioxane, 3 mL) and the resulting mixture was stirred at 25° C. for 2 h. LCMS analysis showed consumption of the starting material. The solvent was removed under reduced pressure to give provide (3R)-3-fluoro-3-(hydroxymethyl)piperidinium chloride (183) (360 mg, 99% yield) as a white solid. $^1$H NMR (400 MHz, DMSO-$d_6$) δ 8.68 (s, 1H), 5.31 (s, 1H), 3.59-3.39 (m, 3H), 3.19-2.97 (m, 2H), 2.82 (m, 1H), 1.86-1.55 (m, 4H). LCMS (ESI) m/z 134 (M+H).

Step 2:

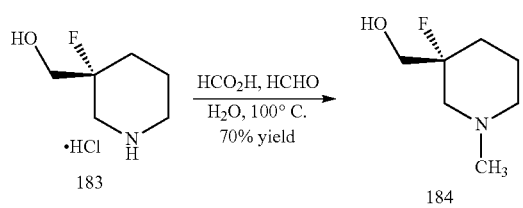

A mixture of (3R)-3-fluoro-3-(hydroxymethyl)piperidinium chloride (183) (360 mg, 2.12 mmol), aqueous formaldehyde (3 mL), and formic acid (6 mL) in a sealed tube was heated to 100° C. for 23 h. LCMS analysis showed consumption of the starting material. The reaction was concentrated to dryness. Concentrated HCl (5 mL) was added to the residue and stirred for 2 h and then the mixture was concentrated. To the residue was added H$_2$O (30 mL). The mixture was carefully basified with solid K$_2$CO$_3$ and then extracted with 10:1 DCM/MeOH (3×30 mL). The combined organics were dried over Na$_2$SO$_4$ and concentrated to provide [(3R)-3-fluoro-1-methylpiperidin-3-yl]methanol (184) (220 mg, 70% yield) as a light yellow oil. $^1$H NMR (400 MHz, DMSO-$d_6$) δ 4.89 (t, J=5.9 Hz, 1H), 3.43 (m, 2H), 2.47-2.31 (m, 2H), 2.23 (m, 1H), 2.14 (s, 3H), 2.13-2.06 (m, 1H), 1.67-1.44 (m, 4H). LCMS (ESI) m/z 148 (M+H).

Preparation of [(3S)-3-fluoro-1-methylpiperidin-3-yl]methanol (187)

Step 1:

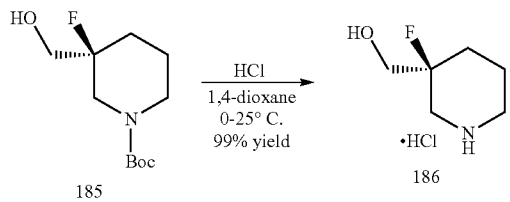 [SMILES: CC(C)(C)OC(=O)N1CCC[C@@](F)(CO)C1 ; Cl ; OC[C@]1(F)CCCNC1 ; Cl]

To a stirred solution of tert-butyl (3S)-3-fluoro-3-(hydroxymethyl)piperidine-1-carboxylate (185) (500 mg, 2.14 mmol) in DCM (3 mL) was added HCl (4 M in 1,4-dioxane, 3 mL). The resulting mixture was stirred at 25° C. for 2 h. LCMS analysis showed consumption of the starting material. The solvent was removed under reduced pressure to provide (3S)-3-fluoro-3-(hydroxymethyl)piperidinium chloride (186) (360 mg, 99% yield) as a white solid. $^1$H NMR (400 MHz, DMSO-$d_6$) δ 8.61 (s, 1H), 5.28 (s, 1H), 3.57-3.36 (m, 3H), 3.21-2.96 (m, 2H), 2.82 (m, 1H), 1.86-1.56 (m, 4H). LCMS (ESI) m/z 134 (M+H).

Step 2:

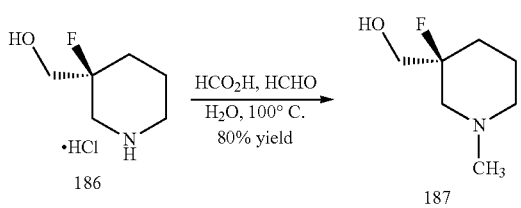

A mixture of (3S)-3-fluoro-3-(hydroxymethyl)piperidinium chloride (186) (230 mg, 0.75 mmol), aqueous formaldehyde (2 mL), and formic acid (4 mL) in a sealed tube was heated to 100° C. for 23 hours. LCMS analysis showed consumption of the starting material. The reaction was concentrated to dryness. Concentrated HCl (5 mL) was added to the residue and stirred for 2 h and then the mixture was concentrated. To the residue was added $H_2O$ (30 mL). The mixture was carefully basified with solid $K_2CO_3$ and then extracted with 10:1 DCM/MeOH (3×30 mL). The combined organics were dried over $Na_2SO_4$ and concentrated to provide [(3S)-3-fluoro-1-methylpiperidin-3-yl]methanol (187) (160 mg, 80% yield) as a light yellow oil. $^1$H NMR (400 MHz, DMSO-$d_6$) δ 4.90 (t, J=5.9 Hz, 1H), 3.44 (dt, J=22.9, 6.7 Hz, 2H), 2.47-2.31 (m, 2H), 2.23 (dd, J=22.0, 11.7 Hz, 1H), 2.14 (s, 3H), 2.10 (d, J=10.4 Hz, 1H), 1.66-1.40 (m, 4H). LCMS (ESI) m/z 148 (M+H).

Preparation of [(3S,4S)-4-methoxy-1-methylpyrrolidin-3-yl]methanol (190)

Step 1:

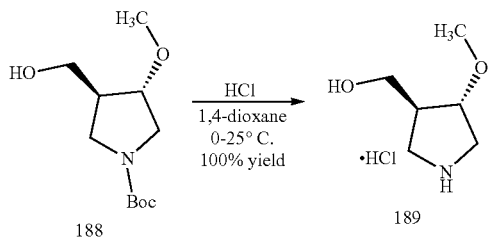

To a stirred solution of tert-butyl (3S,4S)-3-(hydroxymethyl)-4-methoxypyrrolidine-1-carboxylate (188) (*J. Med. Chem.* 2016, 59, 2005-2024) (1.85 g, 8.0 mmol) in 1,4-dioxane (5 mL) was added HCl (4 M in 1,4-dioxane, 10 mL) at 0-10° C. After the addition, the mixture was stirred at 20-25° C. for 16 h. LCMS analysis showed consumption of the starting material. The solvent was removed under reduced pressure to afford (3S,4S)-3-(hydroxymethyl)-4-methoxypyrrolidinium chloride (189) (1.34 g, 100% yield) as a brown oil, which was taken on without further purification. $^1$H NMR (400 MHz, DMSO-$d_6$) δ 9.54 (s, 1H), 9.31 (s, 1H), 5.50-4.50 (br s, 1H), 3.94-3.80 (m, 1H), 3.41 (s, 1H), 3.39 (s, 1H), 3.32-3.06 (m, 6H), 3.03-2.92 (m, 1H), 2.43-2.29 (m, 1H). LCMS (ESI) m/z 132 (M+H).

Step 2:

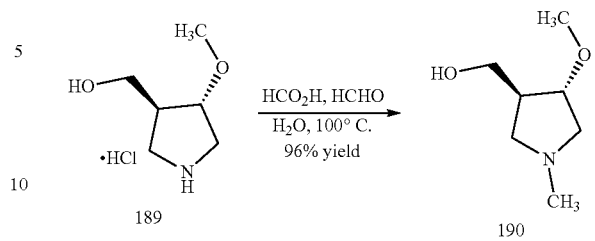

A mixture of (3S,4S)-3-(hydroxymethyl)-4-methoxypyrrolidinium chloride (189) (1.34 g, 8.0 mmol), aqueous formaldehyde (7 mL), and formic acid (14 mL) in a sealed tube was heated to 100° C. for 4 days. LCMS analysis showed consumption of the starting material and formation of the product. The reaction was cooled to 25° C. The solvent was removed under reduced pressure. Concentrated HCl (10 mL) was added to the residue and the mixture was stirred for 2 h. The mixture was concentrated to dryness. The residue was carefully basified with aqueous $K_2CO_3$ and then extracted with DCM (3×50 mL). The combined organics were dried over $Na_2SO_4$, filtered, and concentrated to provide [(3S,4S)-4-methoxy-1-methylpyrrolidin-3-yl]methanol (190) (1.12 g, 96% yield) as a brown oil. $^1$H NMR (400 MHz, DMSO-$d_6$) δ 4.64 (m, 1H), 3.53-3.47 (m, 1H), 3.39-3.34 (m, 1H), 3.32-3.28 (m, 1H), 3.16 (s, 3H), 2.60-2.53 (m, 2H), 2.38 (dd, J=9.8, 3.7 Hz, 1H), 2.16 (s, 3H), 2.14-2.10 (m, 1H), 2.04 (m, 1H). LCMS (ESI) m/z 146 (M+H).

Preparation of [(3R,4R)-4-methoxy-1-methylpyrrolidin-3-yl]methanol (193)

Step 1:

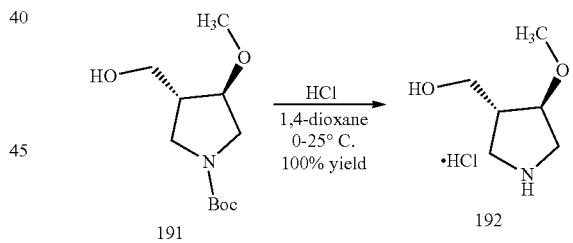

To a stirred solution of tert-butyl (3R,4R)-3-(hydroxymethyl)-4-methoxypyrrolidine-1-carboxylate (191) (*J. Med. Chem.* 2016, 59, 2005-2024) (1.90 g, 8.22 mmol) in 1,4-dioxane (5 mL) was added HCl (4 M in 1,4-dioxane, 10 mL) at 0-10° C. After the addition, the mixture was stirred at 20-25° C. for 16 h. LCMS analysis showed consumption of the starting material. The solvent was removed under reduced pressure to afford crude (3R,4R)-3-(hydroxymethyl)-4-methoxypyrrolidinium chloride (182) (1.38 g, yield 100% yield) as a brown oil, which was taken on without further purification. $^1$H NMR (400 MHz, DMSO-$d_6$) δ 9.54 (s, 1H), 9.31 (s, 1H), 5.70-4.20 (br, s, 1H), 3.94-3.80 (m, 1H), 3.41 (s, 1H), 3.39 (s, 1H), 3.32-3.06 (m, 6H), 3.03-2.92 (m, 1H), 2.43-2.29 (m, 1H). LCMS (ESI) m/z 132 (M+H).

Step 2:

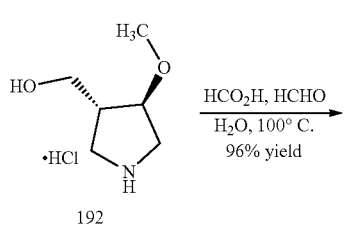

A mixture of (3R,4R)-3-(hydroxymethyl)-4-methoxypyrrolidinium chloride (192) (1.38 g, 8.2 mmol), aqueous formaldehyde (7 mL), and formic acid (14 mL) in a sealed tube was heated to 100° C. for 4 days. LCMS analysis showed consumption of the starting material and formation of the product. The reaction was cooled to 25° C. The solvent was removed under reduced pressure. Concentrated HCl (10 mL) was added to the residue and the mixture was stirred for 2 h. The mixture was concentrated to dryness. The residue was carefully basified with aqueous $K_2CO_3$ and then extracted with DCM (3×50 mL). The combined organics were dried over $Na_2SO_4$, filtered, and concentrated to provide [(3R,4R)-4-methoxy-1-methylpyrrolidin-3-yl]methanol (193) (1.12 g, 96% yield) as a brown oil. $^1$H NMR (400 MHz, DMSO-$d_6$) δ 4.64 (m, 1H), 3.51 (m, 1H), 3.37 (m, 1H), 3.33-3.28 (m, 1H), 3.16 (s, 3H), 2.60-2.53 (m, 1H), 2.38 (dd, J=9.8, 3.7 Hz, 1H), 2.16 (s, 3H), 2.15-2.11 (m, 1H), 2.05 (m, 1H). LCMS (ESI) m/z 146 (M+H).

Preparation of
(3R,4R)-4-methoxy-1-methylpyrrolidin-3-ol (196)

Step 1:

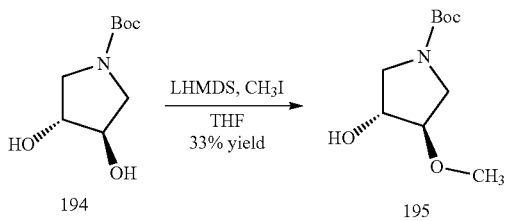

To a mixture of tert-butyl (3R,4R)-3,4-dihydroxypyrrolidine-1-carboxylate (194) (400 mg, 1.97 mmol) and $CH_3I$ (838 mg, 5.90 mmol) in THF (10 mL) was added LHMDS (2.95 mL, 2.95 mmol, 1.0 M in THF) and the mixture was stirred at 20° C. for 16 h. LCMS analysis showed approximately 50% of the desired product with 30% remaining starting material and trace amounts of the dimethyl byproduct. $H_2O$ (10 mL) was added and the mixture was extracted with EtOAc (3×20 mL). The combined organics were washed with brine (10 mL), dried over $Na_2SO_4$, filtered, and concentrated. The crude residue was purified by flash chromatography ($SiO_2$, 1:1 petroleum ether/EtOAc) to afford tert-butyl (3R,4R)-3-hydroxy-4-methoxypyrrolidine-1-carboxylate (195) as a colorless oil (140 mg, 33% yield). $^1$H NMR (400 MHz, DMSO-$d_6$) δ 5.19 (d, J=3.5 Hz, 1H), 4.06 (s, 1H), 3.60 (s, 1H), 3.35 (d, J=4.2 Hz, 1H), 3.30-3.21 (m, 5H), 3.14 (d, J=11.5 Hz, 1H), 1.39 (s, 9H). LCMS (ESI) m/z 240 (M+Na).

Step 2:

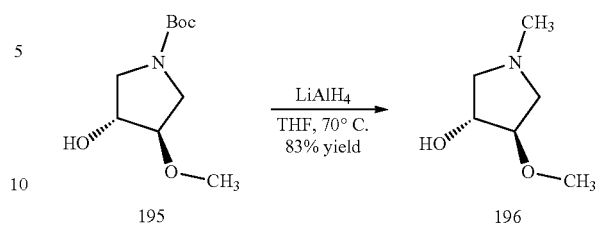

To a solution of tert-butyl (3R,4R)-3-hydroxy-4-methoxypyrrolidine-1-carboxylate (195) (140 mg, 0.64 mmol) in THF (10 mL) was added $LiAlH_4$ (49 mg, 1.29 mmol) and the mixture was stirred at 70° C. for 2 h. LCMS analysis showed formation of the product. After cooling to 20° C., $Na_2SO_4 \cdot 10H_2O$ was added and the mixture was stirred for 10 min. The mixture was filtered to afford (3R,4R)-4-methoxy-1-methylpyrrolidin-3-ol (196) as colorless oil (70 mg, 83% yield). $^1$H NMR (400 MHz, DMSO-$d_6$) δ 5.00 (d, J=5.1 Hz, 1H), 3.96-3.90 (m, 1H), 3.53 (ddd, J=6.3, 3.9, 2.3 Hz, 1H), 3.22 (d, J=2.0 Hz, 3H), 2.72-2.63 (m, 2H), 2.34 (dd, J=9.9, 4.0 Hz, 1H), 2.21 (dd, J=9.5, 4.7 Hz, 1H), 2.16 (s, 3H). LCMS (ESI) m/z 132 (M+H).

Preparation of
(3S,4S)-4-methoxy-1-methylpyrrolidin-3-ol (199)

Step 1:

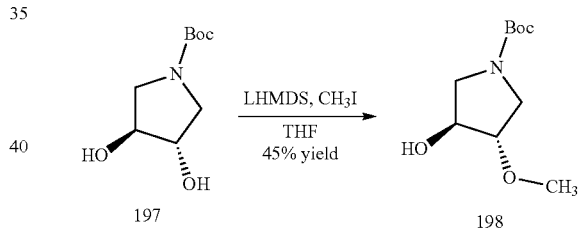

To a mixture of tert-butyl (3S,4S)-3,4-dihydroxypyrrolidine-1-carboxylate (197) (500 mg, 2.46 mmol) and $CH_3I$ (1.05 mg, 7.38 mmol) in THF (10 mL) was added LHMDS (3.69 mL, 3.69 mmol, 1.0 M in THF) and the mixture was stirred at 20° C. for 16 h. LCMS analysis showed approximately 50% of the desired product with 30% remaining starting material and trace amounts of the dimethyl byproduct. $H_2O$ (10 mL) was added and the mixture was extracted with EtOAc (3×20 mL). The combined organics were washed with brine (10 mL), dried over $Na_2SO_4$, filtered, and concentrated. The crude residue was purified by flash chromatography ($SiO_2$, 1:1 petroleum ether/EtOAc) to afford tert-butyl (3S,4S)-3-hydroxy-4-methoxypyrrolidine-1-carboxylate (198) as a colorless oil (240 mg, 45% yield). $^1$H NMR (400 MHz, DMSO-$d_6$) δ 5.19 (d, J=3.5 Hz, 1H), 4.06 (s, 1H), 3.60 (s, 1H), 3.35 (d, J=4.2 Hz, 1H), 3.29-3.22 (m, 5H), 3.13 (d, J=11.5 Hz, 1H), 1.39 (s, 9H). LCMS (ESI) m/z 240 (M+Na).

Step 2:

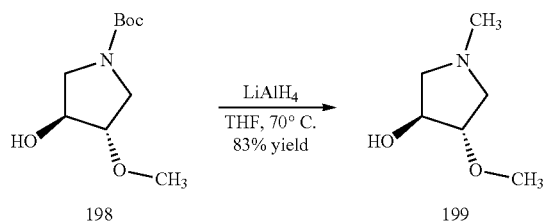

To a solution of tert-butyl (3R,4R)-3-hydroxy-4-methoxypyrrolidine-1-carboxylate (199) (240 mg, 1.10 mmol) in THF (10 mL) was added LiAlH$_4$ (84 mg, 2.21 mmol) and the mixture was stirred at 70° C. for 16 h. LCMS analysis showed formation of the product. After cooling to 20° C., Na$_2$SO$_4$.10H$_2$O was added and the mixture and stirred for 10 min. The mixture was filtered to afford (3S,4S)-4-methoxy-1-methylpyrrolidin-3-ol (199) as colorless oil (120 mg, 83% yield). $^1$H NMR (400 MHz, DMSO-d$_6$) δ 5.00 (d, J=5.1 Hz, 1H), 3.93 (d, J=4.4 Hz, 1H), 3.57-3.50 (m, 1H), 3.24 (d, J=13.8 Hz, 3H), 2.68 (dd, J=16.0, 8.4 Hz, 2H), 2.34 (dd, J=9.9, 4.0 Hz, 1H), 2.21 (dd, J=9.4, 4.6 Hz, 1H), 2.16 (s, 3H). LCMS (ESI) m/z 132 (M+H).

Preparation of 6-fluoro-5-methyl-1-(tetrahydro-2H-pyran-2-yl)-1H-indazol-4-ol (202)

Step 1:

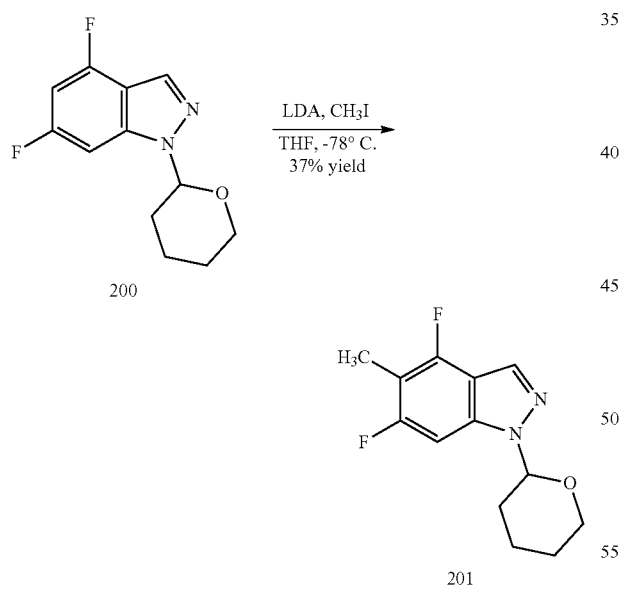

To a solution of diisopropylamine (3.18 g, 31.5 mmol) in THF (100 mL) was added n-BuLi (2.5 M, 10.5 mL, 26.25 mmol) dropwise at −70° C. under an atmosphere of N$_2$. The mixture was stirred for 30 min at the same temperature and then a solution of 4,6-difluoro-1-(tetrahydro-2H-pyran-2-yl)-1H-indazole (200) (5 g, 21 mmol) in THF (3 mL) was added dropwise at −78° C. After 0.5 h CH$_3$I (5.96 g, 42 mmol) was added. The mixture was stirred for 1 h. The mixture was quenched with saturated aqueous NH$_4$Cl and then extracted with EtOAc (3×200 mL). The combined organics were dried over Na$_2$SO$_4$, filtered, and concentrated. The residue was purified by flash chromatography (SiO$_2$, 10:1 petroleum ether/EtOAc) to afford 4,6-difluoro-5-methyl-1-(tetrahydro-2H-pyran-2-yl)-1H-indazole (201) as a white solid (2 g, 38% yield). An additional 2 g of mixed fractions were collected containing 30% of starting material (200). $^1$H NMR (400 MHz, DMSO-d$_6$) δ 8.19 (s, 1H), 7.51 (d, J=9.7 Hz, 1H), 5.83-5.79 (m, 1H), 3.91-3.83 (m, 1H), 3.81-3.71 (m, 1H), 2.36 (tdd, J=13.2, 9.6, 3.8 Hz, 1H), 2.22 (t, J=1.9 Hz, 3H), 2.07-1.92 (m, 2H), 1.79-1.67 (m, 1H), 1.63-1.53 (m, 2H). LCMS (ESI) m/z 253 (M+H).

Step 2:

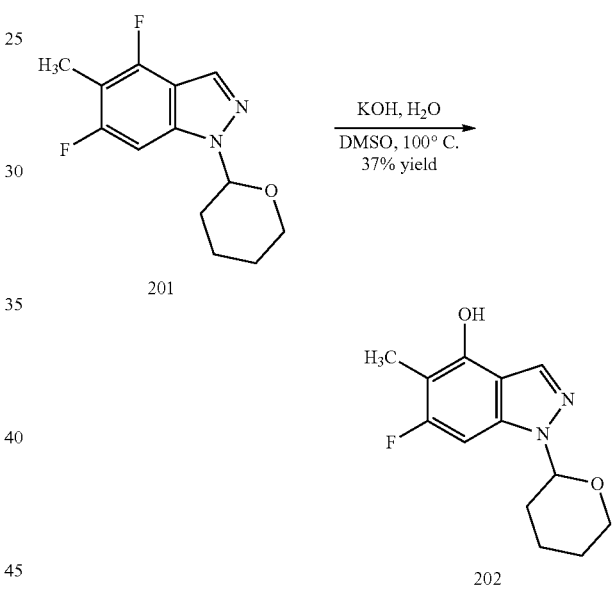

To a solution of 4,6-difluoro-5-methyl-1-(tetrahydro-2H-pyran-2-yl)-1H-indazole (201) (2 g, 7.93 mmol) in DMSO (24 mL) was added KOH (1.78 g, 31.7 mmol) and H$_2$O (571 mg, 31.7 mmol). The mixture was stirred at 100° C. for 6 h. LCMS analysis showed formation of the product. The reaction was quenched with H$_2$O (30 mL) and then the mixture was extracted with EtOAc (3×50 mL). The combined organics were washed with brine (30 mL), dried over Na$_2$SO$_4$, filtered, and concentrated. The residue was purified by flash chromatography (SiO$_2$, 2:1 petroleum ether/EtOAc) to afford a solid, which was triturated with 5:1 petroleum ether/EtOAc to afford 6-fluoro-5-methyl-1-(tetrahydro-2H-pyran-2-yl)-1H-indazol-4-ol (202) (730 mg, 37% yield) as a white solid. $^1$H NMR (400 MHz, DMSO-d$_6$) δ 10.33 (s, 1H), 8.16 (s, 1H), 6.97 (d, J=10.0 Hz, 1H), 5.67 (dd, J=9.7, 2.5 Hz, 1H), 3.91-3.81 (m, 1H), 3.77-3.64 (m, 1H), 2.44-2.27 (m, 1H), 2.10 (d, J=2.0 Hz, 3H), 2.06-1.97 (m, 1H), 1.97-1.87 (m, 1H), 1.79-1.64 (m, 1H), 1.55 (dt, J=9.8, 4.0 Hz, 2H). LCMS (ESI) m/z 251, 253 (M+H).

Preparation of (3S,4S)-4-methoxy-1-methylpyrrolidin-3-ol (207)

Step 1:

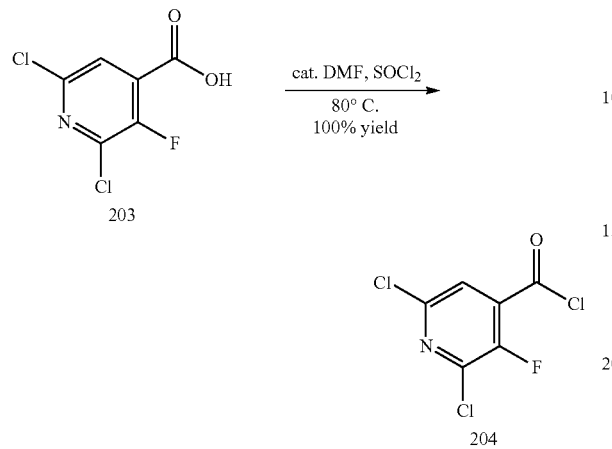

To a stirred mixture of 2,6-dichloro-3-fluoropyridine-4-carboxylic acid (203) (21.6 g, 103 mmol) in $SOCl_2$ (75 mL) was added three drops of DMF. The mixture was heated to 80° C. and stirred at this temperature for 3 h. LCMS analysis in MeOH indicates formation of methyl ester. The mixture was concentrated and azeotroped with toluene to provide crude 2,6-dichloro-3-fluoropyridine-4-carbonyl chloride (204) (23.5 g, 100% yield) as an oil, which was taken on immediately to the next transformation.

Step 2:

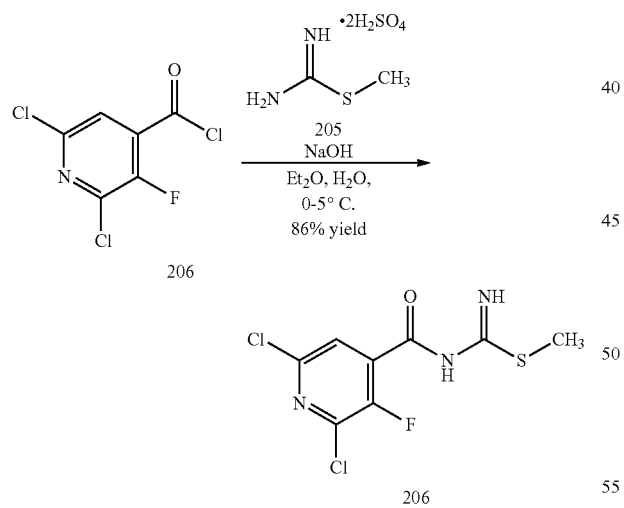

To a solution of NaOH (18.5 g, 463 mmol) in $H_2O$ (400 mL) was added 2-methyl-2-thiopseudourea sulfate (51.5 g, 185 mmol) portionwise at 0° C. The mixture was stirred for 10 mins and then a solution of 2,6-dichloro-3-fluoropyridine-4-carbonyl chloride (204) (23.5 g, 103 mmol) in dry $Et_2O$ (300 mL) was added dropwise. After the addition, the reaction was stirred at 0-5° C. for 30 mins. LCMS analysis showed consumption of the starting material and formation of the desired product. The mixture was separated. The aqueous layer was extracted with EtOAc (2×300 mL). The combined organics were washed with $H_2O$ (2×200 mL) and brine (200 mL), dried over $Na_2SO_4$, and concentrated to provide crude methyl N-[(2,6-dichloro-3-fluoropyridin-4-yl)carbonyl]carbamimidothioate (206) (25.0 g, 86% yield) as a yellow solid, which was taken on directly without purification. $^1H$ NMR (400 MHz, DMSO-$d_6$) δ 9.25 (s, 2H), 7.85 (d, J=4.2 Hz, 1H), 2.46 (s, 3H). LCMS (ESI) m/z 282, 284 (M+H).

Step 3:

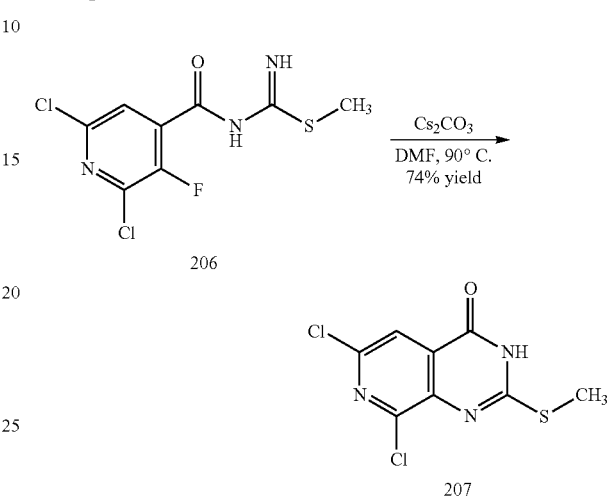

A mixture of methyl N-[(2,6-dichloro-3-fluoropyridin-4-yl)carbonyl]carbamimidothioate (206) (28.9 g, 102 mmol) and $Cs_2CO_3$ (46.7 g, 143 mmol) in dry DMF (150 mL) was stirred at 90° C. for 5 h. LCMS analysis showed consumption of the starting material and formation of the desired product. The mixture was cooled to 25° C., diluted with $H_2O$ (800 mL), and acidified to pH<7 by addition of 3 M aqueous HOAc. The resultant solid was collected by filtration. The filter cake was washed with $H_2O$ (3×100 mL) and then dried under vacuum. The crude product was slurried in EtOAc (60 mL) for 30 min and then filtered. The solid was collected by filtration and dried to afford 6,8-dichloro-2-(methylsulfanyl)pyrido[3,4-d]pyrimidin-4(3H)-one (207) (19.8 g, 74% yield) as a light yellow solid. $^1H$ NMR (400 MHz, DMSO-$d_6$) δ 13.27 (s, 1H), 7.94-7.83 (m, 1H), 2.62 (s, 3H). LCMS (ESI) m/z 262, 264 (M+H).

PREPARATION OF EXAMPLES

The following examples were prepared according to general method G:

Preparation of 1-[4-(6-chloro-8-[(5-chloro-6-fluoro-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one (Example 1G)

Step 1:

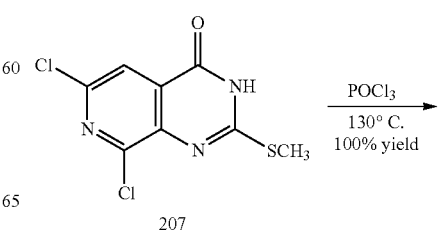

-continued

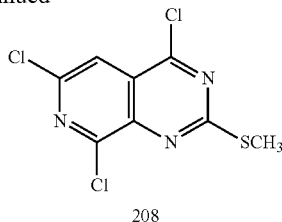

208

A mixture of 6,8-dichloro-2-(methylsulfanyl)pyrido[3,4-d]pyrimidin-4(3I-O-one (207) (10.0 g, 38 mmol) in POCl₃ (70 mL) was heated to 130° C. for 3 h. LCMS analysis showed consumption of the starting material. The mixture was cooled to 25° C. and the solvent was removed under reduced pressure to afford crude 4,6,8-trichloro-2-(methylsulfanyl)pyrido[3,4-d]pyrimidine (208) (11.0 g, 100% yield) as a yellow solid, which was used in the next step without further purification.

Step 2:

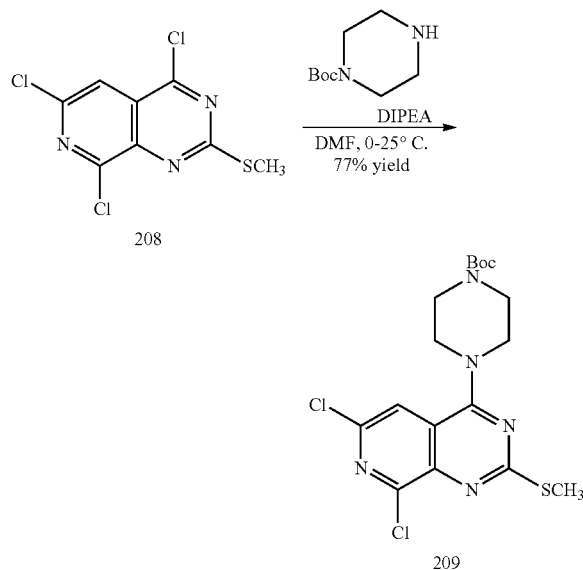

To a stirred suspension 4,6,8-trichloro-2-(methylsulfanyl) pyrido[3,4-d]pyrimidine (208) (10.7 g, 38.1 mmol) in dry DMF (60 mL) was added DIPEA (246 mg, 1.91 mmol) at 0° C., followed by tert-butyl piperazine-1-carboxylate (8.52 g, 45.8 mmol). The resultant mixture was stirred at 20-25° C. for 2 h. LCMS analysis showed consumption of the starting material. The mixture was diluted with H₂O (500 mL), stirred for 30 mins, and then filtered. The filter cake was dissolved in DCM (500 mL). The mixture was washed with H₂O (2×400 mL) and brine (400 mL), dried over Na₂SO₄, filtered, and concentrated to dryness. The residue was slurried with EtOAc (50 mL) for 1 h and then cooled to 0° C. The solid was collected by filtration and dried under vacuum to afford tert-butyl 4-[6,8-dichloro-2-(methylsulfanyl)pyrido[3,4-d]pyrimidin-4-yl]piperazine-1-carboxylate (209) (12.6 g, 76% yield) as a yellow solid. ¹H NMR (400 MHz, DMSO-d₆) δ 7.90 (s, 1H), 3.94-3.81 (m, 4H), 3.63-3.45 (m, 4H), 2.57 (s, 3H), 1.43 (s, 9H). LCMS (ESI) m/z 430, 432 (M+H).

Step 3:

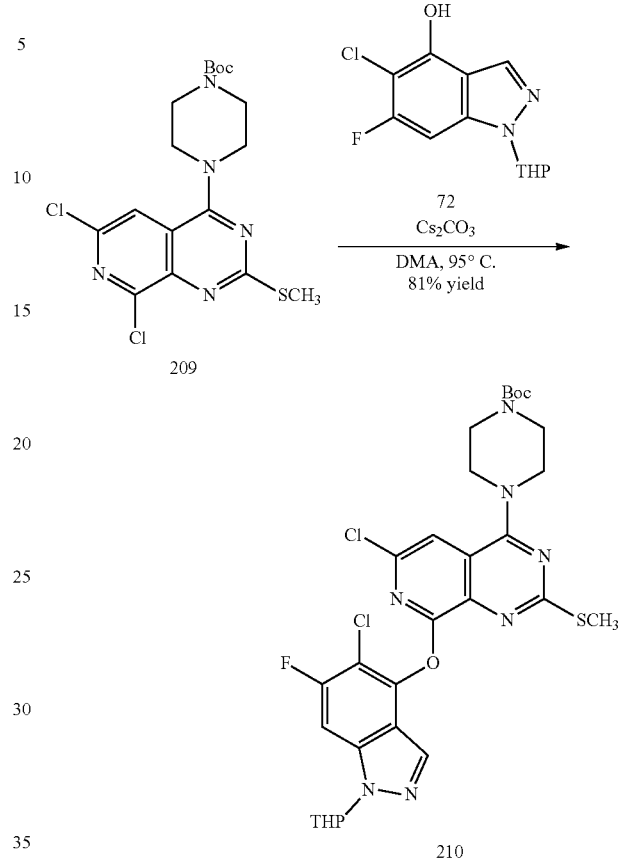

A mixture of 5-chloro-6-fluoro-1-(tetrahydro-2H-pyran-2-yl)-1H-indazol-4-ol (72) (4.19 g, 15.5 mmol), tert-butyl 4-[6,8-dichloro-2-(methylsulfanyl)pyrido[3,4-d]pyrimidin-4-yl]piperazine-1-carboxylate (209) (6.99 g, 16.3 mmol) and Cs₂CO₃ (7.57 g, 23.2 mmol) in dry DMA (50 mL) was heated to 95° C. for 16 h. LCMS analysis showed consumption of the starting material. The reaction was cooled to 25° C., diluted with H₂O (300 mL) and extracted with EtOAc (3×200 mL). The combined organics were washed with H₂O (2×200 mL) and brine (200 mL), dried over Na₂SO₄, and concentrated to dryness. The crude residue was purified by flash chromatography (SiO₂, 0-50% EtOAc/petroleum ether) to afford tert-butyl 4-[6-chloro-8-{[5-chloro-6-fluoro-1-(tetrahydro-2H-pyran-2-yl)-1H-indazol-4-yl]oxy}-2-(methylsulfanyl)pyrido[3,4-d]pyrimidin-4-yl]piperazine-1-carboxylate (210) (8.37 g, 81% yield) as a yellow solid. ¹H NMR (400 MHz, DMSO-d₆) δ 7.99 (s, 1H), 7.93 (dd, J=9.2, 0.7 Hz, 1H), 7.64 (s, 1H), 5.89 (dd, J=9.7, 2.2 Hz, 1H), 3.97-3.85 (m, 5H), 3.83-3.73 (m, 1H), 3.65-3.46 (m, 4H), 2.53 (s, 3H), 2.43-2.28 (m, 1H), 2.08-1.98 (m, 2H), 1.81-1.66 (m, 1H), 1.65-1.53 (m, 2H), 1.44 (s, 9H). LCMS (ESI) m/z 664, 666 (M+H).

Step 5:

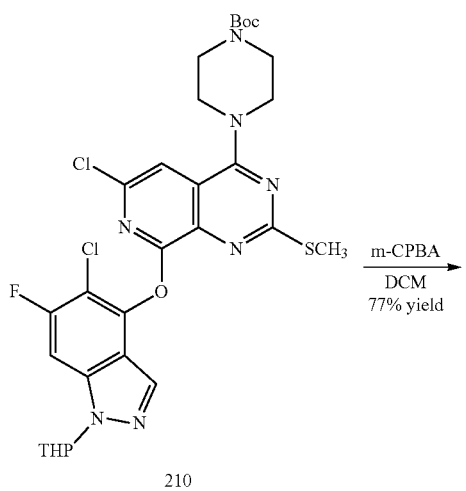

To a stirred solution tert-butyl 4-[6-chloro-8-{[5-chloro-6-fluoro-1-(tetrahydro-2H-pyran-2-yl)-1H-indazol-4-yl]oxy}-2-(methylsulfanyl)pyrido[3,4-d]pyrimidin-4-yl]piperazine-1-carboxylate (210) (9.33 g, 14 mmol) in DCM (100 mL) was added m-CPBA (7.7 mg, 37.9 mmol) portionwise at 25° C. The reaction was stirred at the same temperature for 5 h. LCMS analysis showed that the reaction was complete. The mixture was diluted with DCM (100 mL) and washed successively with saturated aqueous NaHCO₃ (200 mL), aqueous Na₂SO₃ (100 mL), and brine (100 mL). The combined organics were dried over Na₂SO₄ and concentrated to dryness. The crude product was purified by flash chromatography (SiO₂, 10-80% EtOAc/petroleum ether) to afford tert-butyl 4-[6-chloro-8-{[5-chloro-6-fluoro-1-(tetrahydro-2H-pyran-2-yl)-1H-indazol-4-yl]oxy}-2-(methylsulfonyl)pyrido[3,4-d]pyrimidin-4-yl]piperazine-1-carboxylate (211) (7.5 g, 77% yield) as a yellow solid. ¹H NMR (400 MHz, DMSO-d₆) δ 8.04 (s, 1H), 7.98 (d, J=9.2 Hz, 1H), 7.83 (s, 1H), 5.91 (dd, J=9.7, 2.0 Hz, 1H), 4.14-3.98 (m, 4H), 3.95-3.86 (m, 1H), 3.85-3.74 (m, 1H), 3.68-3.50 (m, 4H), 3.42 (s, 3H), 2.44-2.28 (m, 1H), 2.10-1.96 (m, 2H), 1.80-1.66 (m, 1H), 1.64-1.53 (m, 2H), 1.44 (s, 9H). LCMS (ESI) m/z 696, 698 (M+H).

Step 6:

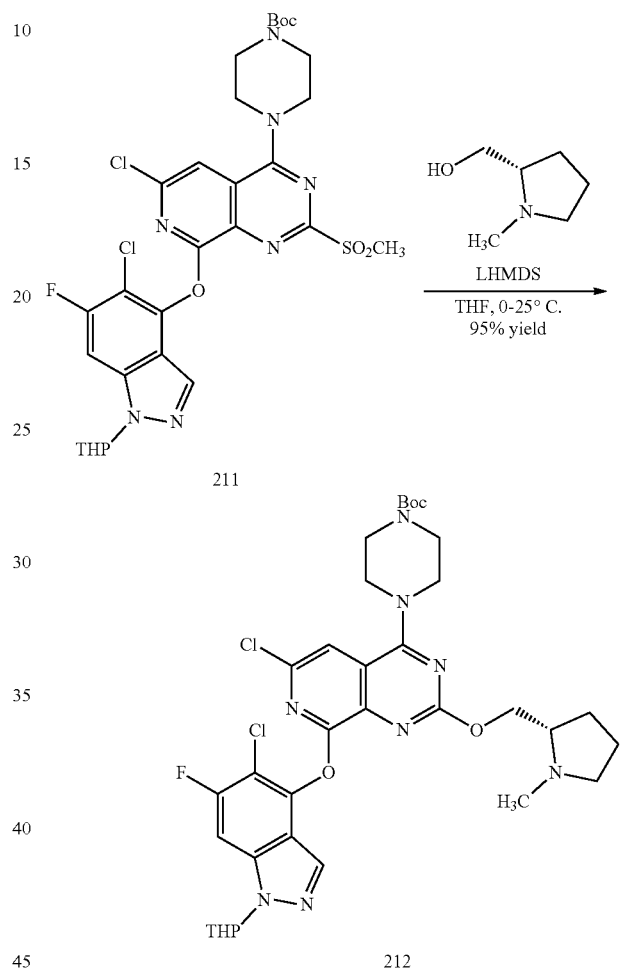

To a solution of tert-butyl 4-[6-chloro-8-{[5-chloro-6-fluoro-1-(tetrahydro-2H-pyran-2-yl)-1H-indazol-4-yl]oxy}-2-(methylsulfonyl)pyrido[3,4-d]pyrimidin-4-yl]piperazine-1-carboxylate (211) (200 mg, 0.287 mmol) and (S)-(1-methylpyrrolidin-2-yl)methanol (165 mg, 1.44 mmol) in THF (3 mL) was added LiHMDS (1.0 M in THF, 0.373 mL, 0.373 mmol) at 0° C. and the mixture was stirred at rt for 1 h. LCMS analysis showed the reaction was complete. The reaction was quenched by the addition of saturated aqueous NH₄Cl. The mixture was extracted with EtOAc (3×30 mL). The combined organics were dried over Na₂SO₄ and concentrated to dryness. The crude residue was purified by flash chromatography (SiO₂, 0-10% MeOH/DCM) to provide tert-butyl 4-(6-chloro-8-{[5-chloro-6-fluoro-1-(tetrahydro-2H-pyran-2-yl)-1H-indazol-4-yl]oxy}-2-{[(2S)-1-methyl-pyrrolidin-2-yl]methoxy}pyrido[3,4-d]pyrimidin-4-yl)piperazine-1-carboxylate (212) (200 mg, 95% yield) as a yellow solid. LCMS (ESI) m/z 731, 733 (M+H).

Step 7:

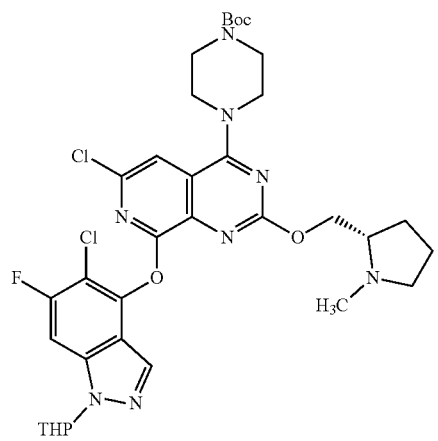

212

Step 8:

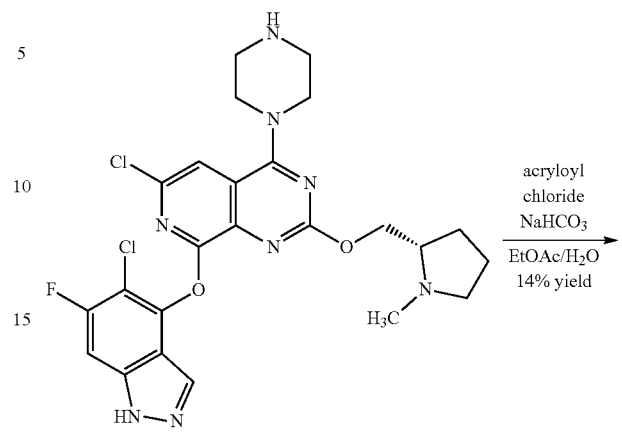

213

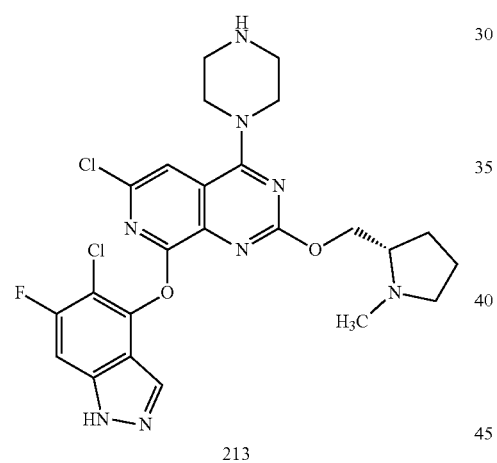

213

To a mixture of tert-butyl 4-(6-chloro-8-{[5-chloro-6-fluoro-1-(tetrahydro-2H-pyran-2-yl)-1H-indazol-4-yl]oxy}-2-{[(2S)-1-methylpyrrolidin-2-yl]methoxy}pyrido[3,4-d]pyrimidin-4-yl)piperazine-1-carboxylate (212) (200 mg, 0.237 mmol) in DCM (2 mL) was added a solution of HCl (2 mL, 4.0 M in 1,4-dioxane). The resulting mixture was stirred at ambient temperature for 4 h. LCMS analysis showed complete consumption of the starting material. The mixture was concentrated to dryness to provide 6-chloro-8-[(5-chloro-6-fluoro-1H-indazol-4-yl)oxy]-2-{[(2S)-1-methylpyrrolidin-2-yl]methoxy}-4-(piperazin-1-yl)pyrido[3,4-d]pyrimidine (213) (150 mg, 100% yield) as a yellow solid, which was taken on without further purification. LCMS (ESI) m/z 547, 549 (M+H).

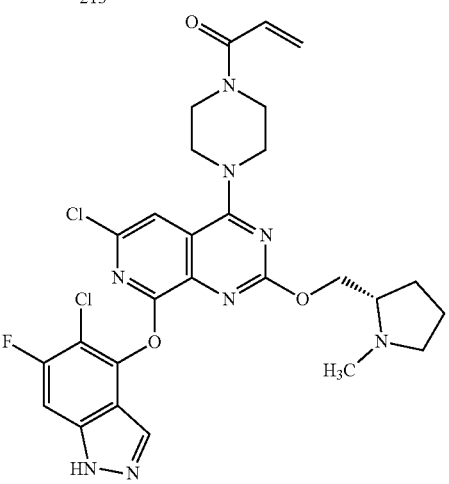

Example-1G

To a solution of 6-chloro-8-[(5-chloro-6-fluoro-1H-indazol-4-yl)oxy]-2-{[(2S)-1-methylpyrrolidin-2-yl]methoxy}-4-(piperazin-1-yl)pyrido[3,4-d]pyrimidine (213) (150 mg, 0.274 mmol) in EtOAc (20 mL) and saturated aqueous NaHCO$_3$ (20 mL) was added acryloyl chloride (37.2 mg, 0.41 mmol) and the mixture was stirred at rt for 30 min. LCMS analysis showed conversion to the product. The mixture was extracted with EtOAc (3×20 mL) and the combined organics were dried over Na$_2$SO$_4$, filtered and concentrated. The residue was purified by Prep-HPLC (column: Gemini-C 18; 100×21.2 mm, 5 μm; mobile phase: ACN-H$_2$O (0.1% FA); gradient: 15-25% ACN; flowrate: 25 mL/min) to afford 6-chloro-8-[(5-chloro-6-fluoro-1H-indazol-4-yl)oxy]-2-{[(2S)-1-methylpyrrolidin-2-yl]methoxy}-4-(piperazin-1-yl)pyrido[3,4-d]pyrimidine (Example-1G) (23 mg, 14% yield) as a white solid. $^1$H NMR (400 MHz, DMSO-d$_6$) δ 13.63 (s, 1H), 7.88 (s, 1H), 7.73 (s, 1H), 7.64 (d, J=8.7 Hz, 1H), 6.82 (dd, J=16.7, 10.4 Hz, 1H), 6.18 (dd, J=16.7, 2.4 Hz, 1H), 5.76 (dd, J=10.4, 2.4 Hz, 1H), 4.86-4.43 (m, 2H), 4.07-3.90 (m, 4H), 3.90-3.69 (m, 5H), 3.16-3.05 (m, 1H), 2.93 (s, 3H), 2.58-2.47 (m, 1H), 2.24 (s, 1H), 2.09-1.78 (m, 3H). LCMS (ESI) m/z 601, 603 (M+H).

363

Preparation of 1-{4-(4-acryloylpiperazin-1-yl)-6-chloro-8-[(5-chloro-6-fluoro-1H-indazol-4-yl)oxy]pyrido[3,4-d]pyrimidin-2-yl}-3-methylazetidine-3-carbonitrile (Example 2G)

Step 1:

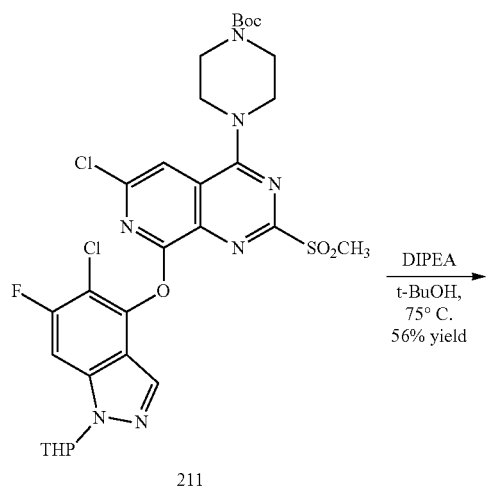

A slurry of tert-butyl 4-[6-chloro-8-{[5-chloro-6-fluoro-1-(tetrahydro-2H-pyran-2-yl)-1H-indazol-4-yl]oxy}-2-(methylsulfonyl)pyrido[3,4-d]pyrimidin-4-yl]piperazine-1-carboxylate (211) (900 mg, 1.29 mmol), 3-cyano-3-methylazetidinium chloride (343 mg, 2.58 mmol), and DIPEA (668 mg, 5.17 mmol, 0.900 mL) in t-BuOH (12.9 mL, c=0.1 M) was heated to 75° C. in a sealed 20 dram vial for 1 hr. LCMS analysis showed formation of the product. The solvent was removed in vacuo. The residue was diluted with EtOAc and water. The organic phase was washed with brine and concentrated to dryness. The residue was purified by flash chromatography (ISCO, 24 g SiO$_2$, 20-60% EtOAc/heptane) to provide tert-butyl 4-[6-chloro-8-{[5-chloro-6-fluoro-1-(tetrahydro-2H-pyran-2-yl)-1H-indazol-4-yl]oxy}-2-(3-cyano-3-methylazetidin-1-yl)pyrido[3,4-d]pyrimidin-

364

4-yl]piperazine-1-carboxylate (214) (519 mg, 56% yield) as a pale solid. LCMS (APCI) m/z 712 (M+H).

Step 2:

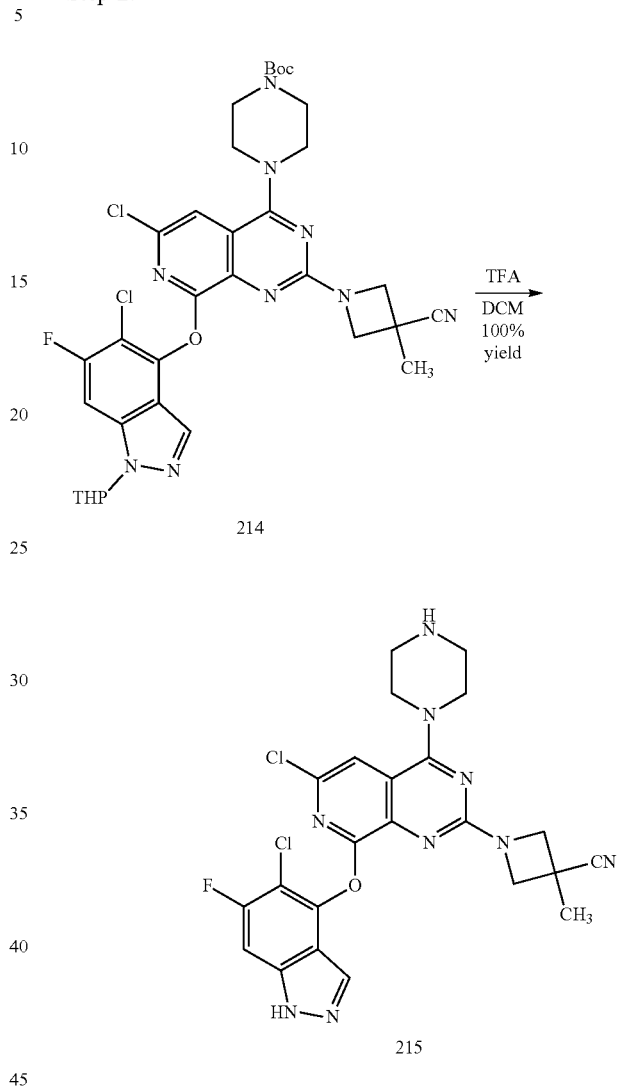

To a solution of tert-butyl 4-[6-chloro-8-{[5-chloro-6-fluoro-1-(tetrahydro-2H-pyran-2-yl)-1H-indazol-4-yl]oxy}-2-(3-cyano-3-methylazetidin-1-yl)pyrido[3,4-d]pyrimidin-4-yl]piperazine-1-carboxylate (214) (100 mg, 0.140 mmol) in DCM (0.52 mL) was added TFA (708 mg, 6.31 mmol, 0.475 mL) to provide a brown solution, which was stirred at room temperature for 40 min. LCMS analysis showed conversion to the product. The reaction mixture was concentrated to dryness. The resultant solid was slurried with MTBE and then centrifuged. The solvent was decanted and the solid was dried provide 1-{6-chloro-8-[(5-chloro-6-fluoro-1H-indazol-4-yl)oxy]-4-(piperazin-1-yl)pyrido[3,4-d]pyrimidin-2-yl}-3-methylazetidine-3-carbonitrile (215) (131 mg, 100% yield) as a pale solid. LCMS (APCI) m/z 561 (M+H).

Step 3:

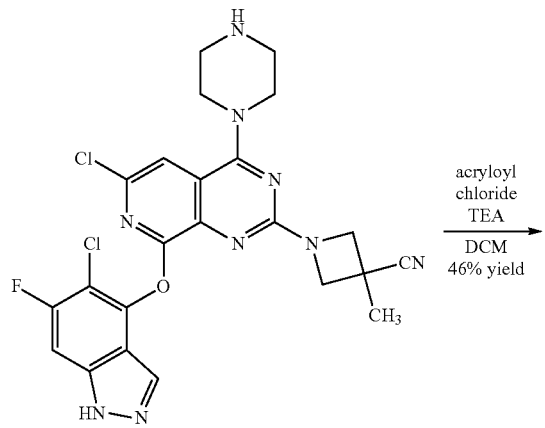

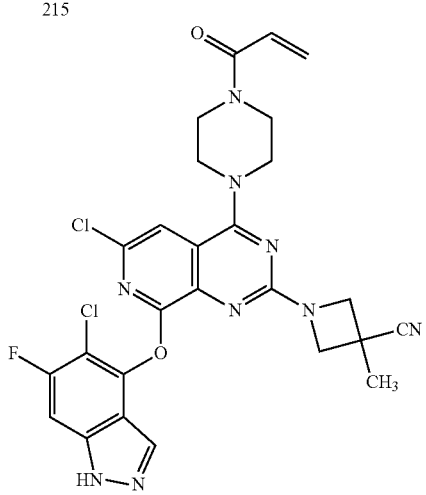

Example-2G

To a solution of 1-{6-chloro-8-[(5-chloro-6-fluoro-1H-indazol-4-yl)oxy]-4-(piperazin-1-yl)pyrido[3,4-d]pyrimidin-2-yl}-3-methylazetidine-3-carbonitrile (215) (74.0 mg, 0.140 mmol) and triethylamine (46.8 mg, 0.46 mmol, 64 µL) in DCM (1 mL) was added a solution of acryloyl chloride (12.7 mg, 0.140 mmol, 11.4 µL) in DCM (0.3 mL) at −65° C. The temperature was raised to −10° C. over 1.5 h. LCMS analysis showed conversion to the desired product with trace amounts of remaining starting material. The reaction was concentrated to dryness. The residue was purified by reverse phase preparatory HPLC on an ISCO ACCQPrep HP-125 system with a Phenomenex Luna Omega Polar C18 column (21×250 mm, 5 µm particle size) with a flow rate of 35 mL/min and a 25 min gradient of 30-75% MeCN/water (+1% AcOH). The collected fractions were dried on a lyophilizer to provide of 1-{4-(4-acryloylpiperazin-1-yl)-6-chloro-8-[(5-chloro-6-fluoro-1H-indazol-4-yl)oxy]pyrido[3,4-d]pyrimidin-2-yl}-3-methylazetidine-3-carbonitrile (Example-2G) as a pale cotton (32.1 mg, 46% yield). ¹H NMR (400 MHz, DMSO-d$_6$) δ 13.55 (br. s, 1H), 7.86 (s, 1H), 7.59 (dd, J=8.9, 0.9 Hz, 1H), 7.53 (s, 1H), 6.82 (dd, J=16.7, 10.45 Hz, 1H), 6.17 (dd, J=16.7, 2.4 Hz, 1H), 5.69-5.77 (m, 1H), 4.41 (d, J=8.9 Hz, 2H), 4.09 (d, J=9.0 Hz, 2H), 3.79-3.90 (m, 5H), 3.75 (d, J=5.0 Hz, 3H), 1.67 (s, 3H). LCMS (ESI) m/z 582 (M+H).

Preparation of 1-[4-(6-chloro-8-[(5,6-dichloro-1H-indazol-4-yl)oxy]-2-{[(3R,4R)-4-methoxy-1-methyl-pyrrolidin-3-yl]oxy}pyrido[3,4-d]pyrimidin-4-yl)piperazin-1-yl]prop-2-en-1-one (Example 29G)

Step 1:

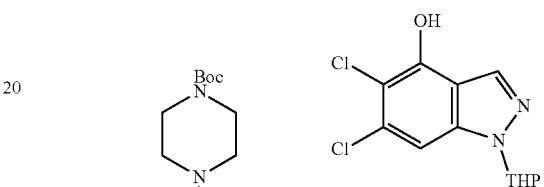
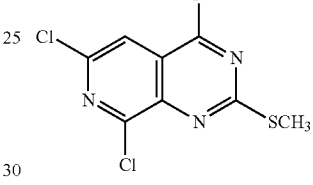

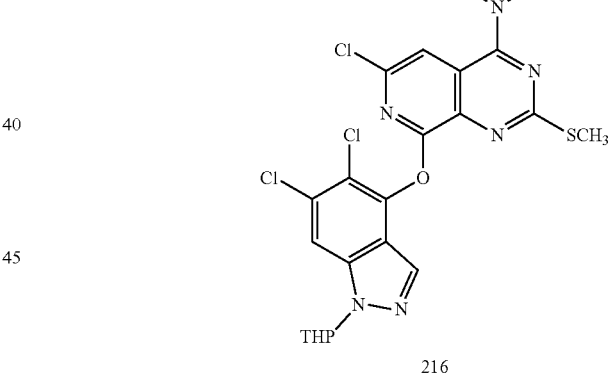

To a vial was added tert-butyl 4-[6,8-dichloro-2-(methyl-sulfanyl)pyrido[3,4-d]pyrimidin-4-yl]piperazine-1-carboxylate (209), 5,6-dichloro-1-(oxan-2-yl)-1H-indazol-4-ol (153), Cs$_2$CO$_3$ (2.18 g, 6.69 mmol), and DMA (12.1 mL). The mixture was degassed with nitrogen and then stirred overnight at 90° C. LCMS analysis showed consumption of the starting material with formation of the product. The reaction mixture was cooled to room temperature and water was added. The resultant precipitate was collected by filtration. The filter cake was washed thoroughly with water and then dried overnight at 50° C. under vacuum to provide tert-butyl 4-[6-chloro-8-{[5,6-dichloro-1-(oxan-2-yl)-1H-indazol-4-yl]oxy}-2-(methylsulfanyl)pyrido[3,4-d]pyrimidin-4-yl]piperazine-1-carboxylate (216) (2.33 g, 77% yield) as an off-white solid that was taken on directly to the next step without further purification. LCMS (ESI) m/z 680 (M+H).

Step 2:

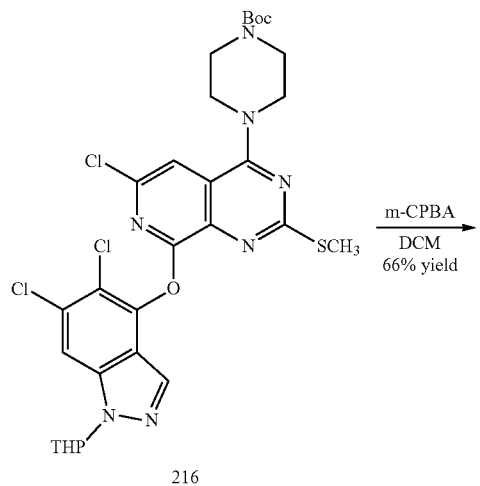

To a solution of tert-butyl 4-[6-chloro-8-{[5,6-dichloro-1-(oxan-2-yl)-1H-indazol-4-yl]oxy}-2-(methylsulfanyl)pyrido[3,4-d]pyrimidin-4-yl]piperazine-1-carboxylate (216) (700 mg, 1.03 mmol) in DCM (20.6 mL) was added m-CPBA (622 mg, 2.78 mmol). The mixture was stirred at room temperature for 2.5 h. LCMS analysis showed consumption of the starting material with formation of the desired product. The mixture was washed with saturated aqueous NaHCO₃. The combined organics were dried over Na₂SO₄, filtered, and concentrated. Purification by flash chromatography (ISCO, 12 g SiO₂, 40-80% EtOAc/heptanes) provided tert-butyl 4-[6-chloro-8-{[5,6-dichloro-1-(oxan-2-yl)-1H-indazol-4-yl]oxy}-2-(methanesulfonyl)pyrido[3,4-d]pyrimidin-4-yl]piperazine-1-carboxylate (217) (480 mg, 66% yield) as a pale solid. ¹H NMR (400 MHz, DMSO-d₆) δ 8.23 (s, 1H), 8.06 (s, 1H), 7.82 (s, 1H), 5.97 (d, J=9.7 Hz, 1H), 4.03-4.12 (m, 4H), 3.87-3.95 (m, 1H), 3.77-3.86 (m, 1H), 3.59 (br. s, 4H), 3.42 (s, 3H), 2.28-2.43 (m, 1H), 2.03 (d, J=11.0 Hz, 2H), 1.66-1.81 (m, 1H), 1.54-1.63 (m, 2H), 1.44 (s, 9H). LCMS (ESI) m/z 712 (M+H).

Step 3:

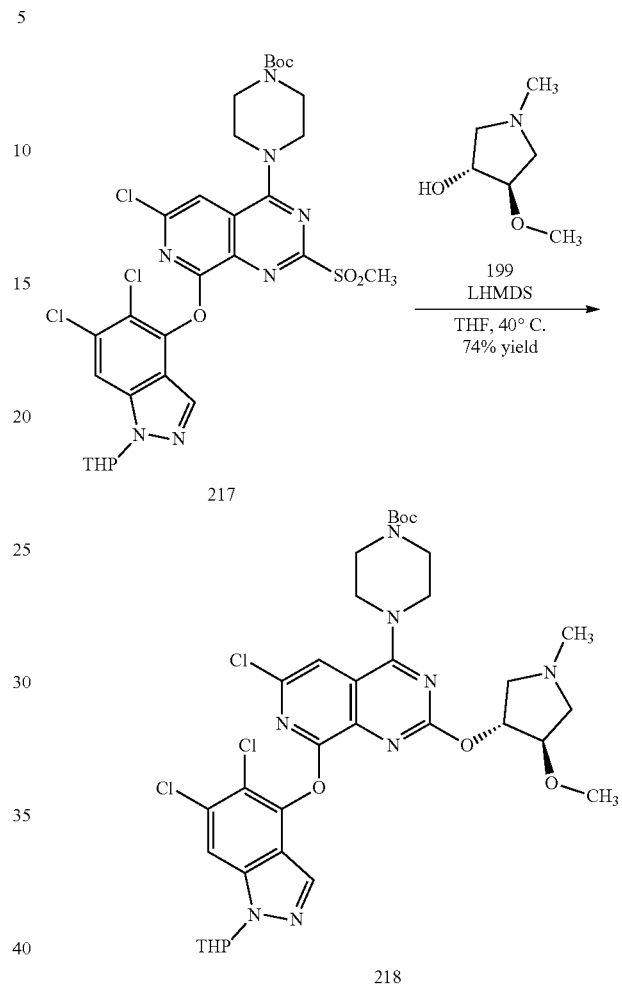

To a solution of tert-butyl 4-[6-chloro-8-{[5,6-dichloro-1-(oxan-2-yl)-1H-indazol-4-yl]oxy}-2-(methanesulfonyl)pyrido[3,4-d]pyrimidin-4-yl]piperazine-1-carboxylate (217) (1.57 g, 2.2 mmol) and (3R,4R)-4-methoxy-1-methylpyrrolidin-3-ol (199) (491 mg, 3.74 mmol) in THF was added LHMDS (3.74 mL, 3.74 mmol, 1.0 M in THF). The resulting red solution was stirred at 40° C. for 20 min. LCMS analysis showed consumption of the product. The reaction was diluted with EtOAc (40 mL) and water (15 mL). The layers were separated. The aqueous layer was extracted with EtOAc (40 mL). The combined organics were dried over Na₂SO₄, filtered and concentrated. The residue was purified by flash chromatography (ISCO, 40 g SiO₂, 10% EtOH/EtOAc) to provide tert-butyl 4-(6-chloro-8-{[5,6-dichloro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (218) (1.24 g, 72% yield). ¹H NMR (400 MHz, DMSO-d₆) δ 8.18 (s, 1H), 7.94 (d, J=4.5 Hz, 1H), 7.66 (s, 1H), 5.95 (dd, J=9.7, 2.1 Hz, 1H), 5.18-5.25 (m, 1H), 3.93-3.98 (m, 1H), 3.88 (br. s, 5H), 3.75-3.84 (m, 1H), 3.56 (br. s, 4H), 3.33 (s, 3H), 3.01 (dd, J=9.7, 6.5 Hz, 1H), 2.78-2.88 (m, 1H), 2.59-2.66 (m, 1H), 2.25-2.41 (m, 2H), 2.22 (s, 3H), 2.01 (d, J=8.0 Hz, 2H), 1.66-1.80 (m, 1H), 1.59 (d, J=4.0 Hz, 2H) 1.44 (s, 9H). LCMS (ESI) m/z 763 (M+H).

Step 4:

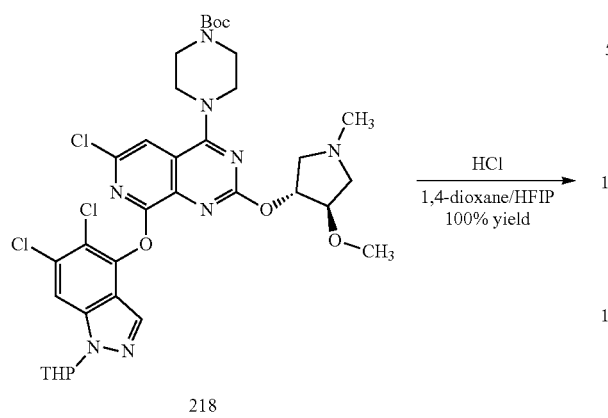
218

Step 5:

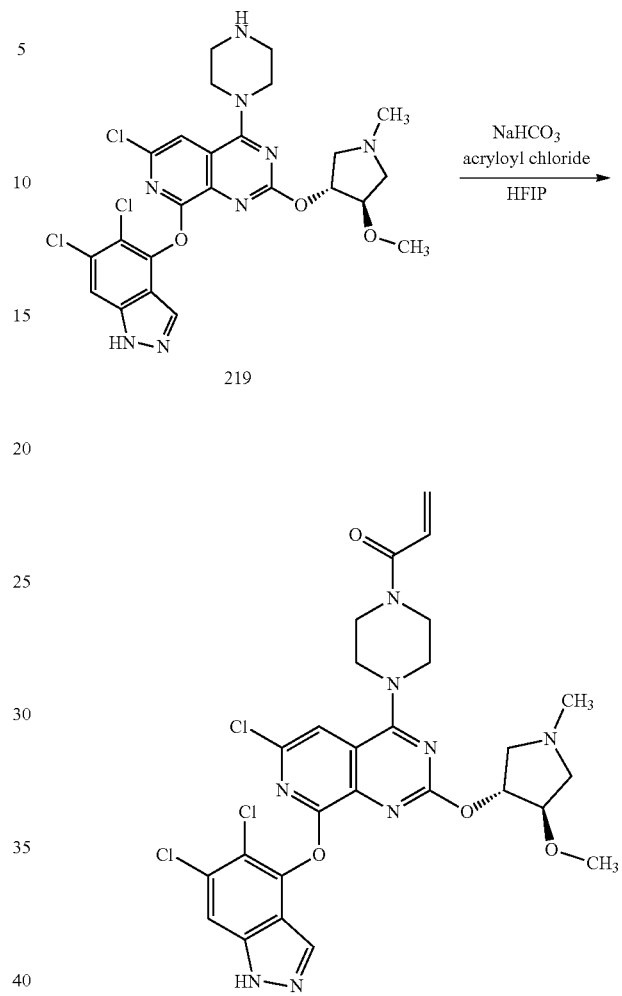

A solution of tert-butyl 4-(6-chloro-8-{[5,6-dichloro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (218) in HFIP was cooled to 0° C. with an ice bath and a solution of HCl (0.33 mL, 1.31 mmol, 4.0 N in 1,4-dioxane) was added. The solution was stirred for a further 10 min at 0° C. to provide an orange solution, which was allowed to warm to room temperature. After 1 h, LCMS analysis showed conversion to the product. The crude reaction mixture was cooled to 0° C. MTBE (5 mL) was slowly added to give a white precipitate. The solvent was removed under reduced pressure. Additional MTBE (5 mL) was added and the mixture was concentrated to provide 6-chloro-8-[(5,6-dichloro-1H-indazol-4-yl)oxy]-2-{[(3R,4R)-4-methoxy-1-methylpyrrolidin-3-yl]oxy}-4-(piperazin-1-yl)pyrido[3,4-d]pyrimidine (219) (90 mg, 100% yield) as an orange solid, which was taken on without further purification. LCMS (ESI) m/z 579 (M+H).

To a slurry of 6-chloro-8-[(5,6-dichloro-1H-indazol-4-yl)oxy]-2-{[(3R,4R)-4-methoxy-1-methylpyrrolidin-3-yl]oxy}-4-(piperazin-1-yl)pyrido[3,4-d]pyrimidine (219) (89.6 mg, 0.13 mmol) in HFIP (1.3 ml) was added $NaHCO_3$(109 mg, 1.3 mmol). The resultant suspension was stirred for 15 h overnight to provide a brown solution. Acryoyl chloride (11 μl, 0.13 mmol) was added. After 5 minutes LCMS analysis showed conversion to the product. The reaction mixture was filtered to remove insolubles. The filter cake was washed with EtOAc. The combined organics were concentrated to dryness. The residue was purified by flash chromatography (Biotage, 10 g $SiO_2$, 2-10% MeOH/DCM+ 0.1% $NH_3$) to provide 1-[4-(6-chloro-8-[(5,6-dichloro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-29G) (37 mg, 45% yield) as a white solid. $^1$H NMR (400 MHz, DMSO-$d_6$) δ 13.63 (br. s, 1H), 7.87 (s, 1H), 7.86 (s, 1H), 7.68 (s, 1H), 6.82 (dd, J=16.6, 10.4 Hz, 1H), 6.18 (dd, J=17.1, 1.4 Hz, 1H), 5.75 (dd, J=10.0, 2.1 Hz, 1H), 5.12-5.26 (m, 1H), 3.95 (br. s, 5H), 3.69-3.87 (m, 4H), 3.33 (s, 3H), 2.93-3.05 (m, 1H), 2.81-2.84 (m, 1H), 2.58-2.71 (m, 1H), 2.25-2.34 (m, 1H), 2.15-2.24 (m, 3H). LCMS (ESI) m/z 633 (M+H).

Preparation of 1-[4-(6-chloro-8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example 24G)

Step 1:

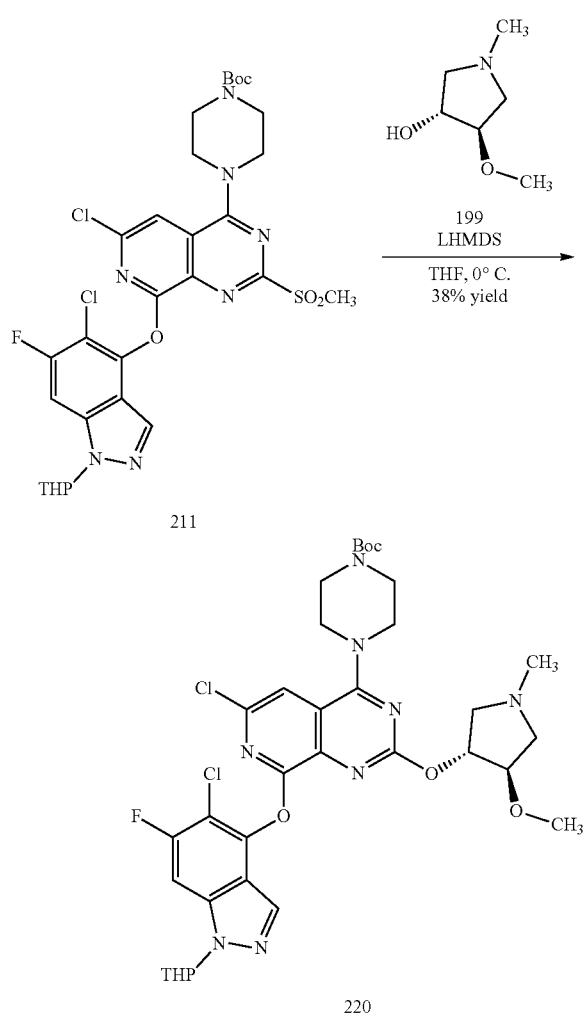

Step 2:

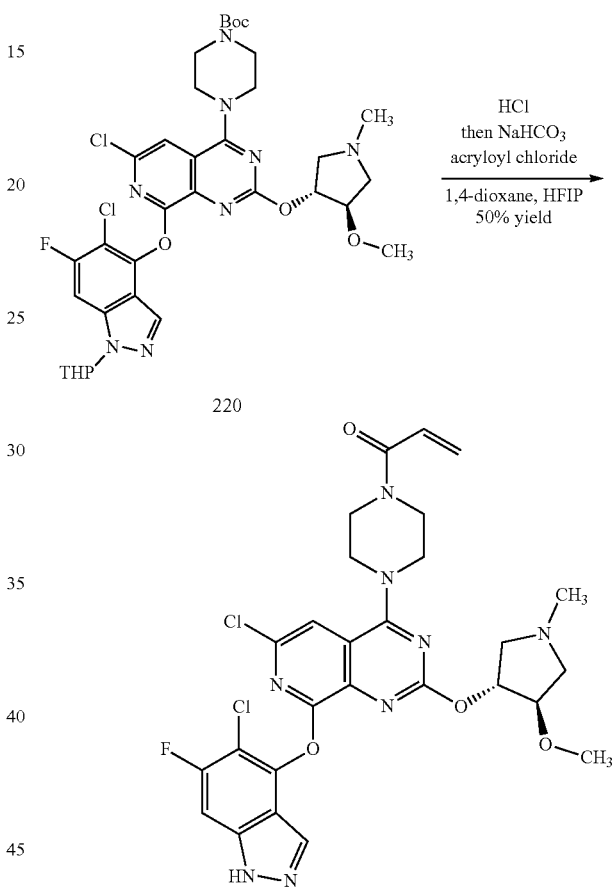

Example-24G pyrimidin-4-yl)piperazine-1-carboxylate (220) (6.9 g, 38% yield) as a yellow oil which was azeotroped with $Et_2O$ to provide an off-white solid. $^1H$ NMR (400 MHz, DMSO-$d_6$) δ 7.96-7.87 (m, 2H), 7.70-7.57 (m, 1H), 5.89 (dd, J=2.2, 9.7 Hz, 1H), 5.28-5.08 (m, 1H), 4.01-3.92 (m, 1H), 3.88 (t, J=4.8 Hz, 5H), 3.82-3.74 (m, 1H), 3.61-3.50 (m, 4H), 3.33 (s, 3H), 3.00 (dd, J=6.5, 9.7 Hz, 1H), 2.88-2.79 (m, 1H), 2.67-2.57 (m, 1H), 2.41-2.26 (m, 2H), 2.21 (s, 3H), 2.10-1.94 (m, 2H), 1.81-1.66 (m, 1H), 1.64-1.54 (m, 2H), 1.44 (s, 9H). LCMS (ESI) m/z 747 (M+H).

A solution of (3R,4R)-4-methoxy-1-methylpyrrolidin-3-ol (199) (3.2 g, 24.4 mmol) in THF (25 mL) was cooled to 0° C. with an ice bath. A solution of LHMDS (1.0 M in THF, 24.4 mL, 24.4 mmol) was added dropwise to provide a light yellow solution. After 30 min at 0° C. the solution was added dropwise to a solution of tert-butyl 4-[6-chloro-8-{[5-chloro-6-fluoro-1-(oxan-2-yl)-1H-indazol-4-yl]oxy}-2-(methanesulfonyl)pyrido[3,4-d]pyrimidin-4-yl]piperazine-1-carboxylate (211) (12.8 g, 18.8 mmol) in THF (50 mL) at 0° C. under nitrogen. The resultant red solution was stirred for 15 min at the same temperature. LCMS analysis indicated complete consumption of the starting material. The mixture was diluted with EtOAc and washed with water and brine. The combined organics were dried over $Na_2SO_4$, filtered, and concentrated. The residue was purified by flash chromatography (ISCO, 300 g $SiO_2$, 100:0:0-95:5:2 DCM: MeOH:TEA) to provide tert-butyl 4-(6-chloro-8-{[5-chloro-6-fluoro-1-(oxan-2-yl)-1H-indazol-4-yl]oxy}-2-{[(3R,4R)-4-methoxy-1-methylpyrrolidin-3-yl]oxy}pyrido[3,4-d]

A solution of tert-butyl 4-(6-chloro-8-{[5-chloro-6-fluoro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (220) (50 mg, 0.07 mmol) in HFIP (0.7 mL) was cooled to 0° C. A solution of HCl (4 M in 1,4-dioxane, 0.1 mL, 0.4 mmol) was added to provide a yellow solution. After 10 min at 0° C. the orange solution was allowed to warm to room temperature. After 1 h, LCMS analysis showed residual starting material. Additional HCl (4 M in 1,4-dioxane, 0.05 mL) was added. After stirring a further 30 min LCMS analysis indicated consumption of the starting material. Solid $NaHCO_3$ (70.6 mg, 12 mmol) was added and the mixture was stirred for 18 h overnight. Acryloyl chloride (0.006 mL, 0.07 mmol) was added. After 5 min the reaction was diluted with EtOAc (20 mL) and water (20 mL). The layers were separated and the aqueous layer was extracted with EtOAc (20 mL). The combined organics were washed with brine, dried over MgSO₄, filtered, and concentrated. The residue was purified by flash chromatography (Biotage, 10 g SiO₂, 2-10% MeOH/DCM+0.1% NH₄OH) to provide 1-[4-(6-chloro-8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example 24G) (20 mg, 50% yield) as a white solid. ¹H NMR (400 MHz, DMSO-d₆) δ 2.17-2.27 (m, 3H), 2.27-2.34 (m, 1H), 2.63 (dd, J=10.6, 2.9 Hz, 1H), 2.81-2.86 (m, 1H), 2.99-3.03 (m, 1H), 3.33 (s, 3H), 3.75 (br. s, 2H), 3.84 (br. s, 2H), 3.95 (br. s, 5H), 5.11-5.32 (m, 1H), 5.75 (dd, J=10.5, 2.5 Hz, 1H), 6.18 (dd, J=16.7, 2.4 Hz, 1H), 6.82 (dd, J=16.7, 10.4 Hz, 1H), 7.61 (d, J=8.9 Hz, 1H), 7.69 (s, 1H), 7.84 (s, 1H), 13.59 (br. s, 1H). LCMS (ESI) m/z 617 (M+H).

The examples in the following table were prepared using Method G and the procedure used to prepare 6-chloro-8-[(5-chloro-6-fluoro-1H-indazol-4-yl)oxy]-2-{[(2S)-1-methylpyrrolidin-2-yl]methoxy}-4-(piperazin-1-yl)pyrido[3,4-d]pyrimidine (Example-1G), 1-{4-(4-acryloylpiperazin-1-yl)-6-chloro-8-[(5-chloro-6-fluoro-1H-indazol-4-yl)oxy]pyrido[3,4-d]pyrimidin-2-yl}-3-methylazetidine-3-carbonitrile (Example-2G), 1-[4-(6-chloro-8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-24G), and 1-[4-(6-chloro-8-[(5,6-dichloro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-29G). The following examples were made with non-critical changes or substitutions to the exemplified procedure used to prepare Example-1G, Example-2G, Example-24G, and Example-29G that someone who is skilled in the art would be able to realize.

| Example | Structure | Compound Name | LCMS m/z | ¹H NMR |
|---|---|---|---|---|
| 3G | 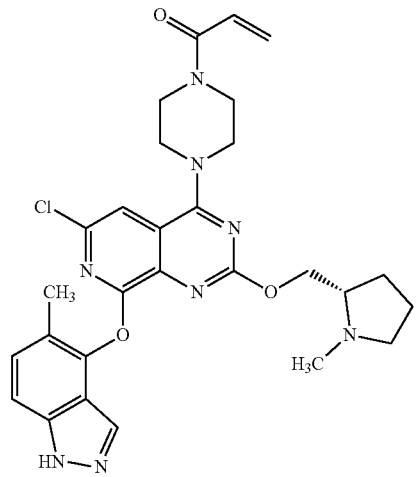 [SMILES: C=CC(=O)N1CCN(c2nc(OC[C@@H]3CCCN3C)nc3c(Oc4c(C)ccc5[nH]ncc45)nc(Cl)cc23)CC1] | 1-[4-(6-chloro-8-[(5-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 563 (M + H) | ¹H NMR (400 MHz, DMSO-d₆) δ 13.18 (s, 1H), 7.61 (d, J = 34.0 Hz, 2H), 7.37 (dd, J = 31.0, 7.3 Hz, 2H), 6.83 (dd, J = 16.7, 10.2 Hz, 1H), 6.18 (d, J = 16.7 Hz, 1H), 5.75 (d, J = 10.5 Hz, 1H), 4.50-4.34 (m, 1H), 4.33-4.14 (m, 1H), 4.01-3.69 (m, 8H), 3.09-2.91 (m, 1H), 2.69-2.61 (m, 1H), 2.38 (s, 3H), 2.30-2.13 (m, 4H), 2.05-1.88 (m, 1H), 1.82-1.52 (m, 3H) |
| 4G | 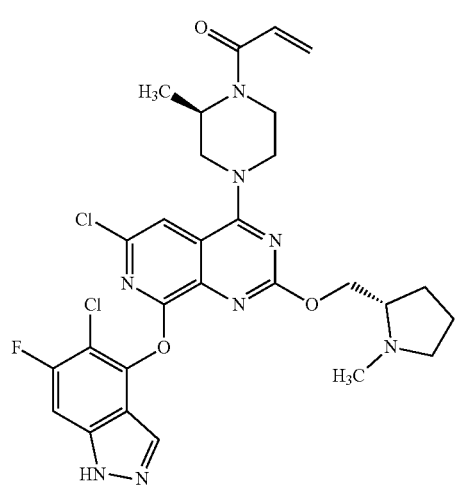 [SMILES: C=CC(=O)N1CCN(c2nc(OC[C@@H]3CCCN3C)nc3c(Oc4c(Cl)c(F)cc5[nH]ncc45)nc(Cl)cc23)C[C@H]1C] | 1-[(2R)-4-(6-chloro-8-[(5-chloro-6-fluoro-1H-indazol-4-yl)oxy]-2-{[(2S)-1-methylpyrrolidin-2-yl]methoxy}pyrido[3,4-d]pyrimidin-4-yl)-2-methylpiperazin-1-yl]prop-2-en-1-one | 615 (M + H) | ¹H NMR (600 MHz, DMSO-d₆) δ 7.85-7.74 (m, 1H), 7.63 (s, 1H), 7.58-7.48 (m, 1H), 6.73 (dd, J = 10.5, 16.7 Hz, 1H), 6.12 (d, J = 15.1 Hz, 1H), 5.68 (d, J = 7.5 Hz, 1H), 4.65-4.38 (m, 1H), 4.34-4.22 (m, 2H), 4.21-3.98 (m, 2H), 3.75 (d, J = 13.4 Hz, 1H), 2.95-2.81 (m, 1H), 2.56-2.50 (m, 1H), 2.48-2.42 (m, 3H), 2.36-2.24 (m, 3H), 2.16-2.06 (m, 1H), 1.99-1.83 (m, 1H), 1.73-1.51 (m, 3H), 1.18 (br. s, 4H) |

| Example | Structure | Compound Name | LCMS m/z | ¹H NMR |
|---|---|---|---|---|
| 5G | 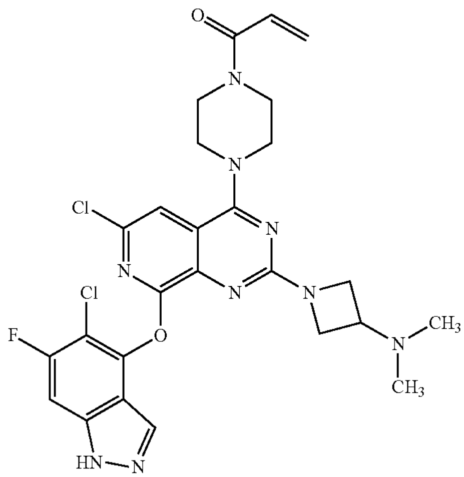 [SMILES: C=CC(=O)N1CCN(c2nc(N3CC(N(C)C)C3)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-[3-(dimethylamino)azetidin-1-yl]pyrido[3,4-d]pyrimidin-4-yl}piperazin-1-yl)prop-2-en-1-one | 586 (M + H) | ¹H NMR (400 MHz, DMSO-d₆) δ 8.52 (s, 1H), 7.86 (s, 1H), 7.61 (d, J = 8.8 Hz, 1H), 7.49 (s, 1H), 6.83 (dd, J = 16.7, 10.4 Hz, 1H), 6.17 (dd, J = 16.7, 2.4 Hz, 1H), 5.74 (dd, J = 10.4, 2.4 Hz, 1H), 4.11 (t, J = 8.0 Hz, 2H), 3.98-3.68 (m, 10H), 3.14 (td, J = 12.6, 11.2, 5.2 Hz, 1H), 2.12 (s, 6H). |
| 6G | 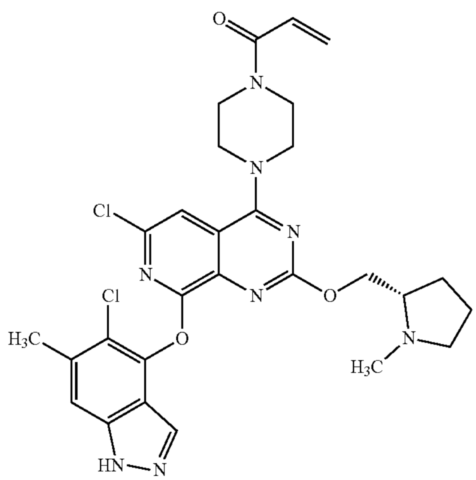 [SMILES: C=CC(=O)N1CCN(c2nc(OC[C@@H]3CCCN3C)nc3c(Oc4c(Cl)c(C)cc5[nH]ncc45)nc(Cl)cc23)CC1] | 1-[4-(6-chloro-8-[(5-chloro-6-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 597 (M + H) | ¹H NMR (400 MHz, DMSO-d₆) δ 13.36 (s, 1H), 7.76 (s, 1H), 7.64 (s, 1H), 7.52 (s, 1H), 6.83 (dd, J = 16.7, 10.4 Hz, 1H), 6.18 (dd, J = 16.7, 2.4 Hz, 1H), 5.75 (dd, J = 10.3, 2.5 Hz, 1H), 4.61-4.20 (m, 2H), 4.20-3.67 (m, 9H), 3.19-2.96 (m, 2H), 2.18-1.93 (m, 1H), 1.92-1.63 (m, 3H). 3 protons obscured by solvent peak, |
| 7G | 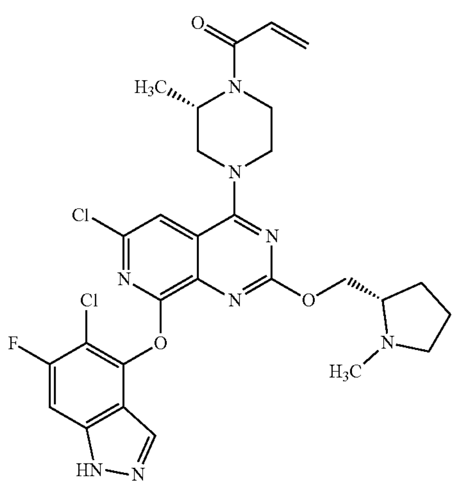 [SMILES: C=CC(=O)N1CCN(c2nc(OC[C@@H]3CCCN3C)nc3c(Oc4c(Cl)c(F)cc5[nH]ncc45)nc(Cl)cc23)C[C@@H]1C] | 1-[(2S)-4-(6-chloro-8-[(5-chloro-6-fluoro-1H-indazol-4-yl)oxy]-2-{[(2S)-1-methylpyrrolidin-2-yl]methoxy}pyrido[3,4-d]pyrimidin-4-yl)-2-methylpiperazin-1-yl]prop-2-en-1-one | 615 (M + H) | ¹H NMR (600 MHz, DMSO-d₆) δ 13.52 (s, 1H), 7.80 (s, 1H), 7.64 (s, 1H), 7.54 (d, J = 8.8 Hz, 1H), 6.72 (dd, J = 16.6, 10.4 Hz, 1H), 6.10 (d, J = 17.4 Hz, 1H), 5.66 (d, J = 10.2 Hz, 1H), 4.69-3.86 (m, 7H), 3.74 3.85-3.64 (m, 2H), 3.60-3.49 (m, 1H), 2.96 (s, 1H), 2.36 (s, 3H), 2.26-2.15 (m, 1H), 1.99-1.81 (m, 1H), 1.63 (dt, J = 26.1, 8.0 Hz, 3H), 1.17 (d, J = 7.8 Hz, 3H) |

| Example | Structure | Compound Name | LCMS m/z | ¹H NMR |
|---|---|---|---|---|
| 8G | 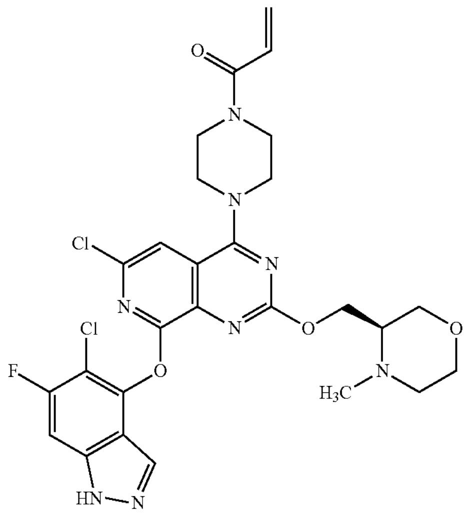 [SMILES: C=CC(=O)N1CCN(c2nc(OC[C@H]3COCCN3C)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(3R)-4-methylmorpholin-3-yl]methoxy}pyrido[3,4-d]pyrimidin-4-yl)piperazin-1-yl]prop-2-en-1-one | 617 (M + H) | ¹H NMR (400 MHz, DMSO-d₆) δ 13.60 (s, 1H), 7.87 (s, 1H), 7.69 (s, 1H), 7.62 (d, J = 8.8 Hz, 1H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 4.47 (dd, J = 11.6, 3.6 Hz, 1H), 4.39-4.30 (m, 1H), 3.95 (s, 4H), 3.84 (s, 5H), 3.75 (s, 1H), 3.69 (d, J = 11.2 Hz, 1H), 3.50 (t, J = 10.8 Hz, 1H), 3.44-3.34 (m, 1H), 2.73-2.64 (m, 1H), 2.47-2.19 (m, 4H) |
| 9G | 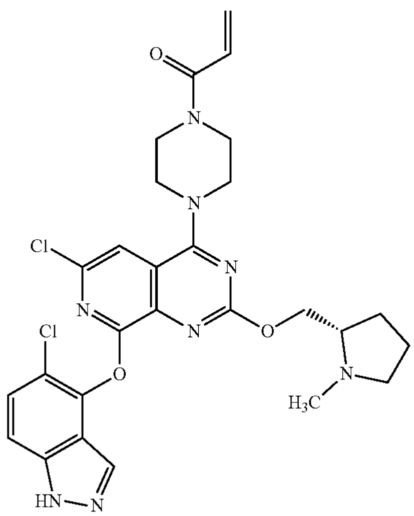 [SMILES: C=CC(=O)N1CCN(c2nc(OC[C@@H]3CCCN3C)nc3c(Oc4c(Cl)ccc5[nH]ncc45)nc(Cl)cc23)CC1] | 1-[4-(6-chloro-8-[(5-chloro-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 583, 585 (M + H) | ¹H NMR (400 MHz, DMSO-d₆) δ 13.50 (s, 1H), 7.84 (s, 1H), 7.63 (s, 1H), 7.53 (d, J = 3.0 Hz, 2H), 6.82 (dd, J = 16.6, 10.5 Hz, 1H), 6.18 (dd, J = 16.7, 2.3 Hz, 1H), 5.75 (dd, J = 10.4, 2.2 Hz, 1H), 4.38 (dd, J = 10.8, 4.5 Hz, 1H), 4.20 (dd, J = 10.8, 6.3 Hz, 1H), 4.01-3.89 (m, 4H), 3.87-3.72 (m, 4H), 2.98-2.90 (m, 1H), 2.63-2.56 (m, 1H), 2.36 (s, 3H), 2.20-2.12 (m, 1H), 2.05-1.86 (m, 1H), 1.71-1.64 (m, 3H) |
| 10G | 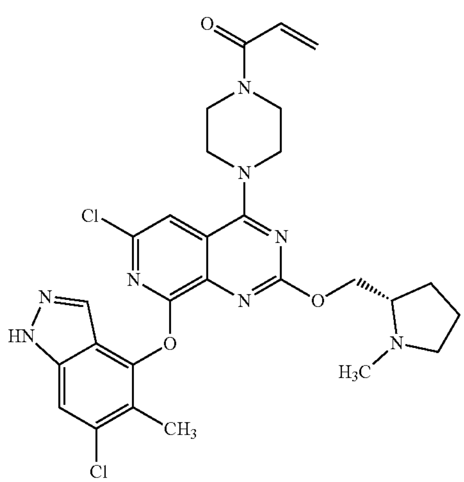 [SMILES: C=CC(=O)N1CCN(c2nc(OC[C@@H]3CCCN3C)nc3c(Oc4c(C)c(Cl)cc5[nH]ncc45)nc(Cl)cc23)CC1] | 1-[4-(6-chloro-8-[(6-chloro-5-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 597 (M + H) | ¹H NMR (400 MHz, DMSO-d₆) δ 13.31 (br. s, 1H), 7.57-7.75 (m, 2H), 6.82 (dd, J = 16.7, 10.45 Hz, 1H), 6.18 (dd, J = 16.8, 2.3 Hz, 1H), 5.67-5.78 (m, 1H), 4.34-4.55 (m, 1H) 4.29 (br. s, 1H), 3.93 (br. s, 3H) 3.84 (br. s, 2H), 3.75 (br. s, 2H), 3.70 (br. s, 1H), 3.06 (d, J = 12.1 Hz, 1H), 2.67 (d, J = 1.8 Hz, 1H), 2.61 (br. s, 1H), 2.54 (br. s, 1H), 2.44 (br. s, 2H), 2.23 (s, 3H), 2.07 (s, 1H), 1.95-2.04 (m, 1H), 1.71 (br. s, 3H) |

| Example | Structure | Compound Name | LCMS m/z | ¹H NMR |
|---|---|---|---|---|
| 11G | 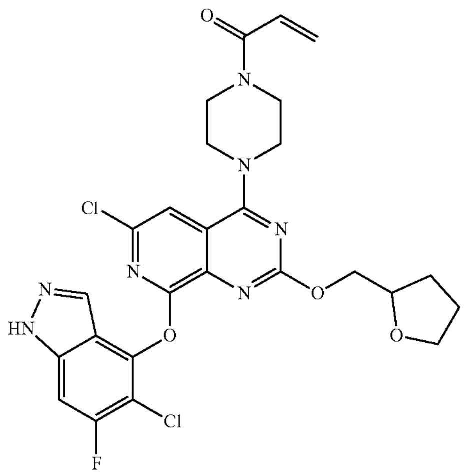 [SMILES: C=CC(=O)N1CCN(c2nc(OCC3CCCO3)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-(tetrahydrofuran-2-ylmethoxy)pyrido[3,4-d]pyrimidin-4-yl}piperazin-1-yl)prop-2-en-1-one | 588, 590 (M + H) | ¹H NMR (400 MHz, DMSO-d₆) δ 13.55 (s, 1H), 7.83 (s, 1H), 7.65 (s, 1H), 7.58 (dd, J = 8.9, 1.1 Hz, 1H), 6.79 (dd, J = 16.7, 10.4 Hz, 1H), 6.14 (dd, J = 16.7, 2.4 Hz, 1H), 5.71 (dd, J = 10.4, 2.3 Hz, 1H), 4.31-4.18 (m, 2H), 4.19-4.08 (m, 1H), 3.93-3.87 (m, 4H), 3.83-3.69 (m, 5H), 3.67-3.60 (m, 1H), 2.02-1.89 (m, 1H), 1.91-1.71 (m, 2H), 1.71-1.51 (m, 1H) |
| 12G | 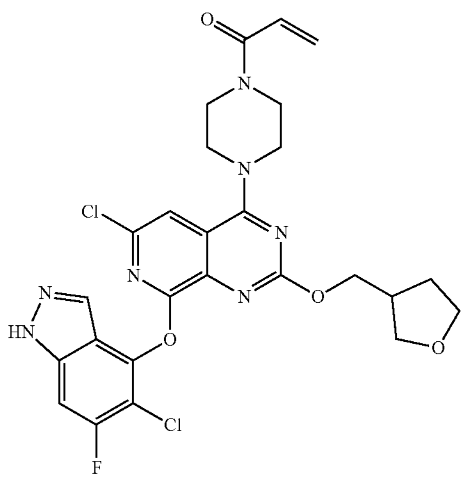 [SMILES: C=CC(=O)N1CCN(c2nc(OCC3CCOC3)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-(tetrahydrofuran-3-ylmethoxy)pyrido[3,4-d]pyrimidin-4-yl}piperazin-1-yl)prop-2-en-1-one | 588, 590 (M + H) | ¹H NMR (400 MHz, DMSO-d₆) δ 13.59 (s, 1H), 7.87 (s, 1H), 7.69 (s, 1H), 7.61 (dd, J = 8.9, 1.1 Hz, 1H), 6.82 (dd, J = 16.7, 10.4 Hz, 1H), 6.18 (dd, J = 16.7, 2.4 Hz, 1H), 5.75 (dd, J = 10.4, 2.3 Hz, 1H), 4.27 (dd, J = 10.6, 6.7 Hz, 1H), 4.19 (dd, J = 10.6, 7.9 Hz, 1H), 3.94 (dd, J = 7.0, 3.6 Hz, 4H), 3.88-3.72 (m, 6H), 3.65 (q, J = 7.6 Hz, 1H), 3.53 (dd, J = 8.7, 5.6 Hz, 1H), 2.74-2.61 (m, 1H), 2.12-1.94 (m, 1H), 1.74-1.59 (m, 1H) |
| 13G | 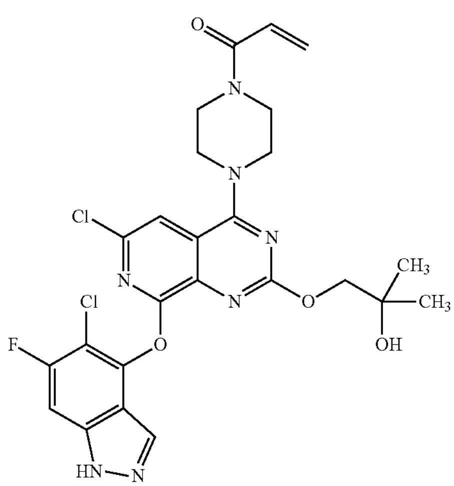 [SMILES: C=CC(=O)N1CCN(c2nc(OCC(C)(C)O)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-(2-hydroxy-2-methylpropoxy)pyrido[3,4-d]pyrimidin-4-yl}piperazin-1-yl)prop-2-en-1-one | 576 (M + H) | ¹H NMR (400 MHz, DMSO-d₆) δ 13.62 (s, 1H), 7.89 (s, 1H), 7.69 (s, 1H), 7.62 (d, J = 8.8 Hz, 1H), 6.83 (dd, J = 16.6, 10.5 Hz, 1H), 6.18 (dd, J = 16.7, 1.7 Hz, 1H), 5.80-5.69 (m, 1H), 4.74 (s, 1H), 4.10 (s, 2H), 4.01-3.69 (m, 8H), 1.21 (s, 6H) |

-continued

| Example | Structure | Compound Name | LCMS m/z | ¹H NMR |
|---|---|---|---|---|
| 14G | 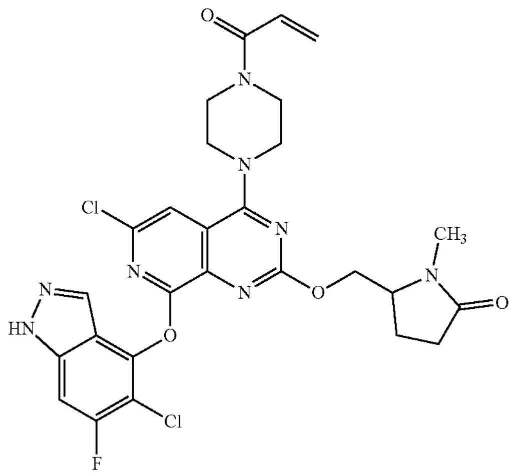 [SMILES: C=CC(=O)N1CCN(c2nc(OCC3CCC(=O)N3C)nc3c(Oc4c(Cl)c(F)cc5[nH]ncc45)nc(Cl)cc23)CC1] | 5-[({4-(4-acryloylpiperazin-1-yl)-6-chloro-8-[(5-chloro-6-fluoro-1H-indazol-4-yl)oxy]pyrido[3,4-d]pyrimidin-2-yl}oxy)methyl]-1-methylpyrrolidin-2-one | 615 (M + H) | ¹H NMR (400 MHz, DMSO-d$_6$) δ 13.61 (br. s, 1H), 7.89 (s, 1H), 7.69 (s, 1H), 7.62 (dd, J = 8.9, 0.8 Hz, 1H), 6.82 (dd, J = 16.7, 10.4 Hz, 1H), 6.18 (dd, J = 16.7, 2.4 Hz, 1H), 5.67-5.83 (m, 1H), 4.59 (dd, J = 11.7, 4.0 Hz, 1H), 4.42 (dd, J = 11.6, 3.8 Hz, 1H), 3.80-4.02 (m, 7H), 3.76 (br. s, 2H), 2.78 (s, 3H), 2.27-2.40 (m, 1H), 2.10-2.23 (m, 2H), 1.84-1.94 (m, 1H) |
| 15G | 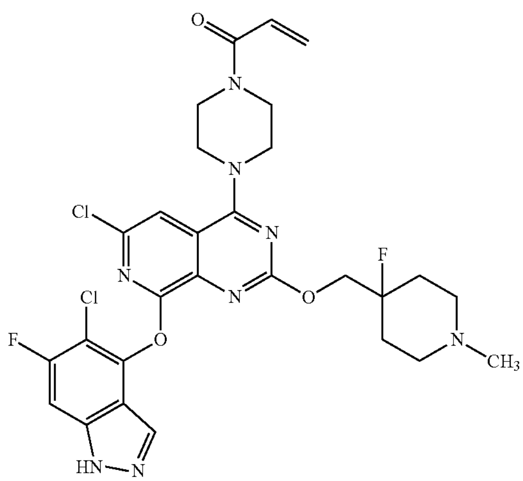 [SMILES: C=CC(=O)N1CCN(c2nc(OCC3(F)CCN(C)CC3)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-[(4-fluoro-1-methylpiperidin-4-yl)methoxy]pyrido[3,4-d]pyrimidin-4-yl}piperazin-1-yl)prop-2-en-1-one | 633 (M + H) | ¹H NMR (600 MHz, DMSO-d$_6$) δ 7.41 (s, 1H), 7.23 (d, J = 0.9 Hz, 1H), 7.14 (d, J = 8.9 Hz, 1H), 6.35 (ddd, J = 1.0, 10.5, 16.7 Hz, 1H), 5.71 (d, J = 16.8 Hz, 1H), 5.28 (d, J = 10.5 Hz, 1H), 3.98-3.82 (m, 2H), 3.55-3.45 (m, 4H), 3.41-3.21 (m, 4H), 2.13 (d, J = 11.4 Hz, 2H), 1.76-1.63 (m, 5H), 1.47-1.39 (m, 2H), 1.38-1.23 (m, 2H) |
| 16G | 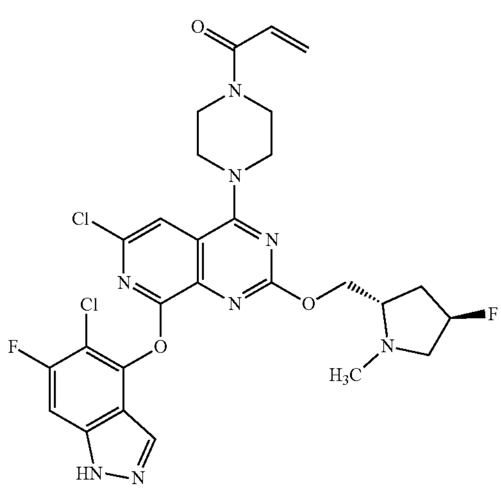 [SMILES: C=CC(=O)N1CCN(c2nc(OC[C@@H]3C[C@@H](F)CN3C)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(2S,4R)-4-fluoro-1-methylpyrrolidin-2-yl]methoxy}pyrido[3,4-d]pyrimidin-4-yl)piperazin-1-yl]prop-2-en-1-one | 619, 621 (M + H) | ¹H NMR (400 MHz, DMSO-d$_6$) δ 13.59 (s, 1H), 7.87 (s, 1H), 7.68 (s, 1H), 7.62 (d, J = 8.8 Hz, 1H), 6.82 (dd, J = 16.7, 10.4 Hz, 1H), 6.18 (dd, J = 16.7, 2.3 Hz, 1H), 5.75 (dd, J = 10.9, 1.8 Hz, 1H), 5.18 (d, J = 55.0 Hz, 1H), 4.45-4.25 (m, 2H), 4.01-3.90 (m, 4H), 3.87-3.70 (m, 4H), 3.51-3.38 (m, 1H), 2.99-2.85 (m, 1H), 2.47-2.41 (m, 1H), 2.40 (s, 3H), 2.21-2.07 (m, 1H), 2.02-1.83 (m, 1H) |

| Example | Structure | Compound Name | LCMS m/z | ¹H NMR |
|---|---|---|---|---|
| 17G | 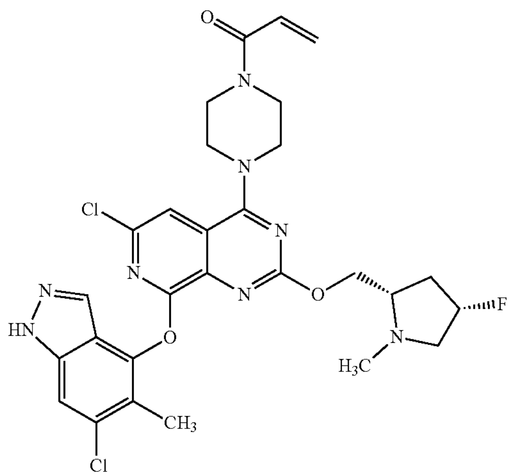 [SMILES: C=CC(=O)N1CCN(c2nc(OC[C@@H]3C[C@H](F)CN3C)nc3c(Oc4c(C)c(Cl)cc5[nH]ncc45)nc(Cl)cc23)CC1] | 1-[4-(6-chloro-8-[(6-chloro-5-methyl-1H-indazol-4-yl)oxy]-2-{[(2S,4S)-4-fluoro-1-methylpyrrolidin-2-yl]methoxy}pyrido[3,4-d]pyrimidin-4-yl)piperazin-1-yl]prop-2-en-1-one | 615 (M + H) | ¹H NMR (600 MHz, DMSO-d$_6$) δ 7.62 (d, J = 1.0 Hz, 1H), 7.59 (s, 1H), 7.54 (s, 1H), 6.74 (dd, J = 16.7, 10.5 Hz, 1H), 6.11 (dd, J = 16.7, 2.3 Hz, 1H), 5.67 (dd, J = 10.5, 2.4 Hz, 1H), 5.08 (dddd, J = 55.1, 6.0, 3.9, 1.5 Hz, 1H), 4.40 (dd, J = 10.9, 4.8 Hz, 1H), 4.23 (dd, J = 10.8, 6.3 Hz, 1H), 3.93-3.83 (m, 5H), 3.77 (s, 2H), 3.69 (s, 2H), 3.09 (ddd, J = 19.1, 11.7, 1.9 Hz, 1H), 2.64-2.54 (m, 1H), 2.41-2.24 (m, 5H), 2.16 (s, 3H), 1.86-1.74 (m, 1H) |
| 18G | 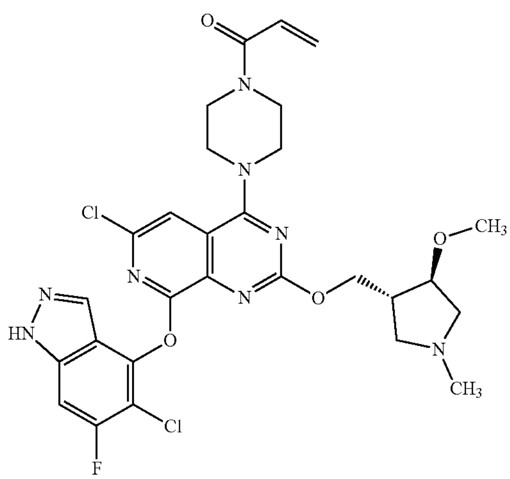 [SMILES: C=CC(=O)N1CCN(c2nc(OC[C@H]3CN(C)C[C@@H]3OC)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(3R,4R)-4-methoxy-1-methylpyrrolidin-3-yl]methoxy}pyrido[3,4-d]pyrimidin-4-yl)piperazin-1-yl]prop-2-en-1-one | 631, 633 (M + H) | ¹H NMR (400 MHz, DMSO-d$_6$) δ 7.87 (s, 1H), 7.69 (s, 1H), 7.61 (dd, J = 8.8, 1.1 Hz, 1H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 4.36 (dd, J = 10.7, 6.4 Hz, 1H), 4.20 (dd, J = 10.7, 8.3 Hz, 1H), 3.98-3.90 (m, 4H), 3.83 (s, 2H), 3.75 (s, 2H), 3.66 (dt, J = 6.5, 3.5 Hz, 1H), 3.20 (s, 3H), 2.77-2.62 (m, 3H), 2.40 (dd, J = 9.8, 3.9 Hz, 1H), 2.35-2.28 (m, 1H), 2.20 (s, 3H) |
| 19G | 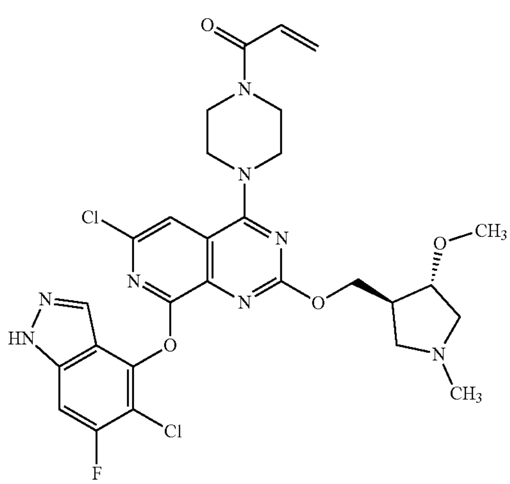 [SMILES: C=CC(=O)N1CCN(c2nc(OC[C@@H]3CN(C)C[C@H]3OC)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(3S,4S)-4-methoxy-1-methylpyrrolidin-3-yl]methoxy}pyrido[3,4-d]pyrimidin-4-yl)piperazin-1-yl]prop-2-en-1-one | 631, 633 (M + H) | ¹H NMR (400 MHz, DMSO-d$_6$) δ 13.60 (s, 1H), 7.87 (s, 1H), 7.69 (s, 1H), 7.61 (dd, J = 8.8, 1.0 Hz, 1H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 4.36 (dd, J = 10.7, 6.5 Hz, 1H), 4.20 (dd, J = 10.7, 8.3 Hz, 1H), 4.02-3.89 (m, 4H), 3.83 (s, 2H), 3.75 (s, 2H), 3.66 (dt, J = 6.6, 3.5 Hz, 1H), 3.20 (s, 3H), 2.76-2.60 (m, 3H), 2.40 (dd, J = 9.8, 3.9 Hz, 1H), 2.34-2.29 (m, 1H), 2.20 (s, 3H) |

-continued

| Example | Structure | Compound Name | LCMS m/z | ¹H NMR |
|---|---|---|---|---|
| 20G | 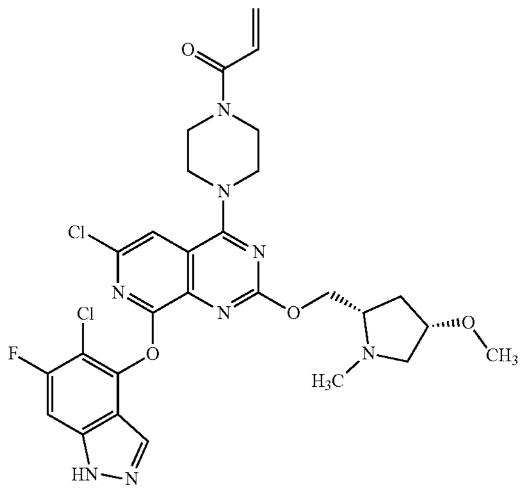 [SMILES: C=CC(=O)N1CCN(c2nc(OC[C@@H]3C[C@H](OC)CN3C)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(2S,4S)-4-methoxy-1-methylpyrrolidin-2-yl]methoxy}pyrido[3,4-d]pyrimidin-4-yl)piperazin-1-yl]prop-2-en-1-one | 631, 633 (M + H) | ¹H NMR (400 MHz, DMSO-d$_6$) δ 13.61 (s, 1H), 8.16 (s, 1H), 7.87 (s, 1H), 7.68 (s, 1H), 7.62 (d, J = 8.8 Hz, 1H), 6.82 (dd, J = 16.7, 10.5 Hz, 1H), 6.18 (dd, J = 16.7, 2.4 Hz, 1H), 5.75 (dd, J = 10.4, 2.4 Hz, 1H), 4.42 (dd, J = 10.9, 5.0 Hz, 1H), 4.27 (dd, J = 10.9, 6.0 Hz, 1H), 3.95 (s, 4H), 3.83 (s, 3H), 3.76 (s, 2H), 3.16 (s, 3H), 3.08 (d, J = 10.6 Hz, 1H), 2.75-2.60 (m, 1H), 2.36 (s, 3H), 2.34-2.24 (m, 2H), 1.71-1.56 (m, 1H) |
| 21G | 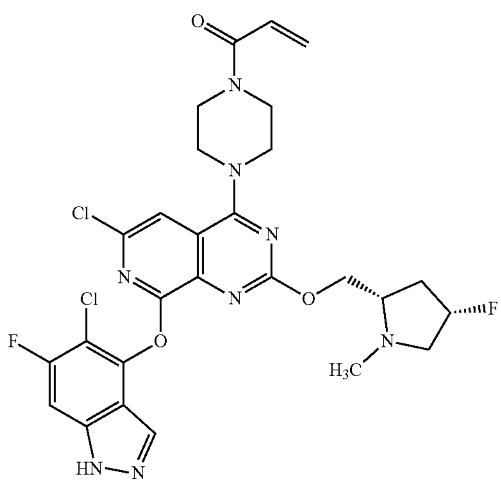 [SMILES: C=CC(=O)N1CCN(c2nc(OC[C@@H]3C[C@H](F)CN3C)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(2S,4S)-4-fluoro-1-methylpyrrolidin-2-yl]methoxy}pyrido[3,4-d]pyrimidin-4-yl)piperazin-1-yl]prop-2-en-1-one | 619 (M + H) | ¹H NMR (400 MHz, MeOD) δ 7.84 (s, 1H), 7.65 (s, 1H), 7.42 (dd, J = 8.6, 1.0 Hz, 1H), 6.80 (dd, J = 16.8, 10.6 Hz, 1H), 6.28 (dd, J = 16.8, 1.9 Hz, 1H), 5.81 (dd, J = 10.6, 1.9 Hz, 1H), 5.24 (dt, J = 53.6, 4.7 Hz, 1H), 4.71-4.44 (m, 2H), 4.06 (s, 4H), 3.91 (s, 4H), 3.47 (t, J = 14.9 Hz, 1H), 3.20 (s, 1H), 2.92-2.48 (m, 5H), 2.10 (ddd, J = 30.1, 15.2, 6.8 Hz, 1H) |
| 22G | | 1-[4-(6-chloro-8-[(5-chloro-6-fluoro-1H-indazol-4-yl)oxy]-2-{[(2R,4R)-4-fluoro-1-methylpyrrolidin-2-yl]methoxy}pyrido[3,4-d]pyrimidin-4-yl)piperazin-1-yl]prop-2-en-1-one | 619 (M + H) | ¹H NMR (400 MHz, DMSO-d$_6$) δ 13.60 (s, 1H), 7.87 (s, 1H), 7.68 (s, 1H), 7.62 (dd, J = 8.8, 1.2 Hz, 1H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 5.25-5.00 (m, 1H), 4.44 (dd, J = 10.9, 4.8 Hz, 1H), 4.27 (dd, J = 10.9, 6.3 Hz, 1H), 3.97-3.91 (m, 4H), 3.84 (s, 2H), 3.76 (d, J = 5.1 Hz, 2H), 3.23-3.00 (m, 1H), 2.65 (d, J = 6.7, 6.1 Hz, 1H), 2.46-2.25 (m, 5H), 1.85 (ddd, J = 31.9, 14.6, 6.6 Hz, 1H) |

| Example | Structure | Compound Name | LCMS m/z | ¹H NMR |
|---|---|---|---|---|
| 23G | 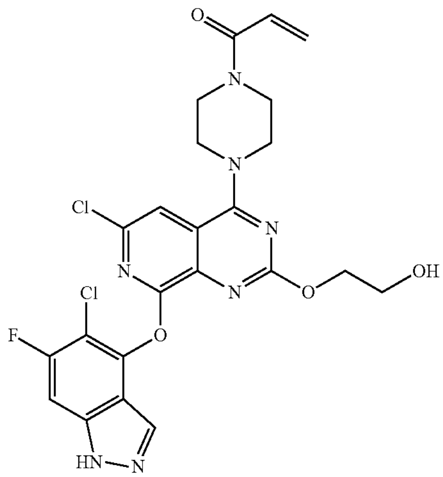 [SMILES: C=CC(=O)N1CCN(c2nc(OCCO)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-(2-hydroxyethoxy)pyrido[3,4-d]pyrimidin-4-yl}piperazin-1-yl)prop-2-en-1-one | 548, 550 (M + H) | ¹H NMR (400 MHz, DMSO-d$_6$) δ 13.64 (s, 1H), 7.89 (s, 1H), 7.68 (s, 1H), 7.62 (d, J = 8.9 Hz, 1H), 6.82 (dd, J = 16.7, 10.4 Hz, 1H), 6.18 (dd, J = 16.7, 2.3 Hz, 1H), 5.75 (dd, J = 10.4, 2.3 Hz, 1H), 4.92 (s, 1H), 4.41-4.29 (m, 2H), 3.94 (s, 4H), 3.83 (s, 2H), 3.79-3.65 (m, 4H) |
| 25G | 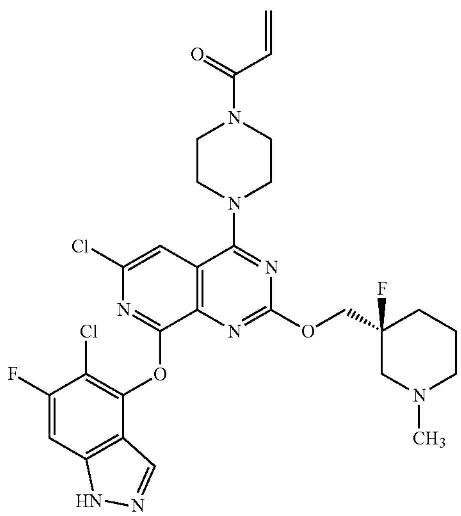 [SMILES: C=CC(=O)N1CCN(c2nc(OC[C@]3(F)CCCN(C)C3)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(3S)-3-fluoro-1-methylpiperidin-3-yl]methoxy}pyrido[3,4-d]pyrimidin-4-yl)piperazin-1-yl]prop-2-en-1-one | 633 (M + H) | ¹H NMR (400 MHz, DMSO-d$_6$) δ 13.60 (s, 1H), 7.87 (s, 1H), 7.70 (s, 1H), 7.62 (d, J = 8.8 Hz, 1H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 4.53 (dd, J = 22.4, 12.2 Hz, 1H), 4.39 (dd, J = 22.4, 12.2 Hz, 1H), 4.00-3.93 (m, 4H), 3.80 (d, J = 32.7 Hz, 4H), 2.64-2.53 (m, 2H), 2.42-2.32 (m, 1H), 2.31-2.22 (m, 1H), 2.20 (s, 3H), 1.85-1.62 (m, 3H), 1.61-1.49 (m, 1H) |
| 26G | 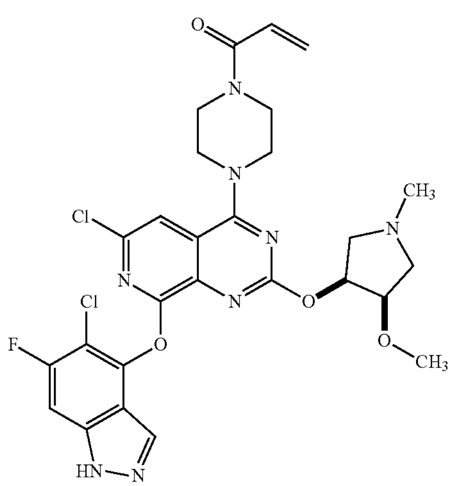 | rac-1-[4-(6-chloro-8-[(5-chloro-6-fluoro-1H-indazol-4-yl)oxy]-2-{[(3R,4S)-4-methoxy-1-methylpyrrolidin-3-yl]oxy}pyrido[3,4-d]pyrimidin-4-yl)piperazin-1-yl]prop-2-en-1-one | 617, 619 (M + H) | ¹H NMR (400 MHz, DMSO-d$_6$) δ 7.85 (d, J = 1.0 Hz, 1H), 7.69 (s, 1H), 7.62 (dd, J = 8.8, 1.0 Hz, 1H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 5.39 (q, J = 5.8 Hz, 1H), 4.03-3.91 (m, 5H), 3.80 (d, J = 34.0 Hz, 4H), 3.17 (s, 3H), 3.07 (dd, J = 10.2, 6.2 Hz, 1H), 2.92 (dd, J = 9.6, 6.3 Hz, 1H), 2.57 (dd, J = 10.3, 5.0 Hz, 1H), 2.49-2.46 (m, 1H), 2.27 (s, 3H) |

| Example | Structure | Compound Name | LCMS m/z | ¹H NMR |
|---|---|---|---|---|
| 27G | 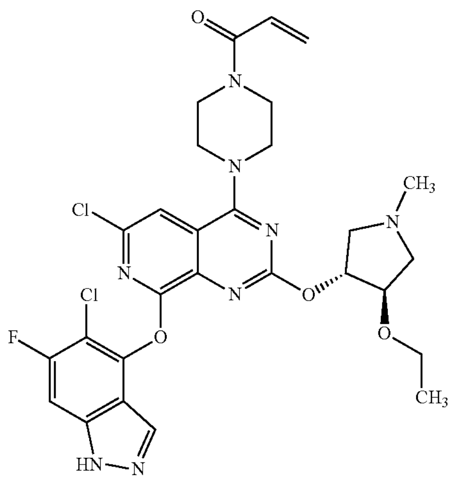 [SMILES: C=CC(=O)N1CCN(c2nc(O[C@@H]3CN(C)C[C@H]3OCC)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(3R,4R)-4-ethoxy-1-methylpyrrolidin-3-yl]oxy}pyrido[3,4-d]pyrimidin-4-yl)piperazin-1-yl]prop-2-en-1-one | 631, 633 (M + H) | ¹H NMR (400 MHz, DMSO-$d_6$) δ 13.62 (s, 1H), 7.85 (s, 1H), 7.69 (s, 1H), 7.62 (d, J = 8.8 Hz, 1H), 6.82 (dd, J = 16.7, 10.4 Hz, 1H), 6.18 (dd, J = 16.7, 2.2 Hz, 1H), 5.75 (dd, J = 10.4, 2.2 Hz, 1H), 5.22 (s, 1H), 4.04 (d, J = 5.0 Hz, 1H), 3.95 (s, 4H), 3.80 (d, J = 34.6 Hz, 4H), 3.70 (dd, J = 9.3, 7.1 Hz, 1H), 3.46 (dd, J = 9.3, 7.0 Hz, 1H), 3.02 (dd, J = 9.5, 6.5 Hz, 1H), 2.83 (dd, J = 10.2, 5.8 Hz, 1H), 2.64 (d, J = 10.4 Hz, 1H), 2.34-2.17 (m, 4H), 1.01 (t, J = 7.0 Hz, 3H) |
| 28G | 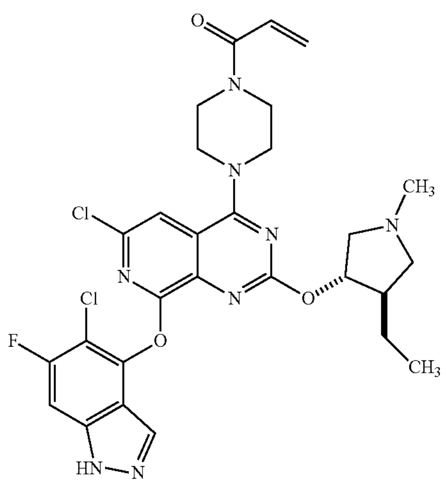 | rac-1-[4-(6-chloro-8-[(5-chloro-6-fluoro-1H-indazol-4-yl)oxy]-2-{[(3S,4R)-4-ethyl-1-methylpyrrolidin-3-yl]oxy}pyrido[3,4-d]pyrimidin-4-yl)piperazin-1-yl]prop-2-en-1-one | 615, 617 (M + H) | ¹H NMR (400 MHz, DMSO-$d_6$) δ 13.60 (s, 1H), 7.83 (s, 1H), 7.68 (s, 1H), 7.61 (d, J = 8.8 Hz, 1H), 6.82 (dd, J = 16.7, 10.4 Hz, 1H), 6.18 (dd, J = 16.7, 2.2 Hz, 1H), 5.75 (dd, J = 10.4, 2.3 Hz, 1H), 4.99 (s, 1H), 4.04-3.61 (m, 8H), 2.98 (t, J = 7.9 Hz, 1H), 2.79 (d, J = 10.5 Hz, 1H), 2.71-2.65 (m, 1H), 2.29 (d, J = 29.5 Hz, 3H), 2.15 (s, 1H), 2.00 (d, J = 16.8 Hz, 1H), 1.77 (d, J = 27.1 Hz, 1H), 1.42-1.37 (m, 1H), 0.84 (t, J = 7.4 Hz, 3H) |
| 30G | 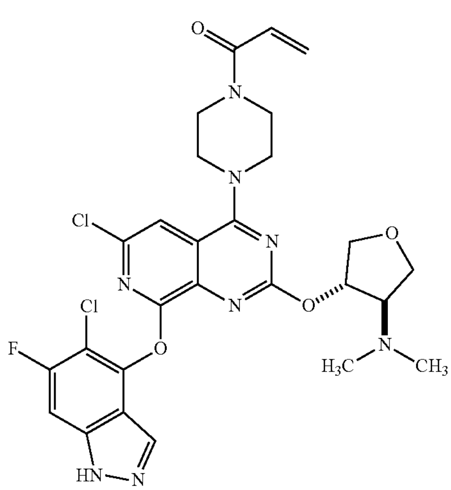 | rac-1-[4-(6-chloro-8-[(5-chloro-6-fluoro-1H-indazol-4-yl)oxy]-2-{[(3S,4R)-4-(dimethylamino)oxolan-3-yl]oxy}pyrido[3,4-d]pyrimidin-4-yl)piperazin-1-yl]prop-2-en-1-one | 617, 619 (M + H) | ¹H NMR (400 MHz, DMSO-$d_6$) δ 13.59 (s, 1H), 7.83 (s, 1H), 7.70 (s, 1H), 7.61 (d, J = 9.0, 1H), 6.82 (dd, J = 16.7, 10.4, 1H), 6.18 (dd, J = 16.7, 2.3, 1H), 5.75 (dd, J = 10.4, 2.3, 1H), 5.43-5.35 (m, 1H), 4.10-3.87 (m, 6H), 3.86-3.72 (m, 5H), 3.62-3.58 (m, 1H), 3.03-2.99 (m, 1H), 2.22 (s, 6H) |

| Example | Structure | Compound Name | LCMS m/z | ¹H NMR |
|---|---|---|---|---|
| 31G | 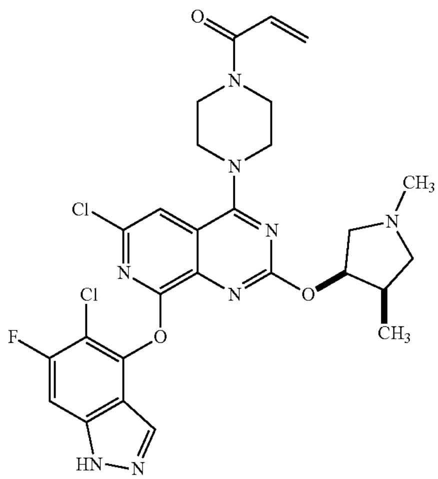 | rac-1-[4-(6-chloro-8-[(5-chloro-6-fluoro-1H-indazol-4-yl)oxy]-2-{[(3R,4R)-1,4-dimethylpyrrolidin-3-yl]oxy}pyrido[3,4-d]pyrimidin-4-yl)piperazin-1-yl]prop-2-en-1-one | 601, 603 (M + H) | ¹H NMR (400 MHz, DMSO-$d_6$) δ 13.62 (s, 1H), 7.85 (s, 1H), 7.68 (s, 1H), 7.61 (d, J = 8.8 Hz, 1H), 6.85-6.77 (m, 1H), 6.18 (dd, J = 16.7, 2.2 Hz, 1H), 5.75 (dd, J = 10.4, 2.3 Hz, 1H), 5.39-5.35 (m, 1H), 3.95-3.75 (m, 8H), 3.21-3.17 (m, 1H), 2.83-2.78 (m, 1H), 2.47-2.42 (m, 2H), 2.31-2.13 (m, 4H), 0.95 (d, J = 7.0 Hz, 3H) |
| 32G | 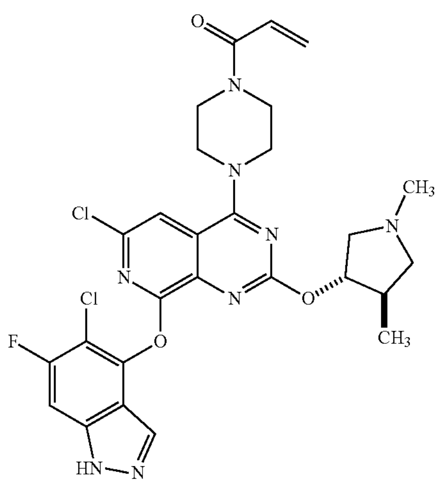 | rac-1-[4-(6-chloro-8-[(5-chloro-6-fluoro-1H-indazol-4-yl)oxy]-2-{[(3S,4R)-1,4-dimethylpyrrolidin-3-yl]oxy}pyrido[3,4-d]pyrimidin-4-yl)piperazin-1-yl]prop-2-en-1-one | 601, 603 (M + H) | ¹H NMR (400 MHz, DMSO-$d_6$) δ 13.62 (s, 1H), 7.85 (s, 1H), 7.67 (s, 1H), 7.62 (d, J = 8.8 Hz, 1H), 6.82 (dd, J = 16.7, 10.4 Hz, 1H), 6.20 (d, J = 2.2 Hz, 1H), 5.75 (d, J = 12.7 Hz, 1H), 4.93 (dd, J = 7.8, 3.9 Hz, 1H), 3.92 (br. s, 4H), 3.73-3.85 (m, 4H), 2.92 (s, 1H), 2.73 (d, J = 4.5 Hz, 2H), 2.21-2.33 (m, 4H), 1.97-1.91 (m, 1H), 1.18 (d, J = 7.1 Hz, 3H) |
| 33G | 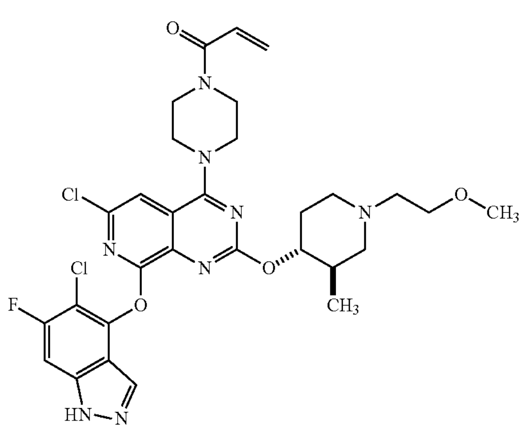 | rac-1-[4-(6-chloro-8-[(5-chloro-6-fluoro-1H-indazol-4-yl)oxy]-2-{[(3R,4R)-1-(2-methoxyethyl)-3-methylpiperidin-4-yl]oxy}pyrido[3,4-d]pyrimidin-4-yl)piperazin-1-yl]prop-2-en-1-one | 659 (M + H) | ¹H NMR (400 MHz, DMSO-$d_6$) δ 13.57 (s, 1H), 7.72 (d, J = 13.8 Hz, 2H), 7.58 (d, J = 8.8 Hz, 1H), 6.82 (dd, J = 16.6, 10.4 Hz, 1H), 6.17 (dd, J = 16.7, 2.3 Hz, 1H), 5.74 (dd, J = 10.4, 2.4 Hz, 1H), 4.47 (s, 1H), 3.93 (s, 8H), 3.43 (s, 2H), 3.23 (s, 3H), 2.76 (m, 2H), 2.48 (s, 2H), 2.13-1.94 (m, 2H), 1.89-1.74 (m, 2H), 1.60-1.41 (m, 1H), 0.82 (d, J = 5.9 Hz, 3H) |

| Example | Structure | Compound Name | LCMS m/z | ¹H NMR |
|---|---|---|---|---|
| 34G | 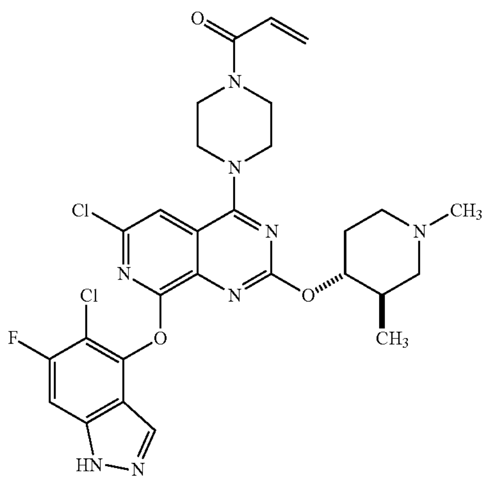 | rac-1-[4-(6-chloro-8-[(5-chloro-6-fluoro-1H-indazol-4-yl)oxy]-2-{[(3R,4R)-1,3-dimethylpiperidin-4-yl]oxy}pyrido[3,4-d]pyrimidin-4-yl)piperazin-1-yl]prop-2-en-1-one | 615 (M + H) | ¹H NMR (400 MHz, DMSO-d₆) δ 13.61 (s, 1H), 7.72 (d, J = 12.1 Hz, 2H), 7.59 (d, J = 8.8 Hz, 1H), 6.82 (dd, J = 16.7, 10.4 Hz, 1H), 6.18 (dd, J = 16.7, 2.3 Hz, 1H), 5.74 (dd, J = 10.4, 2.3 Hz, 1H), 4.47 (td, J = 9.8, 4.2 Hz, 1H), 4.00-3.73 (m, 8H), 2.70 (dd, J = 24.0, 4.4 Hz, 2H), 2.16 (s, 3H), 2.06-1.80 (m, 3H), 1.72 (t, J = 11.0 Hz, 1H), 1.52 (d, J = 10.9 Hz, 1H), 0.83 (d, J = 6.5 Hz, 3H) |
| 35G | 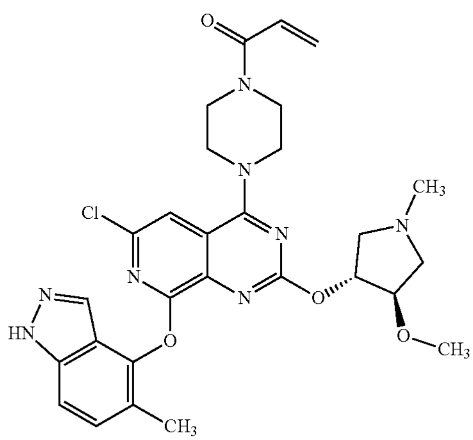 [SMILES: C=CC(=O)N1CCN(c2nc(O[C@@H]3CN(C)C[C@H]3OC)nc3c(Oc4c(C)ccc5[nH]ncc45)nc(Cl)cc23)CC1] | 1-[4-(6-chloro-2-{[(3R,4R)-4-methoxy-1-methylpyrrolidin-3-yl]oxy}-8-[(5-methyl-1H-indazol-4-yl)oxy]pyrido[3,4-d]pyrimidin-4-yl)piperazin-1-yl]prop-2-en-1-one | 579, 581 (M + H) | ¹H NMR (400 MHz, DMSO-d₆) δ 13.18 (s, 1H), 7.63 (s, 1H), 7.57 (s, 1H), 7.40 (d, J = 8.7 Hz, 1H), 7.32 (d, J = 8.6 Hz, 1H), 6.86-6.79 (m, 1H), 6.18 (d, J = 14.4 Hz, 1H), 5.75 (dd, J = 10.4, 2.3 Hz, 1H), 5.30-5.27 (m, 1H), 4.00-3.90 (m, 5H), 3.84 (br. s, 2H), 3.75 (br. s, 2H), 3.35 (s, 3H), 3.01 (d, J = 3.5 Hz, 1H), 2.89 (d, J = 4.6 Hz, 1H), 2.68-2.66 (m, 1H), 2.34-2.32 (m, 1H), 2.23 (s, 3H), 2.19 (s, 3H) |
| 36G | 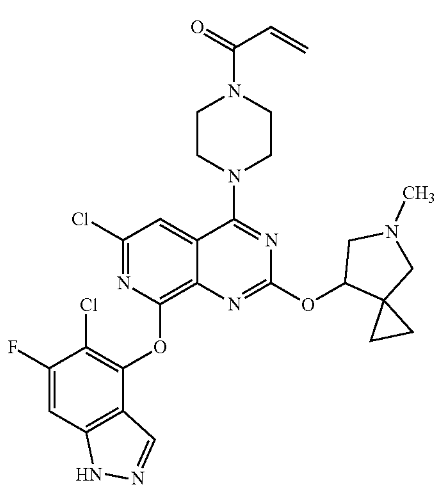 [SMILES: C=CC(=O)N1CCN(c2nc(OC3CN(C)CC34CC4)nc3c(Oc4c(Cl)c(F)cc5[nH]ncc45)nc(Cl)cc23)CC1] | 1-(4-{6-chloro-8-[(5-chloro-6-fluoro-1H-indazol-4-yl)oxy]-2-[(5-methyl-5-azaspiro[2.4]heptan-7-yl)oxy]pyrido[3,4-d]pyrimidin-4-yl}piperazin-1-yl)prop-2-en-1-one | 613, 615 (M + H) | ¹H NMR (400 MHz, DMSO-d₆) δ 13.74 (s, 1H), 7.83 (d, J = 0.8 Hz, 1H), 7.67-7.59 (m, 2H), 6.82 (dd, J = 16.7, 10.4 Hz, 1H), 6.18 (dd, J = 16.7, 2.3 Hz, 1H), 5.75 (dd, J = 10.4, 2.3 Hz, 1H), 5.14 (dd, J = 5.7, 3.3 Hz, 1H), 3.86 (dd, J = 54.7, 18.0 Hz, 8H), 3.14 (dd, J = 10.6, 5.8 Hz, 1H), 2.69 (dd, J = 15.2, 5.9 Hz, 2H), 2.37 (d, J = 8.8 Hz, 1H), 2.27 (s, 3H), 0.99-0.90 (m, 1H), 0.77 (dd, J = 10.0, 3.9 Hz, 1H), 0.65-0.55 (m, 2H) |

-continued

| Example | Structure | Compound Name | LCMS m/z | ¹H NMR |
|---|---|---|---|---|
| 37G | 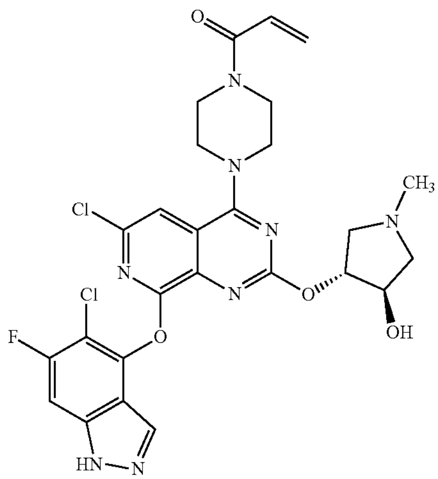 [SMILES: C=CC(=O)N1CCN(c2nc(O[C@@H]3CN(C)C[C@H]3O)nc3c(Oc4c(Cl)c(F)cc5[nH]ncc45)nc(Cl)cc23)CC1] | 1-[4-(6-chloro-8-[(5-chloro-6-fluoro-1H-indazol-4-yl)oxy]-2-{[(3R,4R)-4-hydroxy-1-methylpyrrolidin-3-yl]oxy}pyrido[3,4-d]pyrimidin-4-yl)piperazin-1-yl]prop-2-en-1-one | 603 (M + H) | ¹H NMR (400 MHz, DMSO-d₆) δ 7.88 (s, 1H), 7.70 (s, 1H), 7.63 (d, J = 8.8 Hz, 1H), 6.83 (dd, J = 16.6, 10.4 Hz, 1H), 6.18 (dd, J = 16.6, 2.3 Hz, 1H), 5.75 (dd, J = 10.4, 2.3 Hz, 1H), 5.26 (d, J = 4.2 Hz, 1H), 5.02-5.05 (m, 1H), 4.26 (br. s, 1H), 3.96-3.98 (m, 4H), 3.72-3.90 (m, 4H), 2.83-2.99 (m, 2H), 2.67-2.68 (m, 1H), 2.17-2.28 (m, 5H) |
| 38G | 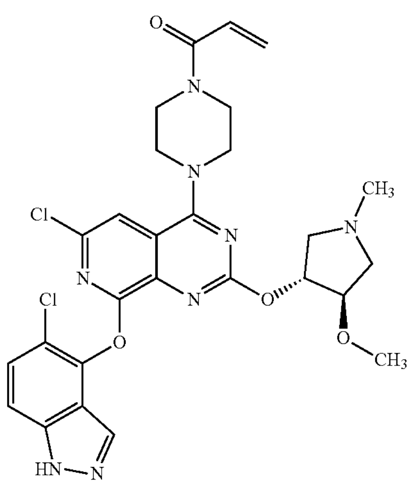 [SMILES: C=CC(=O)N1CCN(c2nc(O[C@@H]3CN(C)C[C@H]3OC)nc3c(Oc4c(Cl)ccc5[nH]ncc45)nc(Cl)cc23)CC1] | 1-[4-(6-chloro-8-[(5-chloro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one | 601 (M + H) | ¹H NMR (400 MHz, DMSO-d₆) δ 13.50 (s, 1H), 7.82 (s, 1H), 7.64 (s, 1H), 7.58-7.42 (m, 2H), 6.82 (dd, J = 16.7, 10.4 Hz, 1H), 6.18 (dd, J = 16.7, 2.4 Hz, 1H), 5.75 (dd, J = 10.4, 2.4 Hz, 1H), 5.33-5.20 (m, 1H), 4.00-3.91 (m, 5H), 3.84 (s, 2H), 3.76 (s, 2H), 3.35 (s, 3H), 3.01 (dd, J = 9.9, 6.4 Hz, 1H), 2.88 (dd, J = 10.7, 6.0 Hz, 1H), 2.69-2.62 (m, 1H), 2.35-2.27 (m, 1H), 2.24 (s, 3H) |
| 39G | 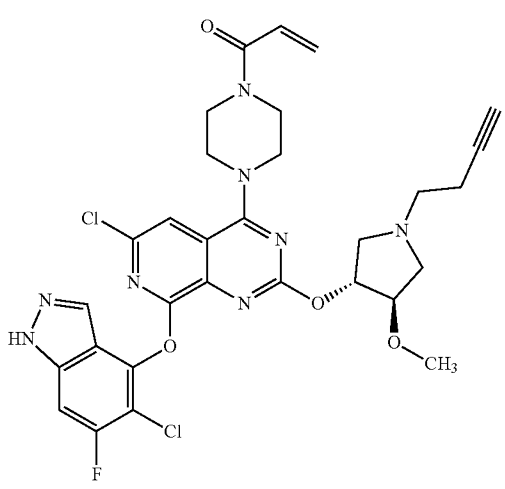 [SMILES: C#CCCN1C[C@@H](OC)[C@H](Oc2nc(N3CCN(C(=O)C=C)CC3)c3cc(Cl)nc(Oc4c(Cl)c(F)cc5[nH]ncc45)c3n2)C1] | 1-[4-(2-{[(3R,4R)-1-(but-3-yn-1-yl)-4-methoxypyrrolidin-3-yl]oxy}-6-chloro-8-[(5-chloro-6-fluoro-1H-indazol-4-yl)oxy]pyrido[3,4-d]pyrimidin-4-yl)piperazin-1-yl]prop-2-en-1-one | 655 (M + H) | ¹H NMR (400 MHz, DMSO-d₆) δ 13.59 (s, 1H), 7.85 (s, 1H), 7.69 (s, 1H), 7.61 (d, J = 8.8 Hz, 1H), 6.82 (dd, J = 16.7, 10.4 Hz, 1H), 6.18 (dd, J = 16.7, 2.3 Hz, 1H), 5.75 (dd, J = 10.4, 2.3 Hz, 1H), 5.24 (s, 1H), 3.96-3.92 (m, 4H), 3.84-3.75 (m, 4H), 3.34 (s, 3H), 3.30 (s, 1H), 3.14-3.07 (m, 1H), 2.95-2.90 (m, 1H), 2.79-2.71 (m, 2H), 2.58-2.53 (m, 2H), 2.41-2.38 (m, 1H), 2.33-2.29 (m, 2H) |

| Example | Structure | Compound Name | LCMS m/z | ¹H NMR |
|---|---|---|---|---|
| 40G | 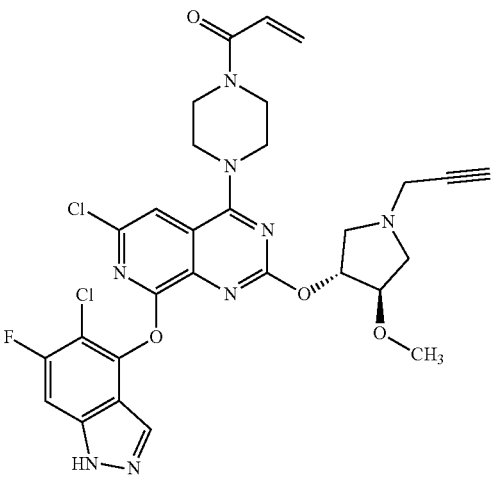 [SMILES: C#CCN1C[C@@H](OC)[C@H](Oc2nc(N3CCN(C(=O)C=C)CC3)c3cc(Cl)nc(Oc4c(Cl)c(F)cc5[nH]ncc45)c3n2)C1] | 1-[4-(6-chloro-8-[(5-chloro-6-fluoro-1H-indazol-4-yl)oxy]-2-{[(3R,4R)-4-methoxy-1-(prop-2-yn-1-yl)pyrrolidin-3-yl]oxy}pyrido[3,4-d]pyrimidin-4-yl)piperazin-1-yl]prop-2-en-1-one | 641 (M + H) | ¹H NMR (400 MHz, DMSO-d₆) δ 13.63 (s, 1H), 7.85 (s, 1H), 7.69 (s, 1H), 7.62 (d, J = 8.8 Hz, 1H), 6.82 (dd, J = 16.7, 10.5 Hz, 1H), 6.18 (dd, J = 16.7, 2.2 Hz, 1H), 5.75 (dd, J = 10.4, 2.2 Hz, 1H), 5.25 (s, 1H), 3.96 (s, 5H), 3.80 (d, J = 33.5 Hz, 4H), 3.39 (s, 2H), 3.35 (s, 3H), 3.17 (s, 1H), 3.08 (dd, J = 9.8, 6.6 Hz, 1H), 3.01 (dd, J = 10.5, 6.1 Hz, 1H), 2.74-2.69 (m, 1H), 2.47-2.44 (m, 1H) |
| 41G | 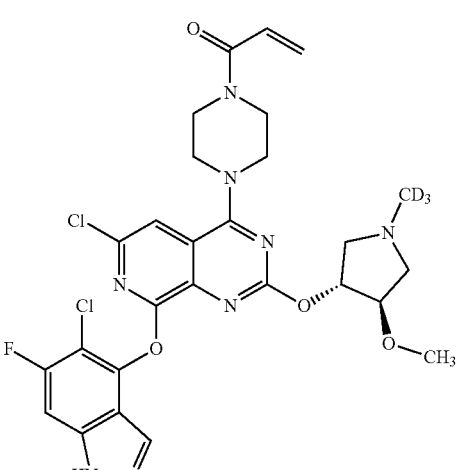 | 1-[4-(6-chloro-8-[(5-chloro-6-fluoro-1H-indazol-4-yl)oxy]-2-{[(3R,4R)-4-methoxy-1-(²H₃)methylpyrrolidin-3-yl]oxy}pyrido[3,4-d]pyrimidin-4-yl)piperazin-1-yl]prop-2-en-1-one | 620 (M + H) | ¹H NMR (400 MHz, DMSO-d₆) δ 13.60 (s, 1H), 7.84 (s, 1H), 7.69 (s, 1H), 7.61 (d, J = 8.9 Hz, 1H), 6.82 (dd, J = 16.6, 10.5 Hz, 1H), 6.18 (dd, J = 16.7, 2.1 Hz, 1H), 5.75 (dd, J = 10.5, 2.1 Hz, 1H), 5.26-5.19 (m, 1H), 4.06-3.91 (m, 5H), 3.86-3.72 (m, 4H), 3.33 (s, 3H), 3.01 (dd, J = 9.5, 6.6 Hz, 1H), 2.84 (dd, J = 10.6, 5.9 Hz, 1H), 2.65-2.60 (m, 1H), 2.32-2.27 (m, 1H) |

The following examples were prepared according to general method H:

Preparation of 1-[4-(8-[(5-chloro-6-fluoro-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one (Example-1H)

Step 1:

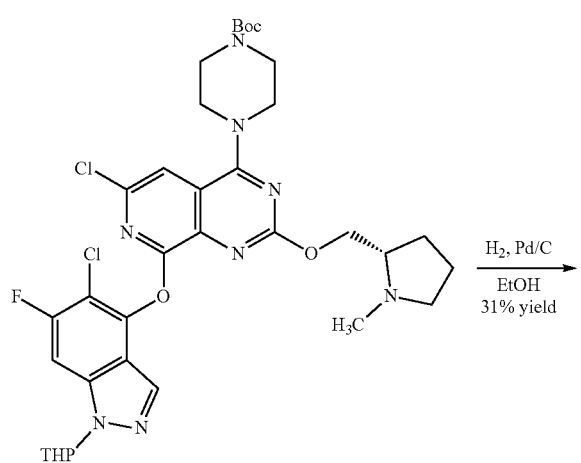

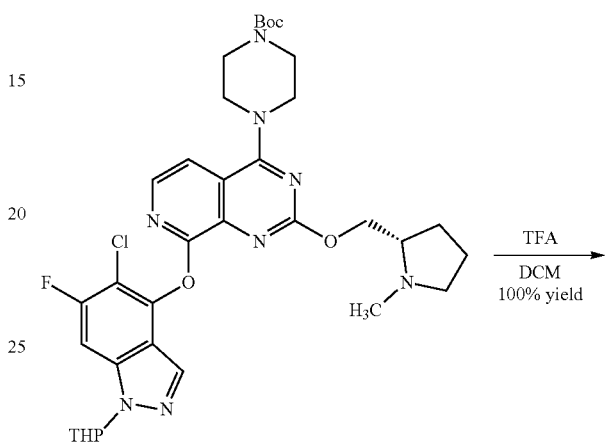

212

222

Step 2:

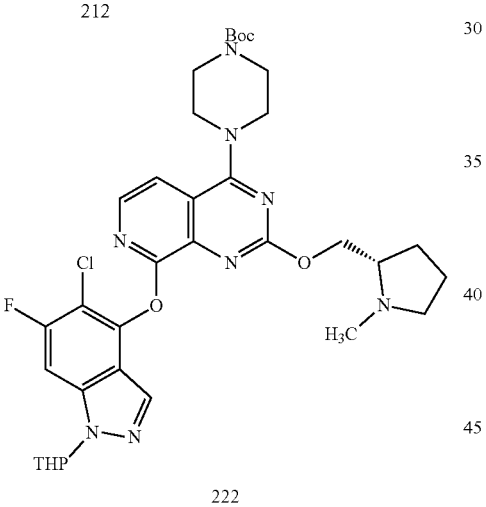

222

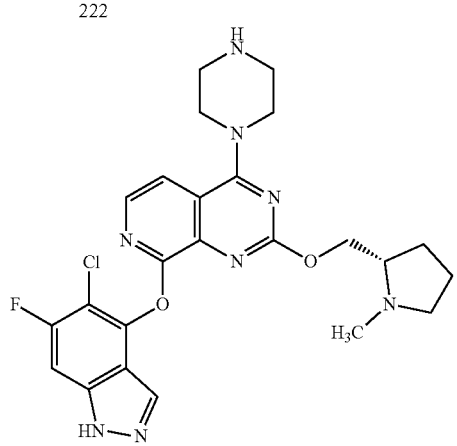

223

To a mixture of tert-butyl 4-(6-chloro-8-{[5-chloro-6-fluoro-1-(tetrahydro-2H-pyran-2-yl)-1H-indazol-4-yl]oxy}-2-{[(2S)-1-methylpyrrolidin-2-yl]methoxy}pyrido[3,4-d]pyrimidin-4-yl)piperazine-1-carboxylate (212) (437 mg, 0.597 mmol) in EtOH (10 mL) was added Pd/C (10% wt loading, 100 mg). A balloon of H₂ was added and the mixture was stirred overnight. LCMS analysis showed 60% conversion to the product. DIPEA (0.21 ml, 1.19 mmol) was added and the mixture was stirred under a balloon of H₂ overnight. LCMS analysis showed consumption of the starting material with formation of the product. The reaction was filtered and then concentrated to dryness. The crude residue was purified by flash chromatography (ISCO, 40 g SiO₂, 100:0:0-95:5:2 DCM/MeOH/TEA) to provide tert-butyl 4-(8-{[5-chloro-6-fluoro-1-(tetrahydro-2H-pyran-2-yl)-1H-indazol-4-yl]oxy}-2-{[(2S)-1-methylpyrrolidin-2-yl]methoxy}pyrido[3,4-d]pyrimidin-4-yl)piperazine-1-carboxylate (222) (130 mg, 31% yield) as an off-white foam. LCMS (ESI) m/z 697 (M+H).

To a solution of tert-butyl 4-(8-{[5-chloro-6-fluoro-1-(tetrahydro-2H-pyran-2-yl)-1H-indazol-4-yl]oxy}-2-{[(2S)-1-methylpyrrolidin-2-yl]methoxy}pyrido[3,4-d]pyrimidin-4-yl)piperazine-1-carboxylate (222) (130 mg, 0.186 mmol) in DCM (2.0 mL) was added TFA (213 mg, 0.139 mL, 1.86 mmol). The reaction was stirred overnight. LCMS analysis showed formation of the desired product. The reaction mixture was concentrated to dryness to provide 8-[(5-chloro-6-fluoro-1H-indazol-4-yl)oxy]-2-{[(2S)-1-methylpyrrolidin-2-yl]methoxy}-4-(piperazin-1-yl)pyrido[3,4-d]pyrimidine (223) (159 mg, 100% yield) as a brown gum, which was taken on without further purification. LCMS (ESI) m/z 513 (M+H).

Step 3:

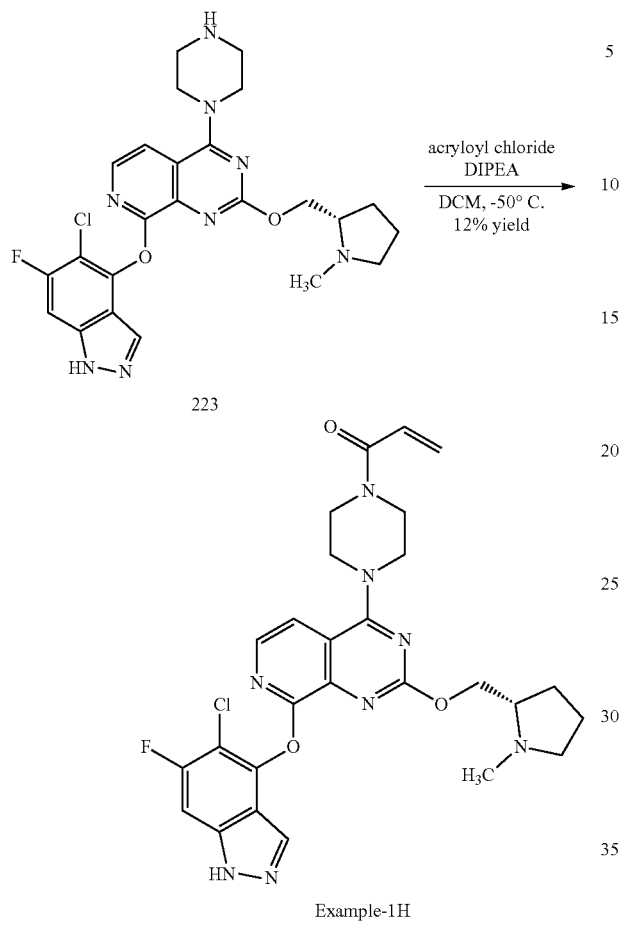

Example-1H

Preparation of 1-[4-(8-[(5,6-dichloro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-19H)

Step 1:

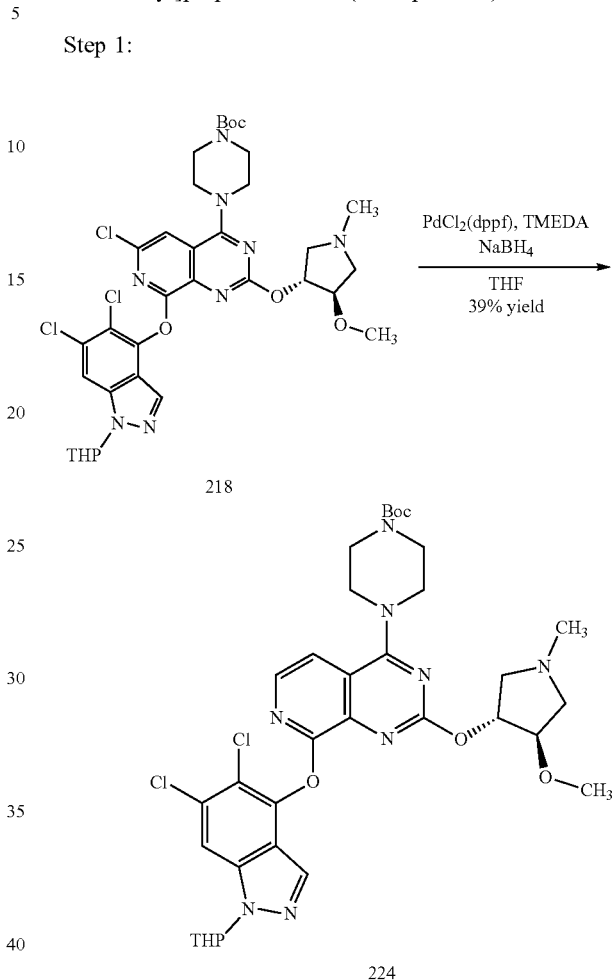

To a slurry of 8-[(5-chloro-6-fluoro-1H-indazol-4-yl)oxy]-2-{[(2S)-1-methylpyrrolidin-2-yl]methoxy}-4-(piperazin-1-yl)pyrido[3,4-d]pyrimidine (223) (236 mg, 0.265 mmol) in DCM (2.0 mL) was added DIPEA (192 mg, 0.258 mL, 1.48 mmol). The mixture was cooled to −50° C. and then treated dropwise with a solution of acryloyl chloride (19.6 mg, 0.212 mmol, 20 μl) in DCM (0.3 mL). The mixture was allowed to slowly warm to room temperature. LCMS analysis showed consumption of the starting material. The mixture was washed with water. The organic layer was dried over $Na_2SO_4$, filtered, and concentrated. Purification by preparatory SFC with a Waters SFC 200 Glacier system on a Princeton HA-Morpholine column (150×21.1 mm, 5 μm particle size), which was eluted with 12%-60% MeCN/$H_2O$ at 35° C. to provide 1-[4-(8-[(5-chloro-6-fluoro-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one (Example-1H) (13.9 mg, 12% yield) as a white solid. $^1$H NMR 400 MHz, DMSO-$d_6$) δ 7.77-7.74 (m, 1H), 7.79-7.69 (m, 1H), 7.73-7.68 (m, 1H), 7.66-7.60 (m, 1H), 7.54 (d, J=8.8 Hz, 1H), 6.87-6.72 (m, 1H), 6.16 (td, J=1.9, 16.8 Hz, 1H), 5.74 (dd, J=2.1, 10.5 Hz, 1H), 4.40-4.28 (m, 1H), 4.18 (dd, J=6.4, 10.7 Hz, 1H), 3.96-3.87 (m, 4H), 3.86-3.70 (m, 4H), 2.93 (dd, J=3.6, 9.0 Hz, 1H), 2.63-2.55 (m, 1H), 2.37-2.29 (m, 3H), 2.21-2.11 (m, 1H), 2.01-1.86 (m, 1H), 1.73-1.57 (m, 3H). LCMS (ESI) m/z 566 (M+H).

To a solution of tert-butyl 4-(6-chloro-8-{[5,6-dichloro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (218) in THF (7.3 mL) under nitrogen was added $NaBH_4$ (47.1 mg, 1.25 mmol), $PdCl_2$(dppf) (53.6 mg, 0.0733 mmol), and TMEDA (0.187 mL, 1.25 mmol). The resultant dark purple solution was stirred at room temperature for 33 h. LCMS analysis showed consumption of the starting material. The reaction was filtered through celite and concentrated to dryness. Purification by flash chromatography (ISCO, 24 g $SiO_2$, 15% IPA/EtOAc) provided 300 mg of material. The material was repurified by preparative HPLC (ISCO ACCQ Prep HP-125 system, Phenomenex Luna Omega Polar C18, 21×250 mm, 5 μm particle size, 35 ml/min flow rate, injection volume of 1 mL) to provide tert-butyl 4-(8-{[5,6-dichloro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (224) as a white cotton (105 mg, 39% yield)$^1$H NMR (400 MHz, DMSO-$d_6$) δ 8.12 (s, 1H), 7.82 (d, J=6.48 Hz, 1H), 7.76 (dd, J=5.8, 1.5 Hz, 1H), 7.59-7.63 (m, 1H), 5.93 (dd, J=9.6, 2.1 Hz, 1H), 5.22-5.27 (m, 1H), 3.93-3.99 (m, 1H), 3.75-3.92 (m, 6H), 3.57 (br. s, 4H), 3.34 (s, 3H), 3.01 (dd, J=9.8, 6.6 Hz, 1H), 2.81-2.89 (m, 1H), 2.58-2.66 (m, 1H), 2.27-2.38 (m, 2H), 2.23 (s, 3H), 1.95-2.07 (m, 2H), 1.71 (d, J=7.5 Hz, 1H), 1.58 (br. s, 2H), 1.44 (s, 9H). LCMS (ESI) m/z 729 (M+H).

Step 2:

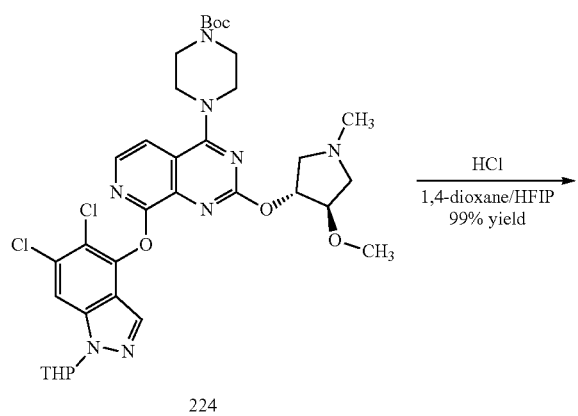

Step 3:

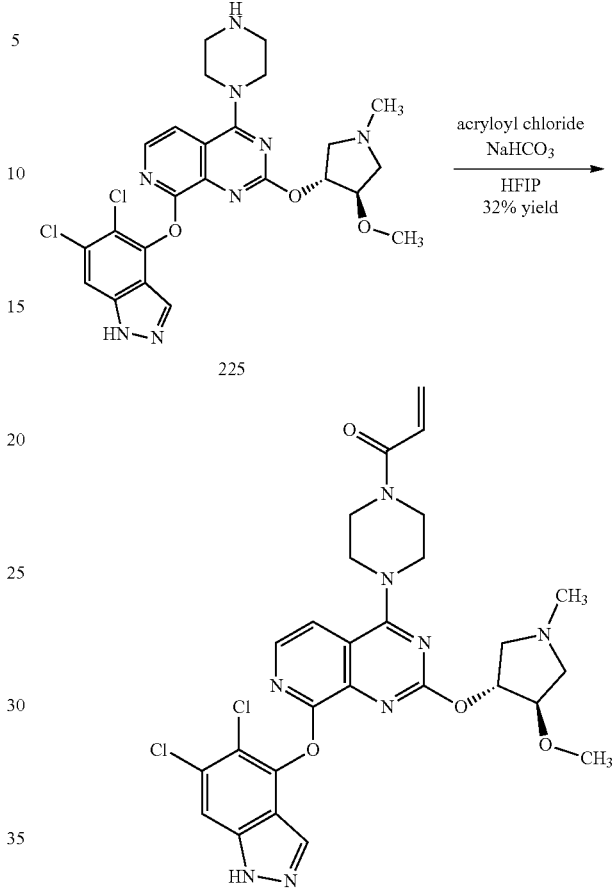

A solution of tert-butyl 4-(8-{[5,6-dichloro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (224) (101 mg, 0.138 mmol) in HFIP (1.48 mL) was cooled to 0° C. A solution of HCl (0.346 mL, 1.38 mmol, 4.0 M in 1,4-dioxane) was added dropwise. The mixture was stirred a further 10 min at 0° C. and then 45 min at room temperature. LCMS analysis of the light brown solution showed formation of the desired product. The crude reaction mixture was cooled to 0° C. and MTBE (5 mL) was slowly added to give a white precipitate. The solvent was removed under reduced pressure. Additional MTBE (5 mL) was added followed by concentration to provide 8-[(5,6-dichloro-1H-indazol-4-yl)oxy]-2-{[(3R,4R)-4-methoxy-1-methylpyrrolidin-3-yl]oxy}-4-(piperazin-1-yl)pyrido[3,4-d]pyrimidine (225) (75.3 mg, 99% yield) as a brown oil that was taken on without further purification. LCMS (ESI) m/z 545 (M+H)

8-[(5,6-dichloro-1H-indazol-4-yl)oxy]-2-{[(3R,4R)-4-methoxy-1-methylpyrrolidin-3-yl]oxy}-4-(piperazin-1-yl)pyrido[3,4-d]pyrimidine (225) (75.3 mg, 0.138 mmol) was dissolved in HFIP (1.38 mL). Solid NaHCO₃ (116 mg, 1.38 mmol) was added and the mixture was stirred at room temperature overnight. To the brown slurry was added acryloyl chloride (11.2 µL, 0.138 mmol). LCMS analysis showed conversion to the product. The crude reaction mixture was filtered to remove a white solid. The filter cake was washed with EtOAc and the filtrate was concentrated under reduced pressure. Purification by flash chromatography (ISCO, 12 g SiO₂, 2-10% MeOH/DCM+0.1% NH₃) provided 1-[4-(8-[(5,6-dichloro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-19H) (26.3 mg, 32% yield) as a white solid. ¹H NMR (400 MHz, DMSO-d₆) δ 13.57 (br. s, 1H), 7.81-7.85 (m, 1H), 7.78 (d, J=5.8 Hz, 1H), 7.75 (s, 1H), 7.63 (d, J=5.9 Hz, 1H), 6.83 (dd, J=16.6, 10.5 Hz, 1H), 6.18 (dd, J=16.7, 2.3 Hz, 1H), 5.71-5.77 (m, 1H), 5.20-5.29 (m, 1H), 3.89-3.98 (m, 5H), 3.84 (br. s, 2H), 3.77 (br. s, 2H), 3.35 (s, 3H), 3.01 (dd, J=9.8, 6.5 Hz, 1H), 2.85 (dd, J=10.6, 5.9 Hz, 1H), 2.63 (dd, J=10.5, 2.7 Hz, 1H), 2.30 (dd, J=9.8, 4.9 Hz, 1H), 2.23 (s, 3H). LCMS (ESI) m/z 599 (M+H).

The examples in the following table were prepared using Method H and the procedure used to prepare 1-(4-{8-[(5-Chloro-6-methyl-1H-indazol-4-yl)oxy]-2-[3-(dimethylamino)azetidin-1-yl]-6-methylpyrido[3,4-d]pyrimidin-4- yl}piperazin-1-yl)prop-2-en-1-one (Example-1H) and 1-[4-(8-[(5,6-dichloro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-19H). The following examples were made with non-critical changes or substitutions to the exemplified procedure used to prepare Example-1H, and Example-19H that someone who is skilled in the art would be able to realize.

| Example | Structure | Compound Name | LCMS m/z | ¹H NMR |
|---|---|---|---|---|
| 2H | 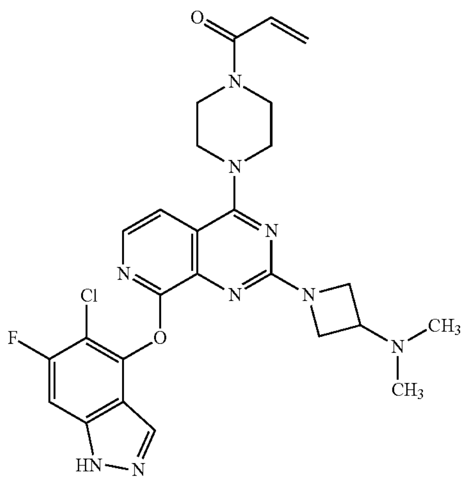 | 1-(4-{8-[(5-chloro-6-fluoro-1H-indazol-4-yl)oxy]-2-[3-(dimethylamino)azetidin-1-yl]pyrido[3,4-d]pyrimidin-4-yl}piperazin-1-yl)prop-2-en-1-one | 522 (M + H) | ¹H NMR (600 MHz, DMSO-$d_6$) δ 7.74 (br. s, 1H), 7.59-7.49 (m, 2H), 7.45 (dd, J = 0.9, 5.7 Hz, 1H), 6.88-6.77 (m, 1H), 6.22-6.07 (m, 1H), 5.79-5.65 (m, 1H), 4.11 (t, J = 7.4 Hz, 2H), 3.93-3.84 (m, 2H), 3.84-3.68 (m, 8H), 3.20-3.07 (m, 1H), 2.12 (s, 6H) |
| 3H | 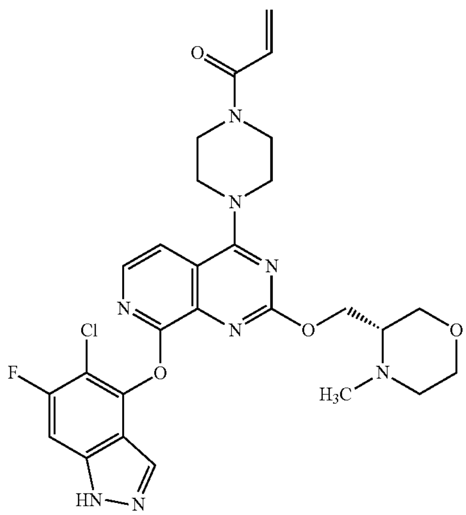 [SMILES: C=CC(=O)N1CCN(c2nc(OC[C@@H]3COCCN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(3S)-4-methylmorpholin-3-yl]methoxy}pyrido[3,4-d]pyrimidin-4-yl)piperazin-1-yl]prop-2-en-1-one | 583, 585 (M + H) | ¹H NMR (400 MHz, DMSO-$d_6$) δ 13.52 (s, 1H), 7.85-7.69 (m, 2H), 7.64 (d, J = 5.8 Hz, 1H), 7.57 (d, J = 8.8 Hz, 1H), 6.83 (dd, J = 16.7, 10.4 Hz, 1H), 6.18 (dd, J = 16.7, 2.4 Hz, 1H), 5.75 (dd, J = 10.5, 2.4 Hz, 1H), 4.47 (s, 1H), 4.34 (s, 1H), 3.93 (s, 4H), 3.80 (d, J = 30.4 Hz, 5H), 3.71-3.66 (m, 1H), 3.56-3.43 (m, 2H), 2.74-2.62 (m, 1H), 2.36-2.11 (m, 4H) |
| 4H | 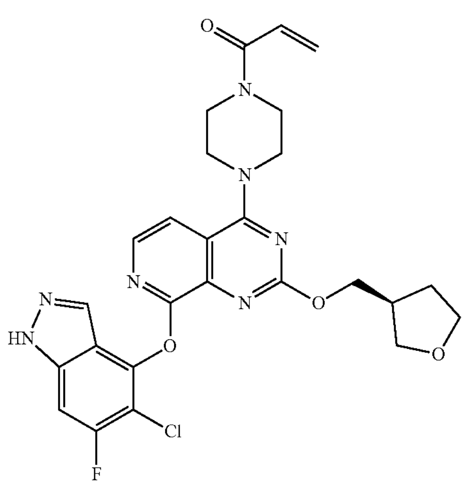 | 1-(4-{8-[(5-chloro-6-fluoro-1H-indazol-4-yl)oxy]-2-[(3S)-tetrahydrofuran-3-ylmethoxy]pyrido[3,4-d]pyrimidin-4-yl}piperazin-1-yl)prop-2-en-1-one | 554, 556 (M + H) | ¹H NMR (400 MHz, DMSO-$d_6$) δ 13.56 (s, 1H), 7.79 (d, J = 5.8 Hz, 1H), 7.75 (d, J = 1.0 Hz, 1H), 7.64 (d, J = 5.8 Hz, 1H), 7.56 (dd, J = 8.9, 1.0 Hz, 1H), 6.83 (dd, J = 16.7, 10.5 Hz, 1H), 6.18 (dd, J = 16.7, 2.4 Hz, 1H), 5.75 (dd, J = 10.4, 2.4 Hz, 1H), 4.29 (dd, J = 10.6, 6.7 Hz, 1H), 4.20 (dd, J = 10.6, 8.0 Hz, 1H), 3.99-3.89 (m, 4H), 3.87-3.73 (m, 6H), 3.66 (q, J = 7.7 Hz, 1H), 3.54 (dd, J = 8.7, 5.6 Hz, 1H), 2.75-2.62 (m, 1H), 2.15-1.95 (m, 1H), 1.73-1.59 (m, 1H) |

| Example | Structure | Compound Name | LCMS m/z | ¹H NMR |
|---|---|---|---|---|
| 5H | 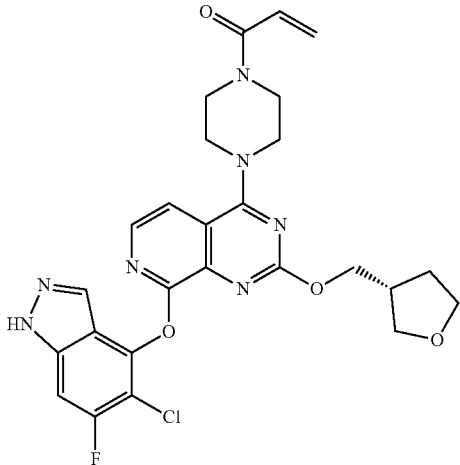 [SMILES: C=CC(=O)N1CCN(c2nc(OC[C@@H]3CCOC3)nc3c(Oc4c(Cl)c(F)cc5[nH]ncc45)nccc23)CC1] | 1-(4-{8-[(5-chloro-6-fluoro-1H-indazol-4-yl)oxy]-2-[(3R)-tetrahydrofuran-3-ylmethoxy]pyrido[3,4-d]pyrimidin-4-yl}piperazin-1-yl)prop-2-en-1-one | 554, 556 (M + H) | ¹H NMR (400 MHz, DMSO-$d_6$) δ 13.53 (s, 1H), 7.79 (d, J = 5.8 Hz, 1H), 7.75 (s, 1H), 7.64 (d, J = 5.8 Hz, 1H), 7.56 (dd, J = 8.9, 1.0 Hz, 1H), 6.83 (dd, J = 16.7, 10.5 Hz, 1H), 6.18 (dd, J = 16.7, 2.4 Hz, 1H), 5.75 (dd, J = 10.5, 2.4 Hz, 1H), 4.29 (dd, J = 10.6, 6.7 Hz, 1H), 4.20 (dd, J = 10.6, 7.9 Hz, 1H), 3.96-3.88 (m, 4H), 3.86-3.73 (m, 6H), 3.66 (q, J = 7.7 Hz, 1H), 3.54 (dd, J = 8.6, 5.6 Hz, 1H), 2.78-2.61 (m, 1H), 2.10-1.91 (m, 1H), 1.73-1.58 (m, 1H) |
| 6H | 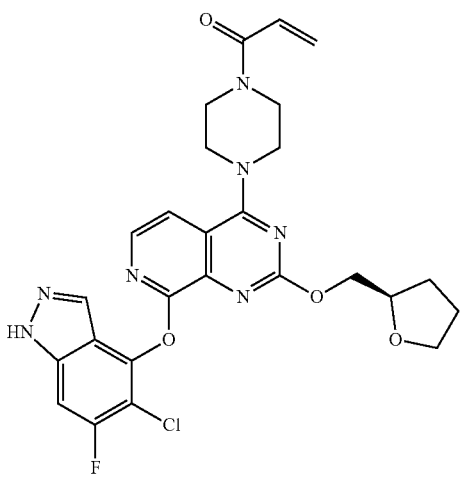 [SMILES: C=CC(=O)N1CCN(c2nc(OC[C@H]3CCCO3)nc3c(Oc4c(Cl)c(F)cc5[nH]ncc45)nccc23)CC1] | 1-(4-{8-[(5-chloro-6-fluoro-1H-indazol-4-yl)oxy]-2-[(2R)-tetrahydrofuran-2-ylmethoxy]pyrido[3,4-d]pyrimidin-4-yl}piperazin-1-yl)prop-2-en-1-one | 554, 556 (M + H) | ¹H NMR (400 MHz, DMSO-$d_6$) δ 13.61 (s, 1H), 7.79 (d, J = 5.8 Hz, 1H), 7.75 (s, 1H), 7.64 (d, J = 5.8 Hz, 1H), 7.57 (d, J = 8.8 Hz, 1H), 6.83 (dd, J = 16.7, 10.5 Hz, 1H), 6.18 (dd, J = 16.7, 2.3 Hz, 1H), 5.75 (dd, J = 10.4, 2.3 Hz, 1H), 4.28 (d, J = 5.3 Hz, 2H), 4.18 (t, J = 6.2 Hz, 1H), 3.99-3.88 (m, 4H), 3.88-3.73 (m, 5H), 3.72-3.63 (m, 1H), 2.05-1.95 (m, 1H), 1.93-1.77 (m, 2H), 1.73-1.61 (m, 1H) |
| 7H | 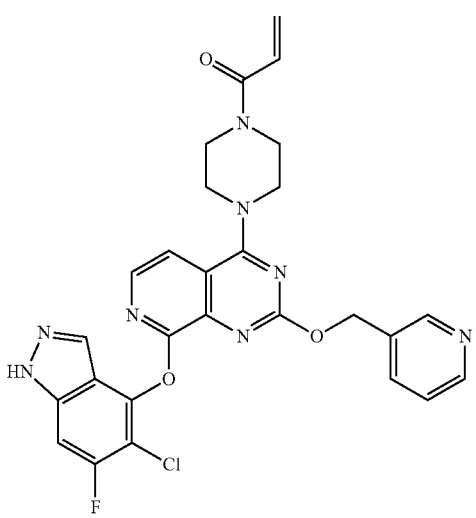 [SMILES: C=CC(=O)N1CCN(c2nc(OCc3cccnc3)nc3c(Oc4c(Cl)c(F)cc5[nH]ncc45)nccc23)CC1] | 1-(4-{8-[(5-chloro-6-fluoro-1H-indazol-4-yl)oxy]-2-(pyridin-3-ylmethoxy)pyrido[3,4-d]pyrimidin-4-yl}piperazin-1-yl)prop-2-en-1-one | 561, 563 (M + H) | ¹H NMR (400 MHz, DMSO-$d_6$) δ 13.59 (s, 1H), 8.78 (s, 1H), 8.54 (dd, J = 4.8, 1.5 Hz, 1H), 7.98 (dd, J = 6.0, 1.8 Hz, 1H), 7.87-7.71 (m, 2H), 7.61 (dd, J = 20.2, 7.4 Hz, 2H), 7.41 (dd, J = 7.8, 4.8 Hz, 1H), 6.82 (dd, J = 16.7, 10.4 Hz, 1H), 6.17 (dd, J = 16.7, 2.3 Hz, 1H), 5.74 (dd, J = 10.4, 2.3 Hz, 1H), 5.49 (s, 2H), 3.93 (dd, J = 6.4, 3.5 Hz, 4H), 3.79 (d, J = 29.7 Hz, 4H) |

-continued

| Example | Structure | Compound Name | LCMS m/z | ¹H NMR |
|---|---|---|---|---|
| 8H | 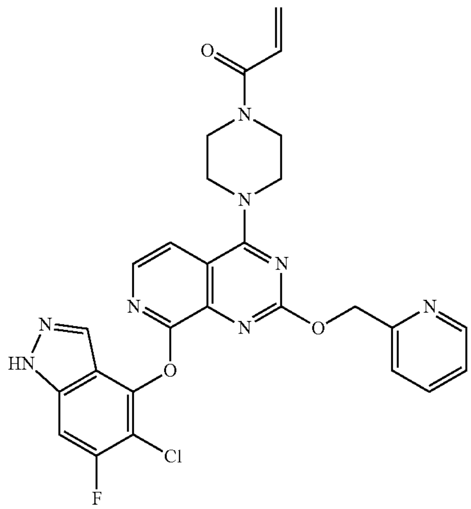 [SMILES: C=CC(=O)N1CCN(c2nc(OCc3ccccn3)nc3c(Oc4c(Cl)c(F)cc5[nH]ncc45)nccc23)CC1] | 1-(4-{8-[(5-chloro-6-fluoro-1H-indazol-4-yl)oxy]-2-(pyridin-2-ylmethoxy)pyrido[3,4-d]pyrimidin-4-yl}piperazin-1-yl)prop-2-en-1-one | 561, 563 (M + H) | ¹H NMR (400 MHz, DMSO-$d_6$) δ 13.61 (s, 1H), 8.57 (dd, J = 4.8, 0.8 Hz, 1H), 8.43 (s, 1H), 7.87-7.72 (m, 3H), 7.64 (d, J = 5.9 Hz, 1H), 7.60-7.52 (m, 2H), 7.34 (dd, J = 7.0, 5.3 Hz, 1H), 6.82 (dd, J = 16.7, 10.5 Hz, 1H), 6.17 (dd, J = 16.7, 2.3 Hz, 1H), 5.74 (dd, J = 10.4, 2.3 Hz, 1H), 5.52 (s, 2H), 3.93 (dd, J = 6.6, 3.5 Hz, 4H), 3.77 (d, J = 28.8 Hz, 4H) |
| 9H | 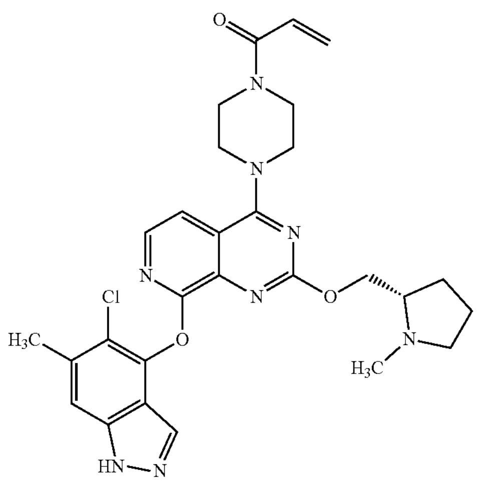 [SMILES: C=CC(=O)N1CCN(c2nc(OC[C@@H]3CCCN3C)nc3c(Oc4c(Cl)c(C)cc5[nH]ncc45)nccc23)CC1] | 1-[4-(8-[(5-chloro-6-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 563 (M + H) | 1H NMR (400 MHz, DMSO-$d_6$) δ 13.27 (s, 1H), 7.74 (d, J = 5.7 Hz, 1H), 7.66 (s, 1H), 7.58 (d, J = 5.8 Hz, 1H), 7.47 (s, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 4.40 (dd, J = 10.8, 4.6 Hz, 1H), 4.21 (dd, J = 10.9, 6.5 Hz, 1H), 3.88-3.81 (m, 8H), 2.95 (dd, J = 8.6, 5.3 Hz, 1H), 2.66-2.55 (m, 1H), 2.37 (s, 3H), 2.18 (q, J = 8.4 Hz, 1H), 1.98-1.89 (m, 1H), 1.82-1.56 (m, 3H). 3 protons obscured by solvent peak, |
| 10H | 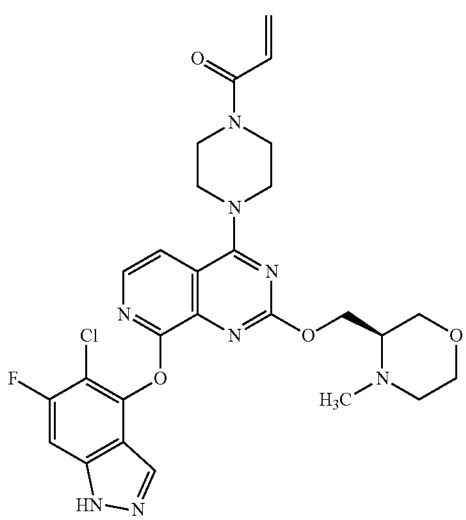 [SMILES: C=CC(=O)N1CCN(c2nc(OC[C@H]3COCCN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R)-4-methylmorpholin-3-yl]methoxy}pyrido[3,4-d]pyrimidin-4-yl)piperazin-1-yl]prop-2-en-1-one | 583, 585 (M + H) | ¹H NMR (400 MHz, DMSO-$d_6$) δ 13.54 (s, 1H), 7.78 (d, J = 5.8 Hz, 1H), 7.76 (s, 1H), 7.64 (d, J = 5.9 Hz, 1H), 7.57 (dd, J = 8.9, 1.0 Hz, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 4.47 (dd, J = 11.6, 3.7 Hz, 1H), 4.33 (dd, J = 11.6, 5.5 Hz, 1H), 3.93 (dd, J = 7.0, 3.6 Hz, 4H), 3.89-3.74 (m, 5H), 3.68 (d, J = 11.2 Hz, 1H), 3.54-3.45 (m, 1H), 3.42-3.36 (m, 1H), 2.72-2.62 (m, 1H), 2.46-2.40 (m, 1H), 2.31 (s, 3H), 2.21 (td, J = 11.1, 3.3 Hz, 1H) |

| Example | Structure | Compound Name | LCMS m/z | ¹H NMR |
|---|---|---|---|---|
| 11H | 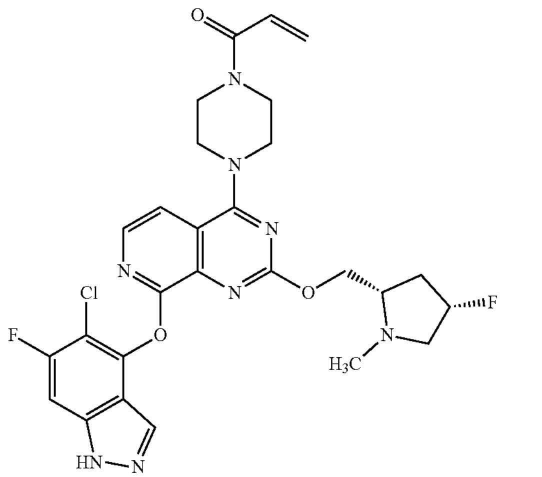 [SMILES: C=CC(=O)N1CCN(c2nc(OC[C@@H]3C[C@H](F)CN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(2S,4S)-4-fluoro-1-methylpyrrolidin-2-yl]methoxy}pyrido[3,4-d]pyrimidin-4-yl)piperazin-1-yl]prop-2-en-1-one | 585 (M + H) | 1H NMR (400 MHz, MeOD) δ 7.83-7.72 (m, 2H), 7.62 (d, J = 5.9 Hz, 1H), 7.38 (dd, J = 8.7, 1.1 Hz, 1H), 6.82 (dd, J = 16.8, 10.6 Hz, 1H), 6.28 (dd, J = 16.8, 2.0 Hz, 1H), 5.81 (dd, J = 10.6, 1.9 Hz, 1H), 5.16 (dt, J = 54.4, 4.4 Hz, 1H), 4.67-4.53 (m, 2H), 4.49 (dd, J = 11.1, 5.7 Hz, 1H), 4.11-4.00 (m, 4H), 3.97-3.89 (m, 4H), 2.97-2.78 (m, 1H), 2.60-2.55 (m, 1H), 2.54 (s, 3H), 2.52-2.45 (m, 1H), 2.12-1.88 (m, 1H) |
| 12H | 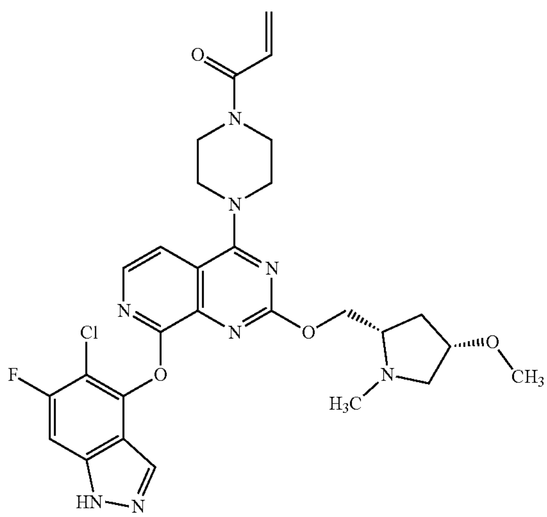 [SMILES: C=CC(=O)N1CCN(c2nc(OC[C@@H]3C[C@H](OC)CN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(2S,4S)-4-methoxy-1-methylpyrrolidin-2-yl]methoxy}pyrido[3,4-d]pyrimidin-4-yl)piperazin-1-yl]prop-2-en-1-one | 597, 599 (M + H) | ¹H NMR (400 MHz, DMSO-d₆) δ 13.54 (s, 1H), 7.82-7.69 (m, 2H), 7.63 (d, J = 5.9 Hz, 1H), 7.57 (dd, J = 8.9, 1.0 Hz, 1H), 6.83 (dd, J = 16.7, 10.5 Hz, 1H), 6.18 (dd, J = 16.7, 2.4 Hz, 1H), 5.75 (dd, J = 10.4, 2.4 Hz, 1H), 4.42 (dd, J = 10.9, 4.9 Hz, 1H), 4.26 (dd, J = 10.9, 6.2 Hz, 1H), 3.97-3.88 (m, 4H), 3.89-3.65 (m, 5H), 3.16 (s, 3H), 3.05 (d, J = 10.6 Hz, 1H), 2.65-2.57 (m, 1H), 2.33 (s, 3H), 2.32-2.20 (m, 2H), 1.71-1.58 (m, 1H) |
| 13H | 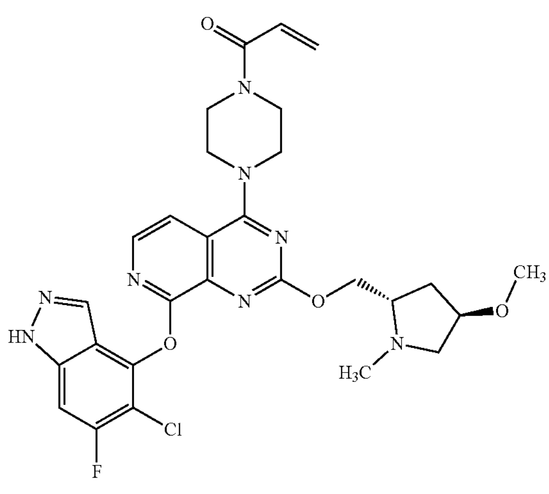 [SMILES: C=CC(=O)N1CCN(c2nc(OC[C@@H]3C[C@@H](OC)CN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(2S,4R)-4-methoxy-1-methylpyrrolidin-2-yl]methoxy}pyrido[3,4-d]pyrimidin-4-yl)piperazin-1-yl]prop-2-en-1-one | 597, 599 (M + H) | ¹H NMR (400 MHz, DMSO-d₆) δ 13.52 (s, 1H), 7.77 (t, J = 5.7 Hz, 2H), 7.63 (d, J = 5.8 Hz, 1H), 7.56 (dd, J = 8.9, 1.0 Hz, 1H), 6.83 (dd, J = 16.7, 10.5 Hz, 1H), 6.18 (dd, J = 16.7, 2.4 Hz, 1H), 5.75 (dd, J = 10.4, 2.4 Hz, 1H), 4.38 (dd, J = 11.1, 4.5 Hz, 1H), 4.26 (dd, J = 10.9, 5.7 Hz, 1H), 4.03-3.71 (m, 9H), 3.32-3.27 (m, 1H), 3.19 (s, 3H), 2.78 (s, 1H), 2.36 (s, 3H), 2.18 (s, 1H), 1.98-1.78 (m, 2H) |

| Example | Structure | Compound Name | LCMS m/z | $^1$H NMR |
|---|---|---|---|---|
| 14H | 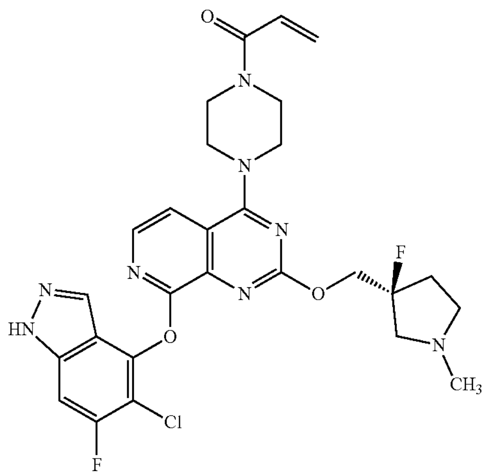 [SMILES: C=CC(=O)N1CCN(c2nc(OC[C@]3(F)CCN(C)C3)nc3c(Oc4c(Cl)c(F)cc5[nH]ncc45)nccc23)CC1] | 1-[4-(8-[(5-chloro-6-fluoro-1H-indazol-4-yl)oxy]-2-{[(3S)-3-fluoro-1-methylpyrrolidin-3-yl]methoxy}pyrido[3,4-d]pyrimidin-4-yl)piperazin-1-yl]prop-2-en-1-one | 585, 587 (M + H) | $^1$H NMR (400 MHz, DMSO-d$_6$) δ 13.54 (s, 1H), 7.80 (d, J = 5.8 Hz, 1H), 7.78 (s, 1H), 7.65 (d, J = 5.9 Hz, 1H), 7.57 (dd, J = 8.9, 0.9 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.60-4.38 (m, 2H), 4.00-3.89 4 (m, 4H), 3.88-3.68 (m, 4H), 2.84-2.66 (m, 3H), 2.47-2.39 (m, 1H), 2.26 (s, 3H), 2.21-1.89 (m, 2H) |
| 15H | 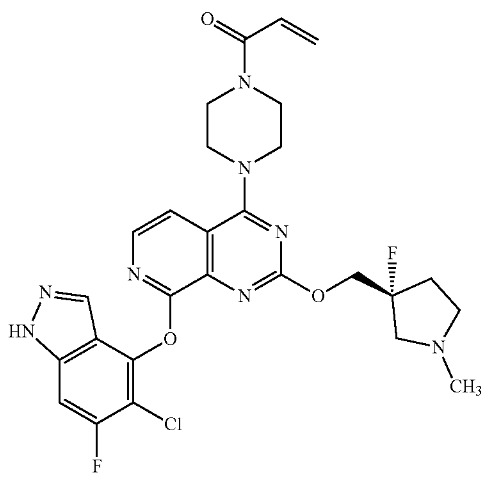 [SMILES: C=CC(=O)N1CCN(c2nc(OC[C@@]3(F)CCN(C)C3)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R)-3-fluoro-1-methylpyrrolidin-3-yl]methoxy}pyrido[3,4-d]pyrimidin-4-yl)piperazin-1-yl]prop-2-en-1-one | 585, 587 (M + H) | $^1$H NMR (400 MHz, DMSO-d$_6$) δ 13.51 (s, 1H), 7.80 (d, J = 5.8 Hz, 1H), 7.77 (s, 1H), 7.65 (d, J = 5.9 Hz, 1H), 7.56 (dd, J = 8.9, 0.9 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.60-4.37 (m, 2H), 4.02-3.90 (m, 4H), 3.87-3.71 (m, 4H), 2.85-2.68 (m, 3H), 2.46-2.40 (m, 1H), 2.26 (s, 3H), 2.21-1.93 (m, 2H) |
| 16H | 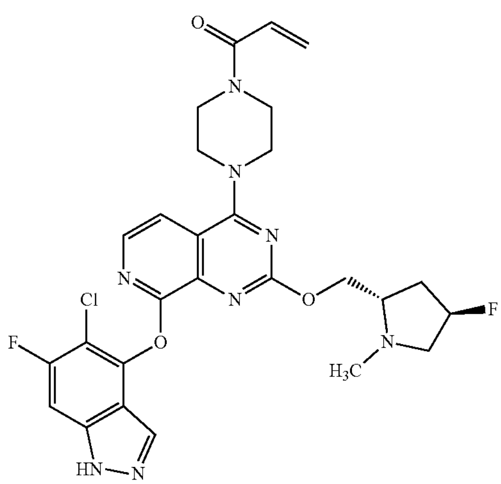 [SMILES: C=CC(=O)N1CCN(c2nc(OC[C@@H]3C[C@@H](F)CN3C)nc3c(Oc4c(Cl)c(F)cc5[nH]ncc45)nccc23)CC1] | 1-[4-(8-[(5-chloro-6-fluoro-1H-indazol-4-yl)oxy]-2-{[(2S,4R)-4-fluoro-1-methylpyrrolidin-2-yl]methoxy}pyrido[3,4-d]pyrimidin-4-yl)piperazin-1-yl]prop-2-en-1-one | 585, 587 (M + H) | $^1$H NMR (400 MHz, DMSO-d$_6$) δ 13.52 (s, 1H), 7.78 (d, J = 5.8 Hz, 1H), 7.76 (s, 1H), 7.63 (d, J = 5.9 Hz, 1H), 7.56 (dd, J = 8.9, 0.9 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 5.30-5.07 (m, 1H), 4.46-4.27 (m, 2H), 4.00-3.87 (m, 4H), 3.86-3.65 (m, 4H), 3.52-3.38 (m, 1H), 2.98-2.88 (m, 1H), 2.49-2.47 (m, 1H), 2.41 (s, 3H), 2.23-2.06 (m, 1H), 2.04-1.82 (m, 1H) |

-continued

| Example | Structure | Compound Name | LCMS m/z | ¹H NMR |
|---|---|---|---|---|
| 17H | 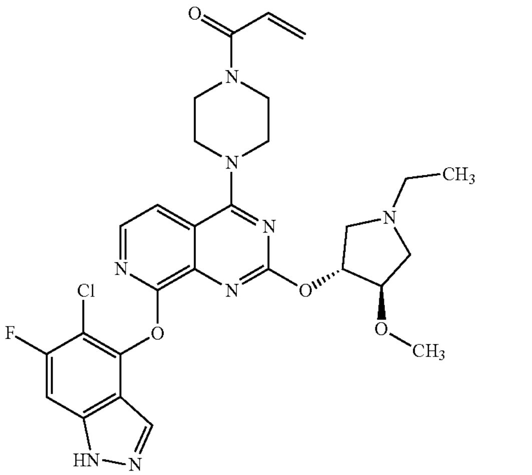 [SMILES: C=CC(=O)N1CCN(c2nc(O[C@@H]3CN(CC)C[C@H]3OC)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R,4R)-1-ethyl-4-methoxypyrrolidin-3-yl]oxy}pyrido[3,4-d]pyrimidin-4-yl)piperazin-1-yl]prop-2-en-1-on | 597, 599 (M + H) | ¹H NMR (400 MHz, DMSO-d₆) δ 13.59 (s, 1H), 7.79 (d, J = 5.7 Hz, 1H), 7.71 (s, 1H), 7.65 (d, J = 5.8 Hz, 1H), 7.56 (d, J = 8.9 Hz, 1H), 6.83 (dd, J = 16.7, 10.5 Hz, 1H), 6.18 (dd, J = 16.7, 2.4 Hz, 1H), 5.75 (dd, J = 10.3, 2.4 Hz, 1H), 5.25 (dt, J = 5.6, 2.6 Hz, 1H), 3.97-3.91 (m, 5H), 3.80 (d, J = 30.9 Hz, 4H), 3.35 (s, 3H), 3.05 (dd, J = 9.8, 6.5 Hz, 1H), 2.86 (dd, J = 10.7, 6.1 Hz, 1H), 2.66 (dd, J = 10.5, 3.0 Hz, 1H), 2.46-2.35 (m, 2H), 2.31 (dd, J = 9.9, 4.8 Hz, 1H), 1.00 (t, J = 7.1 Hz, 3H) |
| 18H | 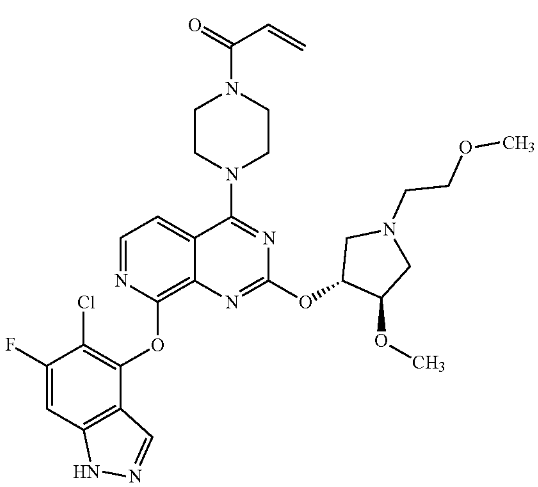 [SMILES: C=CC(=O)N1CCN(c2nc(O[C@@H]3CN(CCOC)C[C@H]3OC)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R,4R)-4-methoxy-1-(2-methoxyethyl)pyrrolidin-3-yl]oxy}pyrido[3,4-d]pyrimidin-4-yl)piperazin-1-yl]prop-2-en-1-one | 627, 629 (M + H) | ¹H NMR (400 MHz, DMSO-d₆) δ 13.53 (s, 1H), 7.79 (d, J = 5.8 Hz, 1H), 7.72 (s, 1H), 7.64 (d, J = 5.8 Hz, 1H), 7.56 (d, J = 8.8 Hz, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 5.24 (s, 1H), 3.98-3.91 (m, 5H), 3.80 (d, J = 30.0 Hz, 4H), 3.40 (t, J = 5.8 Hz, 2H), 3.35 (s, 3H), 3.21 (s, 3H), 3.09 (dd, J = 10.0, 6.5 Hz, 1H), 2.94 (dd, J = 10.7, 6.1 Hz, 1H), 2.70 (dd, J = 11.9, 9.1 Hz, 1H), 2.56 (td, J = 6.0, 2.5 Hz, 2H), 2.38 (dd, J = 10.0, 4.8 Hz, 1H) |

417

The following examples were prepared according to general Method I:

Preparation of (3R,5S)-5-[({8-[(5-chloro-6-fluoro-1H-indazol-4-yl)oxy]-4-[4-(prop-2-enoyl)piperazin-1-yl]pyrido[3,4-d]pyrimidin-2-yl}oxy)methyl]-1-methylpyrrolidine-3-carbonitrile (Example-1I)

Step 1:

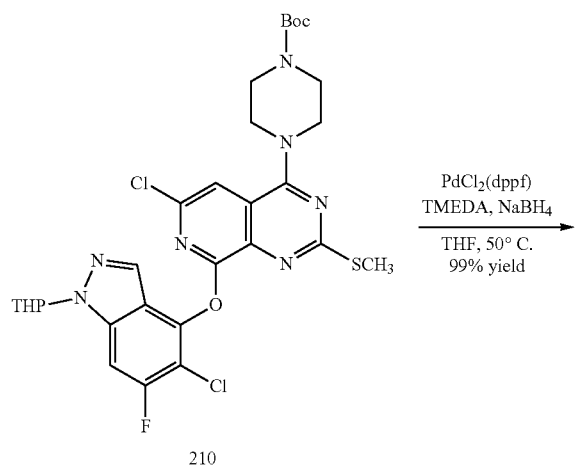

210

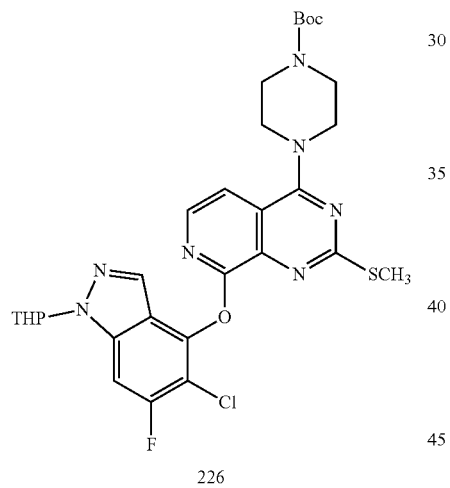

226

A mixture of tert-butyl 4-[6-chloro-8-{[5-chloro-6-fluoro-1-(tetrahydro-2H-pyran-2-yl)-1H-indazol-4-yl]oxy}-2-(methylsulfanyl)pyrido[3,4-d]pyrimidin-4-yl]piperazine-1-carboxylate (210) (35.0 g, 52.8 mmol) in dry THF (595 mL) was degassed by bubbling through with nitrogen for 20 min. Pd(dppf)Cl₂ (3.86 g, 5.28 mmol), TMEDA (12.0 g, 14.8 mL, 100 mmol), and NaBH₄ (3.51 g, 92.4 mmol) were added sequentially. The mixture was stirred in an oil bath at 50° C. (internal temperature of 40° C.) for 1.2 h. LCMS analysis showed consumption of the starting material. The reaction was cooled to room temperature and then 600 mL of brine and 595 mL of EtOAc were added. The layers were separated and the combined organics were dried with Na₂SO₄, filtered, and concentrated. The crude residue was purified by flash chromatography (3:5:2 EtOAc/petroleum ether/DCM) to provide tert-butyl 4-[8-{[5-chloro-6-fluoro-1-(oxan-2-yl)-1H-indazol-4-yl]oxy}-2-(methylsulfanyl)pyrido[3,4-d]pyrimidin-4-yl]piperazine-1-carboxylate (226) (34 g, 100% yield) as a pale yellow solid. ¹H NMR (400 MHz, DMSO-d₆) δ 7.88 (t, J=4.3 Hz, 2H), 7.82 (d, J=5.8 Hz, 1H), 7.60 (d, J=5.9 Hz, 1H), 5.88 (dd, J=9.7, 2.1 Hz, 1H), 3.92-3.73 (m, 6H), 3.57 (s, 4H), 2.54 (s, 3H), 2.34 (dt, J=10.3, 6.7 Hz, 1H), 2.02 (dd, J=13.6, 4.3 Hz, 2H), 1.71 (dd, J=15.8, 8.7 Hz, 1H), 1.59 (d, J=3.9 Hz, 2H), 1.44 (s, 9H). LCMS (ESI) m/z 630 (M+H).

Step 2:

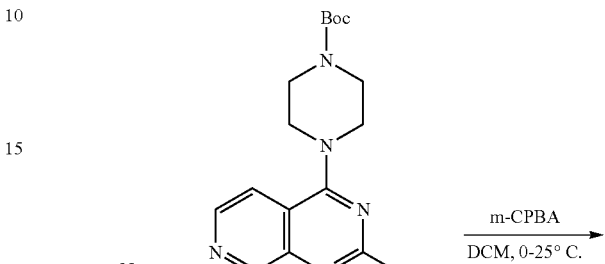

226

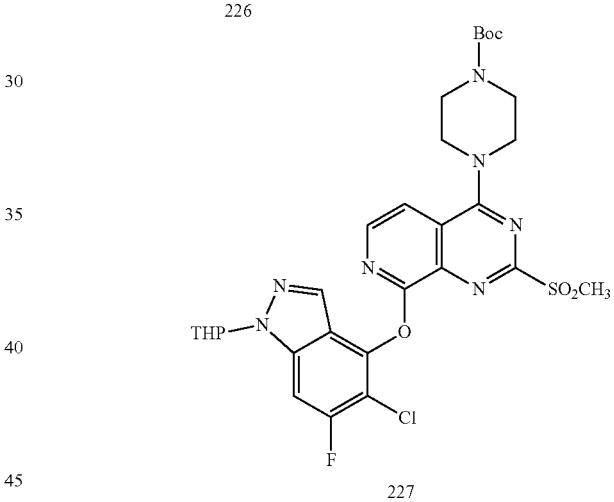

227

A solution of tert-butyl 4-[8-{[5-chloro-6-fluoro-1-(oxan-2-yl)-1H-indazol-4-yl]oxy}-2-(methylsulfanyl)pyrido[3,4-d]pyrimidin-4-yl]piperazine-1-carboxylate (226) in DCM (30 mL) was cooled to 0° C. with an ice bath. m-CPBA (1.92 g, 8.57 mmol) was added, which resulted in an exotherm. The resultant suspension was stirred overnight. LCMS analysis showed persisting sulfoxide intermediate. Additional m-CPBA (100 mg, 4.29 mmol) was added. After 3 h LCMS analysis showed full conversion to the desired product. The reaction mixture was washed with saturated aqueous NaHCO₃. The aqueous layer was extracted with DCM. The combined organics were washed with brine, dried over Na₂SO₄, filtered and concentrated. Purification by flash chromatography (ISCO, 80 g SiO₂, 0-100 EtOAc/heptanes) provided tert-butyl 4-[8-{[5-chloro-6-fluoro-1-(oxan-2-yl)-1H-indazol-4-yl]oxy}-2-(methanesulfonyl)pyrido[3,4-d]pyrimidin-4-yl]piperazine-1-carboxylate (227) (900 mg, 48% yield) as a white solid. ¹H NMR (400 MHz, DMSO-d₆) δ 8.06 (d, J=5.9 Hz, 1H), 7.94 (s, 1H), 7.91 (d, J=9.3 Hz, 1H), 7.77 (d, J=6.0 Hz, 1H), 5.89 (dd, J=2.3, 9.6 Hz, 1H), 4.10-4.01 (m, 4H), 3.94-3.87 (m, 1H), 3.84-3.74 (m, 1H), 3.60 (br. s, 4H), 3.41 (s, 3H), 2.43-2.29 (m, 1H), 2.09-1.96 (m, 2H), 1.72 (br.s, 1H), 1.59 (d, J=3.8 Hz, 2H), 1.44 (s, 9H). LCMS (ESI) m/z 662 (M+H).

Step 3:

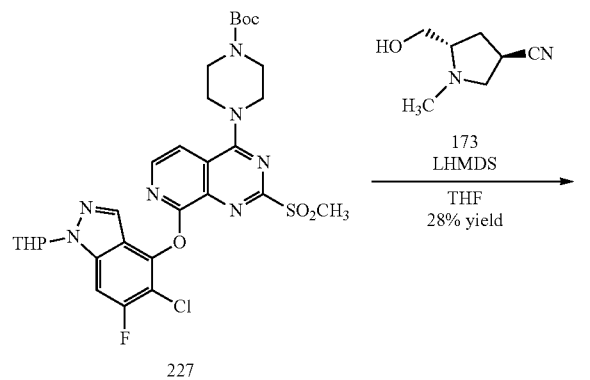

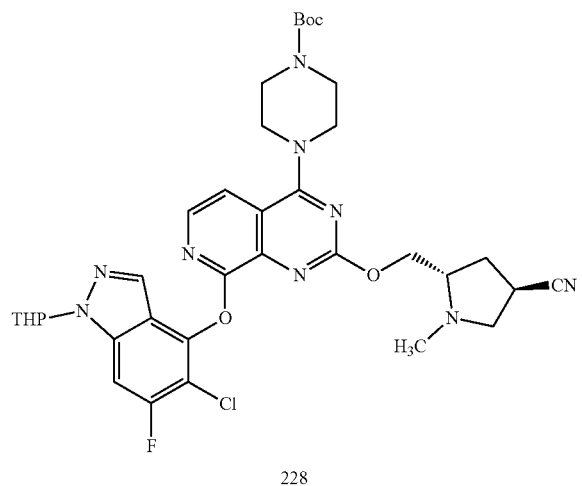

To a mixture tert-butyl 4-[8-{[5-chloro-6-fluoro-1-(oxan-2-yl)-1H-indazol-4-yl]oxy}-2-(methanesulfonyl)pyrido[3,4-d]pyrimidin-4-yl]piperazine-1-carboxylate (227) (400 mg, 0.604 mmol) and (3R,5S)-5-(hydroxymethyl)-1-methylpyrrolidine-3-carbonitrile (173) (169 mg, 1.21 mmol) in THF (10 mL) was added LHMDS (0.785 mL, 0.785 mmol, 1.0 M in THF). The mixture was stirred at 25° C. for 16 h. LCMS analysis showed conversion to the product. H₂O (5 mL) was added and the mixture was extracted with EtOAc (3×20 mL). The combined organics were dried over Na₂SO₄, filtered, and concentrated. The residue was purified by flash chromatography (SiO₂, 2:3 petroleum ether/EtOAc) to provide tert-butyl 4-(8-{[5-chloro-6-fluoro-1-(oxan-2-yl)-1H-indazol-4-yl]oxy}-2-{[(2S,4R)-4-cyano-1-methylpyrrolidin-2-yl]methoxy}pyrido[3,4-d]pyrimidin-4-yl)piperazine-1-carboxylate (228) (120 mg, 28% yield) as yellow oil. LCMS (ESI) m/z 722, 724 (M+H).

Step 4:

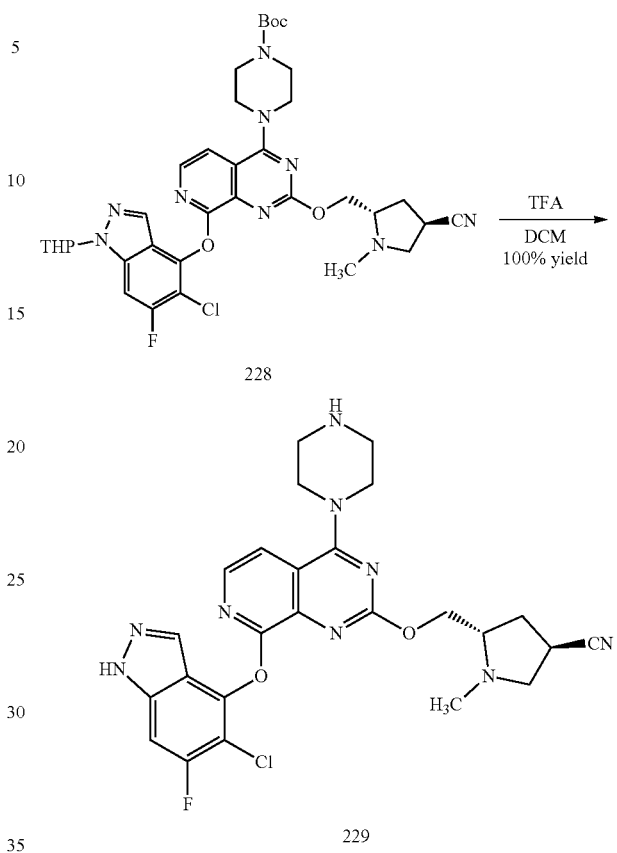

To a solution of tert-butyl 4-(8-{[5-chloro-6-fluoro-1-(oxan-2-yl)-1H-indazol-4-yl]oxy}-2-{[(2S,4R)-4-cyano-1-methylpyrrolidin-2-yl]methoxy}pyrido[3,4-d]pyrimidin-4-yl)piperazine-1-carboxylate (228) (120 mg, 0.166 mmol) in DCM (3 mL) was added TFA (1.5 mL) and the mixture was stirred at 25° C. for 2 h. The mixture was concentrated to afford (3R,5S)-5-[({8-[(5-chloro-6-fluoro-1H-indazol-4-yl)oxy]-4-(piperazin-1-yl)pyrido[3,4-d]pyrimidin-2-yl}oxy)methyl]-1-methylpyrrolidine-3-carbonitrile (229) (108 mg, 100% yield) as yellow oil, which was used in next step without purification. LCMS (ESI) m/z 538, 540 (M+H).

Step 5:

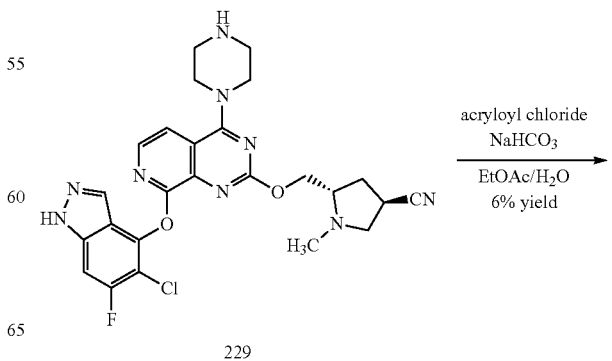

421

-continued

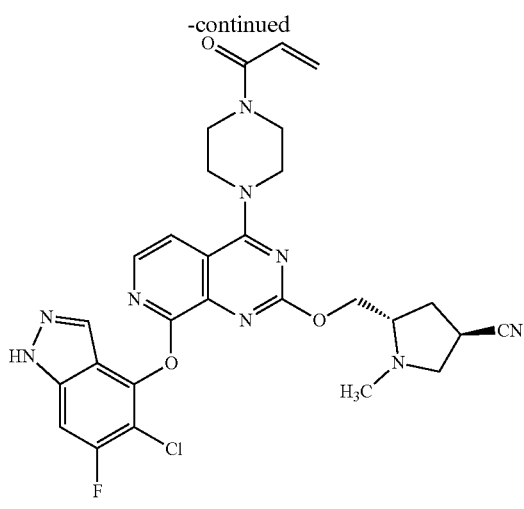

Example-1I

To a solution of (3R,5S)-5-[({8-[(5-chloro-6-fluoro-1H-indazol-4-yl)oxy]-4-(piperazin-1-yl)pyrido[3,4-d]pyrimidin-2-yl}oxy)methyl]-1-methylpyrrolidine-3-carbonitrile (229) (90 mg, 0.166 mmol) in EtOAc (40 mL) and saturated aqueous NaHCO$_3$ (40 mL, sat.) was added acryloyl chloride (15 mg, 0.166 mmol) and the mixture was stirred at 20° C. for 30 min. LCMS analysis showed consumption of the starting material. The mixture was extracted with EtOAc (3×40 mL). The combined organics were washed with brine (20 mL), dried over Na$_2$SO$_4$, and concentrated. The residue was purified by preparative HPLC on a C-18 column which was eluted with MeCN/H$_2$O (+0.05% formic acid)) to afford (3R,5S)-5-[({8-[(5-chloro-6-fluoro-1H-indazol-4-yl)oxy]-4-[4-(prop-2-enoyl)piperazin-1-yl]pyrido[3,4-d]pyrimidin-2-yl}oxy)methyl]-1-methylpyrrolidine-3-carbonitrile (Example-1I) (5.5 mg, 6% yield) as a white solid. $^1$H NMR (400 MHz, MeOD) δ 8.52 (s, 1H), 7.76 (s, 2H), 7.62 (d, J=5.8 Hz, 1H), 7.39 (d, J=8.8 Hz, 1H), 6.82 (dd, J=16.8, 10.6 Hz, 1H), 6.28 (d, J=16.7 Hz, 1H), 5.81 (d, J=12.1 Hz, 1H), 4.46 (d, J=4.9 Hz, 2H), 4.05 (s, 4H), 3.92 (s, 4H), 3.41-3.36 (m, 1H), 3.24 (dd, J=17.1, 7.8 Hz, 1H), 2.99 (s, 1H), 2.58 (t, J=9.5 Hz, 1H), 2.52 (s, 3H), 2.38-2.27 (m, 2H). LCMS (ESI) m/z 592, 594 (M+H).

Preparation of (3R,5S)-5-[({8-[(5-chloro-6-fluoro-1H-indazol-4-yl)oxy]-4-[4-(prop-2-enoyl)piperazin-1-yl]pyrido[3,4-d]pyrimidin-2-yl}oxy)methyl]-1-methylpyrrolidine-3-carbonitrile (Example-2I)

Step 1:

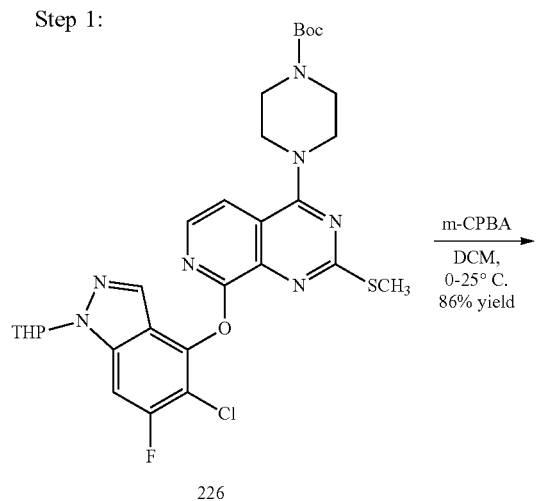

422

-continued

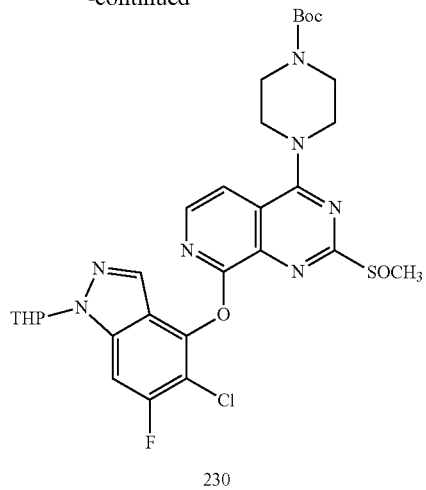

230

To a stirred solution of tert-butyl 4-[8-{[5-chloro-6-fluoro-1-(oxan-2-yl)-1H-indazol-4-yl]oxy}-2-(methylsulfanyl)pyrido[3,4-d]pyrimidin-4-yl]piperazine-1-carboxylate (226) (10.0 g, 15.9 mmol) in DCM (100 mL) was added m-CPBA (85% purity, 9.67 g, 47.6 mmol) portion-wise at 5° C. The reaction was stirred at the same temperature for 2 h. LCMS analysis showed formation of the desired product. The mixture was diluted with DCM (100 mL), washed successively with saturated aqueous NaHCO$_3$ (100 mL), saturated aqueous Na$_2$SO$_3$ (100 mL), and brine (100 mL). The combined organics were dried over Na$_2$SO$_4$, filtered, and concentrated to dryness to provide tert-butyl 4-[8-{[5-chloro-6-fluoro-1-(oxan-2-yl)-1H-indazol-4-yl]oxy}-2-(methanesulfinyl)pyrido[3,4-d]pyrimidin-4-yl]piperazine-1-carboxylate (230) (9.04 g, 86% yield) as a pale yellow solid, which was used without further purification. $^1$H NMR (400 MHz, DMSO-d$_6$) δ 8.00 (d, J=5.9 Hz, 1H), 7.96-7.89 (m, 2H), 7.73 (d, J=5.9 Hz, 1H), 5.89 (dd, J=9.7, 2.2 Hz, 1H), 4.00 (dd, J=9.0, 4.9 Hz, 4H), 3.90 (d, J=11.4 Hz, 1H), 3.83-3.75 (m, 1H), 3.59 (s, 4H), 2.95 (s, 3H), 2.38 (s, 1H), 2.02 (s, 2H), 1.80-1.69 (m, 1H), 1.59 (d, J=3.5 Hz, 2H), 1.44 (s, 9H). LCMS (ESI) m/z 646 (M+H).

Step 2:

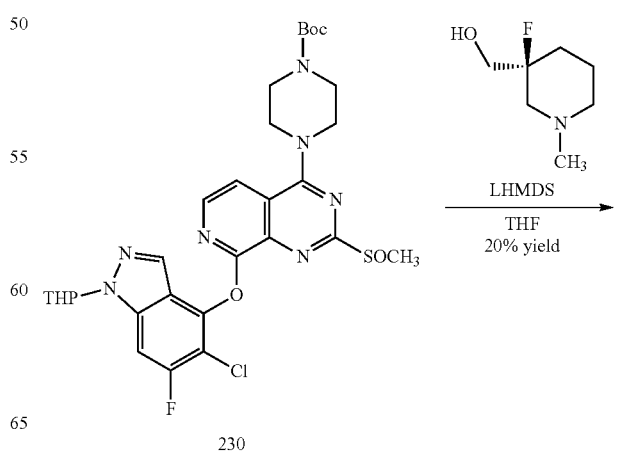

423

-continued

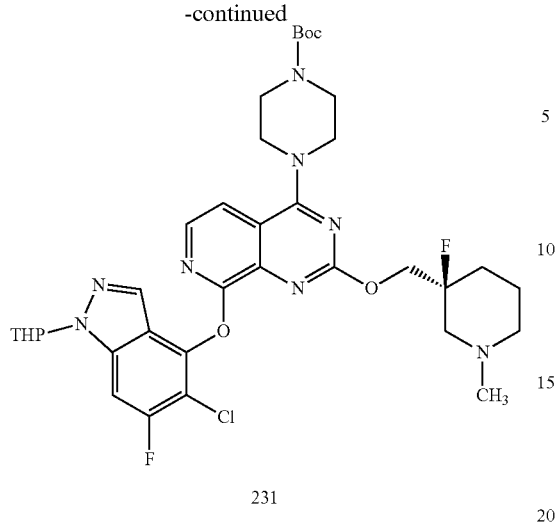

231

424

-continued

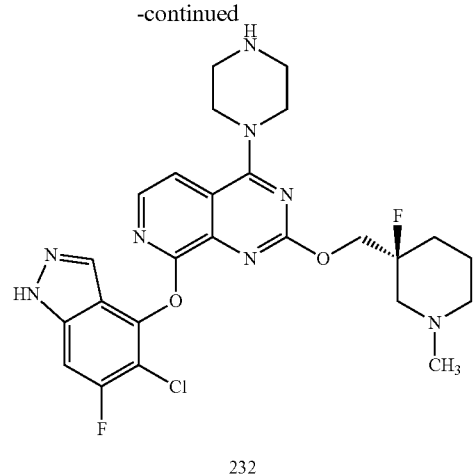

232

To a stirred solution of [(3S)-3-fluoro-1-methylpiperidin-3-yl]methanol (187) (50 mg, 0.34 mmol) in THF (5 mL) was added tert-butyl 4-[8-{[5-chloro-6-fluoro-1-(oxan-2-yl)-1H-indazol-4-yl]oxy}-2-(methanesulfinyl)pyrido[3,4-d]pyrimidin-4-yl]piperazine-1-carboxylate (230) (146 mg, 0.226 mmol) and LHMDS (56.8 mg, 0.340 mmol, 1.0 M in THF). The resulting mixture was stirred at 25° C. for 1.5 hours. LCMS analysis showed consumption of the starting material. The reaction was quenched by the addition of saturated aqueous NH$_4$Cl. The crude reaction mixture was poured into H$_2$O (30 mL) and extracted with EtOAc (3×30 mL). The combined organics were dried over anhydrous Na$_2$SO$_4$, filtered, and concentrated to dryness. The crude residue was purified by reverse phase flash chromatography (0-100% MeCN/H$_2$O (+0.05% FA) to provide tert-butyl 4-(8-{[5-chloro-6-fluoro-1-(oxan-2-yl)-1H-indazol-4-yl]oxy}-2-{[(3S)-3-fluoro-1-methylpiperidin-3-yl]methoxy}pyrido[3,4-d]pyrimidin-4-yl)piperazine-1-carboxylate (231) (50 mg, 20% yield) as a white solid. $^1$H NMR (400 MHz, DMSO-d$_6$) δ 7.87 (d, J=9.2 Hz, 1H), 7.83 (s, 1H), 7.78 (d, J=5.7 Hz, 1H), 7.63 (d, J=5.8 Hz, 1H), 5.87 (d, J=8.8 Hz, 1H), 4.56 (dd, J=22.6, 12.1 Hz, 1H), 4.41 (dd, J=22.3, 12.2 Hz, 1H), 3.93-3.75 (m, 6H), 3.57 (m, 4H), 2.57 (m, 1H), 2.45 (m, 1H), 2.35 (m, 2H), 2.24 (m, 1H), 2.18 (s, 3H), 1.99 (m, 2H), 1.71 (m, 4H), 1.58 (m, 3H), 1.44 (s, 9H). LCMS (ESI) m/z 729, 731 (M+H).

Step 3:

To a stirred solution of tert-butyl tert-butyl 4-(8-{[5-chloro-6-fluoro-1-(oxan-2-yl)-1H-indazol-4-yl]oxy}-2-{[(3S)-3-fluoro-1-methylpiperidin-3-yl]methoxy}pyrido[3,4-d]pyrimidin-4-yl)piperazine-1-carboxylate (231) (50 mg, 0.069 mmol) in DCM (3 mL) was added TFA (1 mL) and the resulting mixture was stirred at 25° C. for 2 h. LCMS analysis showed complete conversion to the product. The solvent was removed under reduced pressure to provide 8-[(5-chloro-6-fluoro-1H-indazol-4-yl)oxy]-2-{[(3S)-3-fluoro-1-methylpiperidin-3-yl]methoxy}-4-(piperazin-1-yl)pyrido[3,4-d]pyrimidine (232) (37 mg, 100% yield) as a brown gum. LCMS (ESI) m/z 545, 547 (M+H).

Step 4:

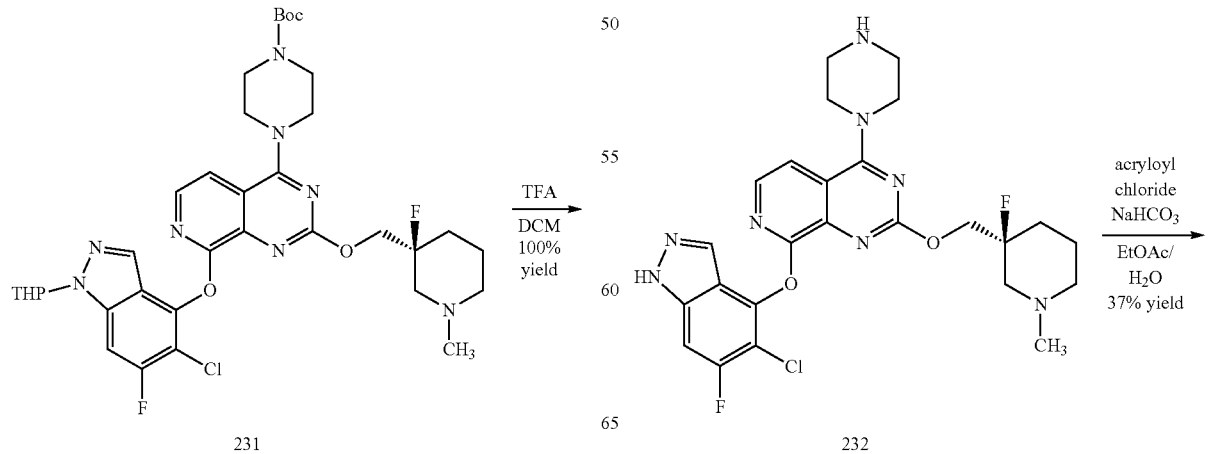

231 → 232

-continued

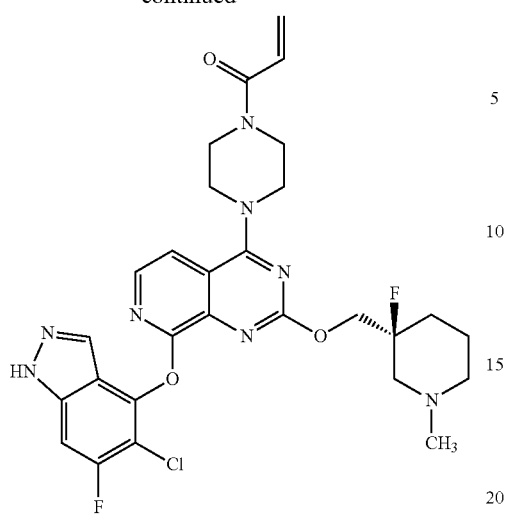

Example-2I

To a solution of 8-[(5-chloro-6-fluoro-1H-indazol-4-yl)oxy]-2-{[(3S)-3-fluoro-1-methylpiperidin-3-yl]methoxy}-4-(piperazin-1-yl)pyrido[3,4-d]pyrimidine (232) (37 mg, 0.068 mmol) in EtOAc (30 mL) and saturated aqueous NaHCO₃ (30 mL) was added a solution of acryloyl chloride (6.14 mg, 0.0679 mmol) in EtOAc (5 mL) dropwise at 25° C. The resultant mixture was stirred at 25° C. for 10 min. LCMS analysis showed complete consumption of the starting material. The reaction was quenched by the addition of several drops of MeOH. The mixture was extracted with EtOAc (3×30 mL). The combined organics were dried over Na₂SO₄, filtered, and concentrated to dryness. The crude product was purified by preparative HPLC on a Kromasil-C18 column (100×21.2 mm, 5 μm particle size), which was eluented with 20-30% MeCN/H₂O (+0.05% NH₃) to provide 1-[4-(8-[(5-chloro-6-fluoro-1H-indazol-4-yl)oxy]-2-{[(3S)-3-fluoro-1-methylpiperidin-3-yl]methoxy}pyrido[3,4-d]pyrimidin-4-yl)piperazin-1-yl]prop-2-en-1-one (Example-2I) (15.2 mg, 37% yield) as a white solid. ¹H NMR (400 MHz, DMSO-d₆) δ 13.53 (s, 1H), 7.80 (d, J=5.8 Hz, 1H), 7.76 (s, 1H), 7.65 (d, J=5.8 Hz, 1H), 7.57 (d, J=8.9 Hz, 1H), 6.83 (dd, J=16.7, 10.4 Hz, 1H), 6.18 (dd, J=16.7, 2.2 Hz, 1H), 5.79-5.71 (m, 1H), 4.55 (dd, J=22.8, 12.2 Hz, 1H), 4.40 (dd, J=22.4, 12.2 Hz, 1H), 3.93 (m, 4H), 3.81 (m, 4H), 2.43 (m, 1H), 2.33 (m, 2H), 2.24 (m, 1H), 2.18 (s, 3H), 1.62 (m, 4H). LCMS (ESI) m/z 599, 601 (M+H).

Preparation of 1-[4-(8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-10I)

Step 1:

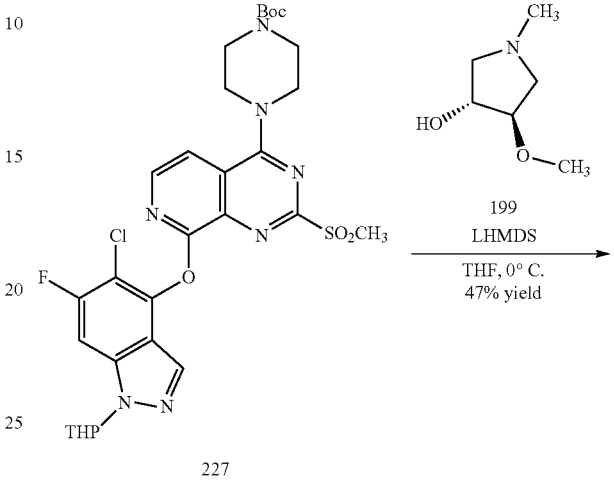

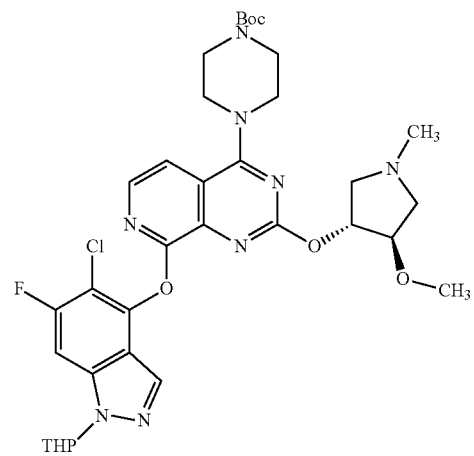

To a mixture of tert-butyl 4-[8-{[5-chloro-6-fluoro-1-(oxan-2-yl)-1H-indazol-4-yl]oxy}-2-(methanesulfonyl)pyrido[3,4-d]pyrimidin-4-yl]piperazine-1-carboxylate (227) (236 mg, 0.356 mmol) and (3R,4R)-4-methoxy-1-methylpyrrolidin-3-ol (199) (70 mg, 0.536 mmol) was added LHMDS (1.0 M in THF, 0.462 mL, 0.462 mmol) and the mixture was stirred at 25° C. for 2 h. The mixture was added to H₂O (5 mL) and extracted with EtOAc (3×20 mL). The combined organics were dried over Na₂SO₄, filtered, and concentrated. The residue was purified by flash chromatography (SiO₂, 20:1 DCM/MeOH) to provide tert-butyl 4-(8-{[5-chloro-6-fluoro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (233) (120 mg, 47% yield) as a brown solid. LCMS (ESI) m/z 713, 715 (M+H).

Step 2:

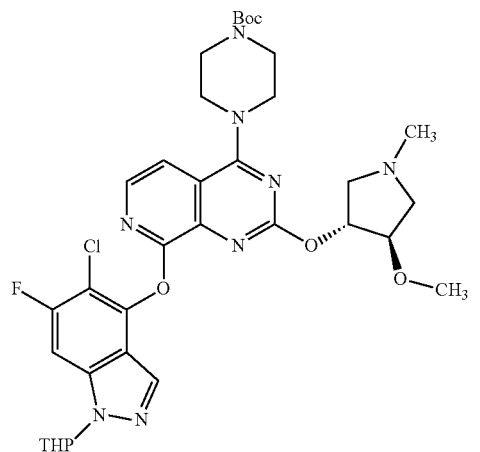

233

Step 3:

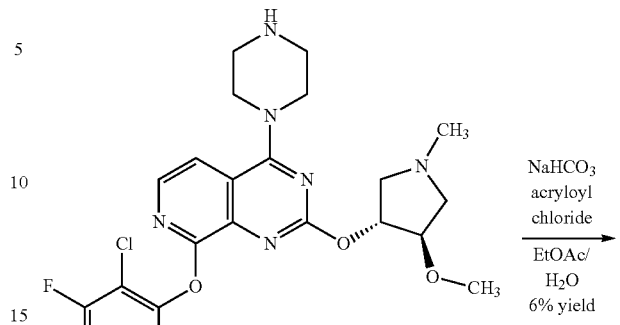

234

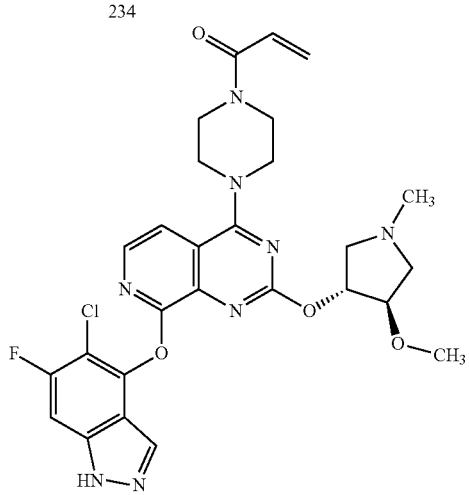

Example-10I

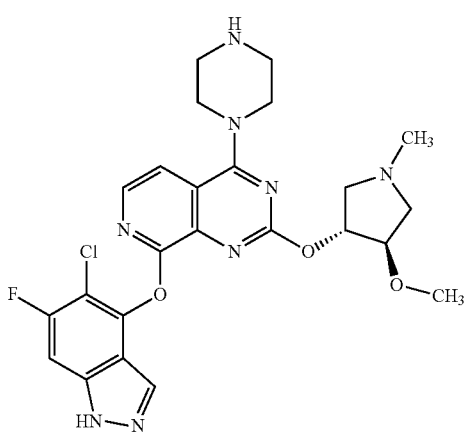

234

To a solution of tert-butyl 4-(8-{[5-chloro-6-fluoro-1-(oxan-2-yl)-1H-indazol-4-yl]oxy}-2-{[(3R,4R)-4-methoxy-1-methylpyrrolidin-3-yl]oxy}pyrido[3,4-d]pyrimidin-4-yl)piperazine-1-carboxylate (233) (120 mg, 0.168 mmol) in DCM (4 mL) was added TFA (2 mL). The mixture was stirred at 25° C. for 2 h. The mixture was concentrated to dryness to provide 8-[(5-chloro-6-fluoro-1H-indazol-4-yl)oxy]-2-{[(3R,4R)-4-methoxy-1-methylpyrrolidin-3-yl]oxy}-4-(piperazin-1-yl)pyrido[3,4-d]pyrimidine (234) (108 mg, 100% yield) as a yellow oil, which was taken onto the next step without further purification. LCMS (ESI) m/z 529, 531 (M+H).

To a solution of 8-[(5-chloro-6-fluoro-1H-indazol-4-yl)oxy]-2-{[(3R,4R)-4-methoxy-1-methylpyrrolidin-3-yl]oxy}-4-(piperazin-1-yl)pyrido[3,4-d]pyrimidine (234) (89 mg, 0.15 mmol) and saturated aqueous NaHCO₃ (40 mL) was added acryloyl chloride (17 mg, 0.186 mmol). The mixture was stirred at 20° C. for 30 min. The mixture was extracted with EtOAc (3×40 mL). The combined organics were washed with brine (20 mL), dried over Na₂SO₄, filtered, and concentrated. The residue was purified by preparatory HPLC on a C18 column, which was eluted with 20-30% MeCN/H₂O (+0.05% formic acid) to provide 1-[4-(8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-10I) (6 mg, 6% yield) as a white solid. $^1$H NMR (400 MHz, DMSO-$d_6$) δ 13.52 (br. s, 1H), 7.79 (d, J=5.9 Hz, 1H), 7.71 (s, 1H), 7.64 (d, J=5.9 Hz, 1H), 7.55 (d, J=8.3 Hz, 1H), 6.83 (dd, J=16.7, 10.4 Hz, 1H), 6.18 (dd, J=16.8, 2.3 Hz, 1H), 5.75 (dd, J=10.3, 2.2 Hz, 1H), 5.11-5.35 (m, 1H), 3.88-4.01 (m, 5H), 3.70-3.86 (m, 4H), 3.34 (s, 3H), 2.98-3.02 (m, 1H), 2.83-2.87 (m, 1H), 2.62 (dd, J=10.8, 2.8 Hz, 1H), 2.28-2.32 (m, 1H), 2.23 (s, 3H). LCMS (ESI) m/z 583 (M+H).

The examples in the following table were prepared using Method I and the procedure used to prepare 1-(4-{8-[(5-Chloro-6-methyl-1H-indazol-4-yl)oxy]-2-[3-(dimethylamino)azetidin-1-yl]-6-methylpyrido[3,4-d]pyrimidin-4-yl}piperazin-1-yl)prop-2-en-1-one (Example-1I), 1-[4-(8-

[(5-chloro-6-fluoro-1H-indazol-4-yl)oxy]-2-{[(3S)-3-fluoro-1-methylpiperidin-3-yl]methoxy}pyrido[3,4-d]pyrimidin-4-yl)piperazin-1-yl]prop-2-en-1-one (Example-2I), and 1-[4-(8-[(5-chloro-6-fluoro-1H-indazol-4-yl)oxy]-2-{[(3R,4R)-4-methoxy-1-methylpyrrolidin-3-yl] oxy}pyrido[3,4-d]pyrimidin-4-yl)piperazin-1-yl]prop-2-en-1-one (Example-10I). The following examples were made with non-critical changes or substitutions to the exemplified procedure used to prepare Example-1I and Example-2I that someone who is skilled in the art would be able to realize.

| Example | Structure | Compound Name | LCMS m/z | $^1$H NMR |
|---|---|---|---|---|
| 3I | 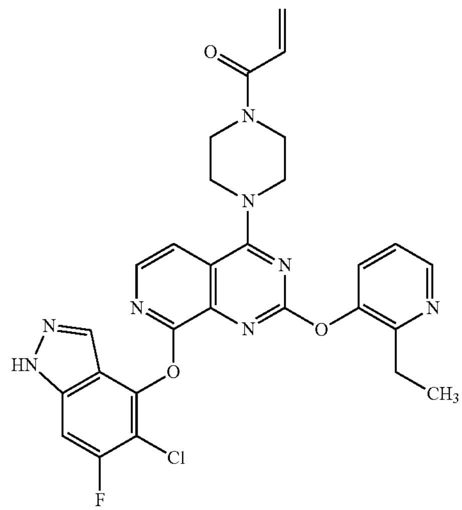 [SMILES: C=CC(=O)N1CCN(c2nc(Oc3cccnc3CC)nc3c(Oc4c(Cl)c(F)cc5[nH]ncc45)nccc23)CC1] | 1-(4-{8-[(5-chloro-6-fluoro-1H-indazol-4-yl)oxy]-2-[(2-ethylpyridin-3-yl)oxy]pyrido[3,4-d]pyrimidin-4-yl}piperazin-1-yl)prop-2-en-1-one | 575, 577 (M + H) | $^1$H NMR (400 MHz, DMSO-d$_6$) δ 13.54 (s, 1H), 8.45-8.36 (m, 1H), 7.83 (d, J = 5.8 Hz, 1H), 7.77-7.60 (m, 3H), 7.54 (d, J = 8.8 Hz, 1H), 7.31 (dd, J = 8.2, 4.7 Hz, 1H), 6.81 (dd, J = 16.7, 10.4 Hz, 1H), 6.16 (dd, J = 16.7, 2.4 Hz, 1H), 5.73 (dd, J = 10.3, 2.4 Hz, 1H), 3.88 (s, 4H), 3.82-3.62 (m, 4H), 2.69 (q, J = 7.5 Hz, 2H), 1.18 (t, J = 7.5 Hz, 3H) |
| 4I | 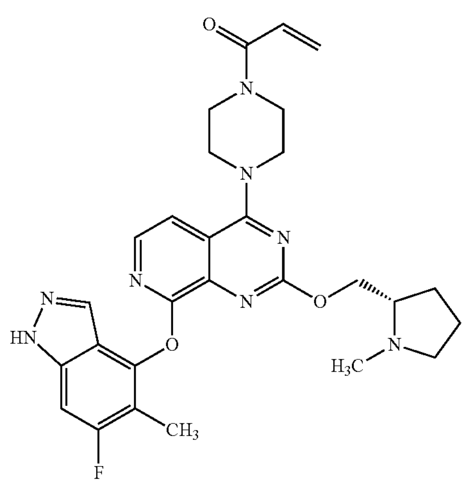 [SMILES: C=CC(=O)N1CCN(c2nc(OC[C@@H]3CCCN3C)nc3c(Oc4c(C)c(F)cc5[nH]ncc45)nccc23)CC1] | 1-[4-(8-[(6-fluoro-5-methyl-1H-indazol-4-yl)oxy]-2-{[(2S)-1-methylpyrrolidin-2-yl]methoxy}pyrido[3,4-d]pyrimidin-4-yl)piperazin-1-yl]prop-2-en-1-one | 547 (M + H) | $^1$H NMR (400 MHz, DMSO-d$_6$) δ 13.22 (s, 1H), 7.75 (d, J = 5.8 Hz, 1H), 7.57 (t, J = 2.8 Hz, 2H), 7.28 (d, J = 9.5 Hz, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.41 (dd, J = 10.9, 4.6 Hz, 1H), 4.22 (dd, J = 10.8, 6.3 Hz, 1H), 3.94-3.87 (m, 4H), 3.80 (m, 4H), 2.96 (dd, J = 7.8, 5.0 Hz, 1H), 2.63 (dd, J = 11.1, 5.9 Hz, 1H), 2.38 (s, 3H), 2.20 (dd, J = 16.9, 8.6 Hz, 1H), 2.10 (d, J = 1.6 Hz, 3H), 2.00-1.91 (m, 1H), 1.75-1.60 (m, 3H) |

| Example | Structure | Compound Name | LCMS m/z | ¹H NMR |
|---|---|---|---|---|
| 5I | 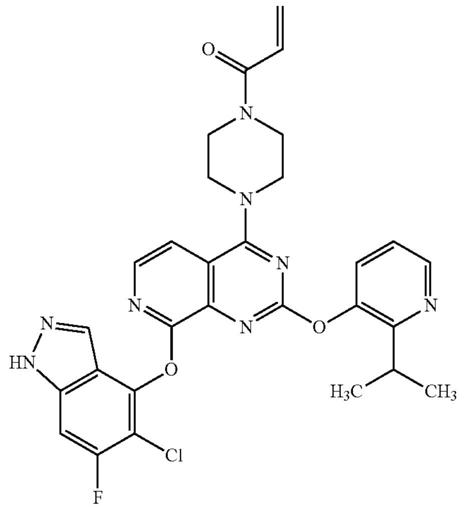 [SMILES: C=CC(=O)N1CCN(c2nc(Oc3cccnc3C(C)C)nc3c(Oc4c(Cl)c(F)cc5[nH]ncc45)nccc23)CC1] | 1-[4-(8-[(5-chloro-6-fluoro-1H-indazol-4-yl)oxy]-2-{[2-(propan-2-yl)pyridin-3-yl]oxy}pyrido[3,4-d]pyrimidin-4-yl)piperazin-1-yl]prop-2-en-1-one | 589, 591 (M + H) | ¹H NMR (400 MHz, DMSO-d₆) δ 13.56 (s, 1H), 8.43 (s, 1H), 7.82 (d, J = 5.6 Hz, 1H), 7.76-7.66 (m, 2H), 7.63 (d, J = 8.1 Hz, 1H), 7.55 (d, J = 8.7 Hz, 1H), 7.29 (d, J = 4.6 Hz, 1H), 6.86-6.78 (m, 1H), 6.16 (d, J = 17.1 Hz, 1H), 5.73 (d, J = 10.6 Hz, 1H), 3.97-3.84 (m, 4H), 3.84-3.63 (m, 4H), 2.69-2.62 (m, 1H), 1.18 (d, J = 6.7 Hz, 6H) |
| 6I | 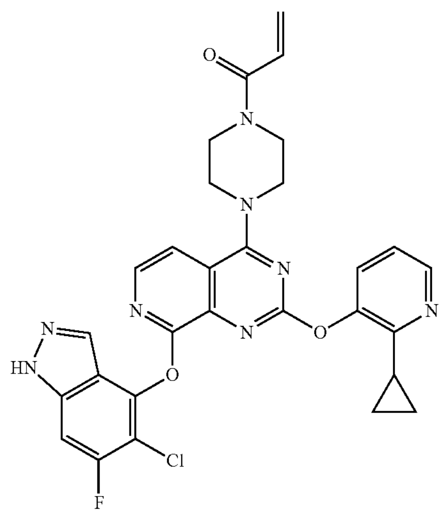 [SMILES: C=CC(=O)N1CCN(c2nc(Oc3cccnc3C3CC3)nc3c(Oc4c(Cl)c(F)cc5[nH]ncc45)nccc23)CC1] | 1-(4-{8-[(5-chloro-6-fluoro-1H-indazol-4-yl)oxy]-2-[(2-cyclopropylpyridin-3-yl)oxy]pyrido[3,4-d]pyrimidin-4-yl}piperazin-1-yl)prop-2-en-1-one | 587, 589 (M + H) | ¹H NMR (400 MHz, DMSO-d₆) δ 13.56 (s, 1H), 8.30 (d, J = 4.6 Hz, 1H), 7.82 (d, J = 5.8 Hz, 1H), 7.74 (s, 1H), 7.68 (d, J = 5.8 Hz, 1H), 7.63 (d, J = 8.0 Hz, 1H), 7.55 (d, J = 8.9 Hz, 1H), 7.21 (dd, J = 8.1, 4.6 Hz, 1H), 6.81 (dd, J = 16.6, 10.5 Hz, 1H), 6.17 (d, J = 16.6 Hz, 1H), 5.73 (d, J = 12.5 Hz, 1H), 3.94-3.84 (m, 4H), 3.84-3.68 (m, 4H), 2.21-2.10 (m, 1H), 1.00-0.92 (m, 2H), 0.92-0.81 (m, 2H) |
| 7I | 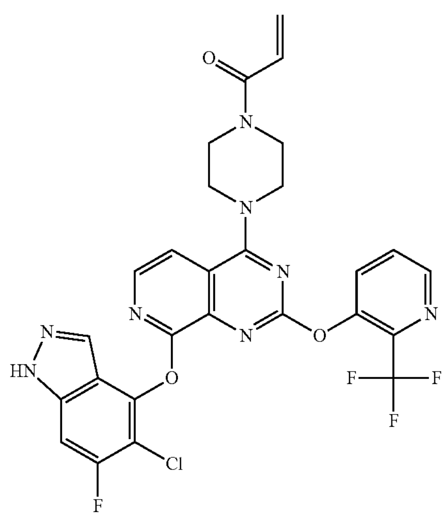 [SMILES: C=CC(=O)N1CCN(c2nc(Oc3cccnc3C(F)(F)F)nc3c(Oc4c(Cl)c(F)cc5[nH]ncc45)nccc23)CC1] | 1-[4-(8-[(5-chloro-6-fluoro-1H-indazol-4-yl)oxy]-2-{[2-(trifluoromethyl)pyridin-3-yl]oxy}pyrido[3,4-s]pyrimidin-4-yl)piperazin-1-yl]prop-2-en-1-one | 615 (M + H) | ¹H NMR (400 MHz, DMSO-d₆) δ 13.56 (s, 1H), 8.62 (d, J = 4.4 Hz, 1H), 8.47 (s, 1H), 8.11 (d, J = 8.2 Hz, 1H), 7.88 (d, J = 5.8 Hz, 1H), 7.82 (dd, J = 8.4, 4.5 Hz, 1H), 7.72 (d, J = 7.6 Hz, 1H), 7.54 (d, J = 9.0 Hz, 1H), 6.80 (dd, J = 16.6, 10.4 Hz, 1H), 6.17 (d, J = 16.7 Hz, 1H), 5.74 (d, J = 10.3 Hz, 1H), 3.90 (s, 4H), 3.75 (m, 4H) |

| Example | Structure | Compound Name | LCMS m/z | ¹H NMR |
|---|---|---|---|---|
| 8I | 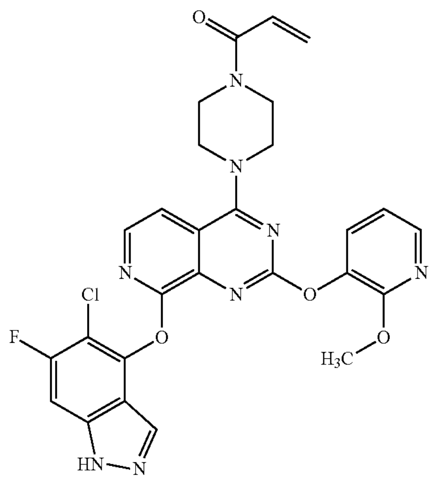 [SMILES: C=CC(=O)N1CCN(c2nc(Oc3cccnc3OC)nc3c(Oc4c(Cl)c(F)cc5[nH]ncc45)nccc23)CC1] | 1-(4-{8-[(5-chloro-6-fluoro-1H-indazol-4-yl)oxy]-2-[(2-methoxy-pyridin-3-yl)oxy]pyrido[3,4-d]pyrimidin-4-yl}piperazin-1-yl)prop-2-en-1-one | 577 (M + H) | ¹H NMR (400 MHz, DMSO-$d_6$) δ 13.54 (s, 1H), 8.06 (dd, J = 4.9, 1.7 Hz, 1H), 7.82 (d, J = 5.8 Hz, 1H), 7.72 (s, 1H), 7.68 (d, J = 1.8 Hz, 1H), 7.67-7.65 (m, 1H), 7.55 (d, J = 8.8 Hz, 1H), 7.06 (dd, J = 7.6, 5.0 Hz, 1H), 6.81 (dd, J = 16.7, 10.4 Hz, 1H), 6.16 (dd, J = 16.7, 2.4 Hz, 1H), 5.73 (dd, J = 10.4, 2.4 Hz, 1H), 3.86 (s, 4H), 3.82 (s, 3H), 3.74 (m, 4H) |
| 9I | 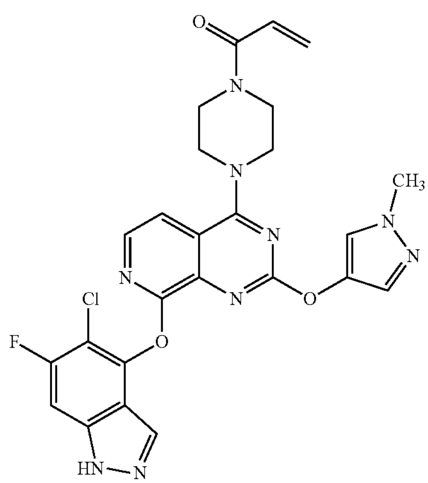 | 1-(4-{8-[(5-chloro-6-fluoro-1H-indazol-4-yl)oxy]-2-[(1-methyl-1H-pyrazol-4-yl)oxy]pyrido[3,4-d]pyrimidin-4-yl}piperazin-1-yl)prop-2-en-1-one | 496 (M + H) | ¹H NMR (400 MHz, DMSO-$d_6$) δ 13.55 (s, 1H), 7.96 (s, 1H), 7.82 (d, J = 5.8 Hz, 1H), 7.79 (s, 1H), 7.68 (d, J = 5.9 Hz, 1H), 7.65-7.64 (m, 2H), 7.58 (dd, J = 8.9, 1.1 Hz, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 4.01-3.92 (m, 4H), 3.88-3.83 (m, 2H), 3.81 (s, 3H), 3.79-3.75 (m, 2H) |
| 11I | 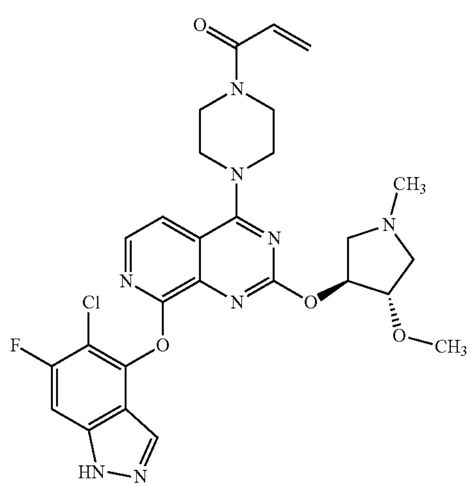 [SMILES: C=CC(=O)N1CCN(c2nc(O[C@H]3CN(C)C[C@@H]3OC)nc3c(Oc4c(Cl)c(F)cc5[nH]ncc45)nccc23)CC1] | 1-[4-(8-[(5-chloro-6-fluoro-1H-indazol-4-yl)oxy]-2-{[(3S,4S)-4-methoxy-1-methyl-pyrrolidin-3-yl]oxy}pyrido[3,4-d]pyrimidin-4-yl)piperazin-1-yl]prop-2-en-1-one | 583, 585 (M + H) | ¹H NMR (400 MHz, DMSO-$d_6$) δ 13.56 (s, 1H), 7.79 (d, J = 5.8 Hz, 1H), 7.72 (s, 1H), 7.65 (d, J = 5.9 Hz, 1H), 7.56 (d, J = 8.9 Hz, 1H), 6.83 (dd, J = 16.7, 10.5 Hz, 1H), 6.18 (dd, J = 16.7, 2.1 Hz, 1H), 5.75 (dd, J = 10.5, 2.1 Hz, 1H), 5.27-5.22 (m, 1H), 3.99-3.91 (m, 5H), 3.84 (s, 2H), 3.77 (s, 2H), 3.35 (s, 4H), 3.01 (dd, J = 9.7, 6.6 Hz, 1H), 2.85 (dd, J = 10.6, 6.0 Hz, 1H), 2.63 (dd, J = 10.5, 2.2 Hz, 1H), 2.30 (dd, J = 9.8, 4.7 Hz, 1H), 2.23 (s, 3H) |

| Example | Structure | Compound Name | LCMS m/z | ¹H NMR |
|---------|-----------|---------------|----------|--------|
| 12I | 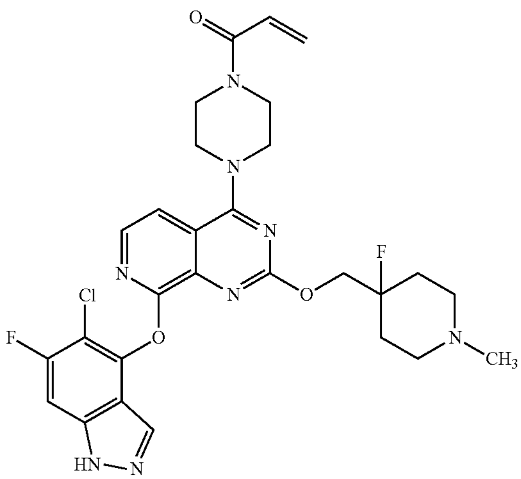 [SMILES: C=CC(=O)N1CCN(c2nc(OCC3(F)CCN(C)CC3)nc3c(Oc4c(Cl)c(F)cc5[nH]ncc45)nccc23)CC1] | 1-(4-{8-[(5-chloro-6-fluoro-1H-indazol-4-yl)oxy]-2-[(4-fluoro-1-methyl-piperidin-4-yl)methoxy]pyrido[3,4-d]pyrimidin-4-yl}piperazin-1-yl)prop-2-en-1-one | 599 (M + H) | ¹H NMR (600 MHz, DMSO-d₆) δ 7.85-7.78 (m, 1H), 7.75 (br. s, 1H), 7.67-7.61 (m, 1H), 7.55 (d, J = 8.8 Hz, 1H), 6.85-6.76 (m, 1H), 6.17 (dd, J = 2.0, 16.7 Hz, 1H), 5.74 (dd, J = 2.1, 10.5 Hz, 1H), 4.48-4.27 (m, 2H), 4.01-3.88 (m, 4H), 3.88-3.69 (m, 4H), 2.60 (d, J = 11.3 Hz, 2H), 2.24-2.13 (m, 5H), 1.93-1.85 (m, 2H), 1.85-1.70 (m, 2H) |
| 13I | 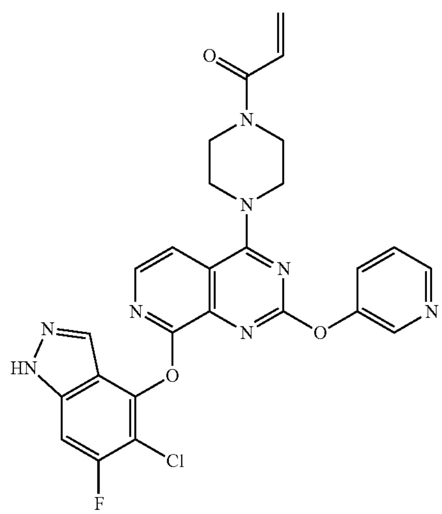 [SMILES: C=CC(=O)N1CCN(c2nc(Oc3cccnc3)nc3c(Oc4c(Cl)c(F)cc5[nH]ncc45)nccc23)CC1] | 1-(4-{8-[(5-chloro-6-fluoro-1H-indazol-4-yl)oxy]-2-(pyridin-3-yloxy)pyrido[3,4-d]pyrimidin-4-yl}piperazin-1-yl)prop-2-en-1-one | 547, 549 (M + H) | ¹H NMR (400 MHz, DMSO-d₆) δ 13.57 (s, 1H), 8.61 (d, J = 2.5 Hz, 1H), 8.46 (t, J = 5.6 Hz, 1H), 7.81 (dd, J = 14.3, 3.6 Hz, 2H), 7.77 (s, 1H), 7.69 (d, J = 5.9 Hz, 1H), 7.56 (d, J = 8.9 Hz, 1H), 7.49 (dd, J = 8.3, 4.7 Hz, 1H), 6.81 (dd, J = 16.7, 10.4 Hz, 1H), 6.17 (dd, J = 16.7, 2.2 Hz, 1H), 5.74 (dd, J = 10.5, 2.1 Hz, 1H), 3.96-3.85 (m, 4H), 3.85-3.67 (m, 4H) |
| 14I | 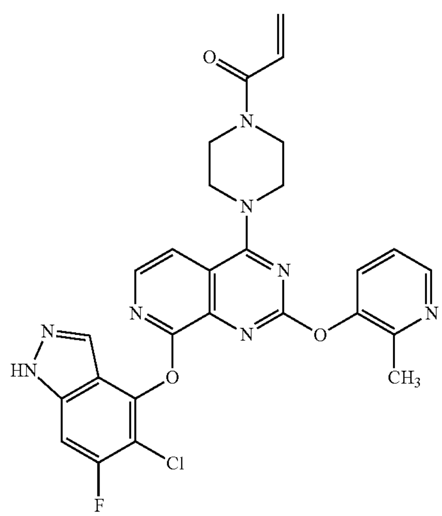 [SMILES: C=CC(=O)N1CCN(c2nc(Oc3cccnc3C)nc3c(Oc4c(Cl)c(F)cc5[nH]ncc45)nccc23)CC1] | 1-(4-{8-[(5-chloro-6-fluoro-1H-indazol-4-yl)oxy]-2-[(2-methyl-pyridin-3-yl)oxy]pyrido[3,4-d]pyrimidin-4-yl}piperazin-1-yl)prop-2-en-1-one | 561, 563 (M + H) | ¹H NMR (400 MHz, DMSO-d₆) δ 13.57 (s, 1H), 8.34 (d, J = 3.9 Hz, 1H), 7.83 (d, J = 5.8 Hz, 1H), 7.71 (s, 1H), 7.67 (dd, J = 14.8, 7.0 Hz, 2H), 7.55 (d, J = 8.8 Hz, 1H), 7.31 (dd, J = 8.1, 4.7 Hz, 1H), 6.85-6.78 (m, 1H), 6.16 (dd, J = 16.7, 2.1 Hz, 1H), 5.73 (dd, J = 10.4, 2.1 Hz, 1H), 3.96-3.83 (m, 4H), 3.83-3.62 (m, 4H), 2.35 (s, 3H) |

| Example | Structure | Compound Name | LCMS m/z | ¹H NMR |
|---|---|---|---|---|
| 15I | 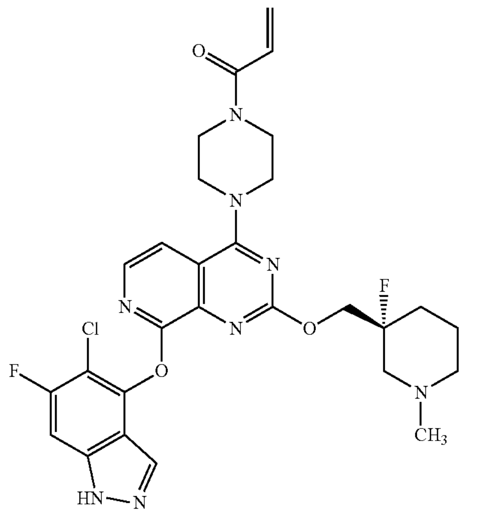 [SMILES: C=CC(=O)N1CCN(c2nc(OC[C@@]3(F)CCCN(C)C3)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R)-3-fluoro-1-methylpiperidin-3-yl]methoxy}pyrido[3,4-d]pyrimidin-4-yl)piperazin-1-yl]prop-2-en-1-one | 599, 601 (M + H) | ¹H NMR (400 MHz, DMSO-d₆) δ 13.54 (s, 1H), 7.80 (d, J = 5.7 Hz, 1H), 7.76 (s, 1H), 7.65 (d, J = 5.9 Hz, 1H), 7.57 (d, J = 8.9 Hz, 1H), 6.83 (dd, J = 16.6, 10.5 Hz, 1H), 6.23-6.12 (m, 1H), 5.79-5.71 (m, 1H), 4.55 (dd, J = 22.5, 12.2 Hz, 1H), 4.40 (dd, J = 22.3, 12.3 Hz, 1H), 3.96-3.90 (m, 4H), 3.88-3.69 (m, 4H), 2.64-2.56 (m, 1H), 2.48-2.41 (m, 1H), 2.40-2.29 (m, 1H), 2.28-2.22 (m, 1H), 2.18 (s, 3H), 1.89-1.46 (m, 4H) |
| 16I | 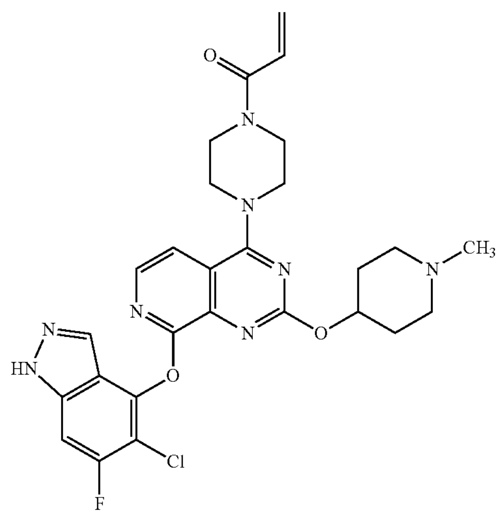 [SMILES: C=CC(=O)N1CCN(c2nc(OC3CCN(C)CC3)nc3c(Oc4c(Cl)c(F)cc5[nH]ncc45)nccc23)CC1] | 1-(4-{8-[(5-chloro-6-fluoro-1H-indazol-4-yl)oxy]-2-[(1-methylpiperidin-4-yl)oxy]pyrido[3,4-d]pyrimidin-4-yl}piperazin-1-yl)prop-2-en-1-one | 567 (M + H) | ¹H NMR (400 MHz, DMSO-d₆) δ 13.52 (s, 1H), 7.81 (d, J = 5.8 Hz, 1H), 7.69-7.61 (m, 2H), 7.54 (dd, J = 8.9, 1.1 Hz, 1H), 6.83 (dd, J = 16.7, 10.4 Hz, 1H), 6.17 (dd, J = 16.7, 2.3 Hz, 1H), 5.75 (dd, J = 10.4, 2.4 Hz, 1H), 5.02-4.83 (m, 1H), 3.95-3.87 (m, 4H), 3.80 (m, 4H), 2.64 (d, J = 5.7 Hz, 1H), 2.24-2.11 (m, 5H), 2.04-1.89 (m, 3H), 1.77-1.58 (m, 2H) |
| 17I | 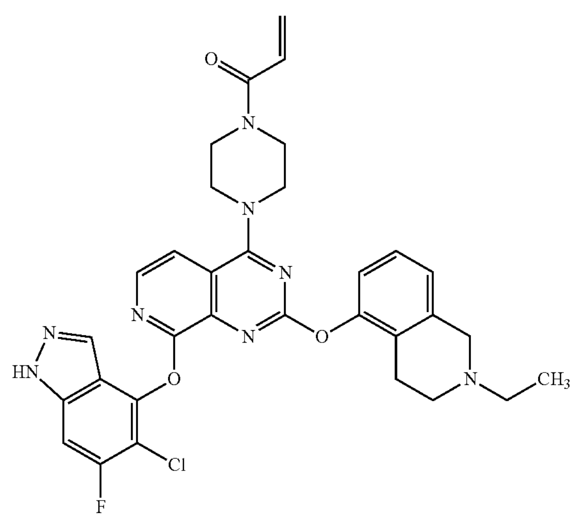 [SMILES: C=CC(=O)N1CCN(c2nc(Oc3cccc4c3CCN(CC)C4)nc3c(Oc4c(Cl)c(F)cc5[nH]ncc45)nccc23)CC1] | 1-(4-{8-[(5-chloro-6-fluoro-1H-indazol-4-yl)oxy]-2-[(2-ethyl-1,2,3,4-tetrahydroisoquinolin-5-yl)oxy]pyrido[3,4-d]pyrimidin-4-yl}piperazin-1-yl)prop-2-en-1-one | 629, 631 (M + H) | ¹H NMR (400 MHz, DMSO-d₆) δ 13.53 (s, 1H), 7.78 (s, 1H), 7.76 (s, 1H), 7.65 (d, J = 5.8 Hz, 1H), 7.55 (d, J = 8.9 Hz, 1H), 7.17 (t, J = 7.8 Hz, 1H), 7.02 (d, J = 7.9 Hz, 1H), 6.97 (d, J = 7.6 Hz, 1H), 6.81 (dd, J = 16.7, 10.4 Hz, 1H), 6.16 (dd, J = 16.6, 2.4 Hz, 1H), 5.73 (dd, J = 10.4, 2.4 Hz, 1H), 3.91-3.83 (m, 4H), 3.73 (d, 4H), 3.57 (s, 2H), 2.67-2.53 (m, 4H), 2.48-2.42 (m, 2H), 1.07 (t, J = 7.1 Hz, 3H) |

| Example | Structure | Compound Name | LCMS m/z | ¹H NMR |
|---|---|---|---|---|
| 18I | 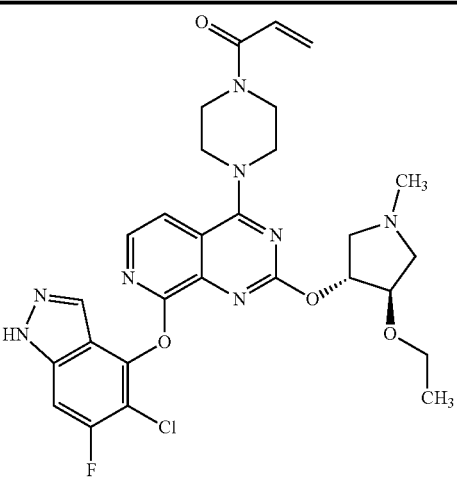 | 1-[4-(8-[(5-chloro-6-fluoro-1H-indazol-4-yl)oxy]-2-{[(3R,4R)-4-ethoxy-1-methyl-pyrrolidin-3-yl]oxy}pyrido[3,4-d]pyrimidin-4-yl)piperazin-1-yl]prop-2-en-1-one | 597, 599 (M + H) | ¹H NMR (400 MHz, DMSO-d₆) δ 13.53 (s, 1H), 7.79 (d, J = 5.8 Hz, 1H), 7.73 (s, 1H), 7.64 (d, J = 5.8 Hz, 1H), 7.56 (d, J = 8.9 Hz, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 5.32-5.13 (m, 1H), 4.11-4.02 (m, 1H), 3.97-3.89 (m, 4H), 3.86-3.66 (m, 4H), 3.47 (dq, J = 9.5, 7.0 Hz, 1H), 3.33 (s, 1H), 3.02 (dd, J = 9.8, 6.4 Hz, 1H), 2.85 (dd, J = 10.8, 6.0 Hz, 1H), 2.64 (dd, J = 10.6, 2.8 Hz, 1H), 2.43-2.11 (m, 4H), 1.02 (t, J = 7.0 Hz, 3H) |
| 19I | 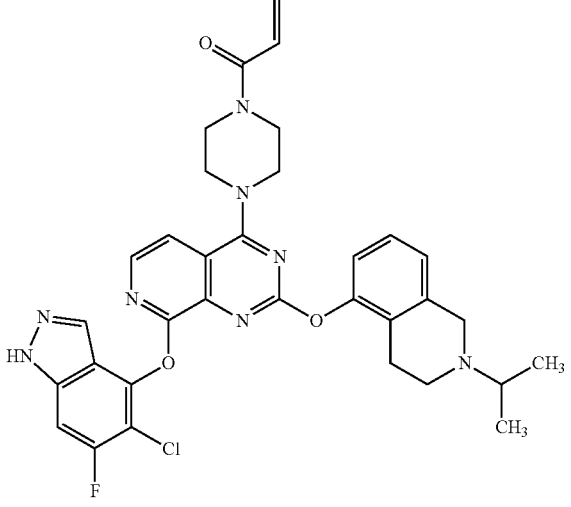 [SMILES: C=CC(=O)N1CCN(c2nc(Oc3cccc4c3CCN(C(C)C)C4)nc3c(Oc4c(Cl)c(F)cc5[nH]ncc45)nccc23)CC1] | 1-[4-(8-[(5-chloro-6-fluoro-1H-indazol-4-yl)oxy]-2-{[2-(propan-2-yl)-1,2,3,4-tetrahydroisoquinolin-5-yl]oxy}pyrido[3,4-d]pyrimidin-4-yl)piperazin-1-yl]prop-2-en-1-one | 643, 645 (M + H) | ¹H NMR (400 MHz, DMSO-d₆) δ 13.51 (s, 1H), 7.79 (d, J = 5.7 Hz, 1H), 7.76 (s, 1H), 7.65 (d, J = 5.9 Hz, 1H), 7.55 (d, J = 8.9 Hz, 1H), 7.17 (t, J = 7.8 Hz, 1H), 6.99 (dd, J = 14.8, 7.8 Hz, 2H), 6.81 (dd, J = 16.7, 10.4 Hz, 1H), 6.16 (dd, J = 16.7, 2.4 Hz, 1H), 5.73 (dd, J = 10.4, 2.4 Hz, 1H), 3.87 (s, 4H), 3.81-3.62 (m, 6H), 2.85 (d, J = 6.4 Hz, 1H), 2.73-2.57 (m, 4H), 1.04 (d, J = 6.5 Hz, 6H |
| 20I | 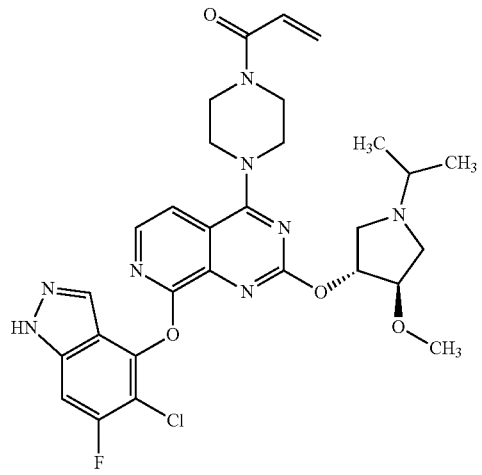 [SMILES: C=CC(=O)N1CCN(c2nc(O[C@@H]3CN(C(C)C)C[C@H]3OC)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R,4R)-4-methoxy-1-(propan-2-yl)pyrrolidin-3-yl]oxy}pyrido[3,4-d]pyrimidin-4-yl)piperazin-1-yl]prop-2-en-1-one | 611, 613 (M + H) | ¹H NMR (400 MHz, DMSO-d₆) δ 13.55 (s, 1H), 7.79 (d, J = 5.8 Hz, 1H), 7.71 (s, 1H), 7.65 (d, J = 5.9 Hz, 1H), 7.56 (d, J = 8.9 Hz, 1H), 6.83 (dd, J = 16.7, 10.4 Hz, 1H), 6.18 (dd, J = 16.7, 2.4 Hz, 1H), 5.75 (dd, J = 10.4, 2.4 Hz, 1H), 5.28-5.17 (m, 1H), 3.98-3.89 (m, 5H), 3.81 (m, 4H), 3.35 (s, 3H), 3.10 (dd, J = 9.8, 6.5 Hz, 1H), 2.94 (dd, J = 10.7, 6.2 Hz, 1H), 2.74-2.62 (m, 1H), 2.40-2.30 (m, 2H), 0.99 (dd, J = 7.6, 6.3 Hz, 6H) |

-continued

| Example | Structure | Compound Name | LCMS m/z | ¹H NMR |
|---|---|---|---|---|
| 21I | 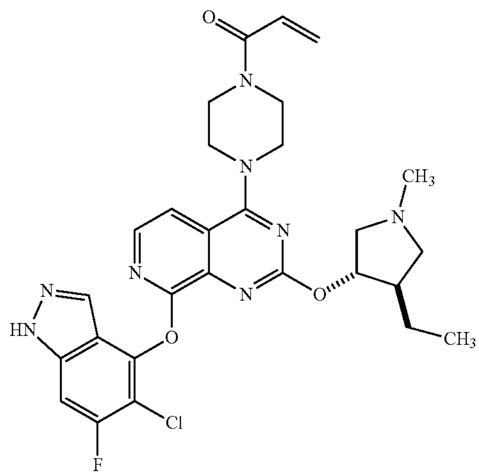 | rac-1-[4-(8-[(5-chloro-6-fluoro-1H-indazol-4-yl)oxy]-2-{[(3S,4R)-4-ethyl-1-methyl-pyrrolidin-3-yl]oxy}pyrido[3,4-d]pyrimidin-4-yl)piperazin-1-yl]prop-2-en-1-one | 581, 583 (M + H) | ¹H NMR (400 MHz, DMSO-d₆) δ 13.53 (s, 1H), 7.79 (d, J = 5.8 Hz, 1H), 7.69 (s, 1H), 7.64 (d, J = 5.9 Hz, 1H), 7.56 (d, J = 8.9 Hz, 1H), 6.83 (dd, J = 16.7, 10.5 Hz, 1H), 6.18 (dd, J = 16.7, 2.3 Hz, 1H), 5.75 (dd, J = 10.4, 2.3 Hz, 1H), 5.05-4.97 (m, 1H), 3.93-3.76 (m, 8H), 2.96 (t, J = 8.1 Hz, 1H), 2.77-2.72 (m, 1H), 2.70-2.65 (m, 1H), 2.24 (s, 3H), 2.08-2.14 (m, 1H), 2.01-1.93 (m, 1H), 1.84-1.74 (m, 1H), 1.44-1.35 (m, 1H), 0.85 (t, J = 7.4 Hz, 3H) |
| 22I | 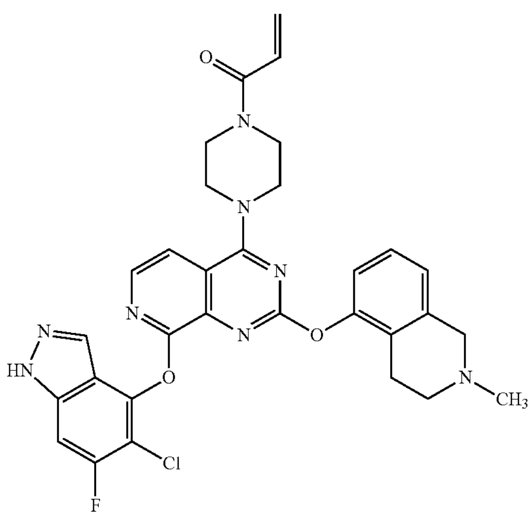 [SMILES: C=CC(=O)N1CCN(c2nc(Oc3cccc4c3CCN(C)C4)nc3c(Oc4c(Cl)c(F)cc5[nH]ncc45)nccc23)CC1] | 1-(4-{8-[(5-chloro-6-fluoro-1H-indazol-4-yl)oxy]-2-[(2-methyl-1,2,3,4-tetrahydroisoquinolin-5-yl)oxy]pyrido[3,4-d]pyrimidin-4-yl}piperazin-1-yl)prop-2-en-1-one | 615 (M + H) | ¹H NMR (400 MHz, DMSO-d₆) δ 13.47 (s, 1H), 7.77 (d, J = 5.8 Hz, 1H), 7.72 (s, 1H), 7.63 (d, J = 5.9 Hz, 1H), 7.52 (d, J = 8.9 Hz, 1H), 7.15 (t, J = 7.8 Hz, 1H), 7.00 (d, J = 7.9 Hz, 1H), 6.93 (d, J = 7.6 Hz, 1H), 6.78 (dd, J = 16.7, 10.4 Hz, 1H), 6.13 (dd, J = 16.7, 2.4 Hz, 1H), 5.71 (dd, J = 10.4, 2.4 Hz, 1H), 3.83 (s, 4H), 3.70 (m, 4H), 3.49 (s, 3H), 2.67-2.58 (m, 2H), 2.56-2.50 (m, 4H) |
| 23I | 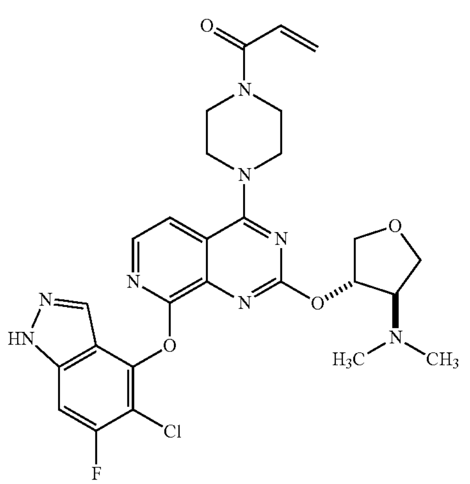 | rac-1-[4-(8-[(5-chloro-6-fluoro-1H-indazol-4-yl)oxy]-2-{[(3S,4R)-4-(dimethylamino)oxolan-3-yl]oxy}pyrido[3,4-d]pyrimidin-4-yl)piperazin-1-yl]prop-2-en-1-one | 583, 585 (M + H) | ¹H NMR (400 MHz, DMSO-d₆) δ = 13.52 (s, 1H), 7.80 (d, J = 5.8, 1H), 7.70 (s, 1H), 7.65 (d, J = 5.8, 1H), 7.56 (d, J = 8.7, 1H), 6.83 (dd, J = 16.6, 10.5, 1H), 6.18 (dd, J = 16.7, 2.2, 1H), 5.75 (dd, J = 10.4, 2.3, 1H), 5.44-5.39 (m, 1H), 4.04-3.97 (m, 2H), 3.96-3.89 (m, 4H), 3.87-3.75 (m, 5H), 3.63-3.57 (m, 1H), 3.04-2.98 (m, 1H), 2.22 (s, 6H) |

-continued

| Example | Structure | Compound Name | LCMS m/z | ¹H NMR |
|---------|-----------|---------------|----------|--------|
| 24I | 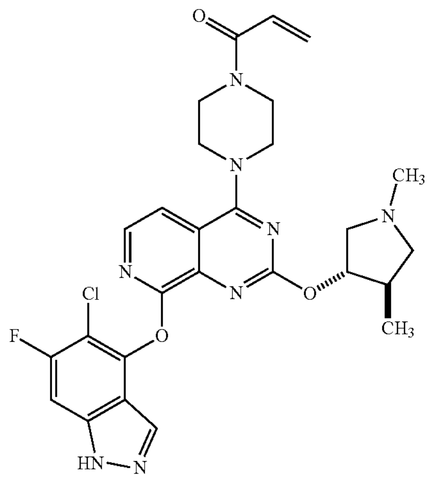 | rac-1-[4-(8-[(5-chloro-6-fluoro-1H-indazol-4-yl)oxy]-2-{[(3S,4R)-1,4-dimethyl-pyrrolidin-3-yl]oxy}pyrido[3,4-d]pyrimidin-4-yl)piperazin-1-yl]prop-2-en-1-one | 567, 569 (M + H) | ¹H NMR (400 MHz, DMSO-d₆) δ 13.58 (s, 1H), 7.78 (d, J = 5.8 Hz, 1H), 7.73 (s, 1H), 7.63 (d, J = 5.9 Hz, 1H), 7.59-7.54 (m, 1H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 4.96-4.92 (m, 1H), 3.98-3.88 (m, 4H), 3.71-3.86 (m, 4H), 2.91 (dd, J = 8.8, 7.4 Hz, 1H), 2.77-2.69 (m, 2H), 2.19-2.31 (m, 4H), 1.94 (dd, J = 8.8, 6.9 Hz, 1H), 1.19 (d, J = 7.1 Hz, 3H) |
| 25I | 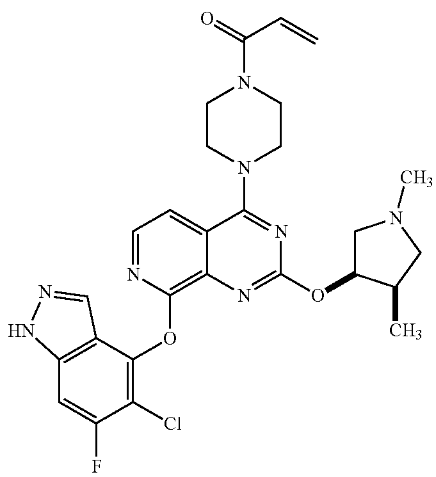 | rac-1-[4-(8-[(5-chloro-6-fluoro-1H-indazol-4-yl)oxy]-2-{[(3S,4S)-1,4-dimethyl-pyrrolidin-3-yl]oxy}pyrido[3,4-d]pyrimidin-4-yl)piperazin-1-yl]prop-2-en-1-one | 567, 569 (M + H) | ¹H NMR (400 MHz, DMSO-d₆) δ 13.61 (s, 1H), 7.78 (d, J = 5.8 Hz, 1H), 7.71 (s, 1H), 7.64 (d, J = 5.8 Hz, 1H), 7.59-7.50 (m, 1H), 6.83 (dd, J = 16.7, 10.4 Hz, 1H), 6.18 (dd, J = 16.7, 2.4 Hz, 1H), 5.75 (dd, J = 10.4, 2.3 Hz, 1H), 5.44-5.29 (m, 1H), 3.98-3.88 (m, 4H), 3.81 (d, J = 30.3 Hz, 4H), 3.19 (dd, J = 10.5, 6.2 Hz, 1H), 2.81 (dd, J = 8.7, 7.0 Hz, 1H), 2.46-2.39 (m, 2H), 2.25 (s, 3H), 2.20 (t, J = 8.6 Hz, 1H), 0.95 (d, J = 7.0 Hz, 3H) |
| 26I | 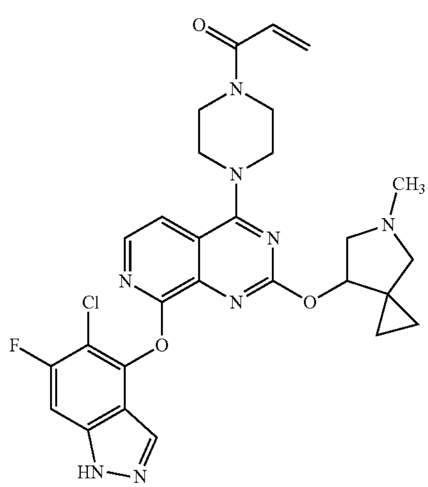 [SMILES: C=CC(=O)N1CCN(c2nc(OC3CN(C)CC34CC4)nc3c(Oc4c(Cl)c(F)cc5[nH]ncc45)nccc23)CC1] | 1-(4-{8-[(5-chloro-6-fluoro-1H-indazol-4-yl)oxy]-2-[(5-methyl-5-azaspiro[2.4]heptan-7-yl)oxy]pyrido[3,4-d]pyrimidin-4-yl}piperazin-1-yl)prop-2-en-1-one | 579, 581 (M + H) | ¹H NMR (400 MHz, DMSO-d₆) δ 13.59 (s, 1H), 7.78-7.69 (m, 2H), 7.64-7.54 (m, 2H), 6.83 (dd, J = 16.7, 10.4 Hz, 1H), 6.18 (dd, J = 16.7, 2.3 Hz, 1H), 5.75 (dd, J = 10.4, 2.3 Hz, 1H), 5.17 (dd, J = 5.7, 3.3 Hz, 1H), 3.94-3.76 (m, 8H), 3.18 (dd, J = 10.6, 5.9 Hz, 1H), 2.71 (dd, J = 15.6, 5.9 Hz, 2H), 2.39 (d, J = 8.8 Hz, 1H), 2.28 (s, 3H), 0.96 (dd, J = 8.2, 3.0 Hz, 1H), 0.82-0.73 (m, 1H), 0.68-0.53 (m, 2H) |

| Example | Structure | Compound Name | LCMS m/z | ¹H NMR |
|---|---|---|---|---|
| 27I | 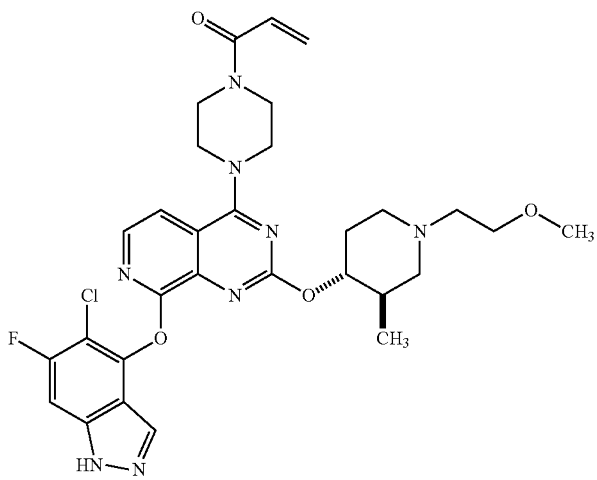 | rac-1-[4-(8-[(5-chloro-6-fluoro-1H-indazol-4-yl)oxy]-2-{[(3R,4R)-1-(2-methoxyethyl)-3-methylpiperidin-4-yl]oxy}pyrido[3,4-d]pyrimidin-4-yl)piperazin-1-yl]prop-2-en-1-one | 625, 627 (M + H) | ¹H NMR (400 MHz, DMSO-d$_6$) δ 13.49 (s, 1H), 7.85 (d, J = 5.8, 1H), 7.67 (d, J = 5.9, 1H), 7.59-7.45 (m, 2H), 6.83 (dd, J = 16.7, 10.5, 1H), 6.17 (dd, J = 16.6, 2.4, 1H), 5.74 (dd, J = 10.4, 2.3, 1H), 4.53-4.44 (m, 1H), 3.92-3.87 (m, 4H), 3.86-3.74 (m, 4H), 3.43 (t, J = 5.9, 2H), 3.24 (s, 3H), 2.86 (d, J = 7.2, 2H), 2.17-1.92 (m, 3H), 1.85-1.78 (m, 2H), 1.54-1.42 (m, 2H), 0.82 (d, J = 5.9, 3H) |
| 28I | 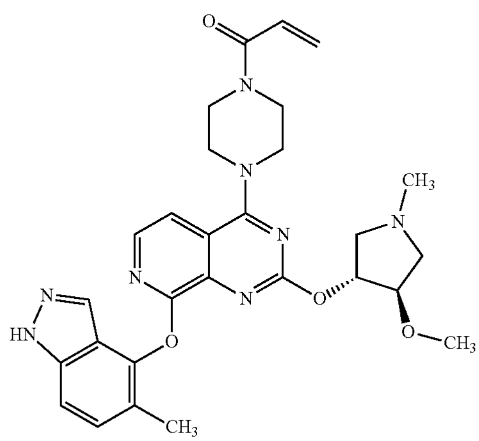 [SMILES: C=CC(=O)N1CCN(c2nc(O[C@@H]3CN(C)C[C@H]3OC)nc3c(Oc4c(C)ccc5[nH]ncc45)nccc23)CC1] | 1-[4-(8-[(5-chloro-6-fluoro-1H-indazol-4-yl)oxy]-2-{[(3S,4S)-1,4-dimethylpyrrolidin-3-yl]oxy}pyrido[3,4-d]pyrimidin-4-yl)piperazin-1-yl]prop-2-en-1-one | 545 (M + H) | ¹H NMR (400 MHz, DMSO-d$_6$) δ 13.11 (s, 1H), 7.72 (d, J = 5.8 Hz, 1H), 7.54-7.53 (m, 2H), 7.37-7.35 (m, 1H), 7.30-7.28 (m, 1H), 6.87-6.80 (m, 1H), 6.18 (dd, J = 16.7, 2.3 Hz, 1H), 5.75 (dd, J = 10.4, 2.3 Hz, 1H), 5.32-5.28 (m, 1H), 4.00-3.97 (m, 1H), 3.93-3.87 (m, 4H), 3.84 (br. s, 2H), 3.76 (br. s, 2H), 3.36 (s, 3H), 3.03-2.99 (m, 1H), 2.93-2.89 (m, 1H), 2.68-2.64 (m, 1H), 2.34-2.31 (m, 1H), 2.24 (s, 3H), 2.17 (s, 3H) |
| 29I | 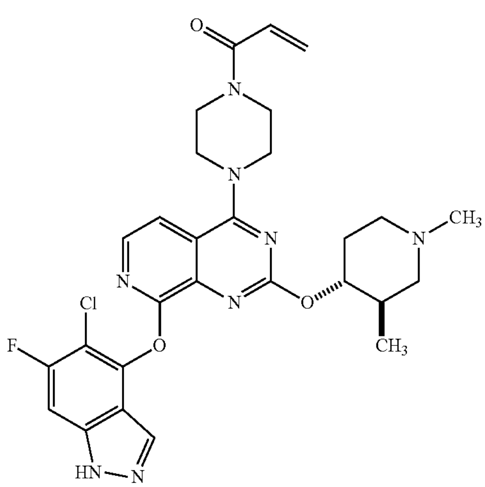 | rac-1-[4-(8-[(5-chloro-6-fluoro-1H-indazol-4-yl)oxy]-2-{[(3R,4R)-1,3-dimethylpiperidin-4-yl]oxy}pyrido[3,4-d]pyrimidin-4-yl)piperazin-1-yl]prop-2-en-1-one | 581 (M + H) | ¹H NMR (400 MHz, DMSO-d$_6$) δ 13.51 (s, 1H), 7.85 (d, J = 5.8 Hz, 1H), 7.68 (d, J = 5.9 Hz, 1H), 7.60-7.47 (m, 2H), 6.83 (dd, J = 16.7, 10.4 Hz, 1H), 6.17 (dd, J = 16.7, 2.4 Hz, 1H), 5.74 (dd, J = 10.4, 2.4 Hz, 1H), 4.49 (td, J = 9.9, 4.3 Hz, 1H), 3.96-3.88 (m, 4H), 3.80 (m, 4H), 2.79-2.69 (m, 2H), 2.17 (s, 3H), 1.98 (dd, J = 13.0, 7.9 Hz, 2H), 1.91-1.82 (m, 1H), 1.72 (t, J = 10.9 Hz, 1H), 1.61-1.40 (m, 1H), 0.82 (d, J = 6.5 Hz, 3H) |

-continued

| Example | Structure | Compound Name | LCMS m/z | ¹H NMR |
|---|---|---|---|---|
| 30I | 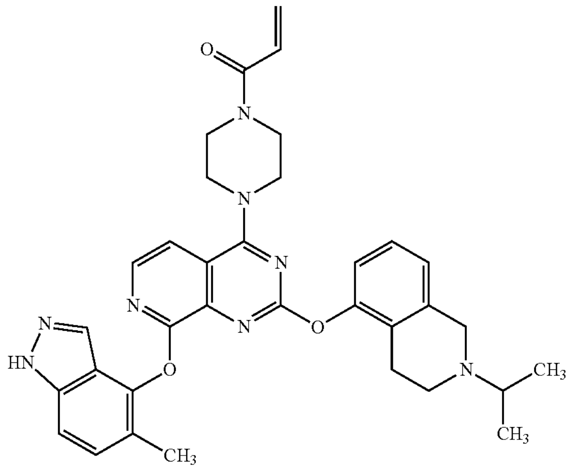 [SMILES: C=CC(=O)N1CCN(c2nc(Oc3cccc4c3CCN(C(C)C)C4)nc3c(Oc4c(C)ccc5[nH]ncc45)nccc23)CC1] | 1-[4-(8-[(5-methyl-1H-indazol-4-yl)oxy]-2-{[2-(propan-2-yl)-1,2,3,4-tetrahydroisoquinolin-5-yl]oxy}pyrido[3,4-d]pyrimidin-4-yl)piperazin-1-yl]prop-2-en-1-one | 605 (M + H) | ¹H NMR (400 MHz, DMSO-d₆) δ 13.09 (s, 1H), 7.73 (d, J = 5.8 Hz, 1H), 7.61-7.51 (m, 2H), 7.34 (d, J = 8.5 Hz, 1H), 7.26 (d, J = 8.5 Hz, 1H), 7.17 (t, J = 7.8 Hz, 1H), 7.03 (d, J = 7.4 Hz, 1H), 6.97 (d, J = 7.5 Hz, 1H), 6.81 (dd, J = 16.7, 10.4 Hz, 1H), 6.16 (dd, J = 16.7, 2.3 Hz, 1H), 5.73 (dd, J = 10.4, 2.3 Hz, 1H), 3.85-3.67 (m, 10H), 2.87-2.80 (m, 1H), 2.70-2.54 (m, 4H), 2.11 (s, 3H), 1.03 (d, J = 6.5 Hz, 6H) |
| 31I | 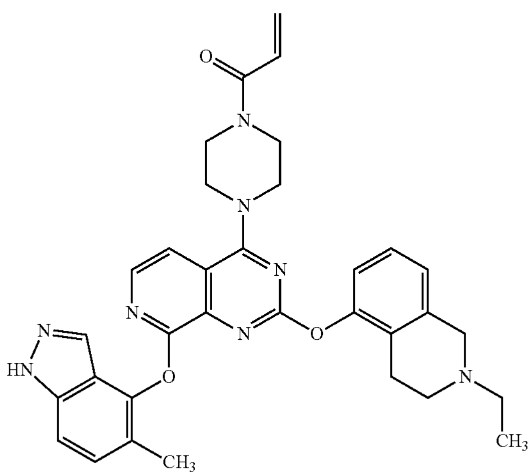 [SMILES: C=CC(=O)N1CCN(c2nc(Oc3cccc4c3CCN(CC)C4)nc3c(Oc4c(C)ccc5[nH]ncc45)nccc23)CC1] | 1-(4-{2-[(2-ethyl-1,2,3,4-tetrahydroisoquinolin-5-yl)oxy]-8-[(5-methyl-1H-indazol-4-yl)oxy]pyrido[3,4-d]pyrimidin-4-yl}piperazin-1-yl)prop-2-en-1-one | 591 (M + H) | ¹H NMR (400 MHz, DMSO-d₆) δ 13.10 (s, 1H), 7.74 (d, J = 5.8 Hz, 1H), 7.57-7.54 (m, 2H), 7.34 (d, J = 8.6 Hz, 1H), 7.26 (d, J = 8.5 Hz, 1H), 7.18 (d, J = 15.6 Hz, 1H), 7.04 (d, J = 7.9 Hz, 1H), 6.97 (d, J = 7.5 Hz, 1H), 6.81 (dd, J = 16.7, 10.4 Hz, 1H), 6.16 (dd, J = 16.7, 2.3 Hz, 1H), 5.73 (dd, J = 10.4, 2.3 Hz, 1H), 3.85-3.70 (m, 8H), 3.57 (s, 2H), 2.68-2.59 (m, 3H), 2.49-2.47 (m, 3H), 2.11 (s, 3H), 1.07 (t, J = 7.1 Hz, 3H) |
| 32I | 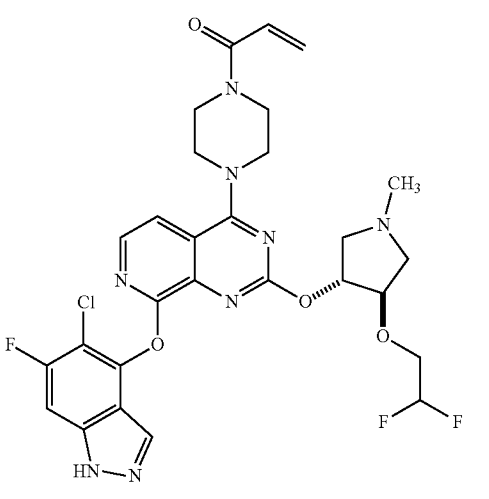 | rac-1-[4-(8-[(5-chloro-6-fluoro-1H-indazol-4-yl)oxy]-2-{[(3R,4R)-4-(2,2-difluoroethoxy)-1-methylpyrrolidin-3-yl]oxy}pyrido[3,4-d]pyrimidin-4-yl)piperazin-1-yl]prop-2-en-1-one | 633, 635 (M + H) | ¹H NMR (400 MHz, DMSO-d₆) δ 13.51 (s, 1H), 7.79 (d, J = 5.8 Hz, 1H), 7.77 (s, 1H), 7.64 (d, J = 5.9 Hz, 1H), 7.56 (dd, J = 8.9, 1.0 Hz, 1H), 6.23-6.11 (m, 2H), 5.96 (dt, J = 55.0, 3.8 Hz, 1H), 5.75 (dd, J = 10.4, 2.4 Hz, 1H), 5.31-5.24 (m, 1H), 4.27-4.18 (m, 1H), 4.18-4.01 (m, 1H), 3.96-3.70 (m, 9H), 3.03 (dd, J = 10.2, 6.3 Hz, 1H), 2.93 (dd, J = 10.8, 5.9 Hz, 1H), 2.73-2.60 (m, 1H), 2.38 (dd, J = 9.9, 3.2 Hz, 1H), 2.26 (s, 3H) |

| Example | Structure | Compound Name | LCMS m/z | ¹H NMR |
|---|---|---|---|---|
| 33I | 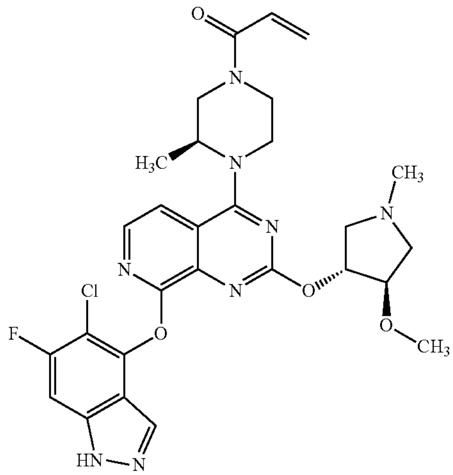 [SMILES: C=CC(=O)N1CCN(c2nc(O[C@@H]3CN(C)C[C@H]3OC)nc3c(Oc4c(Cl)c(F)cc5[nH]ncc45)nccc23)[C@@H](C)C1] | 1-[(3S)-4-(8-[(5-chloro-6-fluoro-1H-indazol-4-yl)oxy]-2-{[(3R,4R)-4-methoxy-1-methyl-pyrrolidin-3-yl]oxy}pyrido[3,4-d]pyrimidin-4-yl)-3-methyl-piperazin-1-yl]prop-2-en-1-one | 597, 599 (M + H) | ¹H NMR (400 MHz, DMSO-d₆) δ 13.54 (s, 1H), 7.78 (d, J = 5.8 Hz, 1H), 7.74 (s, 1H), 7.56 (d, J = 8.9 Hz, 2H), 6.83 (dd, J = 16.3, 10.7 Hz, 1H), 6.20 (d, J = 16.5 Hz, 1H), 5.75 (dd, J = 10.4, 2.2 Hz, 1H), 5.28-5.21 (m, 1H), 4.80 (br. s, 1H), 4.47-3.85 (m, 6H), 3.62-3.60 (m, 1H), 3.35 (s, 3H), 3.04-3.00 (m, 1H), 2.90-2.79 (m, 1H), 2.71-2.64 (m, 1H), 2.30 (dd, J = 9.8, 4.8 Hz, 1H), 2.24 (s, 3H), 1.32 (d, J = 5.8 Hz, 3H) |
| 34I | 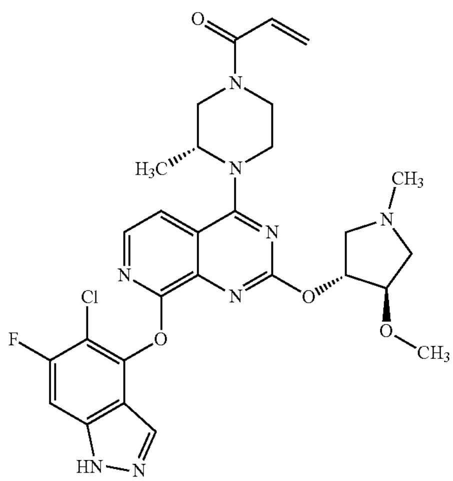 [SMILES: C=CC(=O)N1CCN(c2nc(O[C@@H]3CN(C)C[C@H]3OC)nc3c(Oc4c(Cl)c(F)cc5[nH]ncc45)nccc23)[C@H](C)C1] | 1-[(3R)-4-(8-[(5-chloro-6-fluoro-1H-indazol-4-yl)oxy]-2-{[(3R,4R)-4-methoxy-1-methyl-pyrrolidin-3-yl]oxy}pyrido[3,4-d]pyrimidin-4-yl)-3-methyl-piperazin-1-yl]prop-2-en-1-one | 597, 599 (M + H) | ¹H NMR (400 MHz, DMSO-d₆) δ 13.56 (s, 1H), 7.78 (d, J = 5.8 Hz, 1H), 7.73 (s, 1H), 7.56 (dd, J = 8.9, 0.8 Hz, 2H), 6.92-6.79 (m, 1H), 6.19 (dd, J = 16.7, 6.3 Hz, 1H), 5.75 (dd, J = 10.4, 2.3 Hz, 1H), 5.27-5.20 (m, 1H), 4.78 (br. s, 1H), 4.47-3.85 (m, 6H), 3.62-3.60 (m, 1H), 3.34 (s, 3H), 3.04-3.00 (m, 1H), 2.87-2.83 (m, 1H), 2.66-2.63 (m, 1H), 2.30 (dd, J = 9.8, 4.7 Hz, 1H), 2.24 (s, 3H), 1.33 (d, J = 5.8 Hz, 3H) |
| 35I | 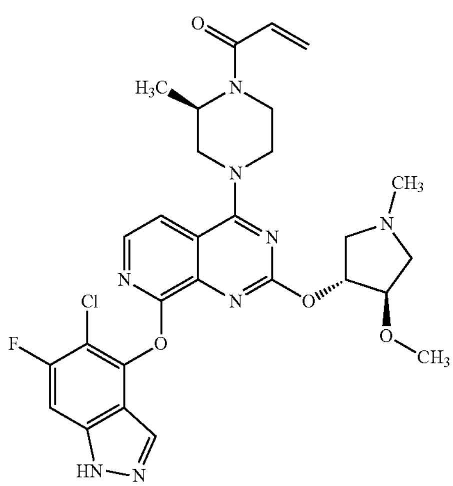 [SMILES: C=CC(=O)N1CCN(c2nc(O[C@@H]3CN(C)C[C@H]3OC)nc3c(Oc4c(Cl)c(F)cc5[nH]ncc45)nccc23)C[C@H]1C] | 1-[(2R)-4-(8-[(5-chloro-6-fluoro-1H-indazol-4-yl)oxy]-2-{[(3R,4R)-4-methoxy-1-methyl-pyrrolidin-3-yl]oxy}pyrido[3,4-d]pyrimidin-4-yl)-2-methyl-piperazin-1-yl]prop-2-en-1-one | 597, 599 (M + H) | ¹H NMR (400 MHz, DMSO-d₆) δ 13.52 (s, 1H), 7.79 (d, J = 5.8 Hz, 1H), 7.72 (s, 1H), 7.66 (d, J = 5.9 Hz, 1H), 7.56 (d, J = 8.9 Hz, 1H), 6.81 (dd, J = 16.6, 10.4 Hz, 1H), 6.17 (d, J = 17.4 Hz, 1H), 5.73 (d, J = 10.7 Hz, 1H), 5.29-5.24 (m, 1H), 4.71-4.46 (m, 2H), 4.34-4.29 (m, 1H), 4.17-4.10 (m, 1H), 3.98-3.92 (m, 1H), 3.80-3.74 (m, 1H), 3.60-3.46 (m, 2H), 3.34 (s, 3H), 3.03 (dd, J = 9.9, 6.4 Hz, 1H), 2.85 (dd, J = 10.7, 6.0 Hz, 1H), 2.66 (d, J = 10.9 Hz, 1H), 2.32 (dd, J = 9.9, 4.6 Hz, 1H), 2.25 (s, 3H), 1.25 (br. s, 3H) |

| Example | Structure | Compound Name | LCMS m/z | ¹H NMR |
|---|---|---|---|---|
| 36I | 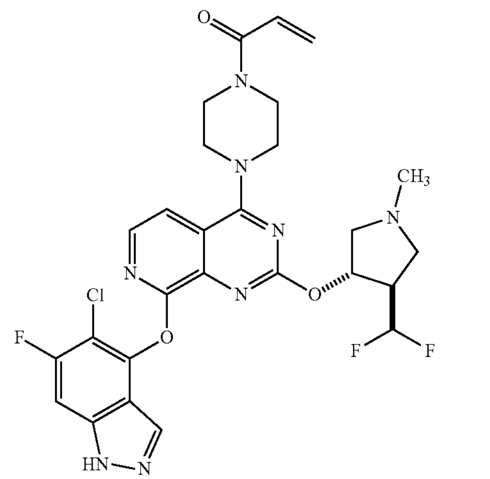 | rac-1-[4-(8-[(5-chloro-6-fluoro-1H-indazol-4-yl)oxy]-2-{[(3S,4R)-4-(difluoromethyl)-1-methylpyrrolidin-3-yl]oxy}pyrido[3,4-d]pyrimidin-4-yl)piperazin-1-yl]prop-2-en-1-one | 603, 605 (M + H) | ¹H NMR (400 MHz, DMSO-$d_6$) δ 13.58 (s, 1H), 7.80 (d, J = 5.8 Hz, 1H), 7.77 (s, 1H), 7.65 (d, J = 5.9 Hz, 1H), 7.58 (dd, J = 8.9, 1.0 Hz, 1H), 6.87-6.80 (m, 1H), 6.79 (dd, J = 114.2, 3.1 Hz, 1H), 6.18 (dd, J = 16.7, 2.4 Hz, 1H), 5.75 (dd, J = 10.4, 2.4 Hz, 1H), 5.33-5.23 (m, 1H), 3.98-3.73 (m, 8H), 2.99-2.73 (m, 3H), 2.71-2.61 (m, 1H), 2.41-2.31 (m, 1H), 2.26 (s, 3H) |
| 37I | 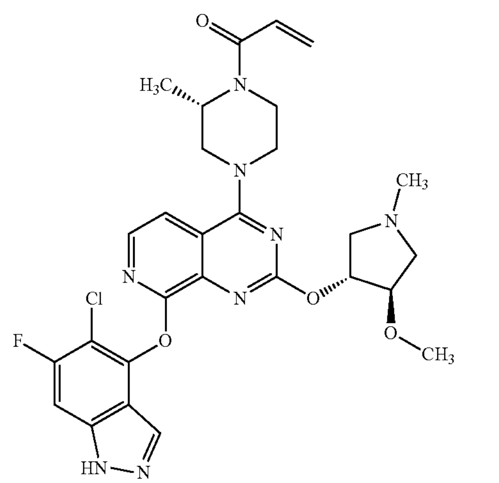 [SMILES: C=CC(=O)N1CCN(c2nc(O[C@@H]3CN(C)C[C@H]3OC)nc3c(Oc4c(Cl)c(F)cc5[nH]ncc45)nccc23)C[C@@H]1C] | 1-[(2S)-4-(8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)-2-methylpiperazin-1-yl]prop-2-en-1-one | 597, 599 (M + H) | ¹H NMR (400 MHz, MeOD) 7.78 (d, J = 5.9 Hz, 1H), 7.75 (s, 1H), 7.65 (d, J = 5.9 Hz, 1H), 7.39 (d, J = 8.6 Hz, 1H), 6.83-6.75 (m, 1H), 6.27 (d, J = 15.8 Hz, 1H), 5.80 (d, J = 10.9 Hz, 1H), 5.60-5.56 (m, 1H), 4.51-4.43 (m, 1H), 4.33-4.27 (m, 1H), 4.26-4.20 (m, 1H), 4.15-4.01 (m, 1H), 3.89 (dd, J = 13.6, 3.9 Hz, 1H), 3.74-3.60 (m, 2H), 3.57-3.53 (s, 1H), 3.51 (s, 3H), 3.42-3.33 (m, 2H), 3.20 (d, J = 12.0 Hz, 1H), 3.06 (d, J = 10.5 Hz, 1H), 2.68 (s, 3H), 1.35 (br. s, 3H) |
| 38I | 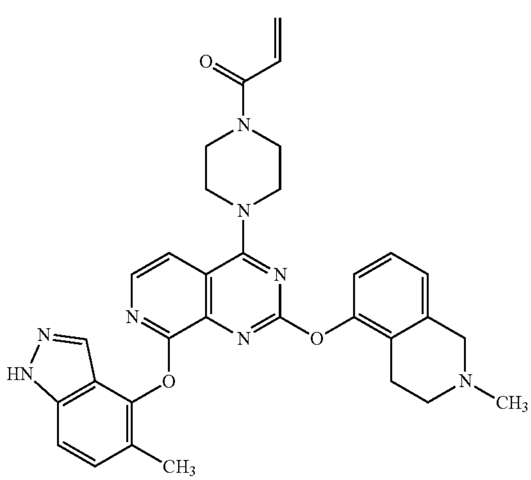 [SMILES: C=CC(=O)N1CCN(c2nc(Oc3cccc4c3CCN(C)C4)nc3c(Oc4c(C)ccc5[nH]ncc45)nccc23)CC1] | 1-(4-{8-[(5-methyl-1H-indazol-4-yl)oxy]-2-[(2-methyl-1,2,3,4-tetrahydroisoquinolin-5-yl)oxy]pyrido[3,4-d]pyrimidin-4-yl}piperazin-1-yl)prop-2-en-1-one | 577 (M + H) | ¹H NMR (400 MHz, DMSO-$d_6$) δ 13.09 (s, 1H), 7.74 (d, J = 5.8 Hz, 1H), 7.57 (s, 1H), 7.55 (d, J = 5.9 Hz, 1H), 7.34 (d, J = 8.4 Hz, 1H), 7.26 (d, J = 8.5 Hz, 1H), 7.18 (t, J = 7.8 Hz, 1H), 7.05 (d, J = 7.9 Hz, 1H), 6.95 (d, J = 7.5 Hz, 1H), 6.81 (dd, J = 16.7, 10.5 Hz, 1H), 6.16 (dd, J = 16.7, 2.4 Hz, 1H), 5.73 (dd, J = 10.4, 2.4 Hz, 1H), 3.88-3.80 (m, 4H), 3.80-3.63 (m, 4H), 3.52 (s, 2H), 2.67 (t, J = 5.1 Hz, 2H), 2.56 (t, J = 6.1 Hz, 2H), 2.32 (s, 3H), 2.11 (s, 3H) |

| Example | Structure | Compound Name | LCMS m/z | ¹H NMR |
|---------|-----------|---------------|----------|--------|
| 39I | 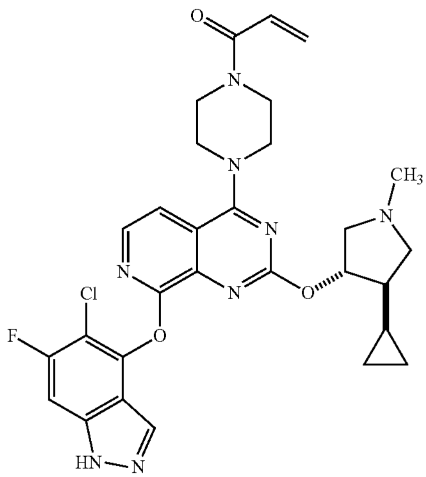 | rac-1-[4-(8-[(5-chloro-6-fluoro-1H-indazol-4-yl)oxy]-2-{[(3S,4R)-4-cyclopropyl-1-methylpyrrolidin-3-yl]oxy}pyrido[3,4-d]pyrimidin-4-yl)piperazin-1-yl]prop-2-en-1-one | 593 (M + H) | ¹H NMR (400 MHz, DMSO-d₆) δ 13.54 (s, 1H), 7.79 (d, J = 5.8 Hz, 1H), 7.71 (s, 1H), 7.64 (d, J = 5.9 Hz, 1H), 7.55 (d, J = 8.9 Hz, 1H), 6.83 (dd, J = 16.7, 10.4 Hz, 1H), 6.18 (dd, J = 16.7, 2.3 Hz, 1H), 5.74 (dd, J = 10.4, 2.3 Hz, 1H), 5.20-5.15 (m, 1H), 3.91 (br. s, 4H), 3.86-3.75 (m, 4H), 2.89-2.84 (m, 1H), 2.80 (dd, J = 10.6, 6.0 Hz, 1H), 2.68-2.65 (m, 1H), 2.23 (s, 3H), 2.17-2.11 (m, 1H), 1.79-1.73 (m, 1H), 0.95-0.88 (m, 1H), 0.43-0.35 (m, 2H), 0.31-0.26 (m, 1H), 0.17 (d, J = 3.1 Hz, 1H) |
| 40I | 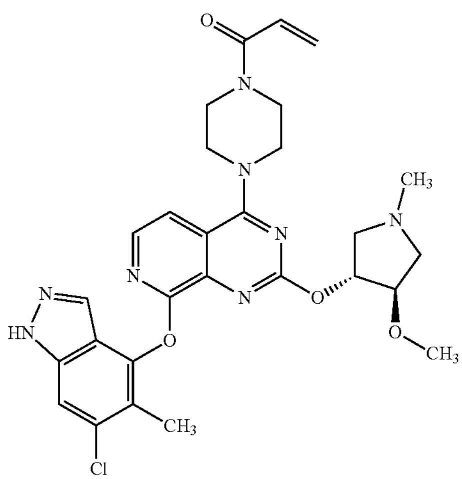 [SMILES: C=CC(=O)N1CCN(c2nc(O[C@@H]3CN(C)C[C@H]3OC)nc3c(Oc4c(C)c(Cl)cc5[nH]ncc45)nccc23)CC1] | 1-[4-(8-[(6-chloro-5-methyl-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one | 579 (M + H) | ¹H NMR (400 MHz, DMSO-d₆) δ 13.24 (s, 1H), 7.75 (d, J = 5.8 Hz, 1H), 7.60 (s, 1H), 7.58 (d, J = 5.8 Hz, 2H), 6.87-6.80 (m, 1H), 6.18 (dd, J = 16.7, 2.3 Hz, 1H), 5.75 (dd, J = 10.4, 2.3 Hz, 1H), 5.31-5.28 (m, 1H), 4.01-3.97 (m, 1H), 3.95-3.89 (m, 4H), 3.86-3.74 (m, 4H), 3.35 (s, 3H), 3.04 (dd, J = 9.7, 6.5 Hz, 1H), 2.94-2.89 (m, 1H), 2.68 (d, J = 11.2 Hz, 1H), 2.35 (d, J = 11.4 Hz, 1H), 2.26 (s, 3H), 2.20 (s, 3H) |
| 41I | 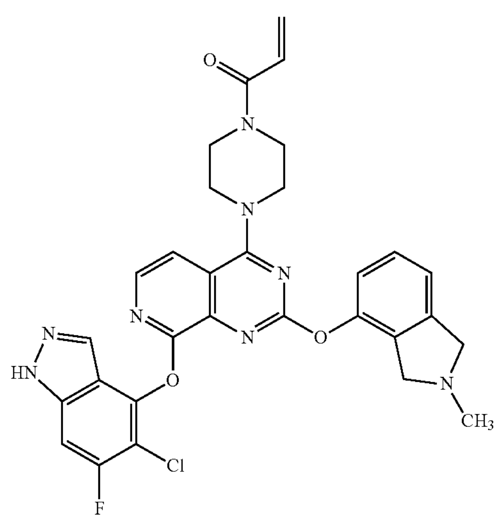 [SMILES: C=CC(=O)N1CCN(c2nc(Oc3cccc4c3CN(C)C4)nc3c(Oc4c(Cl)c(F)cc5[nH]ncc45)nccc23)CC1] | 1-(4-{8-[(5-chloro-6-fluoro-1H-indazol-4-yl)oxy]-2-[(2-methyl-2,3-dihydro-1H-isoindol-4-yl)oxy]pyrido[3,4-d]pyrimidin-4-yl}piperazin-1-yl)prop-2-en-1-one | 601 (M + H) | ¹H NMR (400 MHz, DMSO-d₆) δ 13.58 (s, 1H), 7.81 (d, J = 5.8 Hz, 1H), 7.76 (s, 1H), 7.67 (d, J = 5.8 Hz, 1H), 7.55 (d, J = 8.8 Hz, 1H), 7.25 (t, J = 7.7 Hz, 1H), 7.11 (d, J = 7.4 Hz, 1H), 7.08 (d, J = 8.1 Hz, 1H), 6.82 (dd, J = 16.7, 10.4 Hz, 1H), 6.17 (dd, J = 16.7, 2.4 Hz, 1H), 5.74 (dd, J = 10.5, 2.4 Hz, 1H), 3.98-3.66 (m, 12H), 2.40 (s, 3H) |

| Example | Structure | Compound Name | LCMS m/z | ¹H NMR |
|---|---|---|---|---|
| 42I | 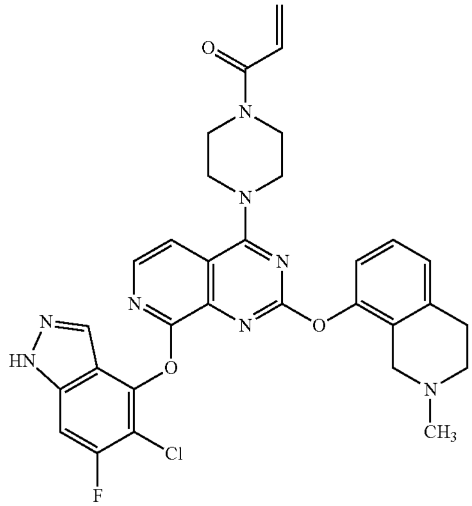 [SMILES: C=CC(=O)N1CCN(c2nc(Oc3cccc4c3CN(C)CC4)nc3c(Oc4c(Cl)c(F)cc5[nH]ncc45)nccc23)CC1] | 1-(4-{8-[(5-chloro-6-fluoro-1H-indazol-4-yl)oxy]-2-[(2-methyl-1,2,3,4-tetrahydro-isoquinolin-8-yl)oxy]pyrido[3,4-d]pyrimidin-4-yl}piperazin-1-yl)prop-2-en-1-one | 615 (M + H) | ¹H NMR (400 MHz, DMSO-d₆) δ 7.80 (d, J = 5.8 Hz, 1H), 7.75 (s, 1H), 7.65 (d, J = 5.9 Hz, 1H), 7.55 (d, J = 8.8 Hz, 1H), 7.18 (t, J = 7.8 Hz, 1H), 7.02 (d, J = 7.9 Hz, 1H), 6.96 (d, J = 7.6 Hz, 1H), 6.81 (dd, J = 16.7, 10.4 Hz, 1H), 6.16 (dd, J = 16.7, 2.4 Hz, 1H), 5.73 (dd, J = 10.4, 2.4 Hz, 1H), 3.93-3.61 (m, 8H), 3.52 (s, 2H), 2.70-2.60 (m, 2H), 2.58-2.53 (m, 2H), 2.33 (s, 3H) |
| 43I | 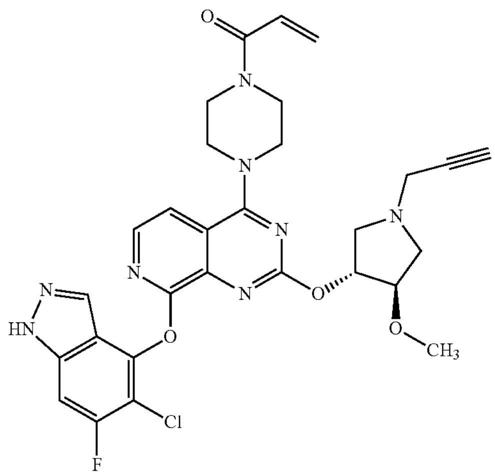 [SMILES: C#CCN1C[C@@H](OC)[C@H](Oc2nc(N3CCN(C(=O)C=C)CC3)c3ccnc(Oc4c(Cl)c(F)cc5[nH]ncc45)c3n2)C1] | 1-[4-(8-[(5-chloro-6-fluoro-1H-indazol-4-yl)oxy]-2-{[(3R,4R)-4-methoxy-1-(prop-2-yn-1-yl)pyrrolidin-3-yl]oxy}pyrido[3,4-d]pyrimidin-4-yl)piperazin-1-yl]prop-2-en-1-one | 607 (M + H) | ¹H NMR (400 MHz, DMSO-d₆) δ 13.56 (s, 1H), 7.79 (d, J = 5.8 Hz, 1H), 7.73 (s, 1H), 7.64 (d, J = 5.8 Hz, 1H), 7.56 (d, J = 8.9 Hz, 1H), 6.83 (dd, J = 16.7, 10.5 Hz, 1H), 6.18 (dd, J = 16.7, 2.3 Hz, 1H), 5.75 (dd, J = 10.5, 2.2 Hz, 1H), 5.27 (s, 1H), 4.04-3.89 (m, 5H), 3.88-3.72 (m, 4H), 3.40 (s, 2H), 3.37 (s, 3H), 3.17 (s, 1H), 3.11-2.99 (m, 2H), 2.73-2.66 (m, 1H), 2.48-2.44 (m, 1H) |
| 44I | 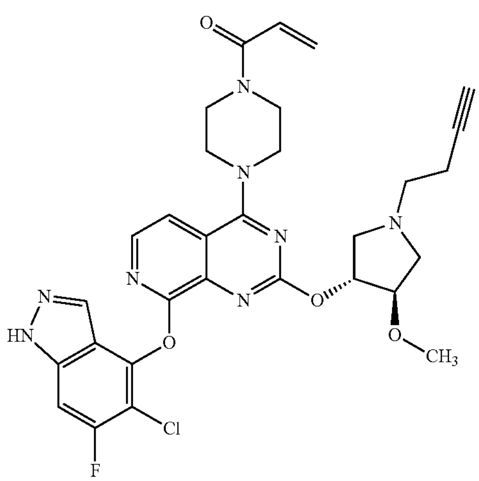 [SMILES: C#CCCN1C[C@@H](OC)[C@H](Oc2nc(N3CCN(C(=O)C=C)CC3)c3ccnc(Oc4c(Cl)c(F)cc5[nH]ncc45)c3n2)C1] | 1-[4-(2-{[(3R,4R)-1-(but-3-yn-1-yl)-4-methoxy-pyrrolidin-3-yl]oxy}-8-[(5-chloro-6-fluoro-1H-indazol-4-yl)oxy]pyrido[3,4-d]pyrimidin-4-yl)piperazin-1-yl]prop-2-en-1-one | 621 (M + H) | ¹H NMR (400 MHz, DMSO-d₆) δ 13.52 (s, 1H), 7.78 (s, 1H), 7.73 (s, 1H), 7.64 (d, J = 5.8 Hz, 1H), 7.56 (d, J = 8.8 Hz, 1H), 6.83 (dd, J = 16.7, 10.5 Hz, 1H), 6.18 (dd, J = 16.7, 2.3 Hz, 1H), 5.75 (dd, J = 10.4, 2.3 Hz, 1H), 5.26 (d, J = 2.5 Hz, 1H), 4.01-3.90 (m, 4H), 3.84-3.76 (m, 4H), 3.35 (s, 3H), 3.30 (s, 1H), 3.12-3.08 (m, 1H), 2.96-2.92 (m, 1H), 2.78 (t, J = 2.5 Hz, 1H), 2.75-2.72 (m, 1H), 2.60-2.53 (m, 2H), 2.39 (dd, J = 9.8, 4.5 Hz, 1H), 2.34-2.28 (m, 2H) |

| Example | Structure | Compound Name | LCMS m/z | ¹H NMR |
|---|---|---|---|---|
| 45I | 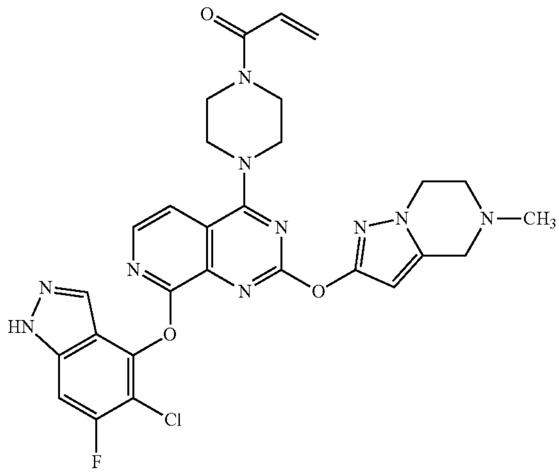 [SMILES: C=CC(=O)N1CCN(c2nc(Oc3cc4n(n3)CCN(C)C4)nc3c(Oc4c(Cl)c(F)cc5[nH]ncc45)nccc23)CC1] | 1-(4-{8-[(5-chloro-6-fluoro-1H-indazol-4-yl)oxy]-2-[(5-methyl-4,5,6,7-tetrahydro-pyrazolo[1,5-a]pyrazin-2-yl)oxy]pyrido[3,4-d]pyrimidin-4-yl}piperazin-1-yl)prop-2-en-1-one | 605 (M + H) | ¹H NMR (400 MHz, DMSO-d₆) δ 13.52 (s, 1H), 7.82 (d, J = 5.8 Hz, 1H), 7.77 (s, 1H), 7.69 (s, 1H), 7.57 (d, J = 8.7 Hz, 1H), 6.83 (dd, J = 16.7, 10.4 Hz, 1H), 6.18 (dd, J = 16.7, 2.3 Hz, 1H), 6.01 (s, 1H), 5.74 (dd, J = 10.4, 2.3 Hz, 1H), 3.99-3.90 (m, 6H), 3.86-3.75 (m, 4H), 3.54 (s, 2H), 2.84 (s, 2H), 2.37 (s, 3H) |
| 46I | 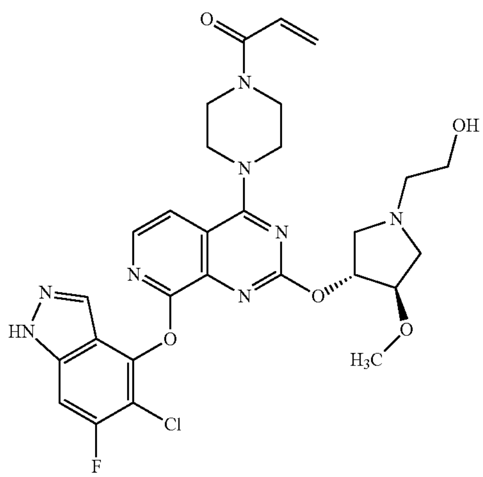 [SMILES: C=CC(=O)N1CCN(c2nc(O[C@@H]3CN(CCO)C[C@H]3OC)nc3c(Oc4c(Cl)c(F)cc5[nH]ncc45)nccc23)CC1] | 1-[4-(8-[(5-chloro-6-fluoro-1H-indazol-4-yl)oxy]-2-{[(3R,4R)-1-(2-hydroxy-ethyl)-4-methoxy-pyrrolidin-3-yl]oxy}pyrido[3,4-d]pyrimidin-4-yl)piperazin-1-yl]prop-2-en-1-one | 613 (M + H) | ¹H NMR (400 MHz, DMSO-d₆) δ 7.78 (d, J = 5.8 Hz, 1H), 7.75 (s, 1H), 7.64 (d, J = 5.8 Hz, 1H), 7.40 (d, J = 8.7 Hz, 1H), 6.81 (dd, J = 16.8, 10.6 Hz, 1H), 6.28 (dd, J = 16.8, 1.7 Hz, 1H), 5.81 (dd, J = 10.6, 1.7 Hz, 1H), 5.65-5.60 (m, 1H), 4.27-4.23 (m, 1H), 4.11-4.02 (m, 4H), 3.96-3.87 (m, 4H), 3.80-3.74 (m, 2H), 3.65-3.59 (m, 1H), 3.53 (s, 3H), 3.50-3.45 (m, 1H), 3.43-3.37 (m, 1H), 3.24-3.18 (m, 1H), 3.14-3.03 (m, 2H) |
| 47I | 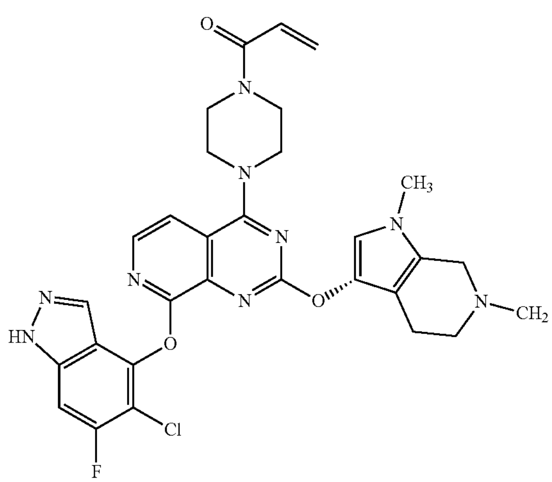 | 1-(4-{8-[(5-chloro-6-fluoro-1H-indazol-4-yl)oxy]-2-[(1,6-dimethyl-4,5,6,7-tetrahydro-1H-pyrazolo[3,4-c]pyridin-3-yl)oxy]pyrido[3,4-d]pyrimidin-4-yl}piperazin-1-yl)prop-2-en-1-one | 619 (M + H) | ¹H NMR (400 MHz, DMSO-d₆) δ 13.53 (s, 1H), 7.79 (t, J = 4.7 Hz, 2H), 7.67 (d, J = 5.9 Hz, 1H), 7.58 (d, J = 8.8 Hz, 1H), 6.83 (dd, J = 16.6, 10.4 Hz, 1H), 6.18 (dd, J = 16.7, 2.4 Hz, 1H), 5.75 (dd, J = 10.3, 2.4 Hz, 1H), 3.99-3.90 (m, 4H), 3.89-3.80 (m, 2H), 3.80-3.67 (m, 2H), 3.59 (s, 2H), 3.44 (s, 3H), 2.65 (d, J = 16.6 Hz, 2H), 2.40 (d, J = 5.5 Hz, 2H), 2.31 (s, 3H) |

| Example | Structure | Compound Name | LCMS m/z | ¹H NMR |
|---|---|---|---|---|
| 48I | 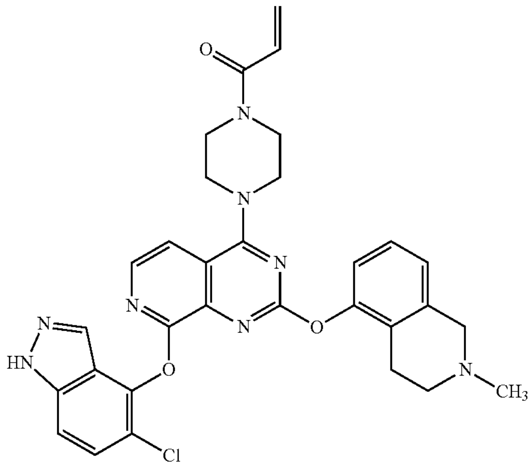 [SMILES: C=CC(=O)N1CCN(c2nc(Oc3cccc4c3CCN(C)C4)nc3c(Oc4c(Cl)ccc5[nH]ncc45)nccc23)CC1] | 1-(4-{8-[(5-chloro-1H-indazol-4-yl)oxy]-2-[(2-methyl-1,2,3,4-tetrahydro-isoquinolin-5-yl)oxy]pyrido[3,4-d]pyrimidin-4-yl}piperazin-1-yl)prop-2-en-1-one | 597 (M + H) | ¹H NMR (400 MHz, DMSO-$d_6$) δ 13.53 (s, 1H), 7.84-7.75 (m, 2H), 7.67 (d, J = 5.8, 1H), 7.58 (d, J = 8.8, 1H), 6.83 (dd, J = 16.6, 10.4, 1H), 6.18 (d, J = 16.6, 1H), 5.75 (d, J = 12.4, 1H), 3.95 (s, 4H), 3.80 (m, 4H), 3.59 (s, 3H), 3.44 (s, 2H), 2.71-2.61 (m, 2H), 2.44-2.36 (m, 2H), 2.31 (s, 3H) |
| 49I | 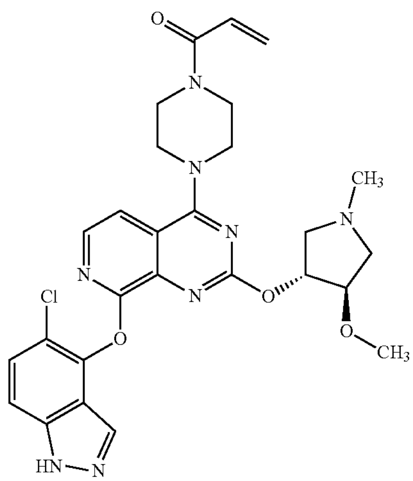 [SMILES: C=CC(=O)N1CCN(c2nc(O[C@@H]3CN(C)C[C@H]3OC)nc3c(Oc4c(Cl)ccc5[nH]ncc45)nccc23)CC1] | 1-[4-(6-chloro-8-[(5-chloro-1H-indazol-4-yl)oxy]-2-{[(3R,4R)-4-methoxy-1-methyl-pyrrolidin-3-yl]oxy}pyrido[3,4-d]pyrimidin-4-yl)piperazin-1-yl]prop-2-en-1-one | 565 (M + H) | ¹H NMR (400 MHz, DMSO-$d_6$) δ 13.43 (s, 1H), 8.16 (d, J = 4.0 Hz, 1H), 7.82-7.68 (m, 2H), 7.60 (d, J = 5.8 Hz, 1H), 7.49 (s, 2H), 6.83 (dd, J = 16.7, 10.4 Hz, 1H), 6.24-6.10 (m, 1H), 5.82-5.69 (m, 1H), 5.30 (s, 1H), 3.97-3.77 (m, 9H), 3.36 (s, 3H), 3.07-3.00 (m, 1H), 2.97-2.87 (m, 1H), 2.73-2.64 (m, 1H), 2.38-2.24 (m, 4H) |
| 50I | 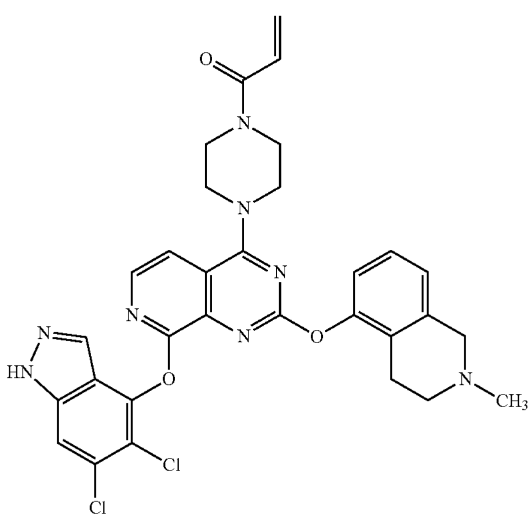 [SMILES: C=CC(=O)N1CCN(c2nc(Oc3cccc4c3CCN(C)C4)nc3c(Oc4c(Cl)c(Cl)cc5[nH]ncc45)nccc23)CC1] | 1-(4-{8-[(5,6-dichloro-1H-indazol-4-yl)oxy]-2-[(2-methyl-1,2,3,4-tetrahydro-isoquinolin-5-yl)oxy]pyrido[3,4-d]pyrimidin-4-yl}piperazin-1-yl)prop-2-en-1-one | 631 (M + H) | ¹H NMR (400 MHz, DMSO-$d_6$) δ 13.58 (s, 1H), 7.84-7.75 (m, 3H), 7.64 (d, J = 5.9 Hz, 1H), 7.18 (t, J = 7.8 Hz, 1H), 7.03 (d, J = 7.8 Hz, 1H), 6.96 (d, J = 7.6 Hz, 1H), 6.81 (dd, J = 16.7, 10.5 Hz, 1H), 6.16 (dd, J = 16.6, 2.1 Hz, 1H), 5.73 (dd, J = 10.4, 2.1 Hz, 1H), 3.85 (br s, 4H), 3.73 (d, J = 29.1 Hz, 4H), 3.52 (s, 2H), 2.68-2.62 (m, 2H), 2.57-2.53 (m, 2H), 2.33 (s, 3H) |

-continued

| Example | Structure | Compound Name | LCMS m/z | ¹H NMR |
|---|---|---|---|---|
| 51I | 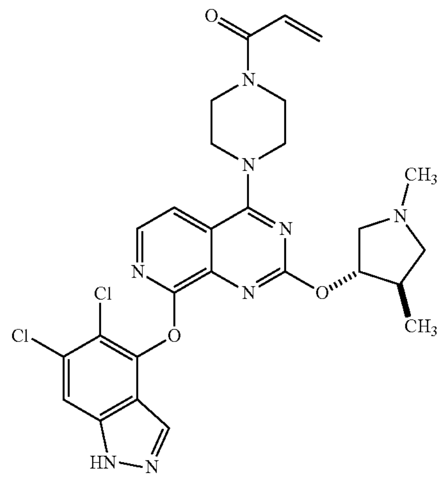 | rac-1-[4-[8-[(5,6-dichloro-1H-indazol-4-yl)oxy]-2-{[(3S,4R)-1,4-dimethyl-pyrrolidin-3-yl]oxy}pyrido[3,4-d]pyrimidin-4-yl)piperazin-1-yl]prop-2-en-1-one | 583 (M + H) | ¹H NMR (400 MHz, DMSO-$d_6$) δ 13.56 (br. s, 1H), 7.83 (s, 1H), 7.80-7.73 (m, 2H), 7.62 (d, J = 5.8 Hz, 1H), 6.86-6.80 (m, 1H), 6.18 (dd, J = 16.7, 2.2 Hz, 1H), 5.75 (dd, J = 10.4, 2.2 Hz, 1H), 4.96-4.92 (m, 1H), 3.96-3.89 (m, 4H), 3.80 (dd, J = 30.3, 3.6 Hz, 4H), 3.22-3.20 (m, 1H), 2.94-2.90 (m, 1H), 2.73 (d, J = 4.4 Hz, 1H), 2.30-2.25 (m, 1H), 2.24 (s, 3H), 1.96-1.91 (m, 1H), 1.19 (d, J = 7.1 Hz, 3H) |
| 52I | 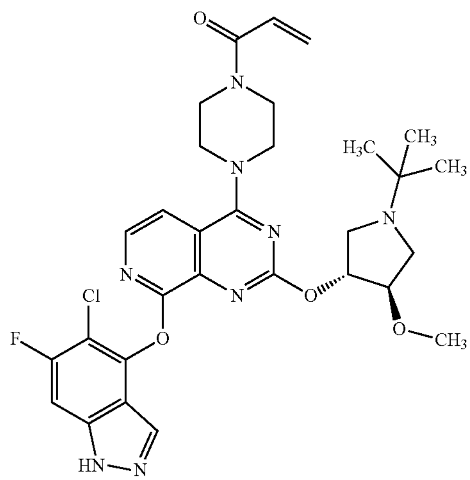 [SMILES: C=CC(=O)N1CCN(c2nc(O[C@@H]3CN(C(C)(C)C)C[C@H]3OC)nc3c(Oc4c(Cl)c(F)cc5[nH]ncc45)nccc23)CC1] | 1-[4-(2-{[(3R,4R)-1-tert-butyl-4-methoxy-pyrrolidin-3-yl]oxy}-8-[(5-chloro-6-fluoro-1H-indazol-4-yl)oxy]pyrido[3,4-d]pyrimidin-4-yl)piperazin-1-yl]prop-2-en-1-one | 625 (M + H) | ¹H NMR (400 MHz, DMSO-$d_6$) δ 13.52 (s, 1H), 7.80 (d, J = 5.8 Hz, 1H), 7.71 (s, 1H), 7.65 (d, J = 5.8 Hz, 1H), 7.56 (d, J = 8.9 Hz, 1H), 6.83 (dd, J = 16.6, 10.4 Hz, 1H), 6.18 (dd, J = 16.7, 2.2 Hz, 1H), 5.75 (dd, J = 10.4, 2.2 Hz, 1H), 5.23 (s, 1H), 4.06-3.67 (m, 8H), 3.35 (s, 3H), 3.30 (s, 1H), 3.09 (s, 1H), 2.67 (s, 1H), 2.33 (s, 1H), 2.00 (d, J = 7.5 Hz, 1H), 1.01-1.23 (m, 9H) |
| 53I | 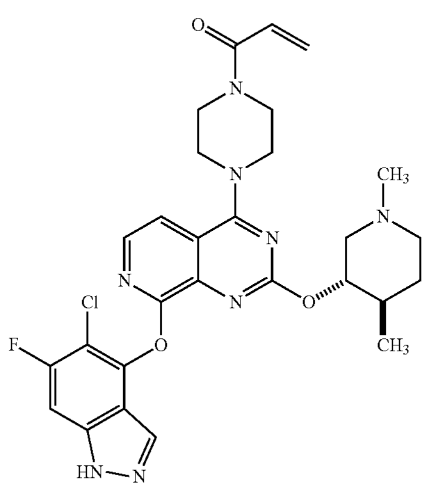 | rac-1-[4-(8-[(5-chloro-6-fluoro-1H-indazol-4-yl)oxy]-2-{[(3S,4R)-1,4-dimethyl-piperidin-3-yl]oxy}pyrido[3,4-d]pyrimidin-4-yl)piperazin-1-yl]prop-2-en-1-one | 581 (M + H) | ¹H NMR (400 MHz, DMSO-$d_6$) δ 13.53 (s, 1H), 7.77 (d, J = 5.8 Hz, 1H), 7.75 (s, 1H), 7.62 (d, J = 5.8 Hz, 1H), 7.56 (d, J = 8.9 Hz, 1H), 6.83 (dd, J = 16.7, 10.4 Hz, 1H), 6.18 (dd, J = 16.7, 2.1 Hz, 1H), 5.75 (dd, J = 10.4, 2.1 Hz, 1H), 4.82-4.76 (m, 1H), 3.94-3.89 (m, 4H), 3.86-3.75 (m, 4H), 3.18 (dd, J = 9.9, 4.1 Hz, 1H), 2.69 (d, J = 12.0 Hz, 1H), 2.17 (s, 3H), 1.91 (t, J = 10.7 Hz, 1H), 1.81 (t, J = 9.9 Hz, 1H), 1.74-1.69 (m, 1H), 1.64-1.56 (m, 1H), 1.38-1.29 (m, 1H), 0.96 (d, J = 6.4 Hz, 3H) |

| Example | Structure | Compound Name | LCMS m/z | ¹H NMR |
|---|---|---|---|---|
| 54I | 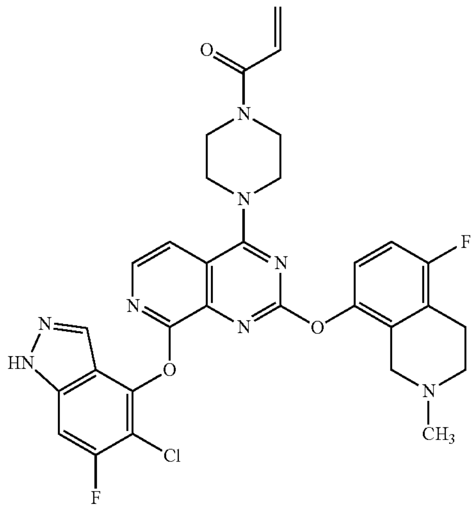 [SMILES: C=CC(=O)N1CCN(c2nc(Oc3ccc(F)c4c3CN(C)CC4)nc3c(Oc4c(Cl)c(F)cc5[nH]ncc45)nccc23)CC1] | 1-(4-{8-[(5-chloro-6-fluoro-1H-indazol-4-yl)oxy]-2-[(5-fluoro-2-methyl-1,2,3,4-tetrahydro-isoquinolin-8-yl)oxy]pyrido[3,4-d]pyrimidin-4-yl}piperazin-1-yl)prop-2-en-1-one | 633 (M + H) | ¹H NMR (400 MHz, DMSO-$d_6$) δ 13.52 (s, 1H), 7.83 (d, J = 5.8, 1H), 7.76-7.64 (m, 2H), 7.54 (d, J = 8.8, 1H), 7.13-6.99 (m, 2H), 6.81 (dd, J = 16.6, 10.4, 1H), 6.17 (d, J = 16.7, 1H), 5.73 (d, J = 11.0, 1H), 3.88 (s, 4H), 3.75 (d, J = 30.8, 4H), 3.36 (s, 2H), 2.79 (t, J = 9.9, 2H), 2.58 (t, J = 5.3, 2H), 2.29 (s, 3H) |
| 55I | 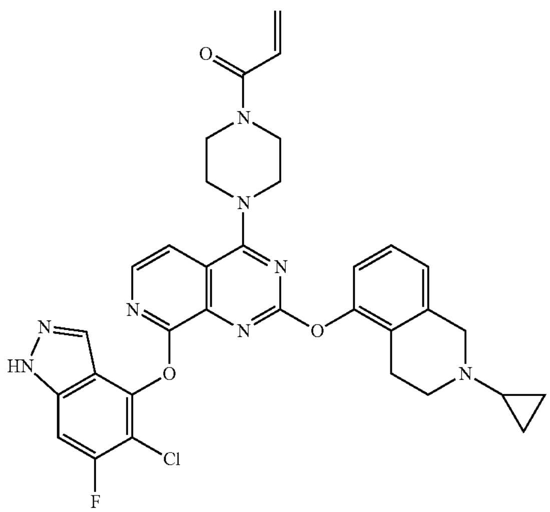 [SMILES: C=CC(=O)N1CCN(c2nc(Oc3cccc4c3CCN(C3CC3)C4)nc3c(Oc4c(Cl)c(F)cc5[nH]ncc45)nccc23)CC1] | 1-(4-{8-[(5-chloro-6-fluoro-1H-indazol-4-yl)oxy]-2-[(2-cyclopropyl-1,2,3,4-tetrahydro-isoquinolin-5-yl)oxy]pyrido[3,4-d]pyrimidin-4-yl}piperazin-1-yl)prop-2-en-1-one | 641 (M + H) | ¹H NMR (400 MHz, DMSO-$d_6$) δ 13.51 (s, 1H), 7.79 (d, J = 5.8 Hz, 1H), 7.73 (s, 1H), 7.65 (d, J = 5.8 Hz, 1H), 7.54 (d, J = 8.9 Hz, 1H), 7.17 (s, 1H), 7.06-6.95 (m, 2H), 6.81 (dd, J = 16.7, 10.4 Hz, 1H), 6.16 (dd, J = 16.7, 2.0 Hz, 1H), 5.73 (dd, J = 10.5, 2.1 Hz, 1H), 3.86 (br. s, 4H), 3.80-3.65 (d, 6H), 2.84-2.73 (m, 2H), 2.64-2.56 (m, 2H), 1.77 (s, 1H), 0.50-0.41 (m, 2H), 0.40-0.33 (m, 2H) |
| 56I | 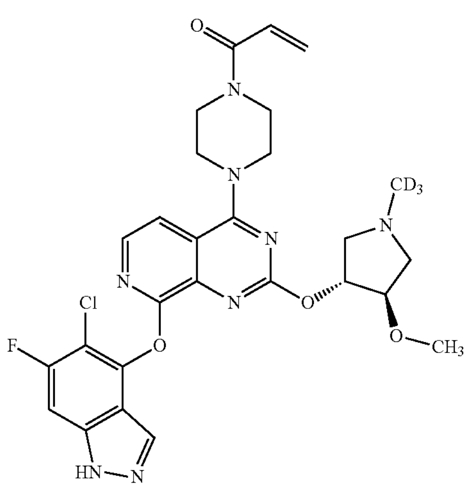 [SMILES: [2H]C([2H])([2H])N1C[C@@H](OC)[C@H](Oc2nc(N3CCN(C(=O)C=C)CC3)c3ccnc(Oc4c(Cl)c(F)cc5[nH]ncc45)c3n2)C1] | 1-[4-(8-[(5-chloro-6-fluoro-1H-indazol-4-yl)oxy]-2-{[(3R,4R)-4-methoxy-1-(²H₃)methyl-pyrrolidin-3-yl]oxy}pyrido[3,4-d]pyrimidin-4-yl)piperazin-1-yl]prop-2-en-1-one | 586 (M + H) | ¹H NMR (400 MHz, DMSO-$d_6$) δ 13.53 (s, 1H), 7.79 (d, J = 5.8 Hz, 1H), 7.72 (s, 1H), 7.64 (d, J = 5.9 Hz, 1H), 7.56 (d, J = 8.9 Hz, 1H), 6.83 (dd, J = 16.7, 10.4 Hz, 1H), 6.18 (dd, J = 16.7, 2.2 Hz, 1H), 5.75 (dd, J = 10.4, 2.2 Hz, 1H), 5.27-5.22 (m, 1H), 3.99-3.90 (m, 5H), 3.92-3.77 (m, 4H), 3.34 (s, 3H), 3.03-2.98 (m, 1H), 2.87-2.83 (m 1H), 2.68-2.59 (m, 1H), 2.34-2.26 (m, 1H) |

| Example | Structure | Compound Name | LCMS m/z | ¹H NMR |
|---|---|---|---|---|
| 57I | 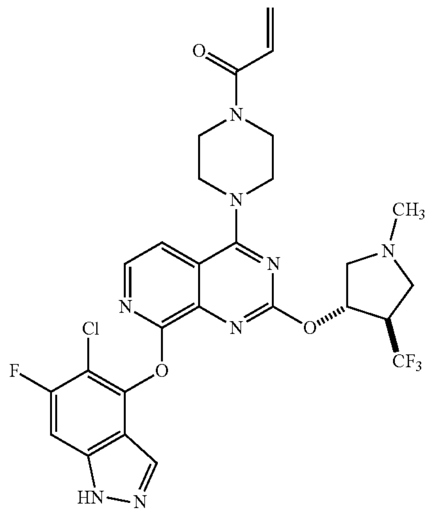 | 1-[4-(8-[(5-chloro-6-fluoro-1H-indazol-4-yl)oxy]-2-{[(3S,4R)-1-methyl-4-(trifluoromethyl)pyrrolidin-3-yl]oxy}pyrido[3,4-d]pyrimidin-4-yl)piperazin-1-yl]prop-2-en-1-one | 621 (M + H) | ¹H NMR (400 MHz, DMSO-d₆) δ 13.56 (s, 1H), 8.37 (s, 1H), 7.84 (d, J = 5.8 Hz, 1H), 7.67 (d, J = 5.4 Hz, 2H), 7.55 (d, J = 8.9 Hz, 1H), 6.82 (dd, J = 16.7, 10.5 Hz, 1H), 6.18 (dd, J = 16.7, 2.2 Hz, 1H), 5.75 (dd, J = 10.5, 2.2 Hz, 1H), 5.43 (d, J = 5.5 Hz, 1H), 3.87 (dd, J = 52.4, 18.2 Hz, 8H), 3.04 (t, J = 9.1 Hz, 1H), 2.84 (dd, J = 10.5, 6.0 Hz, 1H), 2.73-2.65 (m, 1H), 2.47-2.43 (m, 1H), 2.25 (s, 3H) |
| 58I | *denotes relative stereochemistry (first eluting enantiomer) | 1-[4-(8-[(5-chloro-6-fluoro-1H-indazol-4-yl)oxy]-2-{[(3S,4R)-rel-4-(difluoromethyl)-1-methylpyrrolidin-3-yl]oxy}pyrido[3,4-d]pyrimidin-4-yl)piperazin-1-yl]prop-2-en-1-one | 603, 605 (M + H) | ¹H NMR (600 MHz, DMSO-d₆) δ 7.79 (d, J = 5.7 Hz, 1H), 7.75 (s, 1H), 7.65 (d, J = 5.8 Hz, 1H), 7.57 (d, J = 8.7 Hz, 1H), 6.92-6.61 (m, 2H), 6.18 (dd, J = 16.7, 2.3 Hz, 1H), 5.75 (dd, J = 10.4, 2.3 Hz, 1H), 5.35-5.24 (m, 1H), 4.05-3.87 (m, 4H), 3.80 (d, J = 41.1 Hz, 4H), 2.93 (t, J = 8.8 Hz, 1H), 2.89-2.76 (m, 2H), 2.66 (dd, J = 10.7, 6.0 Hz, 1H), 2.36 (dd, J = 9.4, 7.4 Hz, 1H), 2.26 (s, 3H) |
| 59I | *denotes relative stereochemistry (second eluting enantiomer) | 1-[4-(8-[(5-chloro-6-fluoro-1H-indazol-4-yl)oxy]-2-{[(3S,4R)-rel-4-(difluoromethyl)-1-methylpyrrolidin-3-yl]oxy}pyrido[3,4-d]pyrimidin-4-yl)piperazin-1-yl]prop-2-en-1-one | 603, 605 (M + H) | ¹H NMR (600 MHz, DMSO-d₆) δ 7.79 (d, J = 5.8 Hz, 1H), 7.75 (s, 1H), 7.65 (d, J = 5.8 Hz, 1H), 7.57 (dd, J = 8.9, 1.0 Hz, 1H), 6.89-6.54 (m, 2H), 6.18 (dd, J = 16.7, 2.3 Hz, 1H), 5.75 (dd, J = 10.5, 2.3 Hz, 1H), 5.29 (dd, J = 6.0, 3.0 Hz, 1H), 4.00-3.90 (m, 4H), 3.80 (d, J = 42.3 Hz, 4H), 2.93 (t, J = 8.8 Hz, 1H), 2.90-2.76 (m, 2H), 2.66 (dd, J = 10.7, 6.0 Hz, 1H), 2.36 (dd, J = 9.4, 7.3 Hz, 1H), 2.26 (s, 3H) |

The examples in the following table were prepared using Method I in parallel library format and the procedure used to prepare 1-(4-{8-[(5-Chloro-6-methyl-1H-indazol-4-yl)oxy]-2-[3-(dimethylamino)azetidin-1-yl]-6-methylpyrido[3,4-d]pyrimidin-4-yl}piperazin-1-yl)prop-2-en-1-one (Example-1I) and 1-[4-(8-[(5-chloro-6-fluoro-1H-indazol-4-yl)oxy]-2-{[(3S)-3-fluoro-1-methylpiperidin-3-yl]methoxy}pyrido[3,4-d]pyrimidin-4-yl)piperazin-1-yl]prop-2-en-1-one (Example-2I), and 1-[4-(8-[(5-chloro-6-fluoro-1H-indazol-4-yl)oxy]-2-{[(3R,4R)-4-methoxy-1-methylpyrrolidin-3-yl]oxy}pyrido[3,4-d]pyrimidin-4-yl)piperazin-1-yl]prop-2-en-1-one (Example-10I). The following examples were made with non-critical changes or substitutions to the exemplified procedure used to prepare Example-1I, Example-2I, and Example-10I that someone who is skilled in the art would be able to realize.

| Example | Structure | Compound Name | LCMS m/z |
|---|---|---|---|
| 1J | 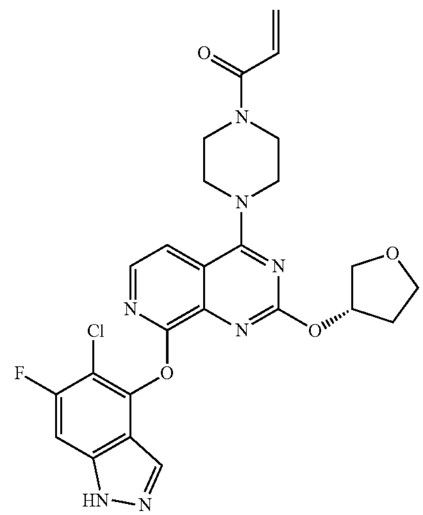 [SMILES: C=CC(=O)N1CCN(c2nc(O[C@H]3CCOC3)nc3c(Oc4c(Cl)c(F)cc5[nH]ncc45)nccc23)CC1] | 1-(4-{8-[(5-chloro-6-fluoro-1H-indazol-4-yl)oxy]-2-[(3S)-tetrahydrofuran-3-yloxy]pyrido[3,4-d]pyrimidin-4-yl}piperazin-1-yl)prop-2-en-1-one | 540 (M + H) |
| 2J | 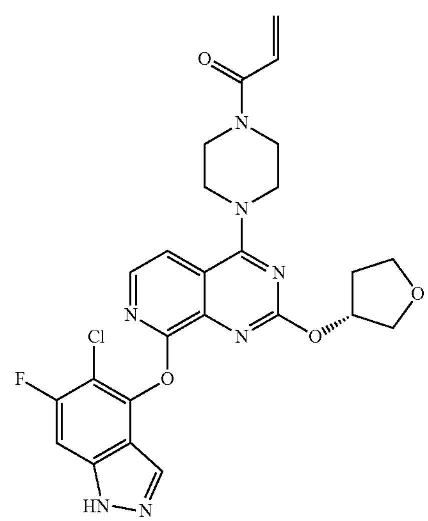 [SMILES: C=CC(=O)N1CCN(c2nc(O[C@@H]3CCOC3)nc3c(Oc4c(Cl)c(F)cc5[nH]ncc45)nccc23)CC1] | 1-(4-{8-[(5-chloro-6-fluoro-1H-indazol-4-yl)oxy]-2-[(3R)-tetrahydrofuran-3-yloxy]pyrido[3,4-d]pyrimidin-4-yl}piperazin-1-yl)prop-2-en-1-one | 540 (M + H) |

-continued

| Example | Structure | Compound Name | LCMS m/z |
|---|---|---|---|
| 3J | 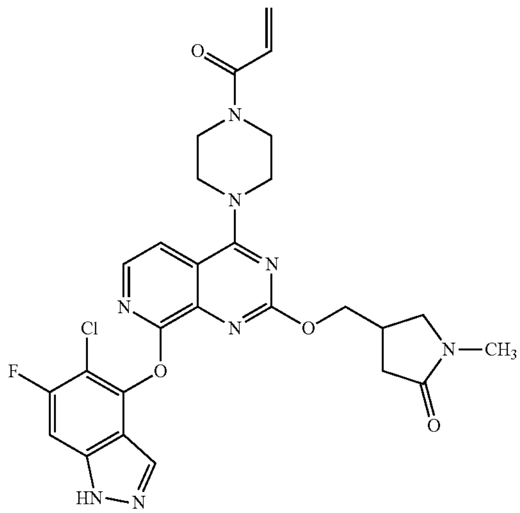 [SMILES: C=CC(=O)N1CCN(c2nc(OCC3CC(=O)N(C)C3)nc3c(Oc4c(Cl)c(F)cc5[nH]ncc45)nccc23)CC1] | 4-[({4-(4-acryloylpiperazin-1-yl)-8-[(5-chloro-6-fluoro-1H-indazol-4-yl)oxy]pyrido[3,4-d]pyrimidin-2-yl}oxy)methyl]-1-methylpyrrolidin-2-one | 581 (M + H) |
| 4J | 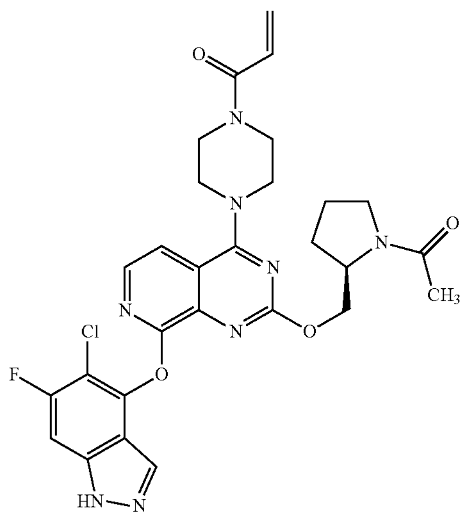 [SMILES: C=CC(=O)N1CCN(c2nc(OC[C@H]3CCCN3C(C)=O)nc3c(Oc4c(Cl)c(F)cc5[nH]ncc45)nccc23)CC1] | 1-[4-(2-{[(2R)-1-acetylpyrrolidin-2-yl]methoxy}-8-[(5-chloro-6-fluoro-1H-indazol-4-yl)oxy]pyrido[3,4-d]pyrimidin-4-yl)piperazin-1-yl]prop-2-en-1-one | 595 (M + H) |
| 5J | 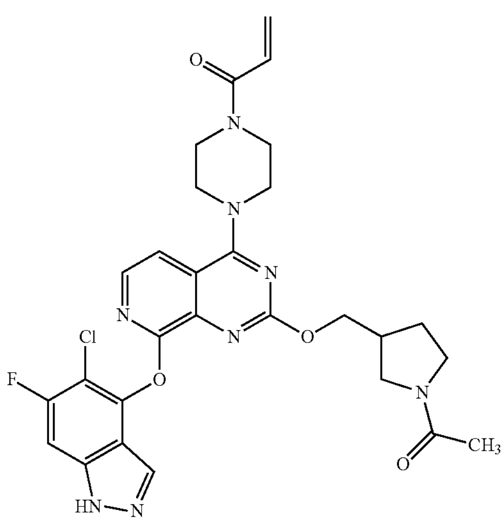 [SMILES: C=CC(=O)N1CCN(c2nc(OCC3CCN(C(C)=O)C3)nc3c(Oc4c(Cl)c(F)cc5[nH]ncc45)nccc23)CC1] | 1-(4-{2-[(1-acetylpyrrolidin-3-yl)methoxy]-8-[(5-chloro-6-fluoro-1H-indazol-4-yl)oxy]pyrido[3,4-d]pyrimidin-4-yl}piperazin-1-yl)prop-2-en-1-one | 595 (M + H) |

-continued

| Example | Structure | Compound Name | LCMS m/z |
|---|---|---|---|
| 6J | 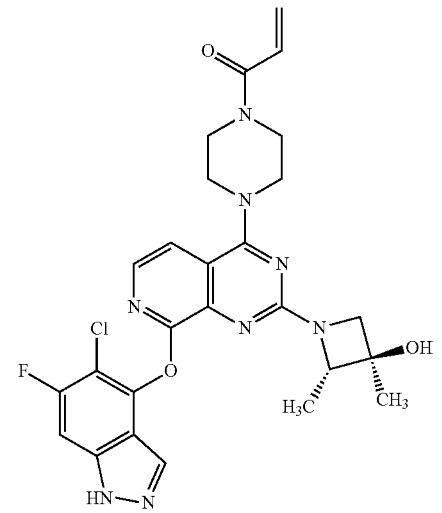 | 1-(4-{8-[(5-chloro-6-fluoro-1H-indazol-4-yl)oxy]-2-[(2S,3R)-3-hydroxy-2,3-dimethylazetidin-1-yl]pyrido[3,4-d]pyrimidin-4-yl}piperazin-1-yl)prop-2-en-1-one | 533 (M + H) |

The following examples were prepared according to general Method K:

Preparation of 1-[4-(8-[(5-chloro-6-fluoro-1H-indazol-4-yl)oxy]-2-{[(3R,4R)-4-methoxy-1-methylpyrrolidin-3-yl]oxy}-6-methylpyrido[3,4-d]pyrimidin-4-yl)piperazin-1-yl]prop-2-en-1-one (Example-1K)

Step 1:

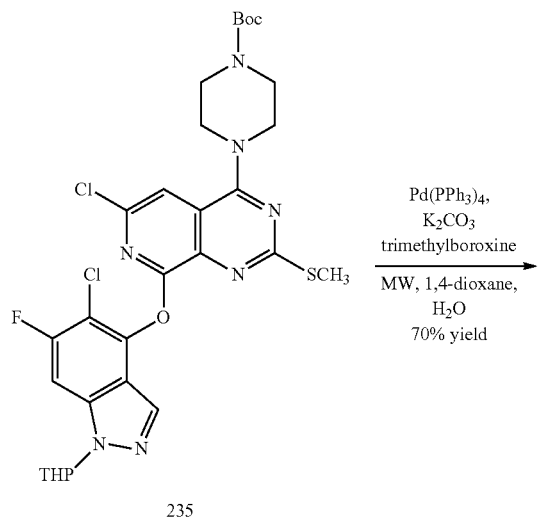

235

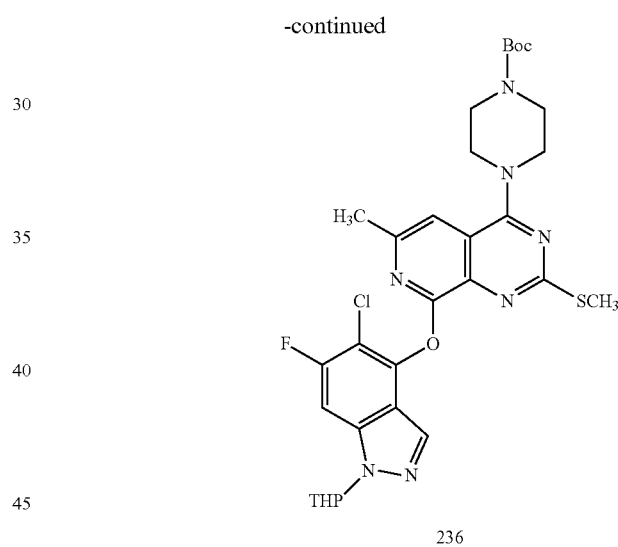

236

A mixture of tert-butyl 4-[6-chloro-8-{[5-chloro-6-fluoro-1-(oxan-2-yl)-1H-indazol-4-yl]oxy}-2-(methylsulfanyl)pyrido[3,4-d]pyrimidin-4-yl]piperazine-1-carboxylate (235) (500 mg, 0.752 mmol), trimethylboroxine (236 mg, 1.88 mmol), $K_2CO_3$ (311 mg, 2.26 mmol), and $Pd(PPh_3)_4$ (86.9 mg, 0.0752 mmol) in 1,4-dioxane (10 mL) and $H_2O$ (1 mL) was degassed with $N_2$ for 2 min. The reaction was heated to 100° C. with MW irradiation for 3 h. LCMS analysis showed consumption of the starting material with formation of the desired product. The reaction was cooled to room temperature and concentrated. The residue was purified by flash chromatography ($SiO_2$, 0-60% EtOAc/petroleum ether) to provide tert-butyl 4-[8-{[5-chloro-6-fluoro-1-(oxan-2-yl)-1H-indazol-4-yl]oxy}-6-methyl-2-(methylsulfanyl)pyrido[3,4-d]pyrimidin-4-yl]piperazine-1-carboxylate (236) (340 mg, 70% yield) as a yellow solid. $^1$H NMR (400 MHz, DMSO-$d_6$) δ 7.85 (d, J=9.4 Hz, 1H), 7.81 (s, 1H), 7.43 (s, 1H), 5.87 (dd, J=9.7, 2.0 Hz, 1H), 3.95-3.74 (m, 6H), 3.62-3.50 (m, 4H), 2.49 (s, 3H), 2.42-2.32 (m, 1H) 2.28 (s, 3H), 2.06-1.94 (m, 2H), 1.82-1.65 (m, 1H), 1.63-1.53 (m, 2H), 1.44 (s, 9H). LCMS (ESI) m/z 644, 646 (M+H).

Step 2:

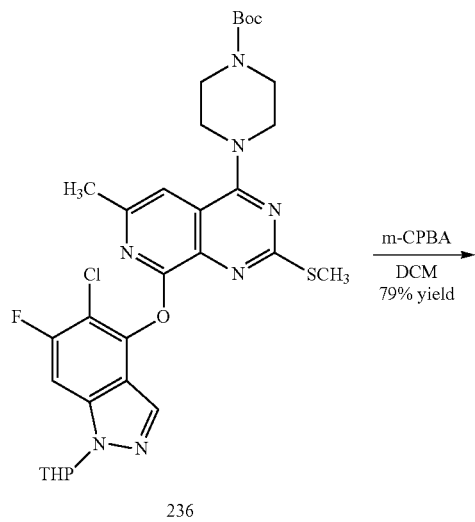

236

237

2.32 (s, 3H), 2.10-1.95 (m, 2H), 1.81-1.66 (m, 1H), 1.65-1.53 (m, 2H), 1.44 (s, 9H). LCMS (ESI) m/z 660, 662 (M+H).

Step 3:

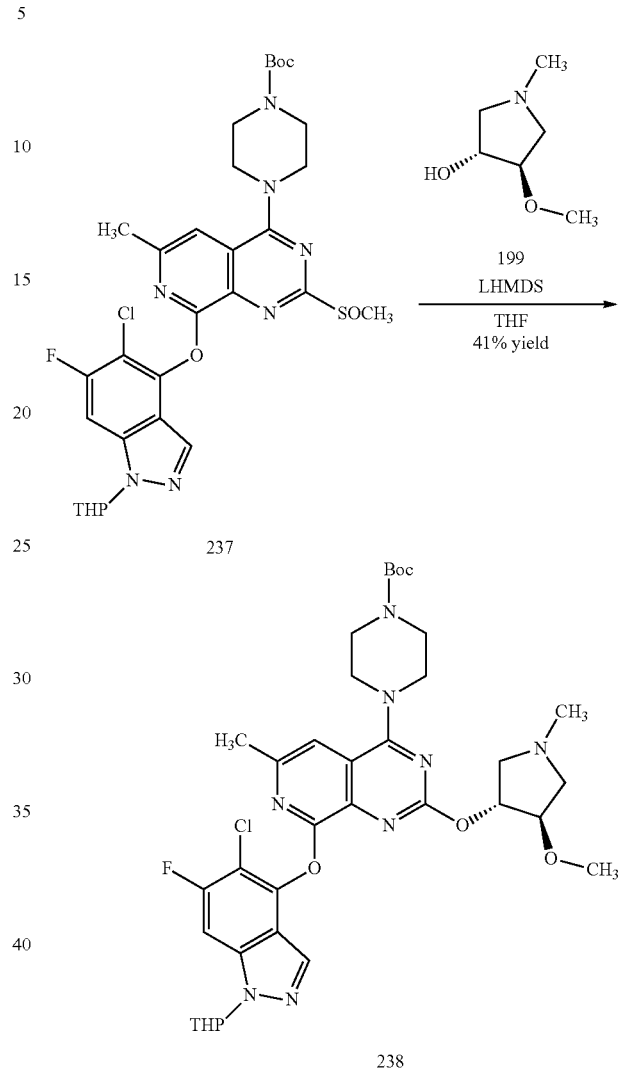

237

238

To a stirred solution of tert-butyl 4-[8-{[5-chloro-6-fluoro-1-(oxan-2-yl)-1H-indazol-4-yl]oxy}-6-methyl-2-(methylsulfanyl)pyrido[3,4-d]pyrimidin-4-yl]piperazine-1-carboxylate (236) (430 mg, 0.528 mmol) in DCM (5 mL) was added m-CPBA (80%, 114 mg, 0.528 mmol) portionwise. After 4 h, LCMS analysis showed consumption of the starting material with formation of the product. The mixture was quenched with saturated aqueous Na$_2$SO$_3$ (10 mL) and diluted with H$_2$O (20 mL). The biphasic mixture was separated. The aqueous layer was extracted with DCM (2×20 mL). The combined organics were washed with saturated aqueous NaHCO$_3$ (20 mL) and brine, dried over Na$_2$SO$_4$, filtered, and concentrated. The residue was purified by flash chromatography (SiO$_2$, 0-100% EtOAc/petroleum ether) to provide tert-butyl 4-[8-{[5-chloro-6-fluoro-1-(oxan-2-yl)-1H-indazol-4-yl]oxy}-2-(methanesulfinyl)-6-methylpyrido[3,4-d]pyrimidin-4-yl]piperazine-1-carboxylate (237) (275 mg, 79% yield) as a yellow oil. $^1$H NMR (400 MHz, DMSO-d$_6$) δ 7.94-7.87 (m, 2H), 7.56 (s, 1H), 5.89 (dd, J=9.7, 2.1 Hz, 1H), 4.03-3.86 (m, 5H), 3.84-3.73 (m, 1H), 3.65-3.50 (m, 4H), 2.93 (s, 3H), 2.43-2.34 (m, 1H), To a stirred solution of tert-butyl 4-[8-{[5-chloro-6-fluoro-1-(oxan-2-yl)-1H-indazol-4-yl]oxy}-2-(methanesulfinyl)-6-methylpyrido[3,4-d]pyrimidin-4-yl]piperazine-1-carboxylate (237) (267 mg, 0.404 mmol) and (3R,4R)-4-methoxy-1-methylpyrrolidin-3-ol (199) (79.6 mg, 0.607 mmol) in dry THF (4 mL) was added dropwise LHMDS (1.0 M in THF, 0.607 ml, 0.607 mmol) at room temperature. The resulting mixture was stirred at room temperature for 3 h. LCMS analysis showed consumption of the starting material with formation of the desired product. The mixture was quenched with saturated aqueous NH$_4$Cl (10 mL), and the aqueous layer was extracted with EtOAc (3×20 mL). The combined organics were dried over Na$_2$SO$_4$, filtered, and concentrated. The crude residue was purified by reverse phase flash chromatography (0-100% MeCN/H$_2$O+0.05% formic acid) to provide tert-butyl 4-(8-{[5-chloro-6-fluoro-1-(oxan-2-yl)-1H-indazol-4-yl]oxy}-2-{[(3R,4R)-4-methoxy-1-methylpyrrolidin-3-yl]oxy}-6-methylpyrido[3,4-d]pyrimidin-4-yl)piperazine-1-carboxylate (238) (120 mg, 41% yield) as a yellow solid. $^1$H NMR (400 MHz, DMSO-d$_6$) δ 7.84 (d, J=9.3 Hz, 1H), 7.70 (d, J=10.2 Hz, 1H), 7.46 (s, 1H), 5.92-5.83 (m, 1H), 5.15 (s, 1H), 3.95-3.70 (m, 7H), 3.56 (br. s, 4H), 3.31 (s, 3H), 3.05-2.92 (m, 1H), 2.84-2.71 (m, 1H), 2.60-2.52 (m, 1H), 2.39-2.32 (m, 1H), 2.29 (s, 3H), 2.28-2.24 (m, 1H), 2.23-2.17 (m, 3H), 2.05-1.95 (m, 2H), 1.79-1.66 (m, 1H), 1.62-1.54 (m, 2H), 1.44 (s, 9H). LCMS (ESI) m/z 727, 729 (M+H).

Step 4:

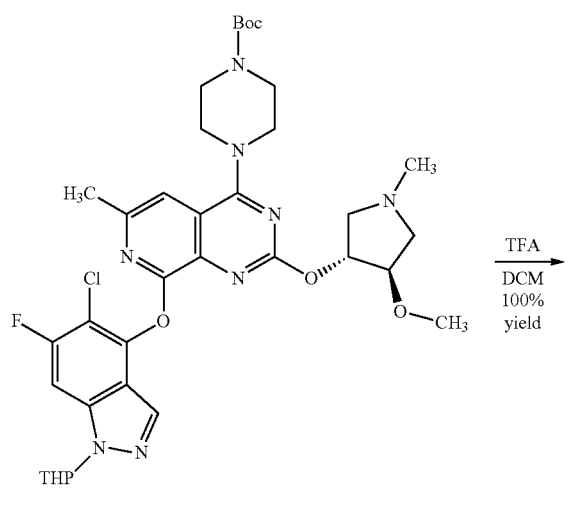

238

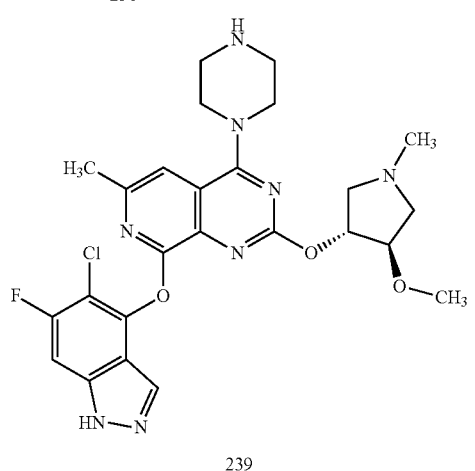

239

To a stirred solution of tert-butyl 4-(8-{[5-chloro-6-fluoro-1-(oxan-2-yl)-1H-indazol-4-yl]oxy}-2-{[(3R,4R)-4-methoxy-1-methylpyrrolidin-3-yl]oxy}-6-methylpyrido[3,4-d]pyrimidin-4-yl)piperazine-1-carboxylate (238) (120 mg, 0.165 mmol) in DCM (4 mL) was added TFA (2 mL). The mixture was stirred at room temperature for 5 h. LCMS analysis showed consumption of the starting material. The reaction was concentrated to dryness to provide 8-[(5-chloro-6-fluoro-1H-indazol-4-yl)oxy]-2-{[(3R,4R)-4-methoxy-1-methylpyrrolidin-3-yl]oxy}-6-methyl-4-(piperazin-1-yl)pyrido[3,4-d]pyrimidine (239) (89.6 mg, 100% yield) as a brown oil. LCMS (ESI) m/z 543, 545 (M+H).

Step 5:

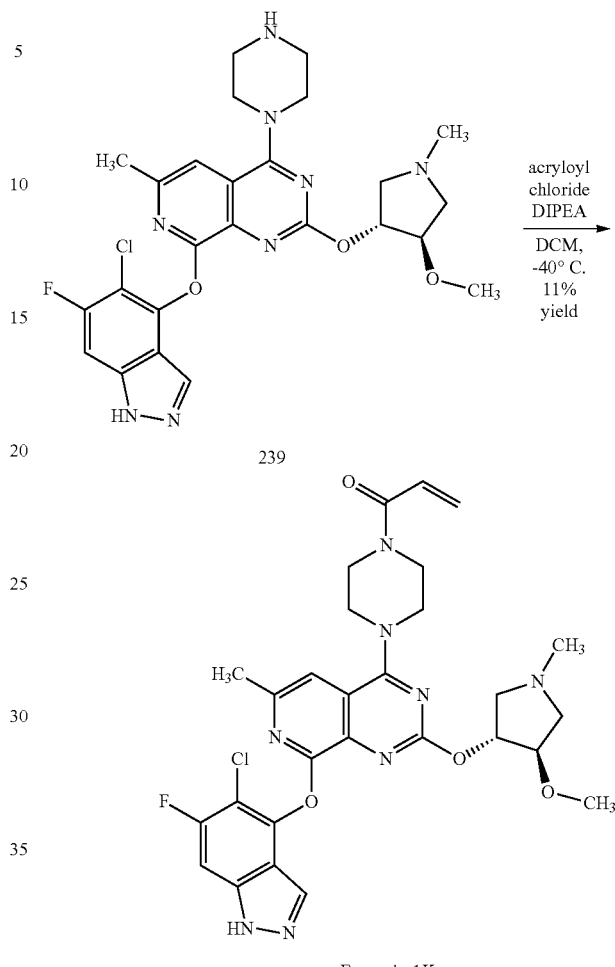

239

Example-1K

To a stirred solution of 8-[(5-chloro-6-fluoro-1H-indazol-4-yl)oxy]-2-{[(3R,4R)-4-methoxy-1-methylpyrrolidin-3-yl]oxy}-6-methyl-4-(piperazin-1-yl)pyrido[3,4-d]pyrimidine (239) (89.6 mg, 0.165 mg) in DCM (4 mL) was added DIPEA (213 mg, 1.65 mmol). The mixture was cooled to −40° C. and a solution of acryloyl chloride (17.9 mg, 0.198 mmol) in DCM (1 mL) was added dropwise. After addition the mixture was stirred at the same temperature for a further 20 min. LCMS analysis showed consumption of the starting material with formation of the desired product. The mixture was quenched with saturated aqueous NaHCO$_3$ (20 mL) and extracted with DCM (3×10 mL). The combined organics were dried over Na$_2$SO$_4$, filtered, and concentrated. The crude residue was purified by reverse phase flash chromatography (0-100% MeCN/H$_2$O+0.05% formic acid) to provide 1-[4-(8-[(5-chloro-6-fluoro-1H-indazol-4-yl)oxy]-2-{[(3R,4R)-4-methoxy-1-methylpyrrolidin-3-yl]oxy}-6-methylpyrido[3,4-d]pyrimidin-4-yl)piperazin-1-yl]prop-2-en-1-one (Example-1K) (11 mg, 11% yield) as a white solid. $^1$H NMR (400 MHz, DMSO-d$_6$) δ 13.50 (s, 1H), 7.62 (s, 1H), 7.53 (dd, J=8.9, 1.0 Hz, 1H), 7.49 (s, 1H), 6.83 (dd, J=16.7, 10.5 Hz, 1H), 6.18 (dd, J=16.7, 2.4 Hz, 1H), 5.75 (dd, J=10.4, 2.4 Hz, 1H), 5.17 (dt, J=5.5, 2.6 Hz, 1H), 3.98-3.87 (m, 5H), 3.80 (d, J=29.2 Hz, 4H), 3.32 (s, 3H), 3.00 (dd, J=9.9, 6.4 Hz, 1H), 2.80 (dd, J=10.7, 6.0 Hz, 1H), 2.58 (dd, J=10.6, 3.0 Hz, 1H), 2.33-2.25 (m, 4H), 2.22 (s, 3H). LCMS (ESI) m/z 597, 599 (M+H).

The following examples were prepared according to general Method L:

Preparation of 1-[4-(8-[(5-chloro-6-fluoro-1H-indazol-4-yl)oxy]-2-{[(3R,4R)-4-methoxy-1-methylpyrrolidin-3-yl]oxy}quinazolin-4-yl)piperazin-1-yl]prop-2-en-1-one (Example-1L)

Step 1:

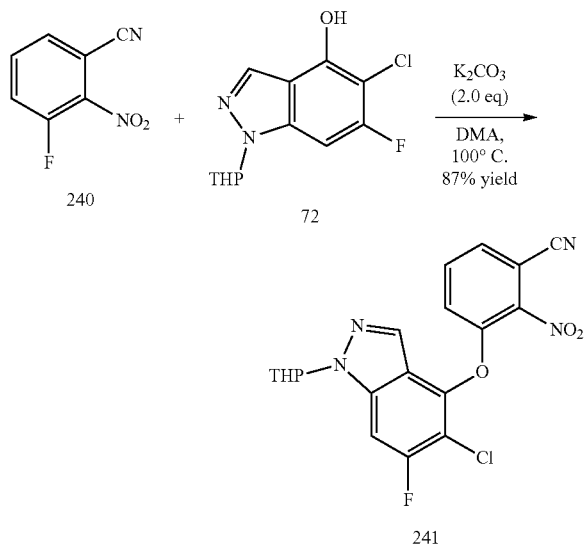

A mixture of 3-fluoro-2-nitrobenzonitrile (240) (4.0 g, 24.1 mmol) and 5-chloro-6-fluoro-1-(oxan-2-yl)-1H-indazol-4-ol (72) (6.5 g, 24.1 mmol) in DMA (20 mL) was stirred at 100° C. for 1 h under $N_2$. The mixture was concentrated and the residue was purified by flash chromatography (SiO$_2$, 7:3 petroleum ether/EtOAc) to afford 3-{[5-chloro-6-fluoro-1-(oxan-2-yl)-1H-indazol-4-yl]oxy}-2-nitrobenzonitrile (241) (8.7 g, 87% yield) as a yellow solid. $^1$H NMR (400 MHz, DMSO-d$_6$) δ 8.02-7.92 (m, 3H), 7.80-7.67 (m, 1H), 7.40 (dd, J=8.6, 0.8 Hz, 1H), 5.89 (dd, J=9.6, 2.2 Hz, 1H), 3.89 (d, J=11.7 Hz, 1H), 3.84-3.70 (m, 1H), 2.41-2.26 (m, 1H), 2.04-1.95 (m, 2H), 1.77-1.66 (m, 1H), 1.58 (t, J=6.2 Hz, 2H). LCMS (ESI) m/z 439, 441 (M+Na).

Step 2:

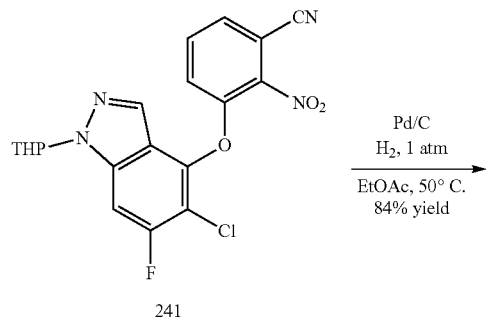

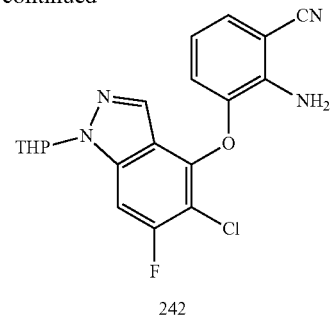

To a solution of 3-{[5-chloro-6-fluoro-1-(oxan-2-yl)-1H-indazol-4-yl]oxy}-2-nitrobenzonitrile (241) (8.5 g, 20.4 mmol) in EtOAc (200 mL) was added Pd/C (10 wt %, 850 mg) and the mixture was stirred at 50° C. for 6 h. The mixture was filtered and the filtrate was concentrated. The residue was purified by flash chromatography (SiO$_2$, 1:1 petroleum ether/EtOAc) to afford 2-amino-3-{[5-chloro-6-fluoro-1-(oxan-2-yl)-1H-indazol-4-yl]oxy}benzonitrile as a white solid (242) (6.6 g, 84% yield). $^1$H NMR (400 MHz, DMSO-d$_6$) δ 7.79 (d, J=8.9 Hz, 1H), 7.43 (s, 1H), 7.30 (dd, J=7.9, 1.2 Hz, 1H), 6.82 (dd, J=8.0, 1.2 Hz, 1H), 6.52 (t, J=7.9 Hz, 1H), 6.22 (s, 2H), 5.83 (dd, J=9.7, 2.4 Hz, 1H), 3.88-3.85 (m, 1H), 3.82-3.71 (m, 1H), 2.36-2.26 (m, 1H), 2.08-1.89 (m, 2H), 1.79-1.65 (m, 1H), 1.58-1.54 (m, 2H). LCMS (ESI) m/z 409, 411 (M+Na).

Step 3:

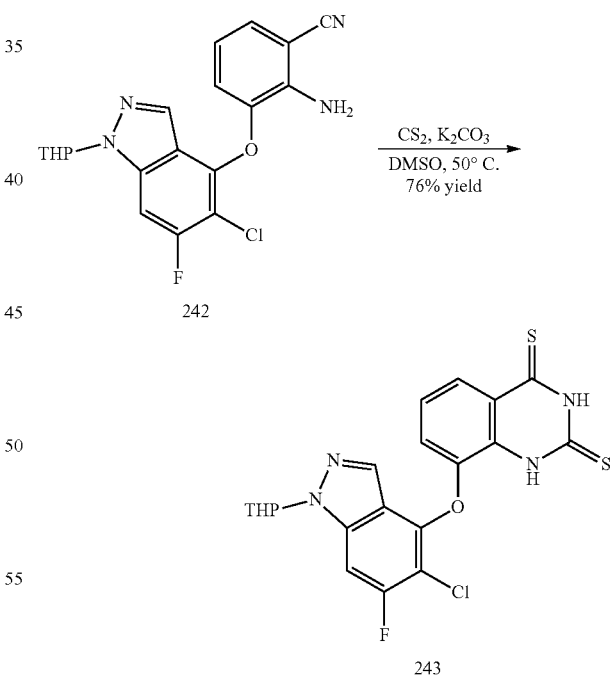

To a mixture of 2-amino-3-{[5-chloro-6-fluoro-1-(oxan-2-yl)-1H-indazol-4-yl]oxy}benzonitrile (242) (6.6 g, 17.2 mmol) and K$_2$CO$_3$ (7.1 g, 51.2 mmol) in DMSO (40 mL) was added CS$_2$ (13 g, 171 mmol) and the mixture was stirred at 50° C. for 2 h. The mixture was poured into water (300 mL), stirred at 25° C. for 30 min, and then filtered. The filter cake was washed with H$_2$O (50 mL) and dried to afford 8-{[5-chloro-6-fluoro-1-(oxan-2-yl)-1H-indazol-4-yl]oxy}quinazoline-2,4(1H,3H)-dithione (243) (6.0 g, 76% yield) as a yellow solid. $^1$H NMR (400 MHz, DMSO-d$_6$) δ 13.80 (s, 1H), 13.02 (s, 1H), 8.12 (dd, J=8.1, 1.3 Hz, 1H), 7.84 (dd, J=8.6, 4.7 Hz, 1H), 7.68 (s, 1H), 7.21-7.14 (m, 1H), 7.12-7.07 (m, 1H), 5.87-5.86 (m, 1H), 3.89-3.86 (m, 1H), 3.80-3.72 (m, 1H), 2.38-2.26 (m, 1H), 2.05-1.91 (m, 2H), 1.77-1.65 (m, 1H), 1.60-1.54 (m, 2H). LCMS (ESI) m/z 485, 487 (M+Na).

Step 4:

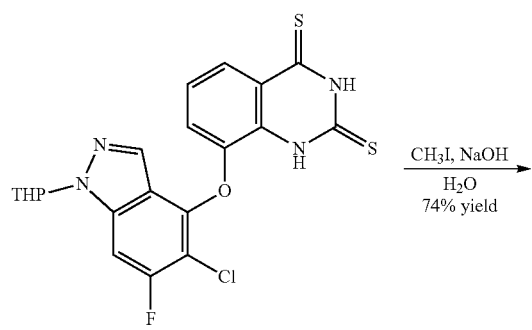

243

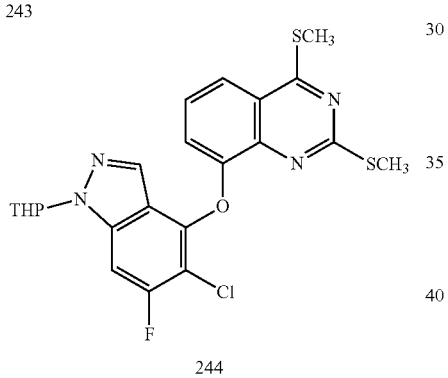

244

To a solution of 8-{[5-chloro-6-fluoro-1-(oxan-2-yl)-1H-indazol-4-yl]oxy}quinazoline-2,4(1H,3H)-dithione (243) (6.0 g, 13.0 mmol) in aqueous NaOH (15 mL, 1 M) was added H$_2$O (20 mL) and the mixture was stirred at 25° C. for 10 min. Methyl iodide (3.7 g, 1.6 mL, 25.9 mmol) was added and the mixture was stirred at 25° C. for 1 h. A yellow solid formed. The mixture was extracted with ethyl acetate (3×200 mL). The combined organics were dried over Na$_2$SO$_4$, filtered, and concentrated. The residue was purified by flash chromatography (SiO$_2$, 4:1 petroleum ether/EtOAc) to afford 8-{[5-chloro-6-fluoro-1-(oxan-2-yl)-1H-indazol-4-yl]oxy}-2,4-bis(methylsulfanyl)quinazoline (244) (4.7 g, 74% yield) as a yellow solid. $^1$H NMR (400 MHz, DMSO-d$_6$) δ 7.94 (dd, J=8.3, 1.2 Hz, 1H), 7.80 (dd, J=7.8, 1.2 Hz, 1H), 7.70 (dd, J=9.3, 0.7 Hz, 1H), 7.62 (t, J=8.1 Hz, 1H), 6.99 (s, 1H), 5.78 (dd, J=9.7, 2.5 Hz, 1H), 3.85-3.83 (m, 1H), 3.77-3.67 (m, 1H), 2.64 (s, 3H), 2.27-2.18 (m, 1H), 2.10 (s, 3H), 1.99-1.92 (m, 1H), 1.90-1.85 (m, 1H), 1.73-1.60 (m, 1H), 1.56-1.50 (m, 2H). LCMS (ESI) m/z 491, 493 (M+H).

Step 5:

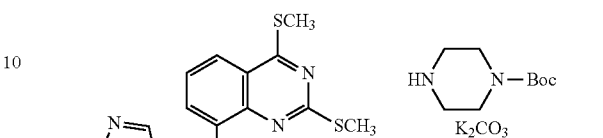

244

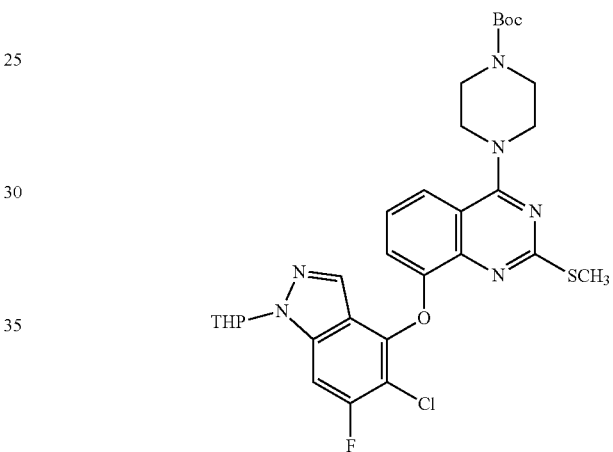

245

To a mixture of 8-{[5-chloro-6-fluoro-1-(oxan-2-yl)-1H-indazol-4-yl]oxy}-2,4-bis(methylsulfanyl)quinazoline (244) (2.0 g, 4.1 mmol) and tert-butyl piperazine-1-carboxylate (1.5 g, 8.2 mmol) in DMA (15 mL) was added K$_2$CO$_3$ (562 mg, 4.1 mmol) and the mixture was stirred at 120° C. for 16 h. The mixture was concentrated and the residue was purified by flash chromatography (SiO$_2$, 3:2 petroleum ether/EtOAc) to afford tert-butyl 4-[8-{[5-chloro-6-fluoro-1-(oxan-2-yl)-1H-indazol-4-yl]oxy}-2-(methylsulfanyl)quinazolin-4-yl]piperazine-1-carboxylate (245) (1.1 g, 41% yield) as a yellow solid. $^1$H NMR (400 MHz, DMSO-d$_6$) δ 7.92-7.85 (m, 1H), 7.73 (dd, J=7.7, 0.9 Hz, 1H), 7.64 (d, J=8.8 Hz, 1H), 7.48 (t, J=8.1 Hz, 1H), 6.88 (s, 1H), 5.80-5.74 (m, 1H), 3.83-3.67 (m, 6H), 3.55 (br. s, 4H), 2.28-2.16 (m, 1H), 2.03-1.92 (m, 4H), 1.89-1.85 (m, 1H), 1.73-1.60 (m, 1H), 1.59-1.49 (m, 2H), 1.43 (s, 9H). LCMS (ESI) m/z 629, 631 (M+H).

Step 6:

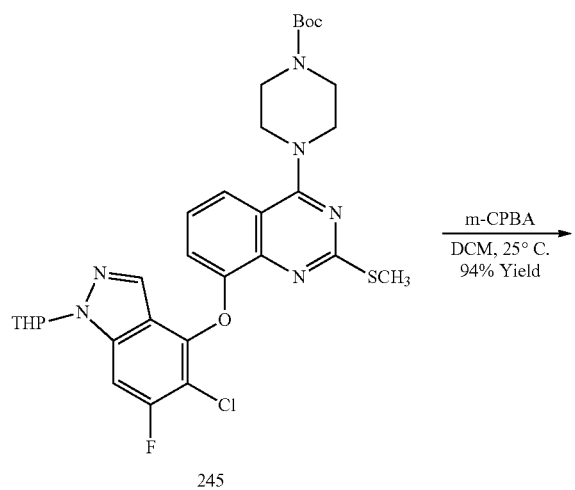

Step 7:

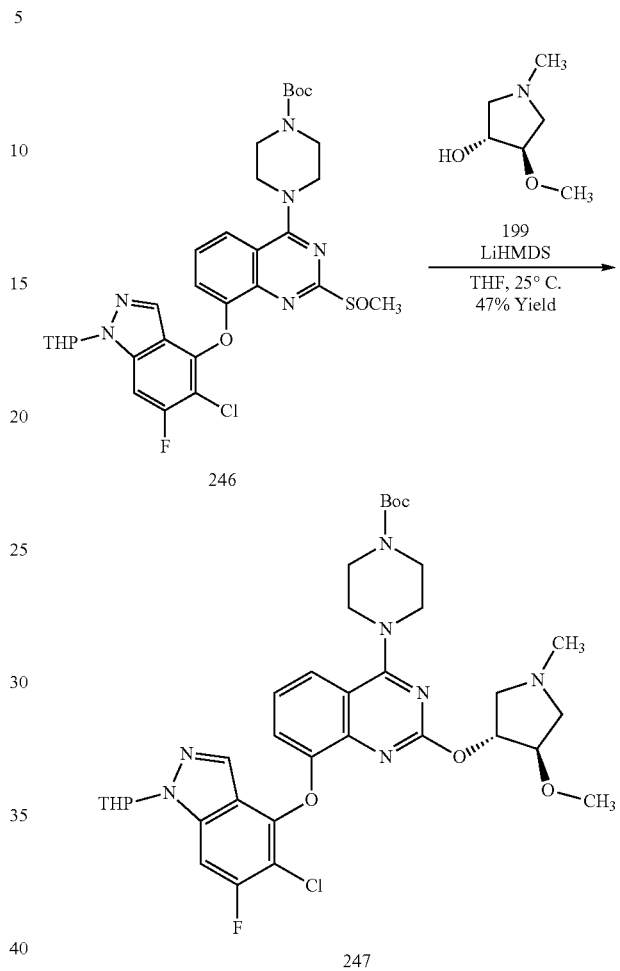

To a solution of tert-butyl 4-[8-{[5-chloro-6-fluoro-1-(oxan-2-yl)-1H-indazol-4-yl]oxy}-2-(methylsulfanyl)quinazolin-4-yl]piperazine-1-carboxylate (245) (1.0 g, 1.6 mmol) in DCM (10 mL) was added m-CPBA (274 mg, 1.6 mmol) and the mixture was stirred at 20° C. for 2 h. LCMS analysis showed conversion to the desired product. The mixture was diluted with DCM (20 mL) and washed with saturated aqueous Na$_2$SO$_3$ (2×20 mL), saturated aqueous NaHCO$_3$ (20 mL), and brine (20 mL). The combined organics were dried over Na$_2$SO$_4$, filtered, and concentrated to afford tert-butyl 4-[8-{[5-chloro-6-fluoro-1-(oxan-2-yl)-1H-indazol-4-yl]oxy}-2-(methanesulfinyl)quinazolin-4-yl]piperazine-1-carboxylate (246) (960 mg, 94% yield) as a yellow solid. $^1$H NMR (400 MHz, DMSO-d$_6$) δ 7.95 (d, J=8.4 Hz, 1H), 7.78 (d, J=9.2 Hz, 1H), 7.54 (t, J=8.1 Hz, 1H), 7.46-7.39 (m, 1H), 7.22 (d, J=6.3 Hz, 1H), 5.82 (dd, J=9.7, 2.3 Hz, 1H), 3.93-3.84 (m, 5H), 3.79-3.69 (m, 1H), 3.59 (br. s, 4H), 2.68 (d, J=5.7 Hz, 3H), 2.34-2.26 (m, 1H), 2.00-1.89 (m, 2H), 1.73-1.66 (m, 1H), 1.60-1.52 (m, 2H), 1.44 (s, 9H). LCMS (ESI) m/z 645, 647 (M+H).

Step 7:

To a mixture of tert-butyl 4-[8-{[5-chloro-6-fluoro-1-(oxan-2-yl)-1H-indazol-4-yl]oxy}-2-(methanesulfinyl)quinazolin-4-yl]piperazine-1-carboxylate (246) (250 mg, 0.388 mmol) and (3R,4R)-4-methoxy-1-methylpyrrolidin-3-ol (199) (67 mg, 0.504 mmol) in THF (5 mL) was added LiHMDS (0.5 mL, 0.5 mmol, 1 M) and the mixture was stirred at 25° C. for 1 h. The mixture was diluted with water (2 mL) and concentrated. The residue was purified by reverse phase flash chromatography (C18, 40 g, 50% MeCN/H$_2$O+0.1% formic acid) to afford tert-butyl tert-butyl 4-(8-{[5-chloro-6-fluoro-1-(oxan-2-yl)-1H-indazol-4-yl]oxy}-2-{[(3R,4R)-4-methoxy-1-methylpyrrolidin-3-yl]oxy}quinazolin-4-yl)piperazine-1-carboxylate (247) (130 mg, 47% yield) as a white solid. $^1$H NMR (400 MHz, DMSO-d$_6$) δ 7.95 (dd, J=8.1, 3.6 Hz, 1H), 7.76 (t, J=6.7 Hz, 1H), 7.63 (dd, J=9.0, 5.8 Hz, 1H), 7.45 (dd, J=8.1, 2.9 Hz, 1H), 6.62 (d, J=27.6 Hz, 1H), 5.74 (dd, J=9.7, 2.1 Hz, 1H), 4.52 (d, J=2.5 Hz, 1H), 3.82-3.71 (m, 7H), 3.56-3.50 (m, 5H), 3.10 (d, J=9.3 Hz, 3H), 2.96-2.93 (m, 1H), 2.25-2.13 (m, 1H), 2.07-2.04 (m, 4H), 1.94-1.84 (m, 3H), 1.70-1.61 (m, 1H), 1.54-1.48 (m, 2H), 1.42 (s, 9H). LCMS (ESI) m/z 712, 714 (M+H).

Step 8:

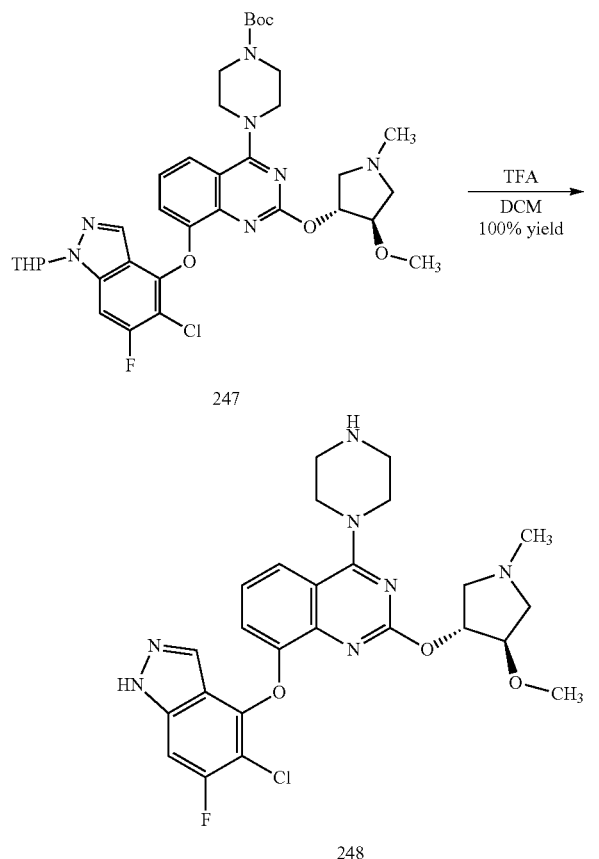

247

To a solution of tert-butyl tert-butyl 4-(8-{[5-chloro-6-fluoro-1-(oxan-2-yl)-1H-indazol-4-yl]oxy}-2-{[(3R,4R)-4-methoxy-1-methylpyrrolidin-3-yl]oxy}quinazolin-4-yl)piperazine-1-carboxylate (247) (130 mg, 0.18 mmol) in DCM (4 mL) was added TFA (2 mL) and the mixture was stirred at 25° C. for 2 h. The mixture was concentrated to afford 8-[(5-chloro-6-fluoro-1H-indazol-4-yl)oxy]-2-{[(3R,4R)-4-methoxy-1-methylpyrrolidin-3-yl]oxy}-4-(piperazin-1-yl)quinazoline (248) (117 mg, 100% yield) as a yellow oil, which was used in next step without purification. LCMS (ESI) m/z 528, 530 (M+H).

Step 9:

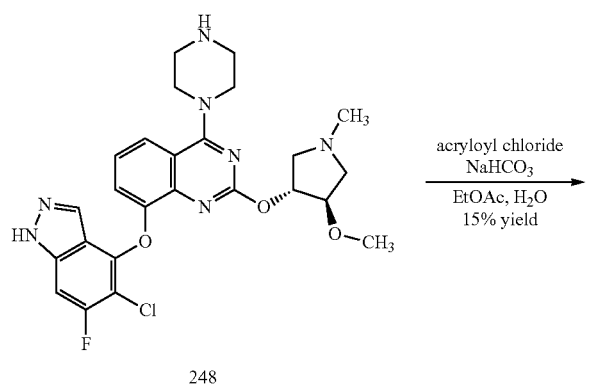

248

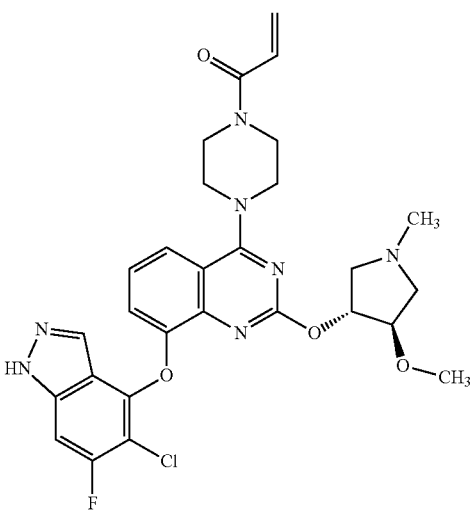

Example-1L

To a solution of 8-[(5-chloro-6-fluoro-1H-indazol-4-yl)oxy]-2-{[(3R,4R)-4-methoxy-1-methylpyrrolidin-3-yl]oxy}-4-(piperazin-1-yl)quinazoline (248) (117 mg, 0.18 mmol) in EtOAc (40 mL) and saturated aqueous NaHCO₃ (40 mL) was added acryloyl chloride (33 mg, 0.36 mmol) and the mixture was stirred at 25° C. for 30 min. The mixture was extracted with EtOAc (3×40 mL). The combined organics were dried over Na₂SO₄, filtered, and concentrated. The residue was purified by reverse phase flash chromatography (C18, 0-25% MeCN/H₂O+0.1% formic acid) to afford 1-[4-(8-[(5-chloro-6-fluoro-1H-indazol-4-yl)oxy]-2-{[(3R,4R)-4-methoxy-1-methylpyrrolidin-3-yl]oxy}quinazolin-4-yl)piperazin-1-yl]prop-2-en-1-one (Example-1L) (16 mg, 15% yield) as a white solid. ¹H NMR (400 MHz, DMSO-d₆) δ 13.35 (s, 1H), 7.97 (d, J=8.4 Hz, 1H), 7.74 (d, J=7.0 Hz, 1H), 7.44 (t, J=8.1 Hz, 1H), 7.31 (d, J=8.8 Hz, 1H), 6.80 (d, J=10.5 Hz, 1H), 6.60 (s, 1H), 6.17 (dd, J=16.7, 2.3 Hz, 1H), 5.74 (dd, J=10.4, 2.3 Hz, 1H), 4.57-4.51 (m, 1H), 3.82-3.76 (m, 9H), 3.10 (s, 3H), 2.93 (s, 1H), 2.15 (dd, J=10.5, 6.0 Hz, 1H), 2.11-2.04 (m, 4H), 1.99 (d, J=8.8 Hz, 1H). LCMS (ESI) m/z 582, 584 (M+H).

The examples in the following table were prepared using Method L and the procedure used to prepare 1-[4-(8-[(5-chloro-6-fluoro-1H-indazol-4-yl)oxy]-2-{[(3R,4R)-4-methoxy-1-methylpyrrolidin-3-yl]oxy}quinazolin-4-yl)piperazin-1-yl]prop-2-en-1-one (Example-1L). The following examples were made with non-critical changes or substitutions to the exemplified procedure used to prepare Example-1L that someone who is skilled in the art would be able to realize.

| Example | Structure | Compound Name | LCMS m/z |
|---|---|---|---|
| 2L | 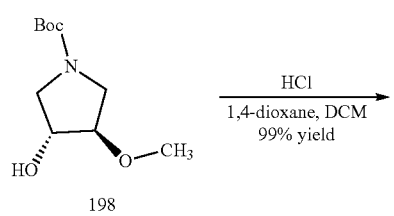 | 1-[4-(8-[(5-chloro-1H-indazol-4-yl)oxy]-2-{[(2S)-1-methylpyrrolidin-2-yl]methoxy}quinazolin-4-yl)piperazin-1-yl]prop-2-en-1-one | 548 (M + H) |

Preparation of Additional Intermediates:

Preparation of (3R,4R)-1-ethyl-4-methoxypyrrolidin-3-ol (250)

Step 1:

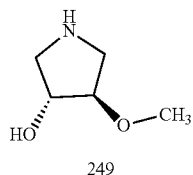

Step 2:

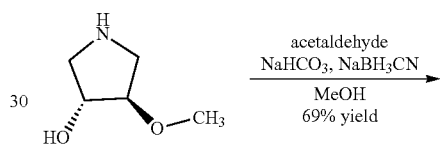

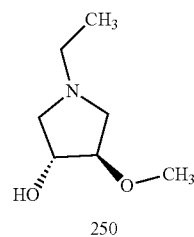

To a solution of tert-butyl (3R,4R)-3-hydroxy-4-methoxypyrrolidine-1-carboxylate (198) (1.3 g, 5.98 mmol) in DCM (20 mL) was added HCl (10 mL, 4 M in 1,4-dioxane) and the mixture was stirred at 20° C. for 2 h. LCMS analysis showed conversion to the product. The mixture was concentrated to dryness to afford (3R,4R)-4-methoxypyrrolidin-3-ol hydrochloride (249) (919 mg, 100% yield) as a white solid, which was taken on without further purification. $^1$H NMR (400 MHz, DMSO-$d_6$) δ 9.59 (s, 2H), 5.77 (s, 1H), 4.26 (d, J=3.0 Hz, 1H), 3.82 (d, J=3.4 Hz, 1H), 3.29 (s, 3H), 3.26-3.11 (m, 3H), 3.09-3.02 (m, 1H). LCMS (ESI) m/z 118 (M+H).

A solution of (3R,4R)-4-methoxypyrrolidin-3-ol hydrochloride (249) (100 mg, 0.651 mmol) in MeOH (1.5 mL) was added acetaldehyde (40% w/w) (0.754 mL) and NaBH$_3$CN (115 mg, 1.82 mmol) portion-wise at 0° C. The mixture was stirred an additional 5 min at 0° C. and then stirred at 20° C. for 2 h. LCMS analysis showed consumption of the starting material with formation of the product. 1.0 M aqueous KOH solution was added to adjust the mixture to pH=9. The mixture was extracted by DCM (5×40 mL). The combined organics were washed with brine (10 mL), dried over anhydrous Na$_2$SO$_4$, filtered, and concentrated to provide (3R,4R)-1-ethyl-4-methoxypyrrolidin-3-ol (250) (68 mg, 72% yield) as a yellow oil, which was taken on without further purification. $^1$H NMR (400 MHz, DMSO-$d_6$) δ 5.02 (d, J=5.0 Hz, 1H), 4.00-3.85 (m, 1H), 3.54 (ddd, J=6.5, 3.9, 2.5 Hz, 1H), 3.23 (s, 3H), 2.73 (ddd, J=11.9, 9.8, 6.4 Hz, 2H), 2.45-2.17 (m, 4H), 0.98 (t, J=7.2 Hz, 3H). LCMS (ESI) m/z 146 (M+H).

Preparation of (3R,4R)-4-methoxy-1-(propan-2-yl)pyrrolidin-3-ol (251)

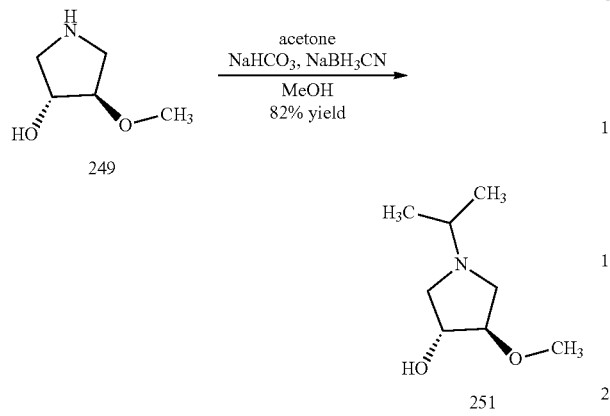

To a solution of (3R,4R)-4-methoxypyrrolidin-3-ol hydrochloride (249) (100 mg, 0.651 mmol) in MeOH (1.5 mL) and acetone (0.25 mL) was added NaBH₃CN (115 mg, 1.82 mmol) portionwise at 0° C. The mixture was stirred a further 5 min at 0° C. and then stirred at 20° C. for 2 h. LCMS analysis showed consumption of the starting material and formation of the product. 1.0 M aqueous KOH solution was added to adjust the mixture to pH=9. The mixture was extracted by DCM (5×40 mL). The combined organics were washed with brine (10 mL), dried over anhydrous Na₂SO₄, filtered, and concentrated to provide (3R,4R)-4-methoxy-1-(propan-2-yl)pyrrolidin-3-ol (251) (254 mg, 82% yield) as a yellow oil, which was used without further purification. ¹H NMR (400 MHz, DMSO-d₆) δ 5.02 (s, 1H), 3.94 (s, 1H), 3.53 (dt, J=6.2, 3.2 Hz, 1H), 3.23 (s, 3H), 2.81 (dd, J=15.6, 6.6 Hz, 2H), 2.46 (s, 1H), 2.33 (s, 2H), 0.98 (t, J=6.1 Hz, 6H). LCMS (ESI) m/z 160 (M+H).

Preparation of (3R,4R)-4-methoxy-1-(2-methoxyethyl)pyrrolidin-3-ol (252)

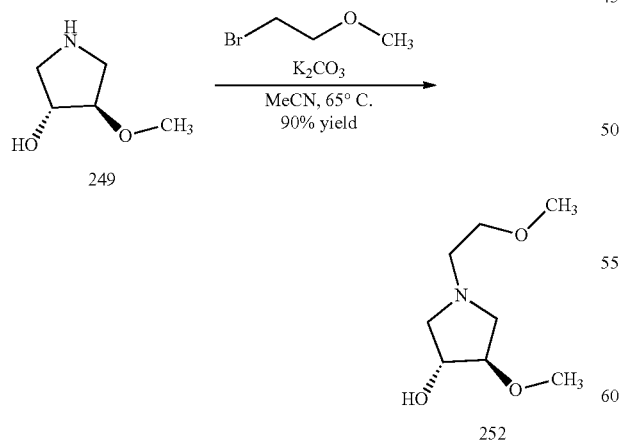

A solution of (3R,4R)-4-methoxypyrrolidin-3-ol hydrochloride (249) (100 mg, 0.651 mmol) and 1-bromo-2-methoxyethane (113 mg, 0.814 mmol) in MeCN (2 mL) was added K₂CO₃ (180 mg, 1.3 mmol) at 20° C. The mixture was stirred at 65° C. for 7 h. LCMS analysis showed consumption of the starting material and formation of the product. To the mixture was added MeCN (10 mL) and DCM (10 mL). The mixture was dried over Na₂SO₄, filtered and concentrated to provide (3R,4R)-4-methoxy-1-(2-methoxyethyl)pyrrolidin-3-ol (252) (102 mg, 90% yield, 75% purity) as a yellow oil, which was taken on without further purification. ¹H NMR (400 MHz, DMSO-d₆) δ 4.99 (d, J=5.0 Hz, 1H), 3.94-3.89 (m, 1H), 3.55-3.47 (m, 1H), 3.37 (t, J=6.0 Hz, 2H), 3.28 (d, J=2.1 Hz, 1H), 3.22 (s, 5H), 2.75 (ddd, J=13.8, 9.8, 6.5 Hz, 2H), 2.53 (s, 1H), 2.49-2.39 (m, 2H), 2.29 (dd, J=9.5, 4.8 Hz, 1H). LCMS (ESI) m/z 176 (M+H).

Preparation of (3R,4R)-4-ethoxy-1-methylpyrrolidin-3-ol (253)

Step 1:

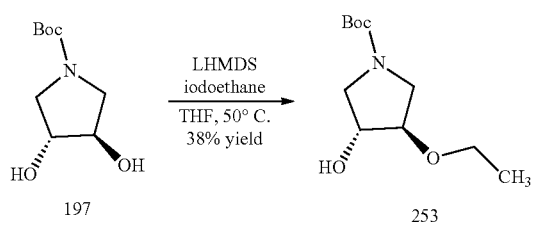 [SMILES: CC(C)(C)OC(=O)N1C[C@@H](O)[C@H](O)C1 ; "LHMDSiodoethane" ; CCO[C@@H]1CN(C(=O)OC(C)(C)C)C[C@H]1O]

To a mixture of tert-butyl (3R,4R)-3,4-dihydroxypyrrolidine-1-carboxylate (197) (1 g, 4.92 mmol) and iodoethane (2.3 g, 14.8 mmol) in THF (30 mL) was added LHMDS (7.38 mL, 7.38 mmol, 1.0 M in THF). The mixture was stirred at 25° C. for 16 h. LCMS analysis showed mostly starting material. The mixture was stirred for 48 h at 50° C. LCMS analysis showed consumption of the starting material and formation of the product. The reaction was cooled to room temperature. The mixture was washed with water. The combined organics were dried over anhydrous sodium sulfate, filtered and concentrated. The crude residue was purified by flash chromatography (SiO₂, 2:3 petroleum ether/EtOAc) to provide tert-butyl (3R,4R)-3-ethoxy-4-hydroxypyrrolidine-1-carboxylate (253) (435 mg, 38% yield) as colorless oil. ¹H NMR (400 MHz, DMSO-d₆) δ 5.17 (d, J=3.5 Hz, 1H), 4.04 (s, 1H), 3.69 (s, 1H), 3.47 (dd, J=7.0, 1.8 Hz, 2H), 3.41-3.25 (m, 2H), 3.20 (d, J=11.8 Hz, 1H), 3.13 (d, J=11.5 Hz, 1H), 1.39 (s, 9H), 1.08 (t, J=7.0 Hz, 3H). LCMS (ESI) m/z 254 (M+Na).

Step 2:

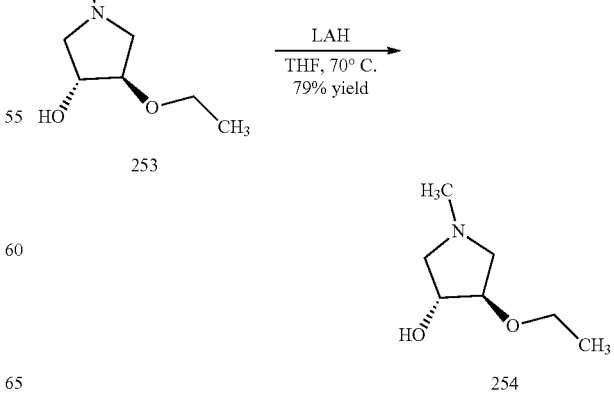

To a solution of tert-butyl (3R,4R)-3-ethoxy-4-hydroxypyrrolidine-1-carboxylate (253) (435 mg, 1.88 mmol) in THF (15 mL) was added LAH (143 mg, 3.76 mmol), and the mixture was stirred at 70° C. for 3 h. LCMS analysis showed formation of the product. The mixture was cooled to room temperature and then Na$_2$SO$_4$.10H$_2$O (2 g) was added. The mixture was stirred for 30 minutes and then filtered through celite. The filtrate was concentrated to afford (3R,4R)-4-ethoxy-1-methylpyrrolidin-3-ol (254) as colorless oil (215 mg, 79% yield). $^1$H NMR (400 MHz, DMSO-d$_6$) δ 4.99 (d, J=3.2 Hz, 1H), 3.92 (d, J=4.0 Hz, 1H), 3.63 (ddd, J=6.5, 4.1, 2.4 Hz, 1H), 3.53-3.35 (m, 2H), 2.72-2.62 (m, 2H), 2.31 (dd, J=9.8, 4.1 Hz, 1H), 2.22 (dd, J=9.5, 4.6 Hz, 1H), 2.16 (s, 3H), 1.09 (t, J=7.0 Hz, 3H). LCMS (ESI) m/z 146 (M+H).

Preparation of rac-(3R,4S)-4-methoxy-1-methylpyrrolidin-3-ol (257)

Step 1:

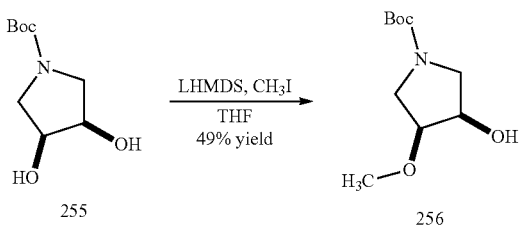

To a mixture of rac-tert-butyl (3R,4S)-3,4-dihydroxypyrrolidine-1-carboxylate (255) (500 mg, 2.46 mmol) and CH$_3$I (1.05 g, 7.38 mmol) in THF (10 mL) was added LHMDS (3.69 mL, 3.69 mmol, 1 M in THF) and the mixture was stirred at 20° C. for 16 h. LCMS analysis showed ~50% product with ~30% remaining starting material and trace amounts of the dimethylated byproduct. To the reaction was added H$_2$O (10 mL). The mixture was extracted with EtOAc (3×20 mL). The combined organics were washed with brine (10 mL), dried over Na$_2$SO$_4$, filtered, and concentrated. The residue was purified by flash chromatography (SiO$_2$, 1:1 petroleum ether/EtOAc) to afford rac-tert-butyl (3R,4S)-3-hydroxy-4-methoxypyrrolidine-1-carboxylate (256) (260 mg, 49% yield) as colorless oil. $^1$H NMR (400 MHz, DMSO-d$_6$) δ 4.14 (d, J=4.1 Hz, 1H), 3.74-3.65 (m, 1H), 3.44-3.32 (m, 3H), 3.30 (s, 3H), 3.11 (ddd, J=12.2, 10.9, 5.2 Hz, 2H), 1.38 (s, 9H). LCMS (ESI) m/z 240 (M+Na).

Step 2:

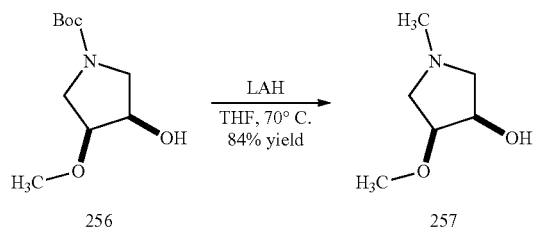

To a stirred solution of rac-tert-butyl 3-hydroxy-4-methoxypyrrolidine-1-carboxylate (256) (256 mg, 1.18 mmol) in dry THF (5 mL) was added LAH (157 mg, 4.12 mmol) at 25° C. The resulting mixture was stirred at 70° C. for 3 h. LCMS analysis showed consumption of the starting material and formation of the desired product. The mixture was cooled to 10° C. and then Na$_2$SO$_4$.10H$_2$O (2 g) was added. The mixture was stirred for 20 minutes and then filtered through celite. The filtrate was concentrated to provide rac-(3R,4S)-4-methoxy-1-methylpyrrolidin-3-ol (257) (130 mg, 84% yield). $^1$H NMR (400 MHz, DMSO-d$_6$) δ 4.41 (d, J=6.6 Hz, 1H), 4.09-4.00 (m, 1H), 3.61 (q, J=6.1 Hz, 1H), 3.28 (s, 3H), 2.83 (dt, J=9.5, 6.2 Hz, 2H), 2.29 (dd, J=9.5, 6.0 Hz, 1H), 2.26-2.21 (dd, 1H), 2.20 (s, 3H). LC-MS (ESI) m/z 132 (M+H).

Preparation of rac-(3S,4R)-4-ethyl-1-methylpyrrolidin-3-ol (259)

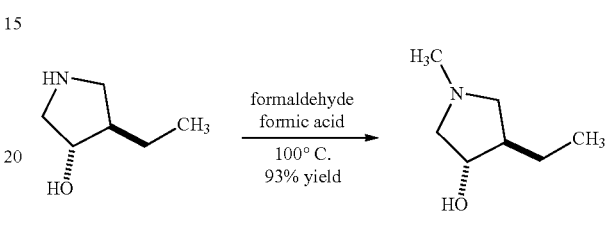

A mixture of rac-(3S,4R)-4-ethylpyrrolidin-3-ol (258) (50 mg, 0.43 mmol) (J. Med. Chem. 2010, 53, 6730-6746), aqueous formaldehyde (3 mL) and formic acid (6 mL) in a sealed tube was stirred at 100° C. for 60 h. LCMS analysis showed consumption of the starting material and formation of the product. The reaction was concentrated to dryness. Concentrated HCl (5 mL) was added to the residue. The mixture was stirred for 2 h and then concentrated to dryness. To the residue was added H$_2$O (30 mL) and the mixture was carefully made basic with solid K$_2$CO$_3$. The mixture was extracted with 10:1 DCM/MeOH (3×30 mL). The combined organics were dried over Na$_2$SO$_4$, filtered, and concentrated to provide rac-(3S,4R)-4-ethyl-1-methylpyrrolidin-3-ol (259) (505 mg, 93% yield) as a pale yellow oil. $^1$H NMR (400 MHz, DMSO-d$_6$) δ 4.72 (s, 1H), 3.71 (d, J=3.1 Hz, 1H), 2.71-2.75 (m, 1H), 2.50-2.53 (m, 1H), 2.36-2.39 (m, 1H), 2.17 (s, 3H), 1.91-1.98 (m, 1H), 1.69-1.75 (m, 1H), 1.39-1.49 (m, 1H), 1.20-1.34 (m, 1H), 0.86 (d, J=14.7 Hz, 3H). LCMS (ESI) m/z 130 (M+H).

Preparation of rac-(3S,4R)-4-cyclopropyl-1-methylpyrrolidin-3-ol (261)

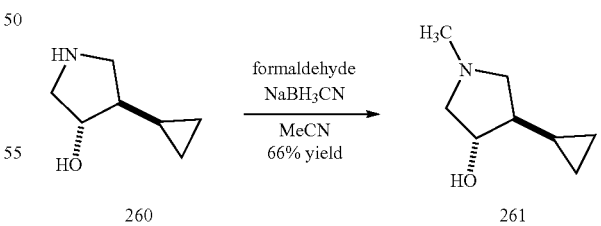

To a stirred solution of rac-(3S,4R)-4-cyclopropylpyrrolidin-3-ol (260) (532 mg, 4.18 mmol) (J. Med. Chem. 2010, 53, 6730-6746), in dry MeOH (10 mL) was added formaldehyde (628 mg, 20.9 mmol) and NaBH$_3$CN (736 mg, 11.7 mmol) at 10° C. The resulting mixture was stirred at 25° C. for 6 h. LCMS analysis showed consumption of the starting material and formation of the desired product. Saturated aqueous NaHCO$_3$ (10 mL) was added to the reaction. The mixture was extracted with DCM (3×15 mL). The combined organics were washed with brine (15 mL), dried over Na$_2$SO$_4$, filtered, and concentrated to provide rac-(3S,4R)-4-cyclopropyl-1-methylpyrrolidin-3-ol (261) (591 mg, 100% yield), which was taken on without further purification. $^1$H NMR (400 MHz, DMSO-d$_6$) δ 4.75 (d, J=5.0 Hz, 1H), 4.29 (d, J=6.4 Hz, 1H), 3.90 (dd, J=6.2, 4.8 Hz, 1H), 2.75-2.68 (m, 1H), 2.64 (dd, J=9.7, 6.4 Hz, 1H), 2.36 (dd, J=9.7, 3.8 Hz, 1H), 2.26-2.07 (m, 4H), 1.35-1.27 (m, 1H), 0.78-0.67 (m, 1H), 0.38-0.35 (m, 1H), 0.23-0.15 (m, 1H), 0.05 (ddd, J=9.2, 4.9, 1.8 Hz, 1H). LCMS (ESI) m/z 142 (M+H).

Preparation of rac-(3S,4R)-1,4-dimethylpyrrolidin-3-ol (263)

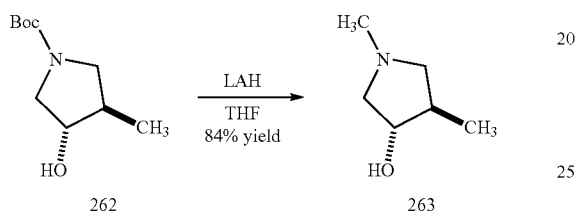

To a stirred solution of rac-tert-butyl (3S,4R)-3-hydroxy-4-methylpyrrolidine-1-carboxylate (262) (469 mg, 2.33 mmol) in dry THF (5 mL) was added LAH (310 mg, 8.16 mmol) at 25° C. The resulting mixture was stirred at 70° C. for 3 h. LCMS analysis showed consumption of the starting material with formation of the product. The mixture was cooled to 10° C. and then Na$_2$SO$_4$·10H$_2$O (2 g) was added. The mixture was stirred for 20 minutes and then filtered through celite. The filtrate was concentrated to afford rac-(3S,4R)-1,4-dimethylpyrrolidin-3-ol (263) (225 mg, 84% yield). $^1$H NMR (400 MHz, DMSO-d$_6$) δ 4.73 (d, J=5.0 Hz, 1H), 3.64 (td, J=9.0, 4.4 Hz, 1H), 2.70 (t, J=7.7 Hz, 1H), 2.56 (dd, J=9.5, 6.6 Hz, 1H), 2.34 (dd, J=9.5, 4.1 Hz, 1H), 2.16 (s, 3H), 1.96-1.84 (m, 2H), 0.97 (d, J=6.8 Hz, 3H). LC-MS (ESI) m/z 116 (M+H).

Preparation of rac-(3S,4S)-1,4-dimethylpyrrolidin-3-ol (265)

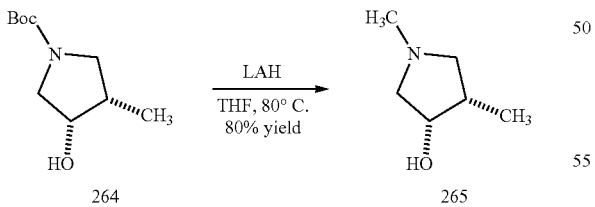

To a stirred solution of rac-tert-butyl (3S,4S)-3-hydroxy-4-methylpyrrolidine-1-carboxylate (264) (500 mg, 2.48 mmol) in dry THF (8 mL) was added LAH (236 mg, 6.21 mmol) at 25° C. The resulting mixture was stirred at 80° C. for 2 h. LCMS analysis showed consumption of the starting material with formation of the product. The mixture was cooled to 10° C. and then Na$_2$SO$_4$·10H$_2$O (2 g) was added. The mixture was stirred for 20 minutes and then filtered through celite. The filtrate was concentrated to afford rac-(3S,4S)-1,4-dimethylpyrrolidin-3-ol (265) (230 mg, 80% yield). $^1$H NMR (400 MHz, DMSO-d$_6$) δ 4.46 (s, 1H), 3.98-4.08 (m, 1H), 2.94-2.98 (m, 1H), 2.69 (t, J=7.4 Hz, 1H), 2.18 (s, 3H), 2.11-1.94 (m, 3H), 0.88 (d, J=6.9 Hz, 3H). LC-MS (ESI) m/z 116 (M+H).

Preparation of rac-(4R)-4-(2,2-difluoroethoxy)-1-methylpyrrolidin-3-ol (267)

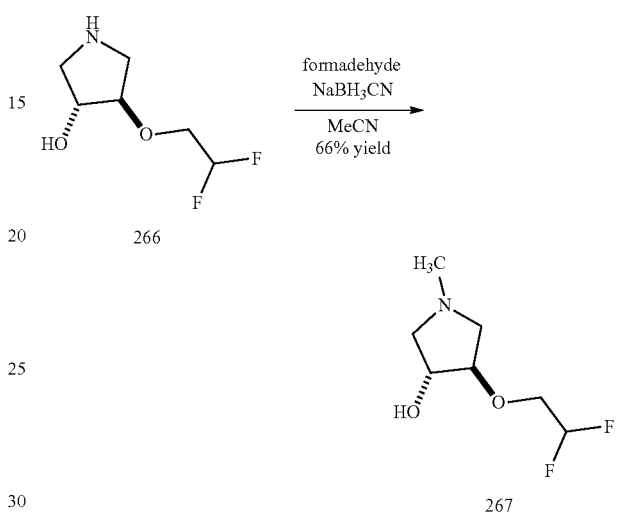

To a solution of rac-(4R)-4-(2,2-difluoroethoxy)pyrrolidin-3-ol (266) (595 mg, 3.56 mmol) in MeOH (10 mL) was added aqueous formaldehyde (2 mL) and NaBH$_3$CN (626 mg, 9.97 mmol) at 0° C. The mixture was stirred an additional 5 min at 0° C. and then 1 h at 20° C. LCMS analysis showed consumption of the starting material and formation of the product. H$_2$O (10 mL) was added and the mixture was extracted with DCM (3×20 mL). The combined organics were washed with brine (20 mL), and dried over Na$_2$SO$_4$, filtered, and concentrated. The residue was purified by flash chromatography (SiO$_2$, 0-10% DCM/MeOH) to afford rac-(4R)-4-(2,2-difluoroethoxy)-1-methylpyrrolidin-3-ol (267) (425 mg, 66% yield) as a brown oil. $^1$H NMR (400 MHz, DMSO-d$_6$) δ=6.14 (dd, J=54.8, 3.6, 1H), 5.71 (d, J=3.5, 1H), 4.23 (s, 1H), 4.08-3.95 (m, 1H), 3.87-3.68 (m, 2H), 3.30 (dd, J=22.2, 5.0, 2H), 3.15 (d, J=12.1, 1H), 2.97 (dd, J=11.6, 1.9, 1H), 2.68 (s, 3H). LCMS (ESI) m/z 182 (M+H).

Preparation of rac-(3R,4R)-1,3-dimethylpiperidin-4-ol (269)

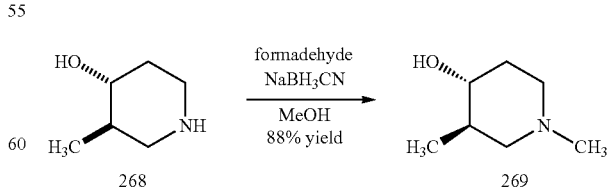

To a solution of rac-(3R,4R)-3-methylpiperidin-4-ol hydrochloride (268) (200 mg, 1.32 mmol) in MeOH (1.5 mL) and acetaldehyde (37-40% w/w) (0.781 mL) was added NaBH$_3$CN (233 mg, 3.70 mmol) portion wise at 0° C. The mixture was stirred for a further 5 min at 0° C. and then 2 h at 20° C. LCMS analysis showed consumption of the starting material with formation of the product. A 1.0 M aqueous KOH solution was added to adjust the mixture to pH=9. The mixture was extracted with DCM (5×40 mL). The combined organics were washed with brine (10 mL), dried over anhydrous $Na_2SO_4$, filtered, and concentrated to provide rac-(3R,4R)-1,3-dimethylpiperidin-4-ol (269) (150 mg, 90% yield) as a yellow oil. $^1$H NMR (400 MHz, DMSO-$d_6$) δ 4.50 (d, J=4.9 Hz, 1H), 2.98-2.77 (m, 1H), 2.77-2.57 (m, 2H), 2.09 (s, 3H), 1.83 (ddd, J=14.3, 8.2, 2.3 Hz, 1H), 1.70 (ddt, J=12.5, 4.6, 2.9 Hz, 1H), 1.52 (t, J=10.8 Hz, 1H), 1.47-1.31 (m, 2H), 0.85 (d, J=6.4 Hz, 3H). LCMS (ESI) m/z 130 (M+H).

Preparation of rac-(3R,4R)-1-(2-methoxyethyl)-3-methylpiperidin-4-ol (270)

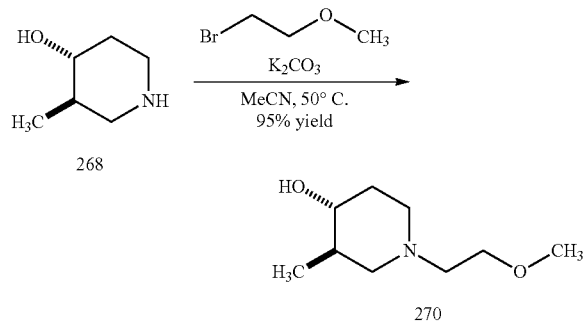

A solution of rac-(3R,4R)-3-methylpiperidin-4-ol hydrochloride (269) (100 mg, 0.659 mmol) and 1-bromo-2-methoxyethane (110 mg, 0.791 mmol) in MeCN (2 mL) was added $K_2CO_3$ (164 mg, 1.19 mmol) at 20° C. The mixture was then stirred at 50° C. for 7 h. LCMS analysis showed consumption of the starting material with formation of the product. The mixture was cooled to room temperature. MeCN (10 mL) and DCM (10 mL) were added. The mixture was dried over $Na_2SO_4$, filtered, and concentrated to provide rac-(3R,4R)-1-(2-methoxyethyl)-3-methylpiperidin-4-ol (270) (114 mg, 100% yield) as a yellow oil, which was taken on without further purification. $^1$H NMR (400 MHz, DMSO-$d_6$) δ 4.50 (s, 1H), 3.38 (t, J=6.0 Hz, 2H), 3.38-3.30 (m, 1H), 3.20 (s, 3H), 2.97-2.47 (m, 3H), 2.39 (t, J=6.0 Hz, 2H), 1.92 (td, J=12.0, 2.5 Hz, 1H), 1.76-1.65 (m, 1H), 1.37 (qdd, J=12.3, 8.7, 6.1 Hz, 2H), 0.85 (d, J=6.5 Hz, 3H). LCMS (ESI) m/z 174 (M+H).

Preparation of 5-methyl-5-azaspiro[2.4]heptan-7-ol (272)

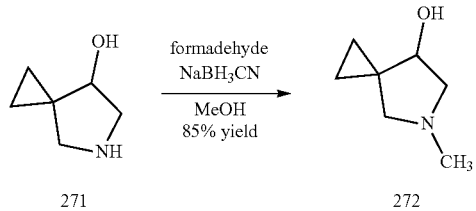

A solution of 5-azaspiro[2.4]heptan-7-ol (271) (200 mg, 1.77 mmol) in MeOH (1.5 mL), acetaldehyde (37-40% w/w) (1.13 mL), and acetic acid (0.1 mL) was added $NaBH_3CN$ (311 mg, 4.95 mmol) portion wise at 0° C. portions. The reaction was stirred for an additional 5 min at 0° C. and then for 2 h at 20° C. LCMS analysis showed consumption of the starting material with formation of the product. A 1.0 M aqueous KOH solution was added to adjust the mixture to pH=9. The mixture was extracted with DCM (5×40 mL). The combined organics were washed with brine (10 mL), dried over anhydrous $Na_2SO_4$, filtered, and concentrated to provide 5-methyl-5-azaspiro[2.4]heptan-7-ol (272) (200 mg, 89% yield) as a yellow oil, which was taken on without further purification. LCMS (ESI) m/z 128 (M+H).

Preparation of (3R,4R)-1-methylpyrrolidine-3,4-diol (273)

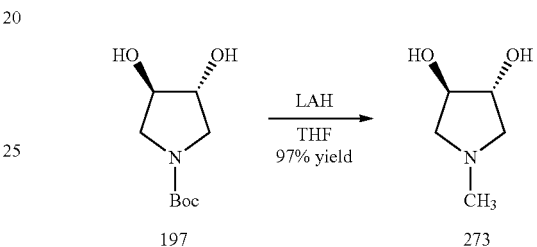

To a solution of tert-butyl (3R,4R)-3,4-dihydroxypyrrolidine-1-carboxylate (197) (922 mg, 4.24 mmol) in THF (15 mL, c=0.28 M) at room temperature under $N_2$ was added LAH (2.0 M in THF, 8.5 mL, 17.0 mmol). Gas evolution was observed. The mixture was then stirred at 60° C. for 9 h. After cooling to 0° C., $H_2O$ (0.65 mL) in THF (10 mL) was added, resulting in a slight exotherm and gas evolution. 15% aqueous NaOH (0.65 mL) and $H_2O$ (1.95 mL) were added. After 15 min the mixture was filtered through celite. The filter cake was washed thoroughly with THF. The filtrate was concentrated to provide (3R,4R)-1-methylpyrrolidine-3,4-diol (273) (481 mg, 97% yield) as an off-white solid, which was taken on without further purification. $^1$H NMR (400 MHz, DMSO-$d_6$) δ 4.78 (d, J=4.8 Hz, 2H), 3.84-3.77 (m, 2H), 2.69 (dd, J=5.9, 9.2 Hz, 2H), 2.27-2.20 (m, 2H), 2.17 (s, 3H).

Preparation of 2-methyl-2,3-dihydro-1H-isoindol-4-ol (275)

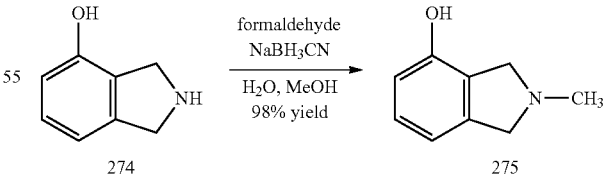

To a solution of 2,3-dihydro-1H-isoindol-4-ol hydrochloride (274) (100 mg, 0.583 mmol) in MeOH (5 mL) was added aqueous formaldehyde (0.3 mL) and $NaBH_3CN$ (293 mg, 4.66 mmol) at 0° C. The reaction was stirred a further 5 min at 0° C. and then 1 h at 20° C. LCMS analysis showed consumption of the starting material with formation of the desired product. The mixture was added to $H_2O$ (10 mL) and extracted with DCM (3×20 mL). The combined organics were washed with brine (20 mL), dried over Na₂SO₄, filtered, and concentrated. Purification by flash chromatography (SiO₂, 0-10% MeOH/DCM) to provide 2-methyl-2,3-dihydro-1H-isoindol-4-ol (275) (80 mg, 98% yield) as a white solid. $^1$H NMR (400 MHz, DMSO-$d_6$) δ 8.37 (s, 1H), 6.97 (t, J=7.7, 1H), 6.64-6.59 (m, 1H), 3.75 (d, J=15.6 Hz, 4H), 2.46 (s, 3H). LCMS (ESI) m/z 150,151 (M+H).

Preparation of 2-methyl-1,2,3,4-tetrahydroisoquinolin-8-ol (277)

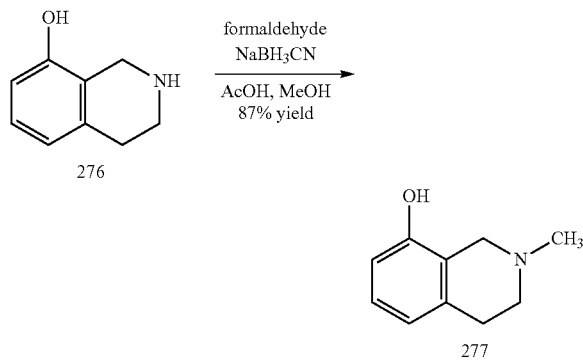

To a solution of 1,2,3,4-tetrahydroisoquinolin-8-ol (276) (150 mg, 1.01 mmol) in MeOH (3 mL) was added formaldehyde (151 mg, 5.03 mmol), NaBH₃CN (177 mg, 2.82 mmol) and acetic acid (1 mL) at 0° C. The mixture was stirred for 5 min at 0° C. and then 1 h at 20° C. LCMS analysis showed consumption of the starting material with formation of the product. The mixture was poured into H₂O (5 mL) and saturated aqueous NaHCO₃ (2 mL) and extracted with DCM (3×20 mL). The combined organics were washed with brine (5 mL), dried over Na₂SO₄, filtered, and concentrated to provide 2-methyl-1,2,3,4-tetrahydroisoquinolin-8-ol (277) (143 mg, 87% yield) as a yellow solid. $^1$H NMR (400 MHz, DMSO-$d_6$) δ 9.23 (s, 1H), 6.90 (t, J=7.7 Hz, 1H), 6.59 (d, J=7.7 Hz, 1H), 6.47 (dd, J=7.7, 3.2 Hz, 1H), 3.38 (s, 2H), 2.62-2.57 (m, 2H), 2.55 (d, J=5.0 Hz, 2H), 2.30 (s, 3H). LCMS (ESI) m/z 164 (M+H).

Preparation of (3R,4R)-4-methoxy-1-(prop-2-yn-1-yl)pyrrolidin-3-ol (278)

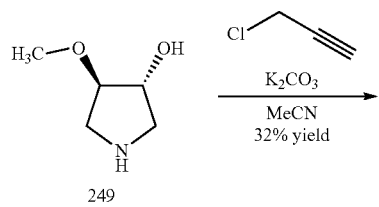

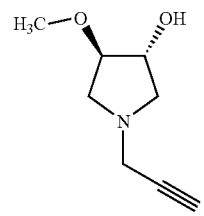

To a stirred solution of (3R,4R)-4-methoxypyrrolidin-3-ol trifluoroacetate (249) (200 mg, 0.23 mmol) and K₂CO₃ (236 mg, 1.71 mmol) in MeCN (3 mL) was added 3-chloroprop-1-yne (127 mg, 1.71 mmol). The resulting mixture was stirred for 16 h. LCMS analysis showed consumption of the starting material with formation of the product. The reaction was filtered and concentrated to dryness. The residue was purified by flash chromatography (SiO₂, 0-8% MeOH/DCM) to provide (3R,4R)-4-methoxy-1-(prop-2-yn-1-yl)pyrrolidin-3-ol (278) (85 mg, 32% yield) as a yellow oil. $^1$H NMR (400 MHz, DMSO-$d_6$) δ 5.05 (d, J=5.0 Hz, 1H), 3.98-3.90 (m, 1H), 3.58-3.51 (m, 1H), 3.30 (d, J=2.3 Hz, 2H), 3.23 (s, 3H), 3.13 (t, J=2.3 Hz, 1H), 2.80 (td, J=9.3, 6.7 Hz, 2H), 2.45 (dd, J=9.8, 3.9 Hz, 1H), 2.35 (dd, J=9.4, 4.7 Hz, 1H).

Preparation of (3R,4R)-1-(but-3-yn-1-yl)-4-methoxypyrrolidin-3-ol (279)

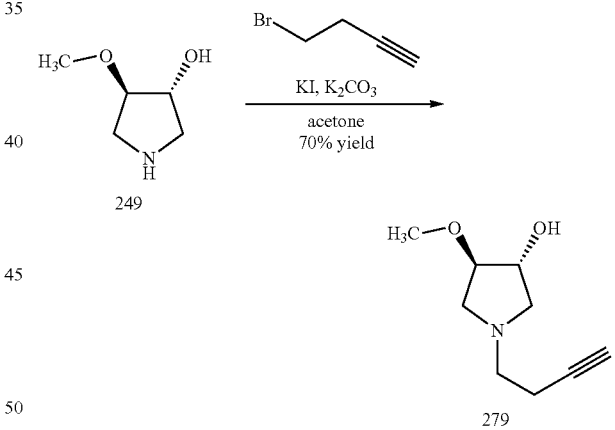

To a mixture of (3R,4R)-4-methoxypyrrolidin-3-ol trifluoroacetate (249) (550 mg, 2.38 mmol), KI (790 mg, 4.76 mmol), and K₂CO₃ (1.31 g, 9.52 mmol) in acetone (15 ml) was added 4-bromobut-1-yne (475 mg, 3.57 mmol). The mixture was stirred at 80° C. for 5 h. LCMS analysis showed formation of the desired product. The reaction was filtered and concentrated to dryness. Purification by reverse phase flash chromatography (40 g C18, 5% MeCN/H₂O+0.1% formic acid) provided (3R,4R)-1-(but-3-yn-1-yl)-4-methoxypyrrolidin-3-ol (279) (360 mg, 70% yield) as a colorless oil. $^1$H NMR (400 MHz, DMSO-$d_6$) δ 3.98-3.94 (m, 1H), 3.58-3.52 (m, 1H), 3.23 (s, 3H), 2.88-2.76 (m, 3H), 2.62-2.52 (m, 3H), 2.37 (dd, J=9.8, 4.5 Hz, 1H), 2.30 (td, J=7.5, 2.6 Hz, 2H).

Preparation of (3R,4R)-1-(2-{[tert-butyl(dimethyl)silyl]oxy}ethyl)-4-methoxypyrrolidin-3-ol (280)

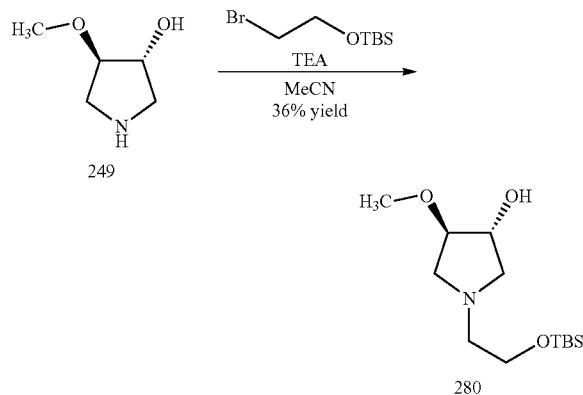

To a solution of (3R,4R)-4-methoxypyrrolidin-3-ol trifluoroacetate (249) (196 mg, 1.67 mmol) in MeCN (15 mL) was added (2-bromoethoxy)(tert-butyl)dimethylsilane (2.0 g, 8.37 mmol) and Et$_3$N (847 mg, 8.37 mmol). The mixture was stirred at 70° C. for 6 h. LCMS analysis showed conversion to the desired. The solvent was removed and the residue was purified by reverse phase flash chromatography (40 g C18, 20-50% MeCN/H$_2$O+0.1% formic acid) to provide (3R,4R)-1-(2-{[tert-butyl(dimethyl)silyl]oxy}ethyl)-4-methoxypyrrolidin-3-ol (280) 164 mg, 36% yield) as a light yellow oil. $^1$H NMR (400 MHz, CDCl$_3$) δ 4.10-4.06 (m, 1H), 3.71 (t, J=6.0 Hz, 2H), 3.69-3.65 (m, 1H), 3.32-3.30 (m, 3H), 3.26 (dd, J=10.6, 6.3 Hz, 1H), 2.83-2.74 (m, 2H), 2.64 (td, J=6.0, 1.0 Hz, 2H), 2.41 (dd, J=10.7, 3.9 Hz, 1H), 0.83 (s, 9H), 0.00 (s, 6H). LCMS (ESI) m/z 276 (M+H).

Preparation of 1,6-dimethyl-4,5,6,7-tetrahydro-1H-pyrazolo[3,4-c]pyridin-3-ol (282)

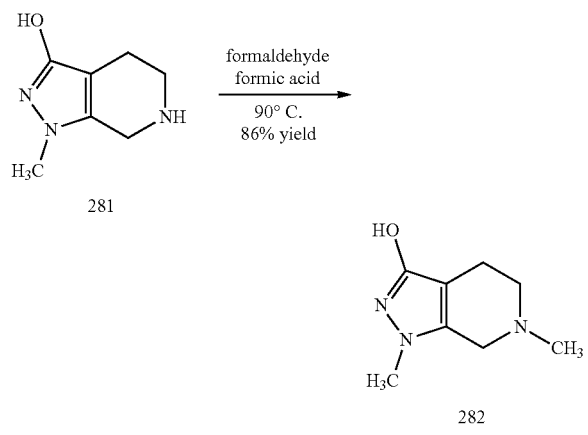

A mixture of 1-methyl-4,5,6,7-tetrahydro-1H-pyrazolo[3,4-c]pyridin-3-ol hydrobromide (281) (Albany Molecular) (130 mg, 0.555 mmol), aqueous formaldehyde (1 mL) and formic acid (3 mL) in a sealed tube was heated to 90° C. for 19 h. LCMS analysis showed consumption of the starting material. The reaction was concentrated. Concentrated HCl (3 mL) was added. The mixture was stirred for 2 h and then the mixture was concentrated. H$_2$O (30 mL) was added and the mixture was carefully basified with solid K$_2$CO$_3$. The mixture was extracted with 10:1 DCM/MeOH (3×30 mL). The combined organics were dried over Na$_2$SO$_4$, filtered, and concentrated. The crude residue was purified by preparative HPLC on a Kromasil-C18 column (100×21.2 mm, 5 μm particle size), which was eluted with MeCN/H$_2$O (+0.1% formic acid) to provide 1,6-dimethyl-4,5,6,7-tetrahydro-1H-pyrazolo[3,4-c]pyridin-3-ol (282) (80 mg, 86% yield) as a white solid. $^1$H NMR (400 MHz, DMSO-d$_6$) δ 3.15 (s, 3H), 3.08 (s, 2H), 2.99 (s, 1H), 2.34 (t, J=5.8 Hz, 2H), 2.21 (s, 3H), 2.13 (t, J=5.8 Hz, 2H). LCMS (ESI) m/z 168 (M+H).

Preparation of rac-(3S,4R)-4-(difluoromethyl)-1-methylpyrrolidin-3-ol (290)

Step 1:

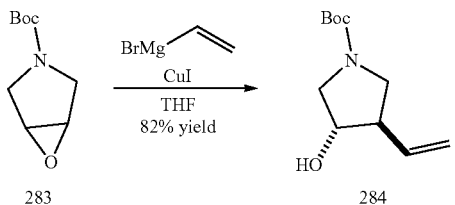

To a suspension of rac-tert-butyl (1R,5S)-6-oxa-3-azabicyclo[3.1.0]hexane-3-carboxylate (283) (7.6 g, 41 mmol) and CuI (1.56 g, 8.2 mmol) in dry THF (100 ml) under N$_2$ was added vinylmagnesium bromide (1.0 M in THF, 82.1 mmol, 82.1 mL) dropwise at −30° C. After 3 h, TLC analysis (3:1 petroleum ether/EtOAc) indicated consumption of the starting material. The reaction was quenched by addition of saturated aqueous NH$_4$Cl (100 mL) and filtered. The filtrate was separated and the aqueous layer was extracted with EtOAc (2×100 mL). The combined organics were washed with brine (100 mL), dried over Na$_2$SO$_4$, filtered, and concentrated. The residue was purified by flash chromatography (Biotage, SiO$_2$, 3:1 petroleum ether/EtOAc) to give a yellow oil (10 g), which was repurified by flash chromatography (Biotage, SiO$_2$, 3:1 petroleum ether/EtOAc) to provide rac-tert-butyl (3R,4S)-3-ethenyl-4-hydroxypyrrolidine-1-carboxylate (284) (7.2 g, 82% yield) as a light yellow oil. $^1$H NMR (400 MHz, CDCl$_3$) δ 5.73 (ddd, J=7.9, 10.0, 17.4 Hz, 1H), 5.26-5.14 (m, 2H), 4.18-4.08 (m, 1H), 3.77-3.62 (m, 2H), 3.32-3.18 (m, 2H), 2.71 (td, J=6.8, 13.5 Hz, 1H), 1.96 (br s, 1H), 1.48 (s, 9H).

Step 2:

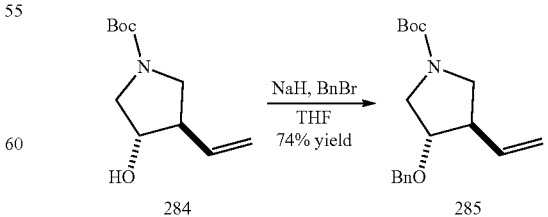

To a solution of rac-tert-butyl (3R,4S)-3-ethenyl-4-hydroxypyrrolidine-1-carboxylate (284) (7.2 g, 33.8 mmol) in THF (100 mL) was added NaH (60% in mineral oil, 2.7 g, 67.5 mmol) at 0° C. The reaction mixture was stirred at 0° C. for 1 h followed by addition of BnBr (6.9 g, 40.5 mmol). After addition the reaction mixture was warmed to 25° C. and stirred at this temperature for 16 h. TLC analysis (4:1 petroleum ether/EtOAc) indicated consumption of the starting material. The mixture was diluted with H₂O (100 mL) and extracted with EtOAc (2×200 mL). The combined organics were washed with brine (100 mL), dried over Na₂SO₄, filtered, and concentrated to dryness. The residue was purified by flash chromatography (Biotage, SiO₂, 10-25% EtOAc/petroleum ether) to provide rac-tert-butyl (3S,4R)-3-(benzyloxy)-4-ethenylpyrrolidine-1-carboxylate (285) (7.55 g, 74% yield) as a yellow oil. ¹H NMR (400 MHz, CDCl₃) δ 7.42-7.30 (m, 5H), 5.82-5.69 (m, 1H), 5.24-5.10 (m, 2H), 4.65-4.54 (m, 2H), 3.87 (br dd, J=5.0, 8.0 Hz, 1H), 3.70-3.55 (m, 2H), 3.44-3.20 (m, 2H), 2.91 (quin, J=6.3 Hz, 1H), 1.48 (s, 9H).

Step 3:

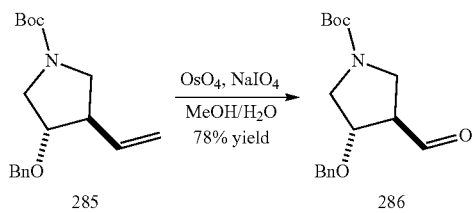 [SMILES: C=C[C@@H]1CN(C(=O)OC(C)(C)C)C[C@H]1OCc1ccccc1 ; CC(C)(C)OC(=O)N1C[C@@H](C=O)[C@H](OCc2ccccc2)C1]

To a solution of rac-tert-butyl (3S,4R)-3-(benzyloxy)-4-ethenylpyrrolidine-1-carboxylate (285) and NaIO₄ (11.7 g, 54.7 mmol) in MeOH (90 mL) and H₂O (30 mL) at 0-5° C. was added OsO₄ (63.3 mg, 0.25 mmol). The reaction mixture was stirred at 0-5° C. for an additional 2 h and then slowly warmed to 25° C. After 16 h at 25° C., TLC analysis (3:1 petroleum ether/EtOAc) showed consumption of the starting material. The reaction mixture was filtered and the filter cake was washed with EtOAc. The filtrate was concentrated on a rotovap to remove MeOH and EtOAc. The aqueous solution was diluted with brine (100 mL) and extracted with EtOAc (45 mL). The combined organics were washed with brine (2×100 mL), dried over Na₂SO₄, filtered, and concentrated. The residue was purified by flash chromatography (SiO₂, 3:1-10:1 petroleum ether/EtOAc) to provide rac-tert-butyl (3S,4R)-3-(benzyloxy)-4-formylpyrrolidine-1-carboxylate (286) (5.9 g, 78% yield) as a light yellow oil. ¹H NMR (400 MHz, CDCl₃) δ 9.68 (d, J=1.0 Hz, 1H), 7.41-7.28 (m, 5H), 4.64-4.49 (m, 2H), 4.36 (br. s, 1H), 3.85-3.57 (m, 2H), 3.56-3.40, (m, 2H), 3.18 (b.r s, 1H), 1.46 (s, 9H).

Step 4:

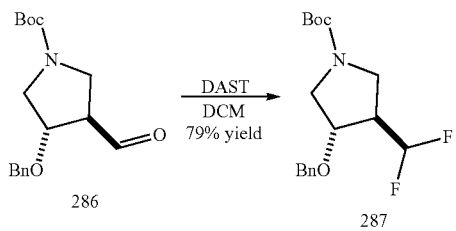 [SMILES: CC(C)(C)OC(=O)N1C[C@@H](C=O)[C@H](OCc2ccccc2)C1 ; "DAST" ; CC(C)(C)OC(=O)N1C[C@@H](OCc2ccccc2)[C@H](C(F)F)C1]

To a solution of rac-tert-butyl (3S,4R)-3-(benzyloxy)-4-formylpyrrolidine-1-carboxylate (286) (5.9 g, 19.3 mmol) in DCM (120 mL) was added DAST (9.34 g, 58 mmol) dropwise while maintaining the internal reaction temperature below 5° C. After addition the reaction mixture was stirred a further 2 h at 0-5° C. The reaction was warmed to room temperature and stirred for 17 h. TLC analysis (4:1 petroleum ether/EtOAc) showed consumption of the starting material. The reaction mixture was quenched with ice-water (40 mL). The organic layer was separated and the aqueous layer was adjusted to pH~8 by addition of saturated aqueous Na₂CO₃. The aqueous mixture was extracted with DCM (2×60 mL). The combined organics were washed with saturated aqueous Na₂CO₃ (40 mL) and brine (40 mL), dried over Na₂SO₄, filtered, and concentrated. The residue was purified by flash chromatography (Biotage, SiO₂, 10-25% EtOAc/petroleum ether) to provide rac-tert-butyl (3S,4R)-3-(benzyloxy)-4-(difluoromethyl)pyrrolidine-1-carboxylate (287) (5.0 g, 79% yield) as a light yellow oil. ¹H NMR (400 MHz, CDCl₃) δ 7.40-7.27 (m, 5H), 5.80 (td, J=56.0, 4.1 Hz, 1H), 4.58-4.48 (m, 2H), 4.20-4.08 (m, 1H), 3.63 (br. s, 2H), 3.45 (br. s, 2H), 2.73 (br dd, J=4.4, 7.9 Hz, 1H), 1.50-1.42 (m, 9H).

Step 5:

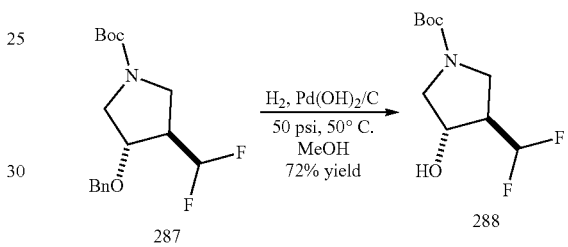

A mixture of rac-tert-butyl (3S,4R)-3-(benzyloxy)-4-(difluoromethyl)pyrrolidine-1-carboxylate (287) (4.6 g, 15 mmol) and Pd(OH)₂/C (10% wt/wt loading, 1.97 g) in MeOH (80 mL) was stirred at 50° C. under H₂ at 50 psi for 17 h. TLC analysis (2:1 petroleum ether/EtOAc) showed consumption of the starting material. The reaction mixture was filtered and concentrated to dryness. The residue was purified by flash chromatography (SiO₂, 7:1-4:1 petroleum ether/EtOAc) to provide rac-tert-butyl (3R,4S)-3-(difluoromethyl)-4-hydroxypyrrolidine-1-carboxylate (288) (2.4 g, 72% yield) as a light yellow oil. ¹H NMR (400 MHz, CDCl₃) δ 5.79 (td, J=56.0, 4.1 Hz, 1H), 5.32 (s, 1H), 4.48 (br. s, 1H), 3.70 (br. s, 2H), 3.51-3.27 (m, 2H), 2.64 (br. s, 1H), 1.52-1.44 (m, 9H). LCMS (ESI) m/z 182 (M-tBu).

Step 6:

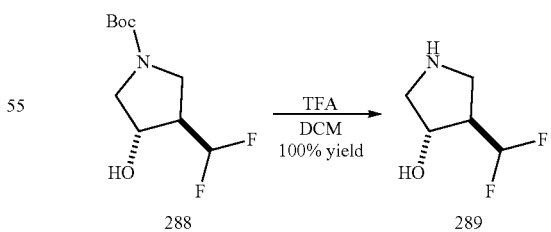

To a solution of rac-tert-butyl (3R,4S)-3-(difluoromethyl)-4-hydroxypyrrolidine-1-carboxylate (288) (920 mg, 3.88 mmol) in DCM (10 mL) was added TFA (4 mL) at 25° C. The resultant mixture was stirred at 25° C. for 2 h. LCMS analysis showed consumption of the starting material with formation of the desired product. The reaction mixture was concentrated to dryness to provide rac-(3S,4R)-4-(difluoromethyl)pyrrolidin-3-ol (289) (532 mg, 100% yield). LCMS (ESI) m/z 138 (M+H).

Step 7:

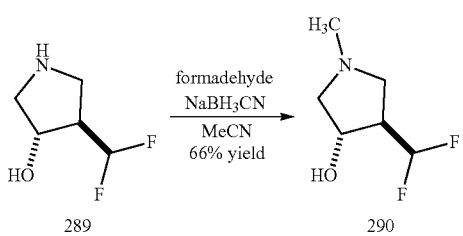

To a solution of rac-(3S,4R)-4-(difluoromethyl)pyrrolidin-3-ol (289) (532 mg, 3.88 mmol) in MeOH (10 mL) was added formaldehyde (582 mg, 19.4 mmol) and NaBH$_3$CN (683 mg, 10.9 mmol) at 10° C. The mixture was stirred for 3 h at 25° C. LCMS analysis showed consumption of the starting material and formation of the product. Saturated aqueous NaHCO$_3$ (10 mL) was added and the mixture was extracted with DCM (3×15 mL). The combined organics were washed with brine (15 mL), and dried over Na$_2$SO$_4$, filtered, and concentrated. The residue was purified by flash chromatography (SiO$_2$, 0-10% DCM/MeOH) to afford rac-(4R)-4-(2,2-difluoroethoxy)-1-methylpyrrolidin-3-ol (290) (472 mg, 81% yield) as a yellow oil. $^1$H NMR (400 MHz, DMSO-d$_6$) δ 6.07-6.01 (m, 1H), 5.13 (d, J=5.4 Hz, 1H), 4.29 (d, J=6.6 Hz, 1H), 4.13-4.06 (m, 1H), 2.64 (dt, J=9.5, 7.3 Hz, 2H), 2.37-2.31 (m, 2H), 2.19 (s, 3H). LCMS (ESI) m/z 125 (M+H).

Preparation of (3R,4R)-1-tert-butyl-4-methoxypyrrolidin-3-ol (292)

Step 1:

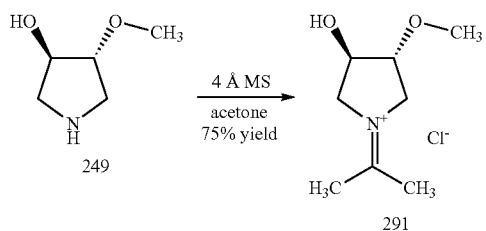

To a solution of (3R,4R)-4-methoxypyrrolidin-3-ol hydrochloride (249) (617 mg, 2.67 mmol) in dry acetone (20 mL) was added 4Å molecular sieves (1.0 g) and the mixture was stirred at 25° C. for 2 h. LCMS analysis showed formation of the desired product. The mixture was filtered through a celite plug and concentrated to afford (3R,4R)-3-hydroxy-4-methoxy-1-(propan-2-ylidene)pyrrolidin-1-ium chloride (291) (700 mg, 96% yield) as a brown gum. LCMS (ESI) m/z 158 (M+H).

Step 2:

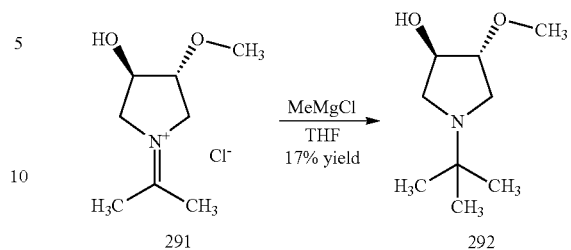

To a solution of (3R,4R)-3-hydroxy-4-methoxy-1-(propan-2-ylidene)pyrrolidin-1-ium chloride (291) (800 mg, 5.1 mmol) in dry THF (12 mL) at −20° C. under N$_2$ was added MeMgCl (3.0 M in THF, 11.8 mL, 35.4 mmol). The resulting solution was stirred at 18-20° C. for 18 h. LCMS analysis showed formation of the desired product with a trace amount of remaining starting material. The reaction was quenched by addition of saturated aqueous NH$_4$Cl (6 mL) and then adjusted to pH~9 by addition of saturated aqueous Na$_2$CO$_3$. The mixture was extracted with EtOAc (4×50 mL). The combined organics were washed with brine, dried over Na$_2$SO$_4$, filtered, and concentrated. The residue was purified by flash chromatography (Biotage, 10-45% MeOH/DCM+0.1% NH$_4$OH) to provide (3R,4R)-1-tert-butyl-4-methoxypyrrolidin-3-ol (292) (150 mg, 17% yield) as a yellow oil. $^1$H NMR (400 MHz, CDCl$_3$) δ 4.32 (br.s, 1H), 3.90-3.92 (m, 1H), 3.55 (d, J=11.6 Hz, 1H), 3.39 (s, 3H), 3.36 (s, 1H), 3.24 (dd, J=11.7, 4.3 Hz, 1H), 3.06 (d, J=12.6 Hz, 1H), 2.08-2.00 (m, 1H), 1.47-1.38 (m, 9H). LCMS (ESI) m/z 174 (M+H).

Preparation of rac-(3S,4R)-1,4-dimethylpiperidin-3-ol (294)

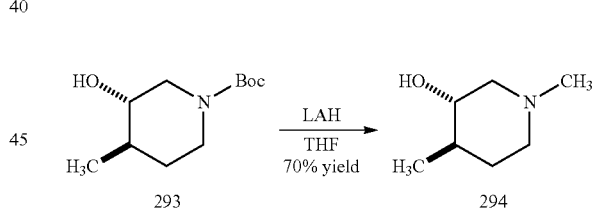

To a solution of rac-tert-butyl (3S,4R)-3-hydroxy-4-methylpiperidine-1-carboxylate (293) (500 mg, 2.32 mmol) in THF (7 mL) was added LAH (177 mg, 4.64 mmol). The mixture was heated to 80° C. and stirred for 2 h at this temperature. LCMS analysis indicated that the starting material was consumed with formation of the desired product. The reaction mixture was cooled to room temperature and diluted with EtOAc (20 mL). Na$_2$SO$_4$.10H$_2$O was added and the mixture was stirred at 25° C. for 2 h. The mixture was filtered and the filter cake was washed with EtOAc. The filtrate was concentrated to provide rac-(3S,4R)-1,4-dimethylpiperidin-3-ol (294) (201 mg, 70% yield) as a colorless oil. $^1$H NMR (400 MHz, DMSO-d$_6$) δ 4.55 (d, J=5.5 Hz, 1H), 3.01-2.95 (m, 1H), 2.81-2.75 (m, 1H), 2.65-2.56 (m, 1H), 2.14 (d, J=12.8 Hz, 3H), 1.72 (td, J=11.5, 2.6 Hz, 1H), 1.60-1.51 (m, 2H), 1.18-1.04 (m, 2H), 0.92 (d, J=6.1 Hz, 3H). LCMS (ESI) m/z 130 (M+H).

Preparation of (3R,4R)-4-methoxy-1-($^2$H$_3$)methyl-pyrrolidin-3-ol (295)

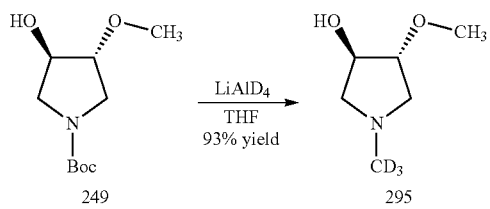

A stirred solution of tert-butyl (3R,4R)-3-hydroxy-4-methoxypyrrolidine-1-carboxylate (249) (1.0 g, 4.6 mmol) in THF (15 mL) was heated to 70° C. and LiAlD$_4$ (386 mg, 9.2 mmol) was added portion-wise. The mixture was stirred a further 30 min at 70° C. LCMS analysis indicated consumption of the starting material with formation of the desired product. After cooling to room temperature the reaction was combined with a parallel reaction run on 200 mg tert-butyl (3R,4R)-3-hydroxy-4-methoxypyrrolidine-1-carboxylate. The mixture was quenched with 15% aqueous NaOH and filtered. The filter cake was washed with EtOAc. The combined filtrate was concentrated to provide (3R,4R)-4-methoxy-1-($^2$H$_3$)methylpyrrolidin-3-ol (295) (690 mg, 93% yield) as a colorless oil. $^1$H NMR (400 MHz, DMSO-d$_6$) δ 5.00 (s, 1H), 3.96-3.90 (m, 1H), 3.56-3.50 (m, 1H), 3.22 (s, 3H), 2.72-2.63 (m, 2H), 2.34 (dd, J=9.9, 3.9 Hz, 1H), 2.21 (dd, J=9.5, 4.7 Hz, 1H). LCMS (ESI) m/z 135 (M+H).

Preparation of rac-(3S,4R)-1-methyl-4-(trifluoromethyl)pyrrolidin-3-ol (300)

Step 1:

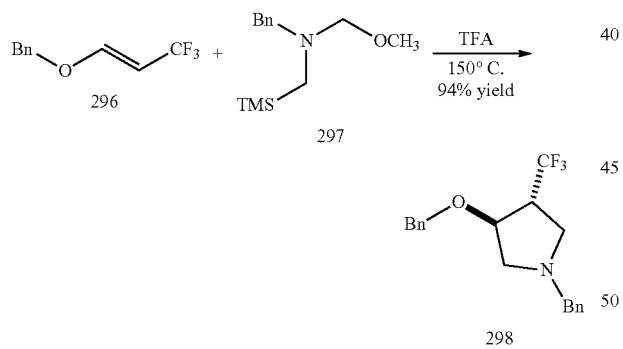

To a 100 mL flask equipped with a reflux condenser was added ({[(1E)-3,3,3-trifluoroprop-1-en-1-yl]oxy}methyl)benzene (296) (2.0 g, 9.9 mmol) and N-benzyl-1-methoxy-N-[(trimethylsilyl)methyl]methanamine (297) (12.2 g, 51.4 mmol). The mixture was heated to 150° C. and then TFA was added dropwise through the reflux condenser over a period of 3 h. After addition the dark reaction mixture was heated at 150° C. for a further 1 h. LCMS analysis showed complete consumption of the starting material. The reaction mixture was cooled to room temperature and purified by flash chromatography (Biotage, 10% EtOAc/petroleum ether) to provide rac-(3S,4R)-1-benzyl-3-(benzyloxy)-4-(trifluoromethyl)pyrrolidine (298) (3.1 g, 93% yield) as a colorless oil. $^1$H NMR (300 MHz, CDCl$_3$) δ 2.49-2.60 (m, 1H), 2.70 (dd, J=10.0, 6.03 Hz, 1H), 2.80 (dd, J=10.1, 3.5 Hz, 1H), 2.92-3.05 (m, 2H), 3.55-3.73 (m, 2H), 4.13-4.25 (m, 1H), 4.44-4.62 (m, 2H), 7.27-7.39 (m, 10H). $^{19}$F NMR (282 MHz, CDCl$_3$) δ −69.42.

Step 2:

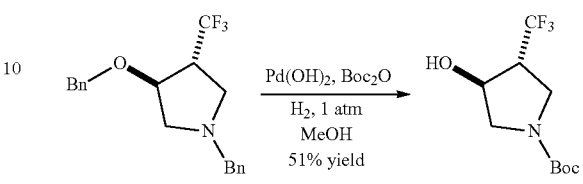

To a solution of rac-(3S,4R)-1-benzyl-3-(benzyloxy)-4-(trifluoromethyl)pyrrolidine (3.6 g, 10.7 mmol) (298) in MeOH (85 ml) was added Pd(OH)$_2$/C (2.26 g, 16.1 mmol) and Boc$_2$O (2.47 g, 11.3 mmol). The mixture was stirred under an atmosphere of H$_2$ for 16 h. LCMS analysis showed ~50% conversion to the desired product. An additional batch of Pd(OH)$_2$/C (2.26 g, 16.1 mmol) was added and the mixture was stirred under H$_2$ at 5 atm for 16 h. LCMS analysis ~65% conversion to the desired product. The reaction was filtered through celite and concentrated. Purification by flash chromatography (ISCO, 20-50% EtOAc/petroleum ether) to provide rac-tert-butyl (3S,4R)-3-hydroxy-4-(trifluoromethyl)pyrrolidine-1-carboxylate (299) (1.6 g, 58% yield) as a colorless oil, which solidified to a white solid upon standing. $^1$H NMR (400 MHz, CDCl$_3$) δ 4.55 (d, J=1.9 Hz, 2H), 4.23 (s, 1H), 3.82-3.51 (m, 4H), 2.98 (d, J=4.2 Hz, 1H), 1.46 (s, 9H). $^{19}$F NMR (376 MHz, CDCl$_3$) δ −70.24. LCMS (ESI) m/z 246 (M-Boc). See jillian—tabulated proton count too high—protons at 7 ppm should not exist.

Step 3:

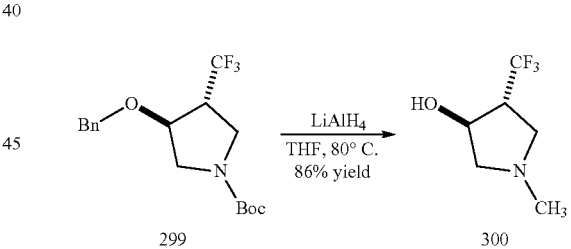

To a stirred solution of rac-tert-butyl (3S,4R)-3-hydroxy-4-(trifluoromethyl)pyrrolidine-1-carboxylate (299) in THF (10 mL) was added LiAlH$_4$ (149 mg, 3.92 mmol) portion-wise at 20-25° C. (vigorous gas emission and exotherm observed). After addition the reaction mixture was stirred for 5 min at 20-25° C. and then heated to 80° C. and stirred at this temperature for 2 h. LCMS analysis showed complete consumption of the starting material. The reaction was cooled to room temperature. Na$_2$SO$_4$.10H$_2$O (300 mg) was added and the mixture was stirred for 10 min. The mixture was filtered to provide rac-(3S,4R)-1-methyl-4-(trifluoromethyl)pyrrolidin-3-ol (300) (285 mg, 86% yield) as a colorless oil. $^1$H NMR (400 MHz, CDCl$_3$) δ 4.39 (dt, J=5.4, 2.7 Hz, 1H), 3.29 (s, 1H), 3.10 (t, J=9.3 Hz, 1H), 2.80 (dd, J=21.9, 10.4 Hz, 2H), 2.54 (dd, J=10.2, 5.6 Hz, 1H), 2.38 (d, J=5.4 Hz, 1H), 2.35 (s, 3H). LCMS (ESI) m/z 170 (M+H).

Preparation of 5-fluoro-2-methyl-1,2,3,4-tetrahydroisoquinolin-8-ol (302)

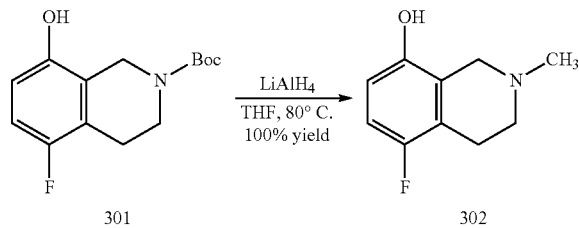 [SMILES: CC(C)(C)OC(=O)N1CCc2c(F)ccc(O)c2C1 ; "LiAlH4" ; CN1CCc2c(F)ccc(O)c2C1]

To a solution of tert-butyl 5-fluoro-8-hydroxy-3,4-dihydroisoquinoline-2(1H-O-carboxylate (301) (200 mg, 0.75 mmol) (US20170348313) in THF (5 mL) was added LiAlH₄ (57 mg, 1.5 mmol). The mixture was stirred at 80° C. for 2 h. LCMS analysis showed consumption of starting material with formation of the desired product. The mixture was cooled to room temperature and Na₂SO₄·10H₂O (8 g) was added. The mixture was stirred for 10 min and then filtered and concentrated to dryness to provide 5-fluoro-2-methyl-1,2,3,4-tetrahydroisoquinolin-8-ol (302) (136 mg, 100% yield) as a white solid. $^1$H NMR (400 MHz, DMSO-$d_6$) δ 9.30 (s, 1H), 6.75 (t, J=9.0, 1H), 6.55 (dd, J=8.7, 4.6, 1H), 3.29 (s, 2H), 2.65 (t, J=5.7, 2H), 2.51 (t, J=5.9, 2H), 2.32 (s, 3H). LCMS (ESI) m/z 182 (M+H).

Preparation of 2-cyclopropyl-1,2,3,4-tetrahydroisoquinolin-5-ol (304)

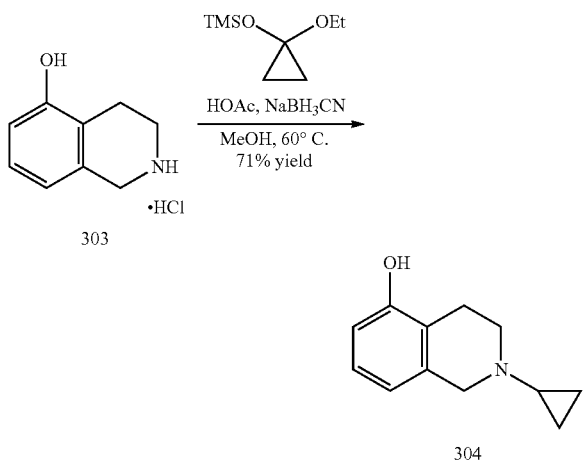

To a mixture of 1,2,3,4-tetrahydroisoquinolin-5-ol hydrochloride (303) (186 mg, 1.0 mmol) and [(1-ethoxycyclopropyl)oxy](trimethyl)silane (210 mg, 1.2 mmol) in MeOH (8 mL) was added NaBH₃CN (76 mg, 1.2 mmol) and AcOH (73 mg, 1.2 mmol). The mixture was stirred at 60° C. for 4 h under N₂. LCMS analysis showed consumption of starting material with formation of the product. The mixture was concentrated. The residue was diluted with DCM (80 mL) and washed with saturated aqueous NaHCO₃ (2×20 mL) and brine (20 mL). The combined organics were dried over Na₂SO₄, filtered, and concentrated. Purification by flash chromatography (SiO₂, 1/15 DCM/petroleum ether) provided (304) (200 mg, 71% yield) as a yellow solid. $^1$H NMR (400 MHz, DMSO-$d_6$) δ 9.20 (s, 1H), 6.89 (t, J=7.8 Hz, 1H), 6.57 (d, J=7.9 Hz, 1H), 6.49 (d, J=7.6 Hz, 1H), 3.62 (s, 2H), 2.79 (t, J=6.0 Hz, 2H), 2.55 (t, J=6.0 Hz, 2H), 1.78-1.67 (m, 1H), 0.53-0.43 (m, 2H), 0.42-0.33 (m, 2H). LCMS (ESI) m/z 190 (M+H).

Biological Examples and Biochemical Assay Methods

Mass Spectrometry Reactivity Assay (MSRA)

Compounds presented in the present invention covalently bind to KRAS G12C using MSRA to detect a covalent adduct of the exemplary compound and KRAS G12C.

GDP-loaded KRAS (1-169) G12C, C51S, C80L, C118S were diluted in the protein assay buffer 25 mM Hepes pH7.5, 200 mM NaCl, 5% glycerol to concentration of 5 μM and 20 μl of protein was transferred into 96-well plate. Initial compound stocks were generated at concentrations 100-fold higher that their desired assay concentrations. See K-Ras (G12C) inhibitors allosterically control GTP affinity and effector interactions; Ostrem J M, Peters U, Sos M L, Wells J A, Shokat K M; Nature. 2013, Nov. 28; 503(7477):548-51.

Exemplary compounds dissolved in DMSO were diluted 100-fold into solution containing 20 μl of 5 μM KRAS protein in the 96-well plate to initiate the reaction. Mosquito (TPP Lab tech) liquid handling robot was used to add compounds to protein solution. Typical final concentration of the compounds was 5 μM or 10 μM. The plates were placed on a shaker for 1 min at RT, sealed and incubated at room temperature for specified time period. 5 μl of reaction mix was added to 10 μl of 0.2% formic acid stop solution and mixed well. Typical end points were 1, 15, 30, and 60 min.

Data were collected using Waters Acquity H-class UPLC system/Xevo G2-XS TOF mass spectrometer. The protein was injected in their liquid phase onto a Bruker Microtrap protein column TR1/15109/03. The following buffers were used to set LC gradient: Buffer A: 0.2% formic acid H2O; B: 0.2% formic acid CAN. The protein was eluted from the column using the following LC Gradient: 0-0.4 min, 10% B to 30% B; 0.4 min-2.4 min, to 90% B, 2.5 min, 10% B, 3 min, 10% B. Initial data analysis was performed using MaxEnt software right after data acquisition.

The standard auto processing function was used to define percentage of unmodified and modified KRAS protein using MexEnt software right after data acquisition. The highest peak was defined as 100% while smaller peak as assigned the number defined by autoprocessing function. The percent of modification corresponding to modified with exemplary compound and unmodified KRAS GDP-loaded KRAS (1-169) G12C, C51S, C80L, C118S were exported to Xcel data analysis software.

The percent of modified protein at the defined concentration of exemplary compound was calculated using the following formula: % mod=Num of modified peak/Sum of modified+unmodified. The resultant value defined as Percent Modification (PM) and an increase in PM reflects that the specific compound is better than other compounds at specified compound concentration at a given time point.

Cell Activity Assay

Compounds presented in the present invention lead to the accumulation of the GDP bound Ras upon treatment of human cancer cell line.

The accumulation of the GDP-bound KRAS G12C in cellular environment was measured based on the principle that KRAS G12C only binds to its downstream kinase; Raf-1 (MAP Kinase Kinase Kinase), when in its active-GTP bound state. In this state, Ras binded to a domain of Raf-1 kinase referred to as the Ras Binding Domain (RBD).

MIAPaCa-2 cells were grown in RPMI 1640 medium (Gibco 11875) supplemented with 10% fetal bovine serum and 1% penicillin/streptomycin. Cells were seeded in 96-well tissue culture plates at a density of 30,000 cells/well and allowed to attach for 16-24 hours. Test compounds were prepared as a 10 mM stock in DMSO and serially diluted in 100% DMSO using a 3-fold dilution scheme. An intermediate 5× concentrated plate in complete growth medium was made and 25 μl/well was added to the 100 μl of cells for a final concentration of 0.3% DMSO. Each concentration of exemplary compound was tested in duplicate. The negative control wells were cells with control inhibitor at 10 μM, and the positive control wells were cells without drugs, DMSO only. Plates were incubated for 6 hours at 37° C., 5% $CO_2$. Following treatment, cells were washed 3× with ice-cold PBS and 115 μl/well ice-cold 1× Assay/Lysis. Buffer with protease inhibitors was added (25 mM HEPES, pH 7.5, 150 mM NaCl, 1% NP-40, 10 mM $MgCl_2$, 1 mM EDTA, 2% Glycerol). Following lysis samples were frozen at −80° C.

Raf-1 RBD (LJIC-1988A1) was diluted to 100 ng/well in PBS and 5 μl/well was spot coated onto MSD high bind SECTOR plates (L15XB). Plates were incubated at room temperature for 1 hour on an orbital shaker. Plates were washed with PBS/0.05% Tween-20 and 50 μl/well of thawed lysate samples were added, followed by 50 μl of 1% MSD Blocker A in PBS/0.05 Tween-20 (R93BA). Plates were incubated for 1 hour on an orbital shaker and washed with PBS/0.05% Tween-20. 25 μl/well of Anti-pan-Ras Antibody (Cell Biolabs 244003) diluted 1:3000 was added in 1% MSD Blocker A solution and plates were incubated for 1 hour on an orbital shaker and washed with PBS/0.05% Tween-20. SULFO-TAG goat anti-mouse secondary antibody (MSD R32AC) was diluted 1:500 in MSD Blocker A solution and added at 25 μL/well. Plates were incubated for 1 hour on an orbital shaker and washed with PBS/0.05% Tween-20. 150 μl/well of Read Buffer T (MSD R92TC) diluted 1:3 in $H_2O$ was added and plates were read on a Meso Scale Discovery Sector Imager S600.

KRAS signal was normalized to maximum inhibition and DMSO control values, and IC50 values were generated using a 4 parameter fit of the dose response curve. The decrease in IC50 reflects that the exemplary compound lead to a higher level of accumulation of GDP-bound KRAS G12C than another exemplary compounds at specific time-point of treatment of cancer cell line.

| MSRA Data and Cell Activity Assay Data | | | | | | |
|---|---|---|---|---|---|---|
| | MSRA (% modification) | | | | $IC_{50}$ (μM) | |
| Example number | 10 μM 0.50 hr | 10 μM 0.25 hr | 5.0 μM 0.25 hr | 5.0 μM 0.017 hr | MiaPACA* | H358 |
| 01 | A | 11 | | | | 11.8 |
| 02 | A | 15 | | | | 5.25 |
| 03 | A | 28 | | | | 2.74 |
| 04 | A | 40 | | | | 2.26 |
| 05 | A | 12 | | | | 8.41 |
| 06 | A | 26 | | | | 6.75 |
| 07 | A | 16 | | | | 7.15 |
| 08 | A | 6 | | | | 11.1 |
| 09 | A | 38 | | | | 1.87 |
| 10 | A | 10 | | | | 7.50 |
| 11 | A | 68 | 44 | | | 0.892 | 2.56 |
| 12 | A | 38 | | | | 2.95 |
| 13 | A | 69 | 44 | | | 0.394 |
| 14 | A | 67 | | 46 | | 0.545 |
| 15 | A | 67 | | | | 0.468 |
| 16 | A | 7 | | | | 29.6 |
| 17 | A | 9 | | | | 24.1 |
| 18 | A | 34 | | | | 6.45 |
| 19 | A | 33 | 21 | | | 28.0 |
| 20 | A | 80 | 73 | 85 | | 0.255 | 0.758 |
| 21 | A | 12 | | | | 10.6 |
| 22 | A | 10 | | | | 15.6 |
| 23 | A | 20 | | | | 11.6 |
| 24 | A | 20 | | | | 4.72 |
| 25 | A | 17 | | | | 8.89 |
| 26 | A | 14 | | | | 27.6 |
| 27 | A | 30 | | | | 13.3 |
| 28 | A | 61 | | | | 1.02 |
| 29 | A | 76 | 70 | | | 0.391 |
| 30 | A | 67 | | | | 0.247 |
| 31 | A | 79 | | | | 0.171 |
| 32 | A | 74 | | | | 0.681 |
| 33 | A | 34 | | | | >30.0 |
| 34 | A | | 47 | 19 | | 1.29 |
| 35 | A | | 64 | | | 4.26 |
| 36 | A | | 31 | | | 4.70 |
| 37 | A | | 63 | | | 0.622 |
| 38 | A | | 56 | | | 0.537 |
| 39 | A | | 74 | | | 0.246 |
| 40 | A | | 6 | | | 20.9 |
| 41 | A | | 31 | | | 3.501 |
| 01 | B | 12 | | | | 16.9 |
| 02 | B | 30 | | | | 7.84 | 8.20 |
| 03 | B | 6 | | | | 27.1 |
| 04 | B | 21 | | | | 23.0 |
| 05 | B | 15 | | | | 4.03 |
| 06 | B | 9 | | | | >30.0 |
| 07 | B | | 15 | | | 6.18 |
| 08 | B | | 44 | | | 2.56 |
| 09 | B | | 43 | | | 3.10 |
| 10 | B | | 60 | | | 13.4 |
| 11 | B | | 21 | | | 4.89 |
| 12 | B | | 21 | | | 5.45 |
| 13 | B | | 74 | 19 | | 0.160 |
| 01 | C | 18 | | | | 5.92 |
| 02 | C | 60 | | 12 | | 1.01 |
| 03 | C | 8 | 3 | | | 24.2 |
| 04 | C | 21 | | | | 18.2 |
| 05 | C | 61 | | | | 1.29 |
| 06 | C | 53 | | | | 1.62 |
| 07 | C | 15 | | | | 5.67 |
| 08 | C | 29 | | | | 2.98 |
| 09 | C | 34 | | | | 2.87 |
| 10 | C | 27 | | | | 5.21 |
| 11 | C | 26 | | | | |
| 12 | C | 34 | | | | 3.91 |
| 13 | C | 36 | | | | 3.74 |
| 14 | C | 20 | | | | 27.8 |
| 15 | C | 12 | | | | |
| 16 | C | 7 | | | | 22.2 |
| 17 | C | 24 | | | | 2.60 |
| 18 | C | 50 | | 36 | | 1.10 |
| 19 | C | 18 | 10 | | | >30.0 |
| 20 | C | 36 | | | | 6.10 |
| 21 | C | 71 | | | | 0.611 |
| 22 | C | 75 | 75 | | | 14.0 |
| 01 | D | 37 | | | | 6.69 |
| 02 | D | 12 | | | | 4.66 |
| 01 | E | 29 | | | | 2.41 |
| 02 | E | 32 | | | | 6.46 |
| 03 | E | 40 | | | | 1.44 |
| 04 | E | 62 | 60 | 71 | | 0.585 |
| 05 | E | 76 | 72 | | | 0.559 |
| 06 | E | 75 | 70 | 35 | | 0.585 |
| 07 | E | 82 | 79 | 67 | | 0.230 | 0.501 |
| 08 | E | 25 | | | | 10.7 |

MSRA Data and Cell Activity Assay Data

| Example number | | MSRA (% modification) | | | | IC$_{50}$ (μM) | |
|---|---|---|---|---|---|---|---|
| | | 10 μM 0.50 hr | 10 μM 0.25 hr | 5.0 μM 0.25 hr | 5.0 μM 0.017 hr | MiaPACA* | H358 |
| 09 | E | 24 | | | | 7.40 | |
| 10 | E | 21 | | | | 2.32 | |
| 11 | E | 68 | | | | 3.95 | |
| 12 | E | 79 | | | | 0.835 | |
| 13 | E | 79 | 75 | | | 0.452 | |
| 14 | E | 65 | | | | 1.01 | |
| 15 | E | 74 | 59 | 56 | | 0.510 | |
| 16 | E | | 11 | | | 0.413 | |
| 17 | E | 83 | 80 | 76 | | 0.197 | |
| 18 | E | | 80 | | | 0.262 | |
| 19 | E | | 33 | | | 29.8 | |
| 20 | E | | 8 | | | 1.02 | |
| 21 | E | | 65 | | | 0.180 | |
| 22 | E | 83 | 81 | 83 | | 0.056 | |
| 01 | F | 35 | | | | 9.34 | |
| 02 | F | 14 | | | | >30.0 | |
| 03 | F | 12 | | | | >30.0 | |
| 04 | F | 43 | | | | 7.28 | |
| 05 | F | 22 | | | | 28.5 | |
| 06 | F | 46 | | | | 3.24 | |
| 07 | F | 75 | 74 | 22 | | 21.2 | |
| 08 | F | 72 | 58 | | | 1.60 | |
| 09 | F | 75 | 64 | | | 3.00 | |
| 10 | F | 65 | 53 | | | 6.07 | |
| 11 | F | 55 | 34 | | | 8.14 | |
| 12 | F | 20 | | | | 29.1 | |
| 13 | F | 26 | | | | 17.0 | |
| 14 | F | 12 | | | | 29.0 | |
| 15 | F | 13 | | | | >30.0 | |
| 16 | F | 16 | | | | >30.0 | |
| 17 | F | 60 | 36 | | | 4.59 | |
| 18 | F | 23 | | | | 29.3 | |
| 19 | F | | 24 | | | 3.70 | |
| 20 | F | | 17 | | | 2.99 | |
| 21 | F | | | 61 | | 0.283 | |
| 22 | F | | | 33 | | 0.535 | |
| 23 | F | | | 66 | 55 | 0.944 | |
| 01 | G | | 82 | | | 0.040 | 0.060 |
| 02 | G | | 75 | 73 | | 0.584 | |
| 03 | G | | 72 | | | 0.155 | |
| 04 | G | | 49 | | | 0.393 | |
| 05 | G | 82 | 81 | 80 | | 0.164 | |
| 06 | G | | 82 | 52 | 23 | 0.064 | |
| 07 | G | | 77 | | | 0.404 | |
| 08 | G | | 80 | | | 0.148 | |
| 09 | G | | 81 | | | 0.069 | 0.123 |
| 10 | G | | 53 | | | 0.071 | |
| 11 | G | | 77 | | | 0.102 | 0.448 |
| 12 | G | | 75 | | | 0.071 | |
| 13 | G | 80 | 78 | 70 | | 0.160 | |
| 14 | G | | 79 | 78 | | 0.401 | |
| 15 | G | | | 80 | | 0.019 | |
| 16 | G | | 14 | | | 0.111 | |
| 17 | G | | 79 | | | 0.054 | |
| 18 | G | 84 | 81 | 88 | 43 | 0.034 | 0.087 |
| 19 | G | | 60 | | | 0.051 | 0.109 |
| 20 | G | | 79 | | 26 | 0.080 | 0.152 |
| 21 | G | | 80 | | | 0.075 | |
| 22 | G | | 81 | | | 0.072 | |
| 23 | G | | | 35 | | 0.688 | |
| 24 | G | | | 84 | 83 | 0.004 | |
| 25 | G | | | | 73 | 0.009 | |
| 26 | G | | | | 35 | 0.195 | |
| 27 | G | | | | 67 | 0.029 | |
| 28 | G | | | | 60 | 0.037 | |
| 29 | G | | | | 82 | 0.005 | |
| 30 | G | | | | 53 | 0.026 | |
| 31 | G | | | | 26 | 0.135 | |
| 32 | G | | | | 44 | 0.016 | |
| 33 | G | | | | 51 | 0.052 | |
| 34 | G | | | | 47 | 0.063 | |
| 35 | G | | | | 75 | 0.027 | |
| 36 | G | | | | 35 | 0.109 | |
| 37 | G | | | | 37 | 0.338 | |
| 38 | G | | | | 75 | 0.021 | |
| 39 | G | | | | 76 | 0.014 | |
| 40 | G | | | | 83 | 0.008 | |
| 41 | G | | | | 83 | 0.007 | |
| 01 | H | | 81 | 66 | | 0.117 | 0.191 |
| 02 | H | | 53 | | | 0.505 | |
| 03 | H | 72 | | 51 | | 0.842 | |
| 04 | H | | 73 | 65 | | 0.465 | |
| 05 | H | | 68 | 54 | | 0.414 | |
| 06 | H | | 60 | 48 | | 0.611 | |
| 07 | H | | 77 | 66 | | 0.285 | |
| 08 | H | | | 36 | | 0.491 | |
| 09 | H | 83 | 81 | 78 | | 0.239 | |
| 10 | H | 68 | | 47 | | 0.965 | |
| 11 | H | | 80 | | | 0.237 | |
| 12 | H | | 67 | 49 | | 0.691 | |
| 13 | H | | 83 | 65 | | 0.311 | |
| 14 | H | | 81 | 52 | | 0.082 | |
| 15 | H | | 54 | 25 | | 0.461 | |
| 16 | H | | | 57 | | 0.169 | |
| 17 | H | | | | 69 | 0.026 | |
| 18 | H | | | | 52 | 0.070 | |
| 19 | H | | | | 66 | 0.004 | |
| 01 | I | | | 44 | | 0.418 | |
| 02 | I | | | 81 | | 0.049 | |
| 03 | I | | | 52 | | 0.060 | |
| 04 | I | | | 55 | | 0.375 | |
| 05 | I | | | 70 | | 0.074 | |
| 06 | I | | | 74 | | 0.020 | |
| 07 | I | | | 46 | | 0.331 | |
| 08 | I | | | 65 | | 0.265 | |
| 09 | I | | | 44 | | 0.398 | |
| 10 | I | | | 82 | 70 | 0.022 | |
| 11 | I | | | 32 | | 0.321 | |
| 12 | I | | | 78 | | 0.120 | |
| 13 | I | | | 44 | | 0.777 | |
| 14 | I | | | 14 | | 0.366 | |
| 15 | I | | | 81 | | 0.126 | |
| 16 | I | | | 48 | | 0.582 | |
| 17 | I | | | | 82 | 0.005 | |
| 18 | I | | | | 35 | 0.093 | |
| 19 | I | | | | 82 | 0.003 | |
| 20 | I | | | | 73 | 0.016 | |
| 21 | I | | | | 42 | 0.094 | |
| 22 | I | | | | 80 | 0.003 | |
| 23 | I | | | | 12 | 0.348 | |
| 24 | I | | | | 20 | | |
| 25 | I | | | | 6 | | |
| 26 | I | | | | 17 | | |
| 27 | I | | | | 15 | | |
| 28 | I | | | | 11 | 1.00 | |
| 29 | I | | | | 16 | | |
| 30 | I | | | | 45 | 0.030 | |
| 31 | I | | | | 31 | 0.041 | |
| 32 | I | | | | 19 | 0.168 | |
| 33 | I | | | | 74 | 0.039 | |
| 34 | I | | | | 52 | 0.935 | |
| 35 | I | | | | 24 | 0.155 | |
| 36 | I | | | | 57 | 0.029 | |
| 37 | I | | | | 16 | | |
| 38 | I | | | | 55 | 0.055 | |
| 39 | I | | | | 31 | 0.083 | |
| 40 | I | | | | 68 | 0.020 | |
| 41 | I | | | | 70 | 0.021 | |
| 42 | I | | | | 73 | 0.010 | |
| 43 | I | | | | 54 | 0.019 | |
| 44 | I | | | | 56 | 0.032 | |
| 45 | I | | | | 7 | | |

MSRA Data and Cell Activity Assay Data

| Example number | MSRA (% modification) | | | | IC$_{50}$ (μM) | |
|---|---|---|---|---|---|---|
| | 10 μM 0.50 hr | 10 μM 0.25 hr | 5.0 μM 0.25 hr | 5.0 μM 0.017 hr | MiaPACA* | H358 |
| 46 I | | | | 70 | 0.285 | |
| 47 I | | | | 14 | | |
| 48 I | | | | 67 | 0.006 | |
| 49 I | | | | 34 | 0.170 | |
| 50 I | | | | 70 | 0.008 | |
| 51 I | | | | 39 | 0.031 | |
| 52 I | | | | 81 | 0.023 | |
| 53 I | | | | 15 | 0.059 | |
| 54 I | | | | 78 | 0.019 | |
| 55 I | | | | 60 | 0.028 | |
| 56 I | | | | 81 | 0.040 | |
| 57 I | | | | 22 | 0.024 | |
| 58 I | | | | 58 | 0.006 | |
| 59 I | | | | 13 | 0.123 | |
| 01 J | | | 55 | | 0.339 | |
| 02 J | | | 26 | | 0.620 | |
| 03 J | | | 77 | | 0.855 | |
| 04 J | | | 64 | | 0.989 | |
| 05 J | | | 81 | | 1.07 | |
| 06 J | | | 33 | | 0.638 | |
| 01 K | | | | 65 | 0.065 | |
| 01 L | | | | 51 | 0.038 | |
| 02 L | | | 31 | | 0.146 | |
| 01 | 27 | | | | >30.0 | |
| 02 | 19 | | | | >30.0 | |
| 03 | 15 | | | | >30.0 | |
| 04 | 25 | | | | 11.7 | |
| 05 | 5 | | | | 29.3 | |
| 06 | 20 | | | | 29.7 | |

*Assay limit is 30.00

We claim:

1. A compound of Formula (I):

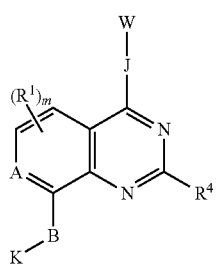

Formula (I)

or a pharmaceutically acceptable salt thereof; wherein:

A is —C(H)— or nitrogen;
B is oxygen or C(R$^6$)$_2$;
J is:

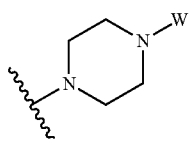

where W* represents the point of attachment to W, and where J is optionally substituted with 1 R$^2$;

K is:

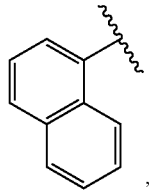 [SMILES: *c1cccc2ccccc12]

or

K is:

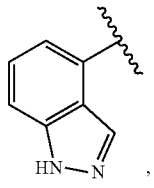

where K is optionally substituted with 1 or 2 R$^3$;
W is selected from the group consisting of:

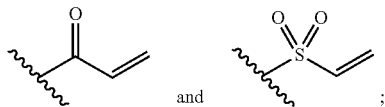

each R$^1$ is independently selected from the group consisting of C$_1$-C$_6$ alkyl, halogen, C$_1$-C$_6$ haloalkyl, cyano and N(R$^6$)$_2$;
R$^2$ is C$_1$-C$_6$ alkyl;
each R$^3$ is independently selected from the group consisting of C$_1$-C$_6$ alkyl, hydroxy, halogen, and C$_1$-C$_6$ haloalkyl;
R$^4$ is —X—Y—Z where:
X is absent or is oxygen,
Y is absent or C$_1$-C$_6$ alkylenyl, and
Z is selected from H, heterocycle having 3-12 ring atoms and C$_3$-C$_6$ cycloalkyl, where R$^4$ is optionally substituted with R$^7$;
each R$^6$ is independently selected from the group consisting of hydrogen, hydroxyl, C$_1$-C$_6$ alkoxy and C$_1$-C$_6$ alkyl, or two R$^6$ optionally join to form heterocycle having 3-12 ring atoms or C$_3$-C$_6$ cycloalkyl;
each R$^7$ is independently R$^{7'}$ or C$_1$-C$_6$ alkyl-R$^{7'}$, where each R$^{7'}$ is independently selected from the group consisting of: C$_1$-C$_6$ alkyl and —N(R$^6$)$_2$; and
m is 0, 1, 2 or 3.

2. The compound or salt of claim 1, wherein J is selected from the group consisting of:

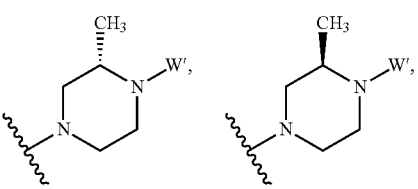

513
-continued
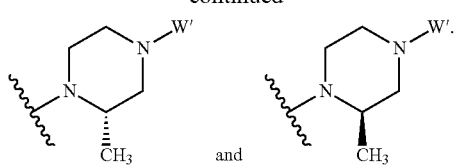
3. The compound or salt of claim 1, wherein $R^4$ is selected from the group consisting of:
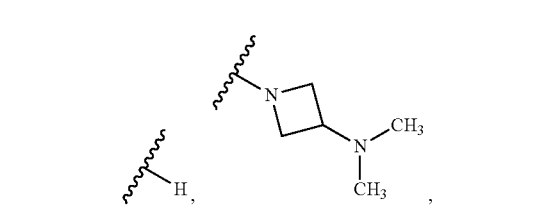
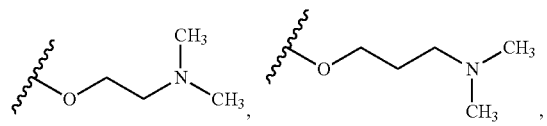
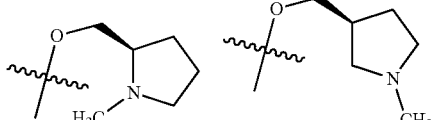
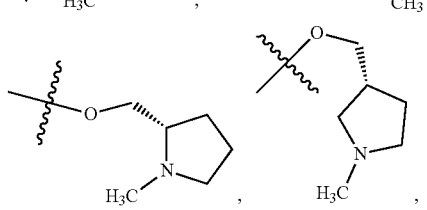
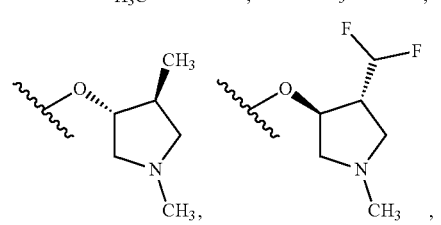
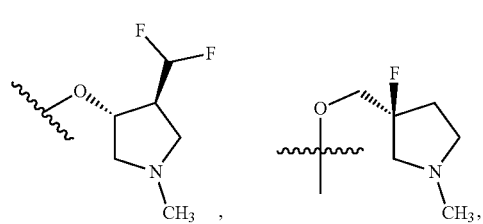
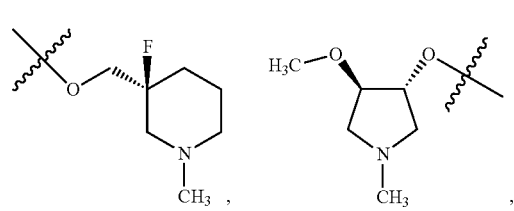
514
-continued
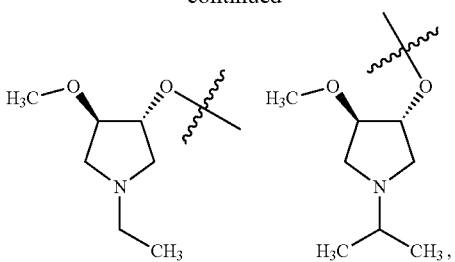
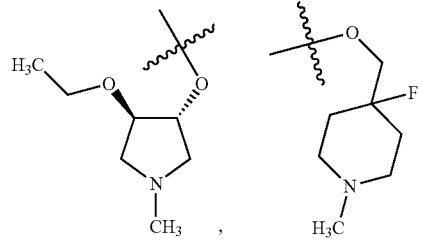
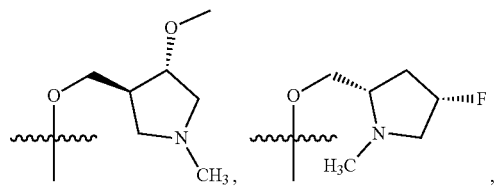
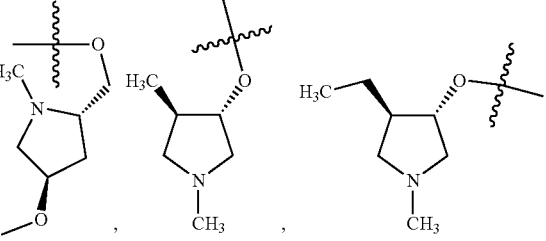
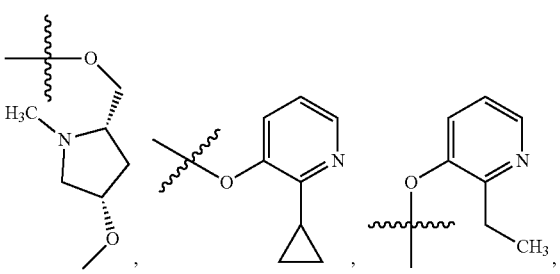
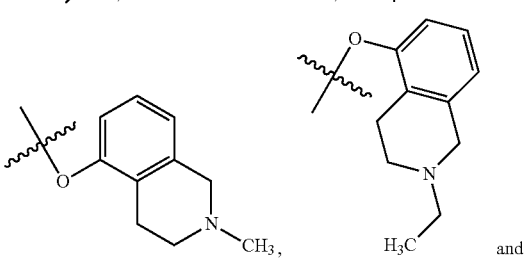
and -continued

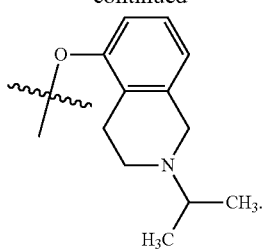

4. The compound or salt of claim 1, wherein R⁴ is selected from the group consisting of:

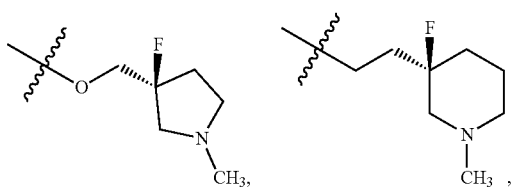

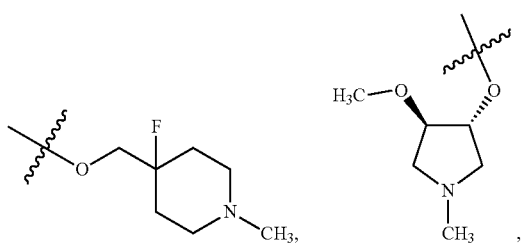

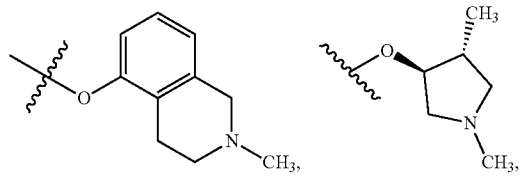

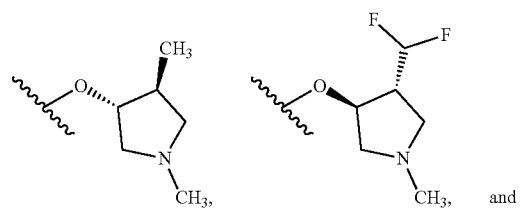

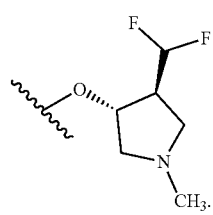

5. A compound of Formula (II):

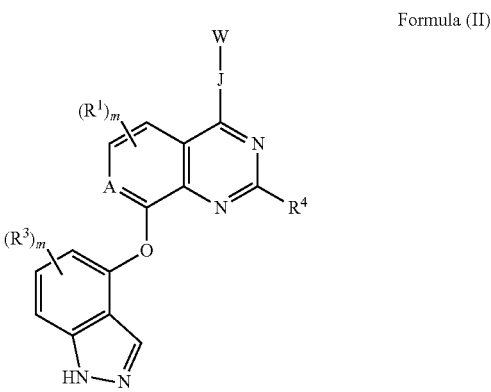

Formula (II)

or a pharmaceutically acceptable salt thereof; wherein:

A is —C(H)— or nitrogen;

J is:

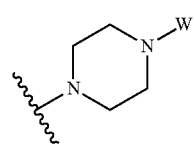

where W* represents the point of attachment to W, and where J is optionally substituted with 1 or more $R^2$;

W is:

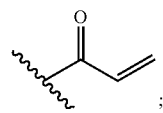 [SMILES: *C(=O)C=C]

each $R^1$ is independently selected from the group consisting of $C_1$-$C_6$ alkyl, halogen, $C_1$-$C_6$ haloalkyl, cyano and $N(R^6)_2$;

$R^2$ is $C_1$-$C_6$ alkyl;

each $R^3$ is independently selected from the group consisting of $C_1$-$C_6$ alkyl, hydroxy, halogen, and $C_1$-$C_6$ haloalkyl;

$R^4$ is —X—Y—Z where:
 X is absent or is oxygen,
 Y is absent or $C_1$-$C_6$ alkylenyl, and
 Z is selected from H, heterocycle having 3-12 ring atoms and $C_3$-$C_6$ cycloalkyl,
where $R^4$ is optionally substituted with $R^7$;

each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;

each $R^7$ is independently $R^{7'}$ or $C_1$-$C_6$ alkyl-$R^{7'}$, where each $R^{7'}$ is independently selected from the group consisting of: $C_1$-$C_6$ alkyl and —$N(R^6)_2$; and each m is independently 0, 1, 2 or 3.

6. The compound or salt of claim 5, wherein
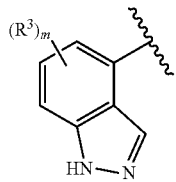
is selected from the group consisting of:
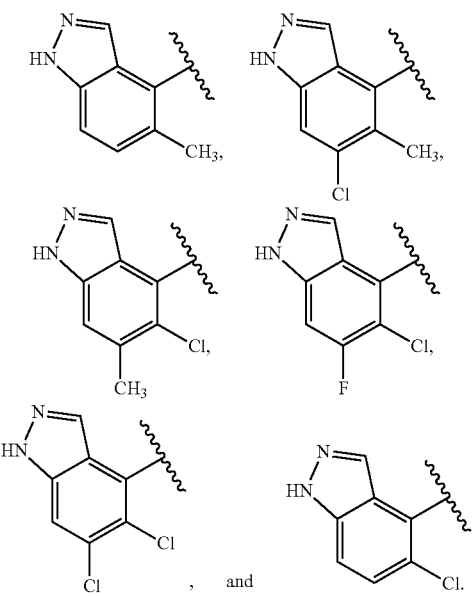
7. The compound or salt of claim 5 or 6, wherein R⁴ is selected from the group consisting of:
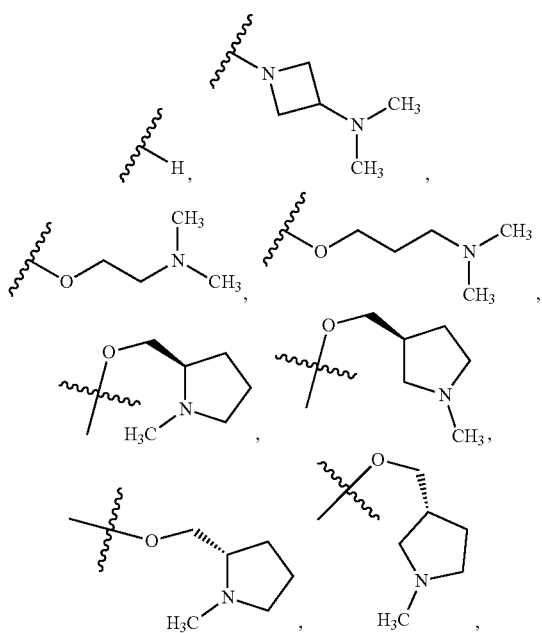
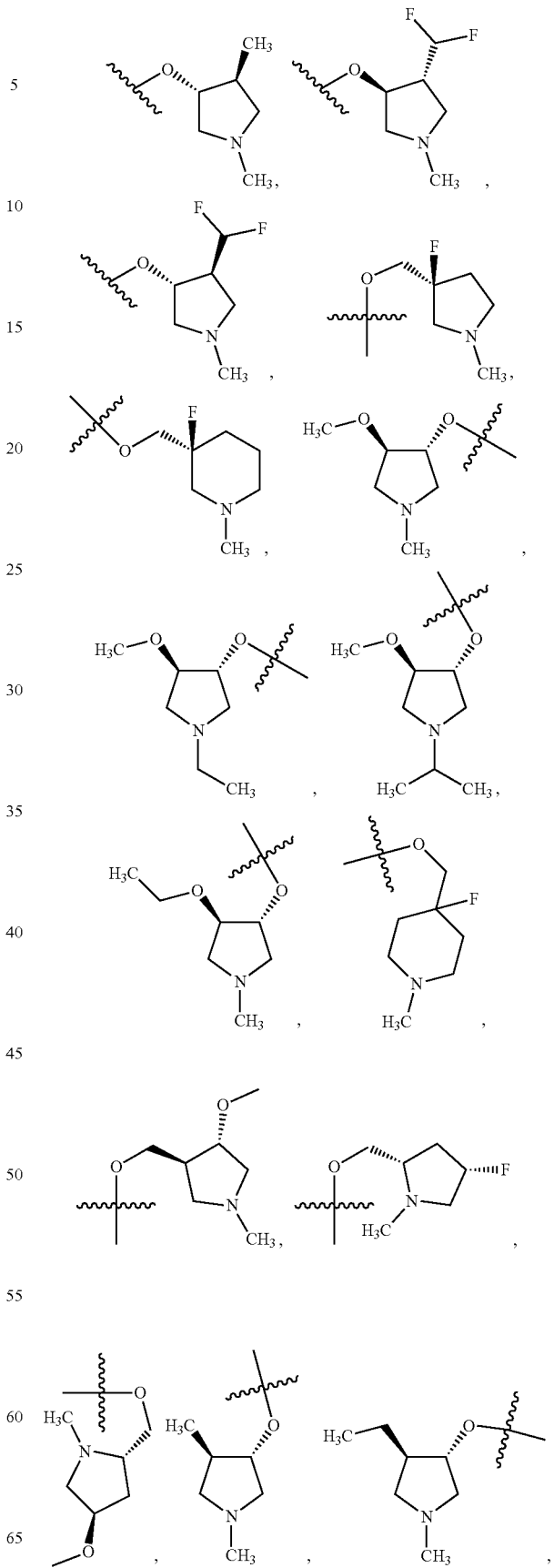

519
-continued

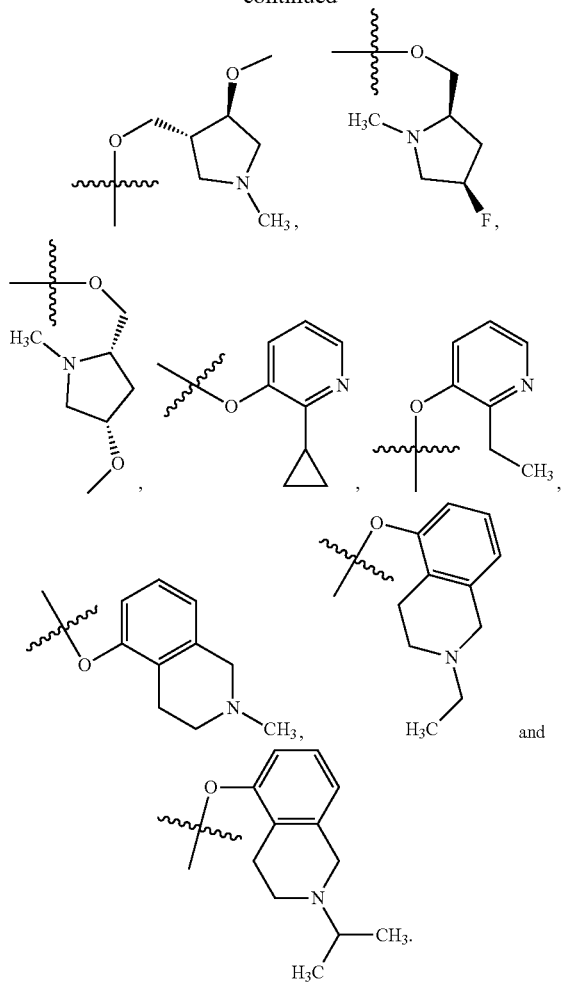

8. The compound or salt of claim 6 or 7, wherein R⁴ is selected from the group consisting of:

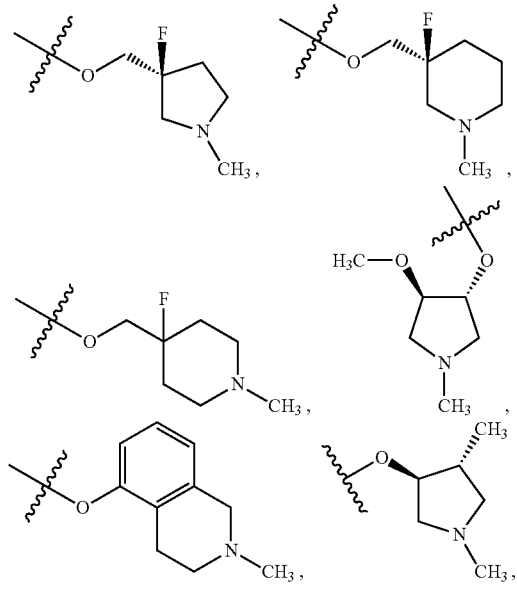

520
-continued

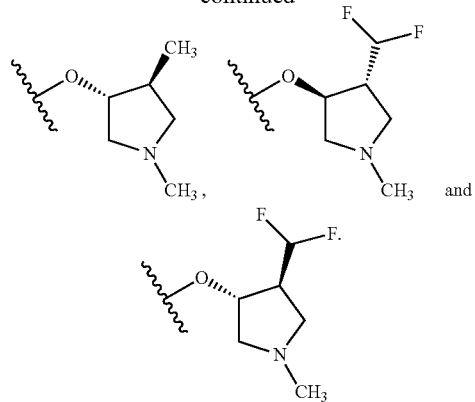

9. A compound of Formula (III):

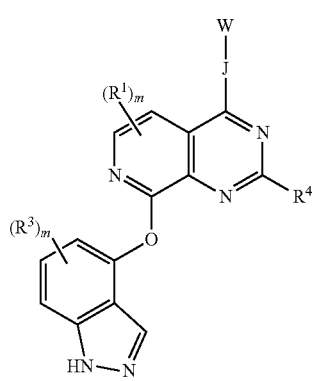
Formula (III)

or a pharmaceutically acceptable salt thereof; wherein:
J is:

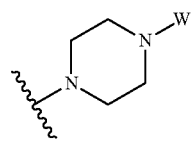

where W* represents the point of attachment to W, and where J is optionally substituted with 1 or more R²;
W is selected from the group consisting of:

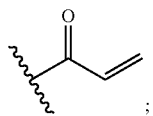 [SMILES: *C(=O)C=C]

each R¹ is independently selected from the group consisting of $C_1$-$C_6$ alkyl, halogen, $C_1$-$C_6$ haloalkyl, cyano and $N(R^6)_2$;
R² is $C_1$-$C_6$ alkyl;
each R³ is independently selected from the group consisting of $C_1$-$C_6$ alkyl, hydroxy, halogen, and $C_1$-$C_6$ haloalkyl;

$R^4$ is —X—Y—Z where:
  X is absent or is oxygen,
  Y is absent or $C_1$-$C_6$ alkylenyl, and
  Z is selected from H, heterocycle having 3-12 ring atoms and $C_3$-$C_6$ cycloalkyl,
where $R^4$ is optionally substituted with $R^7$;
each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;
each $R^7$ is independently $R^{7'}$ or $C_1$-$C_6$ alkyl-$R^{7'}$, where each $R^{7'}$ is independently selected from the group consisting of: $C_1$-$C_6$ alkyl and —N$(R^6)_2$; and
each m is independently 0, 1, 2 or 3.

10. The compound or salt of claim 9, wherein

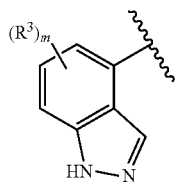

is selected from the group consisting of:

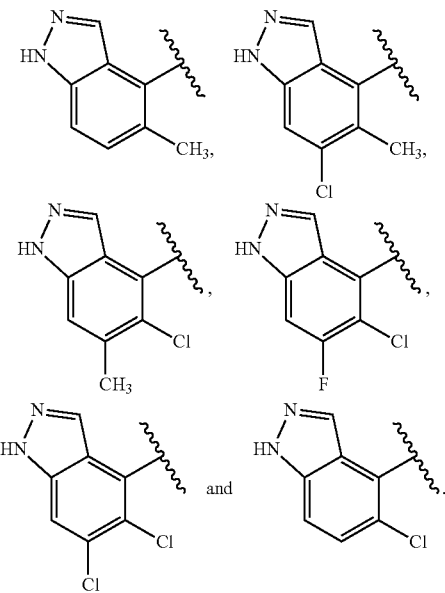

11. The compound or salt of claim 9, wherein $R^4$ is selected from the group consisting of:

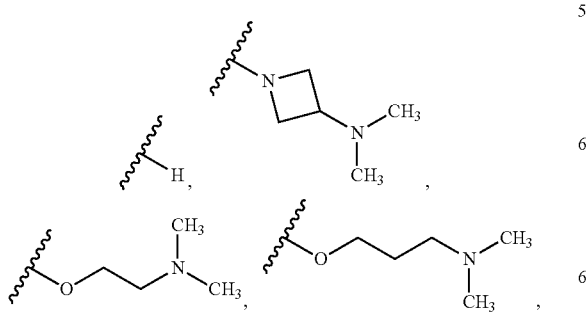

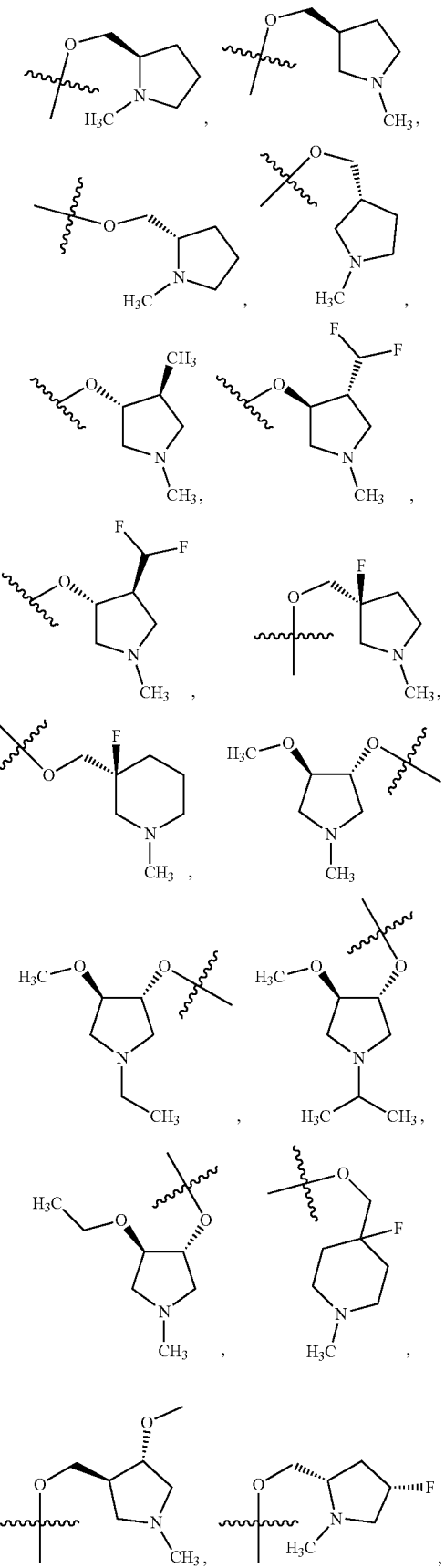

523
-continued
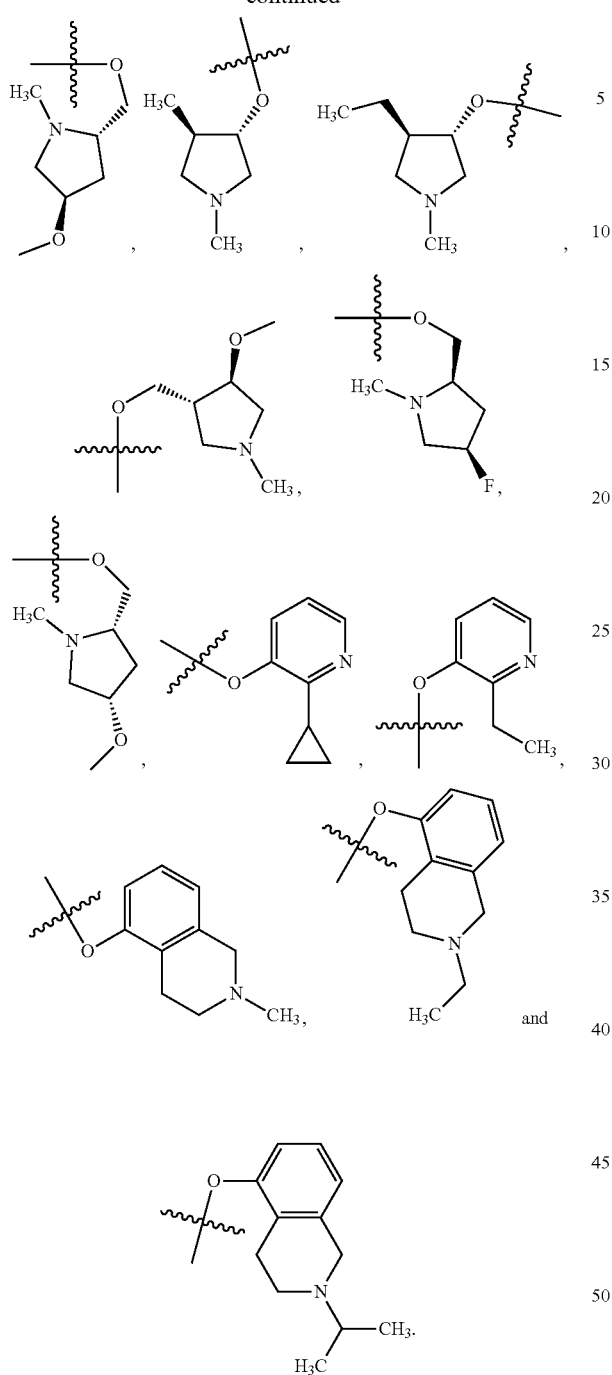
12. The compound or salt of claim 9, wherein $R^4$ is selected from the group consisting of:
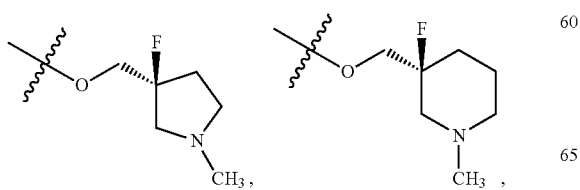
524
-continued
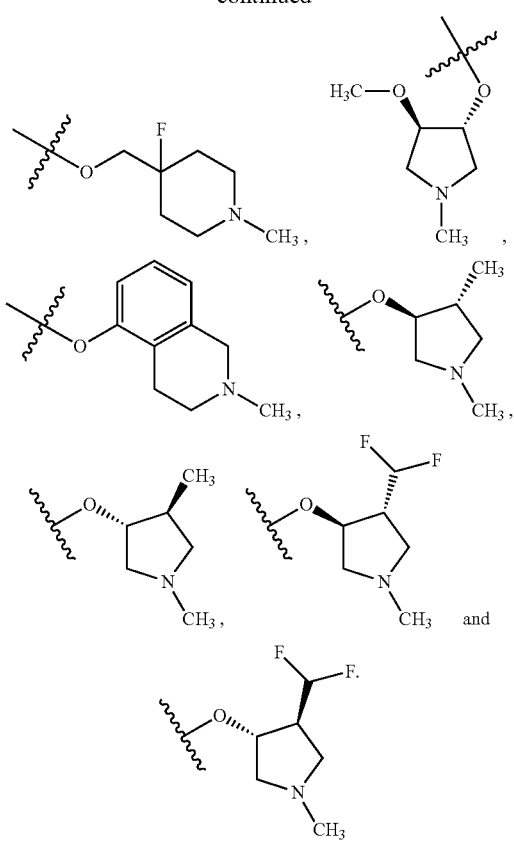
13. A compound of Formula (IV):
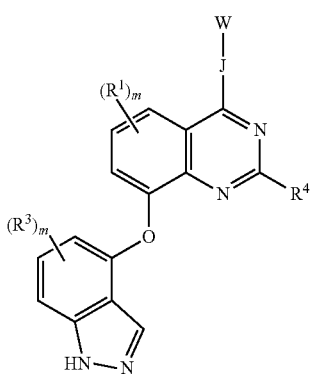
Formula (IV)
or a pharmaceutically acceptable salt thereof; wherein:
J is:
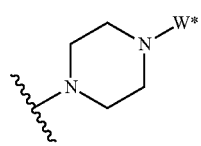
where W* represents the point of attachment to W, and where J is optionally substituted with 1 or more $R^2$;

W is selected from the group consisting of:

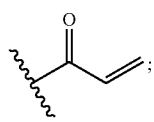 [SMILES: *C(=O)C=C]

each R¹ is independently selected from the group consisting of $C_1$-$C_6$ alkyl, halogen, $C_1$-$C_6$ haloalkyl, cyano and $N(R^6)_2$;
$R^2$ is $C_1$-$C_6$ alkyl;
each $R^3$ is independently selected from the group consisting of $C_1$-$C_6$ alkyl, hydroxy, halogen, and $C_1$-$C_6$ haloalkyl;
$R^4$ is —X—Y—Z where:
  X is absent or is oxygen,
  Y is absent or $C_1$-$C_6$ alkylenyl, and
  Z is selected from H, heterocycle having 3-12 ring atoms and $C_3$-$C_6$ cycloalkyl,
where $R^4$ is optionally substituted with $R^7$;
each $R^6$ is independently selected from the group consisting of hydrogen, hydroxyl, $C_1$-$C_6$ alkoxy and $C_1$-$C_6$ alkyl, or two $R^6$ optionally join to form heterocycle having 3-12 ring atoms or $C_3$-$C_6$ cycloalkyl;
each $R^7$ is independently $R^{7'}$ or $C_1$-$C_6$ alkyl-$R^{7'}$, where each $R^{7'}$ is independently selected from the group consisting of: $C_1$-$C_6$ alkyl and —$N(R^6)_2$; and
each m is independently is 0, 1, 2 or 3.

14. The compound or salt of claim 13, wherein is selected from the group consisting of:

15. The compound or salt of claim 13, wherein $R^4$ is selected from the group consisting of:

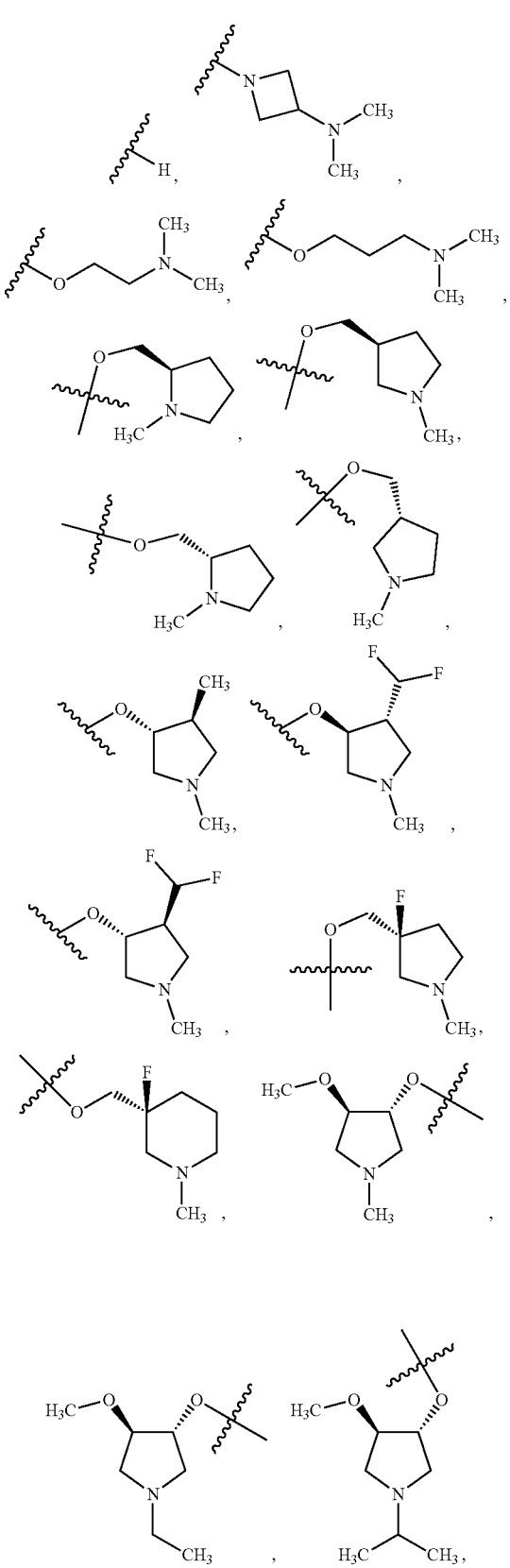

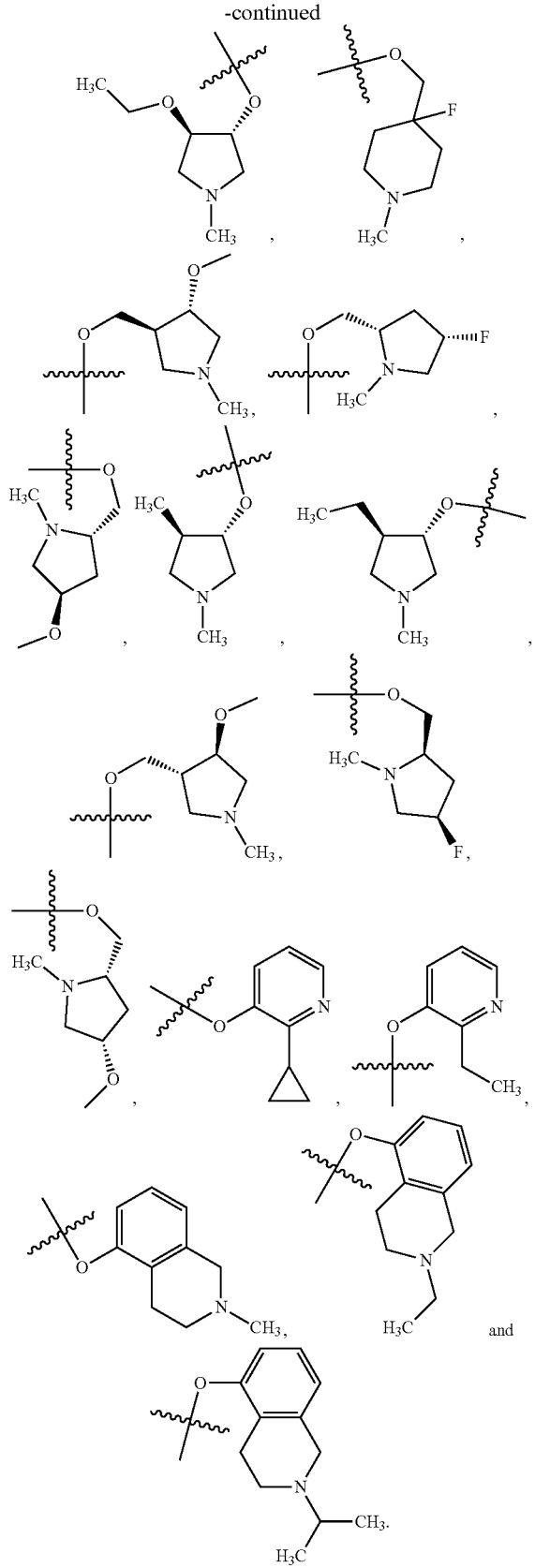
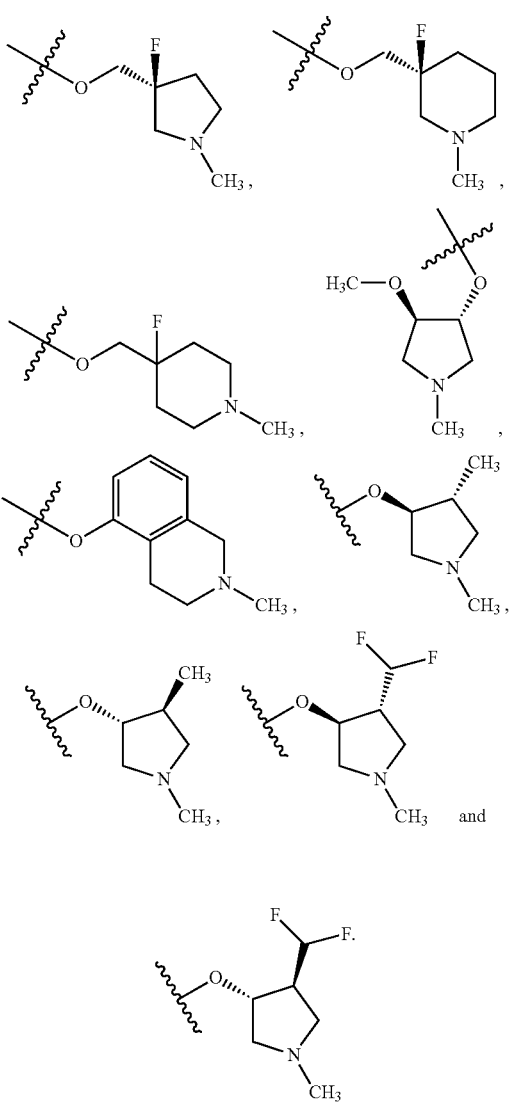
17. A compound selected from the group consisting of:
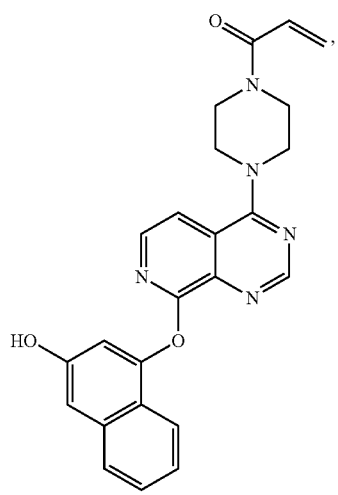
16. The compound or salt of claim 13, wherein $R^4$ is selected from the group consisting of:

529
-continued
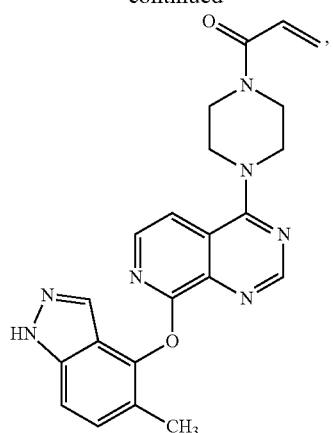
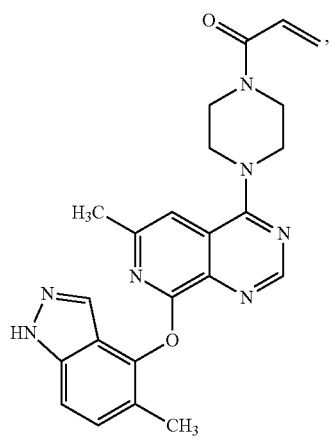
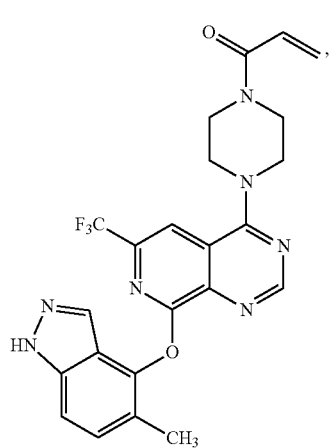
530
-continued
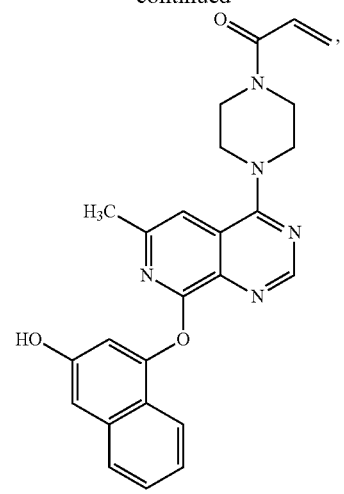
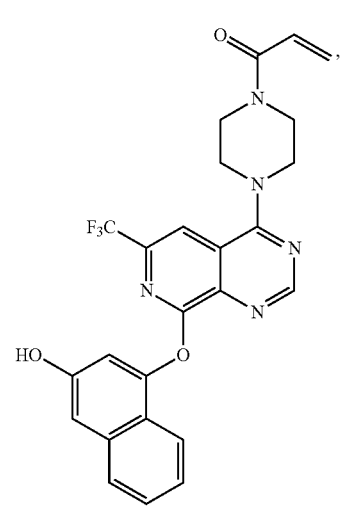
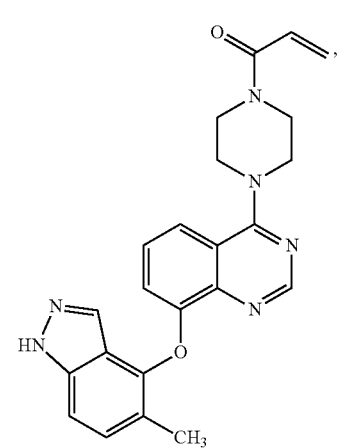

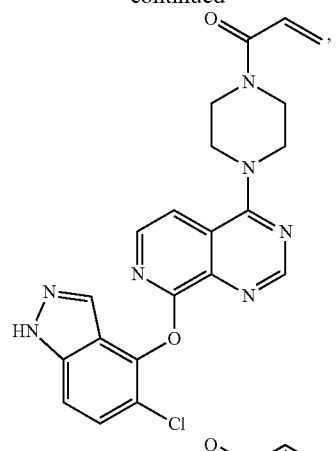
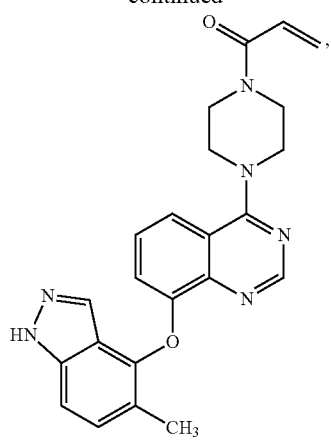
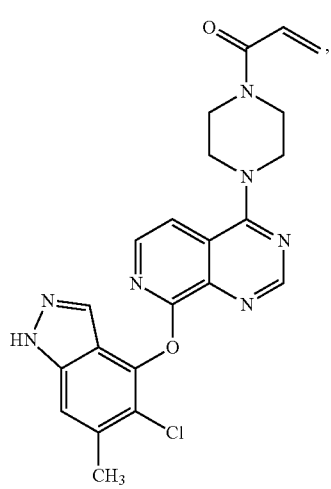
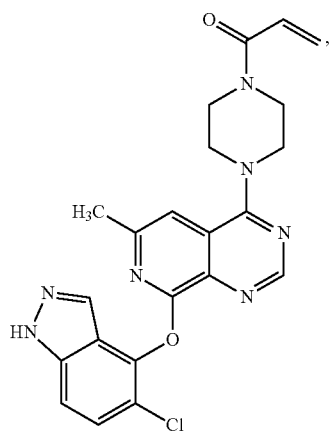

533
-continued
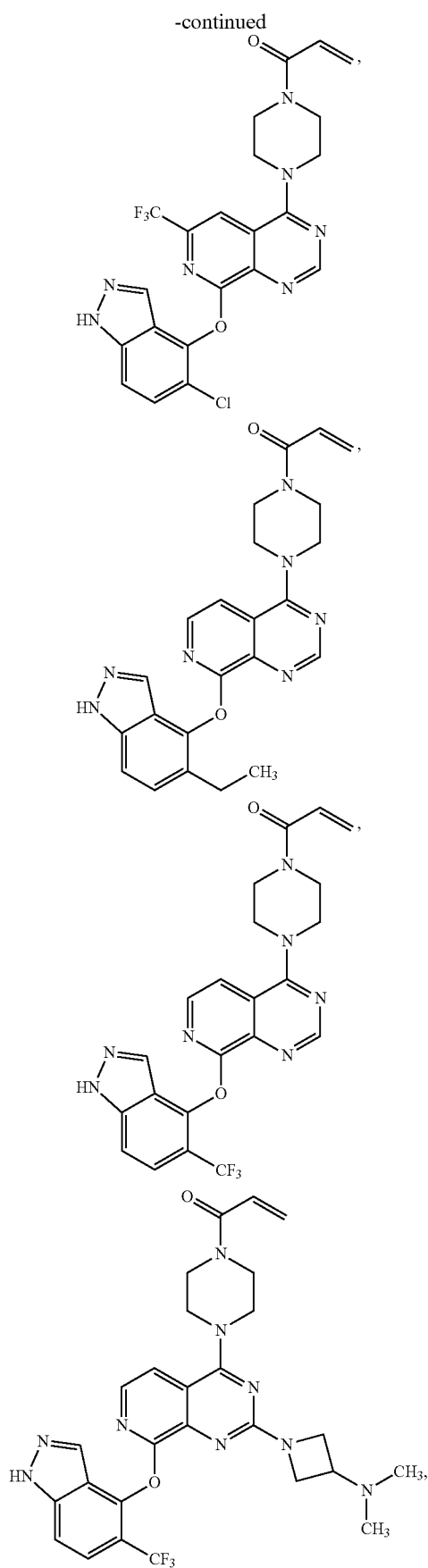
534
-continued
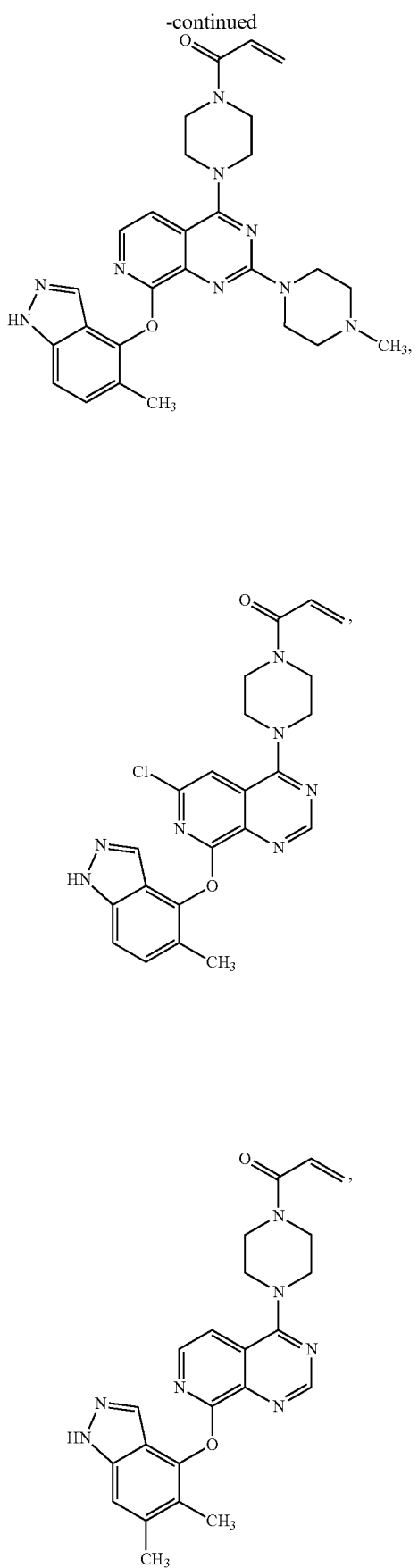

535
-continued
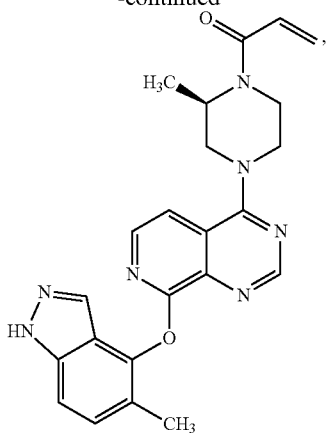
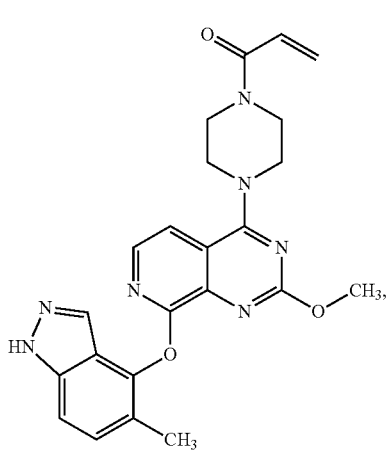
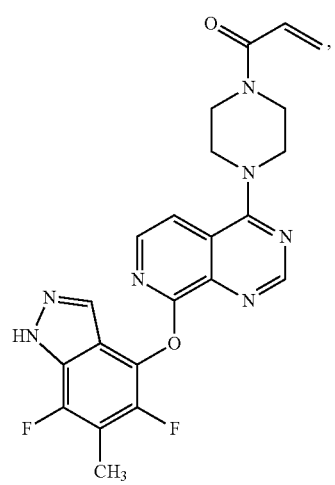
536
-continued
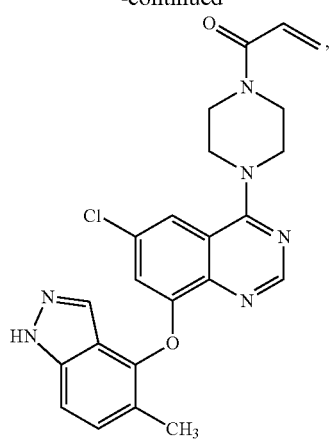
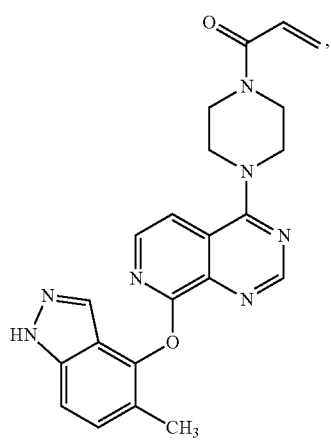
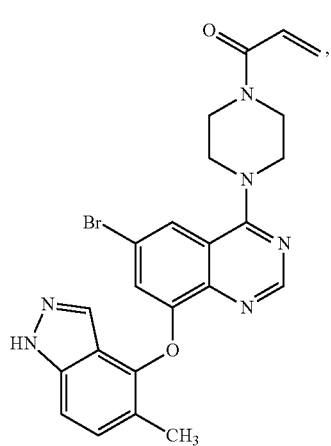

537
-continued
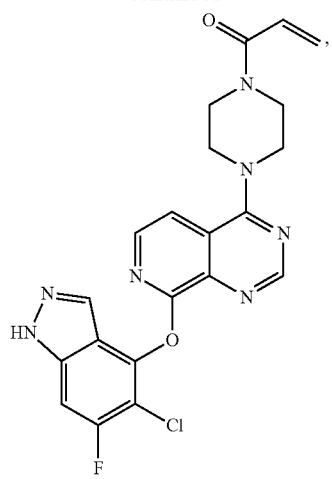
538
-continued
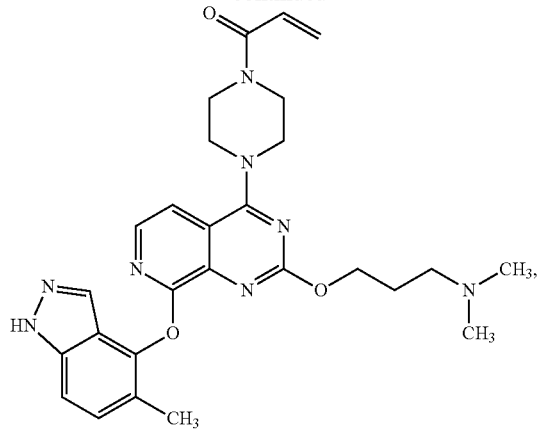
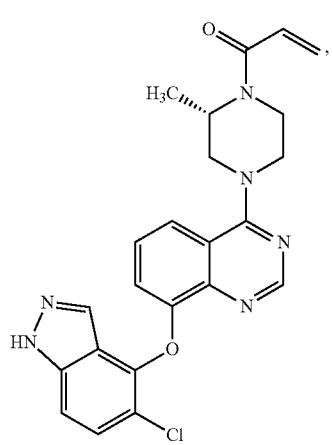
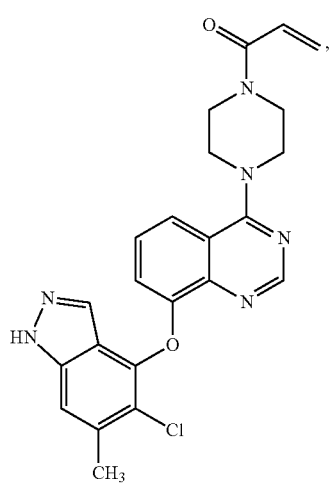
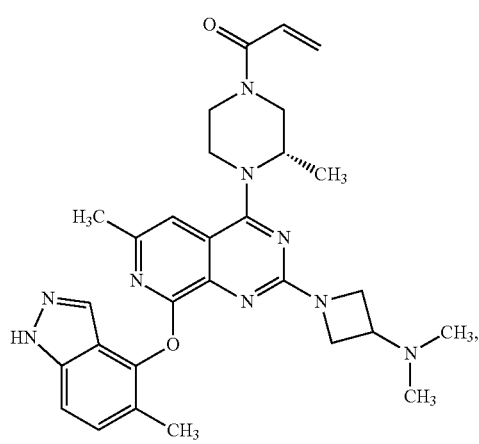
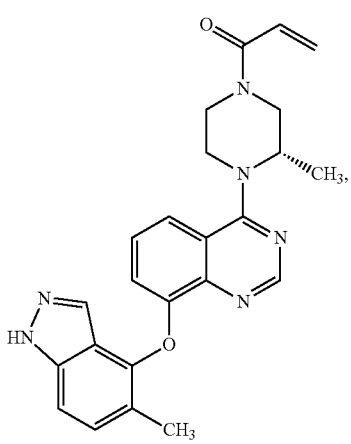

539
-continued
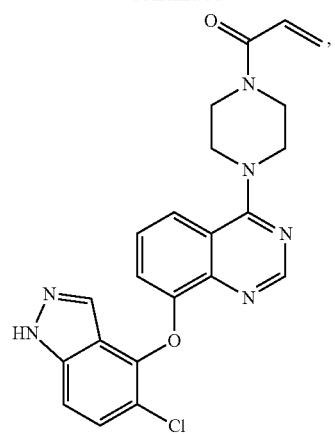
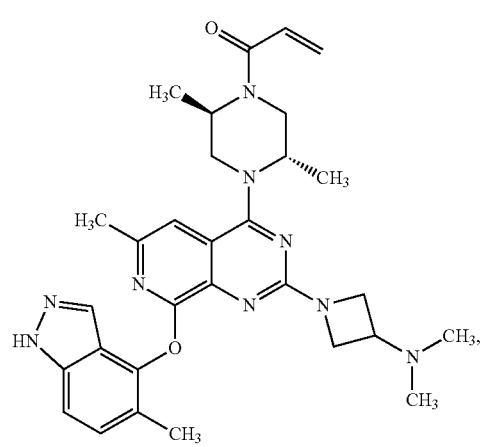
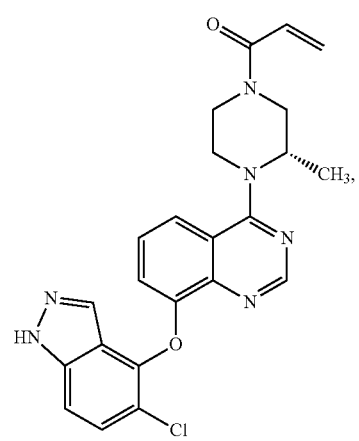
540
-continued
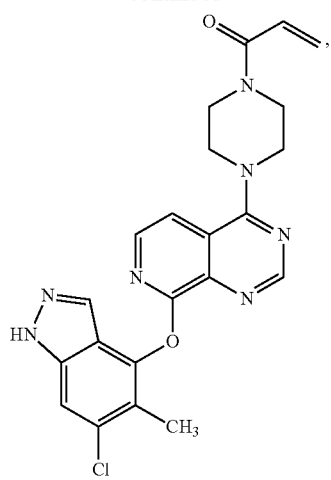
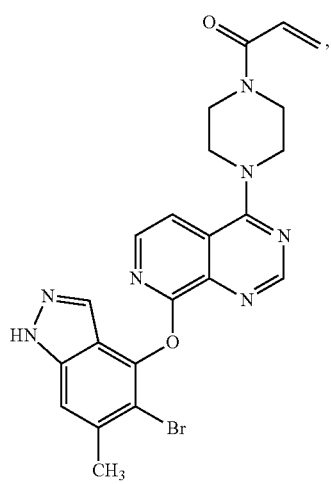
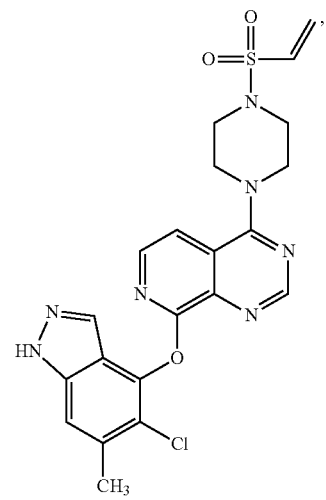

541
-continued
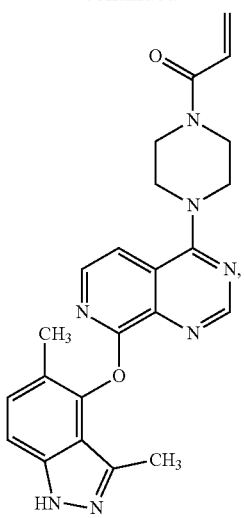
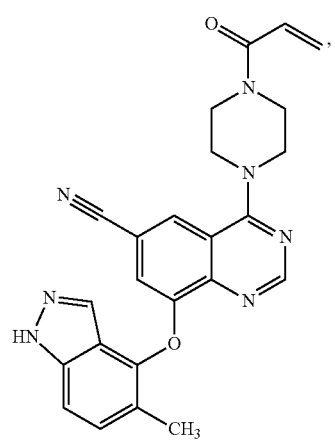
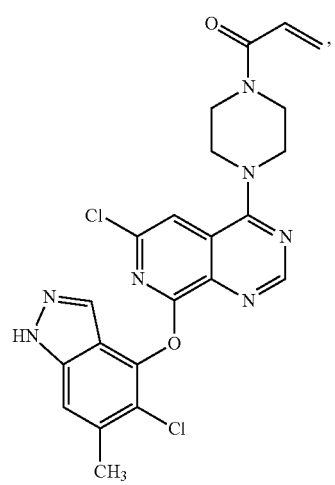
542
-continued
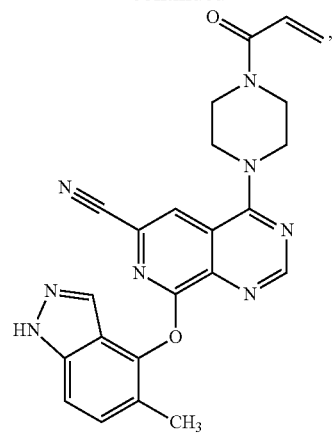
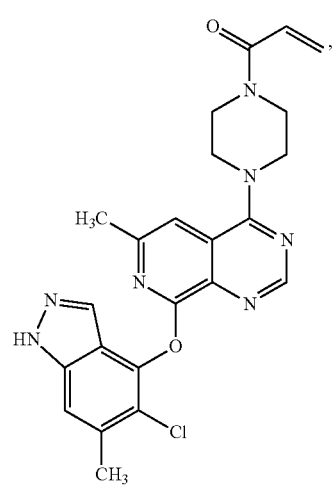
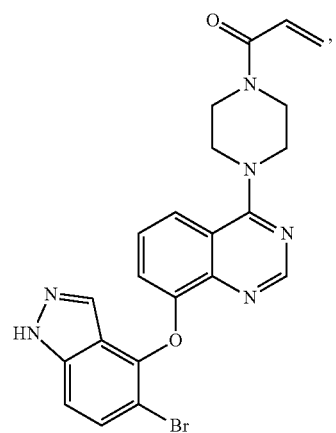

543
-continued
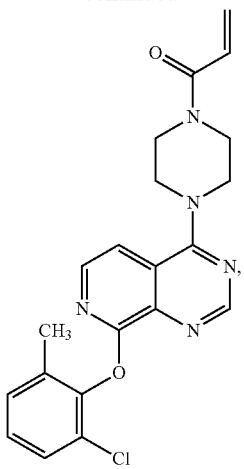
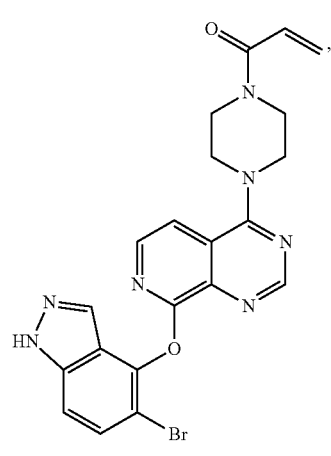
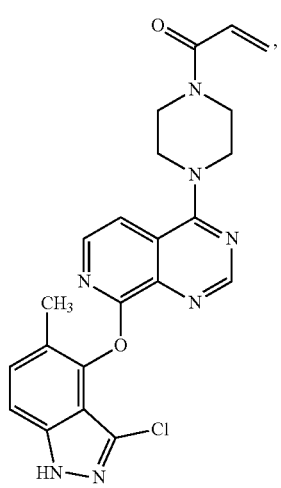
544
-continued
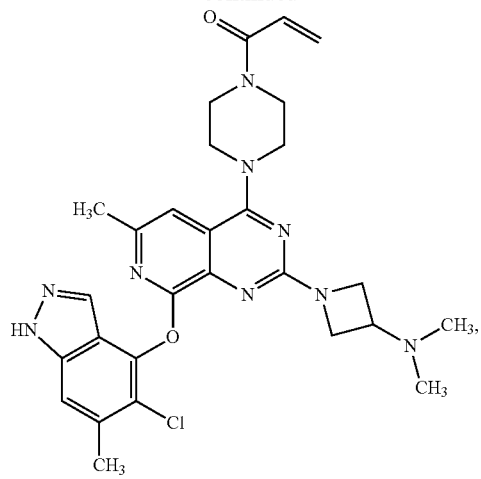
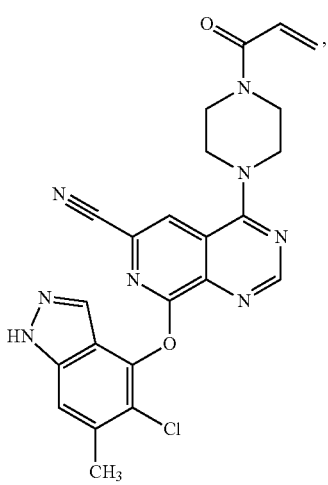
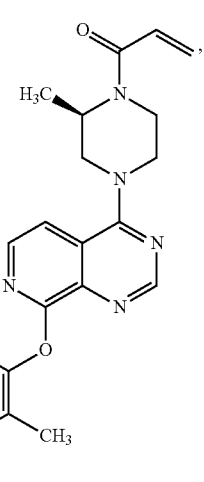

545
-continued
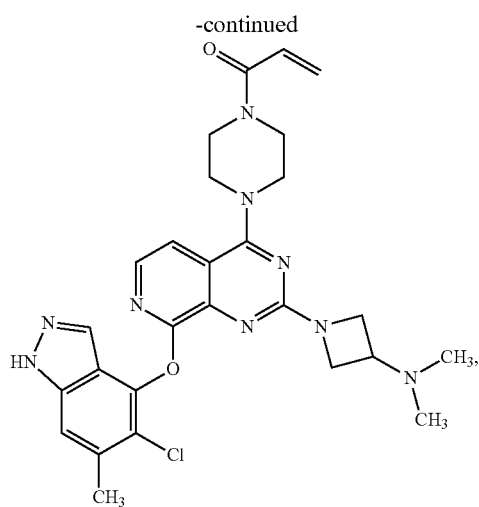
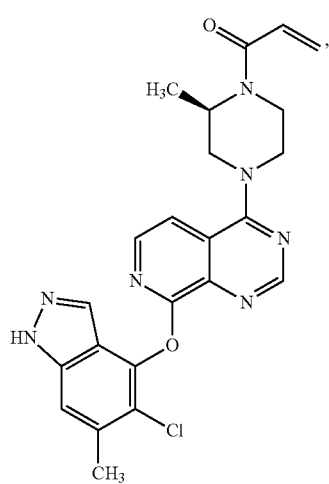
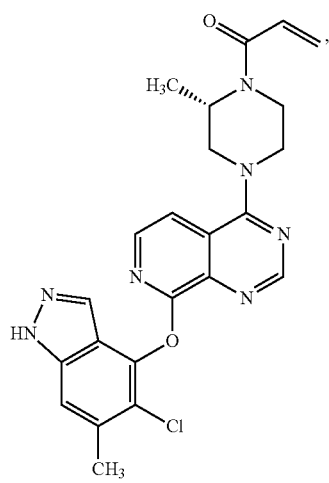
546
-continued
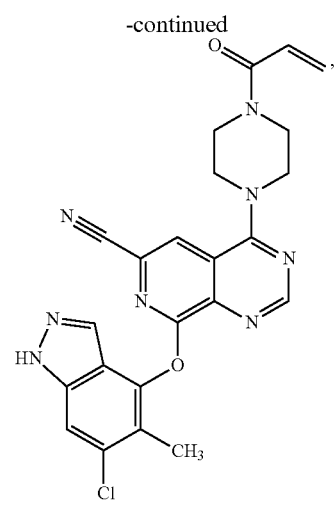
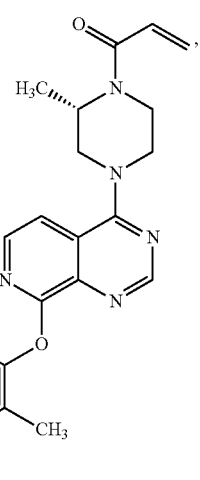
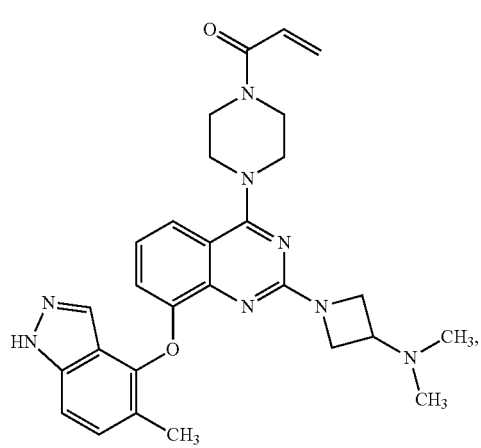

547
-continued
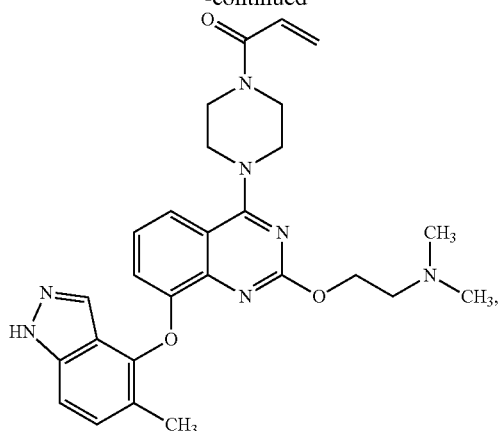
548
-continued
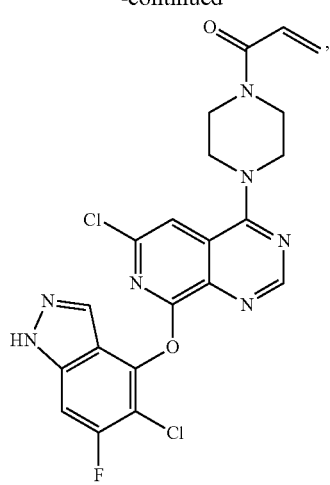
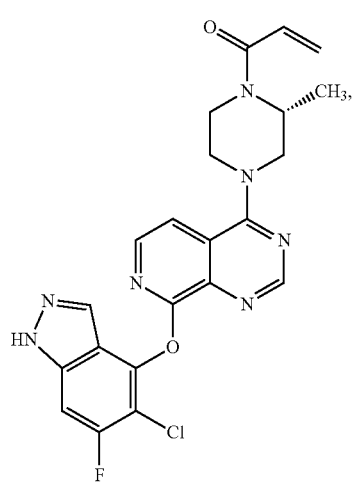
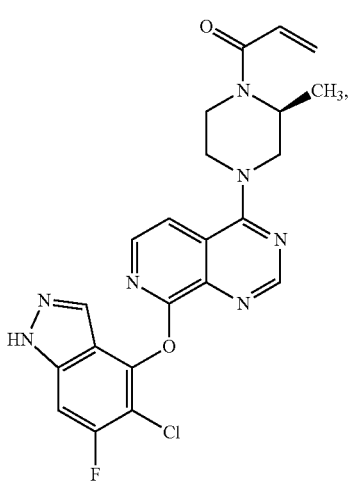
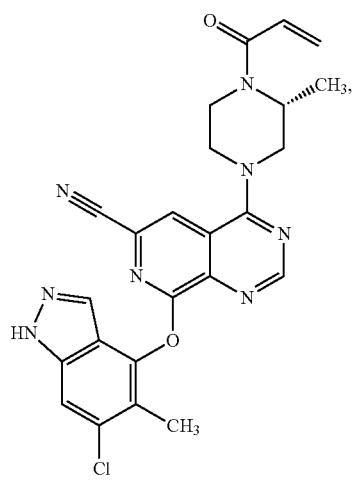
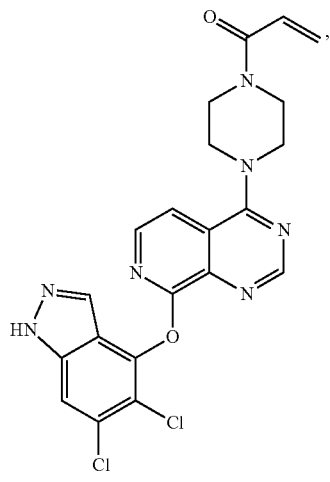

549
-continued
550
-continued
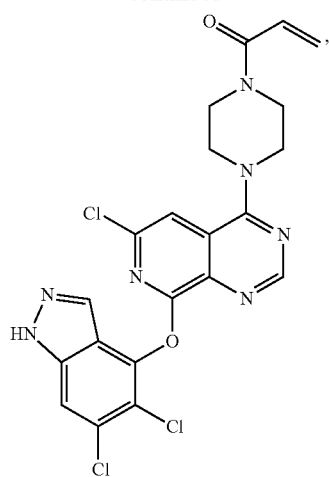
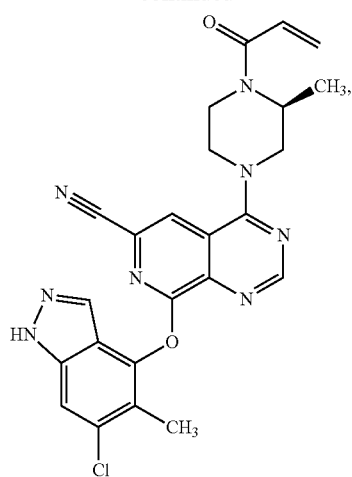
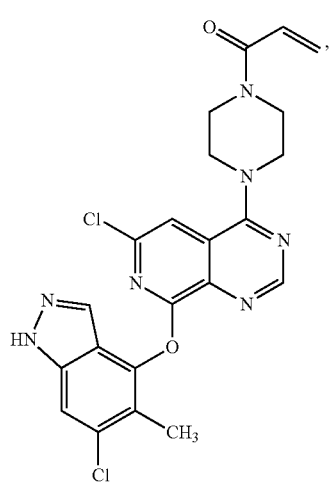
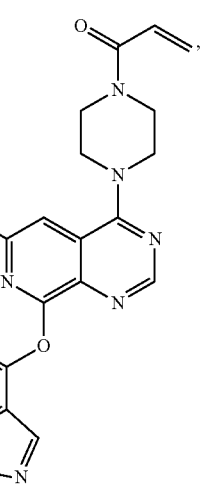
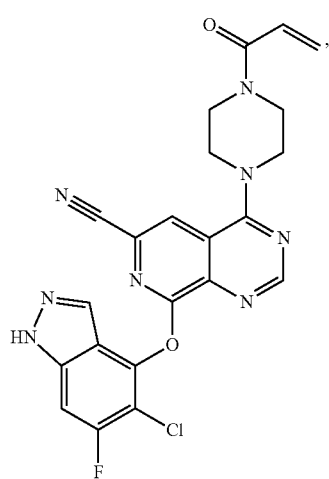
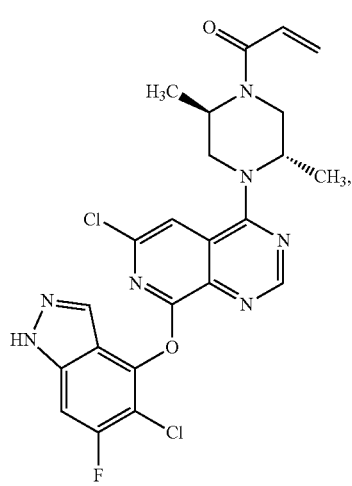

551
-continued
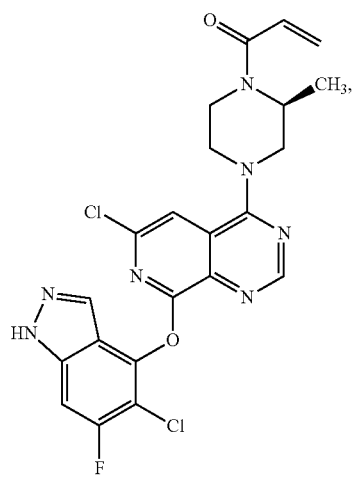
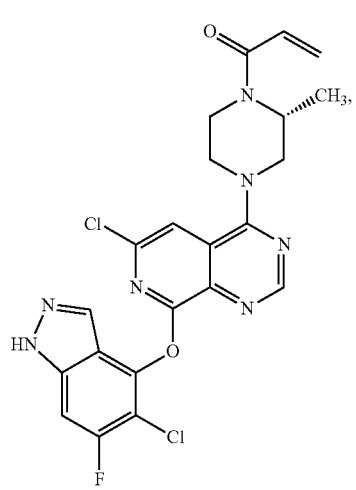
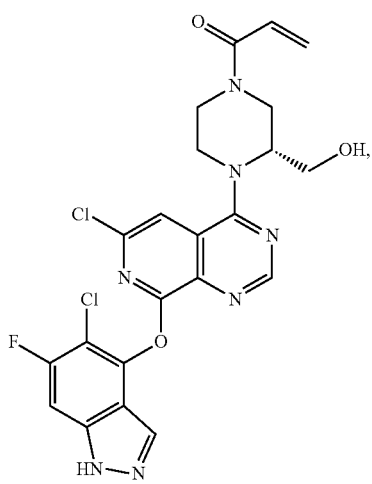
552
-continued
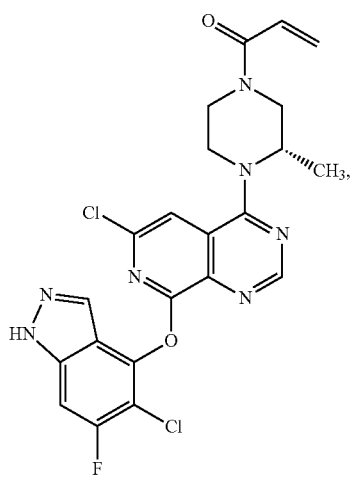
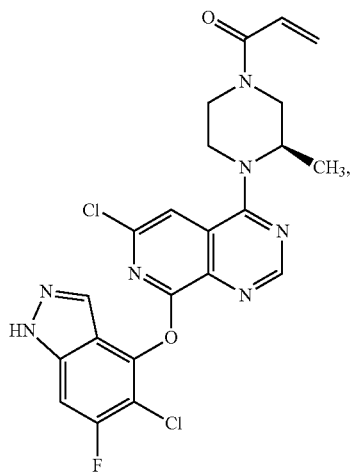
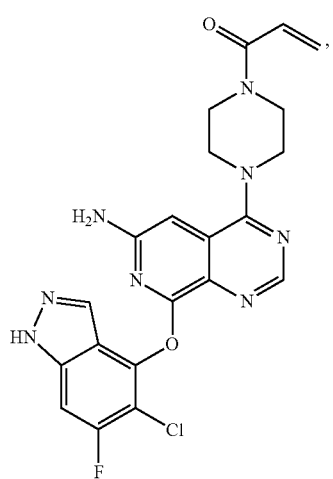

553
-continued
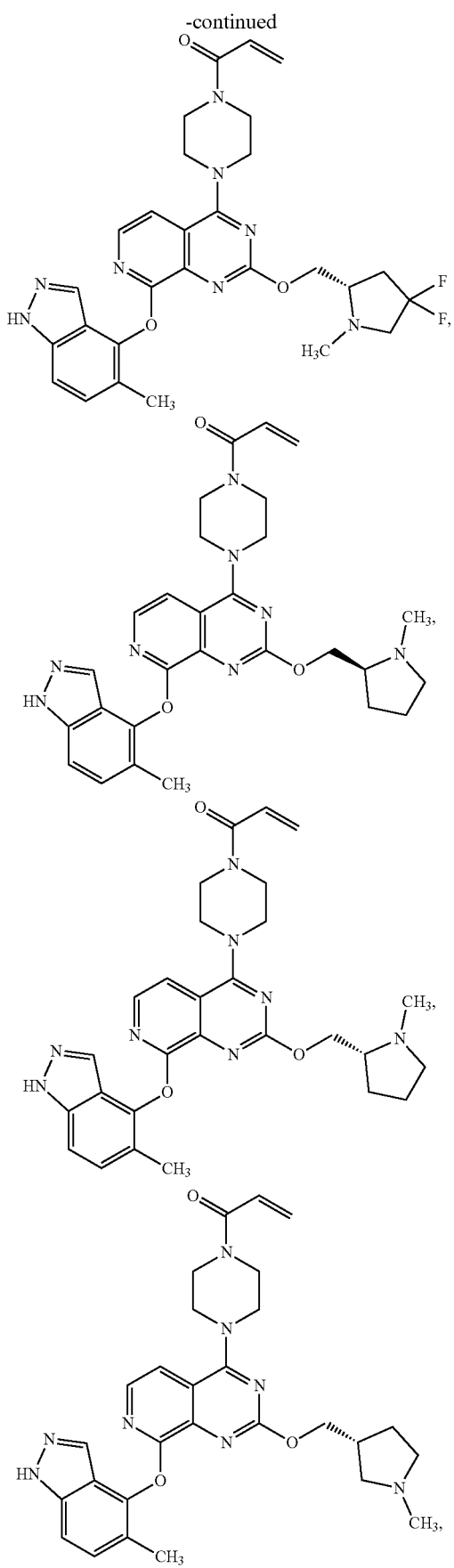
554
-continued
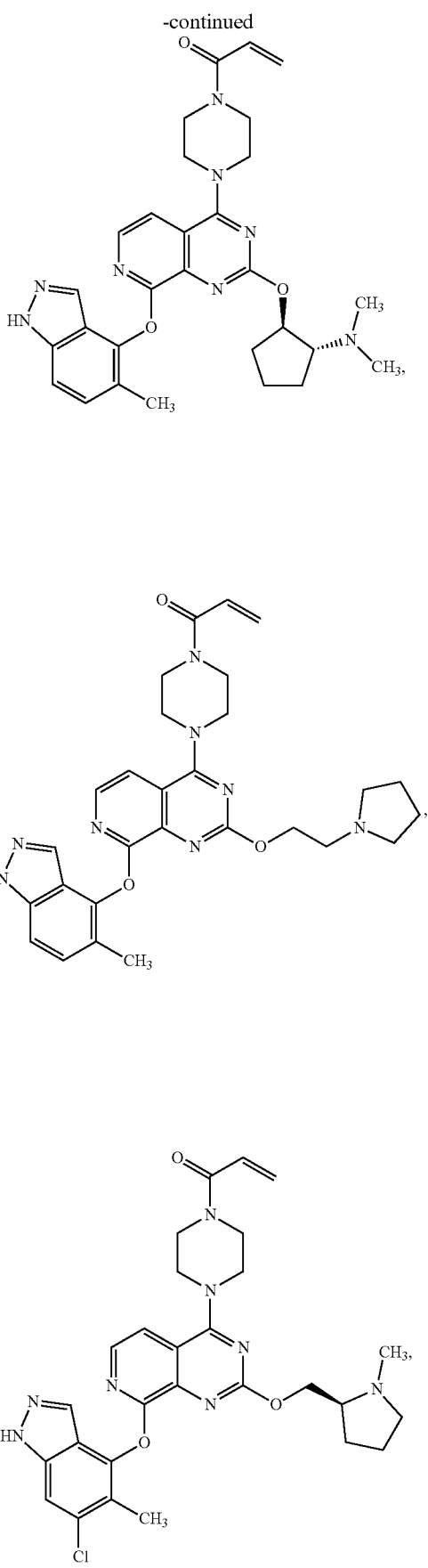

555
-continued
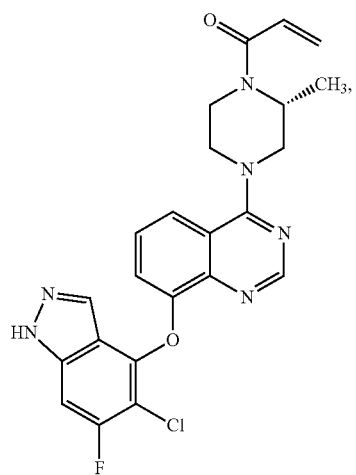
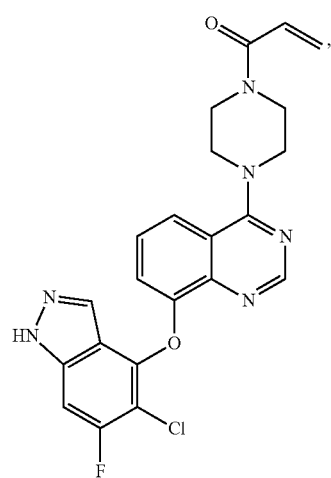
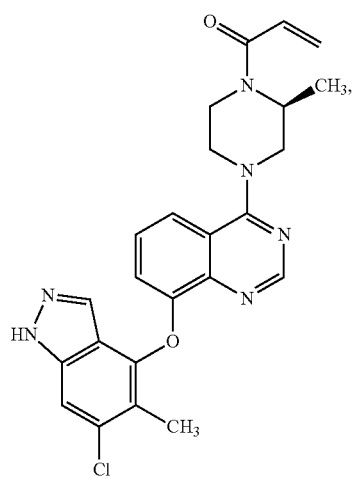
556
-continued
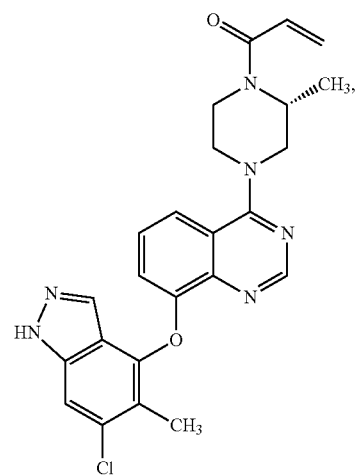
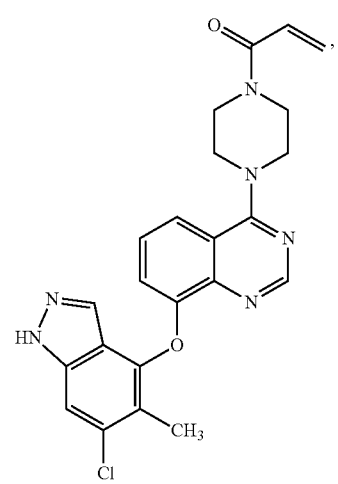
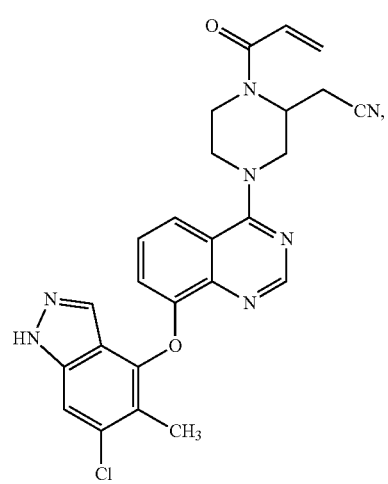

557 -continued

558 -continued

559
-continued
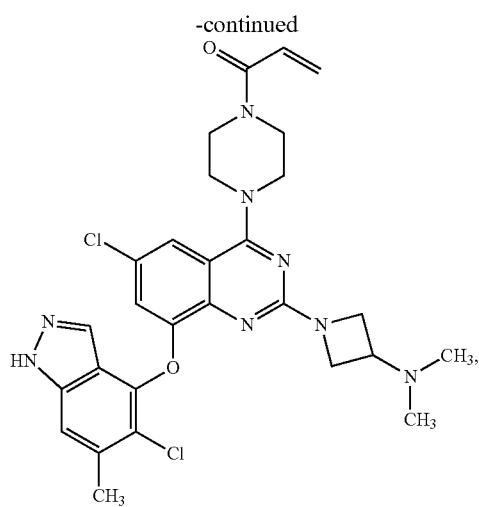
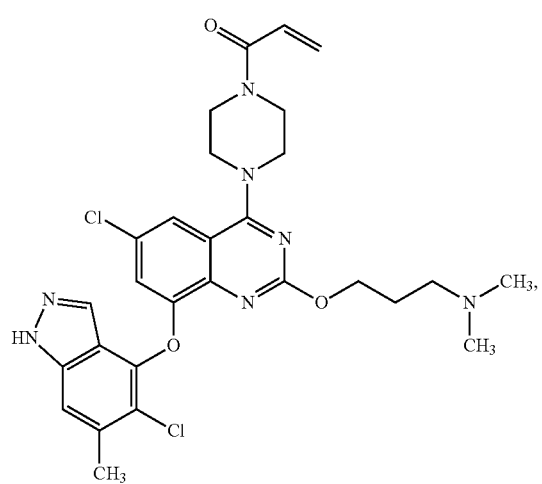
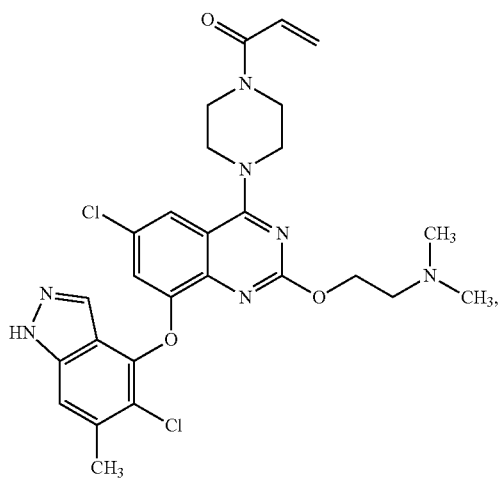
560
-continued
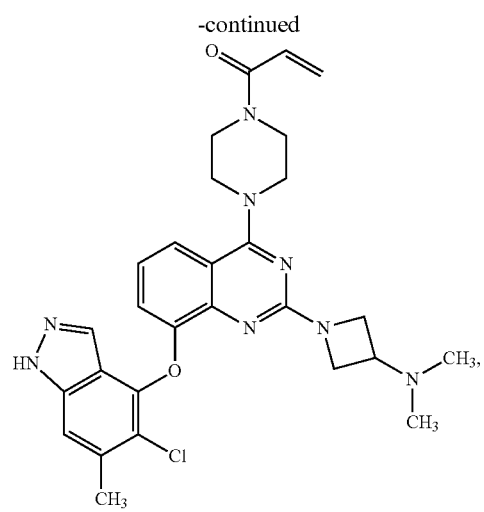
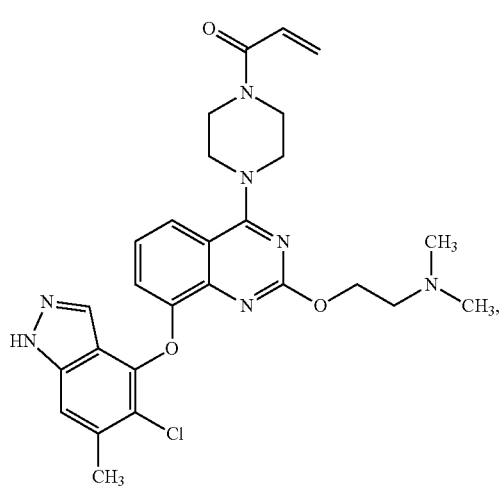
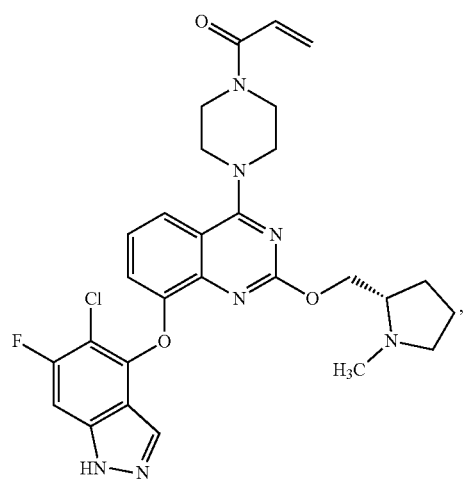

561
-continued
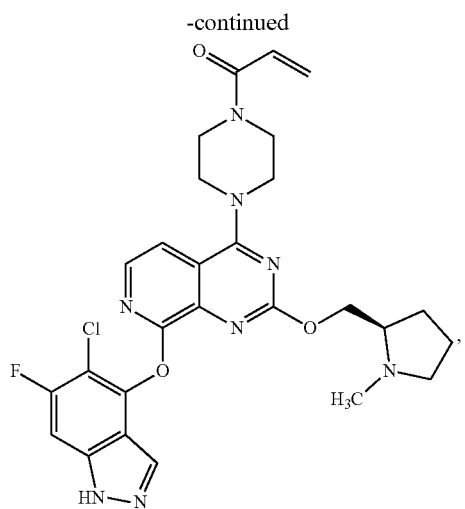
562
-continued
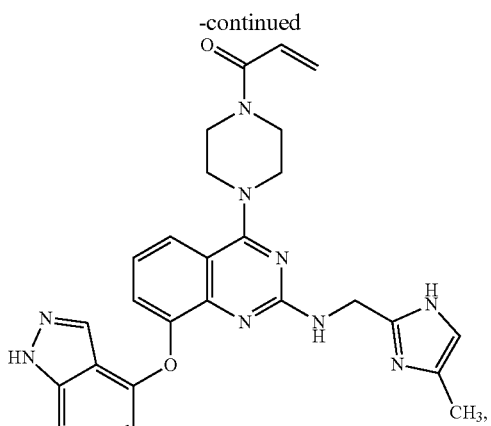
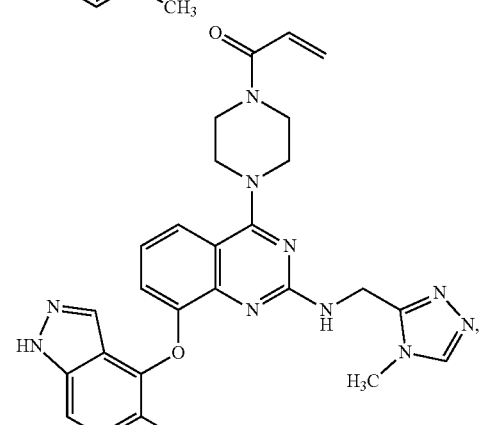
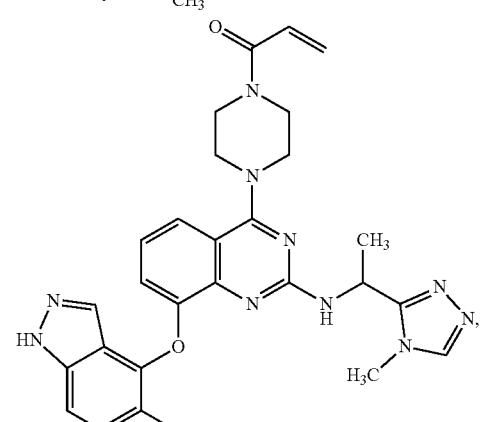
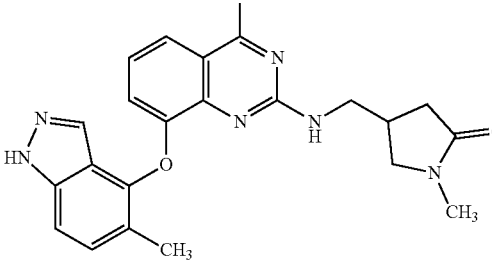

563
-continued
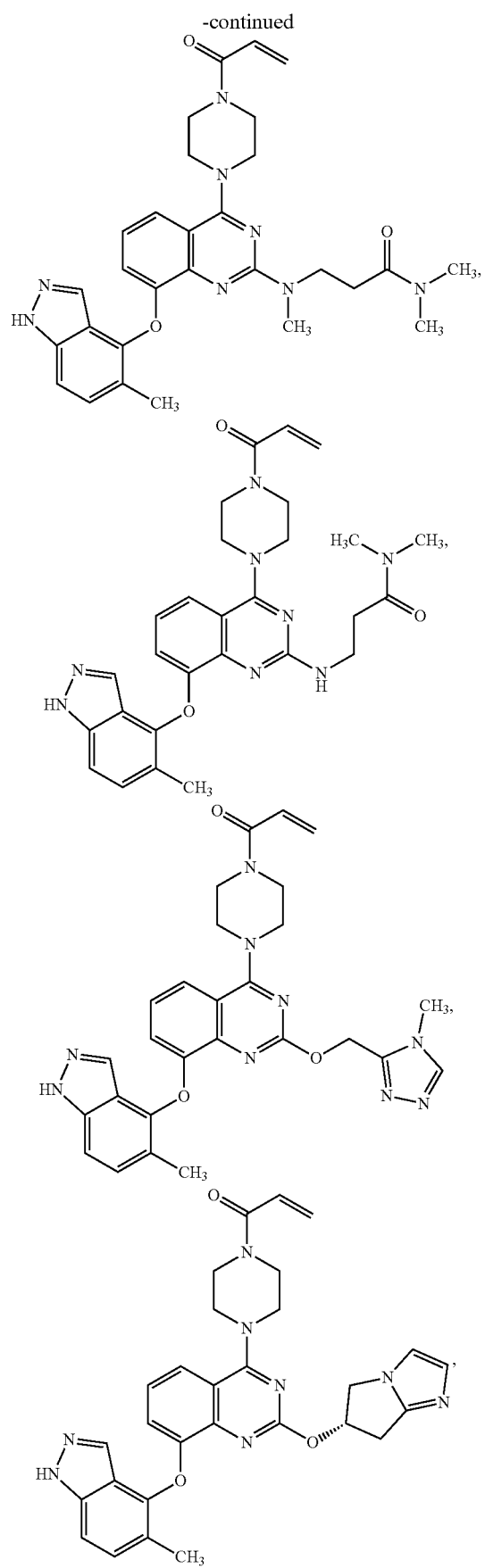
564
-continued
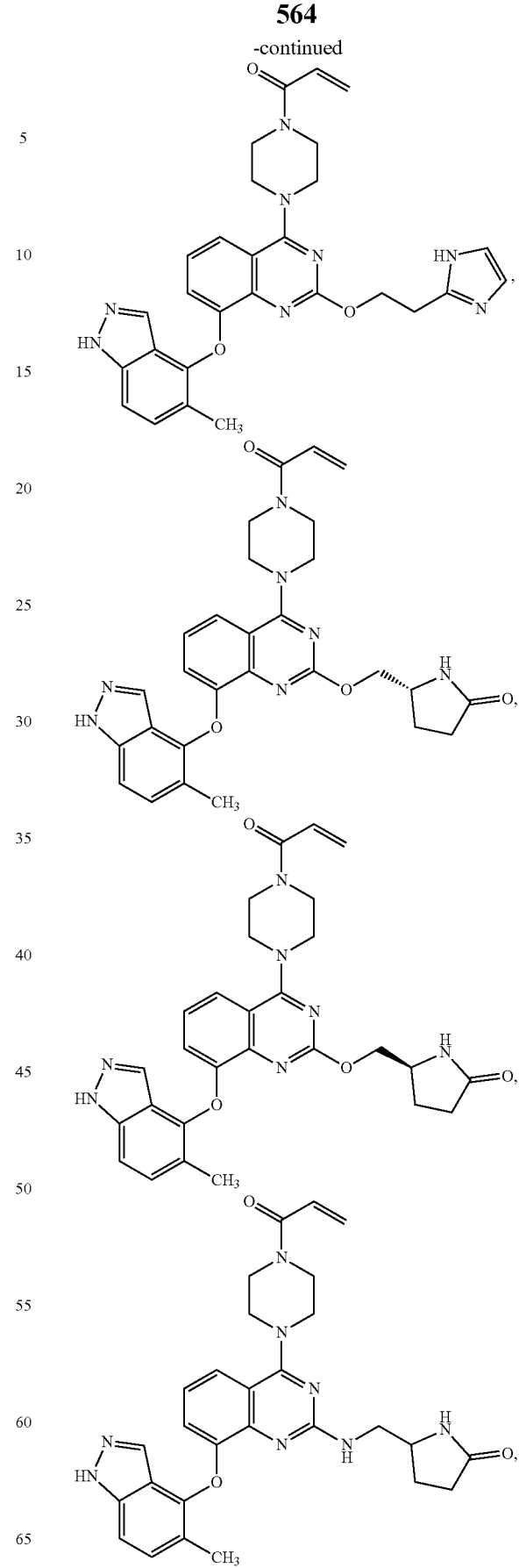

565
-continued
566
-continued
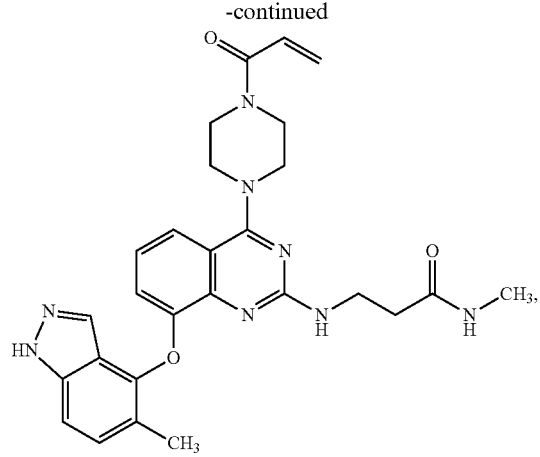
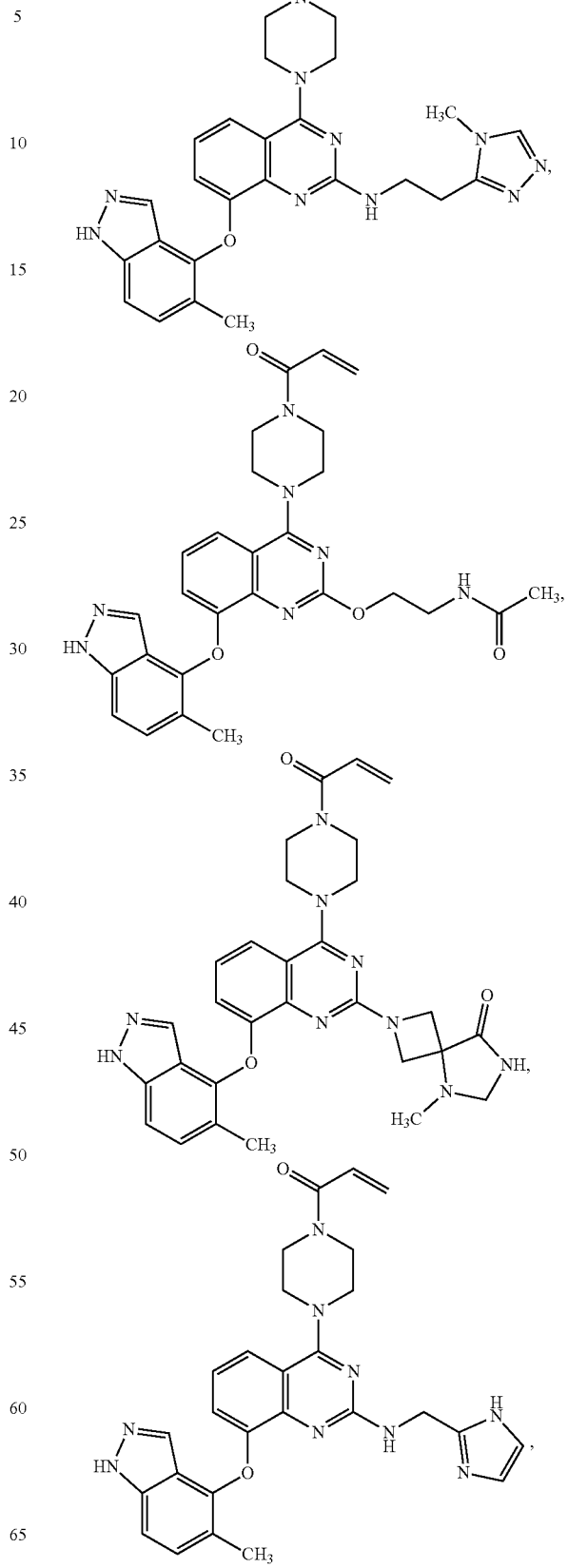

567
-continued
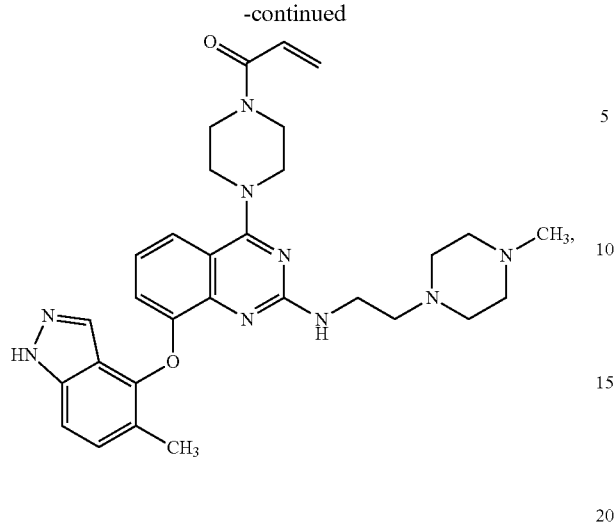
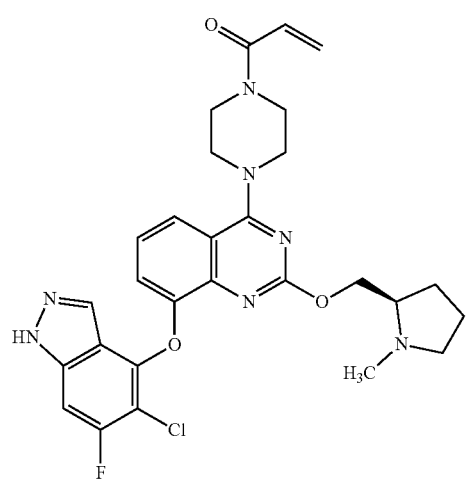
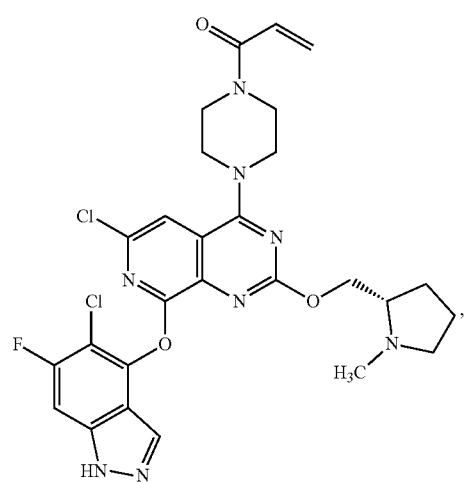
568
-continued
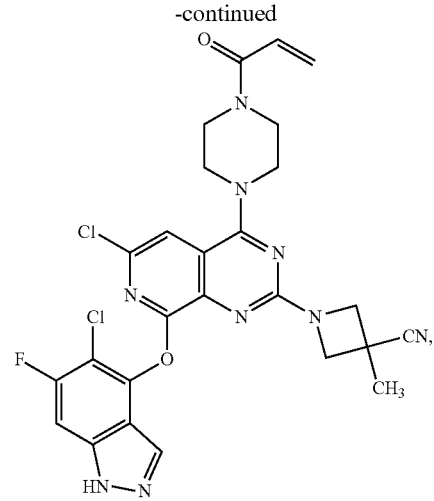
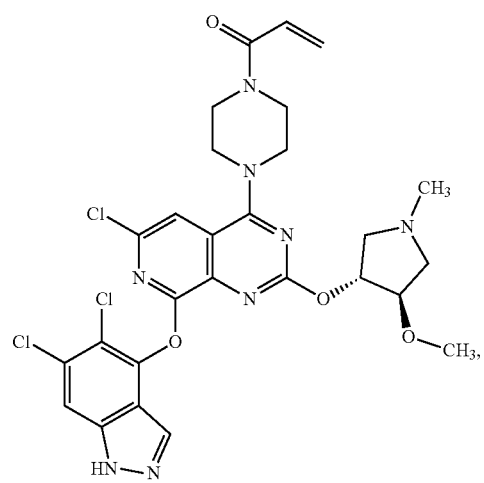
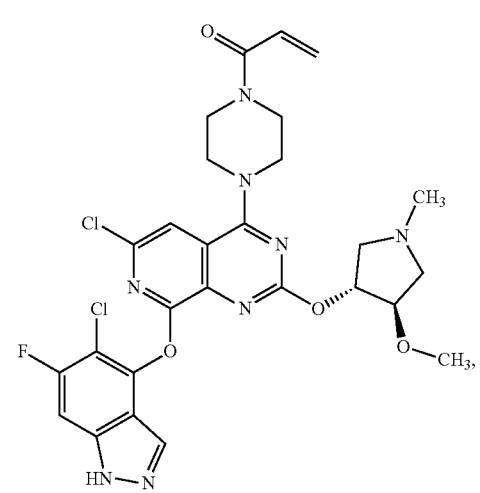

569
-continued
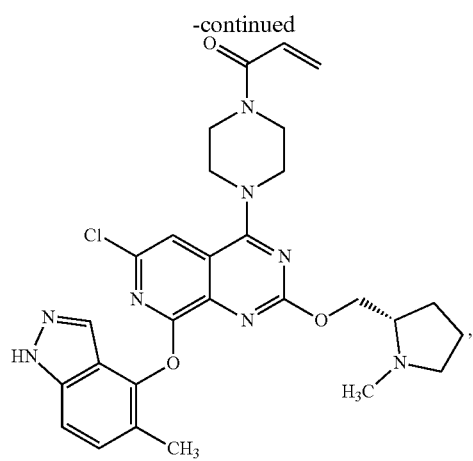
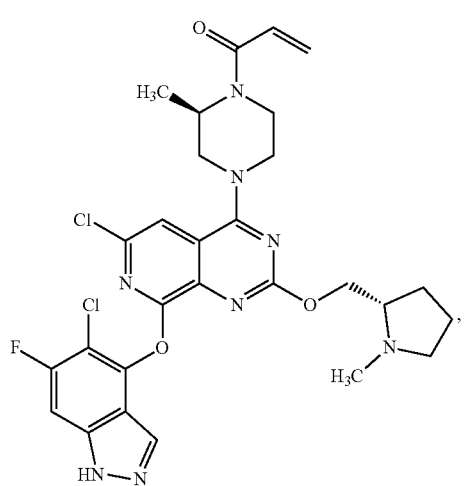
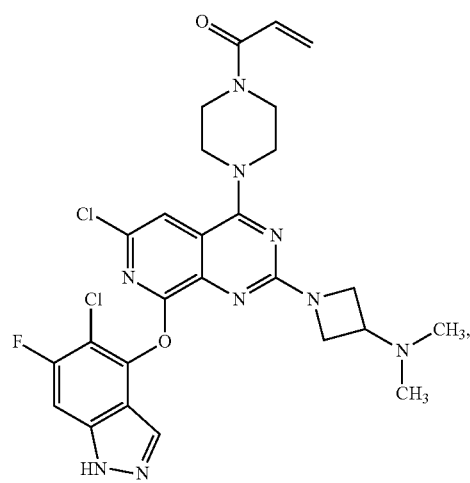
570
-continued
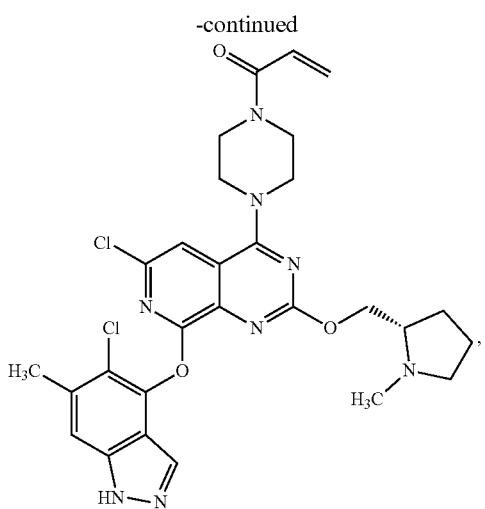
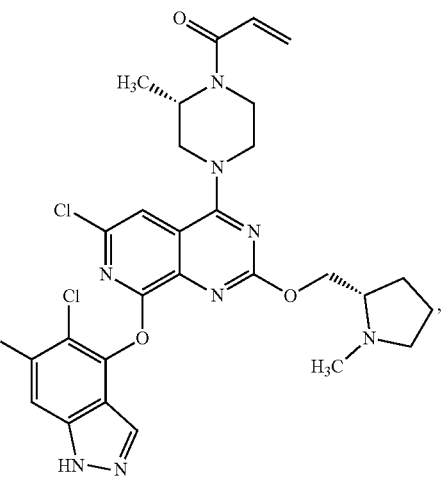
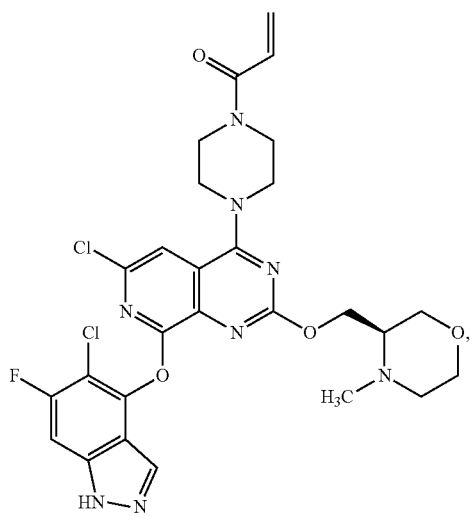

571
-continued
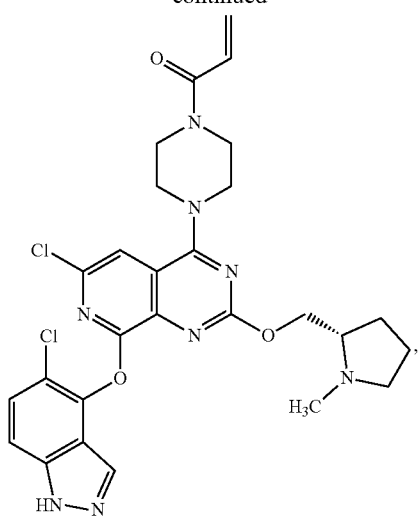
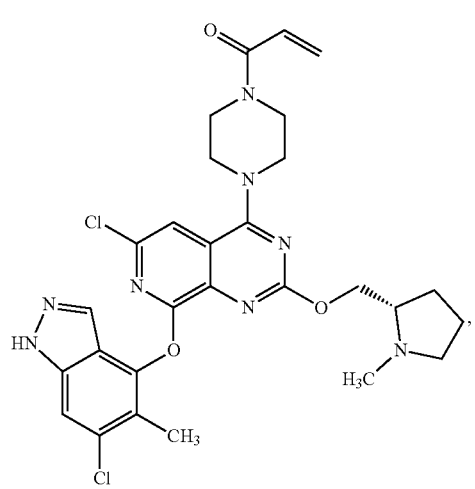
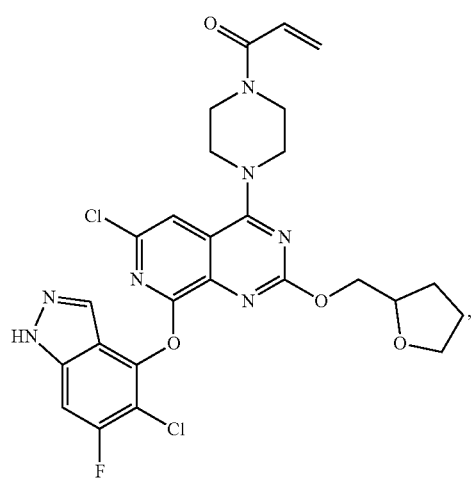
572
-continued
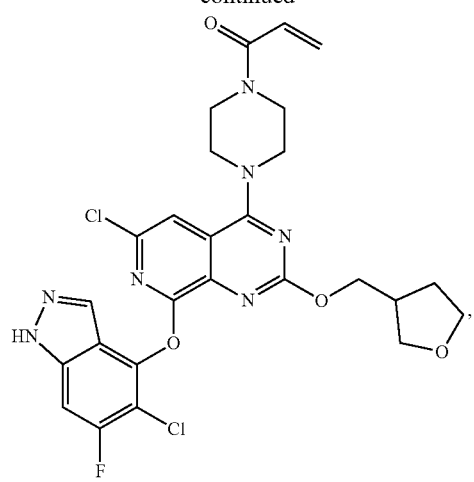
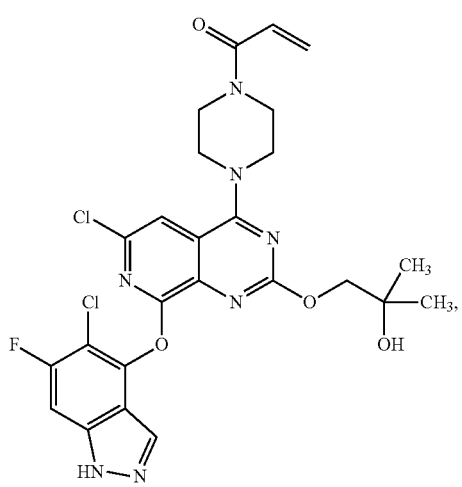
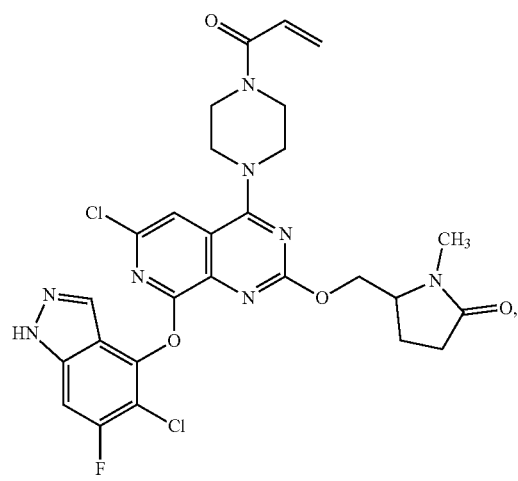

573
-continued
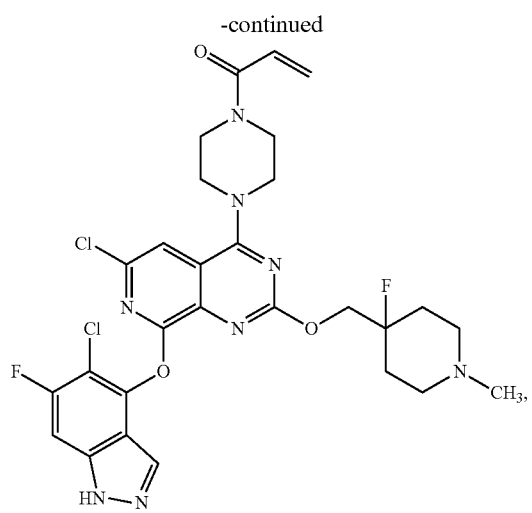
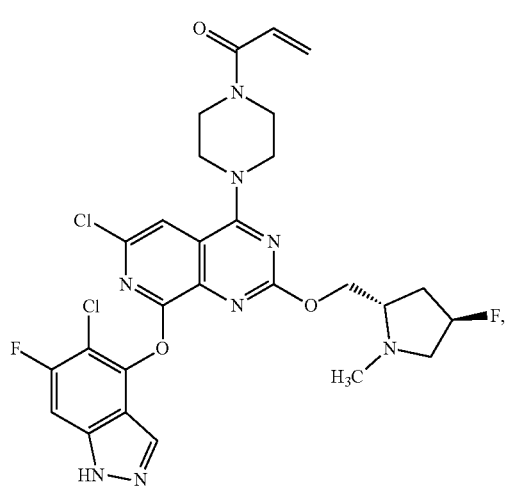 [SMILES: C=CC(=O)N1CCN(c2nc(OC[C@@H]3C[C@@H](F)CN3C)nc3c(Oc4c(Cl)c(F)cc5[nH]ncc45)nc(Cl)cc23)CC1]
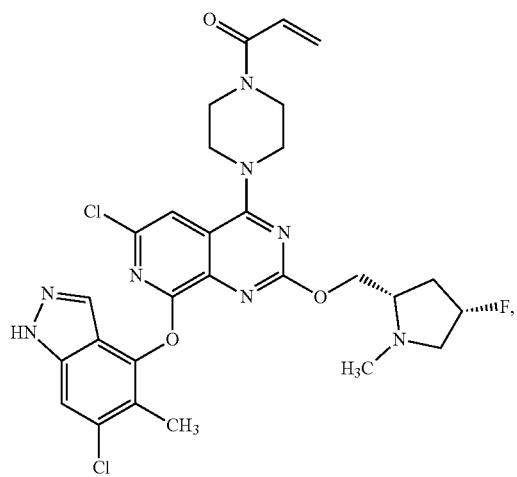
574
-continued
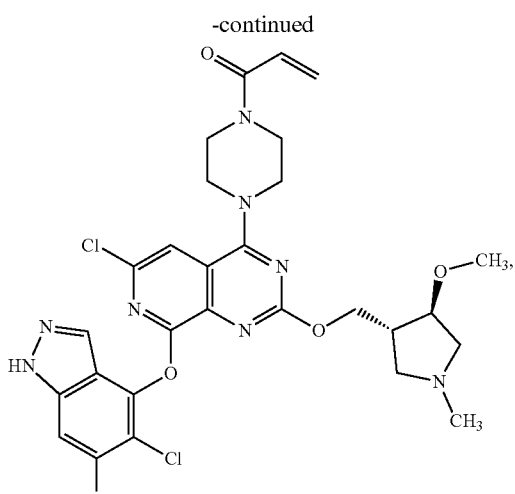
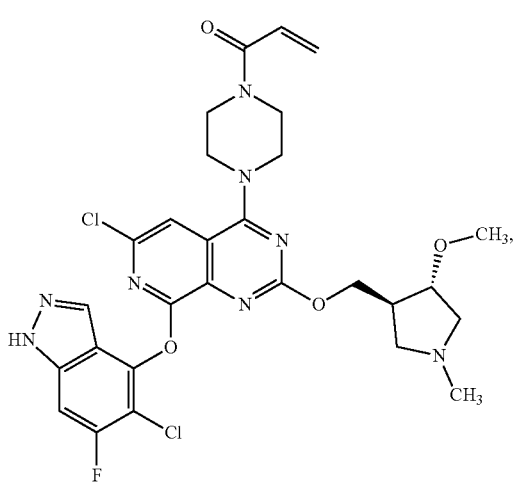
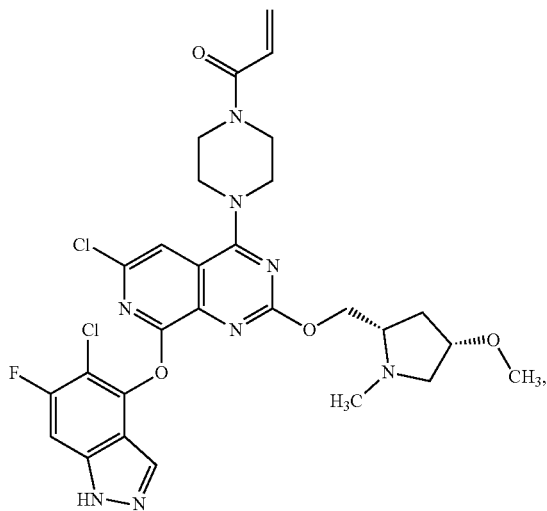

-continued
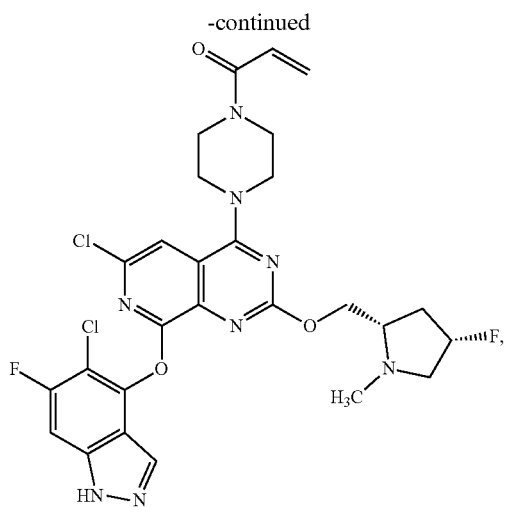
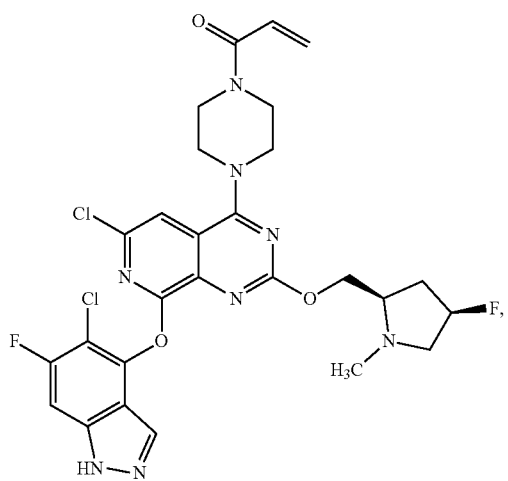
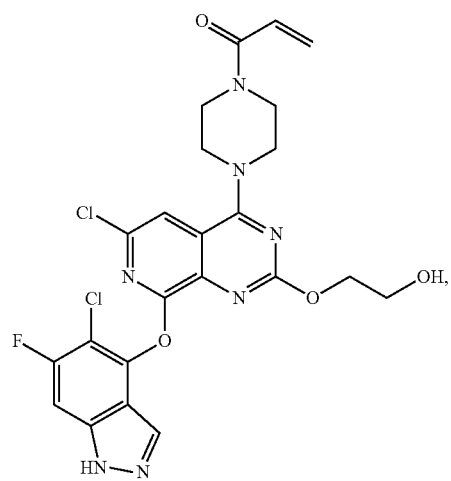
-continued
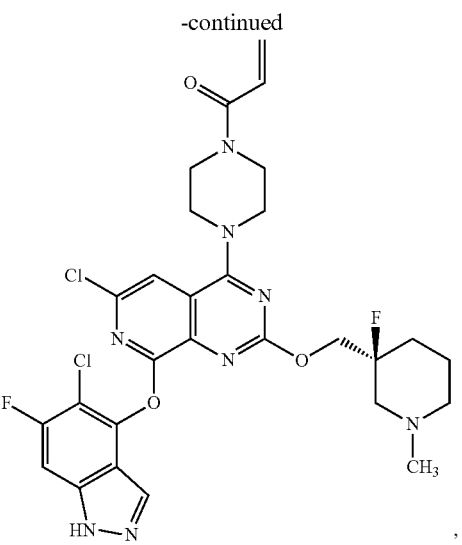
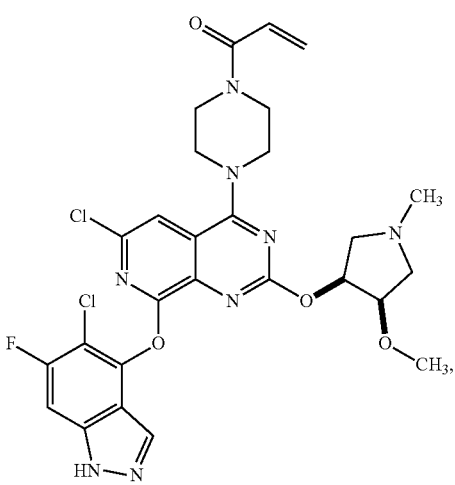
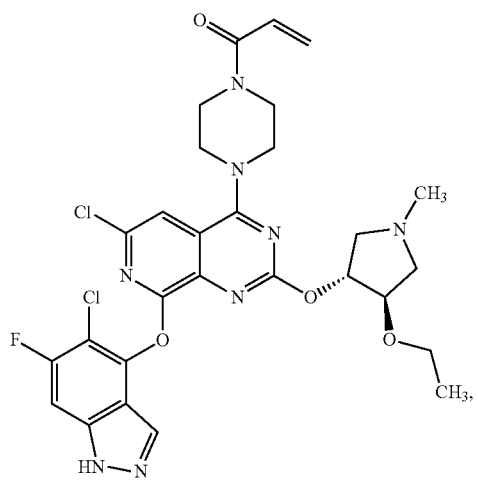

577
-continued
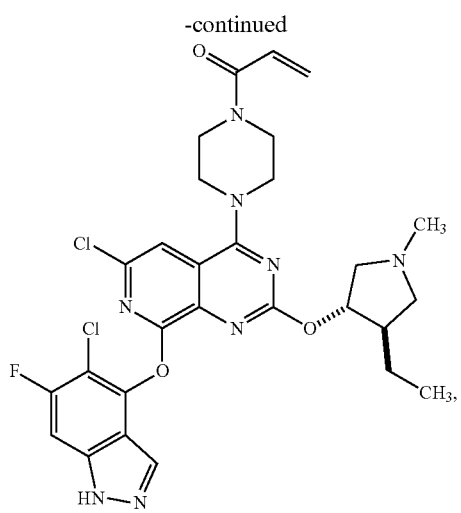
578
-continued
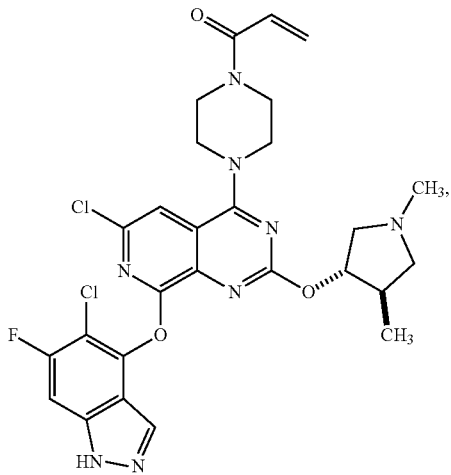
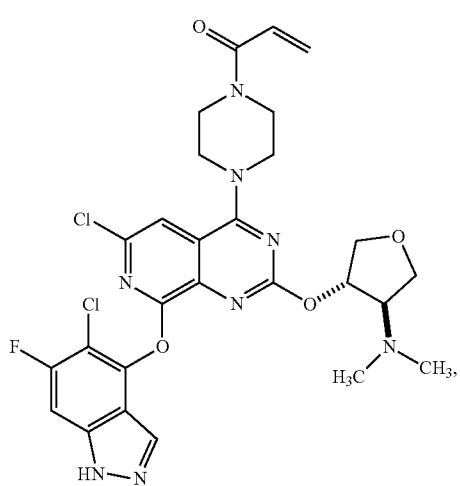
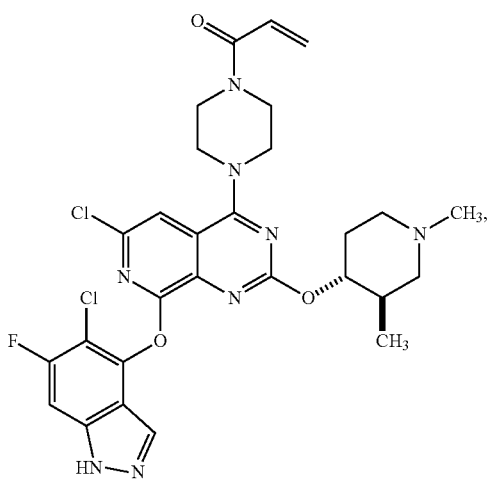
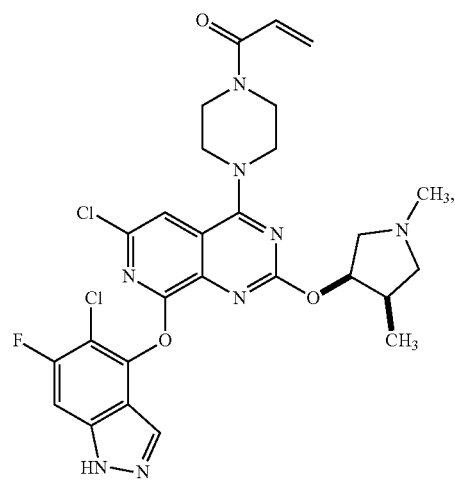
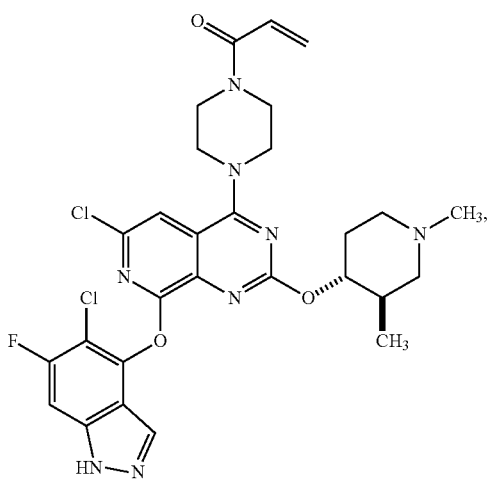

579
-continued
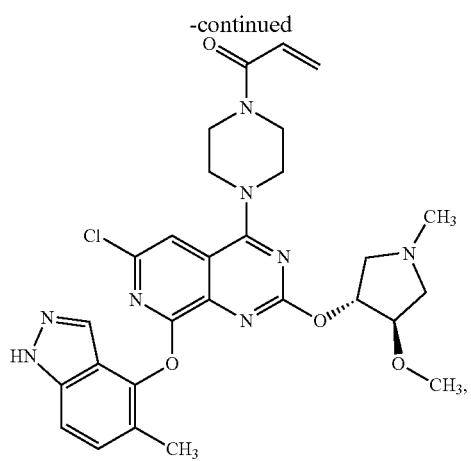
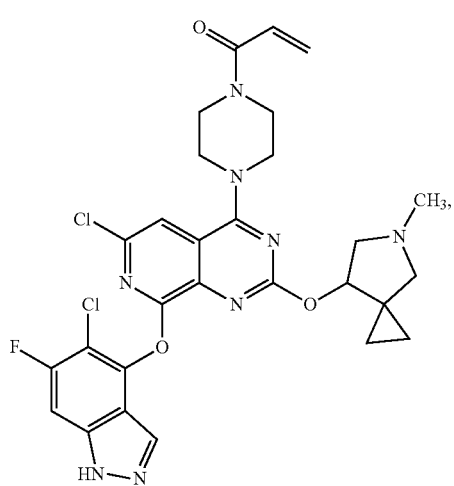
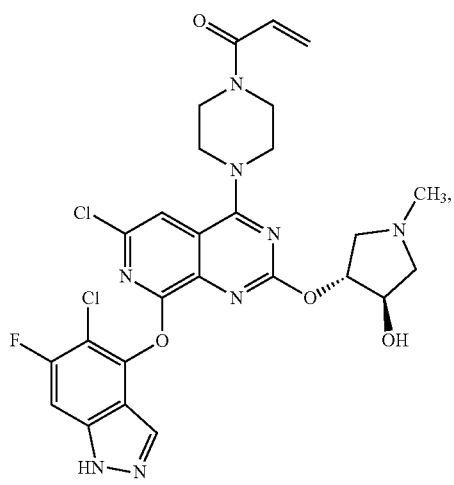
580
-continued
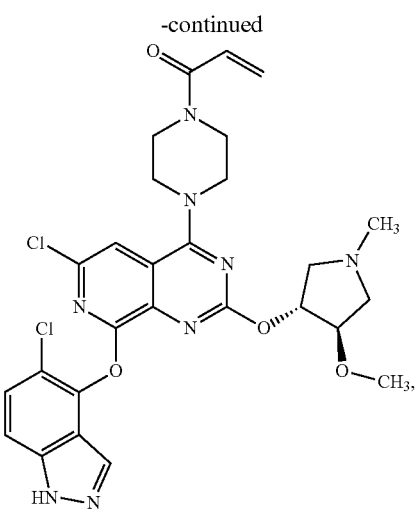
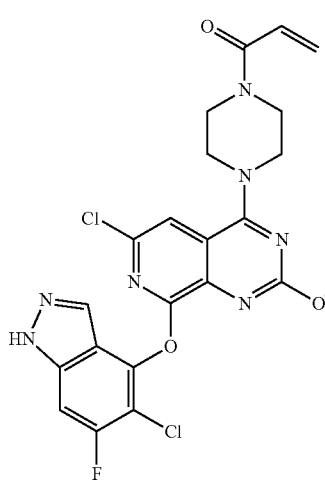
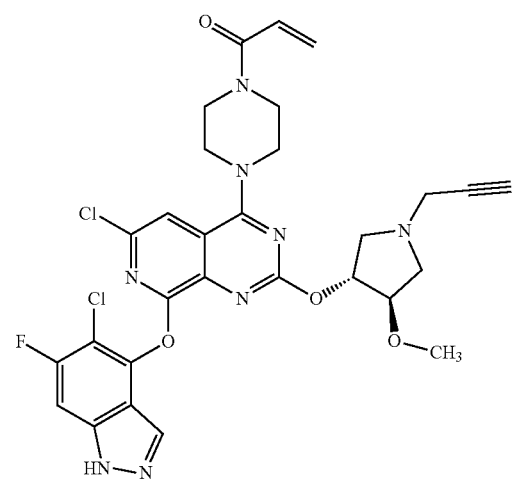

581
-continued
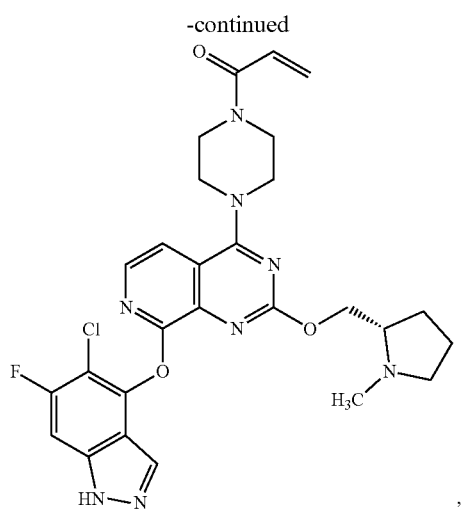
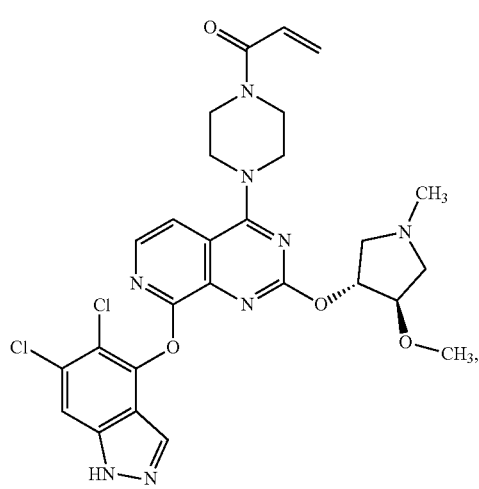
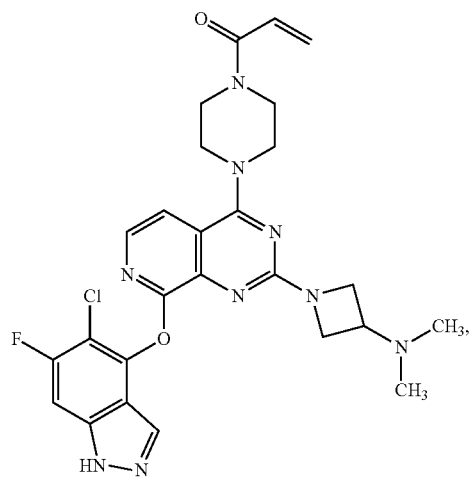
582
-continued
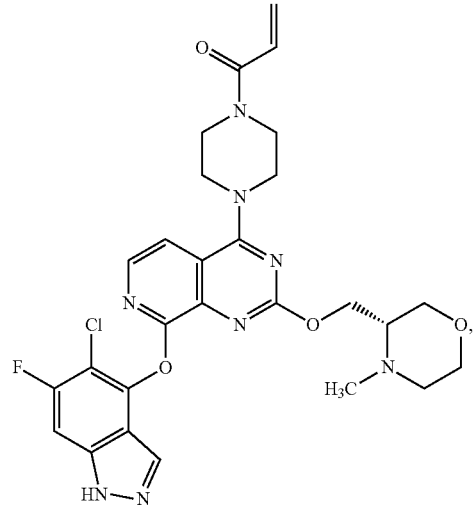
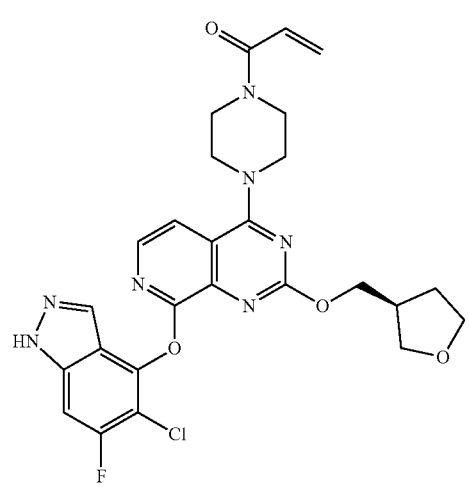
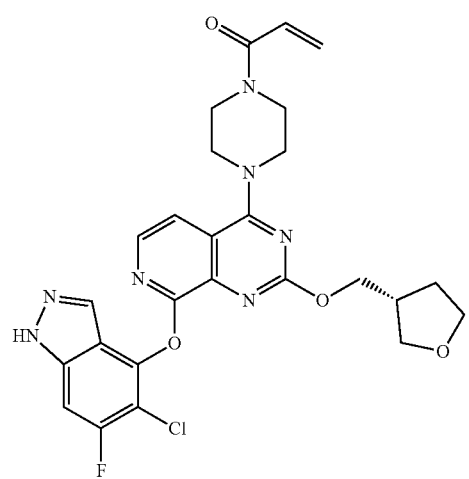

583
-continued
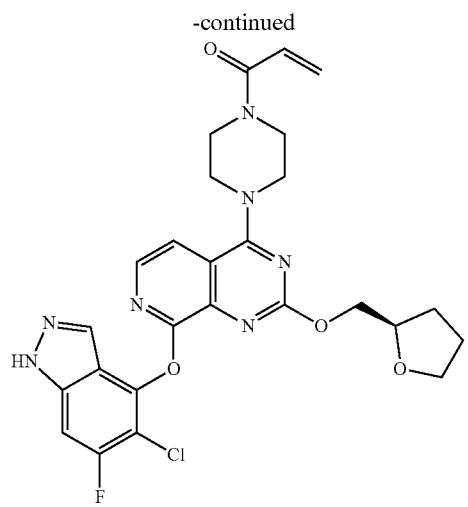
,
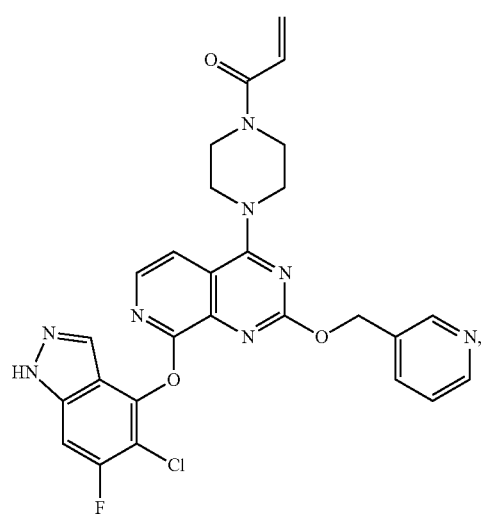
,
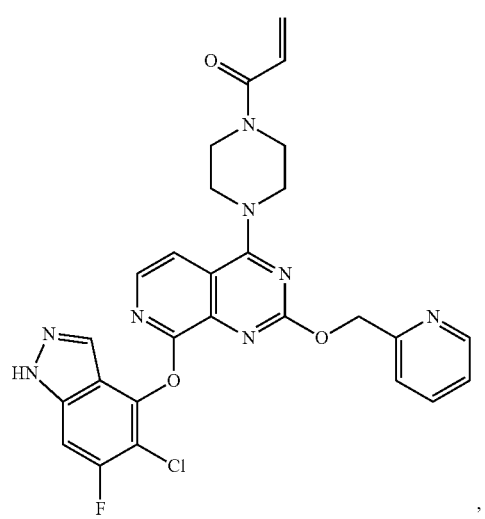
,
584
-continued
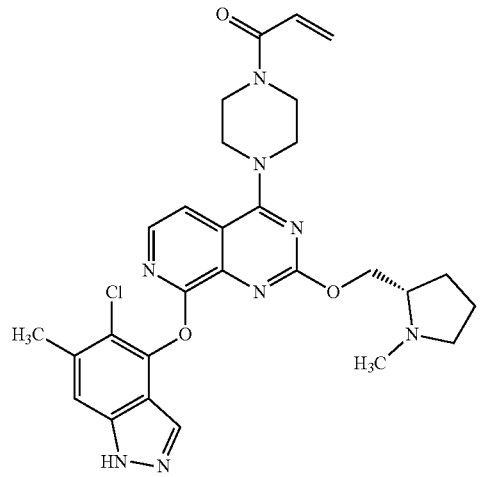
,
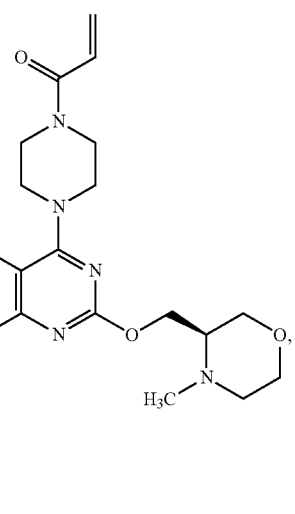
,
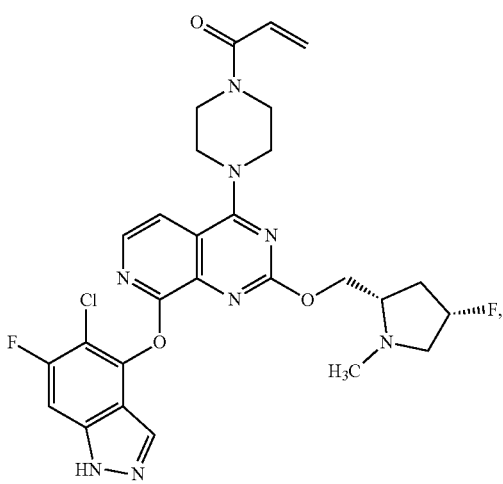
, 585
-continued
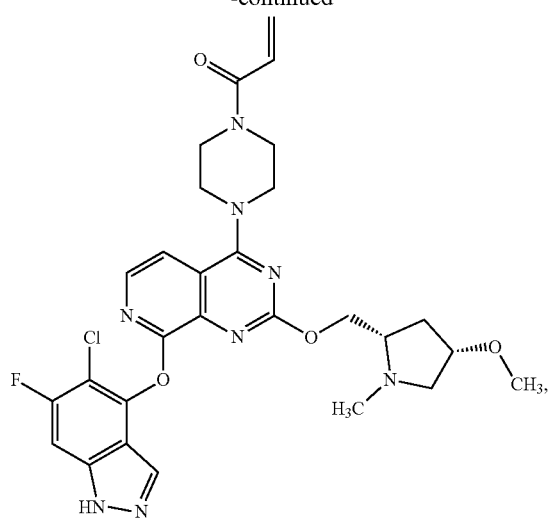
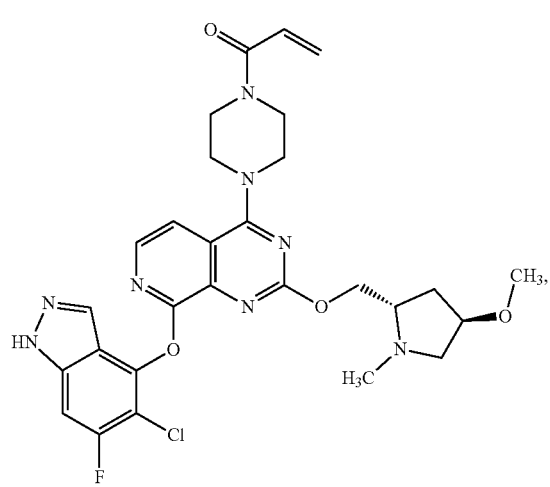
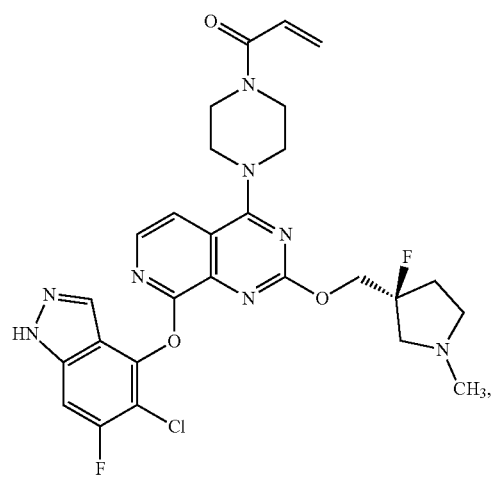
586
-continued
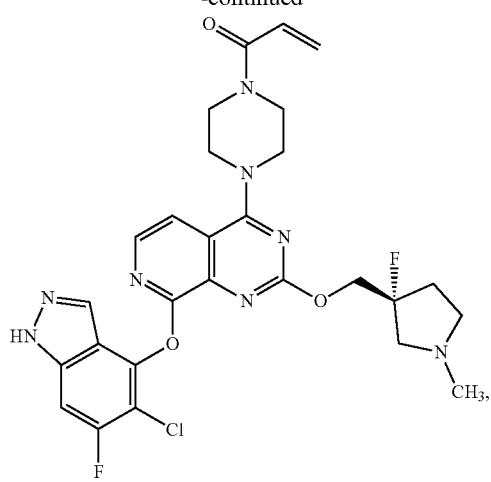
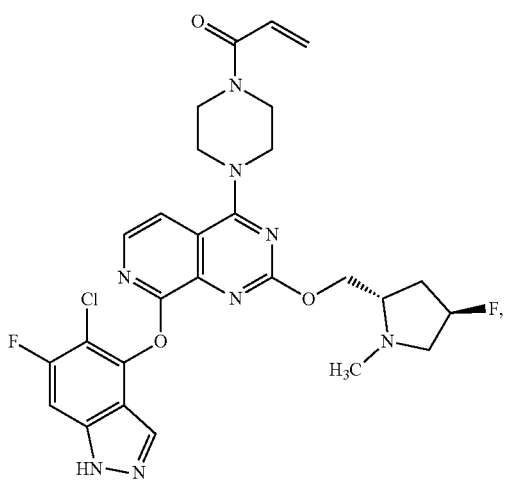
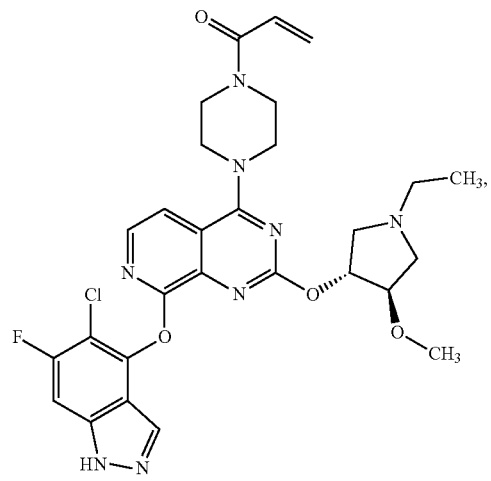

587
-continued
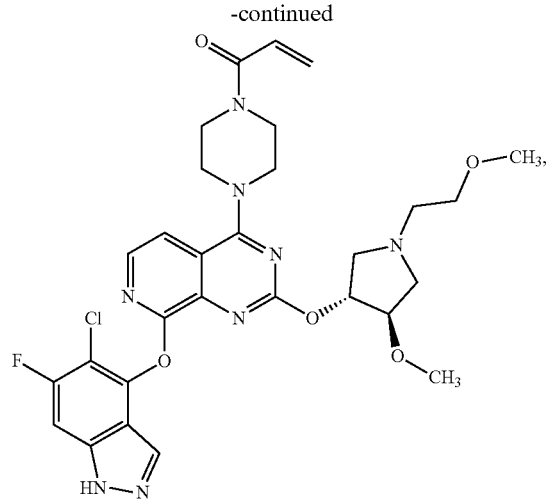
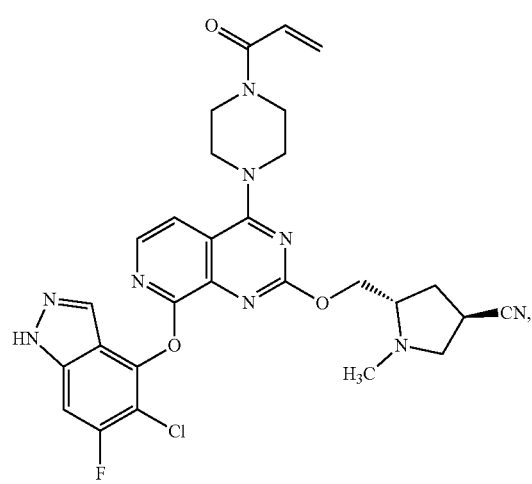
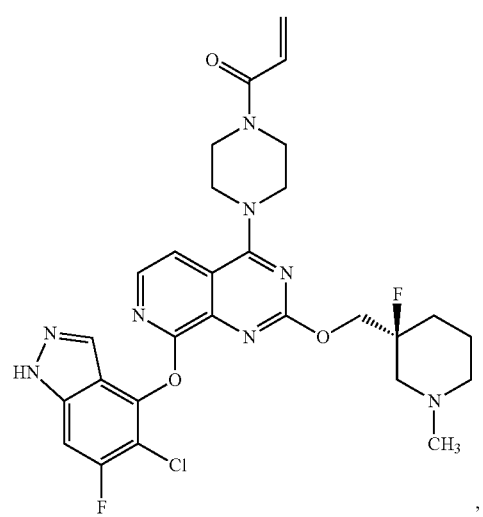
,
588
-continued
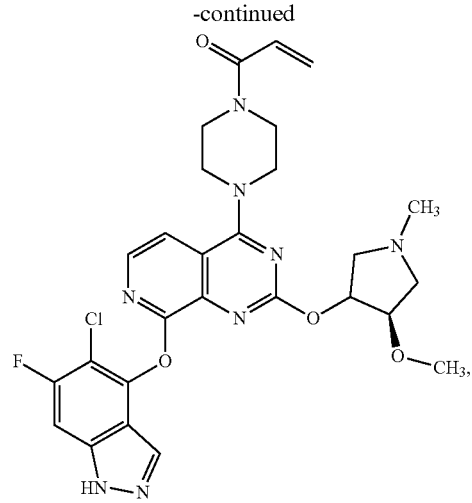
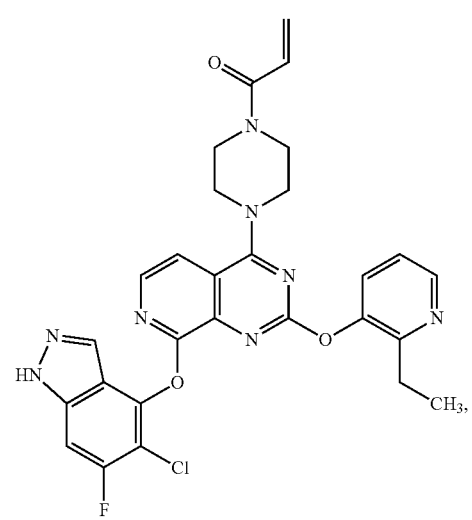
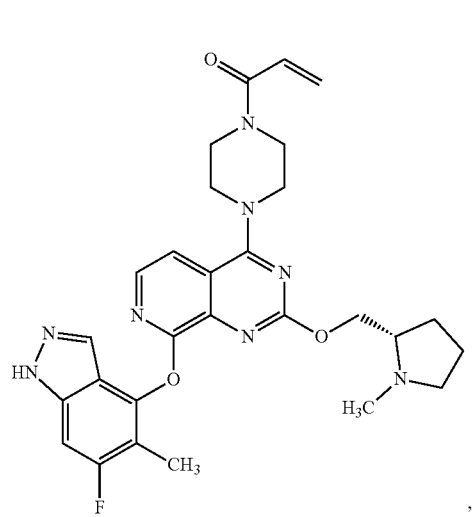
, 589
-continued
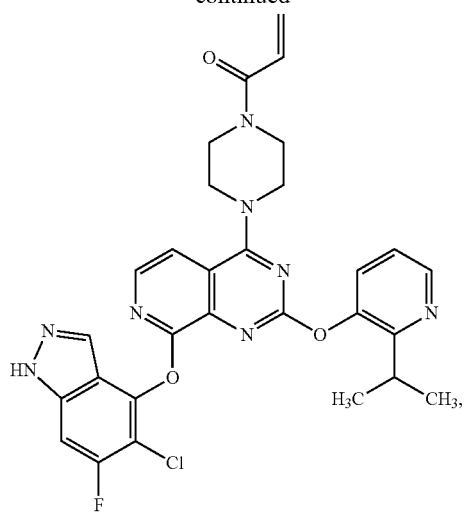
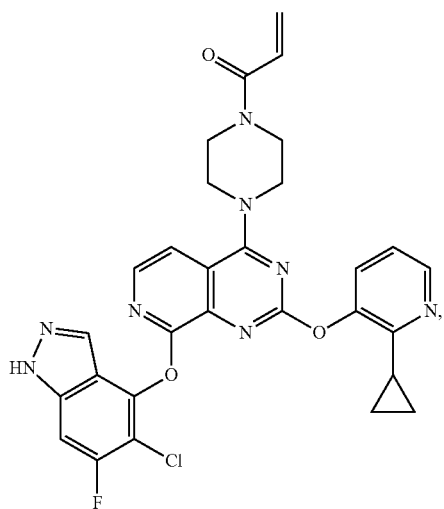
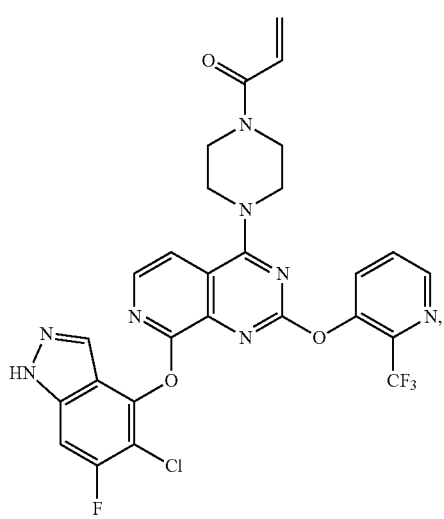
590
-continued
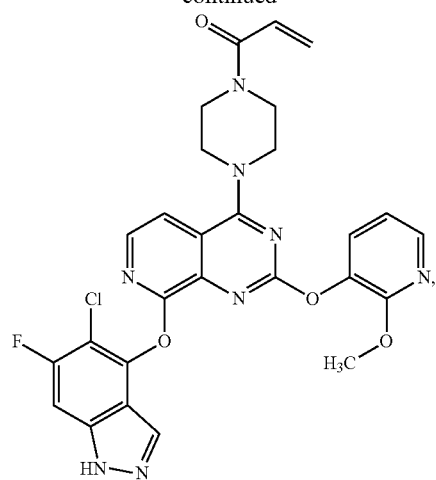
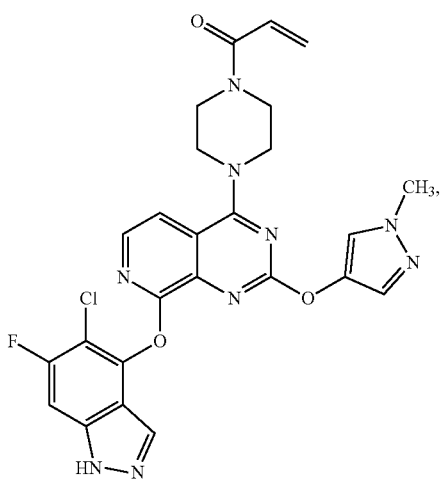
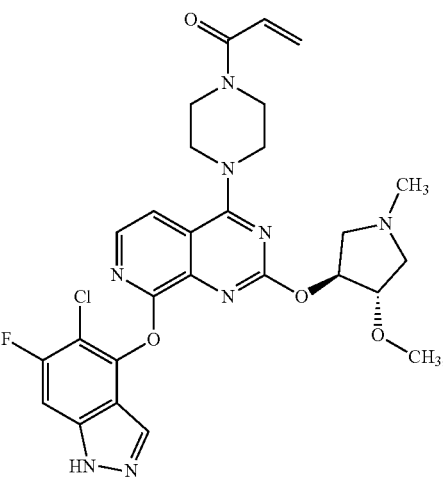

591
-continued
592
-continued
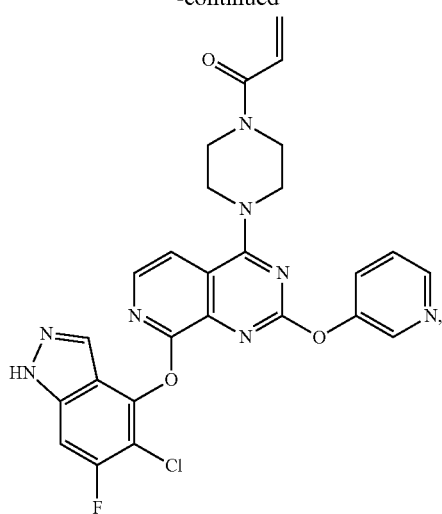
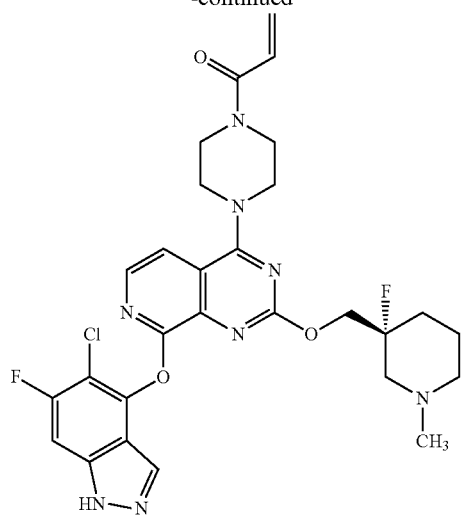
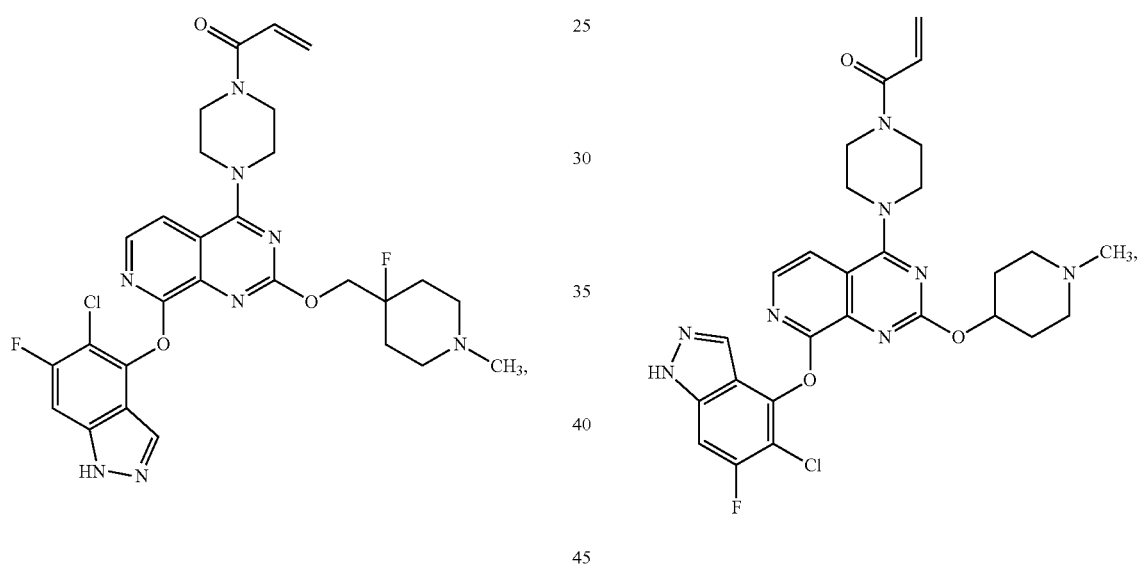
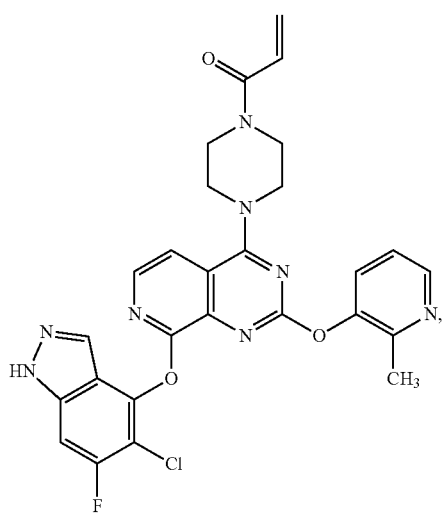
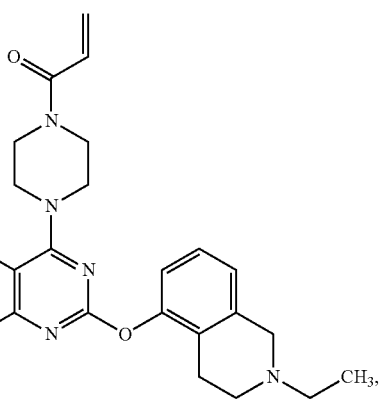

593
-continued
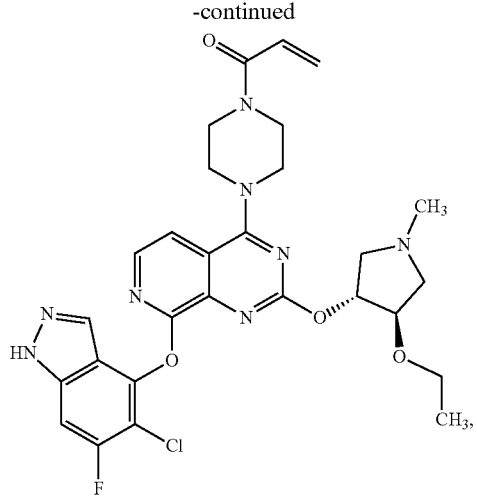
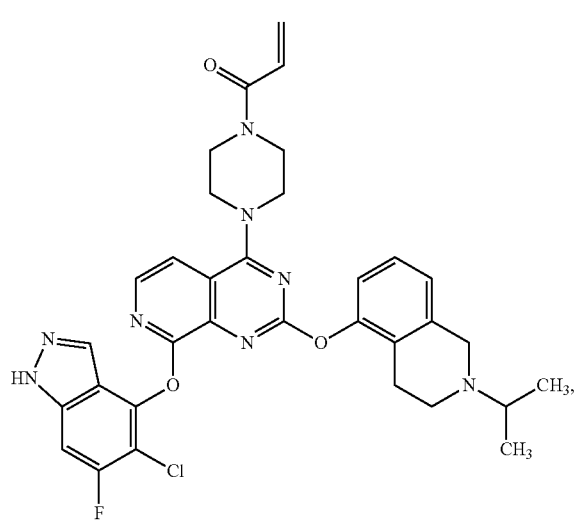
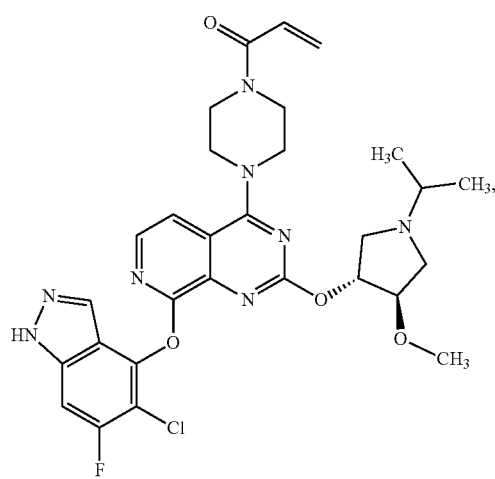
594
-continued
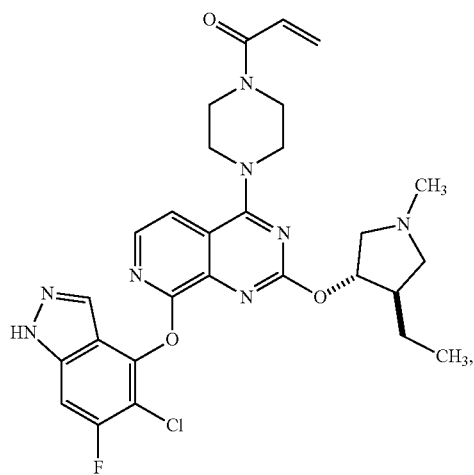
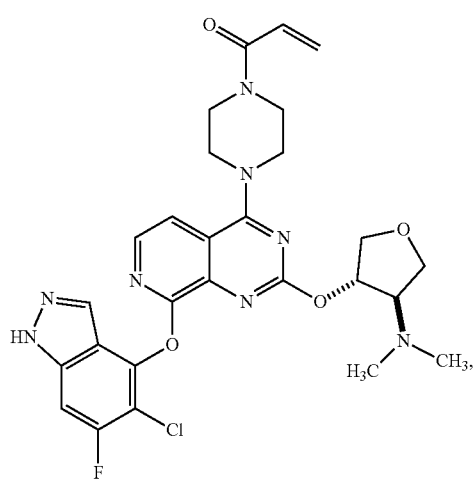

595
-continued
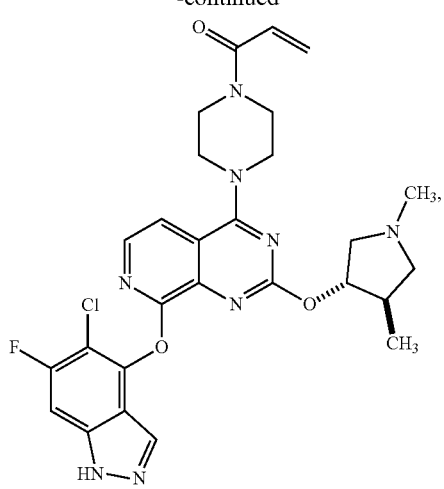
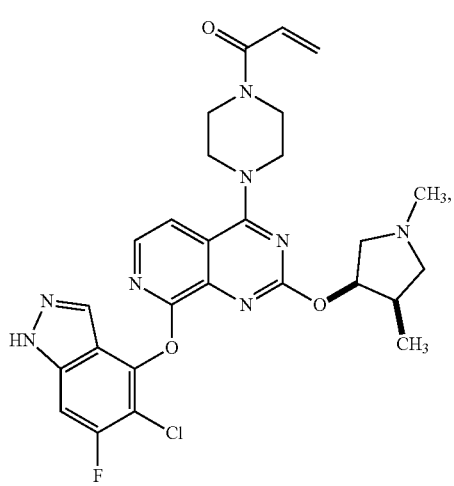
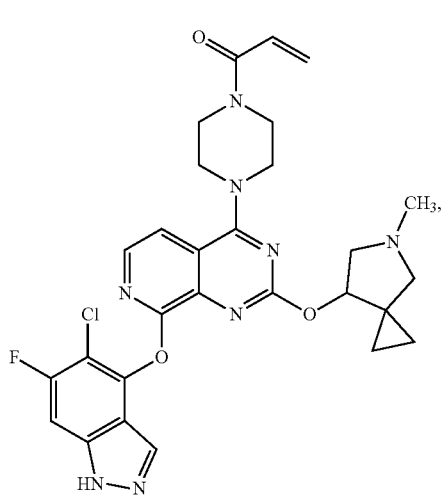
596
-continued
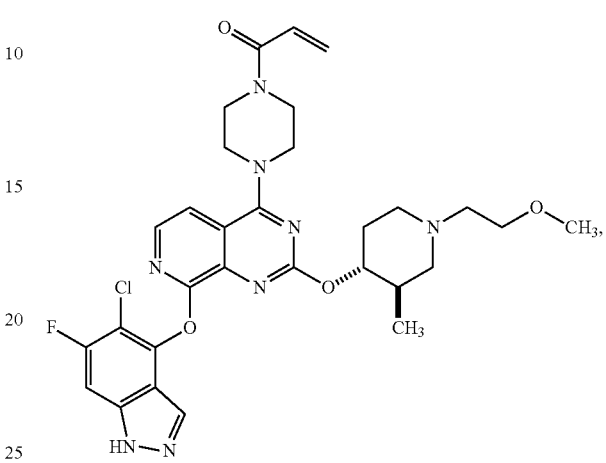
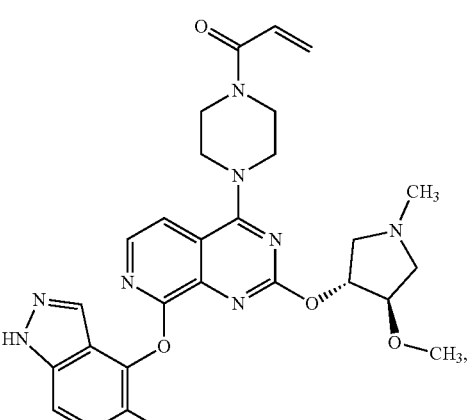
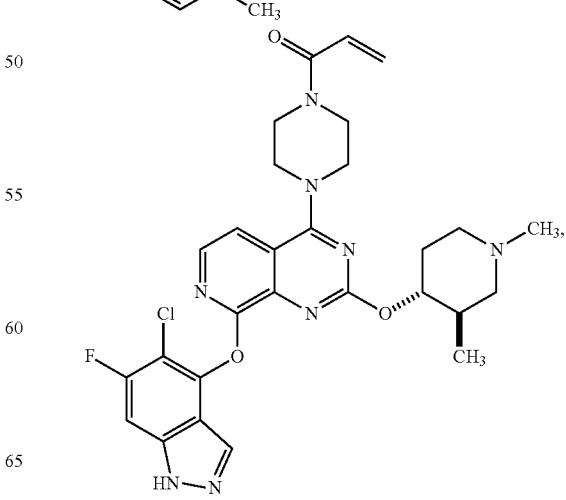

597
-continued
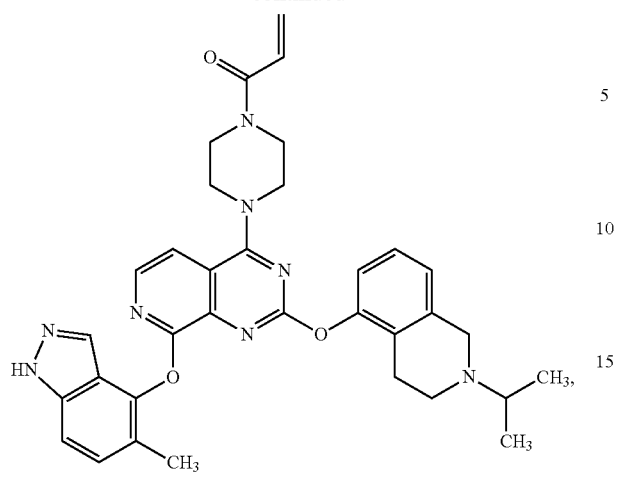
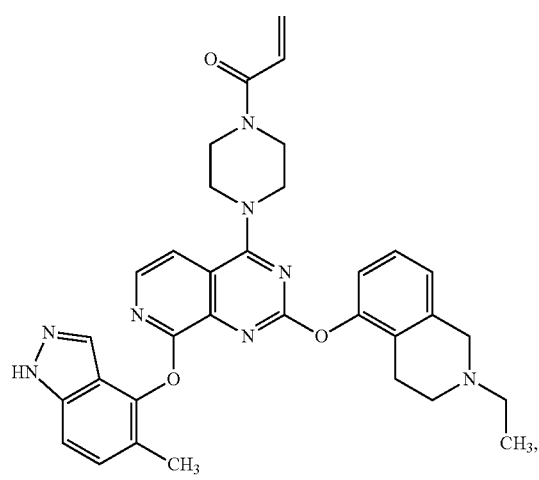
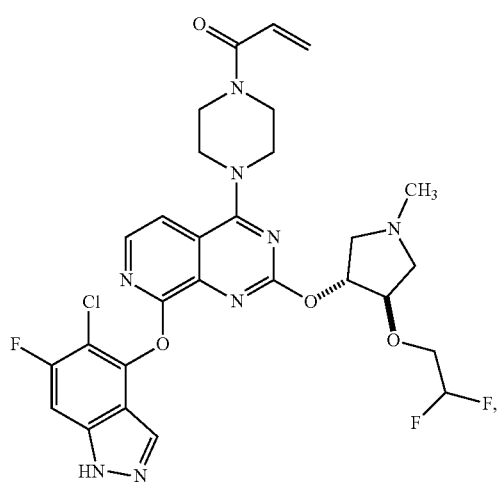
598
-continued
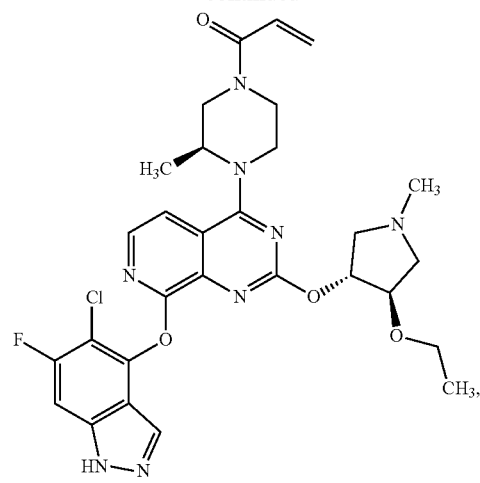
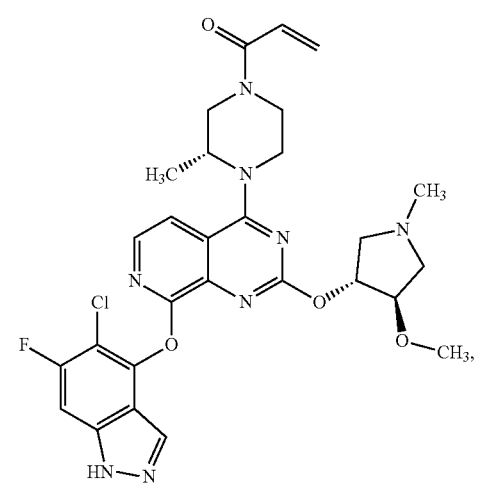
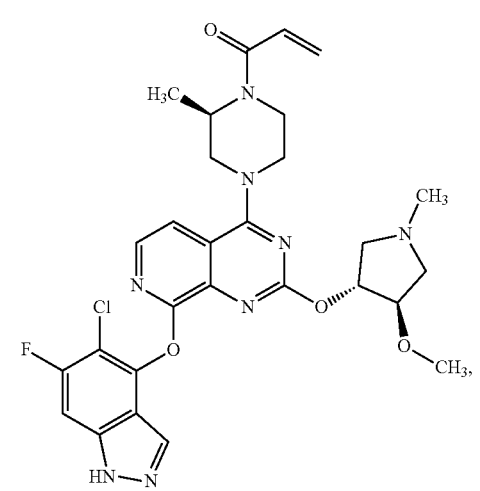

599
-continued
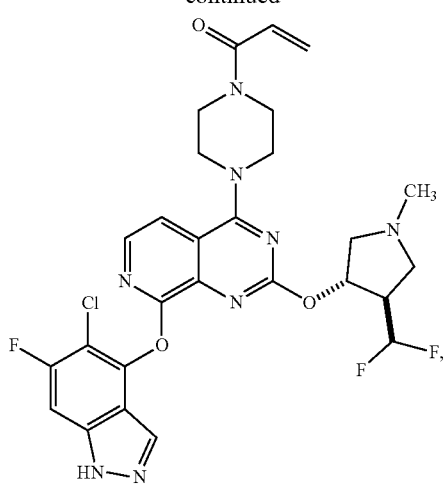
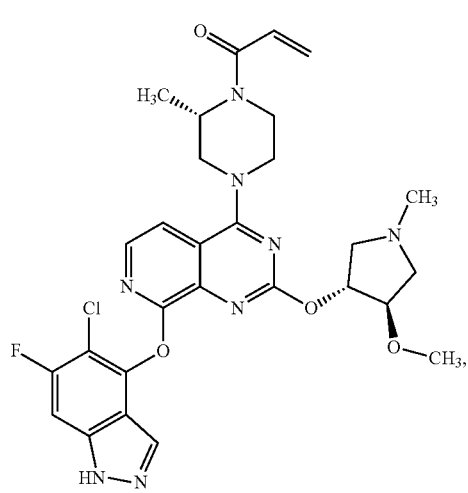
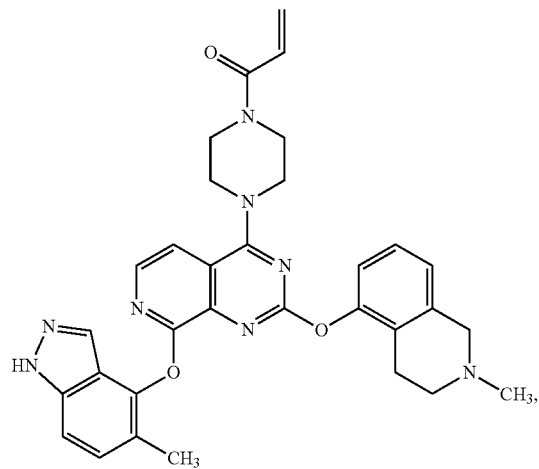
600
-continued
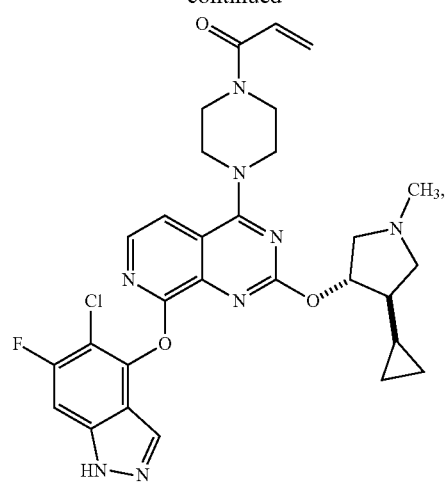
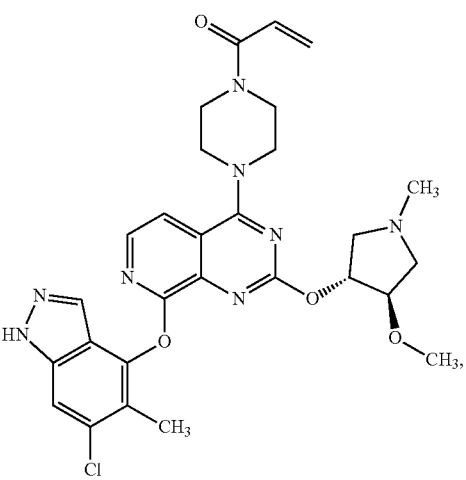
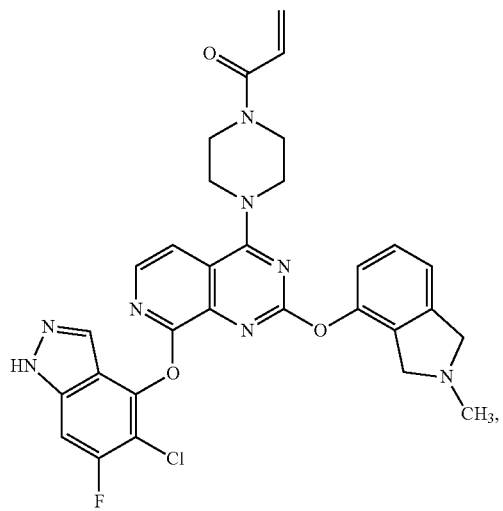

601
-continued
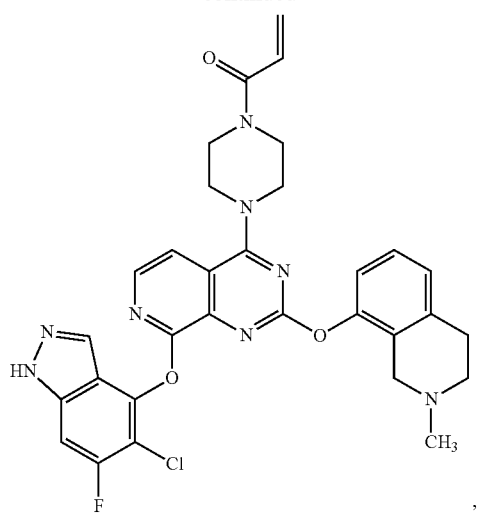
,
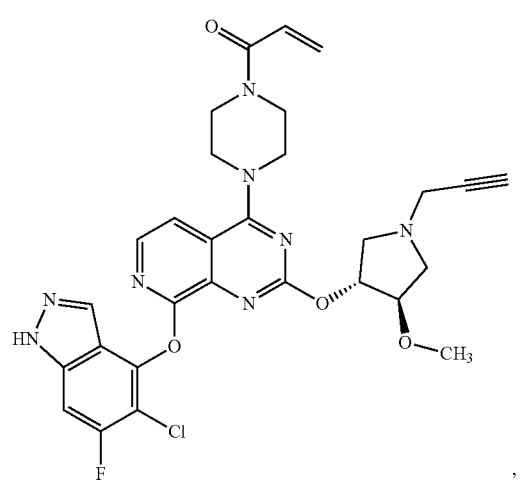
,
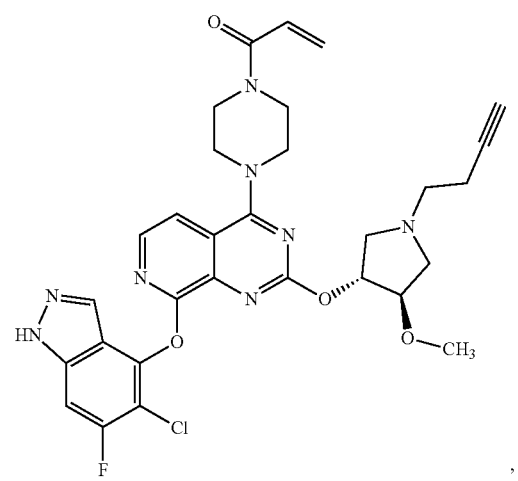
,
602
-continued
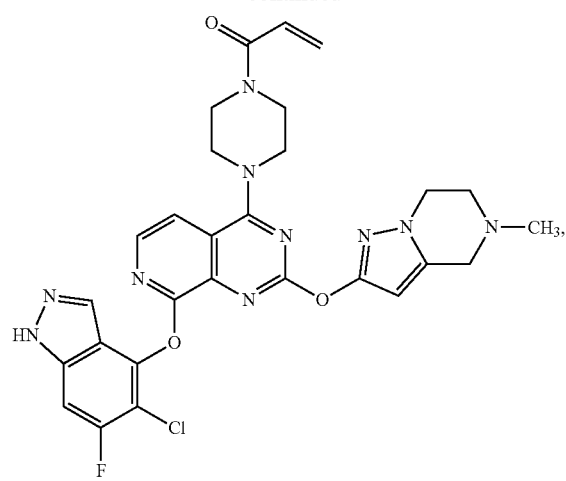
,
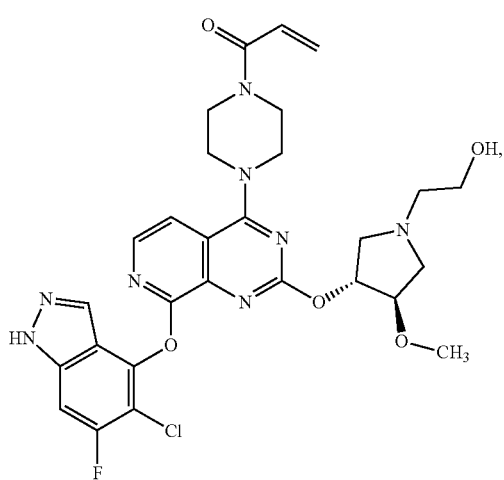
,
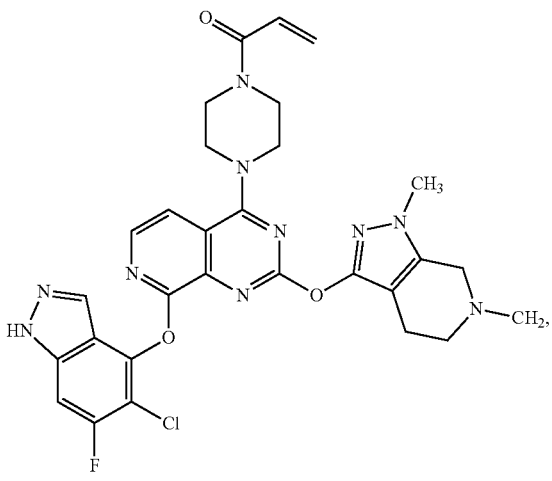
, 603
-continued
604
-continued
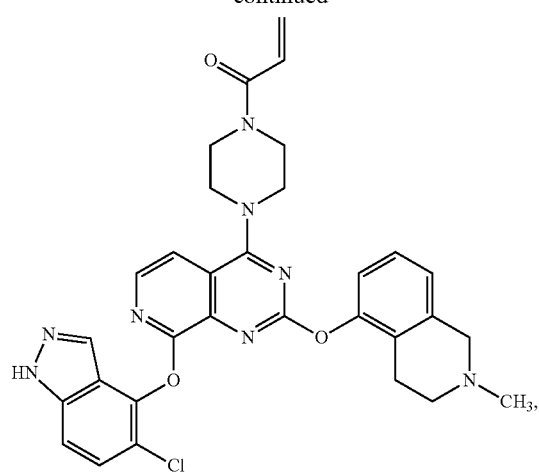
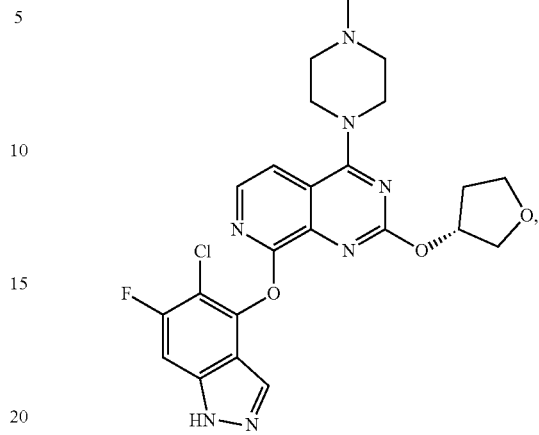
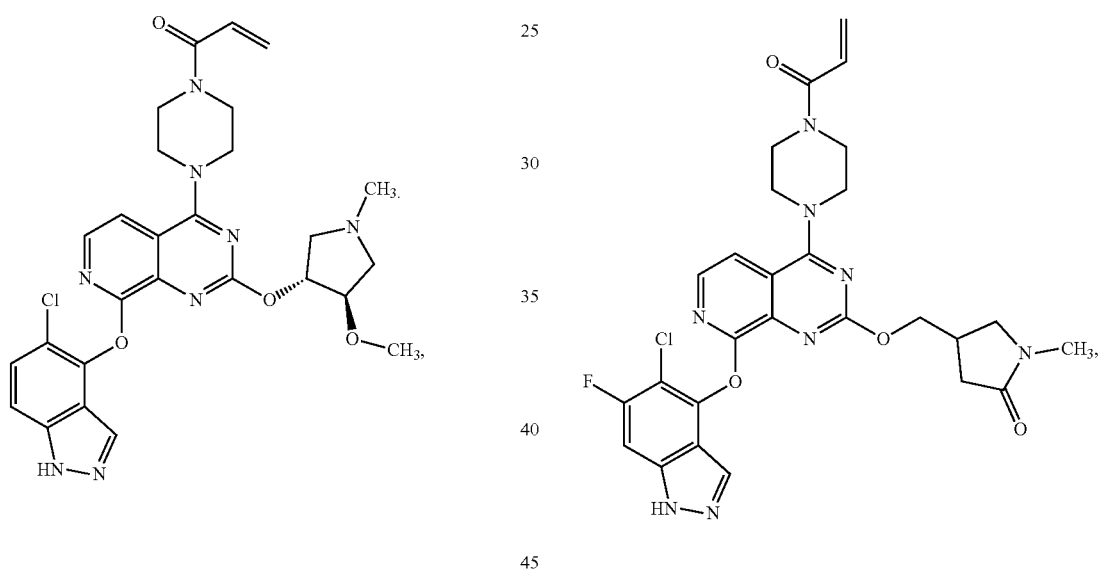
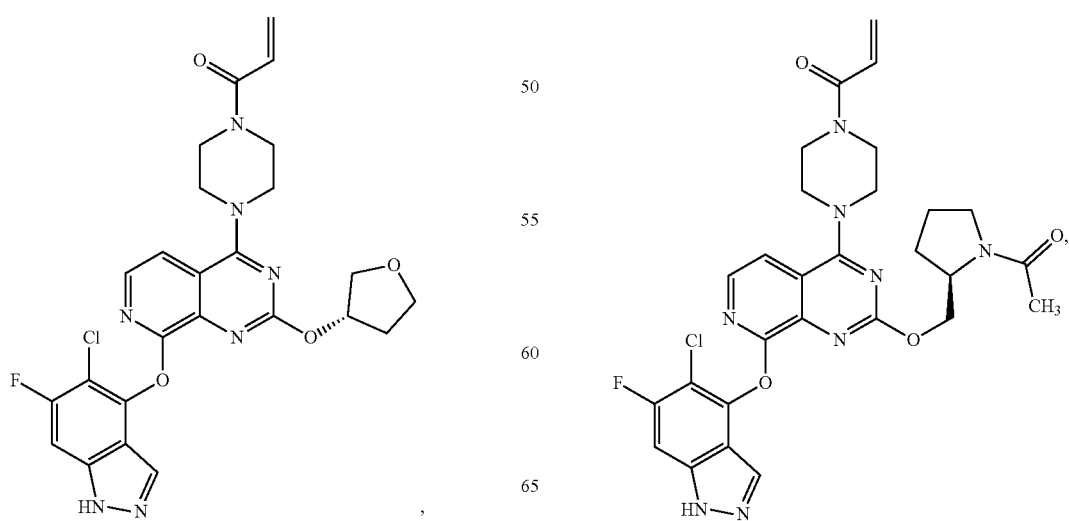

605
-continued
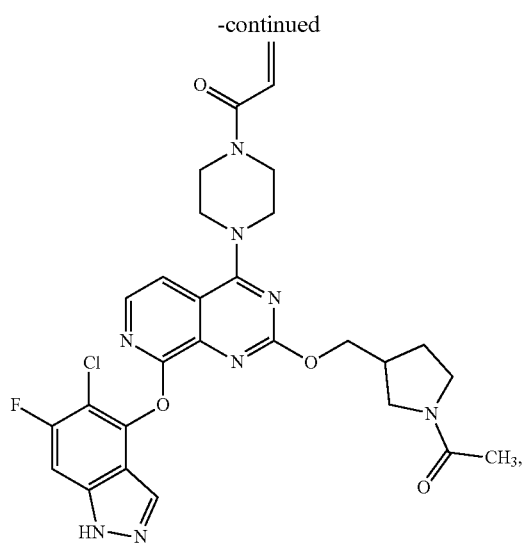
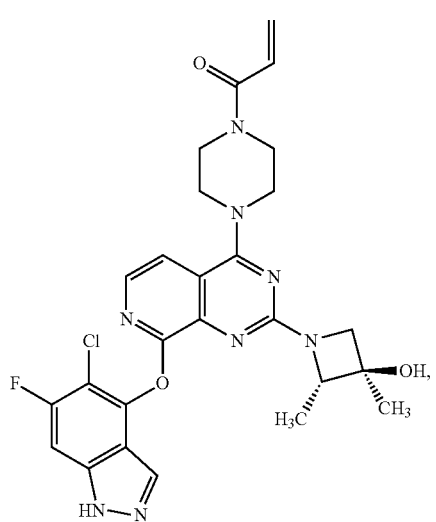
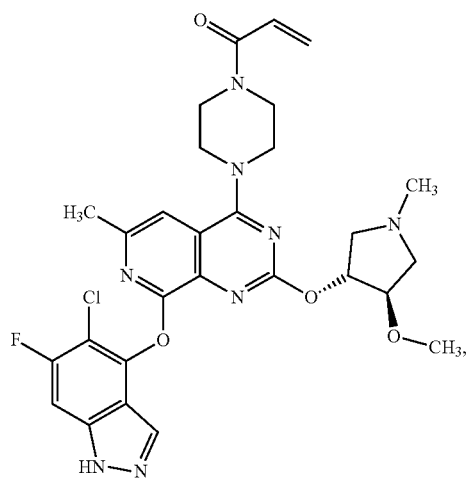
606
-continued
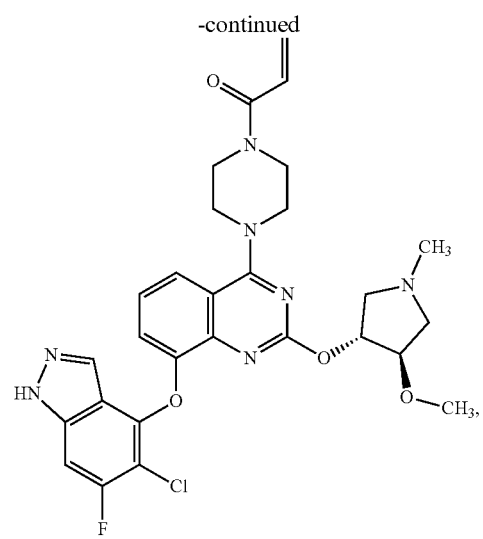
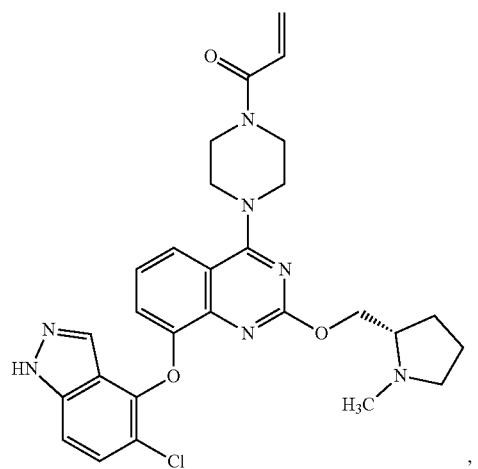

607
-continued
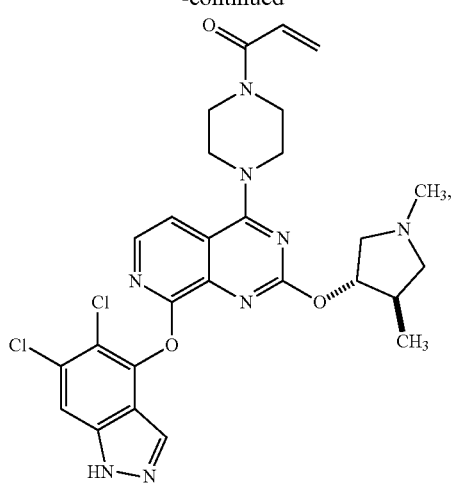
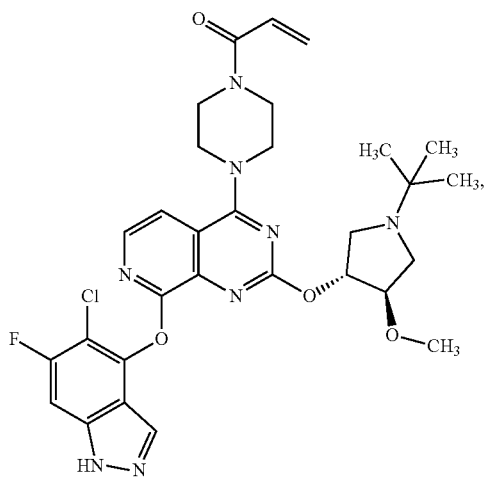
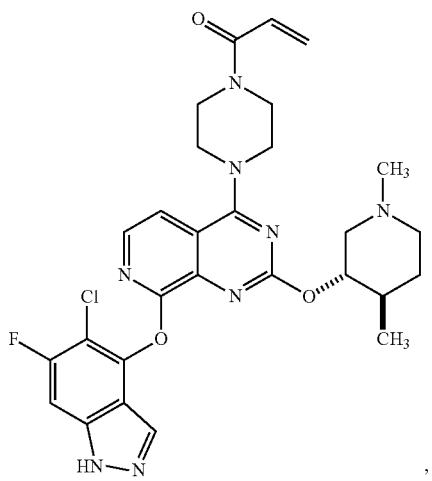
608
-continued
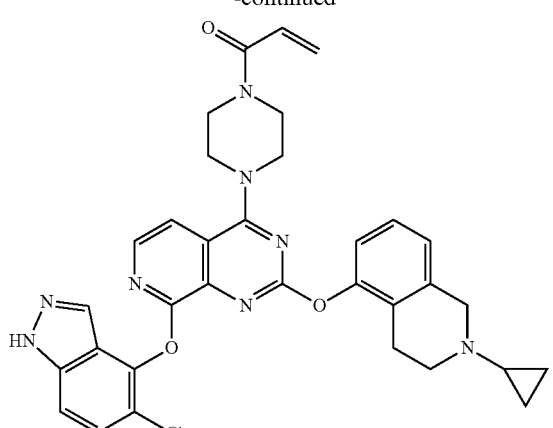
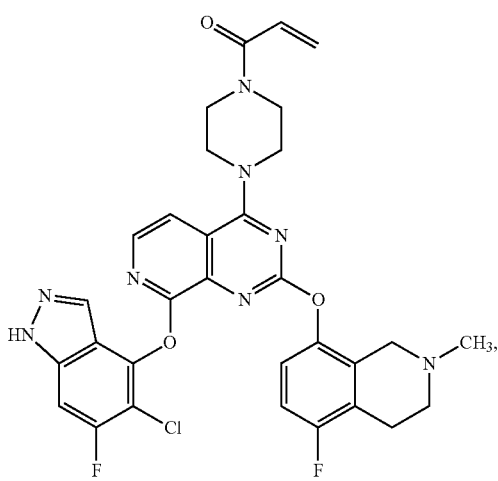
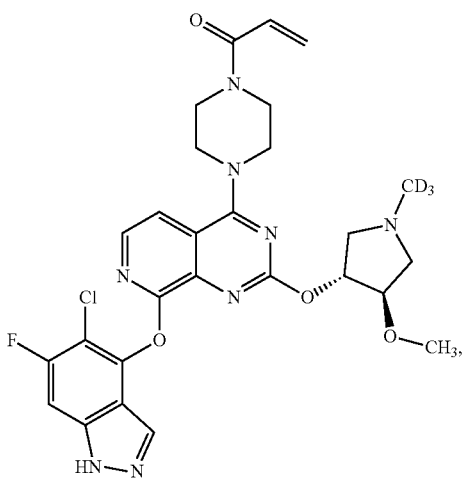

609
-continued
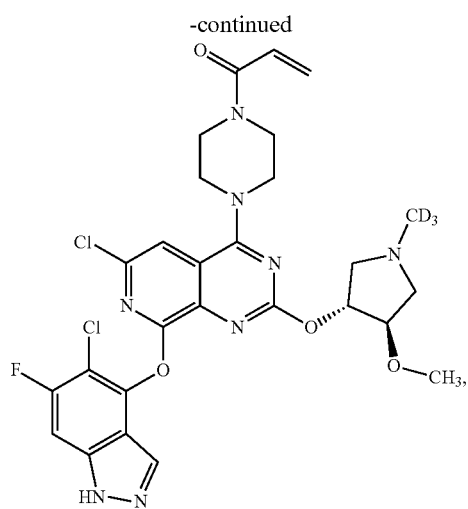
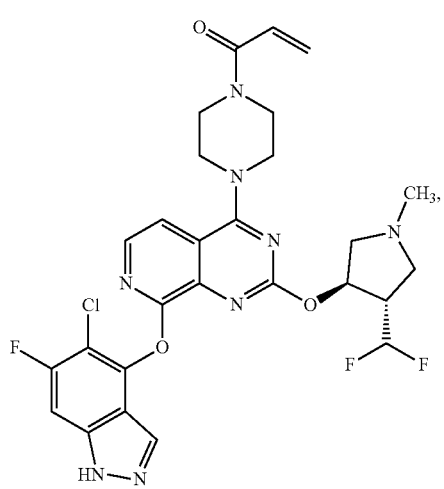
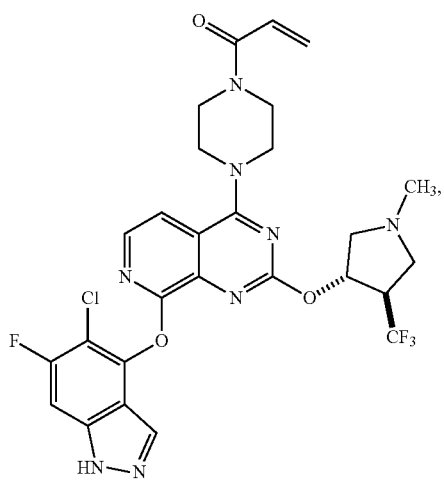
610
-continued
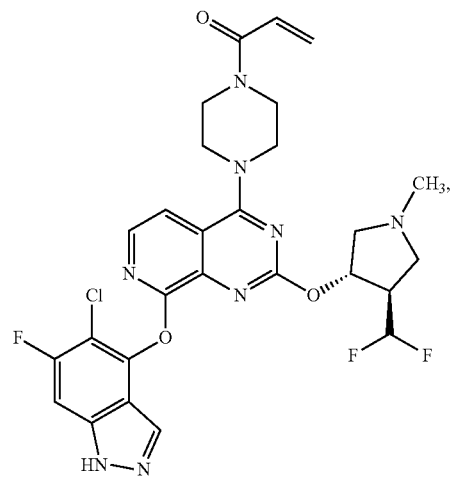
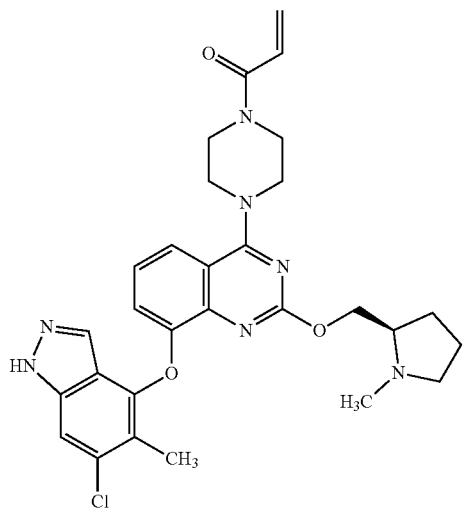
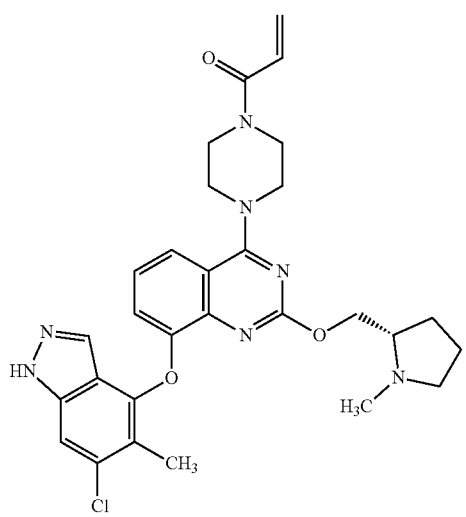

611
-continued
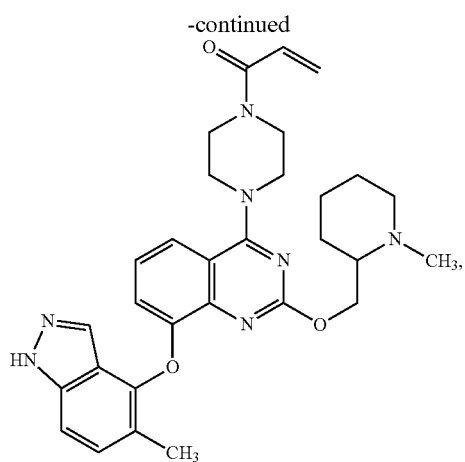
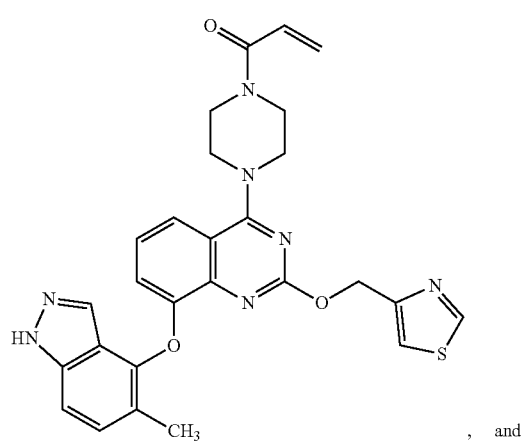
, and
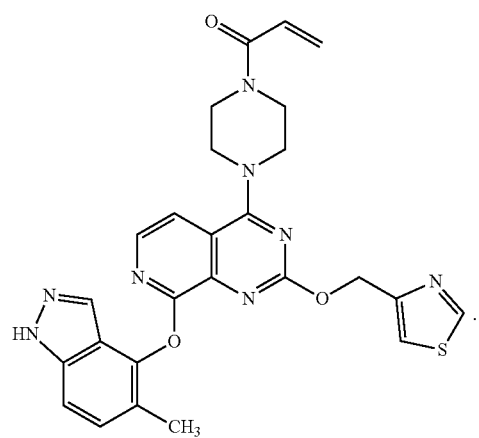
or a pharmaceutically acceptable salt thereof.
18. A compound selected from the group consisting of:
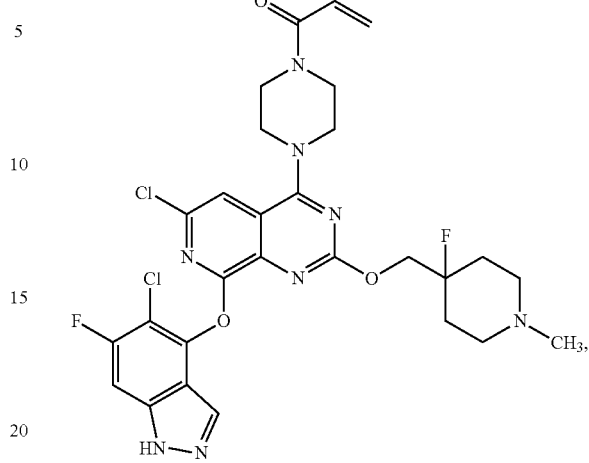
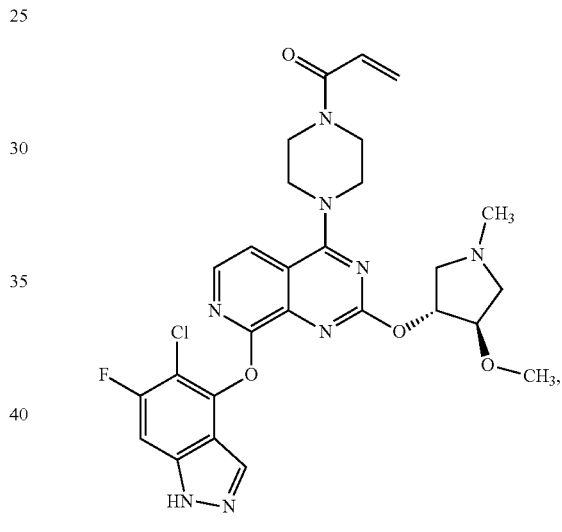
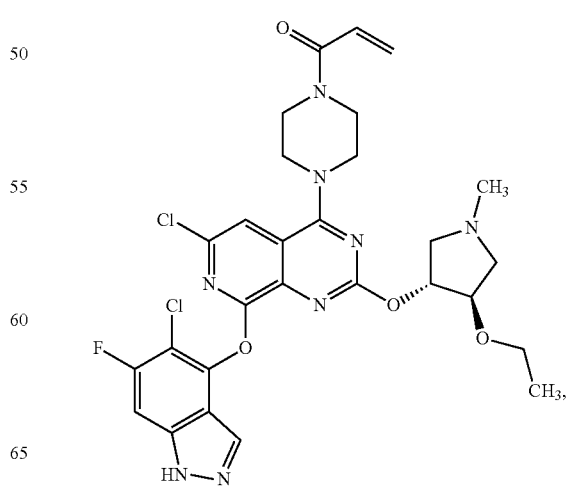

613
-continued
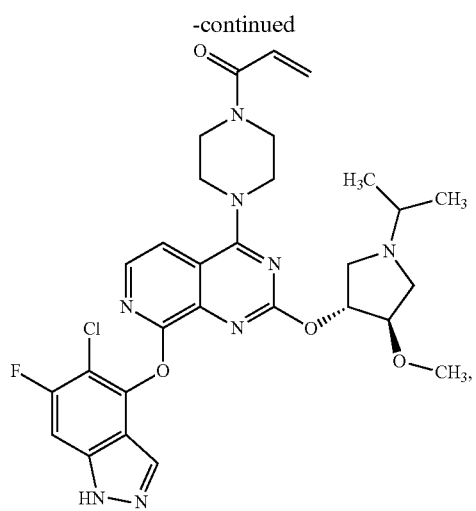
614
-continued
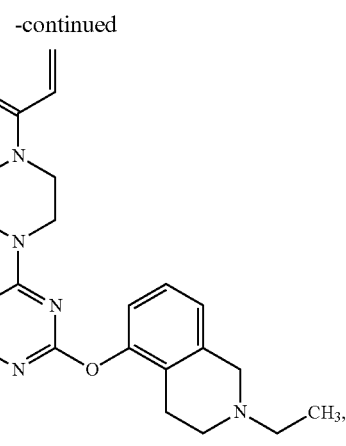
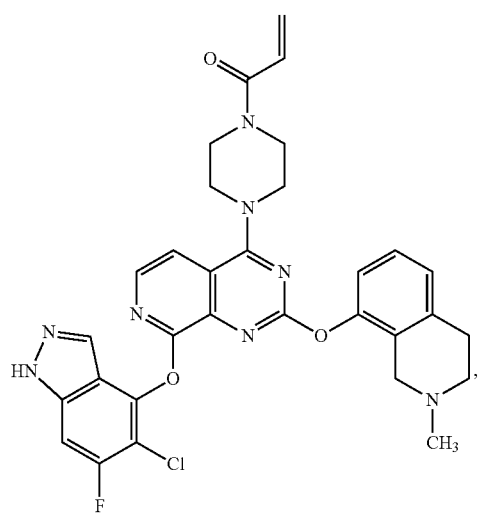
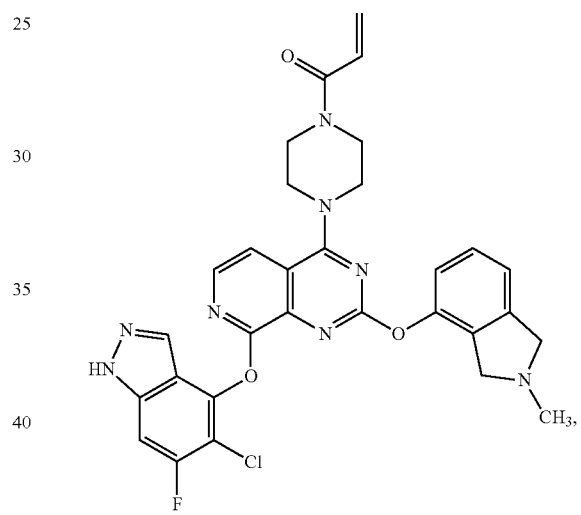
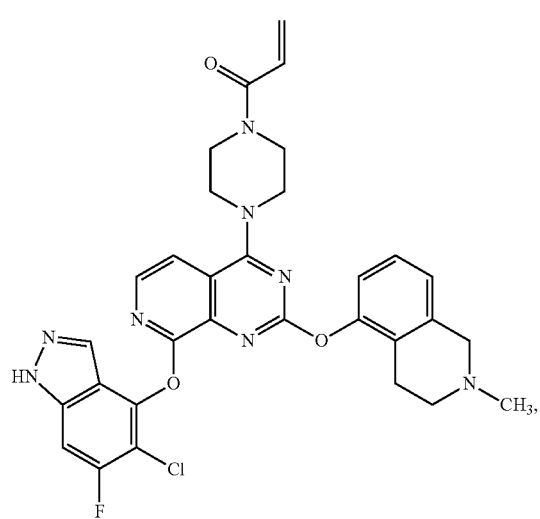
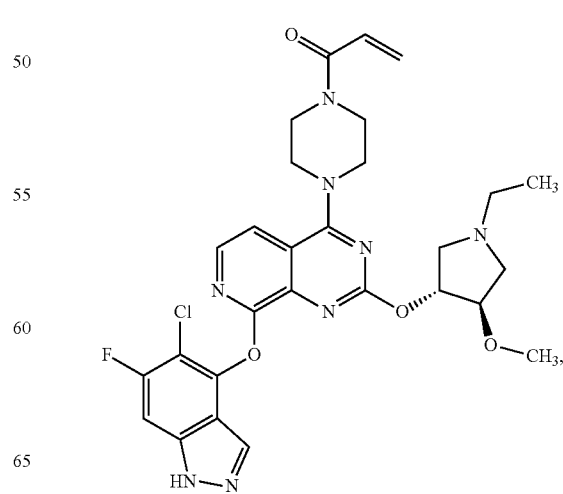

615
-continued
616
-continued
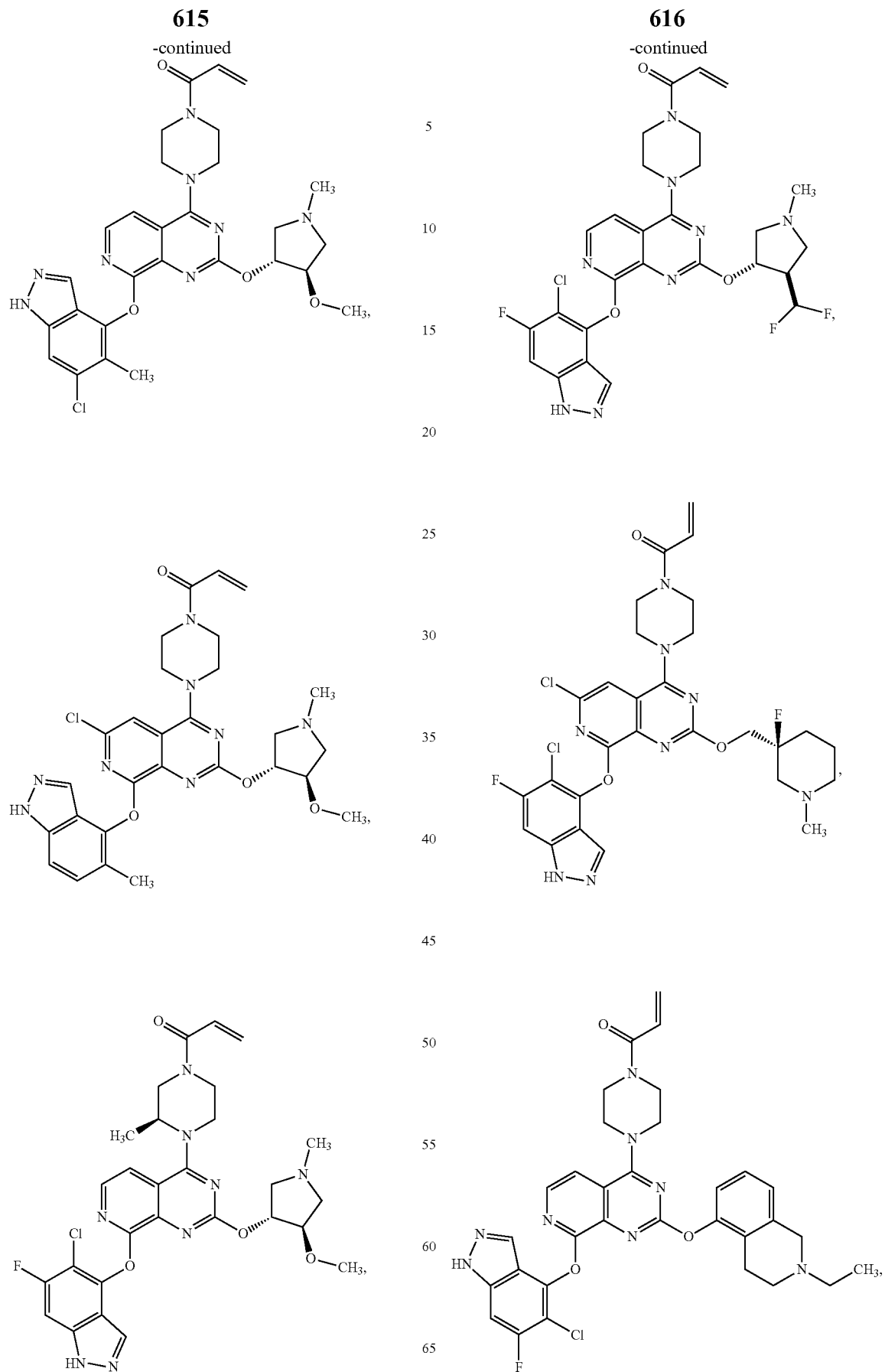

617
-continued
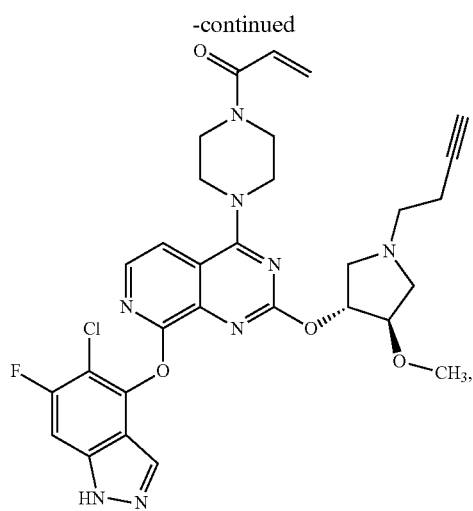
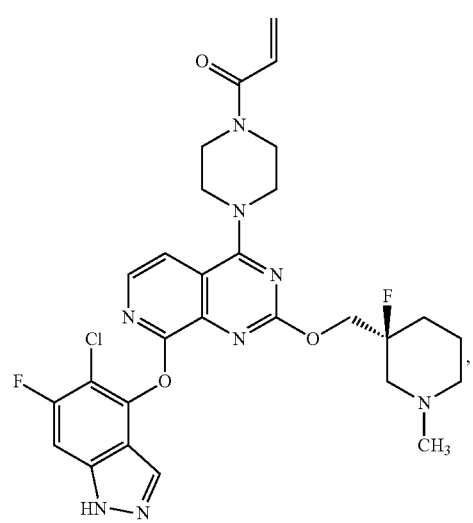
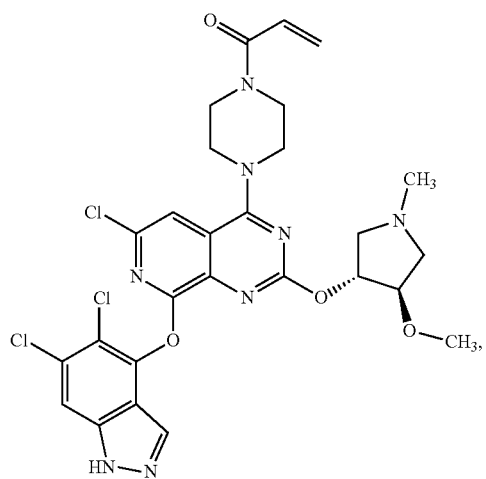
618
-continued
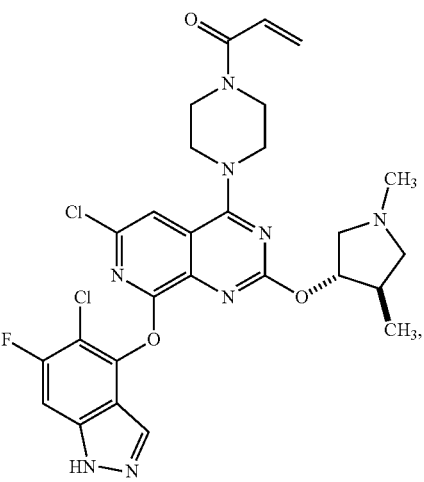
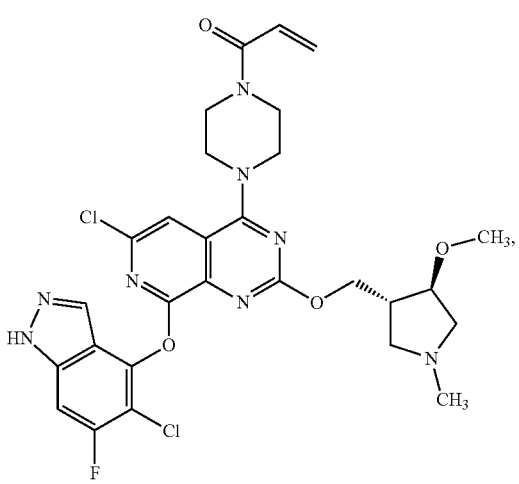
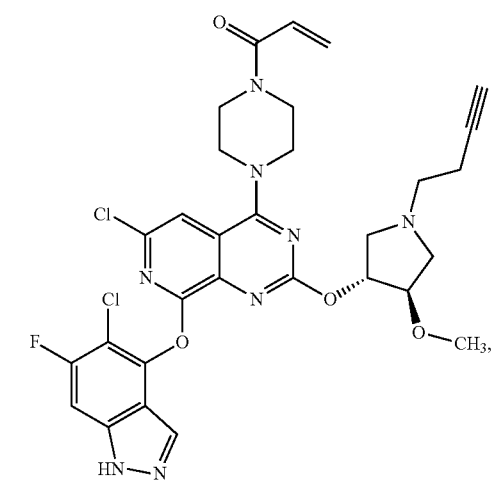

619
-continued
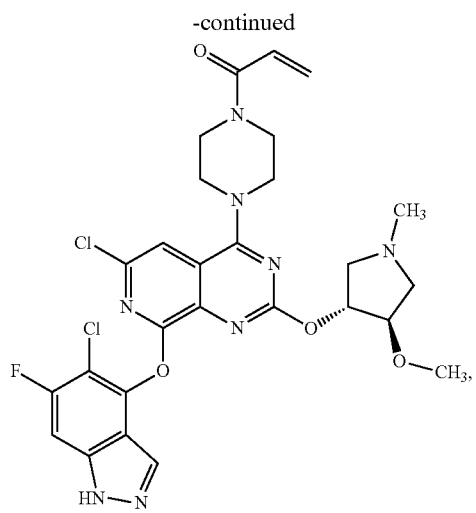
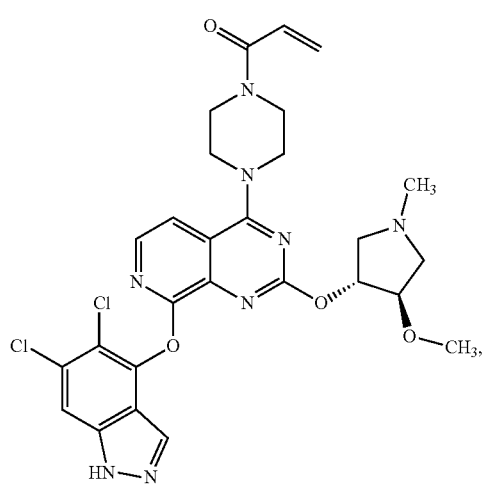
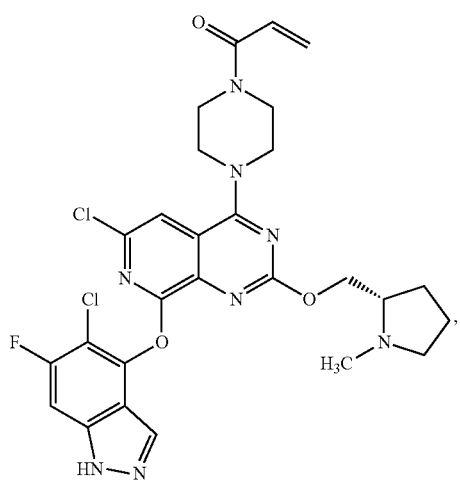
620
-continued
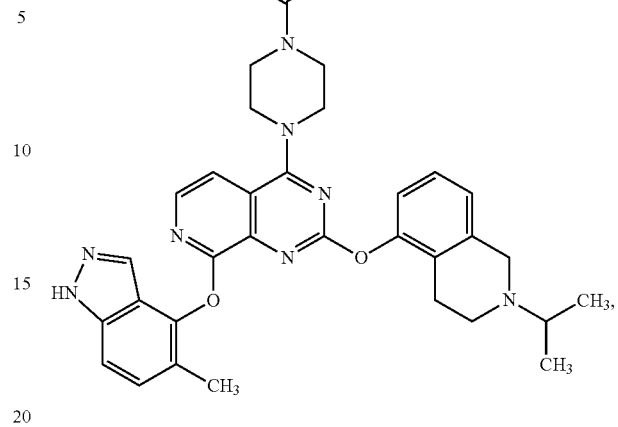
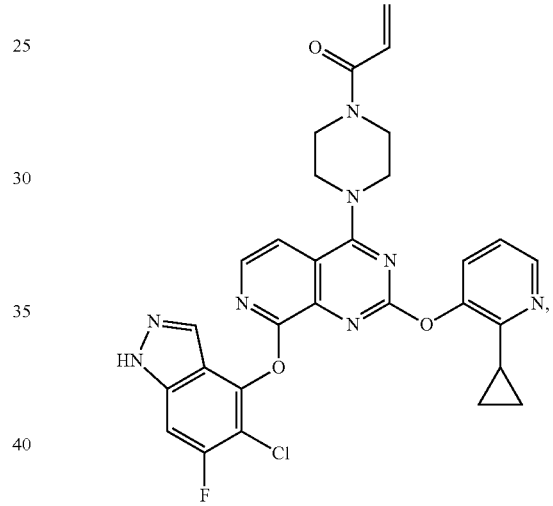
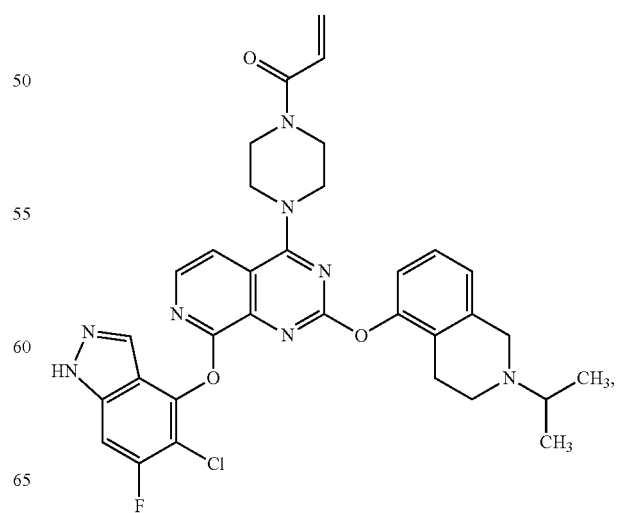

621
-continued
622
-continued
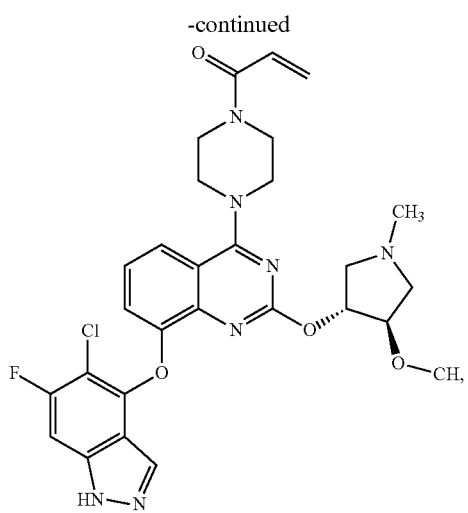
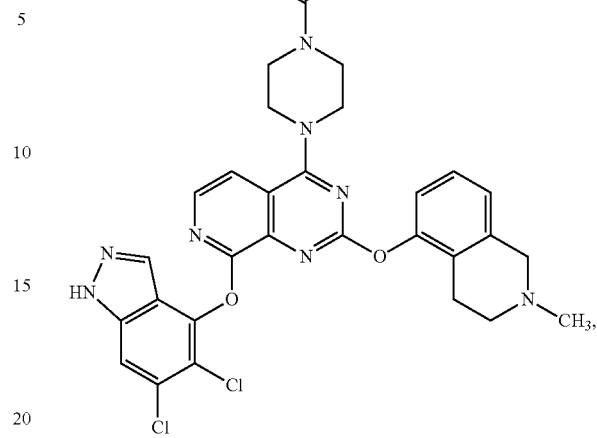
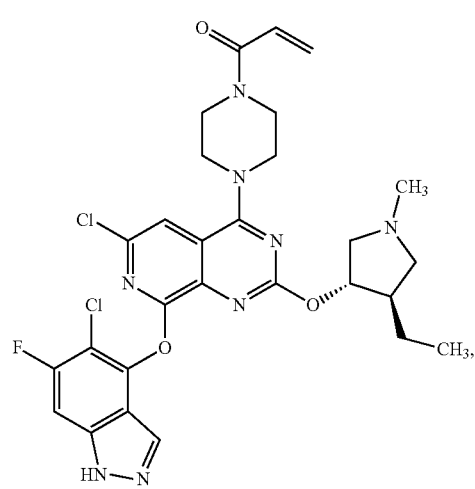
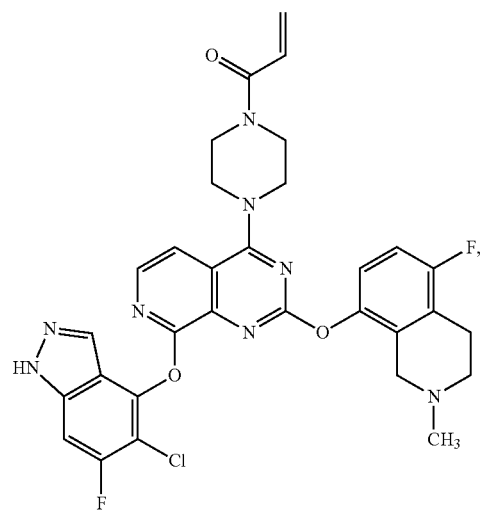
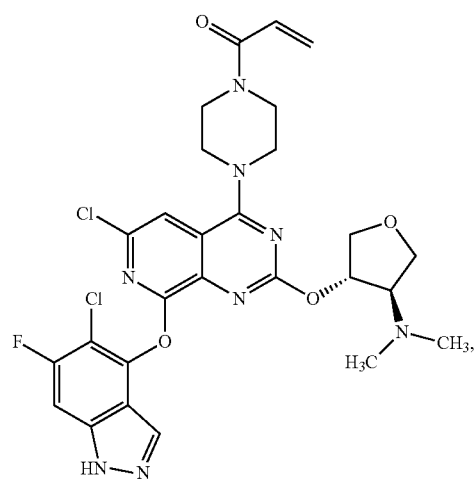
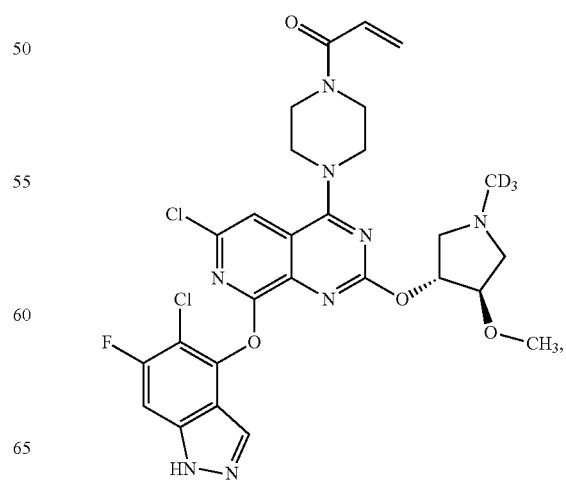

623
-continued
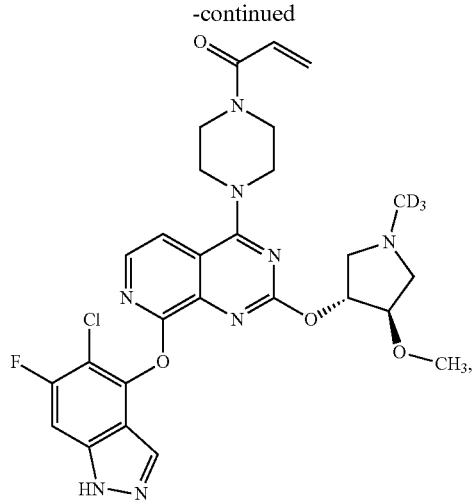
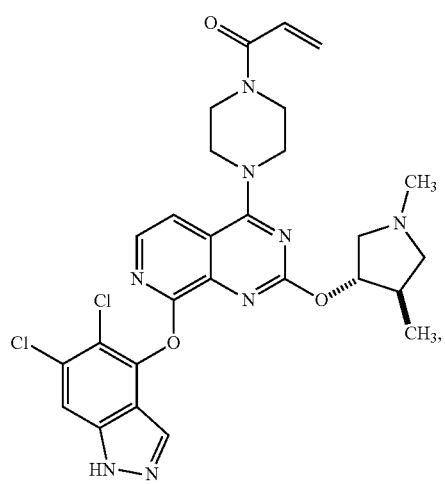
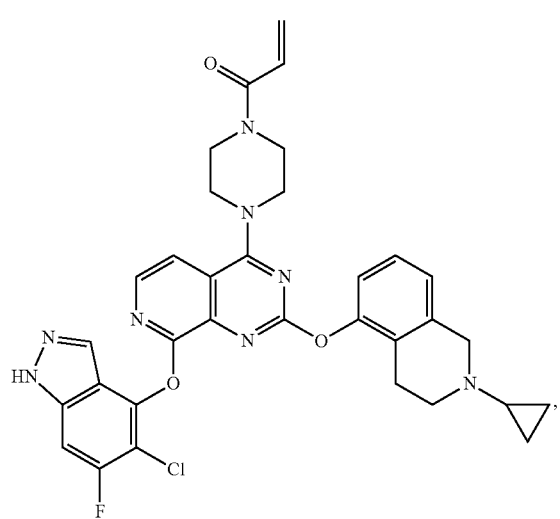
624
-continued
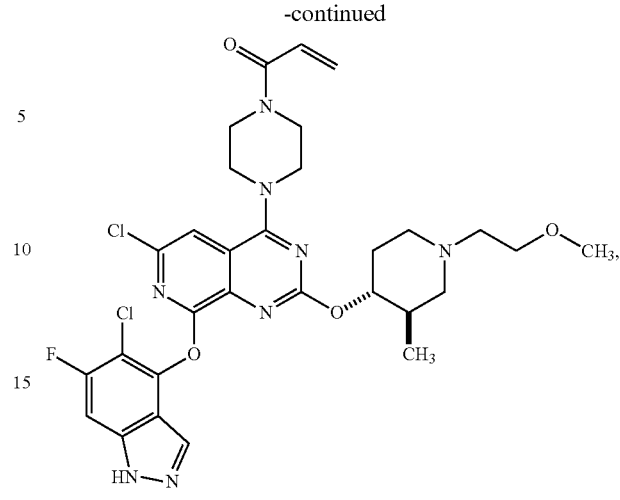
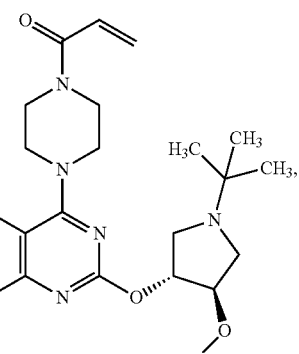
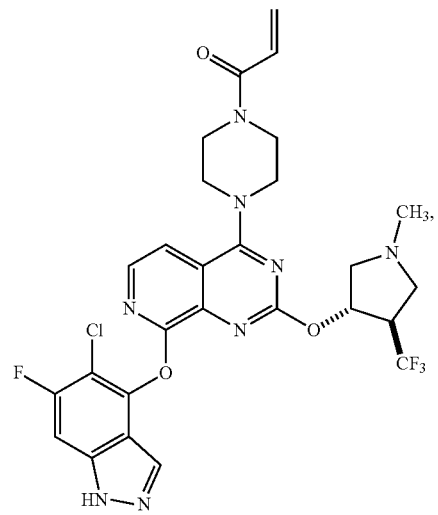

625
-continued
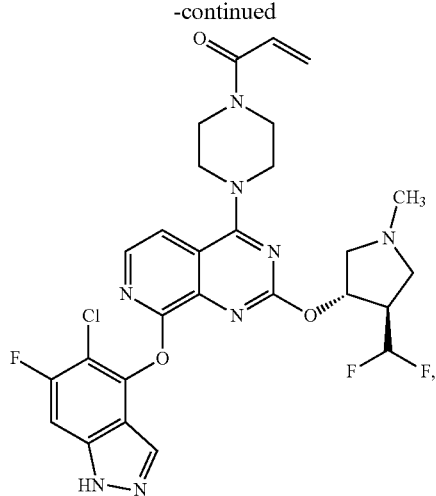
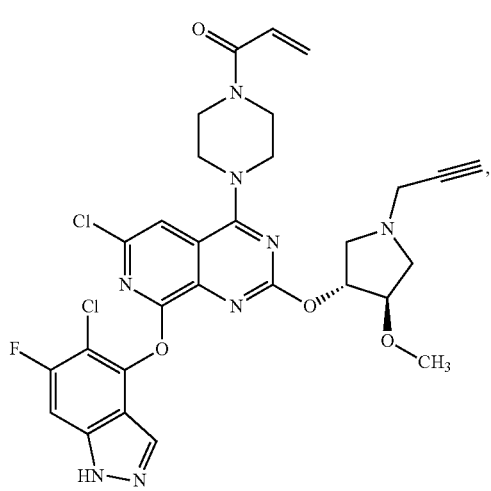
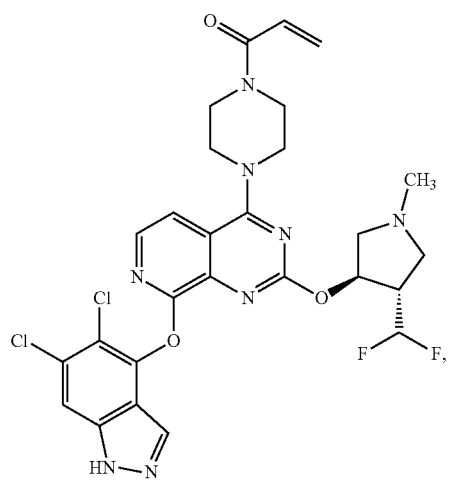
626
-continued
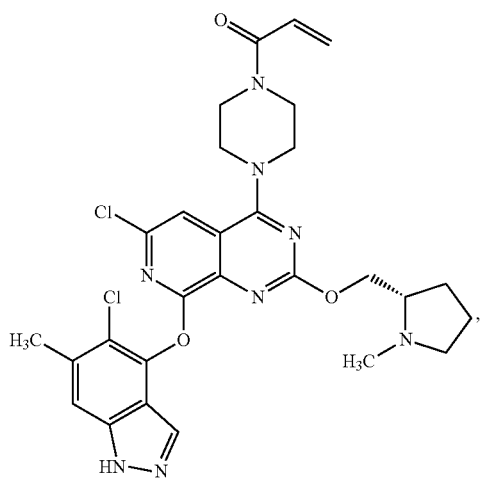
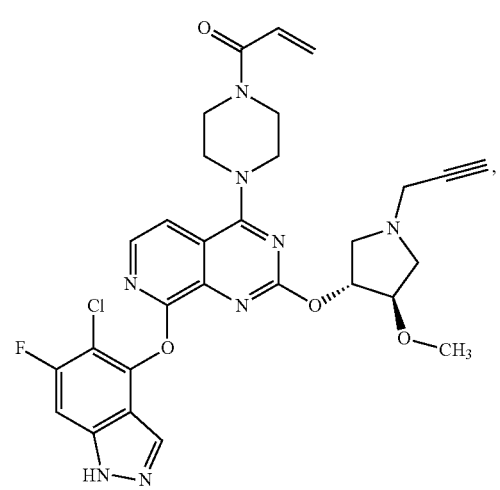
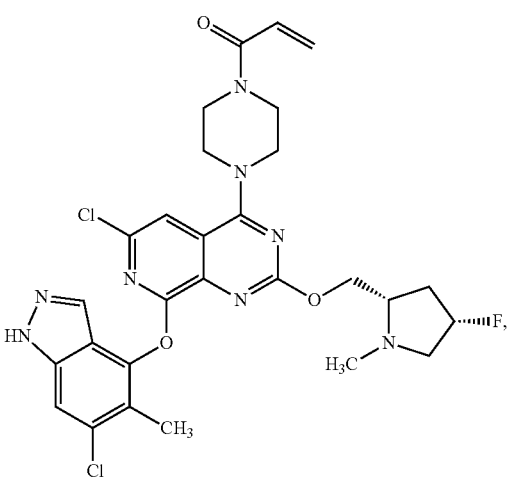

627

-continued

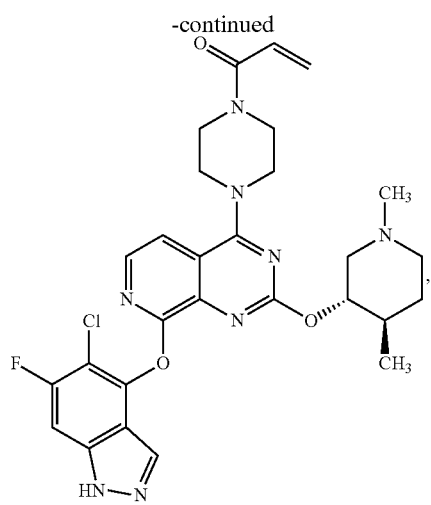

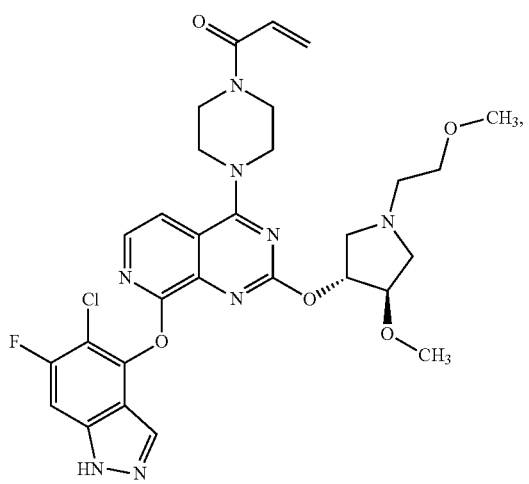

628

-continued

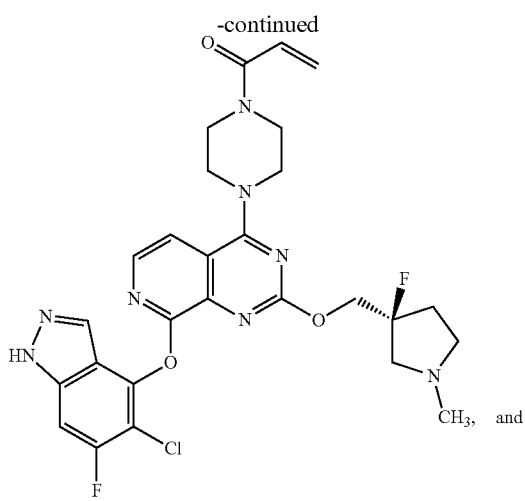

or a pharmaceutically acceptable salt thereof.

19. A compound or pharmaceutically acceptable salt of according claim 1, wherein one or more hydrogen atoms are replaced with deuterium atoms.

20. A pharmaceutical composition, comprising a therapeutically effective amount of a compound according to claim 1, or pharmaceutically acceptable salt thereof, and a pharmaceutically acceptable excipient.

21. A method of treating cancer in a mammal, the method comprising administering to the mammal a therapeutically effective amount of a compound according to any one of claims 1 5, 9, 13, 17 and 18, or a pharmaceutically acceptable salt thereof, wherein the cancer is lung cancer, pancreatic cancer, or colon cancer.

\* \* \* \* \*